US009751894B2

(12) United States Patent
Maiti et al.

(10) Patent No.: US 9,751,894 B2
(45) Date of Patent: Sep. 5, 2017

(54) CEPHEM COMPOUNDS, THEIR PRODUCTION AND USE

(71) Applicant: NAEJA-RGM PHARMACEUTICALS INC., Alberta (CA)

(72) Inventors: Samarendra Nath Maiti, Alberta (CA); Dai Quoc Nguyen, Alberta (CA); Andhe V. N. Reddy, Alberta (CA); Judy Yip, Alberta (CA); Chan Minh Ha, Alberta (CA); Rong Ling, Alberta (CA); Rudong Shan, Alberta (CA); Madhava Reddy Madala, Alberta (CA)

(73) Assignee: NAEJA-RGM PHARMACEUTICALS INC. (CA)

( * ) Notice: Subject to any disclaimer, the term of this patent is extended or adjusted under 35 U.S.C. 154(b) by 0 days.

(21) Appl. No.: 15/369,181

(22) Filed: Dec. 5, 2016

(65) Prior Publication Data
US 2017/0166587 A1    Jun. 15, 2017

Related U.S. Application Data

(60) Provisional application No. 62/265,625, filed on Dec. 10, 2015.

(51) Int. Cl.
*C07D 501/46* (2006.01)
*C07D 501/56* (2006.01)
*A61K 31/546* (2006.01)
*C07D 501/04* (2006.01)

(52) U.S. Cl.
CPC .......... *C07D 501/56* (2013.01); *A61K 31/546* (2013.01); *C07D 501/04* (2013.01)

(58) Field of Classification Search
CPC .............................. C07D 501/46; C07D 501/56
USPC .................... 540/221, 222, 225; 514/202
See application file for complete search history.

(56) References Cited

U.S. PATENT DOCUMENTS

| | | | | |
|---|---|---|---|---|
| 4,406,899 A | * | 9/1983 | Aburaki | C07D 501/46 514/202 |
| 4,748,171 A | * | 5/1988 | Yamauchi | C07D 471/08 514/202 |
| 4,864,022 A | * | 9/1989 | Miyake | C07D 277/587 540/222 |
| 4,910,301 A | * | 3/1990 | Kaplan | C07D 501/46 540/222 |
| 5,010,188 A | * | 4/1991 | Yamauchi | C07D 471/08 540/221 |
| 5,071,979 A | * | 12/1991 | Lattrell | C07D 501/46 540/225 |
| 5,173,485 A | * | 12/1992 | Sakane | C07D 519/00 514/202 |
| 5,215,982 A | * | 6/1993 | Sakane | C07D 501/00 514/202 |
| 5,998,611 A | | 12/1999 | Shinohara et al. | |
| 2012/0264727 A1 | | 10/2012 | Cho et al. | |
| 2013/0079319 A1 | | 3/2013 | Yamawaki et al. | |
| 2014/0256697 A1 | | 9/2014 | Yamawaki et al. | |

FOREIGN PATENT DOCUMENTS

| | | |
|---|---|---|
| EP | 332156 | 9/1989 |
| EP | 0832893 | 4/1998 |
| EP | 2341053 | 7/2011 |
| EP | 2557082 | 2/2013 |
| EP | 2703406 | 3/2014 |
| EP | 2706062 | 3/2014 |
| WO | WO 2004/039814 | 5/2004 |
| WO | WO 2007/119511 | 10/2007 |
| WO | WO 2011/136268 | 11/2011 |
| WO | WO 2013/052568 | 4/2013 |
| WO | WO 2014/068388 | 5/2014 |
| WO | WO 2014/087165 | 6/2014 |

OTHER PUBLICATIONS

Garigipati "An Efficient Conversion of Nitriles to Amidines," Tetrahedron Letters, 1990, vol. 31, No. 14, pp. 1969-1972.
Judkins et al. "A Versatile Synthesis of Amidines From Nitriles Via Amidoximes," Synthetic Communications, 1996, vol. 26, No. 23, pp. 4351-4367.
Nadrah et al. "Preparation of Amidines by Amidoxime Reduction with Potassium Formate," Synlett, May 2007, Iss. 8, pp. 1257-1258.
Ohki et al. "Studies on 3'-Quaternary Ammonium Cephalosporins II1)," The Journal of Antibiotics, Sep. 1995, vol. 48, No. 9, pp. 1049-1051.
Pfaff et al. "A Lewis acid-promoted Pinner reaction," Beilstein Journal of Organic Chemistry, 2013, vol. 9, pp. 1572-1577.
Pinner et al. "Unwandlung der Nitrile in Imide." Berichte der deutschen chemisschen Gesellschaft, Jul.-Dec. 1877, vol. 10, No. 2, pp. 1889-1897.
Weintraub et al. "A Convenient General Synthesis of Amidines," The Journal of Organic Chemistry, Apr. 1968, vol. 33, No. 4, pp. 1679-1681.
Yamawaki et al. "A novel series of parenteral cephalosporins exhibiting potent activities against Pseudomonas aeruginosa and other Gram-negative pathogens: Synthesis and structure-activity relationships," Bioorganic & Medicinal Chemistry, Nov. 2007, vol. 15, No. 21, pp. 6716-6732.

* cited by examiner

*Primary Examiner* — Kahsay Habte
(74) *Attorney, Agent, or Firm* — Sheridan Ross P.C.

(57) ABSTRACT

Cephem compounds, pharmaceutically acceptable salts thereof, and methods of using same, wherein the compound has a bicyclic nitrogen-containing aromatic heterocyclic ring as the quaternary ammoniomethyl group at the 3-position and one or both of a terminal amidine residue (substituted or unsubstituted) attached to an aryl or a 5- or 6-membered heteroaryl group (substituted or unsubstituted) which is further attached through a spacer to the free N-atom of the quaternary nitrogen-containing bicyclic ring at the 3-side chain, or a terminal guanidine residue attached to an aryl or a 5- or 6-membered heteroaryl group (substituted or unsubstituted) which is further attached through a spacer to the free N-atom of the quaternary nitrogen-containing bicyclic ring at the 3-side chain.

12 Claims, No Drawings

CEPHEM COMPOUNDS, THEIR PRODUCTION AND USE

CROSS-REFERENCE TO RELATED APPLICATIONS

This Application claims priority to U.S. Provisional Patent Application No. 62/265,625, filed Dec. 10, 2015, entitled "Cephem Derivatives As Broad-Spectrum Antibacterial Agents", which is hereby incorporated by reference in its entirety.

TECHNICAL FIELD

New cephem compounds, their pharmaceutically acceptable salts, their use, and the methods for preparation of these new compounds are provided. More particularly, cephem compounds having improved antibacterial activity, and combinations of the present cephem antibiotics with β-lactamase inhibitors that are active against a number of resistant pathogenic microorganisms are provided.

BACKGROUND

Cephem antibiotics have been widely used for the treatment of bacterial infections both in hospitals and in the general public. As such, it is highly desirable to use cephem antibiotics showing activity against both gram-positive and gram-negative bacteria. Unfortunately, due to the existence of multiple-drug resistant gram-negative and gram-positive organisms, many bacteria have become highly resistant to a number of β-lactam drugs, including the bacteria that constitute the ESKAPE organisms, generally encompassed by the following six pathogens: *Enterococcus faecium, Staphylococcus aureus, Klebsiella pneumonia, Acinetobacter baumanii, Pseudomonas aeruginosa* and *Enterobacter* species. This includes a resistance to known cephems whereby the bacteria are producing β-lactamases, including Class A (ESBL) and Class D (serine β-lactamases) types, which have an extended substrate spectrum. As a result, the morbidity and mortality caused by bacterial infections in both hospital and community settings continues to rise, and has become a significant public health concern.

There is a demand for development of new cephem compounds which exhibit more potent antimicrobial activity in particular more effective against a variety of β-lactamase producing gram-positive and gram-negative bacteria.

A variety of cephem compounds having a quaternary ammonium group at the 3-side chain and 2-(2-aminothiazol-4-yl)-2-hydroxy-(or substituted hydroxyl)aminoacetamido group at 7-position have been published such as, for example, U.S. Pat. Nos. 4,864,022, 5,173,485 ,5,215,982, 5,071,979, 4,406,899, 4,910,301, 4,748,171, 5,010,188, International Patent Application Nos. PCT/JP2003/013684, PCT/JP2007/056136, PCT/IB2013/002423, European Patent Application No. 2 703 406, European Patent Application No. 2 557 082; European Patent No. 2 341 053; European Patent Application No. 2 70606, United States Patent Application No. 2013/0079319 (Shionogi), United States Patent Application No. 2012/0264727, and European Patent Application No. 2706062.

The above mentioned patents and patent applications disclose cephem compounds whose quaternary ammoniomethyl group at the 3-position has a monocyclic or bicyclic nitrogen-containing heterocyclic or aromatic heterocyclic ring which is optionally substituted with an organic group other than benzamidine, heteroaryl amidine, arylguanidine and heteroaryl guanidine as the terminal residues.

There remains a need for new cephem compounds having increased antibiotic efficacy, particularly in highly resistant gram-positive and gram-negative bacteria, the compounds having structural features are significantly different from the compounds described in the patent references cited above

SUMMARY

According to embodiments herein, cephem compounds and pharmaceutically acceptable salts thereof are provided having a bicyclic nitrogen containing aromatic heterocyclic ring as the quaternary ammoniomethyl group at the 3-position and the free N-atom of the said bicyclic aromatic heterocyclic ring further attached through one or two carbon spacers to a residue like benzamidine, heteroarylamidine, arylguanidine and heteroaryl guanidine or similar basic functionality bearing terminal residues. The present compounds, and pharmaceutically acceptable salts thereof, comprise different structural characteristics to known cephem compounds, providing improved antibacterial activity, particularly when used in combination with one or more β-lactamase inhibitors. It may be an advantage of the present compounds, and pharmaceutically acceptable salts thereof, to provide antibacterial activity against "third-generation" and "fourth-generation" cephalosporin-resistant bacteria including gram-negative and gram-positive strains.

In some embodiments, the present cephem compounds, and pharmaceutically acceptable salts thereof, may comprise the following structural features:

(1) A bicyclic nitrogen containing aromatic heterocyclic ring as the quaternary ammoniomethyl group at the 3-position, and (2) A terminal amidine residue (substituted or unsubstituted) attached to an aryl or a 5- or 6-membered heteroaryl group (substituted or unsubstituted) which is further attached through a spacer to the free N-atom of the quaternary nitrogen containing bicyclic aromatic heterocyclic ring at the 3-side chain, or (3) A terminal guanidine residue attached to an aryl or a 5- or 6-membered heteroaryl group (substituted or unsubstituted) which is further attached through a spacer to the free N-atom of the quaternary nitrogen containing bicyclic aromatic heterocyclic ring at the 3-side chain.

In some embodiments, the present cephem compound may be represented by the general formula (I) or a pharmaceutically acceptable salt thereof:

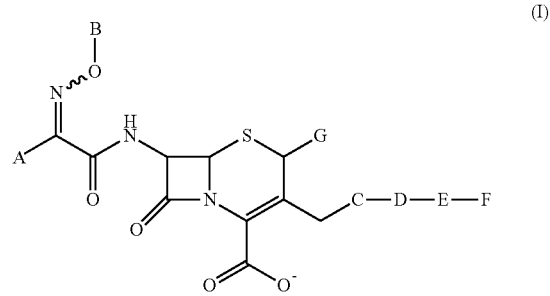

(I)

Accordingly, in some embodiments, cephem compounds and pharmaceutically acceptable salts thereof, i.e., compounds of formula (I) and pharmaceutically acceptable salts thereof are provided. In some aspects, these compounds may exhibit activity against pathogenic microorganisms, therefore useful in the treatment of bacterial infections in humans or animals either alone or in combination with other β-lactam and/or non β-lactam β-lactamase inhibitors.

In other embodiments, pharmaceutical compositions comprising one or more compounds of formula (I), or pharmaceutically acceptable salts thereof, and a pharmaceutically acceptable carrier or diluent are provided. In some aspects, these compositions may exhibit activity against pathogenic organisms.

In other embodiments, processes for the preparation of the new cephem compounds and salts thereof, i.e., the compounds of formula (I) and pharmaceutically acceptable salts thereof are provided.

In other embodiments, pharmaceutical compositions comprising (i) one or more compounds of formula (I), or pharmaceutically acceptable salts thereof, (ii) one or more β-lactamase inhibitors, and (iii) a pharmaceutically acceptable carrier or diluent are provided. In some aspects, these compounds may exhibit activity against pathogenic microorganisms.

In other embodiments, methods for treating bacterial infections in a subject, comprising providing or administering to a subject in need thereof:
(i) a therapeutically effective amount of one or more compounds of formula (I), or pharmaceutically acceptable salts thereof;
(ii) a therapeutically effective amount of a pharmaceutical composition comprising one or more compounds of formula (I), or pharmaceutically acceptable salts thereof, and a pharmaceutically acceptable carrier or diluent;
(iii) a therapeutically effective amount of a combination comprising (a) one or more compounds of formula (I), or pharmaceutically acceptable salts thereof, and (b) one or more β-lactamase inhibitors; or
(iv) a therapeutically effective amount of a pharmaceutical composition comprising (a) one or more compounds of formula (I), or pharmaceutically acceptable salts thereof, (b) one or more β-lactamase inhibitors, and (c) a pharmaceutically acceptable carrier or diluent.

In other embodiments, the use of a compound comprising formula (I) for bacterial infections in a subject is provided. In some aspects, the compound may further comprise a β-lactamase inihibitor, and may involve the preparation of a therapeutically effective medicament.

According to embodiments herein, the present subject may be a human being or an animal, or any other organism in which the present compounds and compositions may provide a beneficial antibacterial effect.

DETAILED DESCRIPTION OF THE EMBODIMENTS

According to embodiments herein, cephem compounds of general formula (I) and pharmaceutically acceptable salts of the compounds of formula (I) are provided, wherein the compounds comprise antibiotics suitable for use either alone or in combination with 3-lactamase inhibitors for the treatment of bacterial infections. The term "antibiotic" refers to a compound or composition which decreases the viability of a microorganism, or which inhibits the growth or proliferation of a microorganism and is further intended to include an antimicrobial, bacteriostatic or bactericidal agent.

More specifically, the present cephem compounds, and pharmaceutically acceptable salts thereof, may be represented by the following general formula (I):

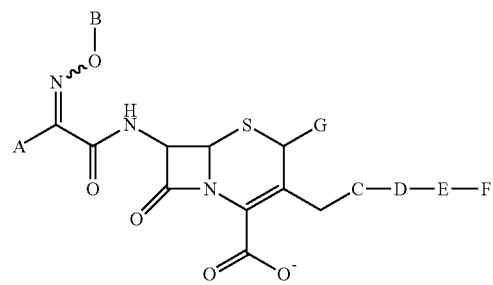

In the formula (I), A is defined by the formula (Ia):

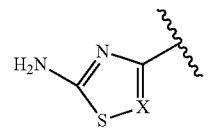

where X is N, C(H), C(F) or C(Cl);
B is defined as hydrogen, methyl, ethyl or represented by the formula (Ib)

wherein, $R^1$ and $R^2$ is independently hydrogen or lower alkyl, or $R^1$ and $R^2$ together may form a 3 to 6-membered spiro ring system; and
m is 0 or 1.

C is defined as a quaternized bicyclic nitrogen containing aromatic heterocyclic ring.

Further, regarding object (1a), it is understood that said objects include syn isomer (Z form), anti isomer (E form) and a mixture thereof.

In some preferred embodiments, the quaternized bicyclic nitrogen containing aromatic heterocyclic rings representing C, may comprise (Ic-Iz):

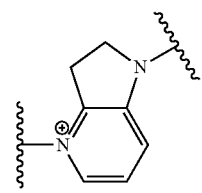

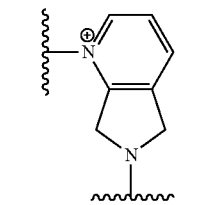

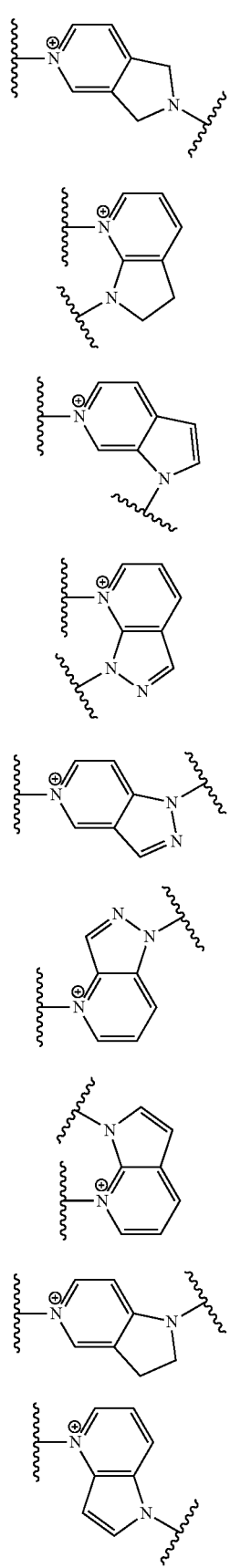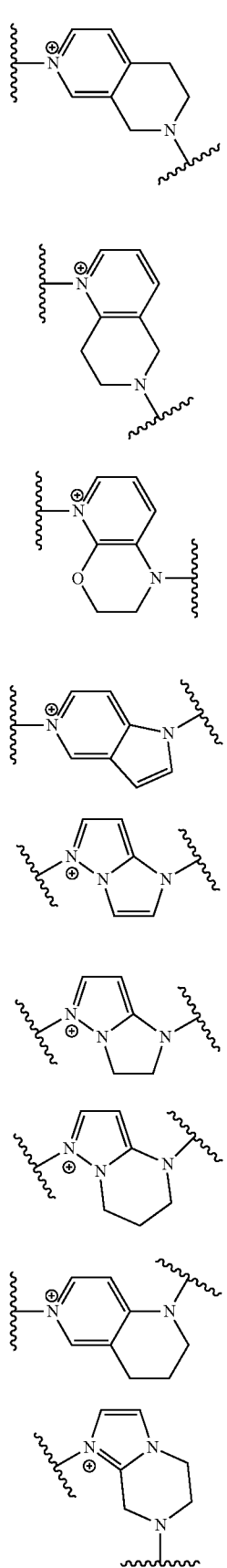

-continued

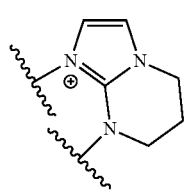
(Iw)

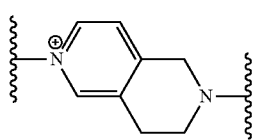
(Ix)

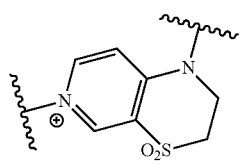
(Iy)

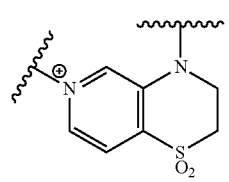
(Iz)

where D is represented by CH$_2$, CH$_2$CH$_2$ or CH$_2$CO; and

E signifies an optionally substituted benzene ring or an optionally substituted 5- or 6-membered aromatic heterocyclic ring having at least one heteroatom selected from O, S and N. Such heteroaromatic rings include pyrrolyl, imidazolyl, pyrazolyl, pyridazinyl, pyrimidinyl, pyrazinyl, triazolyl, isoxazolyl, oxazolyl, oxadiazolyl, isothiazolyl, thiazolyl, thiadiazolyl, furyl, thienyl and the like.

In the above formula (I), E may even more preferably selected from aryl or 5- and 6-membered aromatic heterocyclic rings as indicated below:

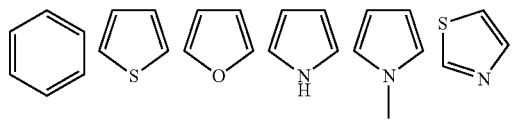

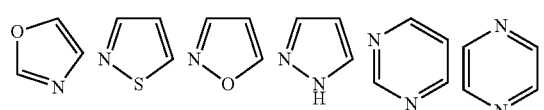

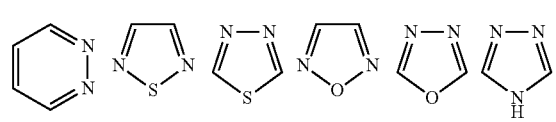

In the above definition, optional substituents include chloro, fluoro, cyano, hydroxy, carboxy, acetyl, methoxy, ethoxy, trifluoromethyl, pyrrolidinyloxy, piperidinyloxy and the like.

Preferably, the substituent is selected from chloro, fluoro, hydroxy, methoxy, trifluoromethyl, pyrrolidinyloxy.

Having further regard to the formula (I), in the definition of E the aryl or aromatic heterocyclic ring can accommodate up to 3 substituents selected from: F, Cl, CH$_3$, C$_2$H$_5$, CF$_3$, NH$_2$, NHCH$_3$, CONH$_2$, CONHCH$_3$, OCH$_3$.

In the formula (I), F is optionally substituted amidine or optionally substituted guanidine, and G is hydrogen, methyl, ethyl, C$_{3-6}$ alkyl, C$_{3-6}$ cycloalkyl or an optionally substituted 5- or 6-membered aliphatic or an optionally substituted 5- or 6-membered aromatic heterocyclic ring, in which the heterocyclic ring is substituted with at least 1-2 hetero atoms selected from N, O, and S (α or β).

In the formula (I), some preferred examples of "-C-D-E-F" include the fragments (1 to 277) as shown below:

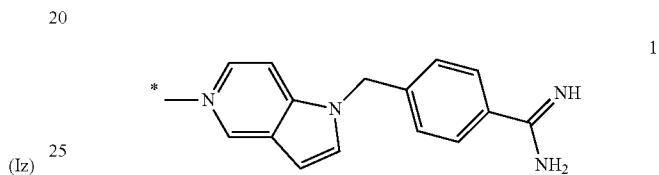
1

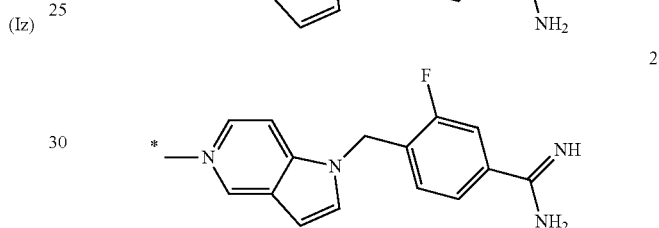
2

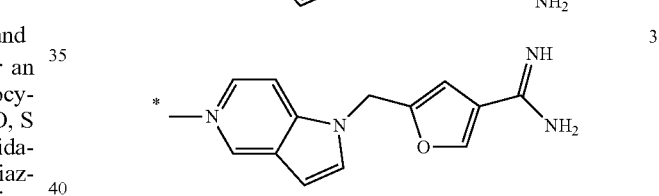
3

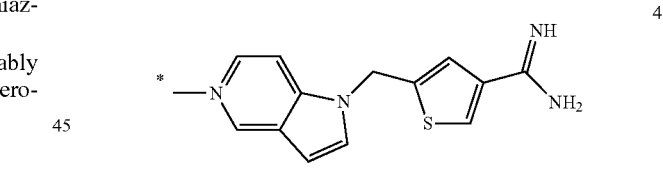
4

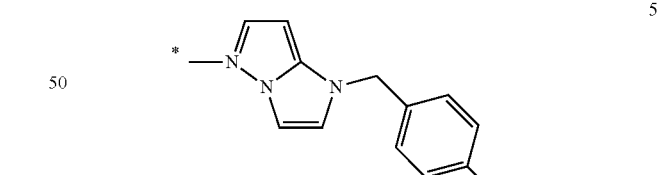
5

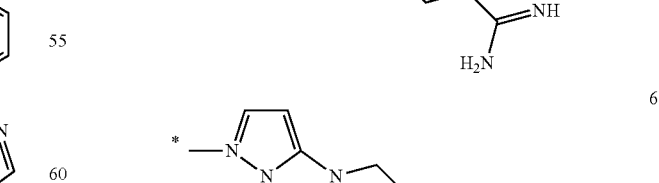
6

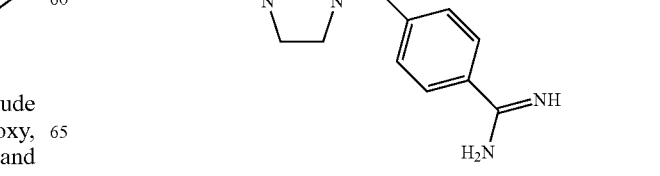

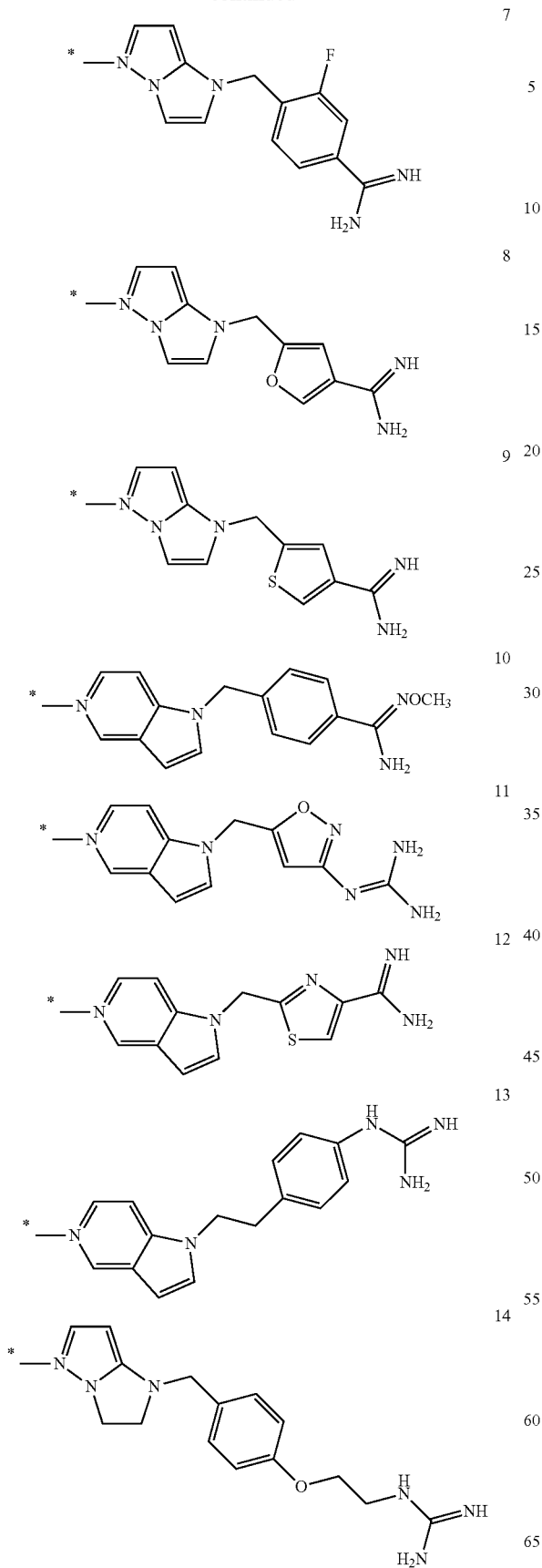
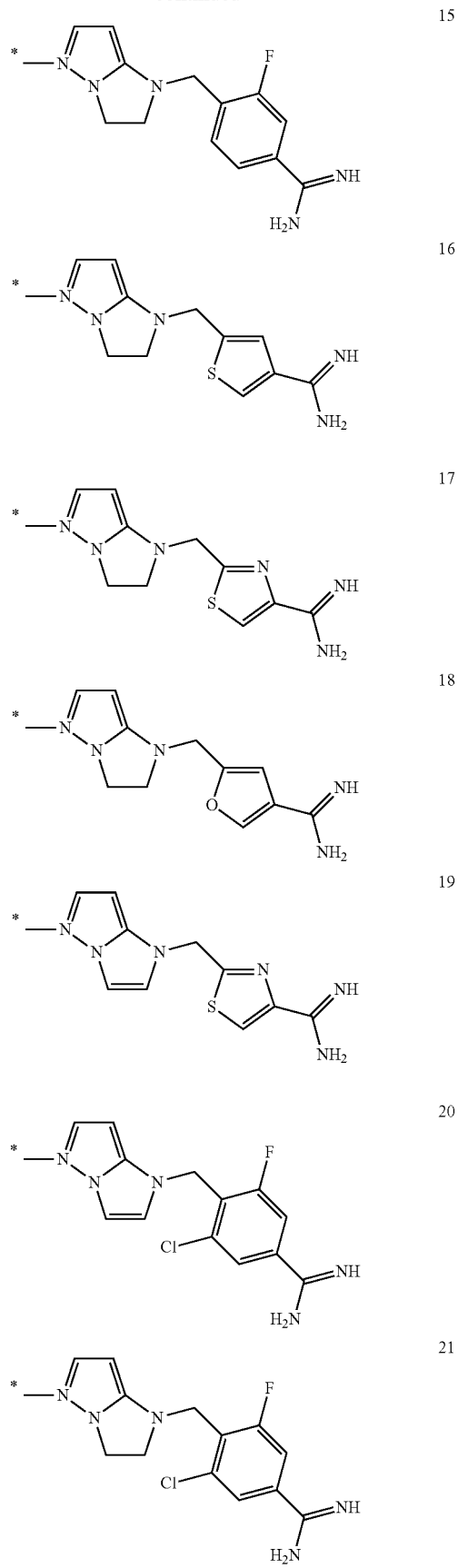

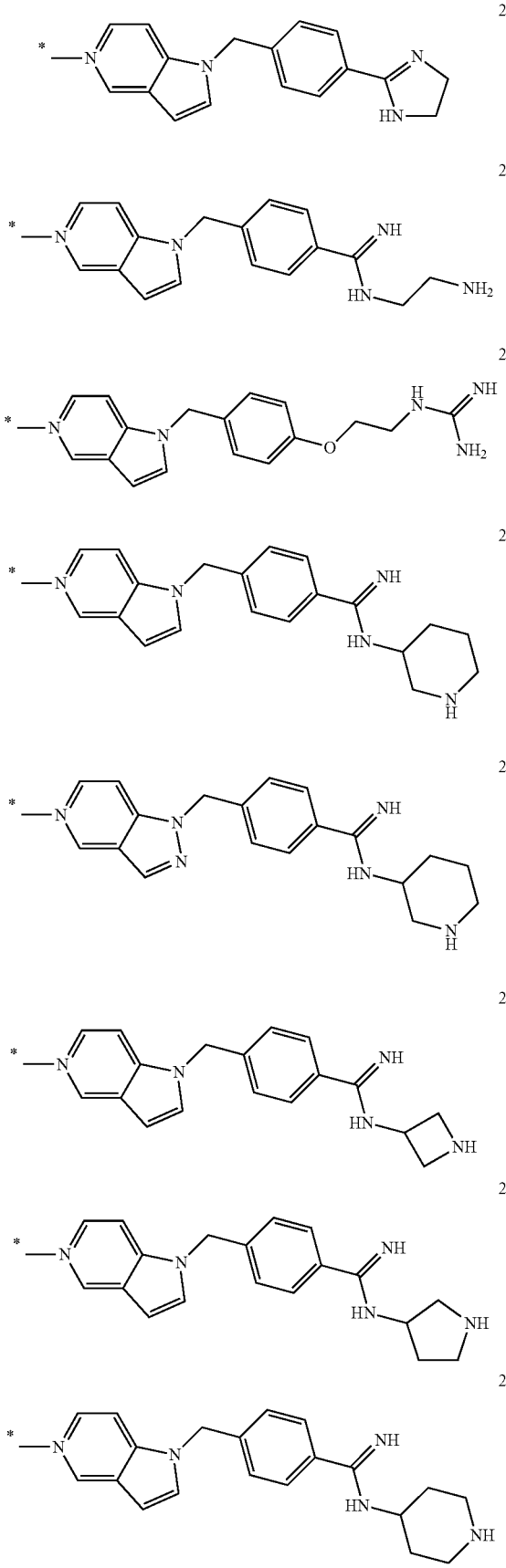
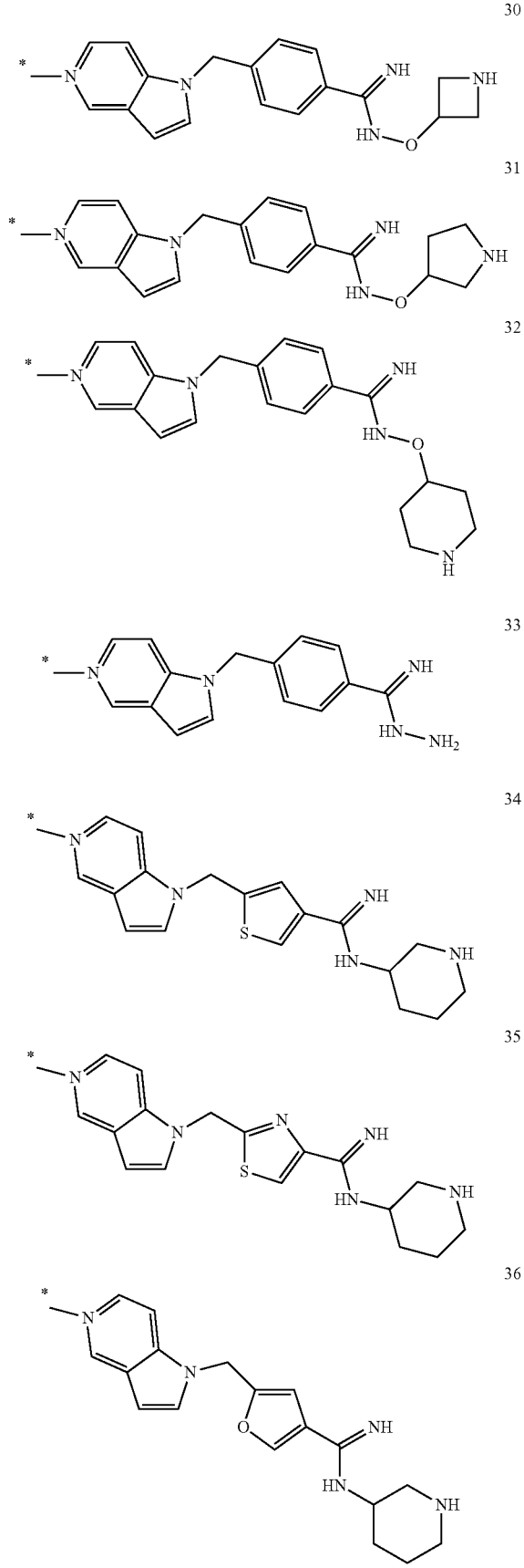

37 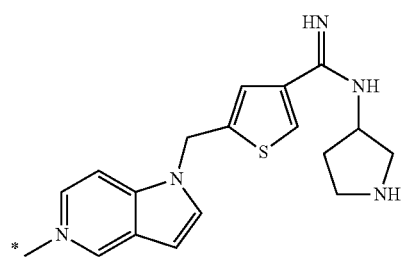
38 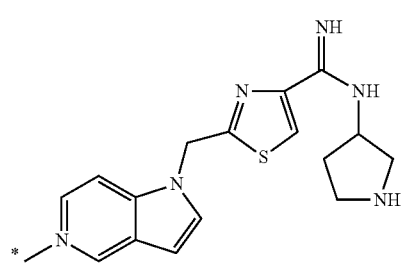
39 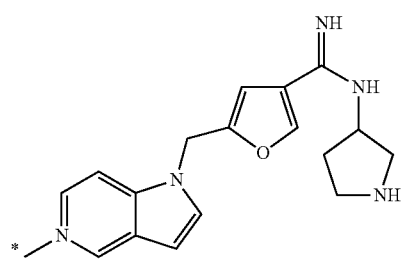
40 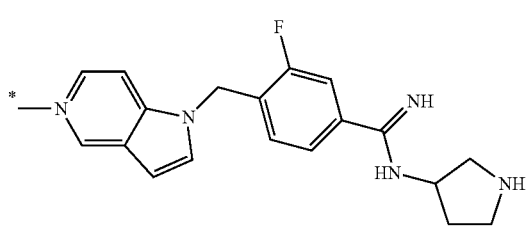
41 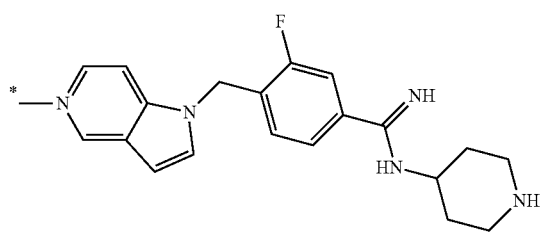
42 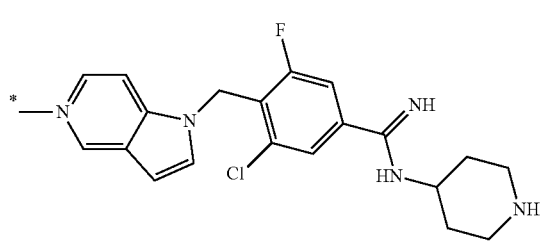
43 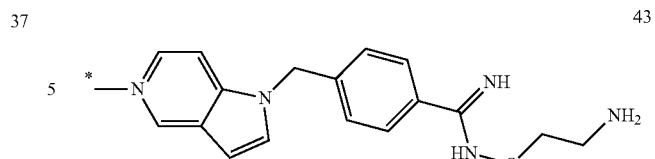
44 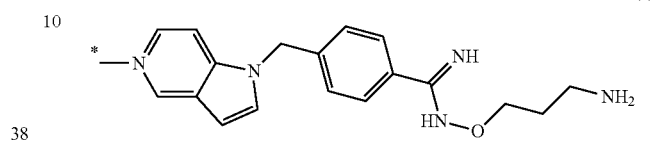
45 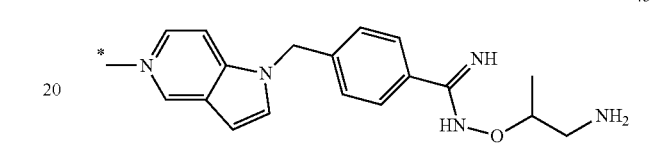
46 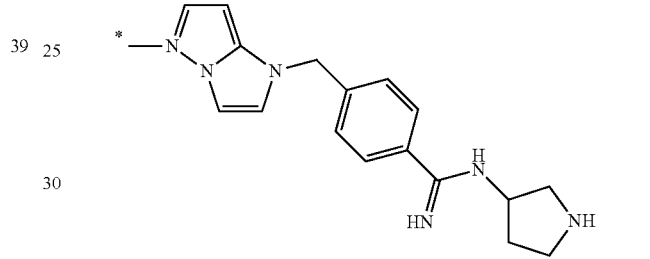
47 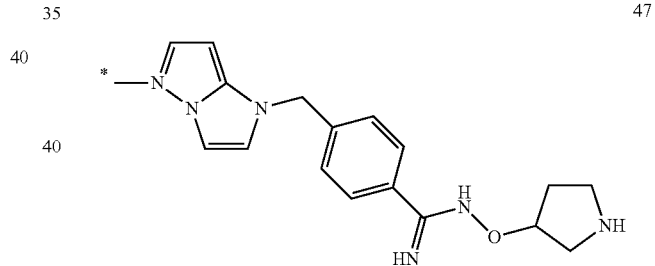
48 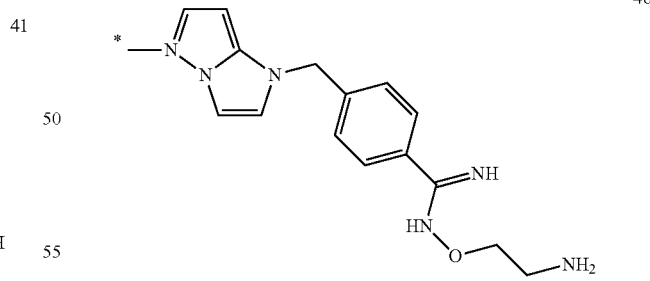
49 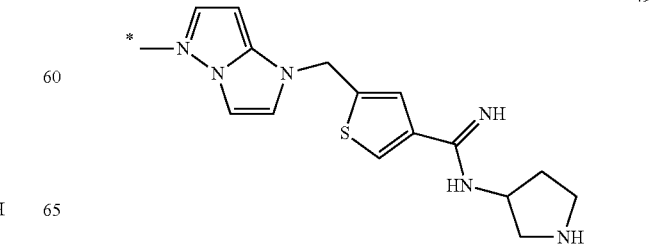

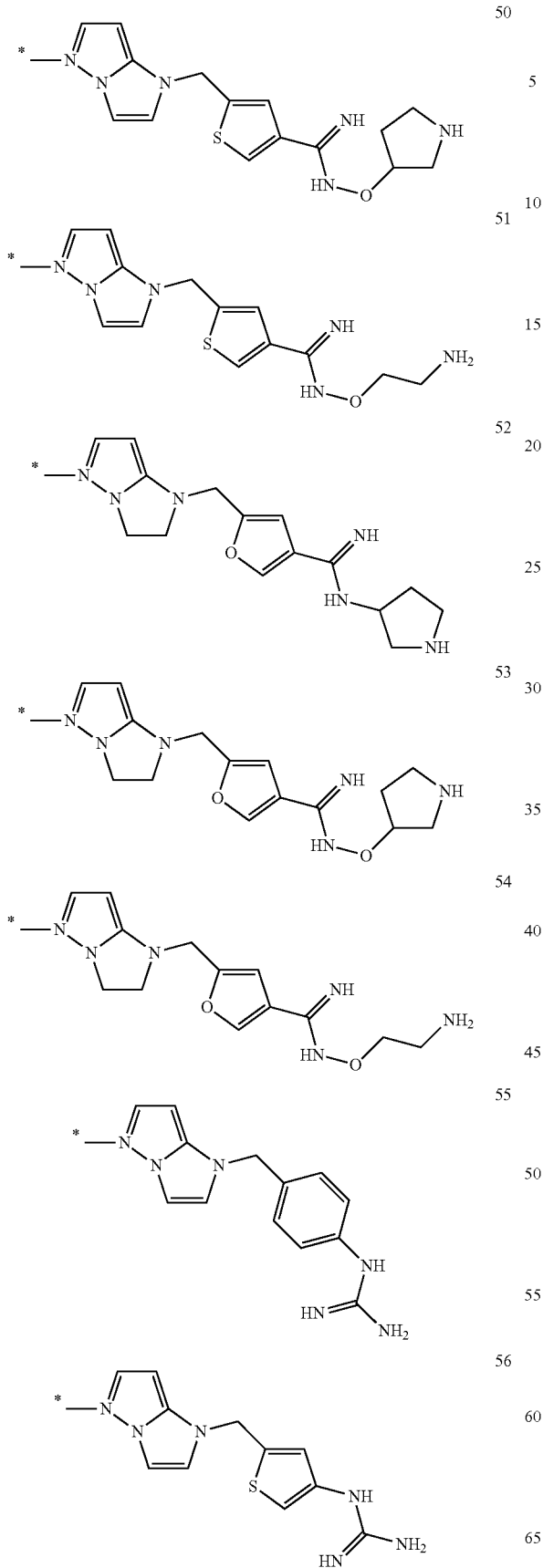
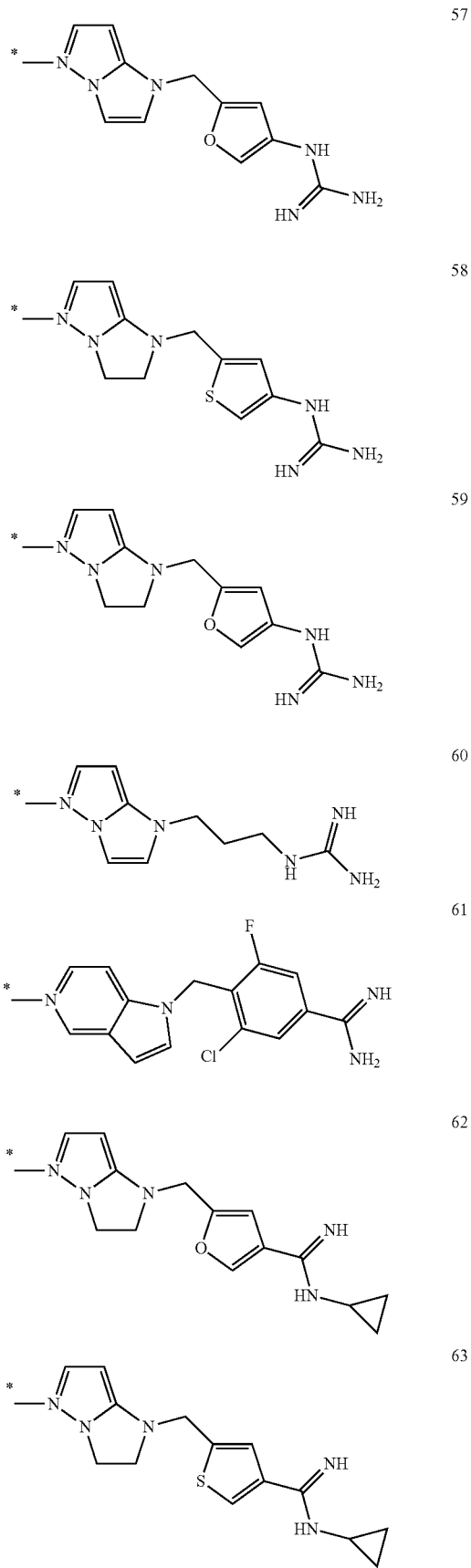

| | |
|---|---|
| 64 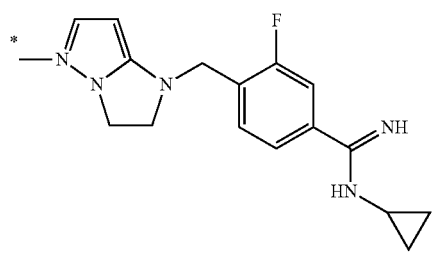 | 70 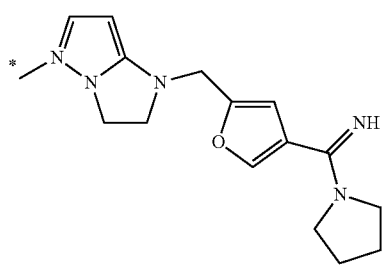 |
| 65 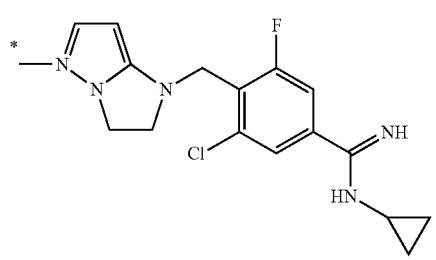 | 71 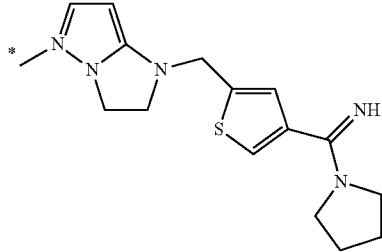 |
| 66 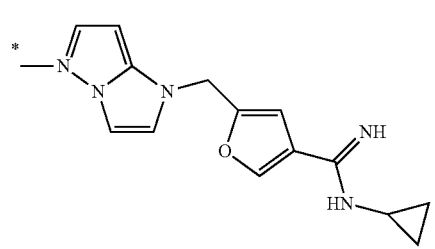 | 72 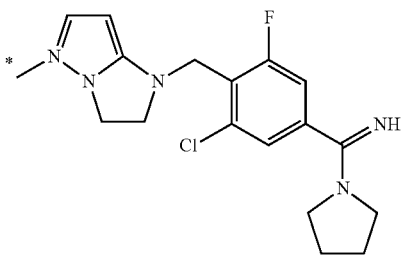 |
| 67 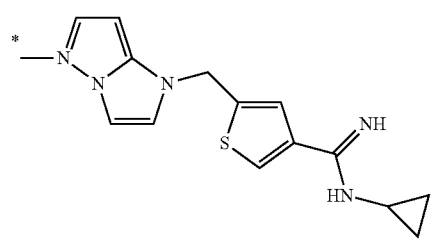 | 73 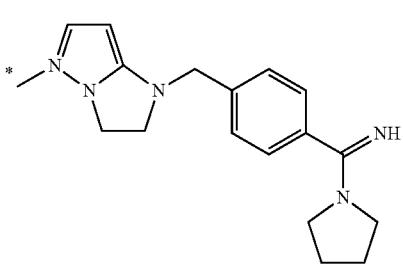 |
| 68 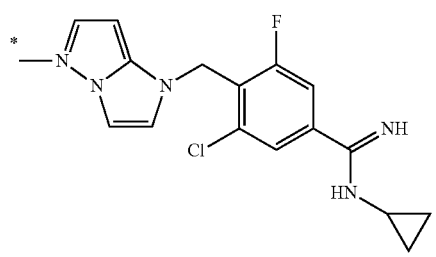 | 74 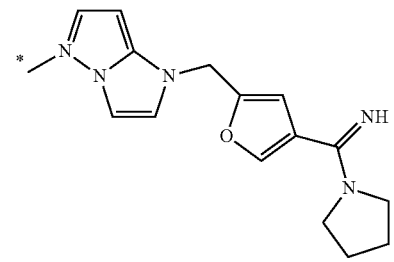 |
| 69 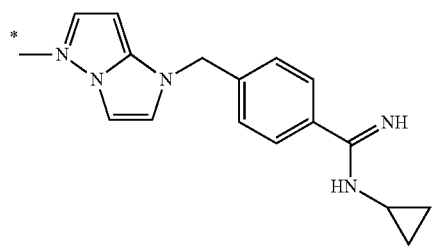 | 75 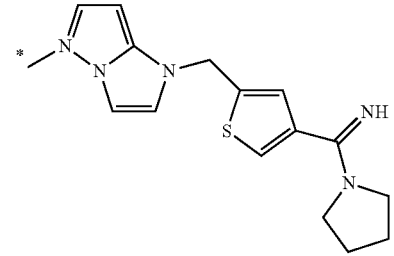 |

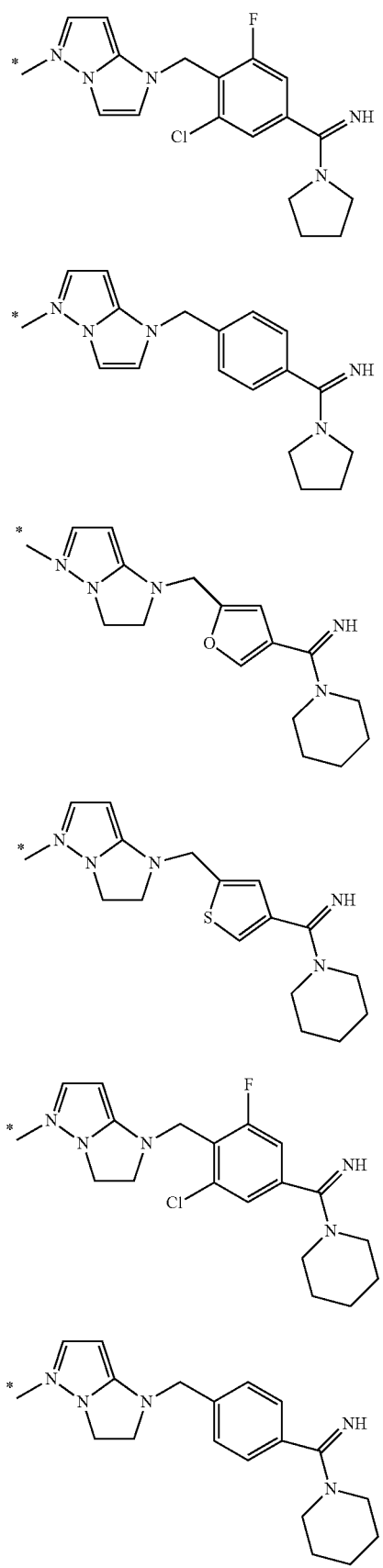

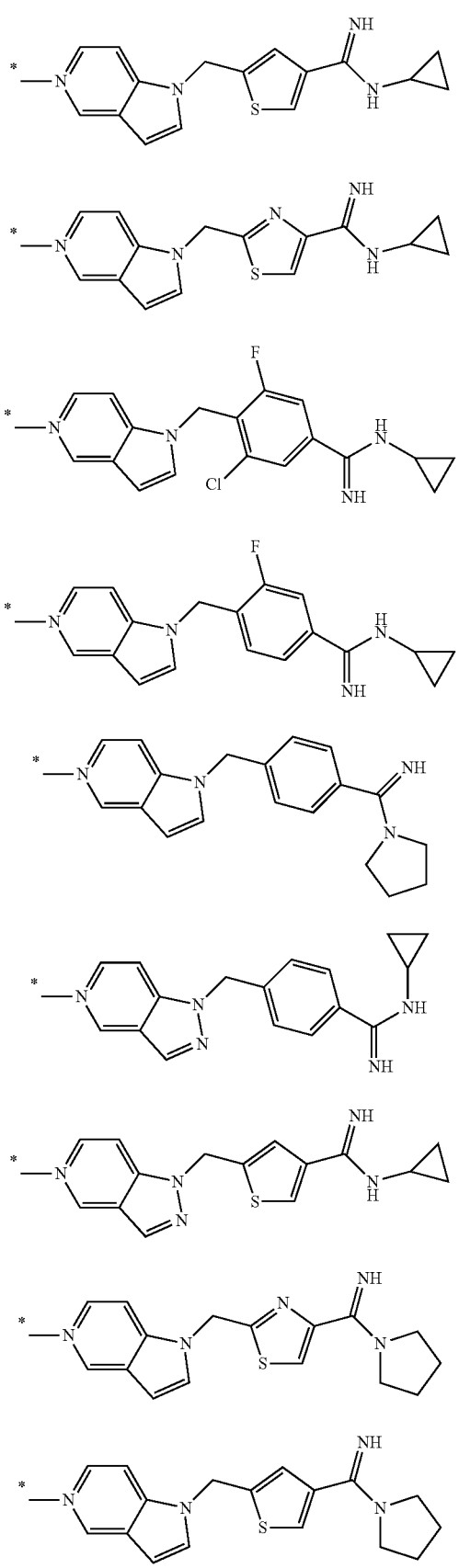
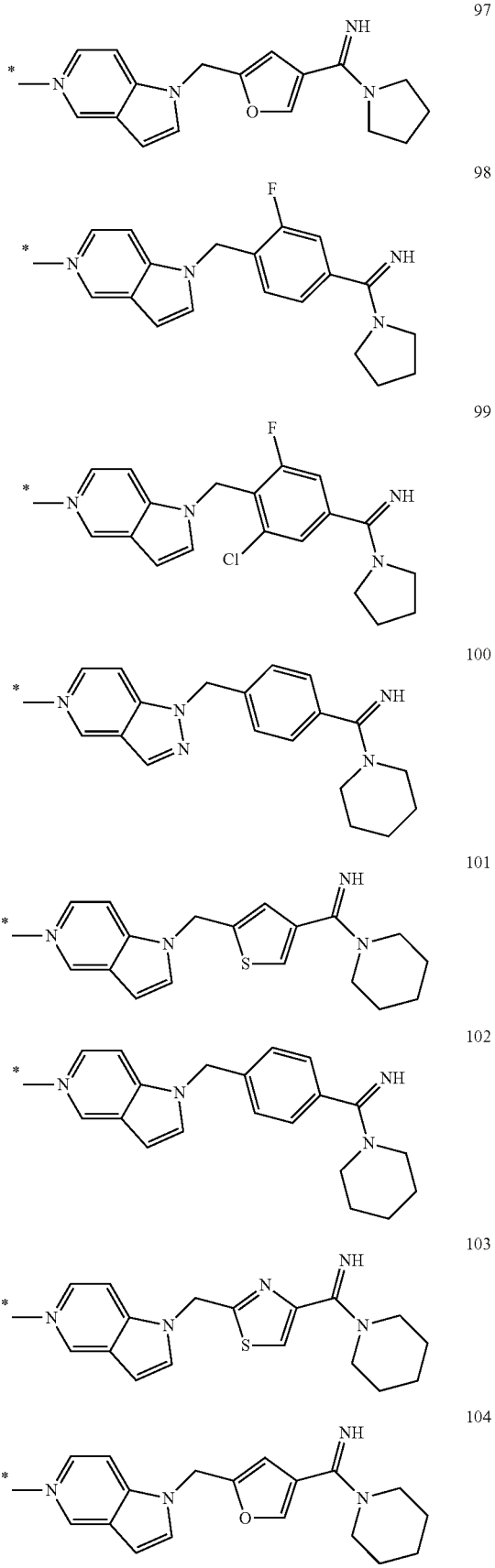

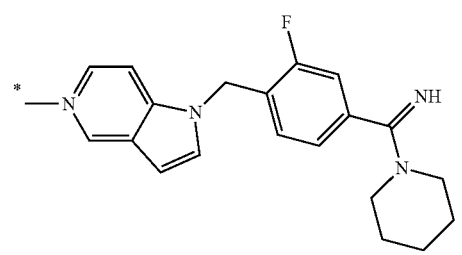
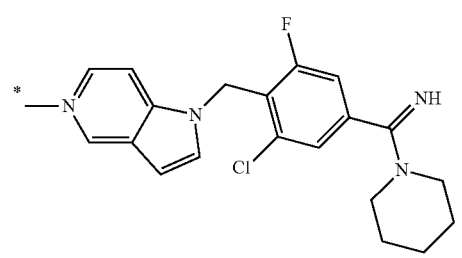
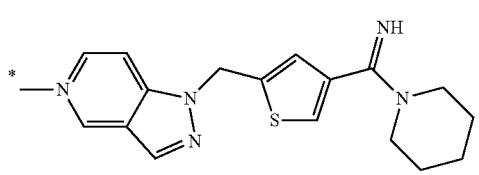
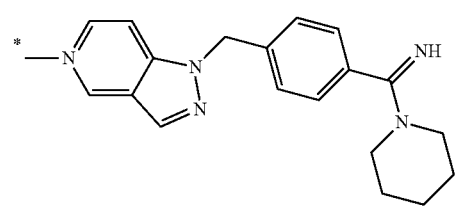
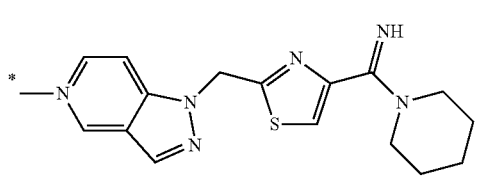
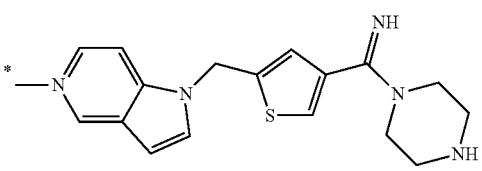
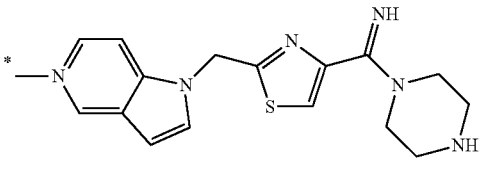
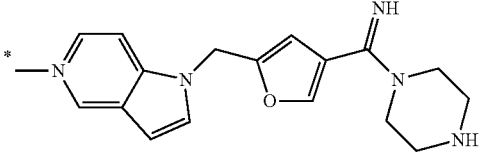
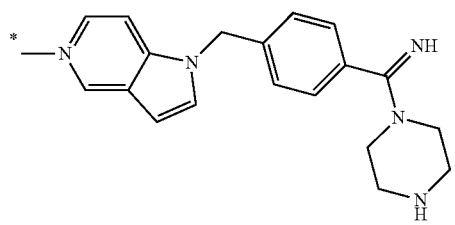
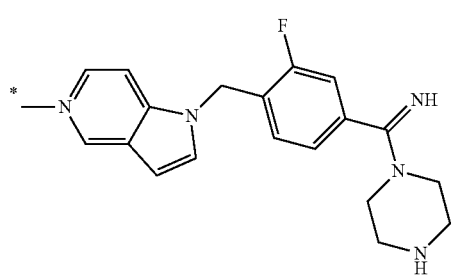
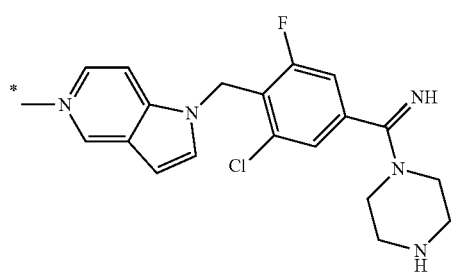
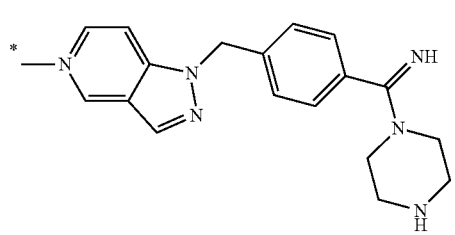
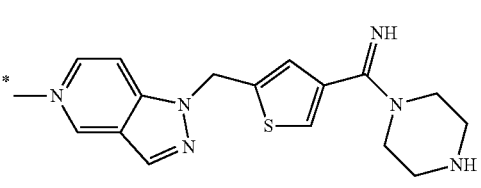
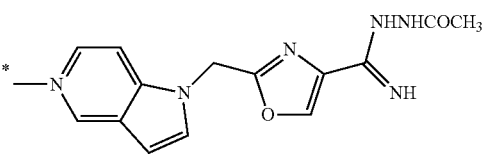
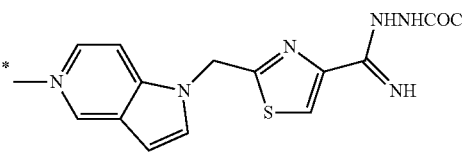

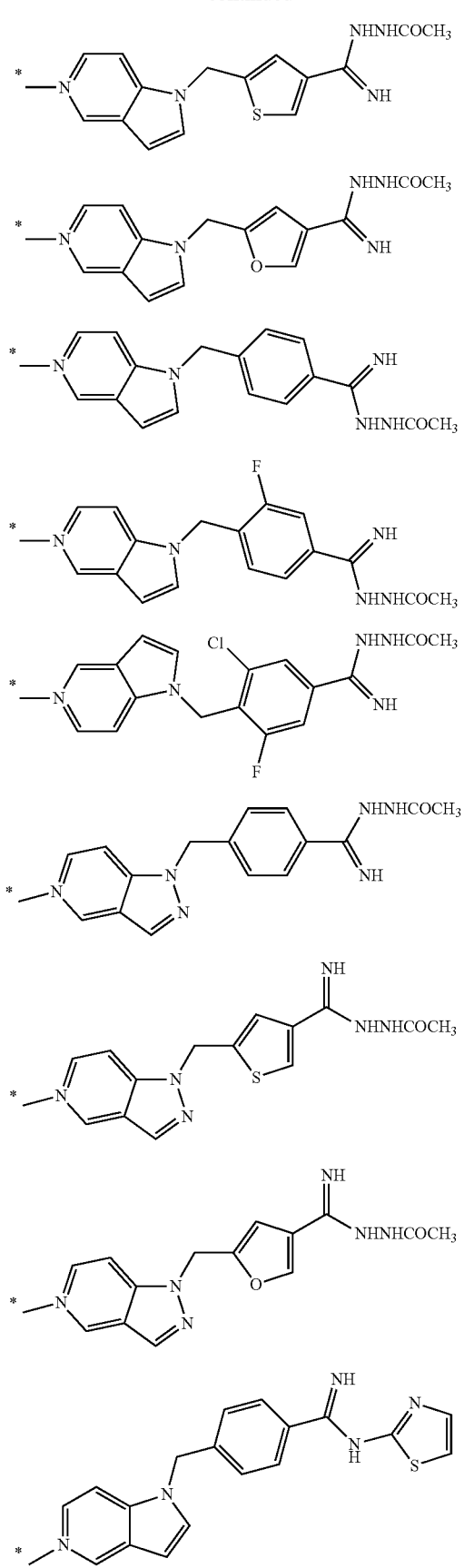
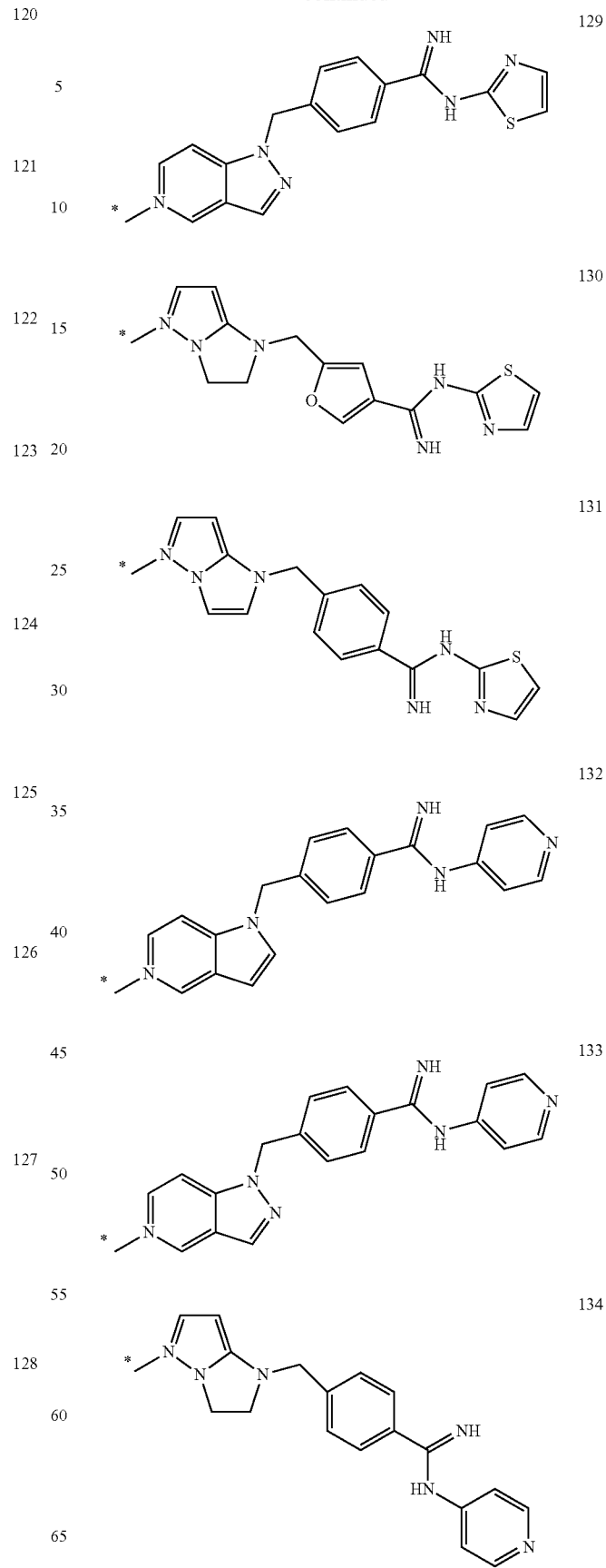

135 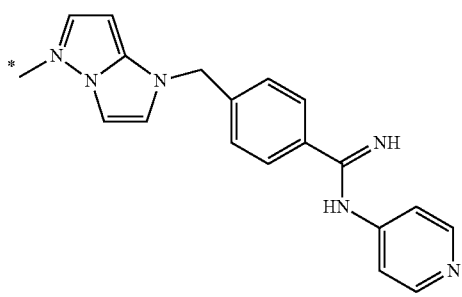
136 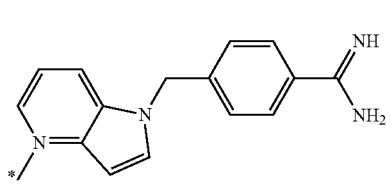
137 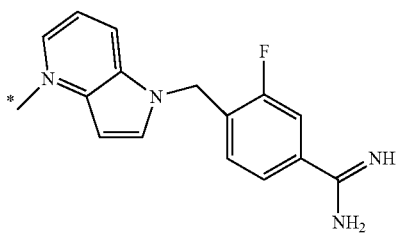
138 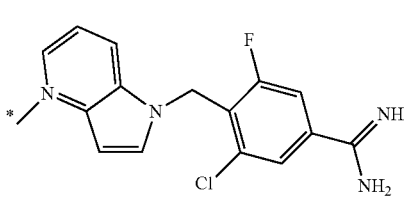
139 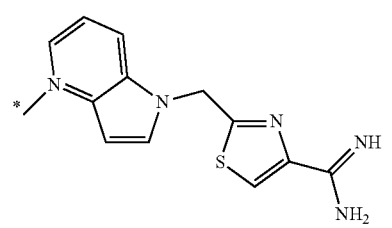
140 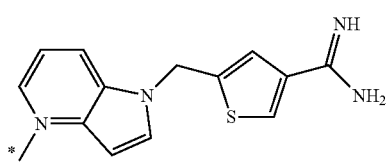
142 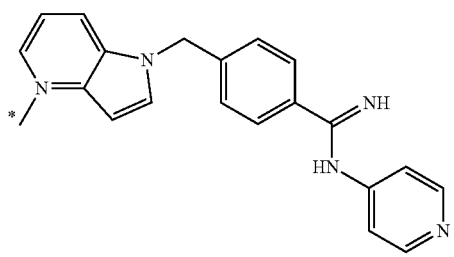
143 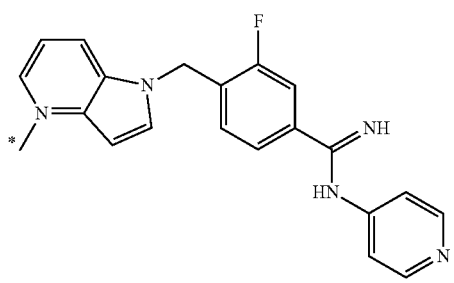
144 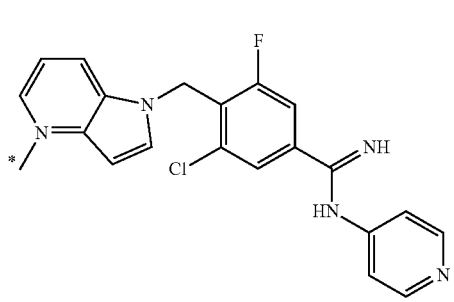
145 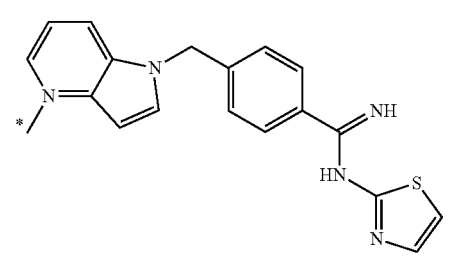
146 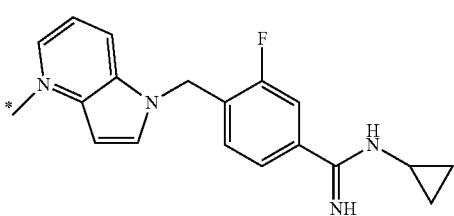
147 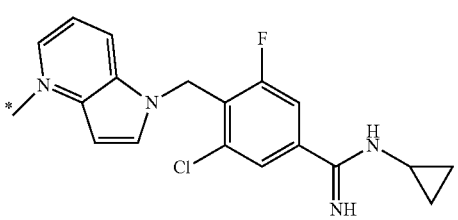

148 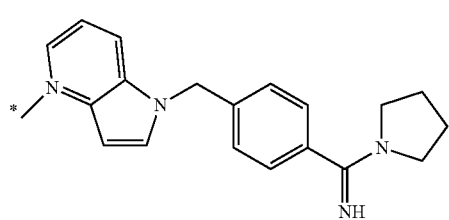
149 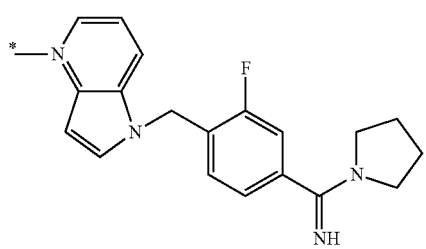
150 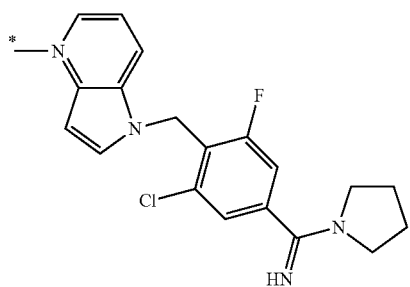
151 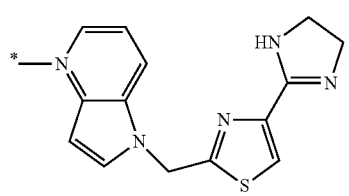
152 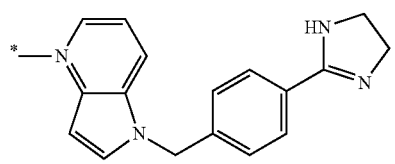
153 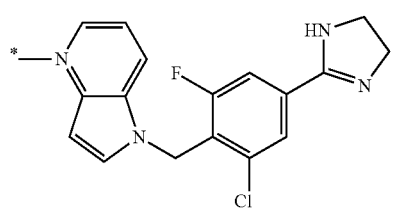
154 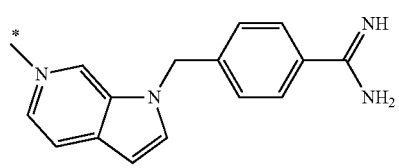
155 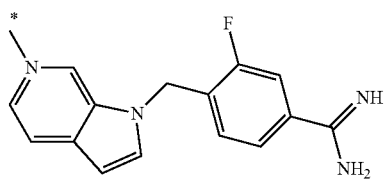
156 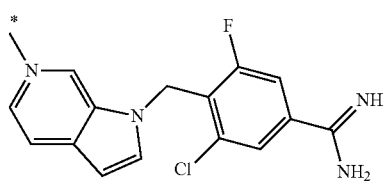
157 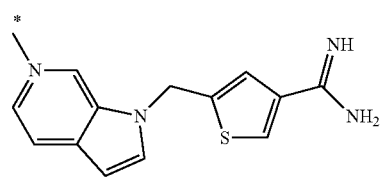
158 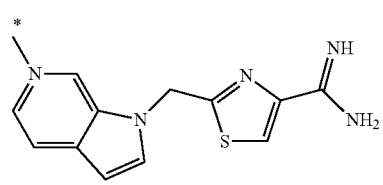
159 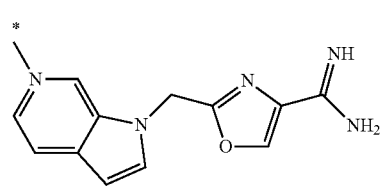
160 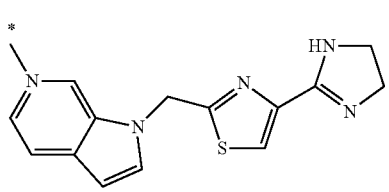
161 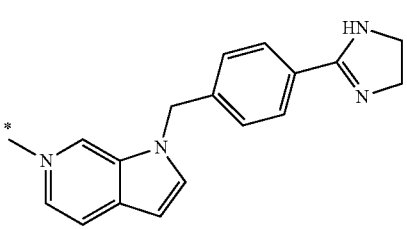
162 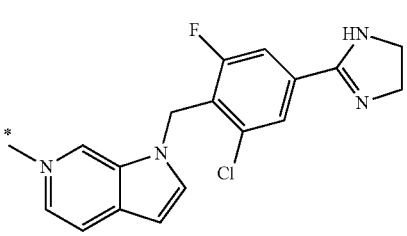

163 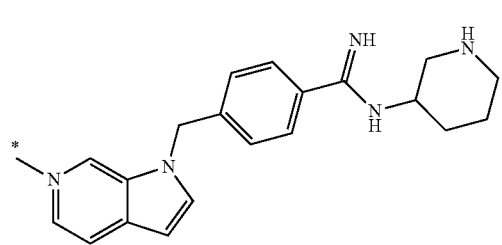
164 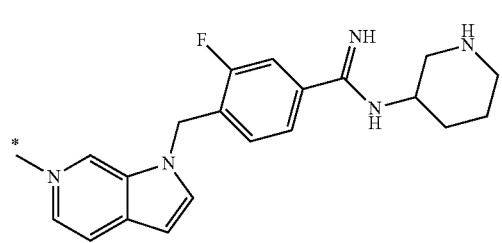
165 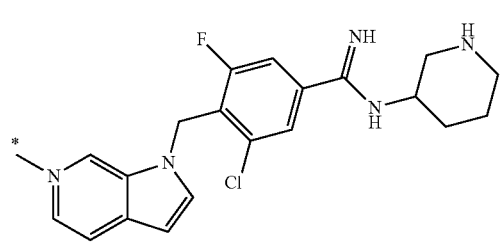
166 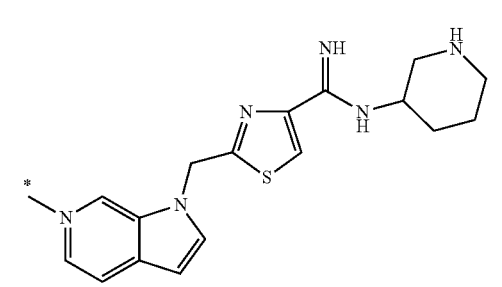
167 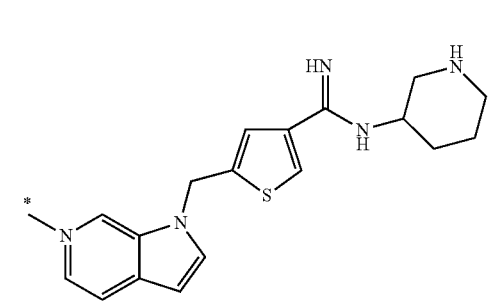
168 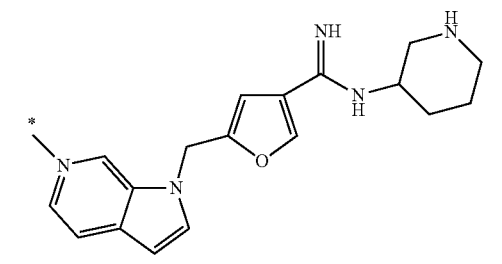
169 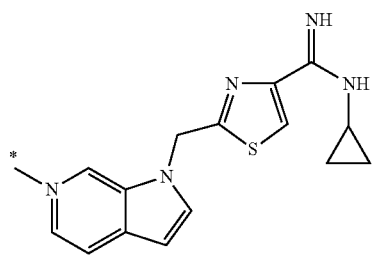
170 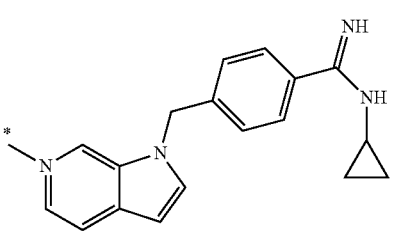
171 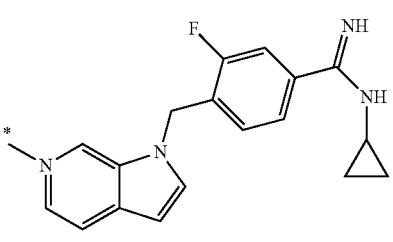
172 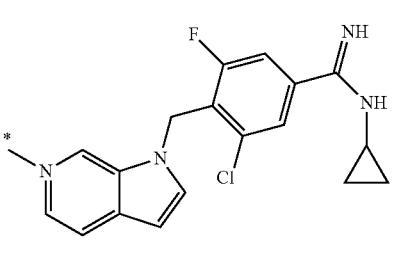
173 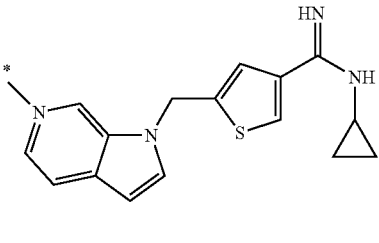
174 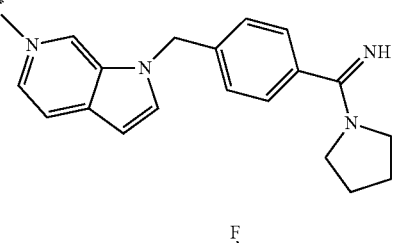
175 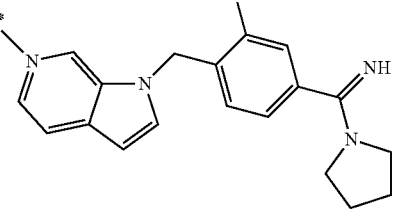

176 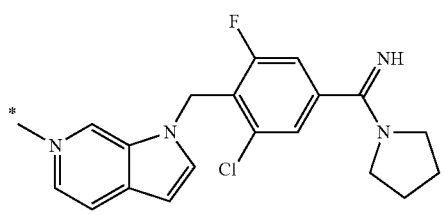
177 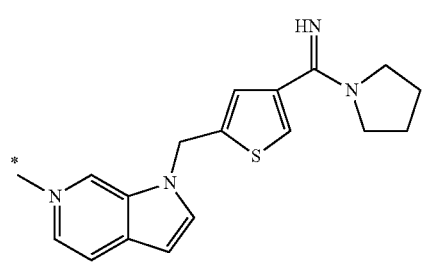
178 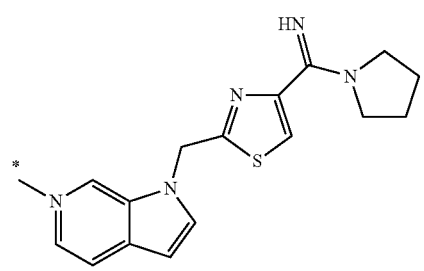
179 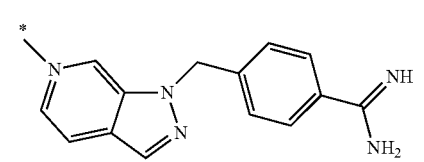
180 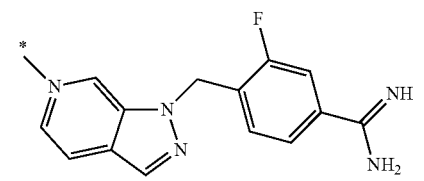
181 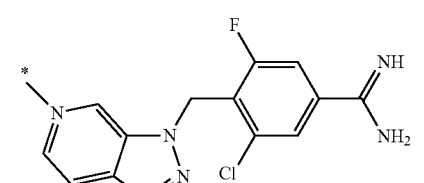
182 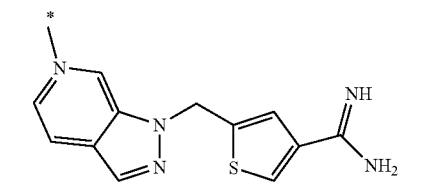
183 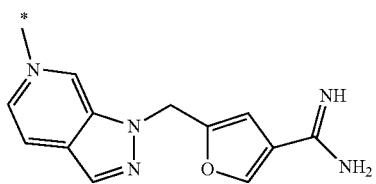
184 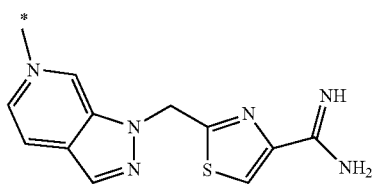
185 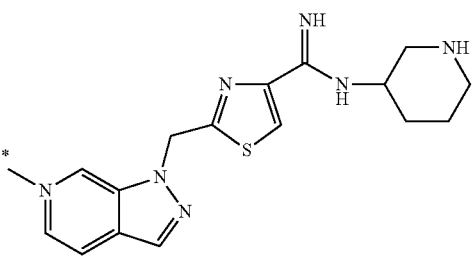
186 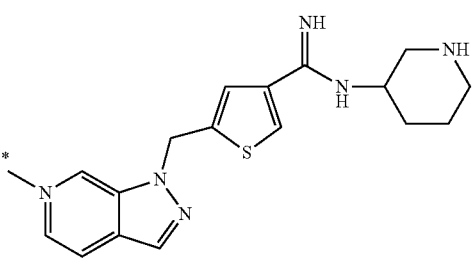
187 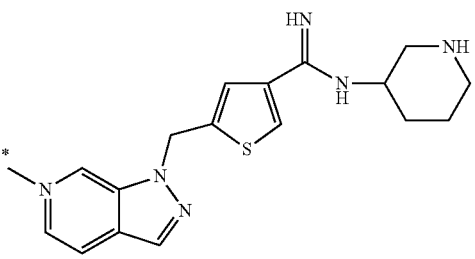
188 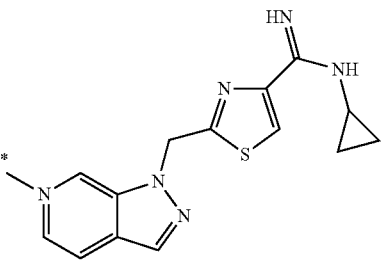

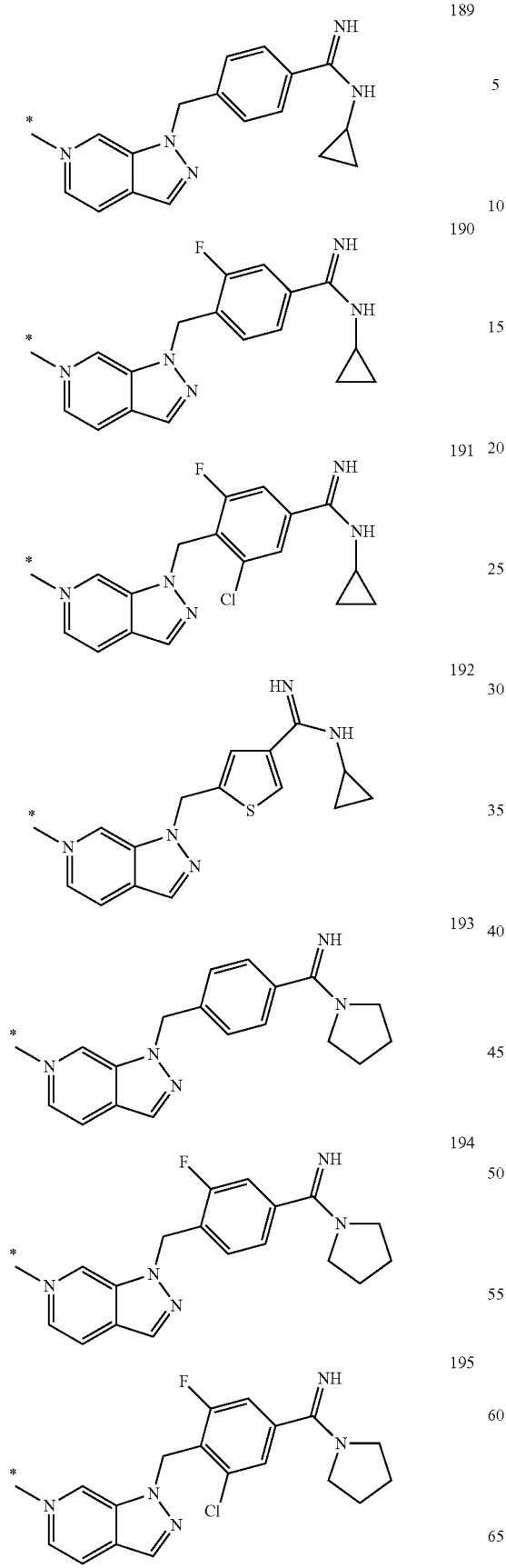

| | |
|---|---|
| 202 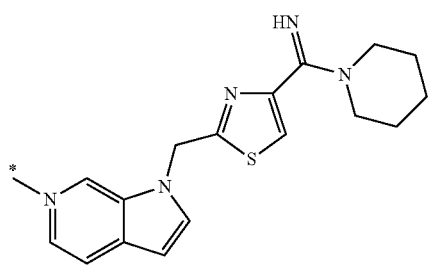 | 208 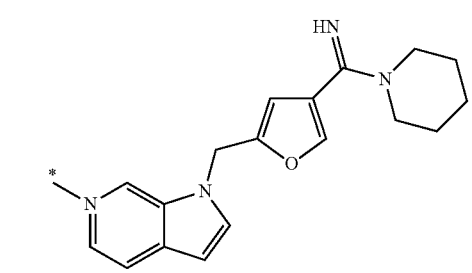 |
| 203 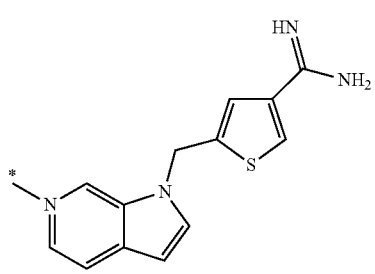 | 209 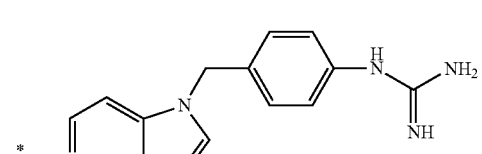 |
| 204 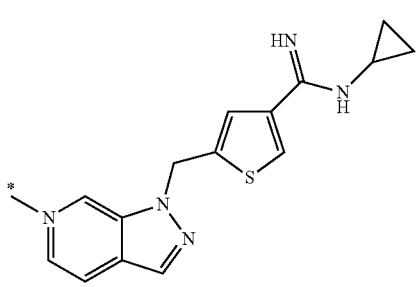 | 210 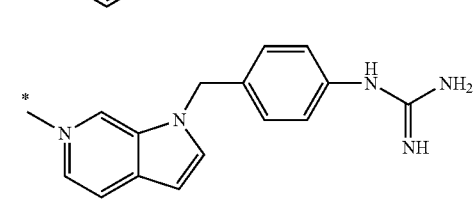 |
| 205 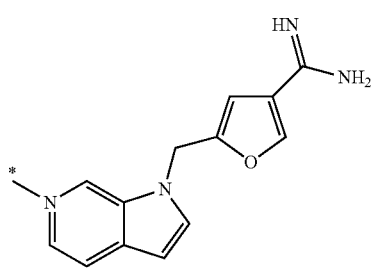 | 211 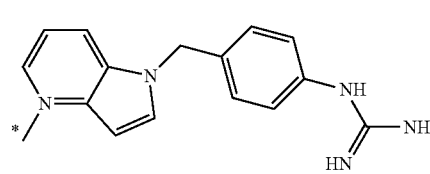 |
| 206 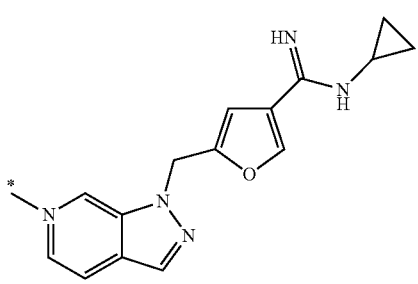 | 212 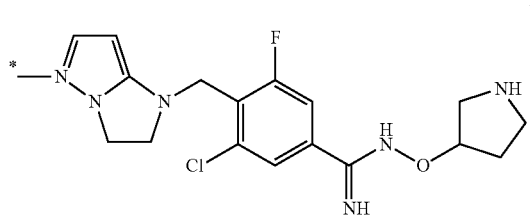 |
| 207 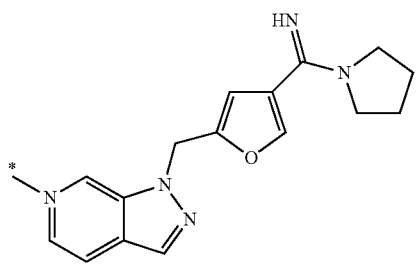 | 213 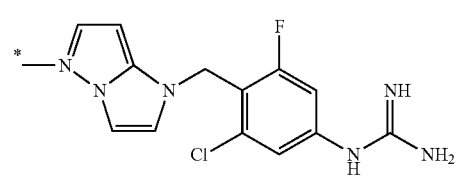 |
| | 214 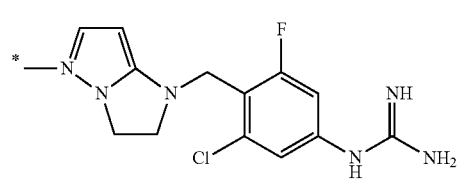 |
| | 215 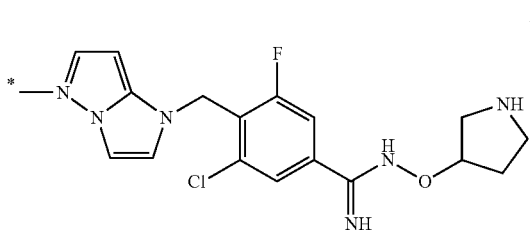 |

-continued
| | |
|---|---|
| 216 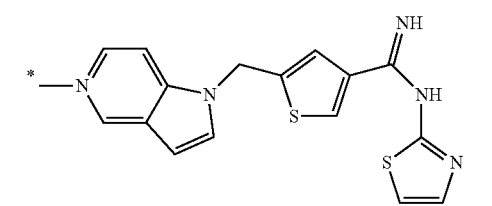 | 223 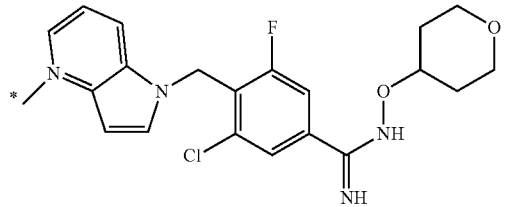 |
| 217 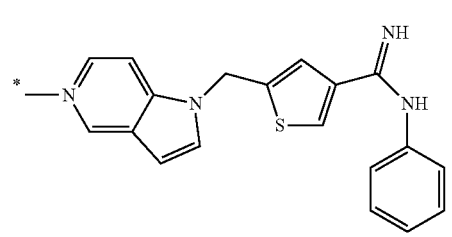 | 224 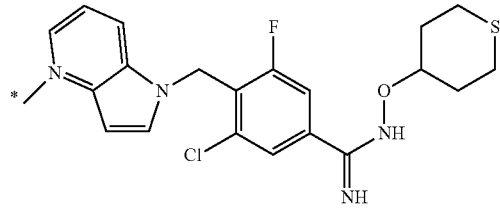 |
| 218 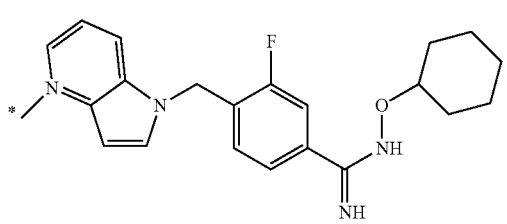 | 225 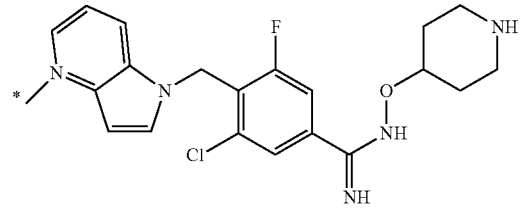 |
| 219 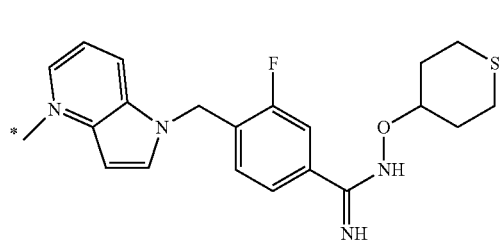 | 226 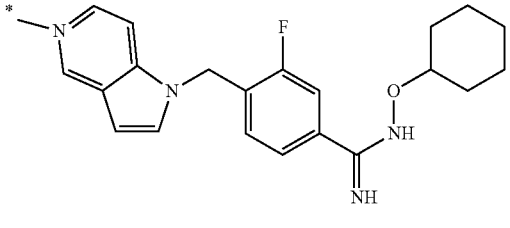 |
| 220 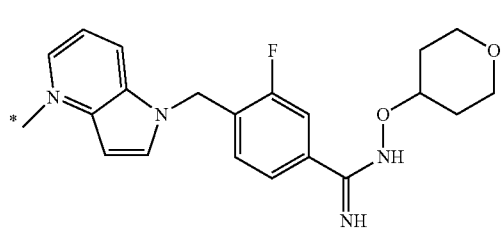 | 227 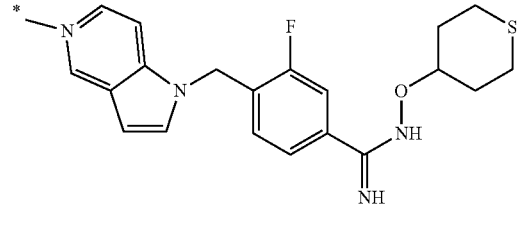 |
| 221 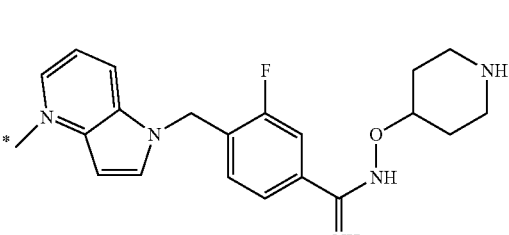 | 228 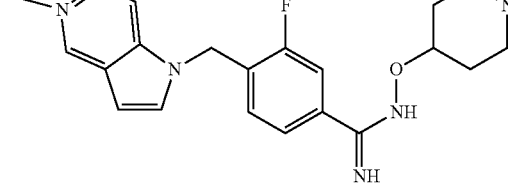 |
| 222 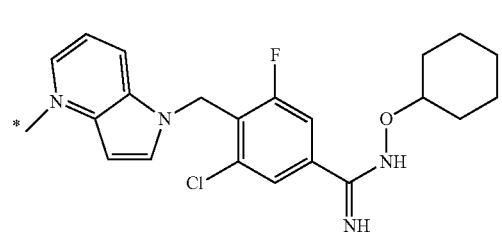 | 229 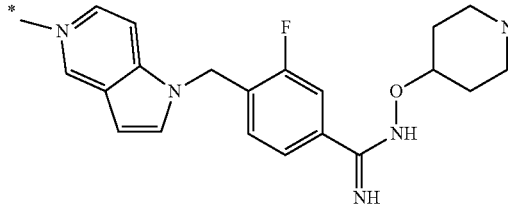 |

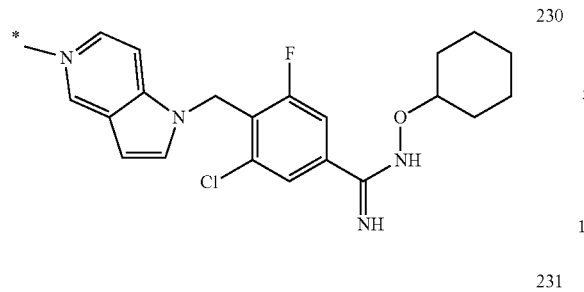
230
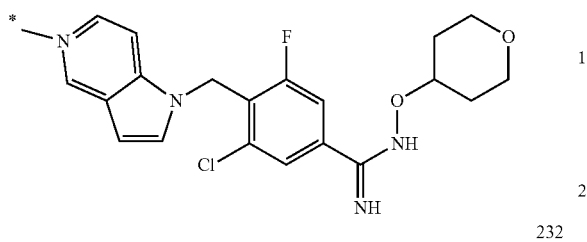
231
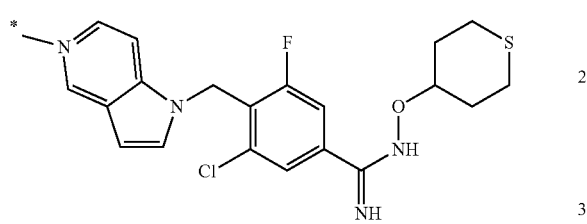
232
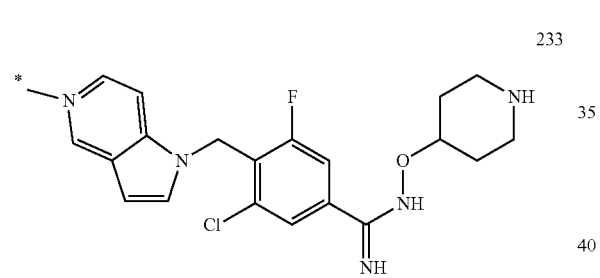
233
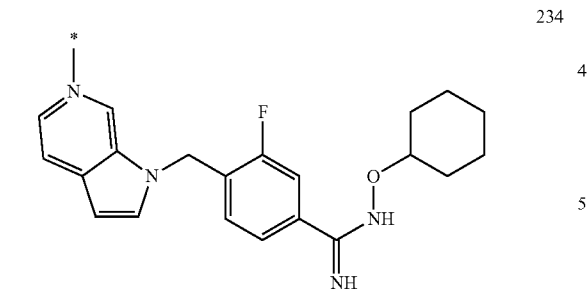
234
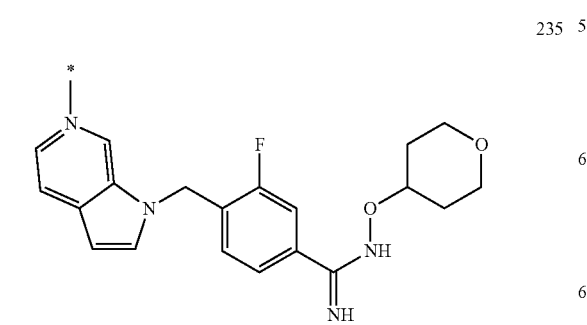
235
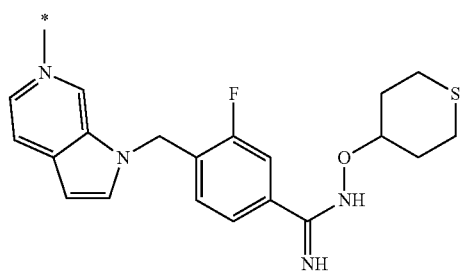
236
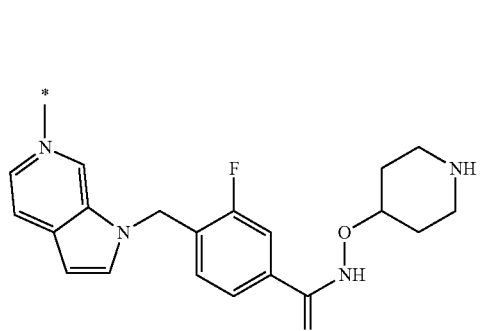
237
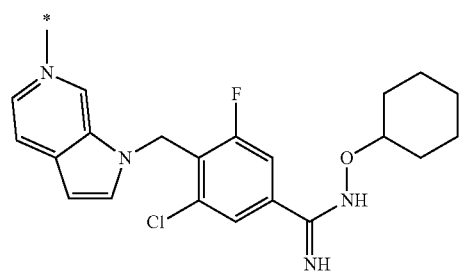
238
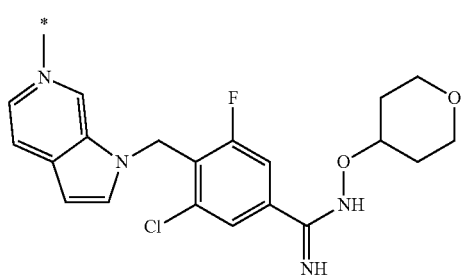
239
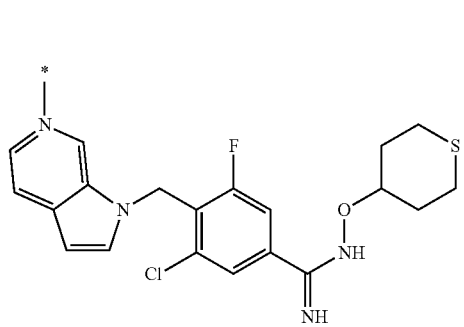
240

| 241 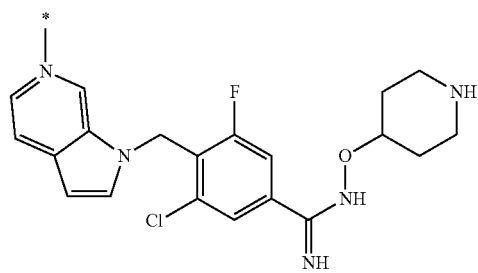 | 248 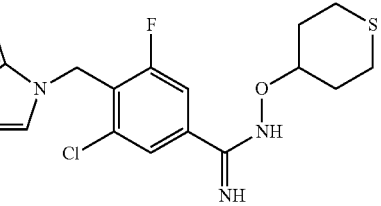 |
| --- | --- |
| 242 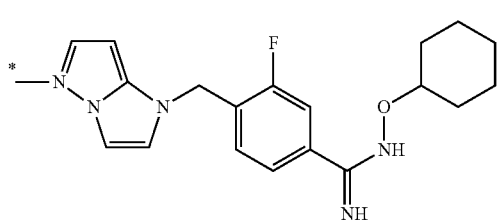 | 249 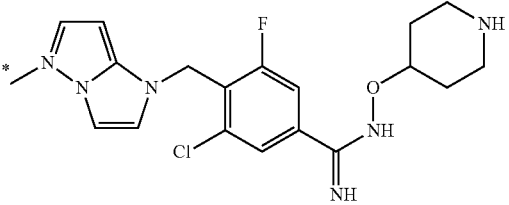 |
| 243 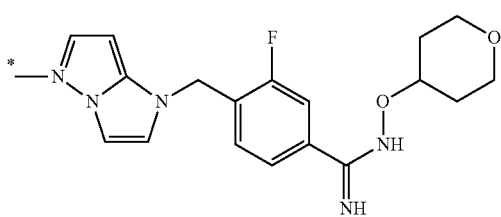 | 250 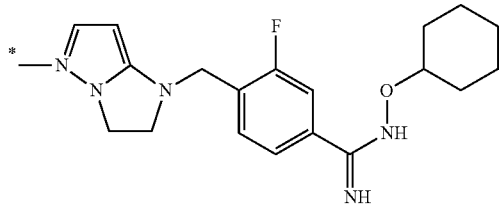 |
| 244 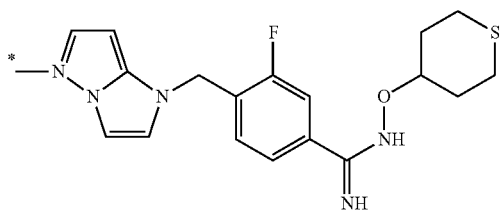 | 251 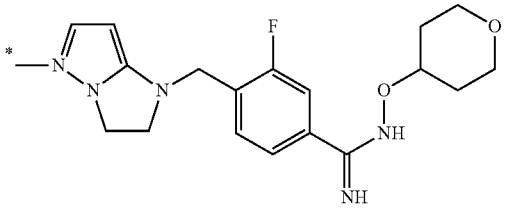 |
| 245 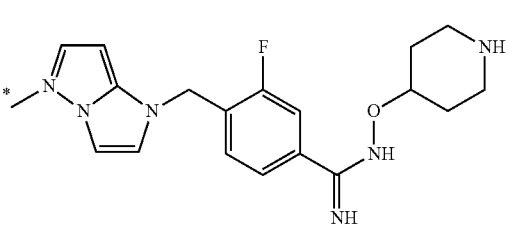 | 252 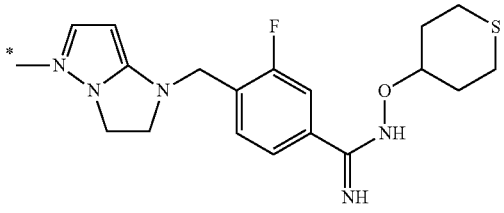 |
| 246 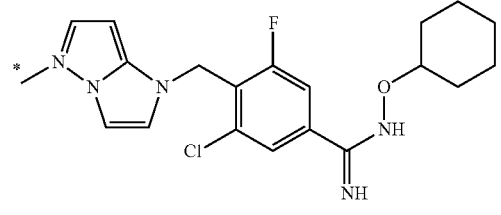 | 253 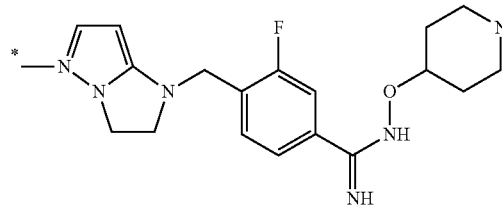 |
| 247 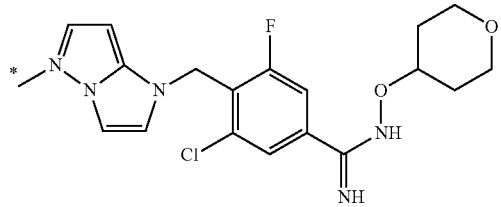 | 254 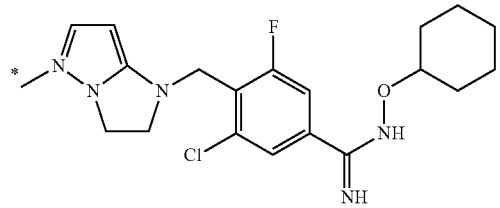 |

255 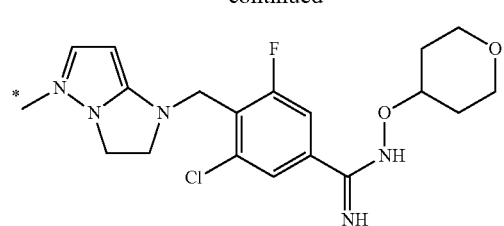
256 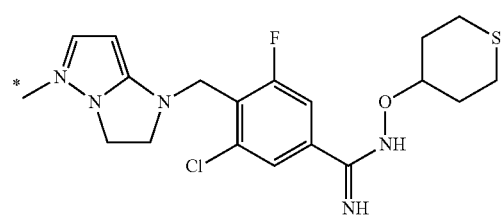
257 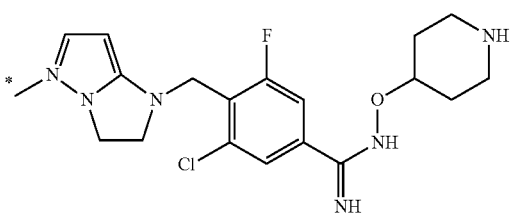
258 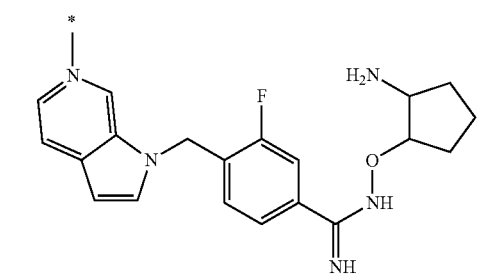
259 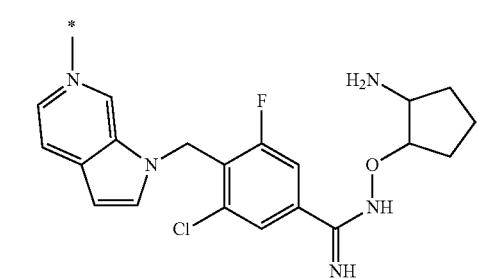
260 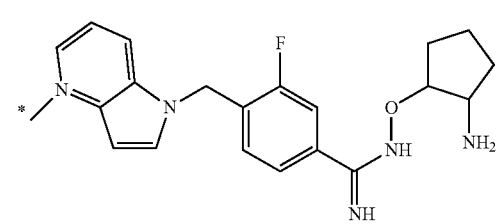
261 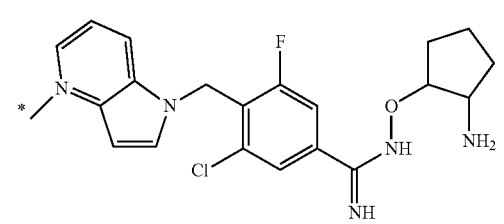
262 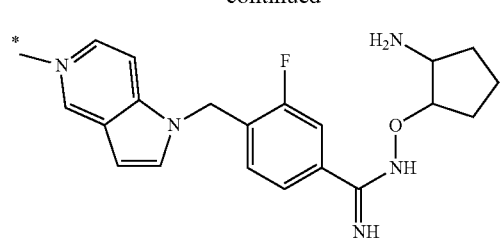
263 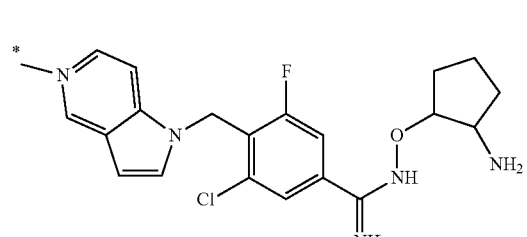
264 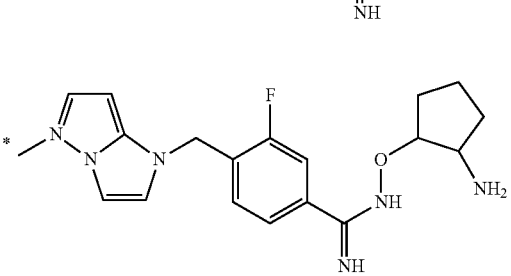
265 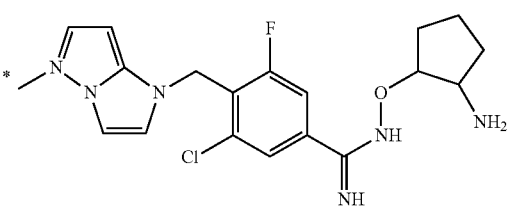
266 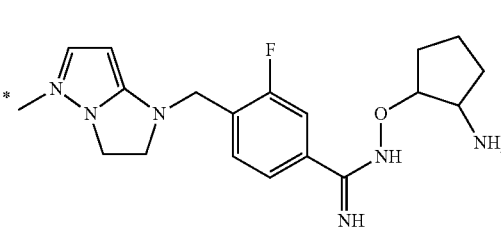
267 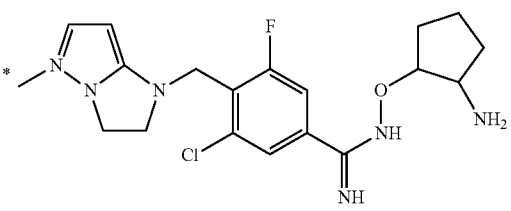
268 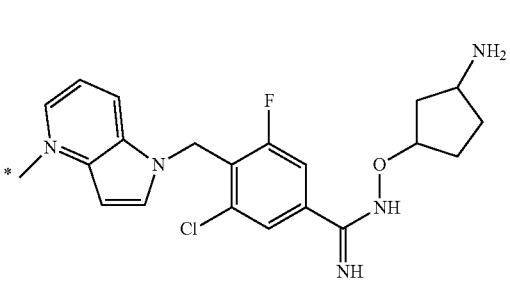

269

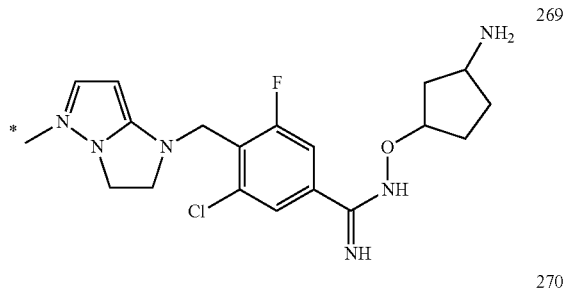

270

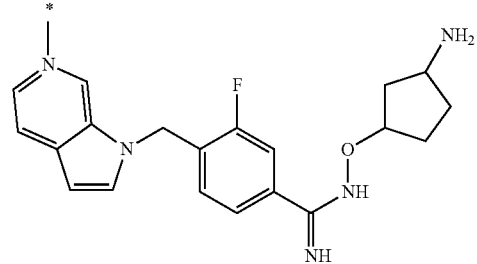

271

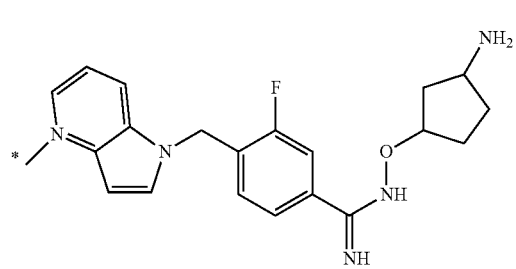

272

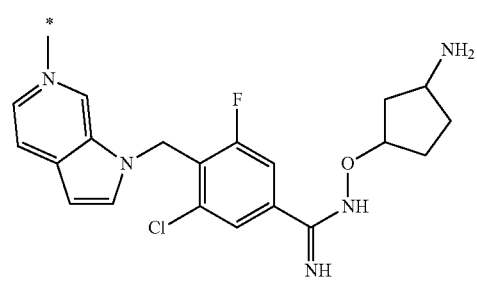

273

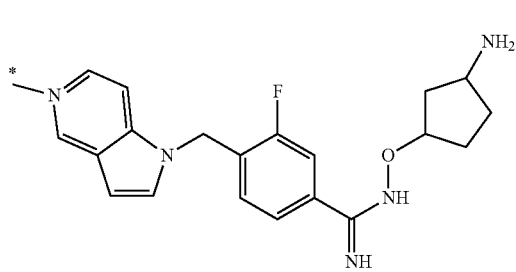

274

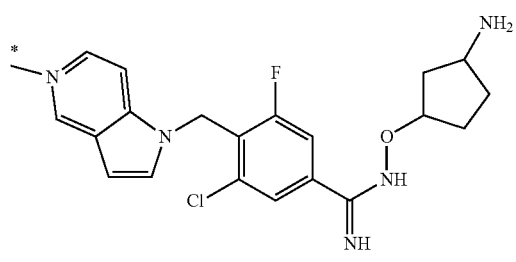

275

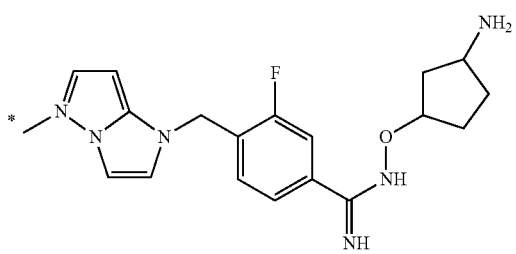

276

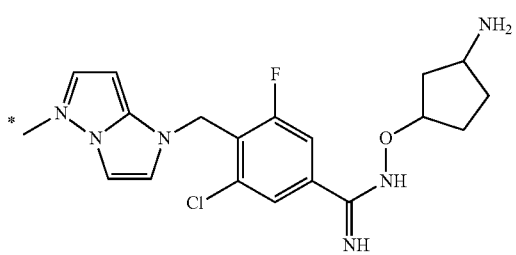

277

Regarding the compounds of general formula (I), it is to be understood that said compounds include syn-isomer, anti-isomer and a mixture thereof. All tautomeric isomers are contemplated, however, for the purposes of example, the object compound (I). As used herein the term 'isomers' refers to different compounds that have the same molecular formula but differ in arrangement and configuration of the atoms, such as geometrical isomers and optical isomers. For a given compound herein, it is to be understood that a substituent may be attached at a chiral center of a carbon atom. Therefore, enantiomers, diastereoisomers or racemates of the compound are contemplated.

It is further understood that isotopically labeled compounds, which are identical to those recited in Formula (I), but for the fact one or more atoms are replaced by an atom having an atomic mass or mass number different from the atomic mass or mass number predominantly found in nature are also contemplated. Examples of isotopes that can be incorporated into the present compounds may include isotopes of hydrogen, carbon, nitrogen, oxygen, phosphorous, fluorine and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S and $^{18}$F respectively. The present compounds, prodrugs thereof, and pharmaceutically acceptable salts of said compounds which contain the above mentioned isotopes and and/or other isotopes of other atoms are contemplated. Isotopically labeled compounds and prodrugs thereof can generally be prepared by carrying out the procedures disclosed in the Schemes and/or in the examples below, by substituting a readily available isotopically labeled reagent.

The term "β-lactamase inhibitor" refers to a compound which is capable of inhibiting β-lactamase activity, where inhibiting β-lactamase activity means inhibiting the activity of a class A, C or D β-lactamase. The term "β-lactamase" denotes an enzyme capable of inactivating a β-lactam antibiotic like a cephem antibiotic. The β-lactamase inhibitor may be, but is not limited to, the following groups:

Group 1: An oxapenam derivative of the general formula (II):

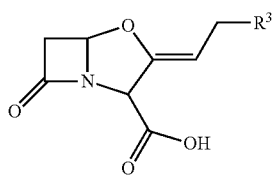

(II)

in which $R^3$ signifies $OR^4$, $S(O)_n R^4$ or a 5-6 membered heteroaromatic ring which may be substituted with 1 to 5 substituents selected from alkyl, hydroxyl, alkoxy, amino, alkylamino, dialkylamino and halogen; whereby n=0, 1, or 2 and $R^4$ is hydrogen, alkyl, ($C_2$-$C_7$)alkene, ($C_2$-$C_7$)alkyne or a 5-6 membered heteroaromatic ring which may be substituted with 1 to 5 substituents selected from alkyl, hydroxyl, alkoxy, amino, alkylamino, dialkylamino and halogen, or a pharmaceutically acceptable salt thereof.

Example of a specific compound from Group 1 is clavulanic acid (IIa):

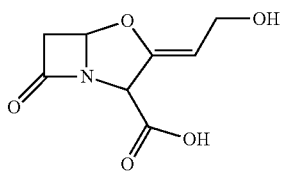

(IIa)

Group 2: A penam sulfone derivative of the general formula (III):

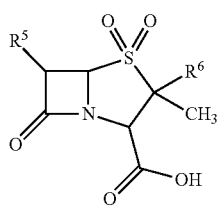

(III)

In which $R^5$ signifies hydrogen or halogen; $R^6$ signifies $CH_2R^7$; $CH=CHR^7$ wherein $R^7$ is hydrogen, halogen, cyano, carboxylic acid, acyl such as acetyl, carboxamide which may be substituted, alkoxycarbonyl or a 5-6 membered heteroaromatic ring which is optionally substituted with 1 to 5 substituents selected from alkyl, hydroxyl, alkoxy, amino, alkylamino, dialkylamino and halogen; or which is optionally fused with a 5-6 membered heteroaromatic ring; $CH=NR^8$ where $R^8$ is amino, alkylamino, dialkylamino, aminocarbonyl, acylamino such as acetylamino, hydroxyl, alkoxy, or a pharmaceutical acceptable salt thereof. Examples of two specific compounds from Group 2 are sulbactam (IIIa) and tazobactam (IIIb):

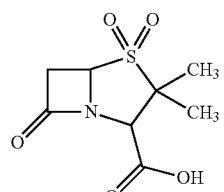

(IIIa)

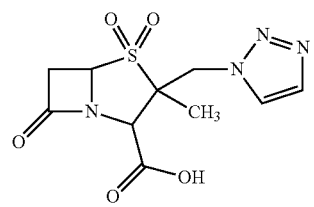

(IIIb)

Group 3: A penem derivative of the general formula (IV):

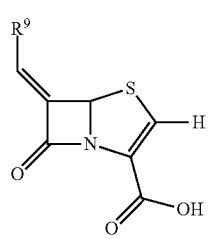

(IV)

In which $R^9$ signifies a 5-6 membered heteroaromatic ring which may be substituted with 1 to 5 substituents selected from alkyl, hydroxyl, alkoxy, amino, alkylamino, dialkylamino and halogen; or which is optionally fused with a 5-6 membered heteroaromatic ring; or a pharmaceutical acceptable salt thereof. Example of a specific compound from Group 3 is BRL-42,715 (IVa):

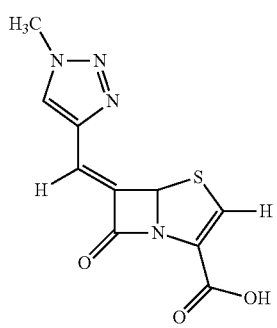

(IVa)

Group 4: A cyclic boronic acid derivative of the general formula (V):

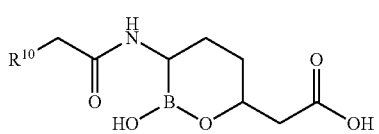

(V)

Wherein, $R^{10}$ signifies a substituted or unsubstituted aryl, substituted or unsubstituted heteroaryl, substituted or unsubstituted carbocyclyl and substituted or unsubstituted heterocyclyl. The substituent is selected from alkyl, hydroxyl, alkoxy, amino, alkylamino, dialkylamino and halogen; or a pharmaceutical acceptable salt thereof. Example of a specific compound from Group 4 is RPX-7009 (Va):

(Va)
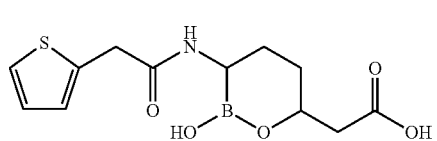

Group 5: A cyclic boronic acid of the general formula (VI):

(VI)
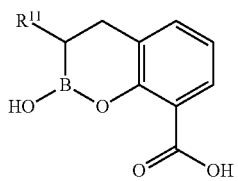

Wherein $R^{11}$ signifies alkoxy, substituted or unsubstituted thioheteroaryl or substituted carboxamide; or a pharmaceutically acceptable salt thereof. Examples of specific compounds from Group 5 are RPX 7262 (VIa), RPX 7282 (VIb), RPX 7381 (VIc), and RPX 7400 (VId):

RPX 7262 (VIa)
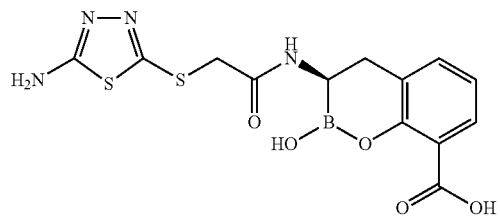

RPX 7282 (VIb)
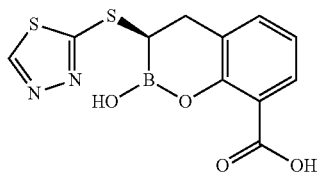

RPX 7381 (VIc)
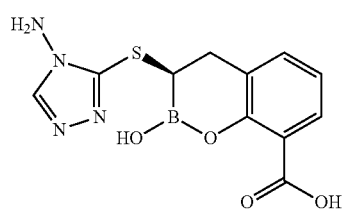

RPX 7400 (VId)
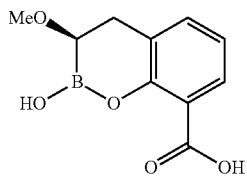

Group 6: A diazabicyclooctane derivative of the general formula (VII):

(VII)
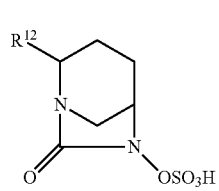

Wherein, $R^{12}$ signifies carboxylic acid, alkoxycarbonyl, heteroaryl, nitrile, or carboxamide which may be substituted; or a pharmaceutical acceptable salt thereof. Examples of several specific compounds from Group 6 are (VIIa-VIIg):

(VIIa, NXL-104)
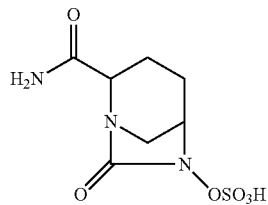

(VIIb, MK-7655)
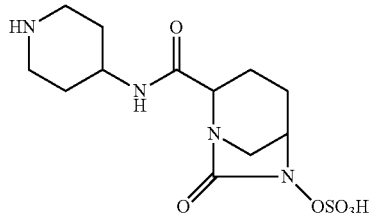

(VIIc)
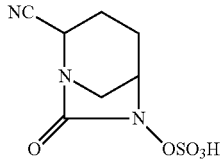

(VIId)
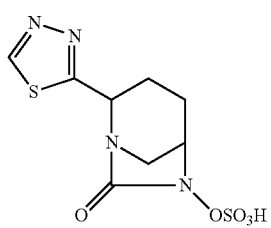

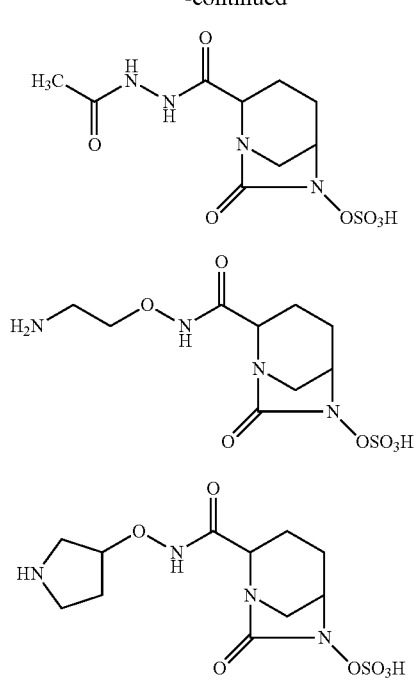

It has been found that the efficacy of cephem compounds of the formula (I) herein against gram-negative bacteria can be potentiated by co-using a β-lactamase inhibitor selected from any one of the formula (II) to (VII).

A "pharmaceutically acceptable salt" of formula (I) refers to a salt which possesses the desired pharmacological activity of the parent compound. Examples of the groups for forming a pharmaceutically acceptable salt include: inorganic base salts, ammonium salts, organic base salts, basic amino acid salts, inorganic acid addition salts, and organic acid addition salts. Inorganic bases that can form the inorganic base salts include alkali metals (e.g., sodium, potassium, and lithium) and alkaline earth metals (e.g., calcium and magnesium). Organic bases that can form the organic base salts include n-propylamine, n-butylamine, cyclohexylamine, benzylamine, octylamine, ethanolamine, diethanolamine, diethylamine, triethylamine, dicyclohexylamine, procaine, choline, picoline, N,N-dibenzylethylenediamine, N-methylglucamine, morpholine, pyrrolidine, pyridine, piperidine, N-ethylpiperidine and N-methylmorpholine. Basic amino acids that can form the basic amino acid salts include lysine, arginine, ornithine and histidine. As will be appreciated by one skilled in the art, the compounds of formula (I) containing a basic nitrogen atom are capable of forming acid addition salts. Such salts with pharmaceutically acceptable acids are included herein. Examples of such acids are hydrochloric, hydrobromic, phosphoric, sulfuric, citric, oxalic, maleic, fumaric, glycolic, mandelic, tartaric, aspartic, succinic, malic, formic, acetic, trifluoroacetic, methanesulfonic, ethanesulfonic, trifluoromethanesulfonic, benzenesulfonic, p-toluenesulfonic and the like.

Moreover, some compounds of formula (I) when they contain a basic group such as NH, $NH_2$ or pyridine and the like may form an inner zwitterionic salt with COOH group. Such inner salts are also contemplated herein.

Pharmaceutically acceptable solvates of the compounds of formula (I) are contemplated herein. 'Pharmaceutically acceptable solvate' refers to a molecular complex of a compound with one or more solvent molecules in a stoichiometric or non-stoichiometric amount. Such solvent molecules are those commonly used in the pharmaceutical art, which are known to be innocuous to recipient, e.g., water, ethanol, and the like. A molecular complex of a compound or moiety of a compound and a solvent can be stabilized by non-covalent intra-molecular forces such as, for example, electrostatic forces, Van der Waals forces or hydrogen bonds. The term hydrate refers to a complex where the one or more solvent molecules are water.

A combination of one or more of the compounds of formula (I) and one or more β-lactamase inhibitors are provided, where the β-lactamase inhibitors may be selected from formula (II) to (VII). Such combinations may exhibit a synergistic effect when used in the treatment of bacterial infections.

A combination of pharmaceutical compositions comprising one or more compounds of formula (I), or pharmaceutically acceptable salts thereof, and one or more pharmaceutically acceptable carriers or diluents are provided. Further, pharmaceutical compositions comprising (i) one or more compounds of formula (I), or pharmaceutically acceptable salts thereof, (ii) one or more β-lactamase inhibitors, and (iii) one or more pharmaceutically acceptable carriers or diluents are also provided. Preferably, the β-lactamase inhibitors may be selected from formula (II) to (VII). It is understood that any of the compositions and combinations herein may be administered to a subject such as, for example, by parenteral, in particular intramuscular route, oral, sublingual, rectal, aerosol or by local route in a topical application on the skin and the mucous membranes. Suitable pharmaceutically acceptable carriers and diluents include excipients such as starch, glucose, lactose, sucrose, gelatin, gum Arabic, malt, rice, flour, chalk, silica gel, sodium stearate, glycerol monostearate, talc, sodium chloride, dried skim milk, glycerol, propylene glycol, water, ethanol, and the like. Compositions of the present disclosure, if desired, can also contain minor amounts of wetting, dispersing or emulsifying agents, or pH buffering agents, and preservatives. In addition, auxiliary, stabilizing, thickening, lubricating, and coloring agents can be included. Pharmaceutical compositions can be formulated in a conventional manner. Proper formulation is dependent upon the route of administration chosen. The present pharmaceutical compositions can take the form of injectable preparations, suspensions, emulsions, sugar-coated tablets, pellets, gelatin-capsules, capsules containing liquids, powders, granules, sustained-release formulations, suppositories, aerosols, sprays, ointments, creams or any other form suitable for use.

In a pharmaceutical composition containing the present compounds, the weight ratio of active ingredient to carrier will normally be in the range of 1:20 to 20:1.

As above, methods for treating bacterial infections in a subject are also provided, said methods comprising administering to a subject in need thereof:

(i) a therapeutically effective amount of one or more compounds formula (I), or pharmaceutically acceptable salts thereof;

(ii) a therapeutically effective amount of a pharmaceutical composition comprising one or more compounds of formula (I), or pharmaceutically acceptable salts thereof, and a pharmaceutically acceptable carrier or diluent;

(iii) a therapeutically effective amount of a combination comprising (a) one or more compounds of formula (I), or pharmaceutically acceptable salts thereof, and (b) one or more β-lactamase inhibitors; or (iv) a therapeutically effective amount of a pharmaceutical composition comprising (a) one or more compounds of formula (I), or pharmaceutically acceptable salts thereof, (b) one or more β-lactamase inhibitors, and (c) a pharmaceutically acceptable carrier or diluent.

In some embodiments, the present methods for preventing bacterial infections in a subject comprise providing a subject in need thereof:
(i) a therapeutically effective amount of one or more compounds formula (I), or pharmaceutically acceptable salts thereof;
(ii) a therapeutically effective amount of a pharmaceutical composition comprising one or more compounds of formula (I), or pharmaceutically acceptable salts thereof, and a pharmaceutically acceptable carrier or diluent;
(iii) a therapeutically effective amount of a combination comprising (a) one or more compounds of formula (I), or pharmaceutically acceptable salts thereof, and (b) one or more β-lactamase inhibitors; or
(iv) a therapeutically effective amount of a pharmaceutical composition comprising (a) one or more compounds of formula (I), or pharmaceutically acceptable salts thereof, (b) one or more β-lactamase inhibitors, and (c) a pharmaceutically acceptable carrier or diluent.

The present methods for treating or preventing a bacterial infection in a subject may comprise administering to a subject in need thereof (i) a therapeutically effective amount of one or more compounds formula (I), or pharmaceutically acceptable salts thereof, and (ii) a therapeutically effective amount of one or more β-lactamase inhibitors. It will thus be apparent that in the treating or preventing of bacterial infections, compounds of formula (I) and β-lactamase inhibitors may be administered to the subject in the same pharmaceutical formulation (e.g., a pharmaceutical composition comprising compounds of formula (I), β-lactamase inhibitors, and a carrier or diluent) or different pharmaceutical formulations (e.g., a first pharmaceutical composition—comprising compounds of formula (I) and a carrier or diluent; and a second pharmaceutical composition—comprising β-lactamase inhibitors and a carrier or diluent). When administered in different formulations, the first and second pharmaceutical compositions may be administered simultaneously, sequentially, or separated in time.

In other embodiments, the use, in the manufacture of a medicament, of a compound of formula (I) as an active ingredient is provided, wherein the active ingredient may be provided in an antibacterial composition in admixture with a carrier. In some embodiments, the use, in the manufacture of a medicament, may further comprise the compound of formula (I) in combination with one or more β-lactamase inhibitors as active ingredients, in an antibacterial composition in admixture with a carrier. In other embodiments, the use, in the manufacture of a medicament, may further comprise the compound of formula (I) in combination with one or more antibiotics β-lactamase inhibitors as active ingredients, or in combination with one or more antibiotics (e.g., a β-lactam antibiotic or some other antibiotic) as active ingredients, in an antibacterial composition in admixture with a carrier.

The parenteral administration which includes intramuscular, intraperitonial, subcutaneous and intravenous use, sterile solutions of the active ingredients are usually prepared and the pH of the solutions are suitably adjusted and buffered. For intravenous use, the total concentration of solutes should be controlled to render the preparation isotonic. Suitable solvents include saline solution (e.g., 0.9% NaCl solution) and a pyrogenic sterile water. Pharmaceutical compositions for oral delivery can be, for example, in the form of tablets, lozenges, aqueous or oily suspensions, granules, powders, emulsions, capsules, syrups, or elixirs. Orally administered compositions can contain one or more optional agents, for example, sweetening agents such as fructose, aspartame, or saccharin, flavoring agents such as peppermint, oil of wintergreen, cherry, coloring agents, and preserving agents to provide a pharmaceutically palatable preparation. Moreover, when in tablet form, the compositions can be coated to delay disintegration and absorption in the gastrointestinal tract, thereby providing a sustained action over an extended period of time. Oral compositions can include standard vehicles such as mannitol, lactose, starch, magnesium stearate, sodium saccharin, cellulose, magnesium carbonate, and the like. For oral liquid preparations, for example, suspensions, elixirs, and solutions, suitable carriers, excipients, or diluents include water, saline, alkyleneglycols (e.g. propylene glycol), polyalkylene glycols (e.g., polyethylene glycol), oils, alcohols, slightly acidic buffers ranging from about pH 4 to about pH 6 (e.g., acetate, citrate, ascorbate ranging from about 5 mM to about 50 mM), and the like. Additionally, flavoring agents, preservatives, coloring agents, bile salts, acylcarnitines, and the like can be added.

For topical formulations of the present compounds, creams, gels, ointments or viscous lotions can be used as appropriate delivery forms. Topical delivery systems also include transdermal patches containing at least one compound of formula (I) to be administered. Delivery through the skin can be achieved by diffusion or by more active energy sources such as iontophoresis or electrotransport. Formulations of a compound herein, for topical use, such as in creams, ointments, and gels, can include an oleaginous or water soluble ointment base, for example, topical compositions can include vegetable oils, animal fats, and in certain embodiments, semisolid hydrocarbons obtained from petroleum. Topical compositions can further include white ointment, yellow ointment, cetyl esters wax, oleic acid, olive oil, paraffin, petrolatum, white petrolatum, spermaceti, starch glycerite, white wax, yellow wax, lanolin, and glyceryl monostearate. Various water-soluble ointment bases can also be used, including glycol ethers and derivatives, polyethylene glycols, polyoxyl 40 stearate, and polysorbates.

In a pharmaceutical composition containing the present cephem compounds, the weight ratio of active ingredient to carrier will normally be in the range of 1:20 to 20:1.

The therapeutically effective amount of the compounds of formula (I) and pharmaceutically acceptable salts thereof and the amounts sufficient to achieve the stated goals of the methods disclosed herein vary depending upon the physical characteristics of the subject, the severity of the subject's symptoms, the formulation and the means used to administer the drug, and the method being practiced. The specific dose for a given subject is usually set by the judgment of the attending physician. However, a therapeutically effective and/or sufficient amount of the compounds and salts of the present compositions is typically between about 1 mg/kg body weight to 500 mg/kg body weight, including from 1 to 100 mg/kg, from 1 to 75 mg/kg, from 1 to 50 mg/kg, from 1 to 25 mg/kg, from 25 to 150 mg/kg, from 25 to 125 mg/kg, from 25 to 100 mg/kg, from 25 to 75 mg/kg, from 25 to 50 mg/kg, from 50 to 150 mg/kg, from 50 to 125 mg/kg, and from 50 to 100 mg/kg, regardless of the formulation. In equally preferred aspects, a therapeutically effective amount is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 mg/kg body weight, regardless of the formulation. In some situations, a dose less than 1 mg/kg body weight or greater than 500 mg/kg body weight may be effective.

In a particular oral formulation for use in the present methods, the compound of formula (I) or a pharmaceutically acceptable salt thereof may be in the form of a capsule containing the compound or salt. Suitable amounts of the compound or salt may range from about 10 to about 3000 mg, with preferred amounts including about 100, 125, 150, 175, 200, 225, 250, 275, 300, 350, 400, 450, 500, 550, 600, 650, 700, 750, 800, 850, 900, 950, 1000, 1050, 1100, 1150, 1200, 1250, 1300, 1350, 1400, 1450 and 1500 mg.

In a particular intravenous (IV) formulation for use in the present methods, the compound of formula (I) or a pharmaceutically acceptable salt thereof is administered in a dosage of between about 100 mg and 2000 mg, preferably about 100, 125, 150, 175, 200, 225, 250, 275, 300, 325, 350, 375, 400, 450, 500, 600, 700, 800, 900, 1000, 1100, 1200, 1300, 1400, 1500 or more mg, by IV infusion over approximately 60, 90, 120 or more minutes, every 6, 12, 18 or 24 hours for 1, 2, 3, 4, 5, 6, 7, 8, 9, 10 or more days. The compound of formula (I) or a pharmaceutically acceptable salt thereof may be reconstituted in sterile water for injection (WFI) or be diluted in 5% dextrose in water, for example.

The terms "dose", "unit dose", "unit dosage", or "effective dose" refer to physically discrete units that contain a predetermined quantity of active ingredient calculated to produce a desired therapeutic effect. These terms are synonymous with the therapeutically effective amounts and amounts sufficient to achieve the stated goals of the methods disclosed herein.

'Therapeutically effective amount' refers to the amount of a compound that, when administered to a subject for treating a disease, or at least one of the clinical symptoms of a disease, is sufficient to affect such treatment of the disease, disorder, or symptom. The therapeutically effective amount can vary depending, for example, on the compound, the disease, disorder, and/or symptoms of the disease, severity of the disease, disorder, and/or symptoms of the disease, the age, weight, and/or health of the patient to be treated, and the judgement of the prescribing physician.

Administration frequencies of doses for the treatment of a bacterial infection include 4, 3, 2 or once daily, every other day, every third day, every fourth day, every fifth day, every sixth day, once weekly, every eight days, every nine days, every ten days, bi-weekly, monthly and bi-monthly. Depending on the means of administration, the dosage may be administered all at once, such as with an oral formulation in a capsule, or slowly over a period of time, such as with an intravenous administration. For slower means of administration, the administering period can be a matter of minutes, such as about 5, 10, 15, 20, 25, 30, 35, 40, 45, 50, 55, 60, 65, 70, 75, 80, 85, 90, 95, 100, 105, 110, 115, 120 or more minutes, or a period of hours, such as about 0.5, 1, 1.5, 2, 2.5, 3, 3.5, 4, 4.5, 5 or more hours.

The weight ratio of (i) the present compounds and (ii) a β-lactamase inhibitor or an antibiotic (if it is being administered with a β-lactamase inhibitor or an antibiotic, e.g., a β-lactam antibiotic or some other antibiotic) will normally be in the range from about 1:20 to about 20:1.

In some embodiments, it is an aim to provide an improved method for the treatment of bacterial infections caused by β-lactamase producing bacteria in a patient in need of such treatment comprising administering to the patient a therapeutically effective amount of at least one compound chosen from formula (I) or a pharmaceutically acceptable salt thereof, either alone or in combination with one or more β-lactamase inhibitors, including the β-lactamase inhibitor of formula (II) to (VII) provided above. In such an embodiment, the compounds may increase the antibacterial effectiveness of β-lactamase susceptible β-lactam antibiotics, that is, they may increase the effectiveness of the antibiotic against infections caused by β-lactamase producing microorganisms in mammalian subjects, particularly in humans. As such, the present compounds of formula (I) and pharmaceutically acceptable salts thereof may valuable for co-administration with β-lactamase inhibitors. In this regard, the present compounds of formula (I) or a pharmaceutically salt thereof can be mixed with the β-lactamase inhibitors, and the two agents thereby administered simultaneously. Alternatively, the two agents can be administered sequentially, either one immediately after the other or separated in time by 1, 5, 10, 15, 30, 45 or 60 minutes, or 1, 2, 3, 4, 5, 6, 7, 8, 9, 10, 11, 12, 13, 14, 15, 16, 17, 18 or more hours, or 1, 2, 3, 4, 5 or more days. When co-administered with a β-lactamase inhibitor, the present compounds and the β-lactamase inhibitor may, in combination, provide a synergistic effect. The term 'synergystic effect' refers to the effect produced when two or more agents are co-administered is greater than the effect produced when the agents are administered individually. Alternatively, the compound of formula (I) or a salt thereof can be administered as a separate agent during a course of treatment with the β-lactamase inhibitor.

In other embodiments, it is an aim to provide an improved method for the treatment of bacterial infections caused by β-lactamase producing bacteria in a patient in need of such treatment comprising administering to the patient a therapeutically effective amount of at least one compound chosen from formula (I) or a pharmaceutically acceptable salt thereof, either alone or in combination with one or more antibiotics, including β-lactam antibiotics and non β-lactam antibiotics. In such an embodiment, the compounds may increase the antibacterial effectiveness of β-lactamase susceptible β-lactam antibiotics, that is, they may increase the effectiveness of the antibiotic against infections caused by β-lactamase producing microorganisms in mammalian subjects, particularly in human. In that regard, the compounds of formula (I) and pharmaceutically acceptable salts thereof may be valuable for co-administration with β-lactam antibiotics. In the treatment of a bacterial infection, the present compounds of formula (I) or a pharmaceutically salt thereof can be mixed with the β-lactam antibiotic, and the two agents thereby administered simultaneously. Alternatively, the two agents can be administered sequentially, either one immediately after the other or separated in time by 1, 5, 10, 15, 30, 45 or 60 minutes, or 1, 2, 3, 4, 5, 6, 7, 8, 9, 10, 11, 12, 13, 14, 15, 16, 17, 18 or more hours, or 1, 2, 3, 4, 5 or more days. When co-administered with a β-lactam antibiotic, the combination of the present compound and the antibiotic can provide a synergistic effect. The term 'synergystic effect' refers to the effect produced when two or more agents are co-administered is greater than the effect produced when the agents are administered individually. Alternatively, the compound of formula (I) or a salt thereof can be administered as a separate agent during a course of treatment with the antibiotic. Examples of compounds of the formula (I), without limiting to the specified compounds, are provided in the following Table 1.

TABLE 1

| Compound No. | Structure | Chemical Name |
|---|---|---|
| 1 | 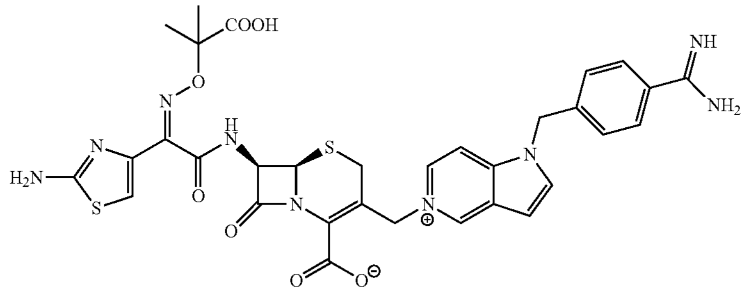 [SMILES: CC(C)(O/N=C(\C(=O)N[C@@H]1C(=O)N2C(C(=O)[O-])=C(C[n+]3ccc4c(ccn4Cc4ccc(C(=N)N)cc4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-{[1-(4-carbamimidoylbenzyl)-1H-pyrrolo[3,2-c]pyridin-5-ium-5-yl]methyl}-8-oxo-5-thia-1-azabicyclo[4.2.0]oct-2-ene-2-carboxylate |
| 2 | 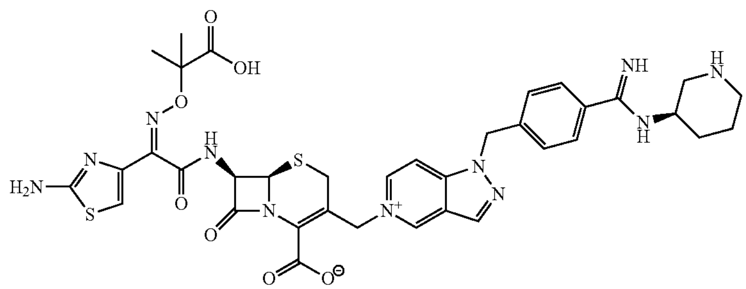 [SMILES: CC(C)(O/N=C(\C(=O)N[C@@H]1C(=O)N2C(C(=O)[O-])=C(C[n+]3ccc4c(cnn4Cc4ccc(C(=N)N[C@@H]5CCCNC5)cc4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-8-oxo-3-[(1-{4-[N-(piperidin-3-yl)carbamimidoyl]benzyl}-1H-pyrazolo[4,3-c]pyridin-5-ium-5-yl)methyl]-5-thia-1-azabicyclo[4.2.0]oct-2-ene-2-carboxylate |
| 3 | 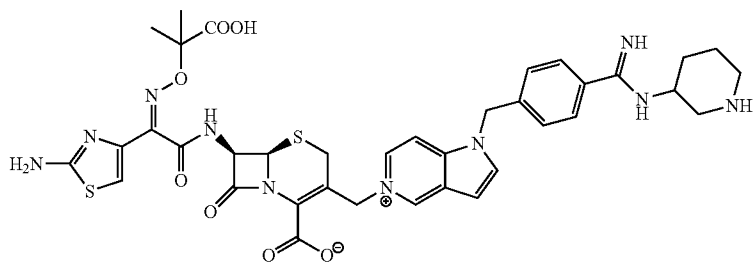 [SMILES: CC(C)(O/N=C(\C(=O)N[C@@H]1C(=O)N2C(C(=O)[O-])=C(C[n+]3ccc4c(ccn4Cc4ccc(C(=N)NC5CCCNC5)cc4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-8-oxo-3-[(1-{4-[N-(piperidin-3-yl)carbamimidoyl]benzyl}-1H-pyrrolo[3,2-c]pyridin-5-ium-5-yl)methyl]-5-thia-1-azabicyclo[4.2.0]oct-2-ene-2-carboxylate |
| 4 | 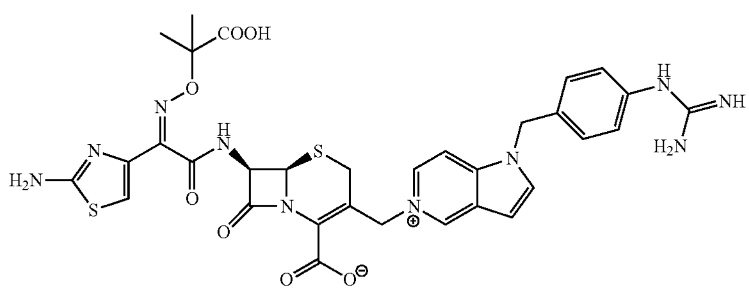 [SMILES: CC(C)(O/N=C(\C(=O)N[C@@H]1C(=O)N2C(C(=O)[O-])=C(C[n+]3ccc4c(ccn4Cc4ccc(NC(=N)N)cc4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-{[1-(4-carbamimidamidobenzyl)-1H-pyrrolo[3,2-c]pyridin-5-ium-5-yl]methyl}-8-oxo-5-thia-1-azabicyclo[4.2.0]oct-2-ene-2-carboxylate |
| 5 | 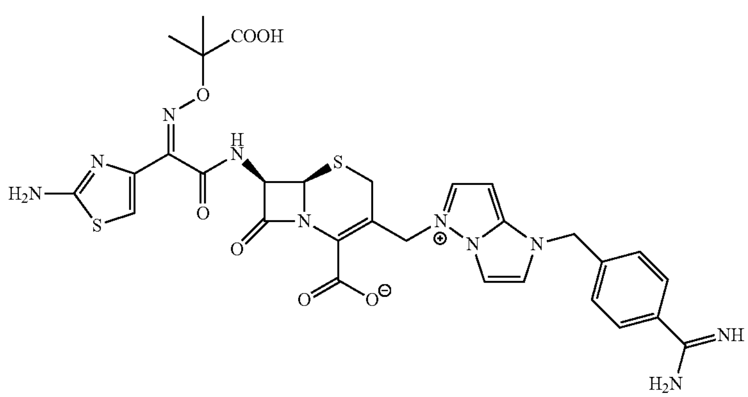 [SMILES: CC(C)(O/N=C(\C(=O)N[C@@H]1C(=O)N2C(C(=O)[O-])=C(C[n+]3ccc4n(Cc5ccc(C(=N)N)cc5)ccn43)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-{[1-(4-carbamimidoylbenzyl)-1H-imidazo[1,2-b]pyrazol-5-ium-5-yl]methyl}-8-oxo-5-thia-1-azabicyclo[4.2.0]oct-2-ene-2-carboxylate |

TABLE 1-continued

| Compound No. | Structure | Chemical Name |
|---|---|---|
| 6 | 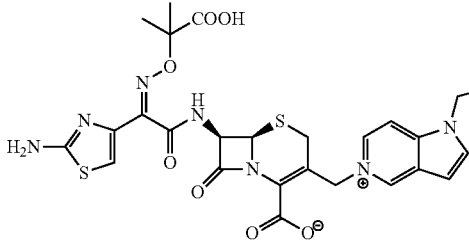 | (6R,7S)-7-{[(2Z)-2-(2-amino-1,3-thiazol-4-yl)-2-{[(2-carboxypropan-2-yl)oxy]imino}acetyl]amino}-3-({1-[4-(2-carbamimidamidoethoxy)benzyl]-1H-pyrrolo[3,2-c]pyridin-5-ium-5-yl}methyl)-8-oxo-5-thia-1-azabicyclo[4.2.0]oct-2-ene-2-carboxylate |
| 7 | 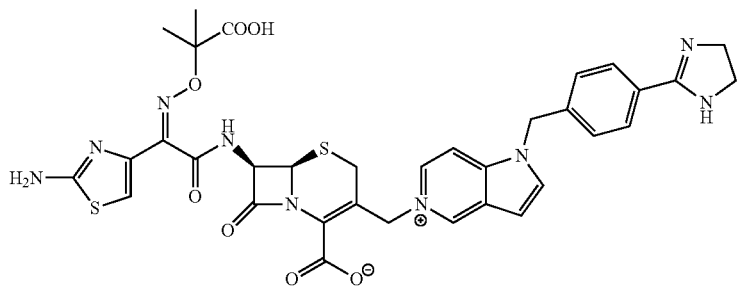 [SMILES: CC(C)(O/N=C(\C(=O)N[C@@H]1C(=O)N2C(C(=O)[O-])=C(C[n+]3ccc4c(ccn4Cc4ccc(C5=NCCN5)cc4)c3)CS[C@H]12)c1csc(N)n1)C(=O)O] | (6R,7R)-3-[(1-{4-[N-(2-aminoethyl)carbamimidoyl]benzyl}-1H-pyrrolo[3,2-c]pyridin-5-ium-5-yl)methyl]-7-{[(2Z)-2-(2-amino-1,3-thiazol-4-yl)-2-{[(2-carboxypropan-2-yl)oxy]imino}acetyl]amino}-8-oxo-5-thia-1-azabicyclo[4.2.0]oct-2-ene-2-carboxylate |
| 8 | 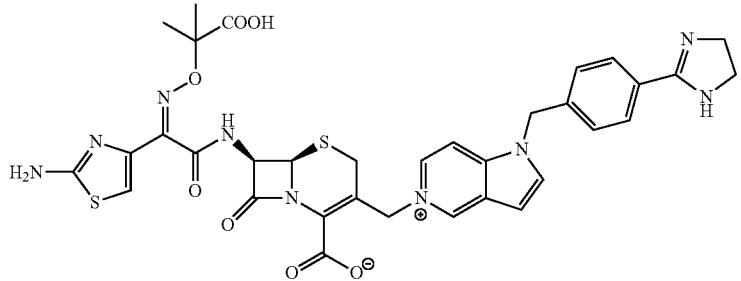 [SMILES: CC(C)(O/N=C(\C(=O)N[C@@H]1C(=O)N2C(C(=O)[O-])=C(C[n+]3ccc4c(ccn4Cc4ccc(C5=NCCN5)cc4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-({1-[4-(4,5-dihydro-1H-imidazol-2-yl)benzyl]-1H-pyrrolo[3,2-c]pyridin-5-ium-5-yl}methyl)-8-oxo-5-thia-1-azabicyclo[4.2.0]oct-2-ene-2-carboxylate |
| 9 | 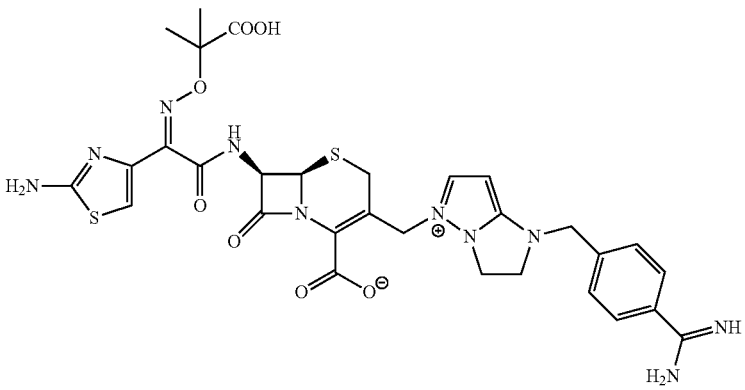 [SMILES: CC(C)(O/N=C(\C(=O)N[C@@H]1C(=O)N2C(C(=O)[O-])=C(C[n+]3ccc4n3CCN4Cc3ccc(C(=N)N)cc3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-{[1-(4-carbamimidoylbenzyl)-2,3-dihydro-1H-imidazo[1,2-b]pyrazol-5-ium-5-yl]methyl}-8-oxo-5-thia-1-azabicyclo[4.2.0]oct-2-ene-2-carboxylate |

TABLE 1-continued

| Compound No. | Structure | Chemical Name |
|---|---|---|
| 10 | 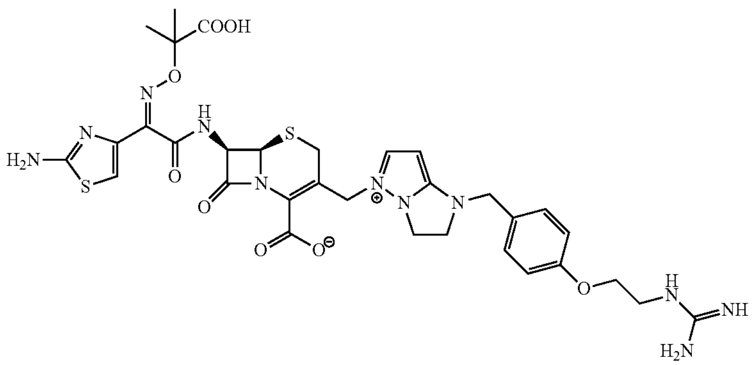 [SMILES: CC(C)(O/N=C(\C(=O)N[C@@H]1C(=O)N2C(C(=O)[O-])=C(C[n+]3ccc4n3CCN4Cc3ccc(OCCNC(=N)N)cc3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-({1-[4-(2-carbamimidamidoethoxy)benzyl]-2,3-dihydro-1H-imidazo[1,2-b]pyrazol-5-ium-5-yl}methyl)-8-oxo-5-thia-1-azabicyclo[4.2.0]oct-2-ene-2-carboxylate |
| 11 | 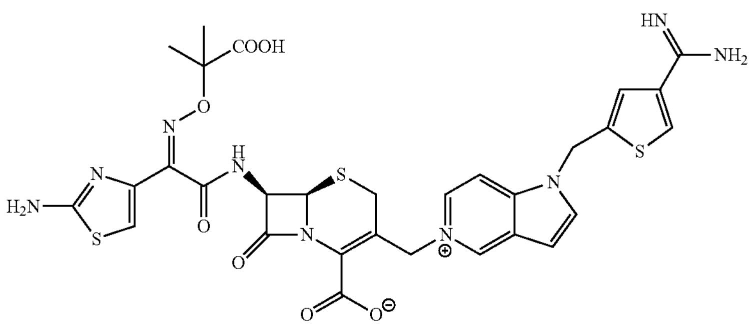 | (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidoylthiophen-2-yl)methyl]-1H-pyrrolo[3,2-c]pyridin-5-ium-5-yl}methyl)-8-oxo-5-thia-1-azabicyclo[4.2.0]oct-2-ene-2-carboxylate |
| 12 | 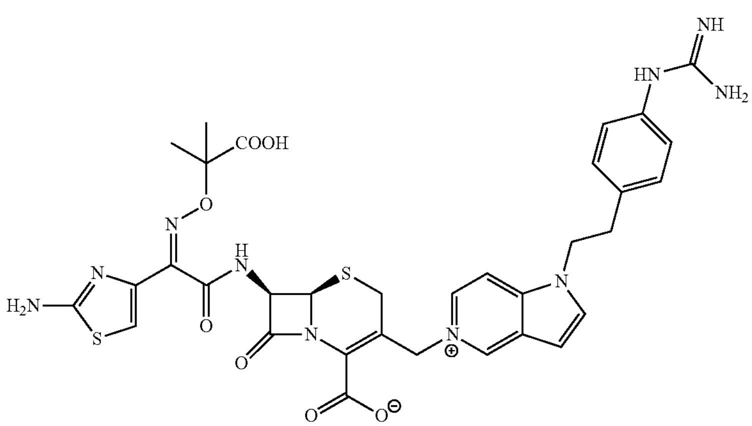 [SMILES: CC(C)(O/N=C(\C(=O)N[C@@H]1C(=O)N2C(C(=O)[O-])=C(C[n+]3ccc4c(ccn4CCc4ccc(NC(=N)N)cc4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-({1-[2-(4-carbamimidamidophenyl)ethyl]-1H-pyrrolo[3,2-c]pyridin-5-ium-5-yl}methyl)-8-oxo-5-thia-1-azabicyclo[4.2.0]oct-2-ene-2-carboxylate |
| 13 | 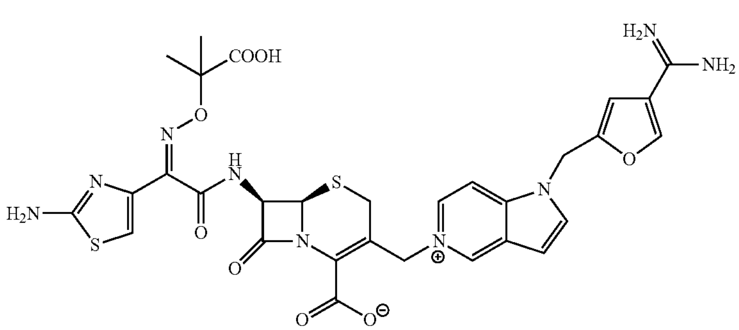 [SMILES: CC(C)(O/N=C(\C(=O)N[C@@H]1C(=O)N2C(C(=O)[O-])=C(C[n+]3ccc4c(ccn4Cc4cc(C(=N)N)co4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidoylfuran-2-yl)methyl]-1H-pyrrolo[3,2-c]pyridin-5-ium-5-yl}methyl)-8-oxo-5-thia-1-azabicyclo[4.2.0]oct-2-ene-2-carboxylate |

TABLE 1-continued

| Compound No. | Structure | Chemical Name |
|---|---|---|
| 14 | 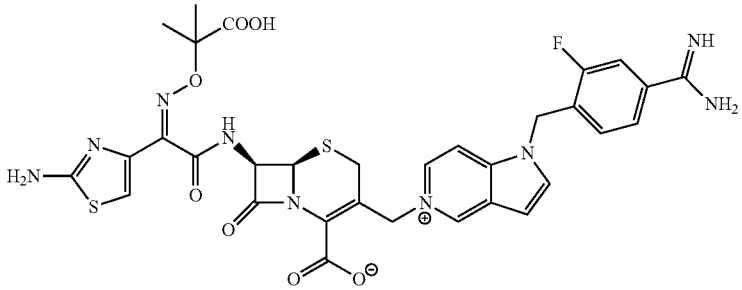 [SMILES: CC(C)(O/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-{[1-(4-carbamimidoyl-2-fluorobenzyl)-1H-pyrrolo[3,2-c]pyridin-5-ium-5-yl]methyl}-8-oxo-5-thia-1-azabicyclo[4.2.0]oct-2-ene-2-carboxylate |
| 15 | 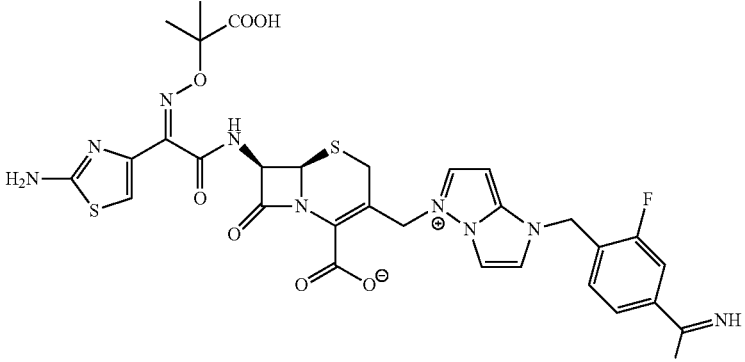 | (6R,7R)-7-{[(2Z)-2-(2-amino-1,3-thiazol-4-yl)-2-{[(2-carboxypropan-2-yl)oxy]imino}acetyl]amino}-3-{[1-(4-carbamimidoyl-2-fluorobenzyl)-1H-imidazo[1,2-b]pyrazol-5-ium-5-yl]methyl}-8-oxo-5-thia-1-azabicyclo[4.2.0]oct-2-ene-2-carboxylate |
| 16 | 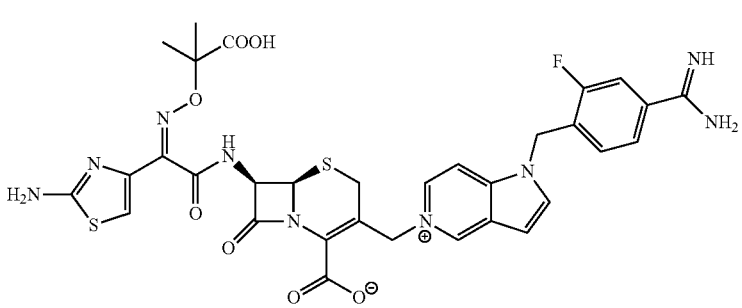 [SMILES: CC(C)(O/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-([1-[(4-carbamimidoyl-1,3-thiazol-2-yl)methyl]-1H-pyrrolo[3,2-c]pyridin-5-ium-5-yl}methyl)-8-oxo-5-thia-1-azabicyclo[4.2.0]oct-2-ene-2-carboxylate |
| 17 | 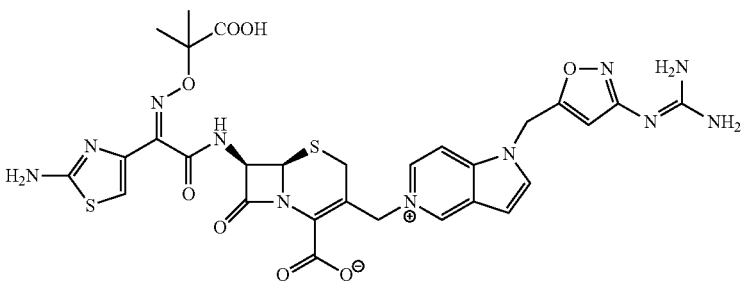 [SMILES: CC(C)(O/N=C(\C(=O)N[C@@H]1C(=O)N2C(C(=O)[O-])=C(C[n+]3ccc4c(ccn4Cc4cc(N=C(N)N)no4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-{[1-({3-[(diaminomethylidene)amino]-1,2-oxazol-5-yl}methyl)-1H-pyrrolo[3,2-c]pyridin-5-ium-5-yl]methyl}-8-oxo-5-thia-1-azabicyclo[4.2.0]oct-2-ene-2-carboxylate |

TABLE 1-continued

| Compound No. | Structure | Chemical Name |
|---|---|---|
| 18 | 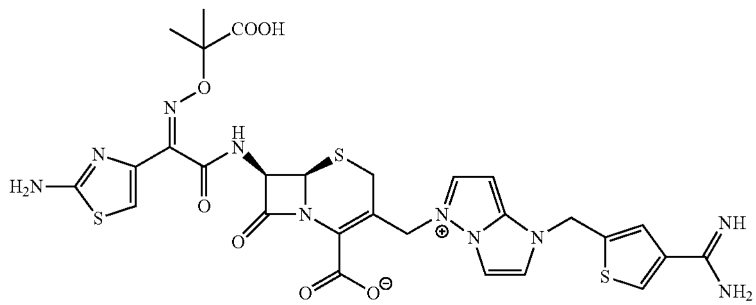 [SMILES: CC(C)(O/N=C(\C(=O)N[C@@H]1C(=O)N2C(C(=O)[O-])=C(C[n+]3ccc4n(Cc5cc(C(=N)N)cs5)ccn43)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidoylthiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 19 | 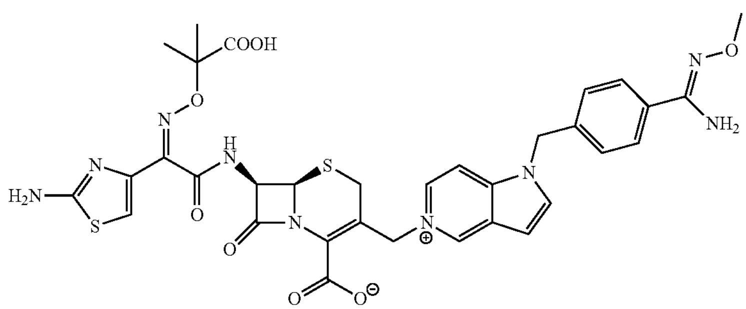 [SMILES: CO/N=C(\N)c1ccc(Cn2ccc3c[n+](CC4=C(C(=O)[O-])N5C(=O)[C@@H](NC(=O)/C(=N\OC(C)(C)C(=O)O)c6csc(N)n6)[C@H]5SC4)ccc32)cc1] | (6R,7R)-7-{[(2Z)-2-(2-amino-1,3-thiazol-4-yl)-2-{[(2-carboxypropan-2-yl)oxy]imino}acetyl]amino}-3-({1-[4-(N'-methoxycarbamimidoyl)benzyl]-1H-pyrrolo[3,2-c]pyridin-5-ium-5-yl}methyl)-8-oxo-5-thia-1-azabicyclo[4.2.0]oct-2-ene-2-carboxylate |
| 20 | 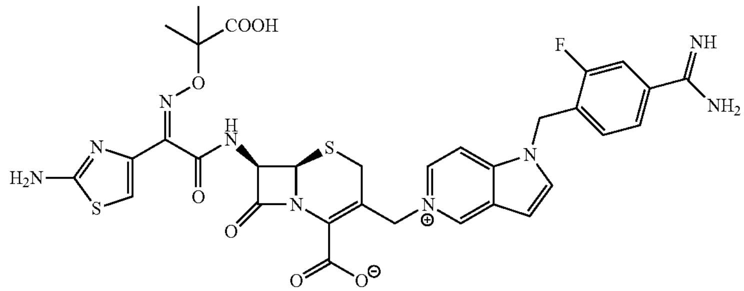 [SMILES: CC(C)(O/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1csc(N)n1)C(=O)O] | (6R,7R)-7-{[(2Z)-2-(5-amino-1,2,4-thiadiazol-3-yl)-2-{[(2-carboxypropan-2-yl)oxy]imino}acetyl]amino}-3-{[1-(4-carbamimidoyl-2-fluorobenzyl)-1H-pyrrolo[3,2-c]pyridin-5-ium-5-yl]methyl}-8-oxo-5-thia-1-azabicyclo[4.2.0]oct-2-ene-2-carboxylate |
| 21 | 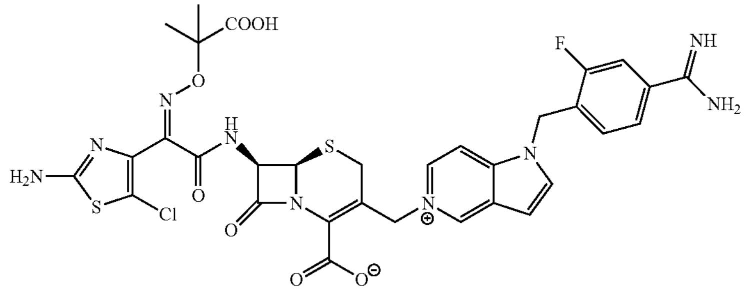 [SMILES: CC(C)(O/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1nc(N)sc1Cl)C(=O)O] | (6R,7R)-7-{[(2Z)-2-(2-amino-5-chloro-1,3-thiazol-4-yl)-2-{[(2-carboxypropan-2-yl)oxy]imino}acetyl]amino}-3-{[1-(4-carbamimidoyl-2-fluorobenzyl)-1H-pyrrolo[3,2-c]pyridin-5-ium-5-yl]methyl}-8-oxo-5-thia-1-azabicyclo[4.2.0]oct-2-ene-2-carboxylate |

TABLE 1-continued

| Compound No. | Structure | Chemical Name |
|---|---|---|
| 22 | 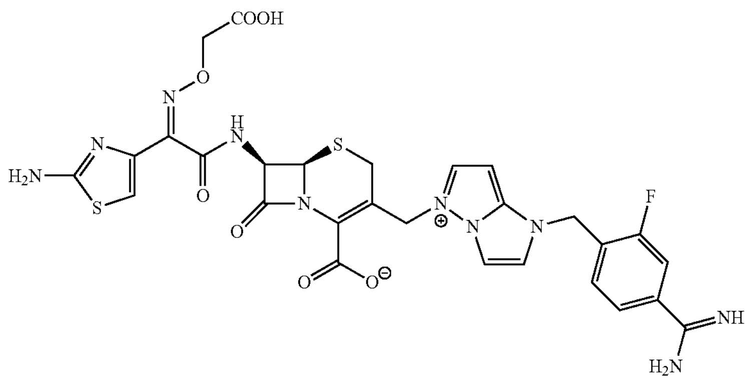 [SMILES: N=C(N)c1ccc(Cn2ccn3c2cc[n+]3CC2=C(C(=O)[O-])N3C(=O)[C@@H](NC(=O)/C(=N\OCC(=O)O)c4csc(N)n4)[C@H]3SC2)c(F)c1] | (6R,7R)-7-({(2Z)-2-(2-amino-1,3-thiazol-4-yl)-2-[(carboxymethoxy)imino]acetyl}amino)-3-{[1-(4-carbamimidoyl-2-fluorobenzyl)-1H-imidazo[1,2-b]pyrazol-5-ium-5-yl]methyl}-8-oxo-5-thia-1-azabicyclo[4.2.0]oct-2-ene-2-carboxylate |
| 23 | 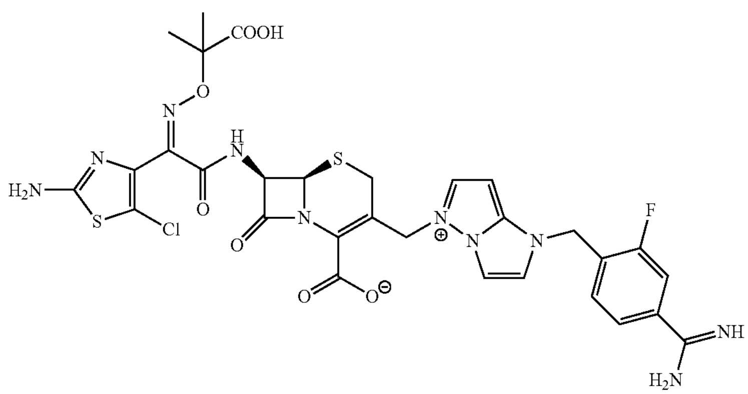 [SMILES: CC(C)(O/N=C(\C(=O)N[C@@H]1C(=O)N2C(C(=O)[O-])=C(C[n+]3ccc4n(Cc5ccc(C(=N)N)cc5F)ccn43)CS[C@H]12)c1nc(N)sc1Cl)C(=O)O] | (6R,7R)-7-{[(2Z)-2-(2-amino-5-chloro-1,3-thiazol-4-yl)-2-{[(2-carboxypropan-2-yl)oxy]imino}acetyl]amino}-3-{[1-(4-carbamimidoyl-2-fluorobenzyl)-1H-imidazo[1,2-b]pyrazol-5-ium-5-yl]methyl}-8-oxo-5-thia-1-azabicyclo[4.2.0]oct-2-ene-2-carboxylate |
| 24 | 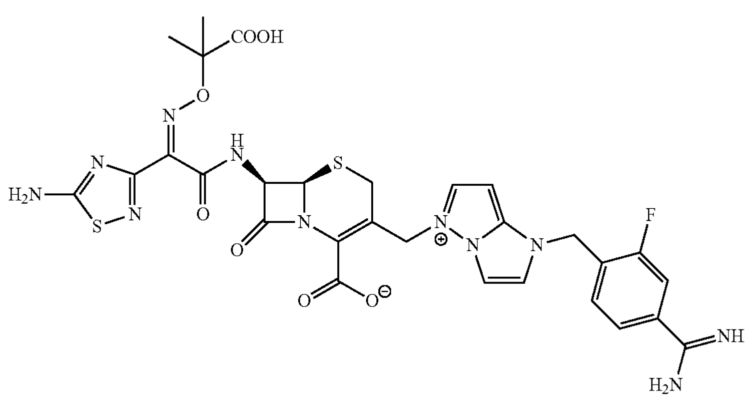 [SMILES: CC(C)(O/N=C(\C(=O)N[C@@H]1C(=O)N2C(C(=O)[O-])=C(C[n+]3ccc4n(Cc5ccc(C(=N)N)cc5F)ccn43)CS[C@H]12)c1nsc(N)n1)C(=O)O] | (6R,7R)-7-{[(2Z)-2-(5-amino-1,2,4-thiadiazol-3-yl)-2-{[(2-carboxypropan-2-yl)oxy]imino}acetyl]amino}-3-{[1-(4-carbamimidoyl-2-fluorobenzyl)-1H-imidazo[1,2-b]pyrazol-5-ium-5-yl]methyl}-8-oxo-5-thia-1-azabicyclo[4.2.0]oct-2-ene-2-carboxylate |
| 25 | 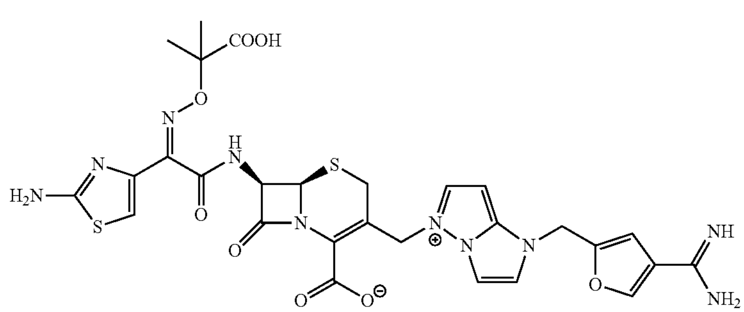 | (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidoylfuran-2-yl)methyl]-1H-imidazo[1,2-b]pyrazol-5-ium-5-yl}methyl)-8-oxo-5-thia-1-azabicyclo[4.2.0]oct-2-ene-2-carboxylate |

TABLE 1-continued

| Compound No. | Structure | Chemical Name |
|---|---|---|
| 26 | 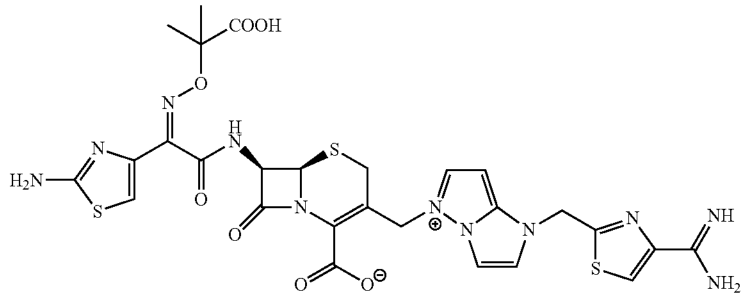 | (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidoyl-1,3-thiazol-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 27 | 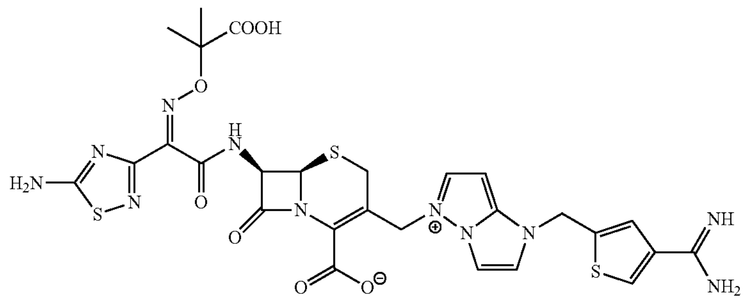 | (6R,7R)-7-{[(2Z)-2-(5-amino-1,2,4-thiadiazol-3-yl)-2-{[(2-carboxypropan-2-yl)oxy]imino}acetyl]amino}-3-({1-[(4-carbamimidoylthiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 28 | 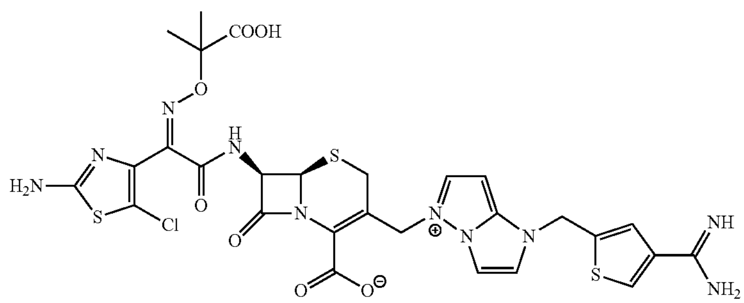 | (6R,7R)-7-{[(2Z)-2-(2-amino-5-chloro-1,3-thiazol-4-yl)-2-{([(2-carboxypropan-2-yl)oxy]imino}acetyl]amino}-3-({1-[(4-carbamimidoylthiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 29 | 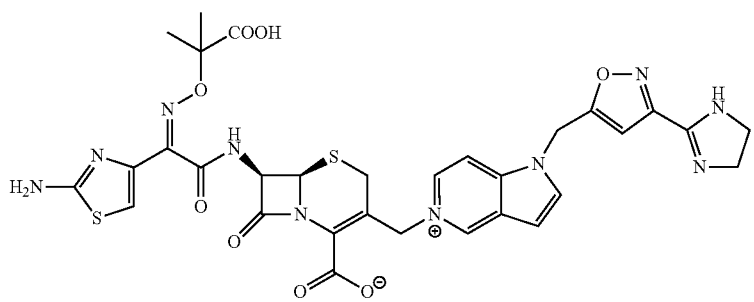 [SMILES: CC(C)(O/N=C(\C(=O)N[C@@H]1C(=O)N2C(C(=O)[O-])=C(C[n+]3ccc4c(ccn4Cc4cc(C5=NCCN5)no4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-[(1-{[3-(4,5-dihydro-1H-imidazol-2-yl)-1,2-oxazol-5-yl]methyl}-1H-pyrrolo[3,2-c]pyridin-5-ium-5-yl)methyl]-8-oxo-5-thia-1-azabicyclo[4.2.0]oct-2-ene-2-carboxylate |
| 30 | 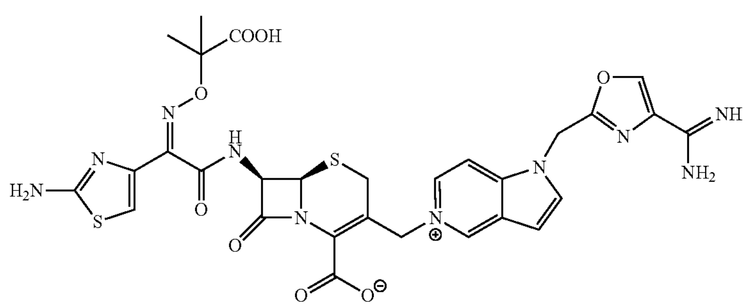 [SMILES: CC(C)(O/N=C(\C(=O)N[C@@H]1C(=O)N2C(C(=O)[O-])=C(C[n+]3ccc4c(ccn4Cc4nc(C(=N)N)co4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidoyl-1,3-oxazol-2-yl)methyl]-1H-pyrrolo[3,2-c]pyridin-5-ium-5-yl}methyl)-8-oxo-5-thia-1-azabicyclo[4.2.0]oct-2-ene-2-carboxylate |

| Compound No. | Structure | Chemical Name |
|---|---|---|
| 31 | 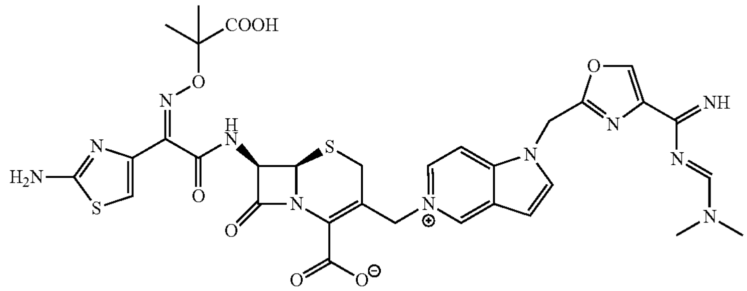 [SMILES: CN(C)/C=N/C(=N)c1coc(Cn2ccc3c[n+](CC4=C(C(=O)[O-])N5C(=O)[C@@H](NC(=O)/C(=N\OC(C)(C)C(=O)O)c6csc(N)n6)[C@H]5SC4)ccc32)n1] | (6R,7R)-7-{[(2Z)-2-(2-amino-1,3-thiazol-4-yl)-2-{[(2-carboxypropan-2-yl)oxy]imino}acetyl]amino}-3-({1-[(4-{N-[(E)-(dimethylamino)methylidene]carbamimidoyl}-1,3-oxazol-2-yl)methyl]-1H-pyrrolo[3,2-c]pyridin-5-ium-5-yl}methyl)-8-oxo-5-thia-1-azabicyclo[4.2.0]oct-2-ene-2-carboxylate |
| 32 | 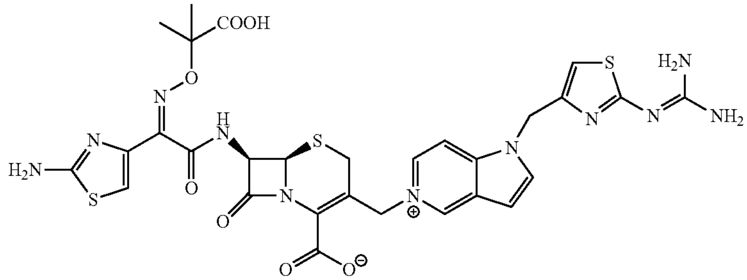 [SMILES: CC(C)(O/N=C(\C(=O)N[C@@H]1C(=O)N2C(C(=O)[O-])=C(C[n+]3ccc4c(ccn4Cc4csc(N=C(N)N)n4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]aminol-3-{[1-({2-[(diaminomethylidene)amino]-1,3-thiazol-4-yl}methyl)-1H-pyrrolo[3,2-c]pyridin-5-ium-5-yl]methyl}-8-oxo-5-thia-1-azabicyclo[4.2.0]oct-2-ene-2-carboxylate |
| 33 | 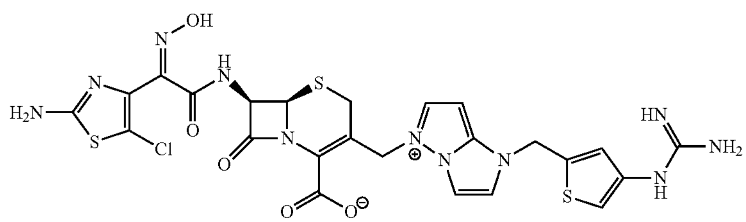 | (6R,7R)-7-{[(2Z)-2-(2-amino-5-chloro-1,3-thiazol-4-yl)-2-(hydroxyimino)acetyl]amino}-3-({1-[(4-carbamimidamidothiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 34 | 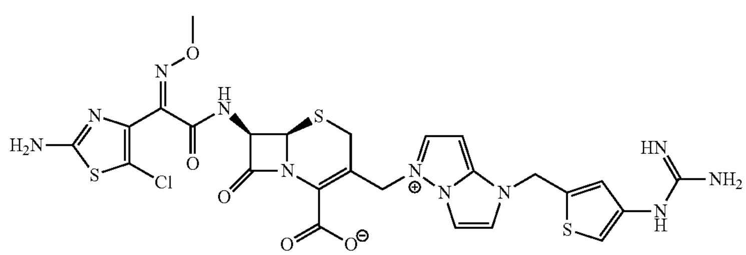 [SMILES: CO/N=C(\C(=O)N[C@@H]1C(=O)N2C(C(=O)[O-])=C(C[n+]3ccc4n(Cc5cc(NC(=N)N)cs5)ccn43)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-({1-[(4-carbamimidamidothiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 35 | 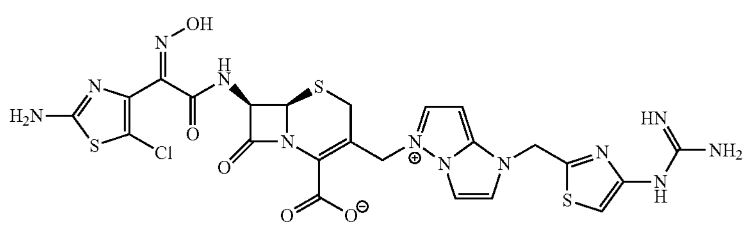 [SMILES: N=C(N)Nc1csc(Cn2ccn3c2cc[n+]3CC2=C(C(=O)[O-])N3C(=O)[C@@H](NC(=O)/C(=N\O)c4nc(N)sc4Cl)[C@H]3SC2)n1] | (6R,7R)-7-{[(2Z)-2-(2-amino-5-chloro-1,3-thiazol-4-yl)-2-(hydroxyimino)acetyl]amino}-3-({1-[(4-carbamimidamido-1,3-thiazol-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 36 | 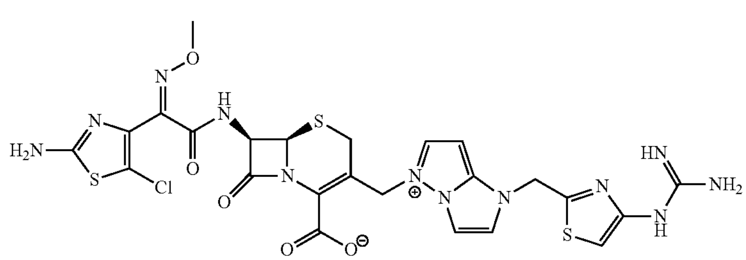 [SMILES: CO/N=C(\C(=O)N[C@@H]1C(=O)N2C(C(=O)[O-])=C(C[n+]3ccc4n(Cc5nc(NC(=N)N)cs5)ccn43)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-({1-[(4-carbamimidamido-1,3-thiazol-2-yl)methyl]-1H-imidazo[1,2-b]pyrazol-5-ium-5-yl}methyl)-8-oxo-5-thia-1-azabicyclo[4.2.0]oct-2-ene-2-carboxylate |

TABLE 1-continued

| Compound No. | Structure | Chemical Name |
|---|---|---|
| 37 | 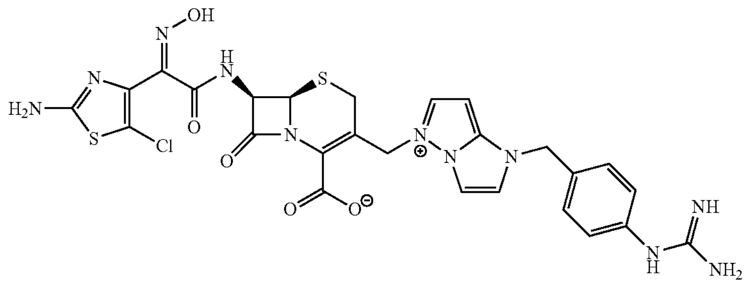 [SMILES: N=C(N)Nc1ccc(Cn2ccn3c2cc[n+]3CC2=C(C(=O)[O-])N3C(=O)[C@@H](NC(=O)/C(=N\O)c4nc(N)sc4Cl)[C@H]3SC2)cc1] | (6R,7R)-7-{[(2Z)-2-(2-amino-5-chloro-1,3-thiazol-4-yl)-2-(hydroxyimino)acetyl]amino}-3-{[1-(4-carbamimidamidobenzyl)-1H-imidazo[1,2-b]pyrazol-5-ium-5-yl]methyl}-8-oxo-5-thia-1-azabicyclo[4.2.0]oct-2-ene-2-carboxylate |
| 38 | 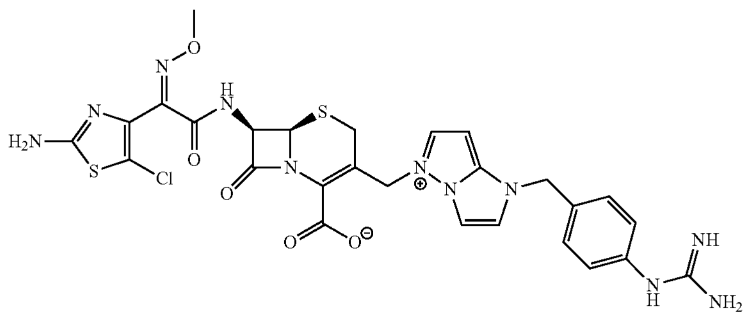 [SMILES: CO/N=C(\C(=O)N[C@@H]1C(=O)N2C(C(=O)[O-])=C(C[n+]3ccc4n(Cc5ccc(NC(=N)N)cc5)ccn43)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-([1-(4-carbamimidamidobenzyl)-1H-imidazo[1,2-b]pyrazol-5-ium-5-yl]methyl}-8-oxo-5-thia-1-azabicyclo[4.2.0]oct-2-ene-2-carboxylate |
| 39 | 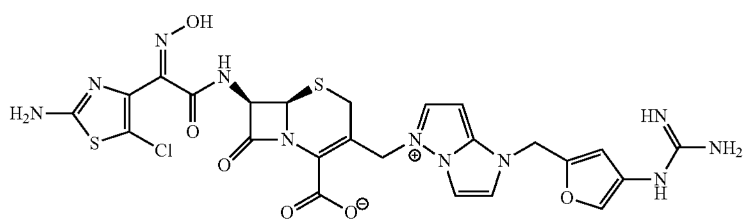 [SMILES: N=C(N)Nc1coc(Cn2ccn3c2cc[n+]3CC2=C(C(=O)[O-])N3C(=O)[C@@H](NC(=O)/C(=N\O)c4nc(N)sc4Cl)[C@H]3SC2)c1] | (6R,7R)-1-{[(2Z)-2-(2-amino-5-chloro-1,3-thiazol-4-yl)-2-(hydroxyimino)acetyl]amino}-3-({1-[(4-carbamimidamidofuran-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 40 | 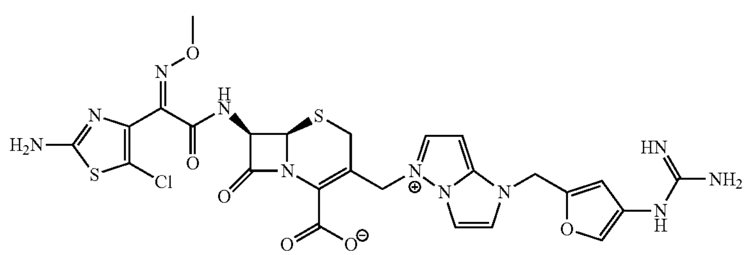 [SMILES: CO/N=C(\C(=O)N[C@@H]1C(=O)N2C(C(=O)[O-])=C(C[n+]3ccc4n(Cc5cc(NC(=N)N)co5)ccn43)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-({1-[(4-carbamimidamidofuran-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 41 | 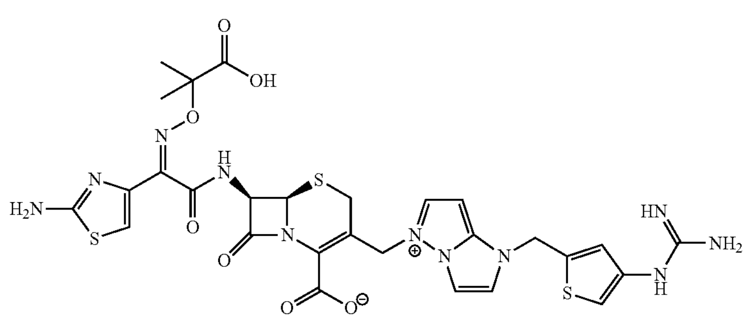 | (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidamidothiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate |

TABLE 1-continued

| Compound No. | Structure | Chemical Name |
|---|---|---|
| 42 | 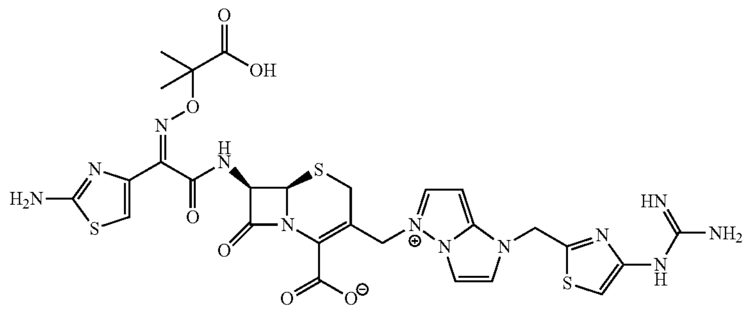 [SMILES: CC(C)(O/N=C(\C(=O)N[C@@H]1C(=O)N2C(C(=O)[O-])=C(C[n+]3ccc4n(Cc5nc(NC(=N)N)cs5)ccn43)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidamido-1,3-thiazol-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 43 | 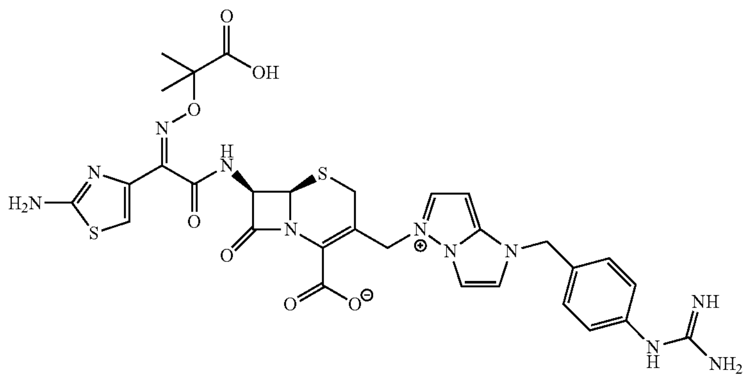 [SMILES: CC(C)(O/N=C(\C(=O)N[C@@H]1C(=O)N2C(C(=O)[O-])=C(C[n+]3ccc4n(Cc5ccc(NC(=N)N)cc5)ccn43)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino]acetyl]amino}-3-{[1-(4-carbamimidamidobenzyl)-1H-imidazo[1,2-b]pyrazol-5-ium-5-yl]methyl}-8-oxo-5-thia-1-azabicyclo[4.2.0]oct-2-ene-2-carboxylate |
| 44 | 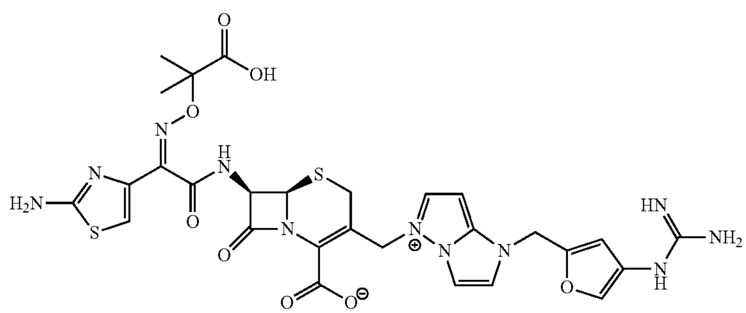 [SMILES: CC(C)(O/N=C(\C(=O)N[C@@H]1C(=O)N2C(C(=O)[O-])=C(C[n+]3ccc4n(Cc5cc(NC(=N)N)co5)ccn43)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino)acetyl]amino}-3-({1-[(4-carbamimidamidofuran-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 45 | 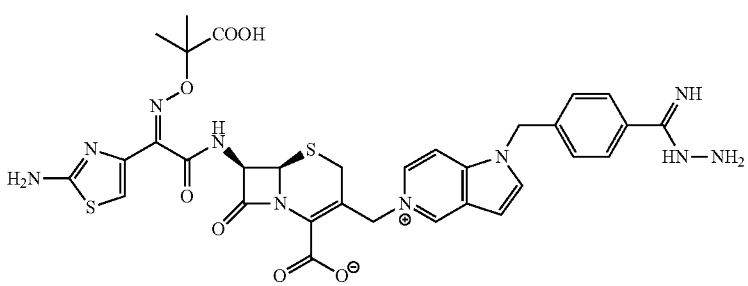 [SMILES: CC(C)(O/N=C(\C(=O)N[C@@H]1C(=O)N2C(C(=O)[O-])=C(C[n+]3ccc4c(ccn4Cc4ccc(C(=N)NN)cc4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-({1-[4-(hydrazinylcarbonoimidoyl)benzyl]-1H-pyrrolo[3,2-c]pyridin-5-ium-5-yl}methyl)-8-oxo-5-thia-1-azabicyclo[4.2.0]oct-2-ene-2-carboxylate |

TABLE 1-continued

| Compound No. | Structure | Chemical Name |
|---|---|---|
| 46 | 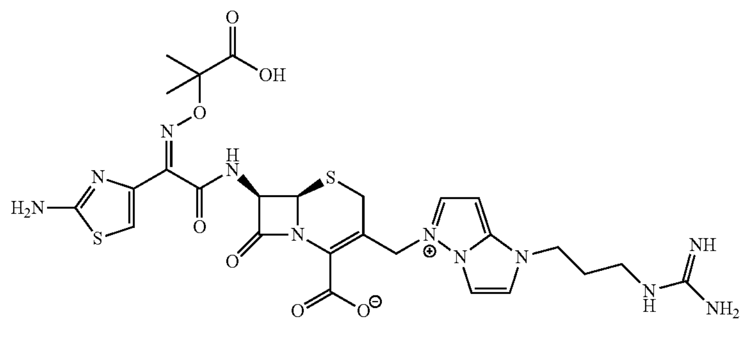 [SMILES: CC(C)(O/N=C(\C(=O)N[C@@H]1C(=O)N2C(C(=O)[O-])=C(C[n+]3ccc4n(CCCNC(=N)N)ccn43)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-{[1-(3-carbamimidamidopropyl)-1H-imidazo[1,2-b]pyrazol-5-ium-5-yl]methyl}-8-oxo-5-thia-1-azabicyclo[4.2.0]oct-2-ene-2-carboxylate |
| 47 | 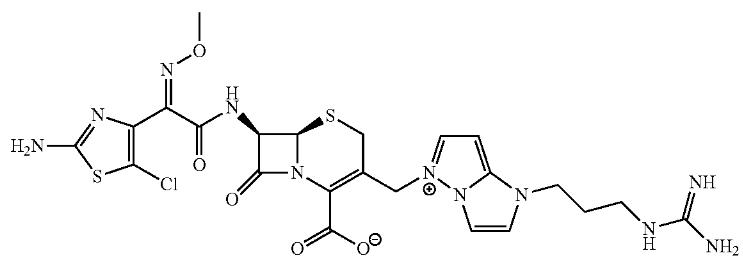 [SMILES: CO/N=C(\C(=O)N[C@@H]1C(=O)N2C(C(=O)[O-])=C(C[n+]3ccc4n(CCCNC(=N)N)ccn43)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-{[1-(3-carbamimidamidopropyl)-1H-imidazo[1,2-b]pyrazol-5-ium-5-yl]methyl}-8-oxo-5-thia-1-azabicyclo[4.2.0]oct-2-ene-2-carboxylate |
| 48 | 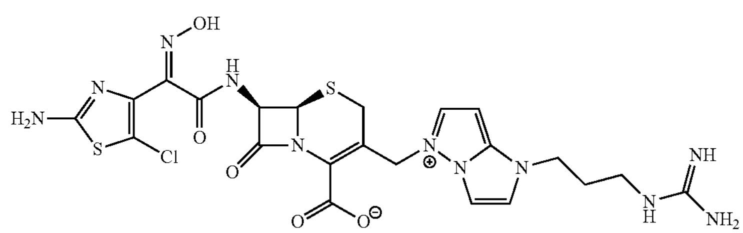 [SMILES: N=C(N)NCCCn1ccn2c1cc[n+]2CC1=C(C(=O)[O-])N2C(=O)[C@@H](NC(=O)/C(=N\O)c3nc(N)sc3Cl)[C@H]2SC1] | (6R,7R)-7-{[(2Z)-2-(2-amino-5-chloro-1,3-thiazol-4-yl)-2-(hydroxyimino)acetyl]amino}-3-{[1-(3-carbamimidamidopropyl)-1H-imidazo[1,2-b]pyrazol-5-ium-5-yl]methyl}-8-oxo-5-thia-1-azabicyclo[4.2.0]oct-2-ene-2-carboxylate |
| 49 | 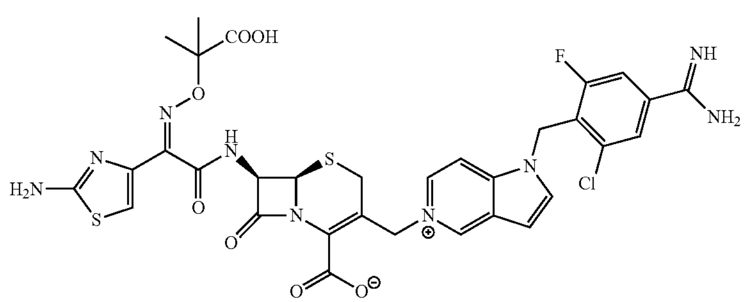 [SMILES: CC(C)(O/N=C(\C(=O)N[C@@H]1C(=O)N2C(C(=O)[O-])=C(C[n+]3ccc4c(ccn4Cc4c(F)cc(C(=N)N)cc4Cl)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino}acetyl]amino}-3-{[1-(4-carbamimidoyl-2-chloro-6-fluorobenzyl)-1H-pyrrolo[3,2-c]pyridin-5-ium-5-yl]methyl}-8-oxo-5-thia-1-azabicyclo[4.2.0]oct-2-ene-2-carboxylate |
| 50 | 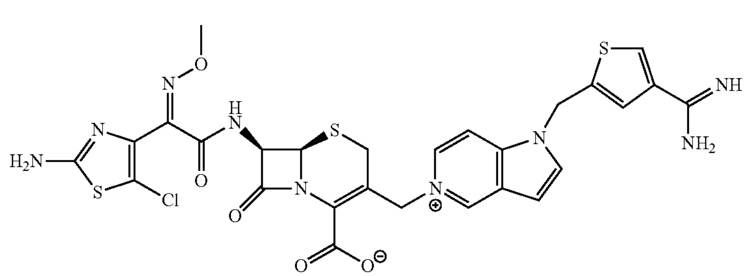 [SMILES: CO/N=C(\C(=O)N[C@@H]1C(=O)N2C(C(=O)[O-])=C(C[n+]3ccc4c(ccn4Cc4cc(C(=N)N)cs4)c3)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-({1-[(4-carbamimidoylthiophen-2-yl)methyl]-1H-pyrrolo[3,2-c]pyridin-5-ium-5-yl}methyl)-8-oxo-5-thia-1-azabicyclo[4.2.0]oct-2-ene-2-carboxylate |

TABLE 1-continued

| Compound No. | Structure | Chemical Name |
|---|---|---|
| 51 | 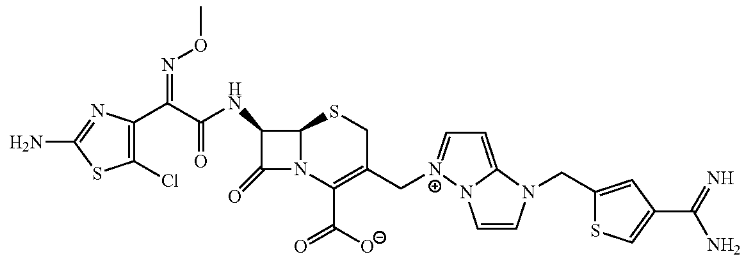 [SMILES: CO/N=C(\C(=O)N[C@@H]1C(=O)N2C(C(=O)[O-])=C(C[n+]3ccc4n(Cc5cc(C(=N)N)cs5)ccn43)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-({1-[(4-carbamimidoylthiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 52 | 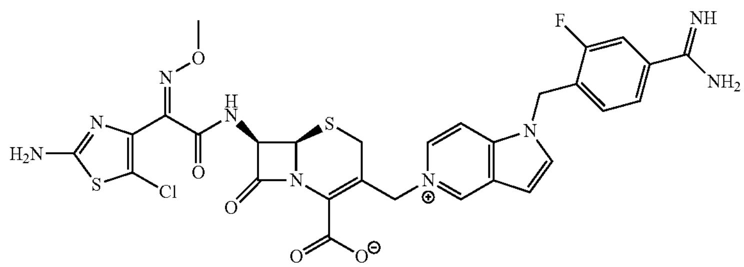 [SMILES: CO/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-{[1-(4-carbamimidoyl-2-fluorobenzyl)-1H-pyrrolo[3,2-c]pyridin-5-ium-5-yl]methyl}-8-oxo-5-thia-1-azabicyclo[4.2.0]oct-2-ene-2-carboxylate |
| 53 | 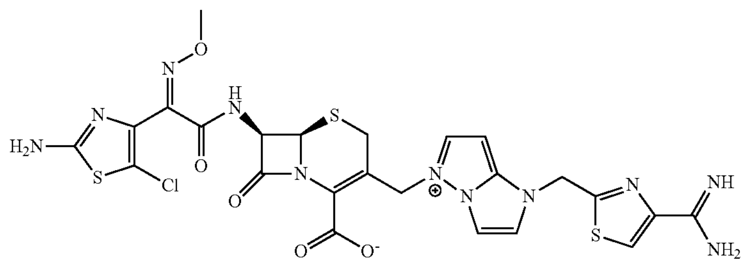 [SMILES: CO/N=C(\C(=O)N[C@@H]1C(=O)N2C(C(=O)[O-])=C(C[n+]3ccc4n(Cc5nc(C(=N)N)cs5)ccn43)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-({1-[(4-carbamimidoyl-1,3-thiazol-2-yl)methyl]-1H-imidazo[1,2-b]pyrazol-5-ium-5-yl}methyl)-8-oxo-5-thia-1-azabicyclo[4.2.0]oct-2-ene-2-carboxylate |
| 54 | 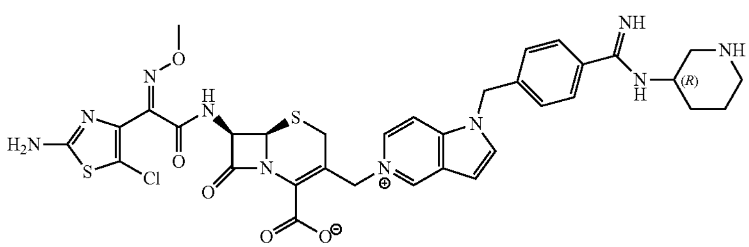 | (6R,7R)-7-{[(2Z)-2-(2-amino-5-chloro-1,3-thiazol-4-yl)-2-(methoxyimino)acetyl]amino}-8-oxo-3-{[1-(4-{N-[(3R)-piperidin-3-yl]carbamimidoyl}benzyl)-1H-pyrrolo[3,2-c]pyridin-5-ium-5-yl]methyl}-5-thia-1-azabicyclo[4.2.0]oct-2-ene-2-carboxylate |
| 55 | 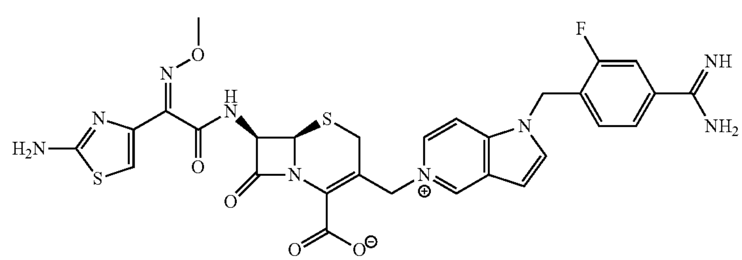 [SMILES: CO/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1csc(N)n1] | (6R,7R)-7-{[(2Z)-2-(2-amino-1,3-thiazol-4-yl)-2-(methoxyimino)acetyl]amino}-3-{[1-(4-carbamimidoyl-2-fluorobenzyl)-1H-pyrrolo[3,2-c]pyridin-5-ium-5-yl]methyl}-8-oxo-5-thia-1-azabicyclo[4.2.0]oct-2-ene-2-carboxylate |
| 56 | 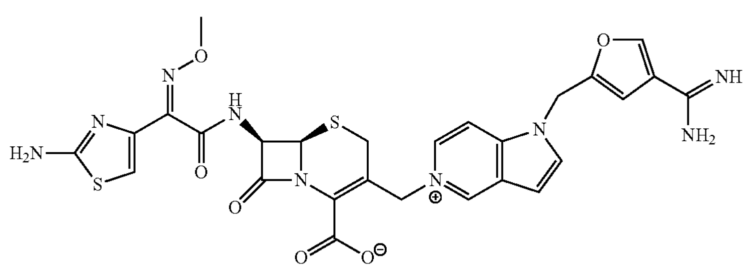 [SMILES: CO/N=C(\C(=O)N[C@@H]1C(=O)N2C(C(=O)[O-])=C(C[n+]3ccc4c(ccn4Cc4cc(C(=N)N)co4)c3)CS[C@H]12)c1csc(N)n1] | (6R,7R)-7-{[(2Z)-2-(2-amino-5-chloro-1,3-thiazol-4-yl)-2-(methoxyimino)acetyl]amino}-3-({1-[(4-carbamimidoylfuran-2-yl)methyl]-1H-pyrrolo[3,2-c]pyridin-5-ium-5-yl}methyl)-8-oxo-5-thia-1-azabicyclo[4.2.0]oct-2-ene-2-carboxylate |

TABLE 1-continued

| Compound No. | Structure | Chemical Name |
|---|---|---|
| 57 | 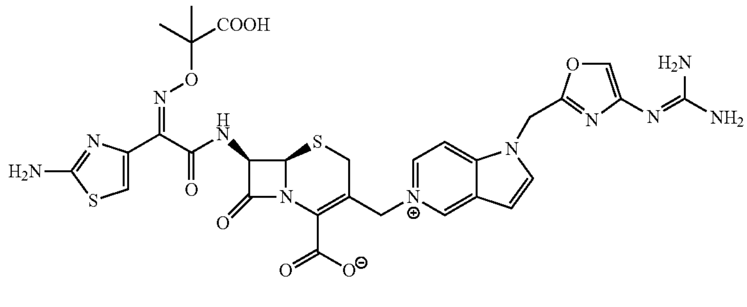 [SMILES: CC(C)(O/N=C(\C(=O)N[C@@H]1C(=O)N2C(C(=O)[O-])=C(C[n+]3ccc4c(ccn4Cc4nc(N=C(N)N)co4)c3)CS[C@H]12)c1csc(N)n1)C(=O)O] | (6R,7R)-7-{[(2Z)-2-(2-amino-1,3-thiazol-4-yl)-2-{[(2-carboxypropan-2-yl)oxy]imino)acetyl]amino}-3-{[1-({3-[(diaminomethylidene)amino]-1,2-oxazol-5-yl}methyl)-1H-pyrrolo[3,2-c]pyridin-5-ium-5-yl]methyl}-8-oxo-5-thia-1-azabicyclo[4.2.0]oct-2-ene-2-carboxylate |
| 58 | 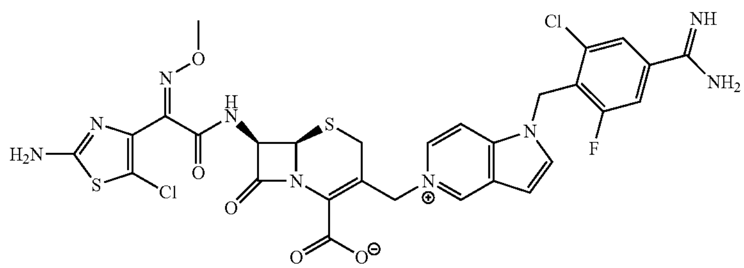 [SMILES: CO/N=C(\C(=O)N[C@@H]1C(=O)N2C(C(=O)[O-])=C(C[n+]3ccc4c(ccn4Cc4c(F)cc(C(=N)N)cc4Cl)c3)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-{[1-(4-carbamimidoyl-2-chloro-6-fluorobenzyl)-1H-pyrrolo[3,2-c]pyridin-5-ium-5-yl]methyl}-8-oxo-5-thia-1-azabicyclo[4.2.0]oct-2-ene-2-carboxylate |
| 59 | 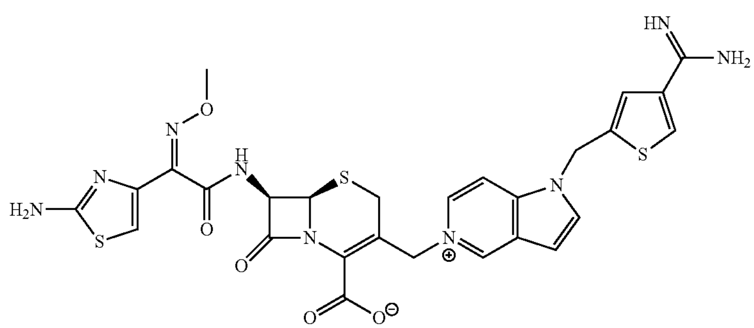 [SMILES: CO/N=C(\C(=O)N[C@@H]1C(=O)N2C(C(=O)[O-])=C(C[n+]3ccc4c(ccn4Cc4cc(C(=N)N)cs4)c3)CS[C@H]12)c1csc(N)n1] | (6R,7R)-7-{[(2Z)-2-(2-amino-1,3-thiazol-4-yl)-2-(methoxyimino)acetyl]amino}-3-({1-[(4-carbamimidoylthiophen-2-yl)methyl]-1H-pyrrolo[3,2-c]pyridin-5-ium-5-yl}methyl)-8-oxo-5-thia-1-azabicyclo[4.2.0]oct-2-ene-2-carboxylate |
| 60 | 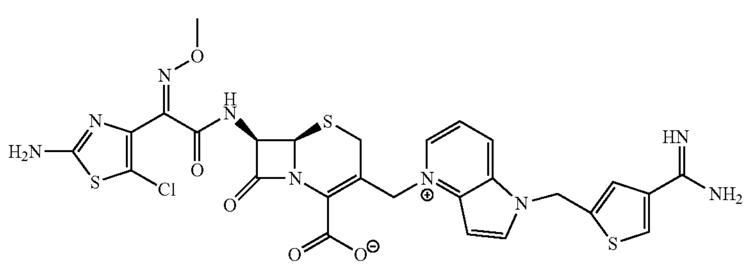 [SMILES: CO/N=C(\C(=O)N[C@@H]1C(=O)N2C(C(=O)[O-])=C(C[n+]3cccc4c3ccn4Cc3cc(C(=N)N)cs3)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-({1-[(4-carbamimidoylthiophen-2-yl)methyl]-1H-pyrrolo[3,2-b]pyridin-4-ium-4-yl}methyl)-8-oxo-5-thia-1-azabicyclo[4.2.0]oct-2-ene-2-carboxylate |
| 61 | 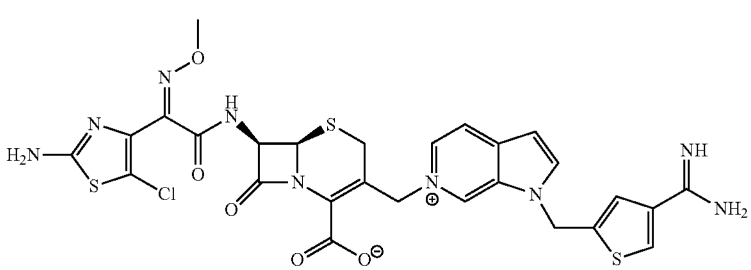 [SMILES: CO/N=C(\C(=O)N[C@@H]1C(=O)N2C(C(=O)[O-])=C(C[n+]3ccc4ccn(Cc5cc(C(=N)N)cs5)c4c3)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-({1-[(4-carbamimidoylthiophen-2-yl)methyl]-1H-pyrrolo[2,3-c]pyridin-6-ium-6-yl}methyl)-8-oxo-5-thia-1-azabicyclo[4.2.0]oct-2-ene-2-carboxylate |

TABLE 1-continued

| Compound No. | Structure | Chemical Name |
|---|---|---|
| 62 | 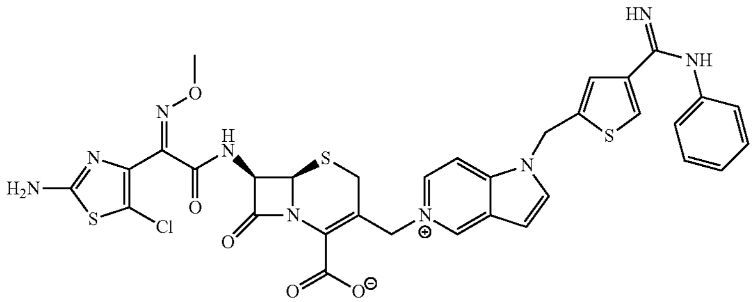 [SMILES: CO/N=C(\C(=O)N[C@@H]1C(=O)N2C(C(=O)[O-])=C(C[n+]3ccc4c(ccn4Cc4cc(C(=N)Nc5ccccc5)cs4)c3)CS[C@H]12)c1nc(N)sc1Cl] | Preparation of (6R,7R)-7-{[(2Z)-2-(2-amino-5-chloro-1,3-thiazol-4-yl)-2-(methoxyimino)acetyl]amino}-8-oxo-3-[(1-{[4-(N-phenylcarbamimidoyl)thiophen-2-yl]methyl}-1H-pyrrolo[3,2-c]pyridin-5-ium-5-yl)methyl]-5-thia-1-azabicyclo[4.2.0]oct-2-ene-2-carboxylate |
| 63 | 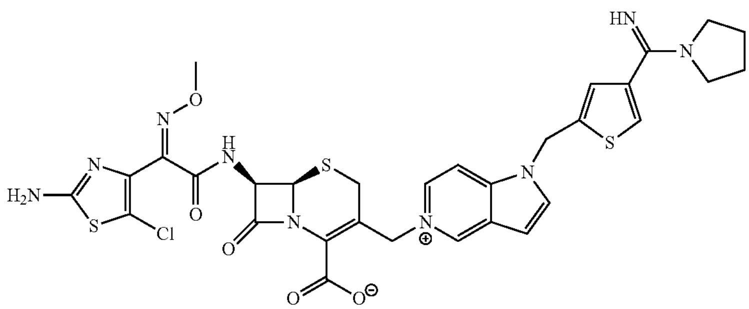 [SMILES: CO/N=C(\C(=O)N[C@@H]1C(=O)N2C(C(=O)[O-])=C(C[n+]3ccc4c(ccn4Cc4cc(C(=N)N5CCCC5)cs4)c3)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-8-oxo-3-[(1-({[4-(pyrrolidin-1-ylcarbonoimidoyl)thiophen-2-yl]methyl}-1H-pyrrolo[3,2-c]pyridin-5-ium-5-yl)methyl]-5-thia-1-azabicyclo[4.2.0]oct-2-ene-2-carboxylate |
| 64 | 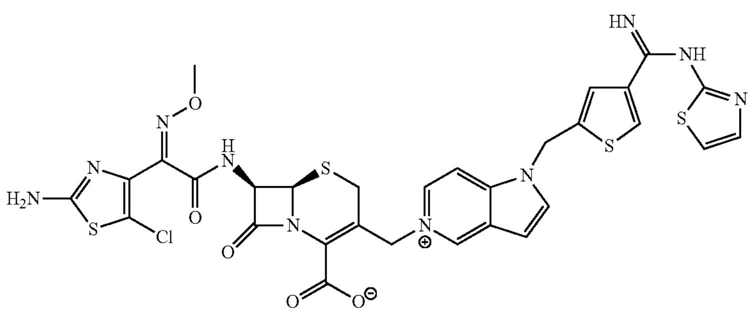 [SMILES: CO/N=C(\C(=O)N[C@@H]1C(=O)N2C(C(=O)[O-])=C(C[n+]3ccc4c(ccn4Cc4cc(C(=N)Nc5nccs5)cs4)c3)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-8-oxo-3-{[1-({4-[N-(1,3-triiazol-2-yl)carbamimidoyl]thiophen-2-yl}methyl)-1H-pyrrolo[3,2-c]pyridin-5-ium-5-yl]methyl}-5-thia-1-azabicyclo[4.2.0]cot-2-ene-2-carboxylate |
| 65 | 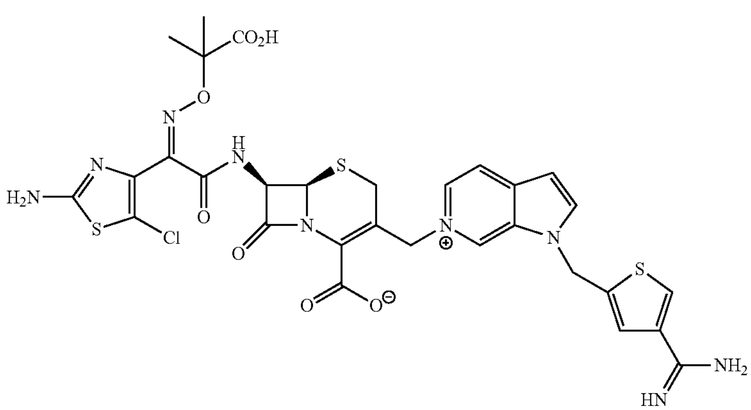 [SMILES: CC(C)(O/N=C(\C(=O)N[C@@H]1C(=O)N2C(C(=O)[O-])=C(C[n+]3ccc4ccn(Cc5cc(C(=N)N)cs5)c4c3)CS[C@H]12)c1nc(N)sc1Cl)C(=O)O] | (6R,7R)-7-{[(2Z)-2-(2-amino-5-chloro-1,3-thiazol-4-yl)-2-{[(2-carboxypropan-2-yl)oxy]imino}acetyl]amino}-3-({1-[(4-carbamimidoylthiophen-2-yl)methyl]-1H-pyrrolo[2,3-c]pyridin-6-ium-6-yl}methyl)-8-oxo-5-thia-1-azabicyclo[4.2.0]oct-2-ene-2-carboxylate |

TABLE 1-continued

| Compound No. | Structure | Chemical Name |
|---|---|---|
| 66 | 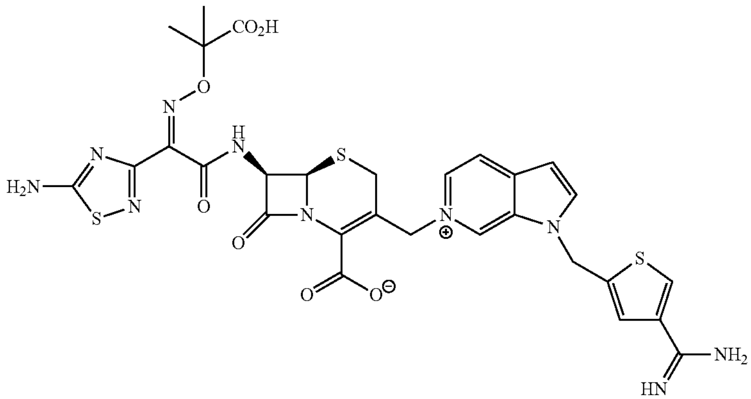 [SMILES: CC(C)(O/N=C(\C(=O)N[C@@H]1C(=O)N2C(C(=O)[O-])=C(C[n+]3ccc4ccn(Cc5cc(C(=N)N)cs5)c4c3)CS[C@H]12)c1nsc(N)n1)C(=O)O] | (6R,7R)-7-{[(2Z)-2-(5-amino-1,2,4-thiadiazol-3-yl)-2-{[(2-carboxypropan-2-yl)oxy]imino}acetyl]amino}-3-({1-[(4-carbamimidoylthiophen-2-yl)methyl]-1H-pyrrolo[2,3-c]pyridin-6-ium-6-yl}methyl)-8-oxo-5-thia-1-azabicyclo[4.2.0]oct-2-ene-2-carboxylate |
| 67 | 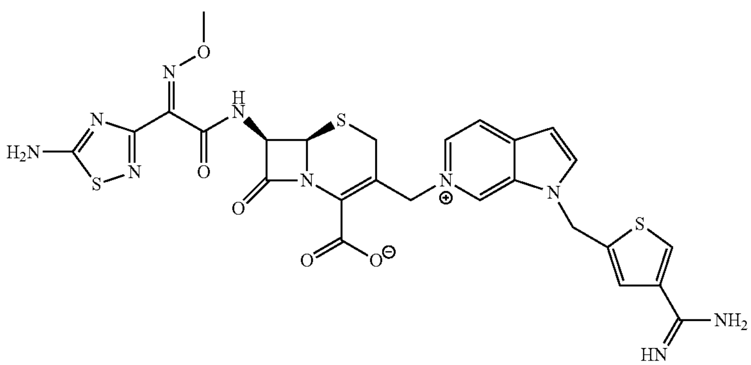 [SMILES: CO/N=C(\C(=O)N[C@@H]1C(=O)N2C(C(=O)[O-])=C(C[n+]3ccc4ccn(Cc5cc(C(=N)N)cs5)c4c3)CS[C@H]12)c1nsc(N)n1] | (6R,7R)-7-{[(2Z)-2-(5-amino-1,2,4-thiadiazol-3-yl)-2-(methoxyimino)acetyl]amino}-3-({1-[(4-carbamimidoylthiophen-2-yl)methyl]-1H-pyrrolo[2,3-c]pyridin-6-ium-6-yl}methyl)-8-oxo-5-thia-1-azabicyclo[4.2.0]oct-2-ene-2-carboxylate |
| 68 | 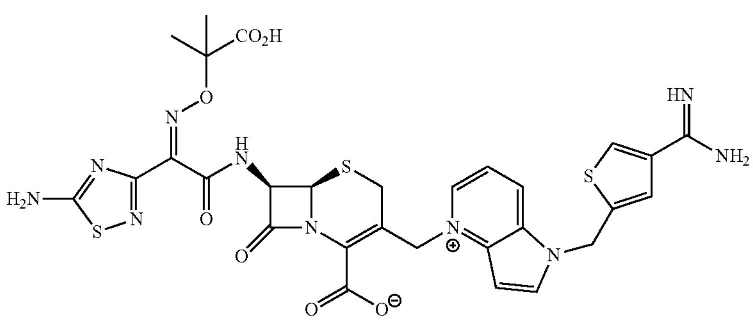 [SMILES: CC(C)(O/N=C(\C(=O)N[C@@H]1C(=O)N2C(C(=O)[O-])=C(C[n+]3cccc4c3ccn4Cc3cc(C(=N)N)cs3)CS[C@H]12)c1nsc(N)n1)C(=O)O] | (6R,7R)-7-{[(2Z)-2-(5-amino-1,2,4-thiadiazol-3-yl)-2-{[(2-carboxypropan-2-yl)oxy]imino}acetyl]amino}-3-({1-[(4-carbamimidoylthiophen-2-yl)methyl]-1H-pyrrolo[3,2-b]pyridin-4-ium-4-yl}methyl)-8-oxo-5-thia-1-azabicyclo[4.2.0]oct-2-ene-2-carboxylate |
| 69 | 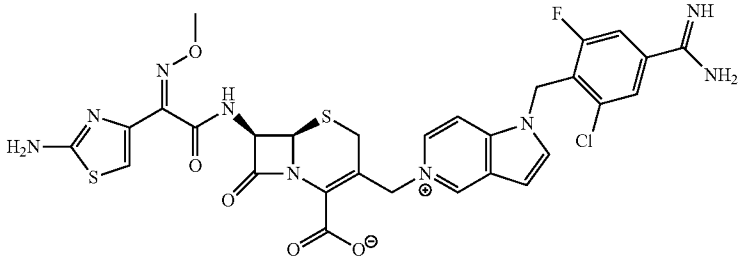 [SMILES: CO/N=C(\C(=O)N[C@@H]1C(=O)N2C(C(=O)[O-])=C(C[n+]3ccc4c(ccn4Cc4c(F)cc(C(=N)N)cc4Cl)c3)CS[C@H]12)c1csc(N)n1] | (6R,7R)-7-{[(2Z)-2-(2-amino-1,3-thiazo]-4-yl)-2-(methoxyimino)acetyl]amino}-3-{[1-(4-carbamimidoyl-2-chloro-6-fluorobenzyl)-1H-pyrrolo[3,2-c]pyridin-5-ium-5-yl]methyl}-8-oxo-5-thia-1-azabicyclo[4.2.0]oct-2-ene-2-carboxylate |

| Compound No. | Structure | Chemical Name |
|---|---|---|
| 70 | 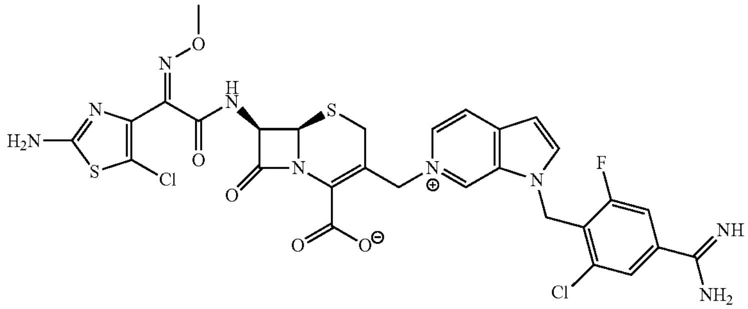 [SMILES: CO/N=C(\C(=O)N[C@@H]1C(=O)N2C(C(=O)[O-])=C(C[n+]3ccc4ccn(Cc5c(F)cc(C(=N)N)cc5Cl)c4c3)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-{[1-(4-carbamimidoyl-2-chloro-6-fluorobenzyl)-1H-pyrrolo[2,3-c]pyridin-6-ium-6-yl]methyl}-8-oxo-5-thia-1-azabicyclo[4.2.0]oct-2-ene-2-carboxylate |
| 71 | 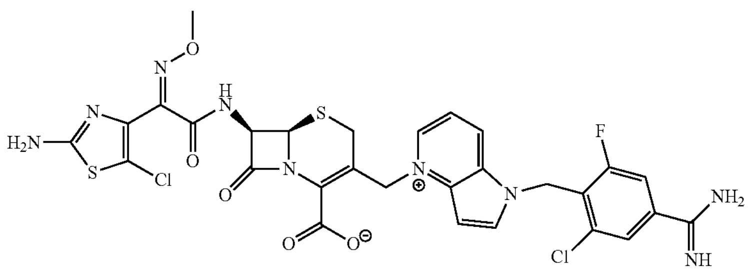 [SMILES: CO/N=C(\C(=O)N[C@@H]1C(=O)N2C(C(=O)[O-])=C(C[n+]3cccc4c3ccn4Cc3c(F)cc(C(=N)N)cc3Cl)CS[C@H]12)c1nc(N)sc1Cl] | (6R,7R)-7-{[(2Z)-2-(2-amino-5-chloro-1,3-thiazol-4-yl)-2-(methoxyimino)acetyl]amino}-3-{[1-(4-carbamimidoyl-2-chloro-6-fluorobenzyl)-1H-pyrrolo[3,2-b]pyridin-4-ium-4-yl]methyl}-8-oxo-5-thia-1-azabicyclo[4.2.0]oct-2-ene-2-carboxylate |
| 72 | 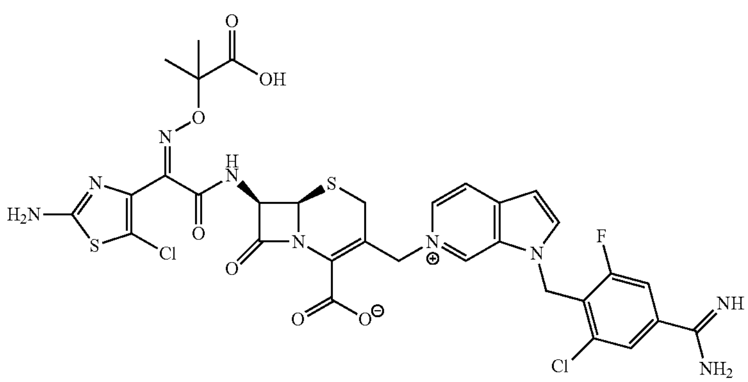 [SMILES: CC(C)(O/N=C(\C(=O)N[C@@H]1C(=O)N2C(C(=O)[O-])=C(C[n+]3ccc4ccn(Cc5c(F)cc(C(=N)N)cc5Cl)c4c3)CS[C@H]12)c1nc(N)sc1Cl)C(=O)O] | (6R,7R)-7-{[(2Z)-2-(2-amino-5-chloro-1,3-thiazol-4-yl)-2-{[(2-carboxypropan-2-yl)oxy]imino}acetyl]amino}-3-{[1-(4-carbamimidoyl-2-chloro-6-fluorobenzyl)-1H-pyrrolo[2,3-c]pyridin-6-ium-6-yl]methyl}-8-oxo-5-thia-1-azabicyclo[4.2.0]oct-2-ene-2-carboxylate |
| 73 | 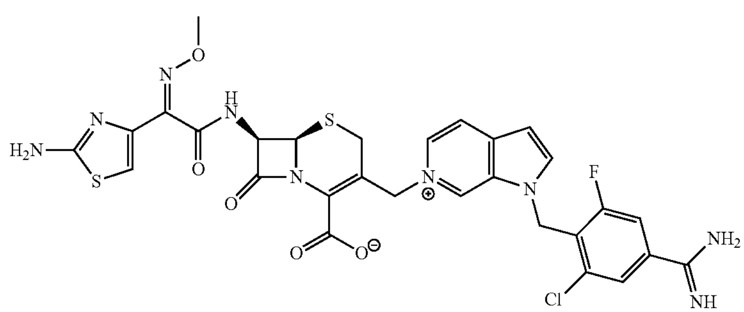 [SMILES: CO/N=C(\C(=O)N[C@@H]1C(=O)N2C(C(=O)[O-])=C(C[n+]3ccc4ccn(Cc5c(F)cc(C(=N)N)cc5Cl)c4c3)CS[C@H]12)c1csc(N)n1] | (6R,7R)-7-{[(2Z)-2-(2-amino-1,3-thiazol-4-yl)-2-(methoxyimino)acetyl]amino}-3-{[1-(4-carbamimidoyl-2-chloro-6-fluorobenzyl)-1H-pyrrolo[2,3-c]pyridin-6-ium-6-yl]methyl}-8-oxo-5-thia-1-azabicyclo[4.2.0]oct-2-ene-2-carboxylate |

| Compound No. | Structure | Chemical Name |
|---|---|---|
| 74 | 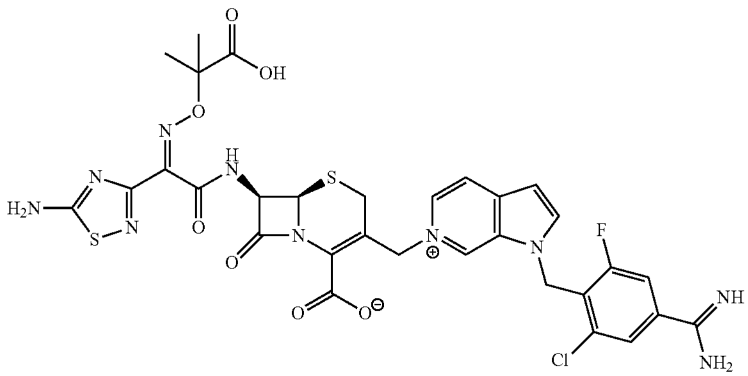 [SMILES: CC(C)(O/N=C(\C(=O)N[C@@H]1C(=O)N2C(C(=O)[O-])=C(C[n+]3ccc4ccn(Cc5c(F)cc(C(=N)N)cc5Cl)c4c3)CS[C@H]12)c1nsc(N)n1)C(=O)O] | (6R,7R)-7-{[(2Z)-2-(5-amino-1,2,4-thiadiazol-3-yl)-2-{[(2-carboxypropan-2-yl)oxy]imino}acetyl]amino}-3-{[1-(4-carbamimidoyl-2-chloro-6-fluorobenzyl)-1H-pyrrolo[2,3-c-]pyridin-6-ium-6-yl]methyl}-8-oxo-5-thia-1-azabicyclo[4.2.0]oct-2-ene-2-carboxylate |

Methods of Preparation:

The compounds of general formula (I) can be prepared as described in the following schemes (Scheme 1 and Scheme 2) which illustrate the general method of preparation only and are not intended to be limiting to any specific compound described herein.

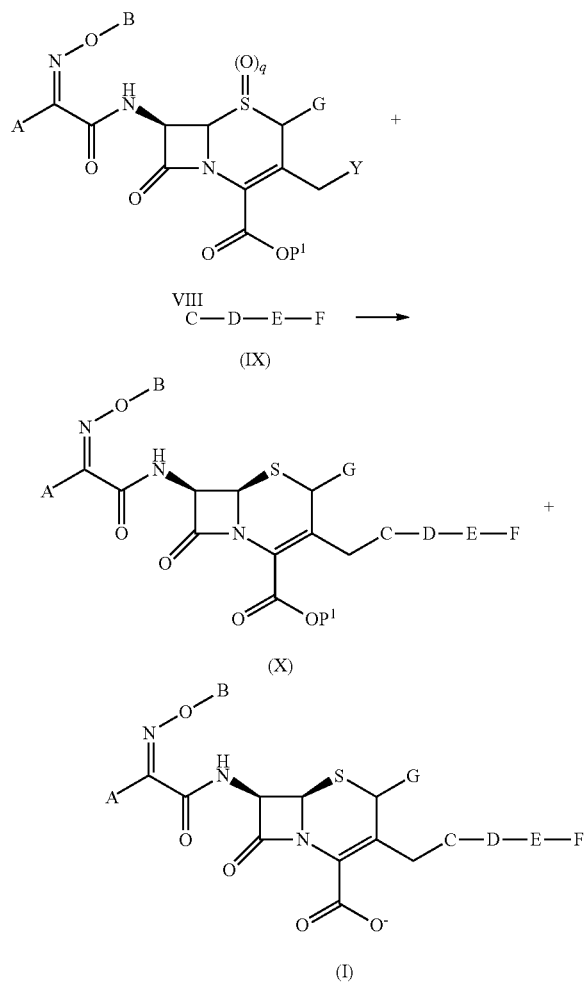

Process I (Scheme 1):

(a) Coupling Step:

Reaction of (VIII, q=0, Y=chloride) with the intermediate (IX) is carried out in a conventional solvent such as water, alcohol (e.g., methanol, ethanol etc.), acetone, dioxane, acetonitrile, chloroform, methylene chloride, ethylene chloride, tetrahydrofuran, ethylacetate, N,N-dimethylformamide, pyridine or any other organic solvent which does not adversely influence the reaction. These conventional solvents may also be used as a co-solvent in a mixture with water. In this reaction, when Y=Cl, the reaction is preferably carried out in the presence of a conventional alkali metal halide such as potassium iodide and in the presence of N,N-dimethylformamide or dimethylacetamide. The reaction is usually carried out ranging from −20° C. to 40° C.

(b) Hydrolysis Step:

The hydrolysis is preferably carried out in the presence of a base or an acid including Lewis acid. Suitable base may include an inorganic base such as an alkali metal (e.g., sodium, potassium etc.); an alkali earth metal (e.g., magnesium, calcium etc.), the hydroxide or carbonate or bicarbonate thereof, and an organic base trialkylamine (e.g., trimethylamine, triethylamine, etc.), picoline or the like. Suitable acid may include an organic acid (e.g., formic acid, acetic acid, propionic acid, trichloroacetic acid, trifluoroacetic acid) and an inorganic acid (e.g., hydrochloric acid, hydrobromic acid, sulfuric acid). The hydrolysis using Lewis acid such as trihaloacetic acid (e.g., trichloroacetic acid, trifluoroacetic acid) or the like and the reaction is preferably carried out in the presence of cation trapping agents (e.g., anisole, phenol etc.). The hydrolysis using Lewis acid such as aluminum trichloride is carried out in a solvent like nitromethane. The hydrolysis reaction is usually carried out in a non-aqueous solvent such as methylene chloride, tetrahydrofuran, a mixture of solvents thereof, or any other solvent that does not adversely influence the reaction. The reaction temperature may be room temperature, or any other temperature as may be appropriate.

Scheme 2

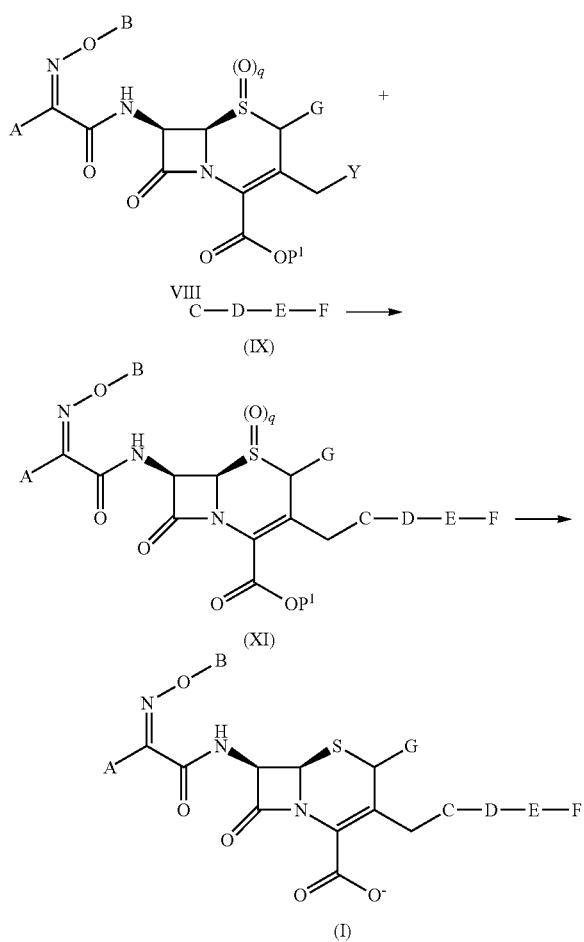

Process II (Scheme 2):

(a) Coupling Step:

Reaction of (VIII, q=1, Y=iodide) with the intermediate (IX) is carried out in a conventional solvent such as water, alcohol (e.g., methanol, ethanol etc.), acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used as a co-solvent in a mixture with water. In this reaction, when Y=Cl, the reaction is preferably carried out in the presence of a conventional alkali metal halide such as potassium iodide and in the presence of N,N-dimethylformamide or dimethylacetamide. The reaction temperature is not critical, and usually carried out under cooling to room temperature, even more preferably ranging from −20° C. to 40° C.

(b) Reduction Step:

Reduction is carried out in a conventional manner. Suitable reducing agents to be used in chemical reduction are a combination of a metal (e.g., tin, zinc, iron etc.) and an organic or inorganic acid (e.g formic acid, acetic acid, propionic acid, trifluoroacetic acid, p-toluenesulfonic acid, hydrochloric acid, hydrobromic acid, etc.). Reduction can also be carried out using a combination of alkali metal halide (e.g., potassium iodide) and acetyl chloride. The reduction is usually carried out in a conventional solvent which does not adversely influence the reaction such as N,N-dimethylformamide, diethyl ether, dioxane, tetrahydrofuran, etc. or a mixture of solvents thereof. The reduction is carried out under cooling to warming, more specifically in the range from −40° C. to 0° C.

(c) Hydrolysis Step:

The hydrolysis is preferably carried out in the presence of a base or an acid including Lewis acid. Suitable base may include an inorganic base such as an alkali metal (e.g., sodium, potassium etc.); an alkali earth metal (e.g., magnesium, calcium etc.), the hydroxide or carbonate or bicarbonate thereof, and an organic base, trialkylamine (e.g., trimethylamine, triethylamine, etc.), picoline or the like. Suitable acid may include an organic acid (e.g., formic acid, acetic acid, propionic acid, trichloroacetic acid, trifluoroacetic acid) and an inorganic acid (e.g., hydrochloric acid, hydrobromic acid, sulfuric acid). The hydrolysis using Lewis acid such as trihaloacetic acid (e.g., trichloroacetic acid, trifluoroacetic acid) or the like and the reaction is preferably carried out in the presence of cation trapping agents (e.g., anisole, phenol etc.). The hydrolysis using Lewis acid such as aluminum trichloride is carried out in a solvent like nitromethane. The hydrolysis reaction is usually carried out in a non-aqueous solvent such as methylene chloride, tetrahydrofuran, a mixture of solvents thereof or any other solvent that does not adversely influence the reaction. The reaction temperature is not critical, but is usually carried out at room temperature.

In the formula (VIII), A and B have the same definitions as described before.

Thus, in formula (VIII), A is defined by the formula (Ia);

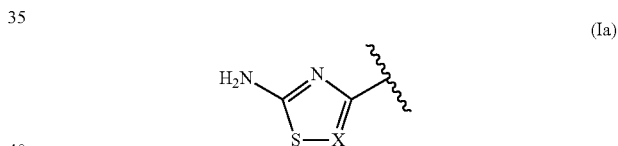

(Ia)

Object (1a) includes syn isomer (Z form) anti isomer (E form) and a mixture thereof.

Wherein X is N, C(H), C(F) or C(Cl);

B is defined as hydrogen, methyl, ethyl or represented by the formula (Ib)

(Ib)

Wherein, $R^1$ and $R^2$ is independently hydrogen or lower alkyl, or $R^1$ and $R^2$ together may form a 3 to 6-membered spiro ring system; and m is 0 or 1.

Furthermore, in the formula (Ib), $R^1$ and $R^2$ together may form a 3- to 6-membered spiro ring system;

Y is halogen, even more preferably chloro or iodo;

q is 0 or 1;

In the organic residue as designated by (IX), objects C, D, E and F have the same definitions as described before, thus C is selected from the following quaternized bicyclic aromatic heterocyclic rings represented by the formulae (Ic) to (Iz);

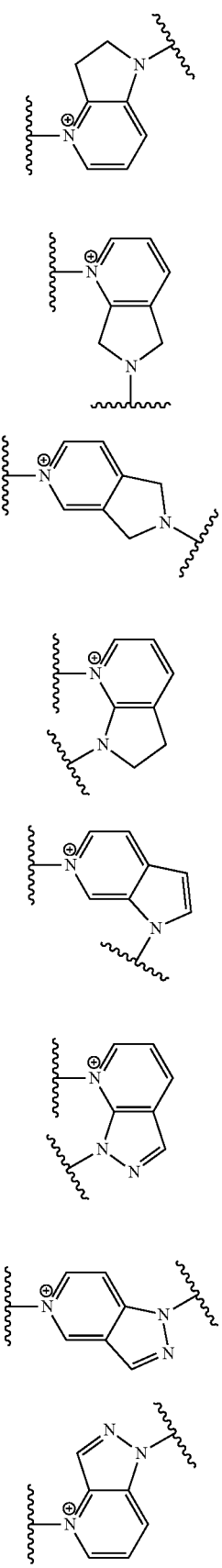
(Ic)
(Id)
(Ie)
(If)
(Ig)
(Ih)
(Ii)
(Ij)
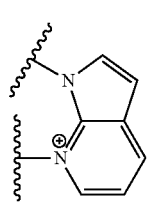
(Ik)
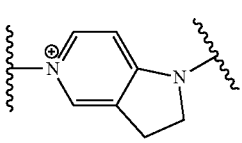
(Il)
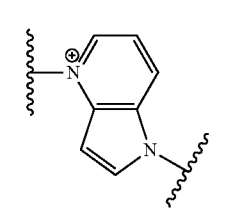
(Im)
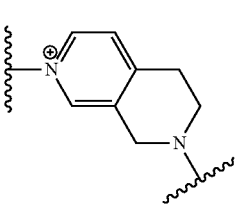
(In)
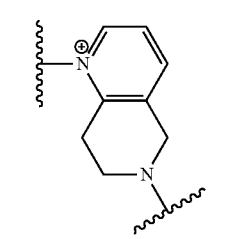
(Io)
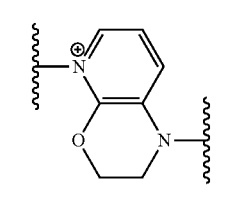
(Ip)
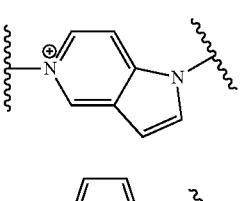
(Iq)
(Ir)
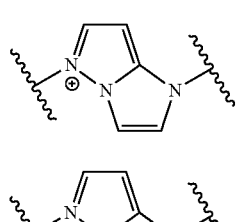
(Is)

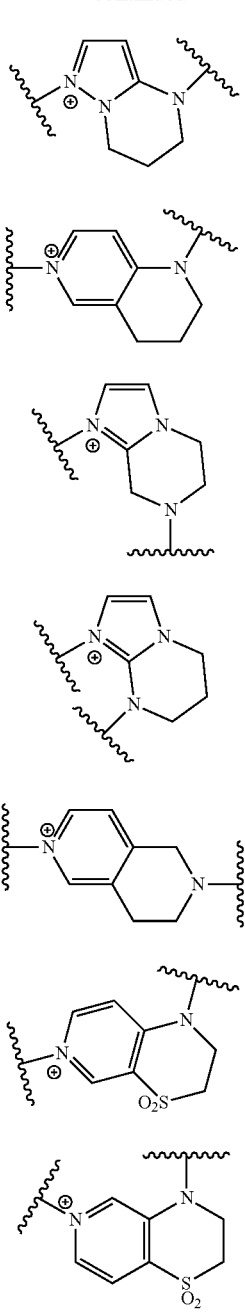

D represents CH$_2$, CH$_2$CH$_2$ or CH$_2$CO;

E is selected from aryl or a 5- to 6-membered aromatic heterocyclic ring as shown below;

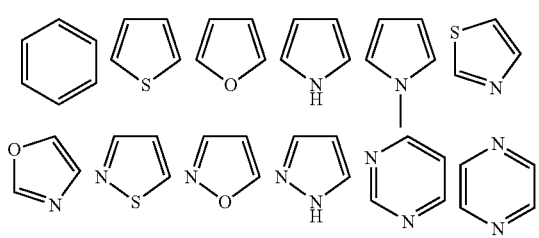

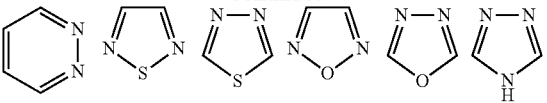

F is optionally substituted amidine or an optionally substituted guanidine; and

G is hydrogen, methyl, ethyl, C$_{3-6}$ alkyl, C$_{3-6}$ cycloalkyl or an optionally substituted 5- or 6-membered aliphatic or an optionally substituted 5- or 6-membered aromatic heterocyclic ring, in which the heterocyclic ring is substituted with at least 1-2 hetero atoms selected from N, O, and S (α or β).

In the formula (VIII), P$^1$ is a suitable carboxy protecting group frequently used in β-lactam chemistry. Suitable examples may be the ones such as lower alkyl ester (e.g., methyl, ethyl, propyl, isopropyl, butyl, isobutyl, t-butyl, pentyl, t-pentyl, hexyl, 1-cyclopropylethyl etc.); lower alkenyl ester (e.g., vinyl, allyl); lower alkynyl ester (e.g., ethynyl, propynyl); lower alkoxyalkyl ester (e.g., methoxymethyl, ethoxymethyl, isopropoxymethyl, 1-methoxyethyl, 1-ethoxyethyl etc.); lower alkylthioalkyl ester (e.g., methylthiomethyl, ethylthiomethyl, ethylthioethyl, isopropylthiomethyl); mono (or di or tri-) halo(lower) alkyl ester (e.g., 2-iodoethyl, 2,2,2-trichloroethyl etc.); lower alkanoyloxy(lower)alkyl ester (e.g., acetoxymethyl, propionyloxymethyl, butyryloxymethyl, valeryloxymethyl, pivaloyloxymethyl, hexanoyloxymethyl, 2-acetoxyethyl, 2-propionyloxyethyl etc.); lower alkanesulfonyl(lower)alkyl ester (e.g., mesylmethyl ester, 2-mesylethyl ester etc.); ar(lower)alkyl ester, for example, phenyl(lower)alkyl ester which may have one or more suitable substituent(s) (e.g., benzyl, 4-methoxybenzyl, 4-nitrobenzyl, phenethyl, trityl, benzhydryl, bis(methoxyphenyl)methyl, 3,4-dimethoxybenzyl, 4-hydroxy-3,5-di-t-butylbenzyl, etc.); aryl ester which may have one or more suitable substituent(s) such as substituted or unsubstituted phenyl ester (e.g., phenyl, tolyl, t-butyl phenyl, xylyl, mesityl, 4-chlorophenyl, 4-methoxyphenyl, etc.); tri(lower)alkyl silyl ester; lower alkylthioester (e.g., methylthioester, ethylthioester, etc.) and the like.

It is understood that in the formula (VIII), when an amino group is present in the molecule, it is to be protected with a suitable protecting group commonly used in the β-lactam chemistry such as benzyl, trityl, t-butoxycarbonyl or the like. Similarly, it is to be understood that in the formula (VIII), when a carboxyl group is present in the molecule, it is to be protected with a suitable protecting group selected from the group as described for P$^1$ above.

The following are provided for illustrative purposes only, and are not intended to be limiting of the present compositions and methods in any way.

EXAMPLES

In the examples the following abbreviations have been used.

Boc: N-tert-butoxycarbonyl
Br s: broad singlet
CDCl$_3$: deuterated chloroform
CD$_3$OD: deuterated methanol
CH$_3$NO$_2$: nitromethane
D$_2$O: deuterium oxide
d: doublet
DCM: dichloromethane
DMAP: 4-dimethylaminopyridine
DMF: N, N'-dimethylformamide DMSO-d$_6$: deuterated dimethylsulfoxide
ES: electron spray
g: gram(s)
h: hour(s)
HPLC: high-performance liquid chromatography
Hz: Hertz
J: coupling constant
m: multiplet
mmol: millimole(s)
MHz: megahertz
MS: mass spectrometry Example 1 (Table 1, Compound 1)

(6R,7R)-7-{[(2Z)-2-(2-Amino-1,3-thiazol-4-yl)-2-{[(2-carboxypropan-2-yl)oxy]imino}acetyl]-amino}-3-{[1-(4-carbamimidoylbenzyl)-1H-pyrrolo[3,2-c]pyridin-5-ium-5-yl]methyl}-8-oxo-5-thia-1-azabicyclo[4.2.0]oct-2-ene-2-carboxylate

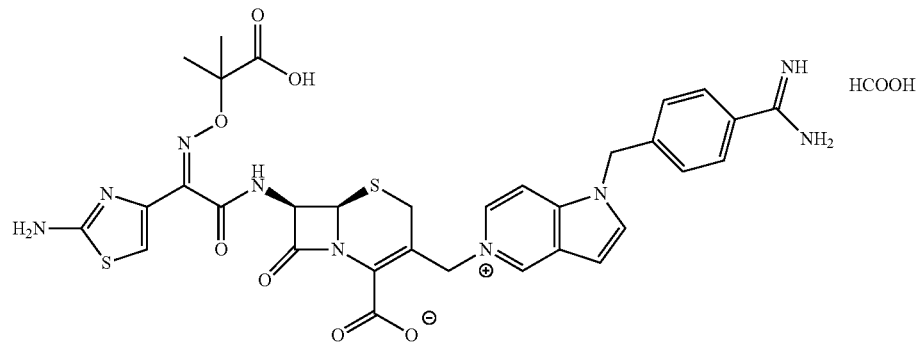 [SMILES: CC(C)(O/N=C(\C(=O)N[C@@H]1C(=O)N2C(C(=O)[O-])=C(C[n+]3ccc4c(ccn4Cc4ccc(C(=N)N)cc4)c3)CS[C@H]12)c1csc(N)n1)C(=O)O ; "HCOOH"]

Step 1: 4-(1H-Pyrrolo[3,2-c]pyridin-1-ylmethyl)benzonitrile

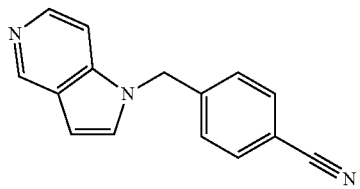

To a solution of 1H-pyrrolo[3,2-c]pyridine (1.0 g, 8.5 mmol) in DMF (40 mL) under nitrogen at 0° C. was added NaH (60% in mineral oil, 0.51 g, 12.8 mmol) in portions and after stirring for 15 min was added 4-(bromomethyl)benzonitrile (2.5 g, 12.8 mmol) in portions. The reaction mixture was stirred at 0° C. for 2 h then at room temperature for 1 h and quenched with saturated ammonium chloride solution then diluted with ethyl acetate (100 mL) and water (100 mL). The organic layer was separated, washed with brine (3×100 mL), dried (Na$_2$SO$_4$) and concentrated.

The crude product was purified by silica gel column chromatography using methylene chloride: ethyl acetate: methanol (5:3:2) to afford 4-(1H-pyrrolo[3,2-c]pyridin-1-ylmethyl)benzonitrile (1.2 g, 60%) as a solid.

$^1$H NMR (400 MHz, CDCl$_3$): δ 5.38 (s, 2H), 6.68 (d, 1H, J=3.2 Hz), 7.11-7.17 (m, 4H), 7.54 (d, 2H, J=8.0 Hz), 8.27 (d, 1H, J=5.6 Hz), 8.94 (s, 1H).

Step 2: Methyl 4-(1H-pyrrolo[3,2-c]pyridin-1-ylmethyl)benzenecarboximidate hydrochloride

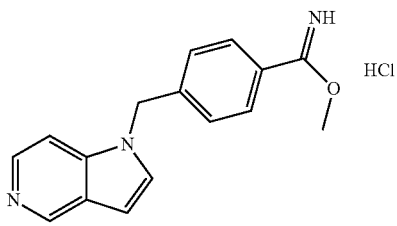 [SMILES: COC(=N)c1ccc(Cn2ccc3cnccc32)cc1 ; Cl]

Through a solution of 4-(1H-pyrrolo[3,2-c]pyridin-1-ylmethyl)benzonitrile (from step 1, 0.7 g, 3.0 mmol) in anhydrous methanol (25 mL) in a pressure vessel at 0° C. was bubbled a stream of anhydrous hydrogen chloride gas for 10 min. The reaction vessel was stoppered and stirred at room temperature for 18 h and the contents were transferred into a flask and evaporated under reduced pressure. The crude product was triturated with ether, then dried under vacuum to provide methyl 4-(1H-pyrrolo[3,2-c]pyridin-1-ylmethyl)benzenecarboximidate hydrochloride (0.85 g, 94%) as a solid.

$^1$H NMR (400 MHz, CD$_3$OD): δ 4.34 (s, 3H), 5.50 (s, 2H), 7.20 (s, 1H), 7.50 (d, 2H, J=8.0 Hz), 7.96-8.11 (m, 4H), 8.39 (d, 1H, J=6.8 Hz), 9.22 (s, 1H). One proton was not observed in CD$_3$OD.

Step 3: 4-(1H-Pyrrolo[3,2-c]pyridin-1-ylmethyl)benzenecarboximidamide

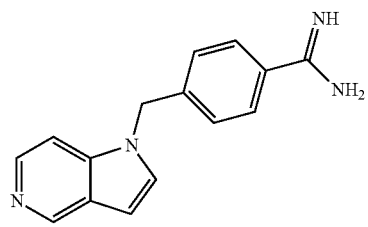 [SMILES: N=C(N)c1ccc(Cn2ccc3cnccc32)cc1]

A pressure vessel containing a suspension of methyl 4-(1H-pyrrolo[3,2-c]pyridin-1-ylmethyl)benzenecarboximidate hydrochloride (from step 2, 0.9 g, 2.85 mol) in methanol (25 mL) was saturated with ammonia gas and stoppered. The reaction mixture was stirred at room temperature for 24 h, then excess ammonia was vented out and the contents were concentrated under reduced pressure. The residue was triturated with hexanes and dried under vacuum to give 4-(1H-pyrrolo[3,2-c]pyridin-1-ylmethyl)benzenecarboximidamide (1.0 g) as a solid.

$^1$H NMR (400 MHz, CD$_3$OD): δ 5.76 (s, 2H), 7.05 (d, 1H, J=3.2 Hz), 7.45 (d, 2H, J=8.0 Hz), 7.79-7.89 (m, 4H), 8.30 (s, 1H), 9.08 (s, 1H). Three protons were not observed in CD$_3$OD.

Step 4: tert-Butyl {[4-(1H-pyrrolo[3,2-c]pyridin-ylmethyl)phenyl]carbonoimidoyl}carbamate

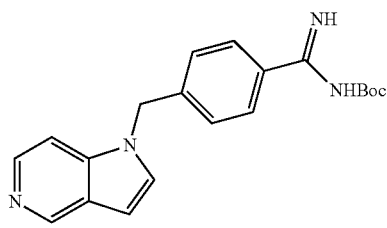 [SMILES: CC(C)(C)OC(=O)NC(=N)c1ccc(Cn2ccc3cnccc32)cc1]

A solution of 4-(1H-Pyrrolo[3,2-c]pyridin-1-ylmethyl)benzenecarboximidamide (from step 3, 0.25 g. 1.0 mmol) in 1,4-dioxane (30 mL) was treated with a saturated sodium carbonate solution (20 mL) followed by di-tert-butyl dicarbonate (1.1 g, 5.0 mmol) and stirred at room temperature for 40 h. The reaction mixture was concentrated under reduced pressure to remove the volatiles and the remaining solution was dissolved in ethyl acetate (60 mL), then washed with water (60 mL), brine solution (60 mL), dried and concentrated. The crude product was purified by silica gel column chromatography using ethyl acetate:methanol:ammonium hydroxide (60:39:1) as eluent to afford tert-butyl {[4-(1H-pyrrolo[3,2-c]pyridin-1-ylmethyl)phenyl]carbonoimidoyl}carbamate (0.12 g, 34%).

$^1$H NMR (400 MHz, CDCl$_3$): δ 1.54 (s, 9H), 5.36 (s, 2H), 6.60 (br s, 1H), 6.66 (d, 1H, J=3.6 Hz), 7.11-7.14 (m, 5H), 7.79 (d, 2H, J=8.4 Hz), 8.23 (d, 1H, J=6.0 Hz), 8.93 (s, 1H).

Step 5: 5-{[(6R,7R)-7-{[(2Z)-2-{2-[(tert-Butoxycarbonyl)amino]-1,3-thiazol-4-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl methyl}-1-{4-[N-(tert-butoxycarbonyl)carbamimidoyl]benzyl}-1H-pyrrolo[3,2-c]pyridin-5-ium iodide

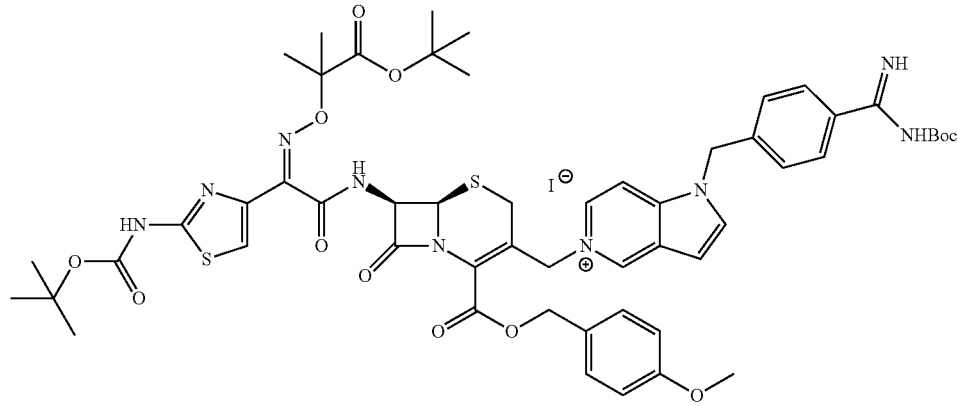 [SMILES: COc1ccc(COC(=O)C2=C(C[n+]3ccc4c(ccn4Cc4ccc(C(=N)NC(=O)OC(C)(C)C)cc4)c3)CS[C@@H]3[C@H](NC(=O)/C(=N\OC(C)(C)C(=O)OC(C)(C)C)c4csc(NC(=O)OC(C)(C)C)n4)C(=O)N23)cc1 ; [I-]]

To a solution of tert-butyl {[4-(1H-pyrrolo[3,2-c]pyridin-1-ylmethyl)phenyl]carbonoimidoyl}carbamate (from step 4, 0.07 g, 0.20 mmol) in dimethylacetamide (1.3 mL) was added 4-methoxybenzyl (6R,7R)-7-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-(chloromethyl)-8-oxo-5-thia-1-azabicyclo[4.2.0]oct-2-ene-2-carboxylate (0.156 g, 0.20 mmol) at 0° C. The reaction mixture was then degassed under reduced pressure for 0.5 h and was added sodium iodide (0.06 g, 0.40 mmol). After stirring at 15° C. for 16 h, the reaction mixture was slowly added to 5% aqueous sodium chloride and sodium thiosulfate solution cooled under ice. The suspension was then filtered, washed with water and the solid was vacuum dried to get a yellow solid (0.22 g) which was used in the next step without further purification.

Step 6: (6R,7R)-7-{[(2Z)-2-(2-Amino-1,3-thiazol-4-yl)-2-{[(2-carboxypropan-2-yl)oxy]imino}acetyl]amino}-3-{[1-(4-carbamimidoylbenzyl)-1H-pyrrolo[3,2-c]pyridin-5-ium-5-yl]methyl}-8-oxo-5-thia-1-azabicyclo[4.2.0]oct-2-ene-2-carboxylate

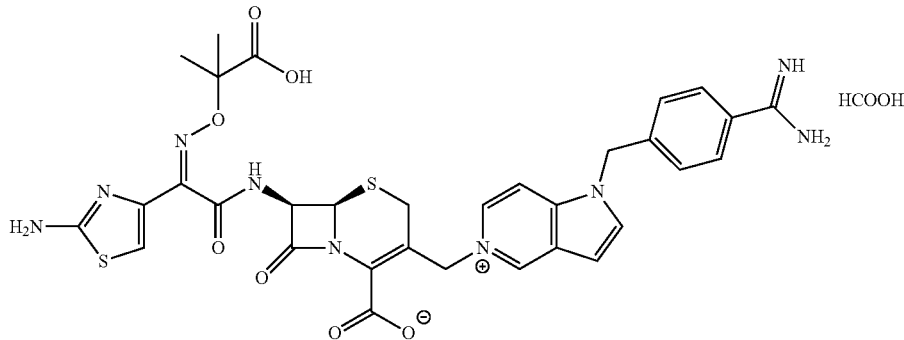 [SMILES: CC(C)(O/N=C(\C(=O)N[C@@H]1C(=O)N2C(C(=O)[O-])=C(C[n+]3ccc4c(ccn4Cc4ccc(C(=N)N)cc4)c3)CS[C@H]12)c1csc(N)n1)C(=O)O ; "HCOOH"]

To a solution of 5-{[(6R,7R)-7-{[(2Z)-2-{5-[(tert-butoxycarbonyl)amino]-1,2,4-thiadiazol-3-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]benzyl}-1H-pyrrolo[3,2-c]pyridin-5-ium iodide (from step 5, 0.22 g) in dry dichloromethane (4.5 mL) at −40° C. was added anisole (0.36 mL, 3.34 mmol) followed by 2M AlCl₃ in CH₃NO₂ (1.7 mL, 3.52 mmol). The liquid was stirred at 0° C. for 30 min. To the reaction mixture were added di-isopropyl ether (5 mL) and water (0.5 mL), and the resultant mixture was stirred to generate a precipitate. The supernatant was removed by decantation. To the insoluble matter adhering to the vessel were added dilute aqueous hydrochloric acid solution (2 mL) and acetonitrile (5 mL) and was stirred to dissolve the matter completely. Thereto was added HP20 resin (0.5 g), stirred for 30 min. and then filtered. The filtrate was concentrated and freeze-dried to give a crude product, which was purified by HPLC to obtain (6R,7R)-7-{[(2Z)-2-(5-amino-1,2,4-thiadiazol-3-yl)-2-{[(2-carboxypropan-2-yl)oxy]imino}acetyl]amino}-3-{[1-(4-carbamimidoylbenzyl)-1H-pyrrolo[3,2-c]pyridin-5-ium-5-yl]methyl}-8-oxo-5-thia-1-azabicyclo[4.2.0]oct-2-ene-2-carboxylate as formic acid salt (0.02 g, 15.5%).

¹H NMR (D₂O): δ 1.25 (s, 6H), 2.94 (d, 1H, J=17.6 Hz), 3.38 (d, 1H, J=18.0 Hz), 5.08-5.13 (m, 2H), 5.33 (d, 1H, J=14.4 Hz), 5.53 (s, 2H), 5.63 (d, 1H, J=4.8 Hz), 6.76 (s, 1H), 6.94 (s, 1H), 7.22 (d, 2H, J=7.2 Hz), 7.55 (d, 2H, J=7.6 Hz), 7.68 (m, 2H), 8.23 (d, 1H, J=7.2 Hz), 9.06 (s, 1H). Seven protons were not observed in D₂O.

Example 2 (Table 1, Compound 9)

(6R,7R)-7-{[(2Z)-2-(2-Amino-1,3-thiazol-4-yl)-2-{[(2-carboxypropan-2-yl)oxy]imino}acetyl]amino}-3-{[1-(4-carbamimidoylbenzyl)-2,3-dihydro-1H-imidazo[1,2-b]pyrazol-5-ium-5-yl]methyl}-8-oxo-5-thia-1-azabicyclo[4.2.0]oct-2-ene-2-carboxylate

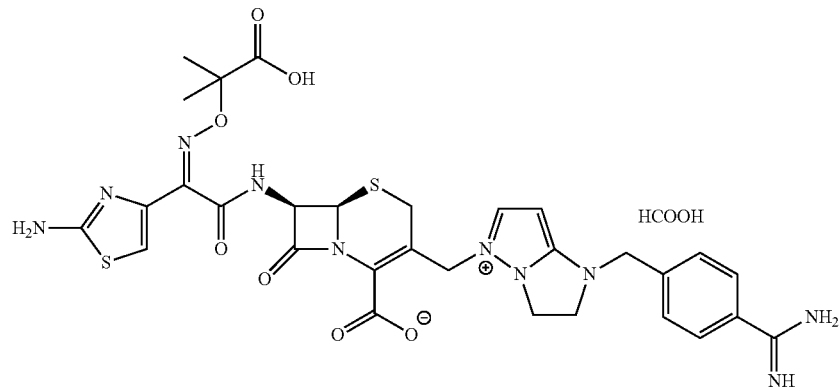 [SMILES: CC(C)(O/N=C(\C(=O)N[C@@H]1C(=O)N2C(C(=O)[O-])=C(C[n+]3ccc4n3CCN4Cc3ccc(C(=N)N)cc3)CS[C@H]12)c1csc(N)n1)C(=O)O ; "HCOOH"]

Step 1: 4-((2,3-Dihydro-1H-imidazo[1,2-b]pyrazol-1-yl)methyl)benzonitrile

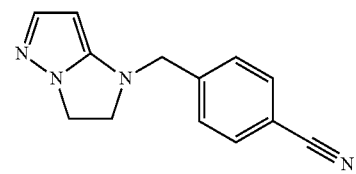

To a solution of 2,3-dihydro-1H-imidazo[1,2-b]pyrazole (1.399 g, 12.84) in dimethyl formamide (10 mL) was added 4-(bromomethyl)benzonitrile (2.86 g, 12.84 mmol) followed by potassium carbonate (2.66 g, 19.26 mmol) and the reaction mixture was stirred under nitrogen 20 h, then diluted with ethyl acetate (100 mL) and water (100 mL). The organic layer was separated, washed with water (3×100 mL) followed by brine solution (200 mL), dried over $Na_2SO_4$ and concentrated under reduced pressure. Purification of the crude product by silica gel column chromatography using ethyl acetate as eluent gave 4-((2,3-dihydro-1H-imidazo[1,2-b]pyrazol-1-yl)methyl)benzonitrile (2.1 g, 72.9%) as a solid.

$^1$H NMR (400 MHz, DMSO-$d_6$): δ 3.66 (t, 2H), 4.07 (t, 2H), 4.31 (s, 2H), 5.22 (d, 2H, J=2.0 Hz), 7.19 (d, 1H, J=1.5 Hz), 7.58 (d, 2H, J=8.2 Hz), 7.85 (d, 2H, J=8.2 Hz)

Step 2: Ethyl 4-(2,3-dihydro-1H-imidazo[1,2-b]pyrazol-1-ylmethyl)benzenecarboximidate hydrochloride

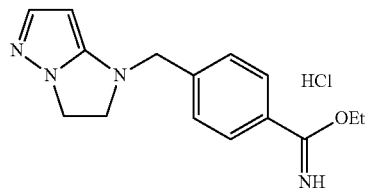 [SMILES: CCOC(=N)c1ccc(CN2CCn3nccc32)cc1 ; Cl]

Through a solution of 4-((2,3-dihydro-1H-imidazo[1,2-b]pyrazol-1-yl)methyl)benzonitrile (from step 1, 1.5 g, 6.69 mmol) in anhydrous methanol in a pressure vessel at 0° C. was bubbled a stream of anhydrous hydrogen chloride gas for 15 min. The reaction vessel was stoppered and stirred at room temperature for 20 h, the contents were transferred to a flask and evaporated in vacuo. The crude product was triturated with ether and dried under vacuum to get ethyl 4-(2,3-dihydro-1H-imidazo[1,2-b]pyrazol-1-ylmethyl)benzenecarboximidate hydrochloride (1.8 g, 87.8%) as a solid.

$^1$H NMR (400 MHz, DMSO-$d_6$): δ 1.49 (t, 3H), 3.77 (dd, 2H, J=4.2 Hz), 4.17 (t, 2H), 4.43 (dd, 2H, 10.0 Hz), 4.63 (q, 2H, J=7.1 Hz), 5.51 (d, 1H, J=2.3 Hz), 6.00 (br s, 2H), 7.63 (d, 2H, J=8.0 Hz), 8.14 (d, 2H, J=8.0 Hz), 12.20 (br s, 2H).

Step 3: 4-(2,3-Dihydro-1H-imidazo[1,2-b]pyrazol-1-ylmethyl)benzenecarboximidamide

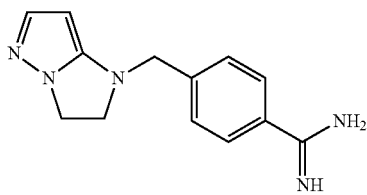 [SMILES: N=C(N)c1ccc(CN2CCn3nccc32)cc1]

A pressure vessel containing a suspension of ethyl 4-(2,3-dihydro-1H-imidazo[1,2-b]pyrazol-1-ylmethyl)benzenecarboximidate hydrochloride (from step 2, 1.8 g, 5.87 mol) in methanol (25 mL) was saturated with ammonia gas and stoppered. The reaction mixture was stirred at room temperature for 24 h, then the excess ammonia was vented out and the contents were concentrated under reduced pressure. The residue was triturated with hexanes and dried under vacuum to give 4-(2,3-dihydro-1H-imidazo[1,2-b]pyrazol-1-ylmethyl)benzenecarboximidamide (0.95 g, 66.9%) as a solid.

$^1$H NMR (400 MHz, DMSO-$d_6$): δ 3.66 (t, 2H), 4.06 (t, 2H), 4.31 (t, 2H), 5.22 (d, 1H, J=2.0 Hz), 7.17 (d, 1H, J=1.6 Hz), 7.71 (d, 2H, J=8.2 Hz), 7.83 (d, 2H, J=8.2 Hz)

Mass: ES$^+$ 242.10

Step 4: tert-Butyl {[4-(2,3-dihydro-1H-imidazo[1,2-b]pyrazol-1-ylmethyl)phenyl]carbonoimidoyl}carbamate

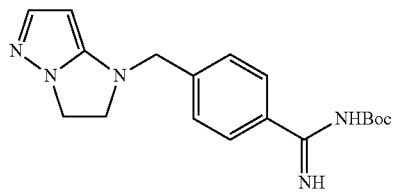 [SMILES: CC(C)(C)OC(=O)NC(=N)c1ccc(CN2CCn3nccc32)cc1]

To a suspension of 4-(2,3-dihydro-1H-imidazo[1,2-b]pyrazol-1-ylmethyl)benzenecarboximidamide (from step 3, 0.95 g, 3.94 mmol) in a mixture of sodium bicarbonate (1.60 g, 19.7 mmol), 1,4-dioxane (25 mL) and water (10 mL) was added di-tert-butyl dicarbonate (2.74 g, 12.54 mmol) and stirred at room temperature for 24 h. The reaction mixture was concentrated under reduced pressure to remove the volatiles and the remaining solution was dissolved in ethyl acetate (80 mL), washed with water (80 mL), brine solution (80 mL), dried and concentrated. The crude product was purified by silica gel column chromatography using ethyl acetate as eluent to afford tert-butyl {[4-(2,3-dihydro-1H-imidazo[1,2-b]pyrazol-1-ylmethyl)phenyl]carbonoimidoyl}carbamate (0.45 g, 33.5%).

$^1$H NMR (400 MHz, DMSO-$d_6$): δ 1.42 (s, 9H), 3.63 (t, 2H), 4.24 (t, 2H), 5.18 (d, 1H, J=2.0 Hz), 7.16 (d, 1H, J=2.0 Hz), 7.45 (d, 2H, J=8.0 Hz), 7.92 (d, 2H, J=8.0 Hz).

Step 5: 5-{[(6R,7R)-7-{[(2Z)-2-{2-[(tert-Butoxycarbonyl)amino]-1,3-thiazol-4-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]benzyl}-2,3-dihydro-1H-imidazo[1,2-b]pyrazol-5-ium iodide

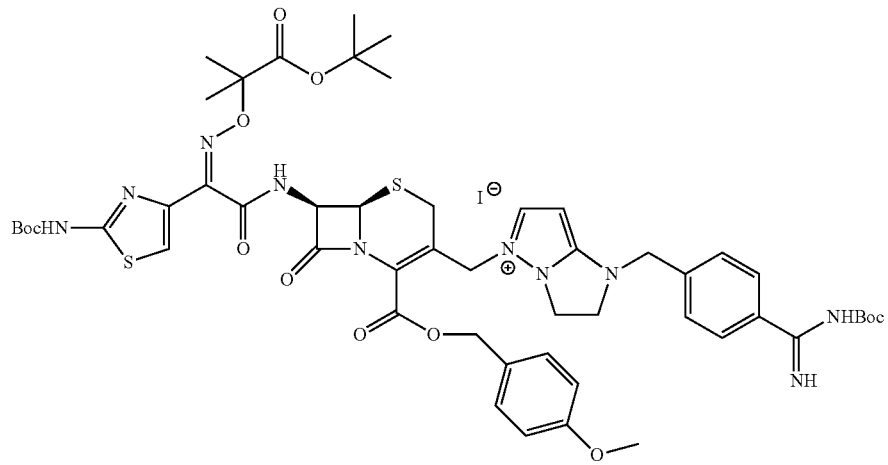 [SMILES: COc1ccc(COC(=O)C2=C(C[n+]3ccc4n3CCN4Cc3ccc(C(=N)NC(=O)OC(C)(C)C)cc3)CS[C@@H]3[C@H](NC(=O)/C(=N\OC(C)(C)C(=O)OC(C)(C)C)c4csc(NC(=O)OC(C)(C)C)n4)C(=O)N23)cc1 ; [I-]]

To a solution of 4-methoxybenzyl (6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(chloromethyl)-8-oxo-5-thia-1-azabicyclo[4.2.0]oct-2-ene-2-carboxylate (0.35 g, 0.449 mmol) in dimethylformamide (8 mL) at room temperature was added potassium iodide (0.149 g, 0.898 mmol) and after stirring for 10 min was added tert-butyl {[4-(2,3-dihydro-1H-imidazo[1,2-b]pyrazol-1-ylmethyl)phenyl]carbonoimidoyl}carbamate (from step 4, 153 mg, 0.449 mmol). The reaction mixture was then stirred under nitrogen at room temperature for 16 h and diluted with a 1:1 mixture of sodium thiosulfate and brine (15 mL) solution. The suspension was then filtered, washed with water and the solid was vacuum dried to get a yellow solid (0.448 g), which was used in the next step without further purification.

Step 6: (6R,7R)-7-{[(2Z)-2-(2-Amino-1,3-thiazol-4-yl)-2-{[(2-carboxypropan-2-yl)oxy]imino}acetyl]amino}-3-{[1-(4-carbamimidoylbenzyl)-2,3-dihydro-1H-imidazo[1,2-b]pyrazol-5-ium-5-yl]methyl}-8-oxo-5-thia-1-azabicyclo[4.2.0]oct-2-ene-2-carboxylate

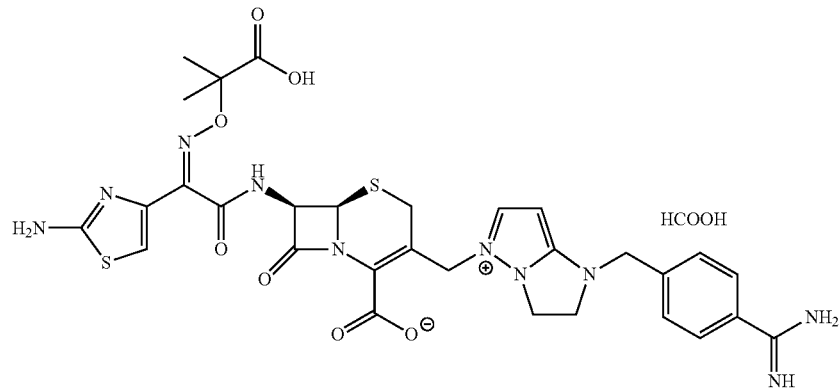 [SMILES: CC(C)(O/N=C(\C(=O)N[C@@H]1C(=O)N2C(C(=O)[O-])=C(C[n+]3ccc4n3CCN4Cc3ccc(C(=N)N)cc3)CS[C@H]12)c1csc(N)n1)C(=O)O ; "HCOOH"]

To a solution of 5-{[(6R,7R)-7-{[(2Z)-2-{2-[(tert-butoxy-carbonyl)amino]-1,3-thiazol-4-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]benzyl}-2,3-dihydro-1H-imidazo[1,2-b]pyrazol-5-ium iodide (from step 5, 0.45 g) in dry dichloromethane (15 mL) under nitrogen at room temperature was added anisole (0.8 mL) followed by trifluoroacetic acid (3 mL) in one portion and stirred for 3 h. The reaction mixture was concentrated under reduced pressure and the residue was suspended in distilled water (20 mL), stirred for 20 min and filtered. The filtrate was lyophilized and the product was purified by HPLC to obtain (6R,7R)-7-{[(2Z)-2-(2-amino-1,3-thiazol-4-yl)-2-{[(2-carboxypropan-2-yl)oxy]imino}acetyl]amino}-3-{[1-(4-carbamimidoylbenzyl)-2,3-dihydro-1H-imidazo[1,2-b]pyrazol-5-ium-5-yl]methyl}-8-oxo-5-thia-1-azabicyclo[4.2.0]oct-2-ene-2-carboxylate as a formic acid salt (0.022 g, 8.4%).

$^1$H NMR (400 MHz, D$_2$O): δ 1.33 (s, 6H), 3.08 (d, 1H, J=18.0 Hz), 3.31 (d, 1H, J=18.0 Hz), 3.86 (t, 2H), 4.12 (q, 1H, J=8.6 Hz), 4.22 (q, 1H, J=8.2 Hz), 4.44 (q, 2H, J=3.5 Hz), 4.85 (dd, 2H, J=15.6 and 19.7 Hz), 5.07 (d, 1H), 5.64 (d, 1H), 5.66 (d, 1H), 6.87 (s, 1H), 7.42 (d, 2H), 7.63 (d, 2H), 7.81 (1H, d), 8.17 (1H, s).

Mass: ES$^+$ 709.19

Example 3 (Table 1, Compound 2)

(6R,7R)-7-{[(2Z)-2-(2-Amino-1,3-thiazol-4-yl)-2-{[(2-carboxypropan-2-yl)oxy]imino}acetyl]-amino}-8-oxo-3-{[1-(4-{N-[(3R)-piperidin-3-yl]carbamimidoyl}benzyl)-1H-pyrazol[4,3-c]pyridin-5-ium-5-yl]methyl}-5-thia-1-azabicyclo[4.2.0]oct-2-ene-2-carboxylate

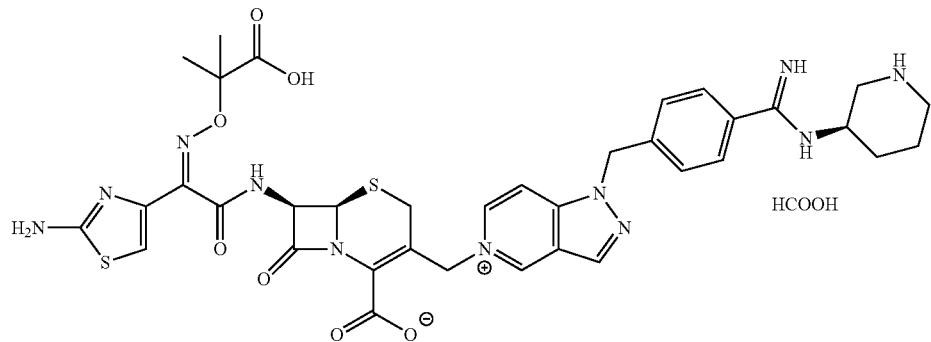 [SMILES: CC(C)(O/N=C(\C(=O)N[C@@H]1C(=O)N2C(C(=O)[O-])=C(C[n+]3ccc4c(cnn4Cc4ccc(C(=N)N[C@@H]5CCCNC5)cc4)c3)CS[C@H]12)c1csc(N)n1)C(=O)O ; "HCOOH"]

Step 1: 4-(1H-Pyrazolo[4,3-c]pyridin-1-ylmethyl)benzonitrile

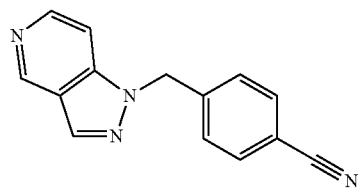 [SMILES: N#Cc1ccc(Cn2ncc3cnccc32)cc1]

A mixture of 1H-pyrazolo[4,3-c]pyridine (0.72 g, 6.04 mmol), 4-(bromomethyl)benzonitrile (1.57 g, 8.01 mmol) and potassium carbonate (1.67 g, 12.08 mmol) in DMF (75 mL) was stirred at 60° C. for 24 h and concentrated. The residue was partitioned between ethyl acetate (100 mL) and water (100 mL). The organic layer was separated, washed with brine (3×100 mL), dried (Na$_2$SO$_4$) and concentrated. The crude product was purified by silica gel column chromatography using ethyl acetate: methanol (9:1) as eluent to afford 4-(1H-pyrazolo[4,3-c]pyridin-1-ylmethyl)benzonitrile (0.42 g, 30.5%) as a solid.

$^1$H NMR (400 MHz, CDCl$_3$): δ 5.66 (s, 2H), 7.24-7.28 (m, 3H), 7.61 (d, 2H, J=8.4 Hz), 8.23 (s, 1H), 8.43 (d, 1H, J=6.4 Hz), 9.15 (s, 1H).

Step 2: Ethyl 4-(1H-pyrazolo[4,3-c]pyridin-1-ylmethyl)benzenecarboximidate hydrochloride

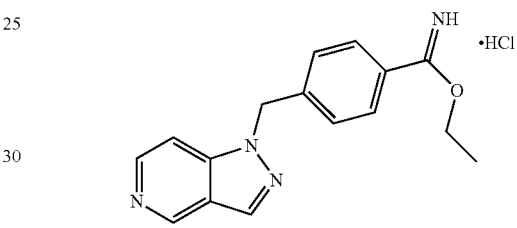

Through a solution of 4-(1H-pyrazolo[4,3-c]pyridin-1-ylmethyl)benzonitrile (from step 1, 0.7 g, 3.0 mmol) in anhydrous ethanol (30 mL) in a pressure vessel at 0° C. was bubbled a stream of anhydrous hydrogen chloride gas for 10 min. The reaction vessel was stoppered, then stirred at room temperature for 18 h and the contents were transferred into a flask and evaporated under reduced pressure. The crude product was triturated with ether and dried under vacuum to provide ethyl 4-(1H-pyrazolo[4,3-c]pyridin-1-ylmethyl)benzenecarboximidate hydrochloride (0.8 g, 84%) as a solid.

$^1$H NMR (400 MHz, CD$_3$OD): δ 1.59 (t, 3H, J=6.6 Hz), 4.63 (q, 2H, J=6.2 Hz), 6.03 (s, 2H), 7.60 (d, 2H, J=6.8 Hz), 8.04 (d, 2H, J=7.2 Hz), 8.37 (s, 1H), 8.58 (s, 1H), 8.84 (s, 1H), 9.59 (s, 1H). One proton was not observed in CD$_3$OD.

Step 3: tert-Butyl (3R)-3-({[4-(1H-pyrazolo[4,3-c]pyridin-1-ylmethyl)phenyl]carbonoimidoyl}amino)piperidine-1-carboxylate

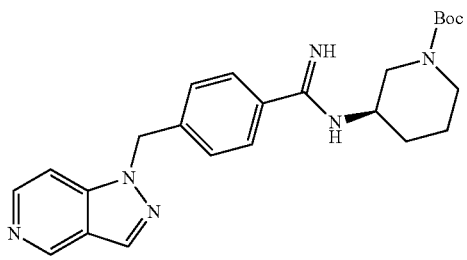 [SMILES: CC(C)(C)OC(=O)N1CCC[C@@H](NC(=N)c2ccc(Cn3ncc4cnccc43)cc2)C1]

To a solution of ethyl 4-(1H-pyrazolo[4,3-c]pyridin-1-ylmethyl)benzenecarboximidate hydrochloride (from step 2, 0.57 g, 1.8 mmol) and triethylamine (0.56 mL, 4.0 mmol) in methanol (5 mL) was added tert-butyl (3R)-3-aminopiperidine-1-carboxylate (0.36 g, 1.8 mmol) in methanol (1 mL) at 0° C. The reaction mixture was stirred at room temperature for 2 days and concentrated. The residue was purified by column chromatography using methanol: ethyl acetate (1:4) as eluent to give tert-butyl (3R)-3-({[4-(1H-pyrazolo[4,3-c]pyridin-1 ylmethyl)phenyl]carbonoimidoyl}amino)piperidine-1-carboxylate (0.5 g, 64%) as a solid.

$^1$H NMR (400 MHz, CDCl$_3$): δ 1.28 (s, 9H), 1.57-1.80 (m, 3H), 2.12 (s, 1H), 3.08-3.30 (m, 2H), 3.36-4.10 (m, 3H), 5.83 (s, 2H), 7.45 (d, 2H, J=8.8 Hz), 7.67-7.69 (m, 3H), 8.33 (d, 1H, J=6.0 Hz), 8.37 (s, 1H), 9.10 (s, 1H). Two protons were not observed in CD$_3$OD.

Step 4: tert-Butyl (3R)-3-[(tert-butoxycarbonyl){[4-(1H-pyrazolo[4,3-c]pyridin-1-ylmethyl)phenyl]carbonoimidoyl}amino]piperidine-1-carboxylate

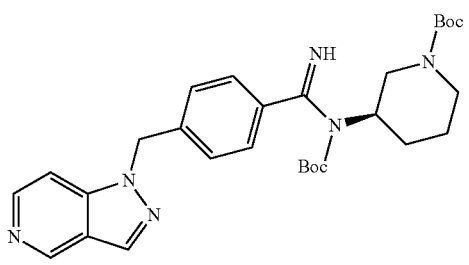 [SMILES: CC(C)(C)OC(=O)N1CCC[C@@H](N(C(=N)c2ccc(Cn3ncc4cnccc43)cc2)C(=O)OC(C)(C)C)C1]

A solution of tert-butyl (3R)-3-({[4-(1H-pyrazolo[4,3-c]pyridin-1 ylmethyl)phenyl]carbonoimidoyl}amino)piperidine-1-carboxylate (from step 3, 0.5 g. 1.15 mmol) in 1,4-dioxane (20 mL) was treated with a saturated sodium carbonate solution (10 mL) followed by di-tert-butyl dicarbonate (1.26 g, 5.78 mmol), then stirred at room temperature for 40 h. The reaction mixture was concentrated under reduced pressure to remove the volatiles and the remaining solution was dissolved in ethyl acetate (100 mL) and washed with water (100 mL), brine solution (100 mL), dried, and concentrated. The crude product was purified by silica gel column chromatography using ethyl acetate: methanol: ammonium hydroxide (60:39:1) as eluent to afford tert-butyl (3R)-3-[(tert-butoxycarbonyl){[4-(1H-pyrazolo[4,3-c]pyridin-1-ylmethyl)phenyl]carbonoimidoyl}amino]piperidine-1-carboxylate (0.48 g, 78%).

$^1$H NMR (400 MHz, CDCl$_3$): δ 1.24-2.05 (m, 22H), 3.05-3.71 (m, 4H), 4.09-4.10 (m, 1H), 5.08 (br s, 1H), 5.62 (s, 2H), 7.22-7.28 (m, 3H), 7.39 (d, 2H, J=8.4 Hz), 8.19 (s, 1H), 8.38 (d, 1H, J=6.0 Hz), 9.12 (s, 1H).

Step 5: 5-{[(6R,7R)-7-{[(2Z)-2-{2-[(tert-Butoxycarbonyl)amino]-1,3-thiazol-4-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-(4-{N-(tert-butoxycarbonyl)-N-[(3R)-1-(tert-butoxycarbonyl)piperidin-3-yl]carbamimidoyl}benzyl)-1H-pyrazolo[4,3-c]pyridin-5-ium iodide

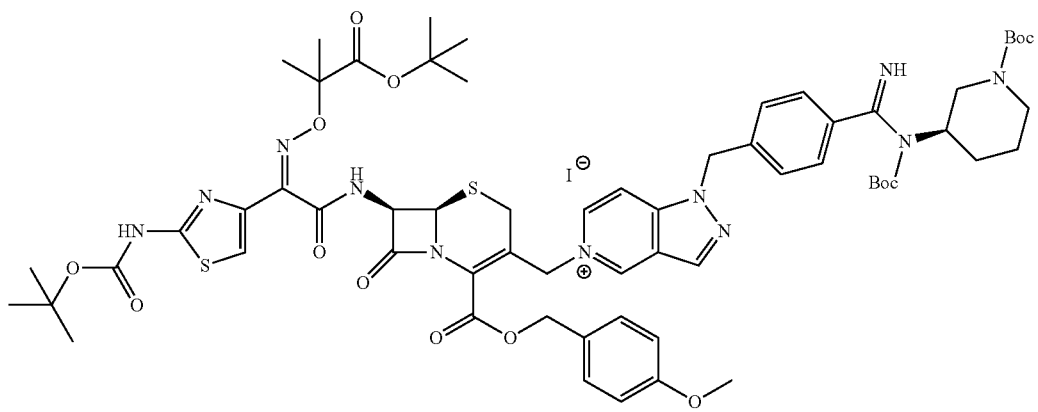 [SMILES: COc1ccc(COC(=O)C2=C(C[n+]3ccc4c(cnn4Cc4ccc(C(=N)N(C(=O)OC(C)(C)C)[C@@H]5CCCN(C(=O)OC(C)(C)C)C5)cc4)c3)CS[C@@H]3[C@H](NC(=O)/C(=N\OC(C)(C)C(=O)OC(C)(C)C)c4csc(NC(=O)OC(C)(C)C)n4)C(=O)N23)cc1 ; [I-]]

To a solution of tert-butyl (3R)-3-[(tert-butoxycarbonyl){[4-(1H-pyrazolo[4,3-c]pyridin-1-ylmethyl)phenyl]carbonoimidoyl}amino]piperidine-1-carboxylate (from step 4, 0.16 g, 0.30 mmol) in dimethylacetamide (2 mL) was added 4-methoxybenzyl (6R,7R)-7-{[(2Z)-2-{5-[(tert-butoxycarbonyl)amino]-1,2,4-thiadiazol-3-yl}-2-{[(1-tert-butoxy-2-methyl-1-oxopropan-2-yl)oxy]imino}acetyl]amino}-3-(chloromethyl)-8-oxo-5-thia-1-azabicyclo[4.2.0]oct-2-ene-2-carboxylate (0.23 g, 0.30 mmol) at 0° C. The reaction mixture was then degassed under reduced pressure for 0.5 h, and thereto was added sodium iodide (0.09 g, 0.60 mmol). After stirring at 15° C. for 16 h, the reaction mixture was slowly added to 5% aqueous sodium chloride and sodium thiosulfate solution cooled under ice. The suspension was then filtered, washed with water and the solid was vacuum dried to get a yellow solid (0.33 g) which was used in the next step without further purification.

Step 6: (6R,7R)-7-{[(2Z)-2-(2-Amino-1,3-thiazol-4-yl)-2-{[(2-carboxypropan-2-yl)oxy]imino}acetyl]amino}-8-oxo-3-{[1-(4-{N-[(3R)-piperidin-3-yl]carbamimidoyl}benzyl)-1H-pyrazolo[4,3-c]pyridin-5-ium-5-yl]methyl}-5-thia-1-azabicyclo[4.2.1]oct-2-ene-2-carboxylate reaction mixture were added di-isopropyl ether (10 mL) and water (0.8 mL), and the resultant was stirred to generate a precipitate. The supernatant was removed by decantation. To the insoluble matter adhering to the vessel were added dilute aqueous hydrochloric acid solution (4 mL) and acetonitrile (15 mL). The resultant was stirred to dissolve the matter completely. Thereto was added HP20 resin (0.8 g), and stirred for 30 min, and then filtered. The filtrate was concentrated and freeze-dried to give a crude product which was purified by HPLC to obtain (6R,7R)-7-{[(2Z)-2-(2-amino-1,3-thiazol-4-yl)-2-{[(2-carboxypropan-2-yl)oxy]imino}acetyl]amino}-8-oxo-3-{[1-(4-{N-[(3R)-piperidin-3-yl]carbamimidoyl}benzyl)-1H-pyrazolo[4,3-c]pyridin-5-ium-5-yl]methyl}-5-thia-1-azabicyclo[4.2.0]oct-2-ene-2-carboxylate as a formic acid salt (0.025 g, 12.5%).

$^1$H NMR (400 MHz, D$_2$O): δ 1.17 (s, 6H), 1.58-1.70 (m, 2H), 1.88-1.92 (m, 1H), 2.08-2.09 (m, 1H), 2.85-2.98 (m, 3H), 3.20 (d, 1H, J=12.0 Hz), 3.45-3.49 (m, 2H), 3.96 (m, 1H), 5.08-5.11 (m, 2H), 5.43 (d, 1H, J=14.8 Hz), 5.58 (d, 1H, J=4.4 Hz), 5.72 (s, 2H), 6.65 (s, 1H), 7.26 (d, 2H, J=8.0 Hz), 7.50 (d, 2H, J=7.2 Hz), 7.90 (d, 1H, J=6.8 Hz), 8.50 (d, 1H, J=7.2 Hz), 8.58 (s, 1H), 9.49 (s, 1H). Seven protons were not observed in D$_2$O.

Mass: ES$^+$ 802.20

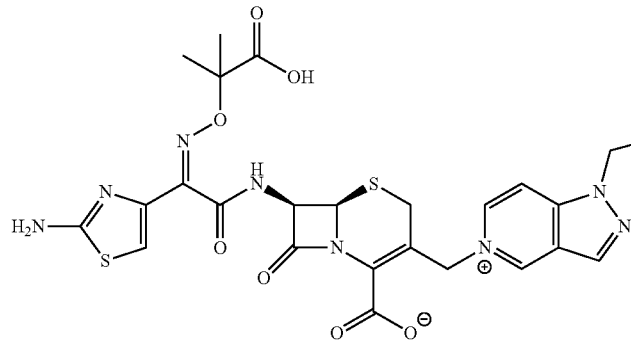 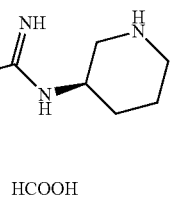

To a solution of 5-{[(6R,7R)-7-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-(4-{N-(tert-butoxycarbonyl)-N-[(3R)-1-(tert-butoxycarbonyl)piperidin-3-yl]carbamimidoyl}benzyl)-1H-pyrazolo[4,3-c]pyridin-5-ium iodide (from step 5, 0.33 g) in dry dichloromethane (6 mL) at −40° C. was added anisole (0.50 mL, 4.64 mmol) and then 2M aluminium chloride in nitromethane (2.33 mL, 4.66 mmol). The liquid was stirred at 0° C. for 30 min. To the Example 4 (Table 1, Compound 5)

(6R,7R)-7-{[(2Z)-2-(2-Amino-1,3-thiazol-4-yl)-2-{[(2-carboxypropan-2-yl)oxy]imino}acetyl]amino}-3-{[1-(4-carbamimidoylbenzyl)-1H-imidazo[1,2-b]pyrazol-5-ium-5-yl]methyl}-8-oxo-5-thia-1-azabicyclo[4.2.0]oct-2-ene-2-carboxylate

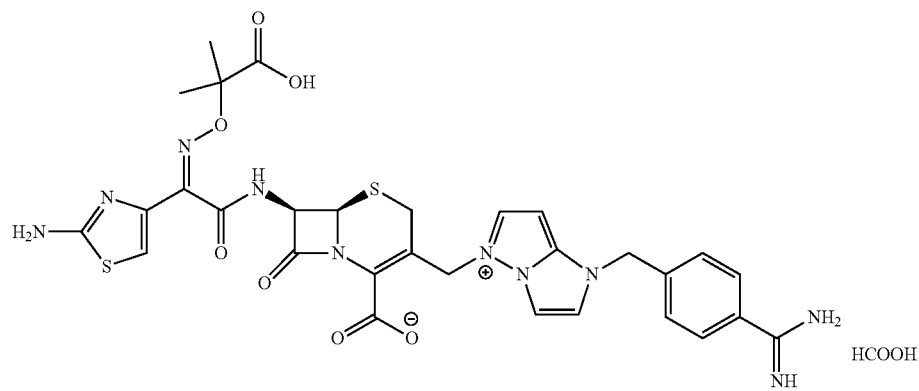 [SMILES: CC(C)(O/N=C(\C(=O)N[C@@H]1C(=O)N2C(C(=O)[O-])=C(C[n+]3ccc4n(Cc5ccc(C(=N)N)cc5)ccn43)CS[C@H]12)c1csc(N)n1)C(=O)O ; "HCOOH"]

Step 1: 4-(1H-Imidazo[1,2-b]pyrazol-1-ylmethyl) benzonitrile

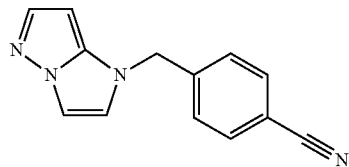 [SMILES: N#Cc1ccc(Cn2ccn3nccc23)cc1]

To a solution of 1H-imidazo[1,2-b]pyrazole (2.158 g, 20.146 mmol) in DMF (30 mL) under nitrogen at 0° C. was added sodium hydride (60.9% in mineral oil, 1.19 g, 30.22 mmol) in portions and after stirring for 15 min was added 4-(bromomethyl)benzonitrile (3.95 g, 20.146 mmol) in portions. The reaction mixture was stirred at 0° C. for 2 h then at room temperature for 1 h and quenched with saturated ammonium chloride solution, then diluted with ethyl acetate (200 mL) and water (200 mL). The organic layer was separated, washed with water (3×200 mL), brine solution, dried (Na$_2$SO$_4$) and concentrated. The crude product was purified by silica gel column chromatography using ethyl acetate to afford 4-(1H-imidazo[1,2-b]pyrazol-1-ylmethyl) benzonitrile (2.2 g, 49%) as a solid.

$^1$H NMR (400 MHz, DMSO-d$_6$): δ 5.25 (s, 2H), 5.62 (d, 1H, J=2.7 Hz), 7.34-7.35 (m, 1H), 7.44-7.47 (m, 3H), 7.59-7.60 (m, 1H), 7.84 (d, 2H, J=8.2 Hz).

Step 2: Ethyl 4-(1H-imidazo[1,2-b]pyrazol-1-ylmethyl)benzenecarboximidate hydrochloride

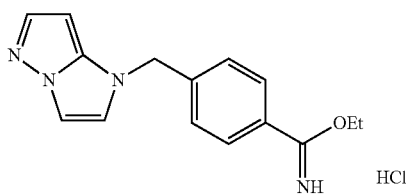 [SMILES: CCOC(=N)c1ccc(Cn2ccn3nccc23)cc1 ; Cl]

Through a solution of 4-(1H-imidazo[1,2-b]pyrazol-1-ylmethyl)benzonitrile (from step 1, 1.2 g, 5.4 mmol) in anhydrous ethanol (25 mL) in a pressure vessel at 0° C. was bubbled a stream of anhydrous hydrogen chloride gas for 15 min. The reaction vessel was stoppered and stirred at room temperature for 18 h, then the contents were transferred into a flask and evaporated under reduced pressure. The crude product was triturated with ether and dried under vacuum to provide ethyl 4-(1H-imidazo[1,2-b]pyrazol-1-ylmethyl)benzenecarboximidate hydrochloride (1.6 g, 97%) as a solid.

$^1$H NMR (400 MHz, DMSO-d$_6$): δ 1.46 (t, 3H, J=7.1 Hz), 4.73 (q, 2H, J=6.9 Hz), 5.41 (s, 2H), 5.98 (d, 1H, J=2.8 Hz), 7.56-7.61 (m, 4H), 7.80 (d, 2H, J=8.6 Hz), 8.14 (d, 2H, J=8.6 Hz), 12.20 (br s, 2H).

Step 3: 4-(1H-Imidazo[1,2-b]pyrazol-1-ylmethyl) benzenecarboximidamide

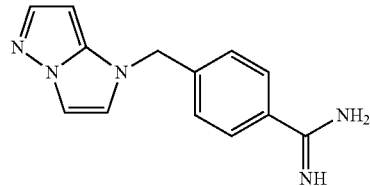 [SMILES: N=C(N)c1ccc(Cn2ccn3nccc23)cc1]

A pressure vessel containing a suspension of ethyl 4-(1H-imidazo[1,2-b]pyrazol-1-ylmethyl)benzenecarboximidate hydrochloride (from step 2, 1.1 g, 3.61 mol) in methanol (25 mL) was saturated with ammonia gas and stoppered. The reaction mixture was stirred at room temperature for 24 h, then excess ammonia was vented out and the contents were concentrated under reduced pressure. The residue was triturated with hexanes and dried under vacuum to give 4-(1H-imidazo[1,2-b]pyrazol-1-ylmethyl)benzenecarboximidamide (1.5 g, 141.5%) as a solid.

$^1$H NMR (400 MHz, DMSO-d$_6$): δ 5.27 (s, 2H), 5.64 (d, 1H, J=2.4 Hz), 7.35-7.60 (m, 5H), 7.80-7.86 (m, 2H)

Step 4: tert-Butyl {[4-(1H-imidazo[1,2-b]pyrazol-1-ylmethyl)phenyl]carbonoimidoyl}carbamate

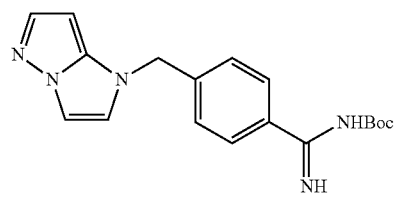 [SMILES: CC(C)(C)OC(=O)NC(=N)c1ccc(Cn2ccn3nccc23)cc1]

To a suspension of 4-(1H-imidazo[1,2-b]pyrazol-1-ylmethyl)benzenecarboximidamide (from step 3, 1.50 g. 6.27 mmol) in a mixture of sodium bicarbonate (1.524 g, 18.81 mmol), 1,4-dioxane (30 mL) and water (10 mL) was added di-tert-butyl dicarbonate (2.74 g, 12.54 mmol) and stirred at room temperature for 20 h. The reaction mixture was concentrated under reduced pressure to remove the volatiles and the remaining solution was dissolved in ethyl acetate (80 mL), washed with water (80 mL), brine solution (80 mL), dried and concentrated. The crude product was purified by silica gel column chromatography using ethyl acetate as eluent to afford tert-butyl {[4-(1H-imidazo[1,2-b]pyrazol-1-ylmethyl)phenyl]carbonoimidoyl}carbamate (0.60 g, 28.17%).

$^1$H NMR (400 MHz, DMSO-d$_6$): δ 1.41 (s, 9H), 5.18 (s, 2H), 5.58 (d, 1H, J=2.3 Hz), 7.32-7.37 (m, 3H), 7.41-7.42 (m, 1H), 7.56 (d, 1H, J=2.8 Hz), 7.88 (d, 2H, J=8.5 Hz).

Mass: ES$^-$ 338.11

Step 5: 5-{[(6R,7R)-7-{[(2Z)-2-{2-[(tert-Butoxycarbonyl)amino]-1,3-thiazol-4-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]benzyl}-1H-imidazo[1,2-b]pyrazol-5-ium iodide

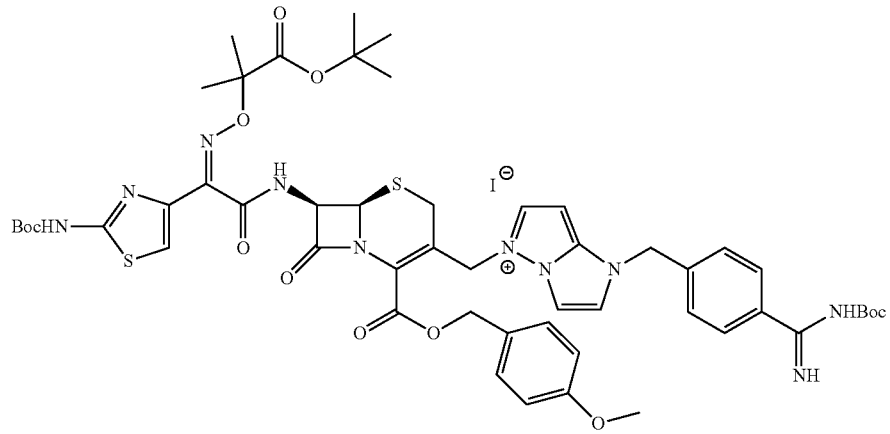 [SMILES: COc1ccc(COC(=O)C2=C(C[n+]3ccc4n(Cc5ccc(C(=N)NC(=O)OC(C)(C)C)cc5)ccn43)CS[C@@H]3[C@H](NC(=O)/C(=N\OC(C)(C)C(=O)OC(C)(C)C)c4csc(NC(=O)OC(C)(C)C)n4)C(=O)N23)cc1 ; [I-]]

To a solution of 4-methoxybenzyl (6R,7R)-7-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-(chloromethyl)-8-oxo-5-thia-1-azabicyclo[4.2.0]oct-2-ene-2-carboxylate (0.35 g, 0.449 mmol) in dimethylformamide (8 mL) at room temperature was added potassium iodide (0.149 g, 0.898 mmol) and after stirring for 10 min was added tert-butyl {[4-(1H-imidazo[1,2-b]pyrazol-1-ylmethyl)phenyl]carbonoimidoyl}carbamate (from step 4, 152 mg, 0.449 mmol). The reaction mixture was then stirred under nitrogen at room temperature for 16 h and diluted with a 1:1 mixture of sodium thiosulfate and brine solution (15 mL). The suspension was then filtered, washed with water and the solid was vacuum dried to get a yellow solid (0.650 g), which was used in the next step without further purification.

Step 6: (6R,7R)-7-{[(2Z)-2-(2-Amino-1,3-thiazol-4-yl)-2-{[(2-carboxypropan-2-yl)oxy]imino}acetyl]amino}-3-{[1-(4-carbamimidoylbenzyl)-1H-imidazo[1,2-b]pyrazol-5-ium-5-yl]methyl}-8-oxo-5-thia-1-azabicyclo[4.2.0]oct-2-ene-2-carboxylate To a solution of 5-{[(6R,7R)-7-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]benzyl}-1H-imidazo[1,2-b]pyrazol-5-ium iodide (from step 5, 0.65 g) in dry dichloromethane under nitrogen at room temperature was added trifluoroacetic acid (5 mL) in one portion and stirred for 3 h. The reaction mixture was concentrated under reduced pressure and the residue was suspended in distilled water (20 mL), stirred for 20 min then filtered. The filtrate was lyophilized and the product was purified by HPLC to obtain (6R,7R)-7-{[(2Z)-2-(2-amino-1,3-thiazol-4-yl)-2-{[(2-carboxypropan-2-yl)oxy]imino}acetyl]amino}-3-{[1-(4-carbamimidoylbenzyl)-1H-imidazo[1,2-b]pyrazol-5-ium-5-yl]methyl}-8-oxo-5-thia-1-azabicyclo[4.2.0]oct-2-ene-2-carboxylate as formic acid salt (0.032 g, 7.9%).

$^1$H NMR (400 MHz, DMSO-$d_6$): δ 1.29 (d, 6H, J=8.2 Hz), 2.94 (d, 1H, J=18.0 Hz), 3.25 (d, 1H, J=18 Hz), 5.05 (d, 1H, J=5.0 Hz), 5.14 (s, 2H), 5.32 (s, 2H), 5.63 (d, 1H, J=4.7 Hz),

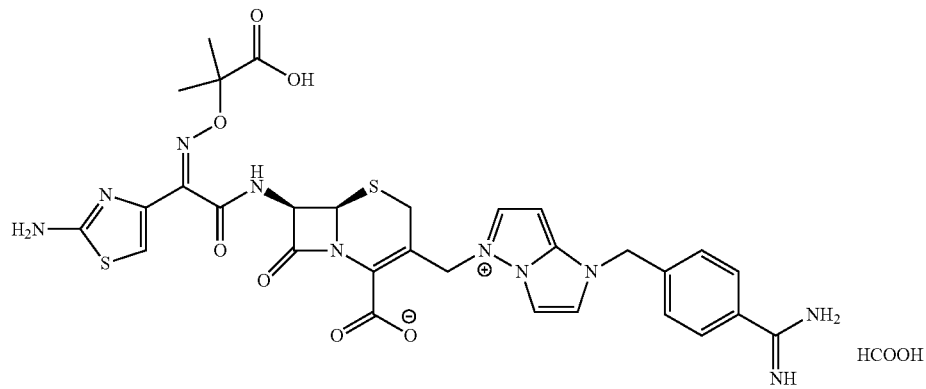 [SMILES: CC(C)(O/N=C(\C(=O)N[C@@H]1C(=O)N2C(C(=O)[O-])=C(C[n+]3ccc4n(Cc5ccc(C(=N)N)cc5)ccn43)CS[C@H]12)c1csc(N)n1)C(=O)O ; "HCOOH"]

6.13 (d, 1H, J=3.5 Hz), 6.86 (s, 1H), 7.37-7.41 (m, 3H), 7.63 (d, 2H, J=8.6 Hz), 7.87 (d, 2H, J=3.2 Hz), 8.16 (s, 1H)
Mass: ES+ 707.17

Example 5 (Table 1, Compound 11)

(6R,7R)-7-{[(2Z)-2-(2-Amino-1,3-thiazol-4-yl)-2-{[(2-carboxypropan-2-yl)oxy]imino}acetyl]amino}-3-({1-[(4-carbamimidoylthiophen-2-yl)methyl]-1H-pyrrolo[3,2-c]pyridin-5-ium-5-yl}methyl)-8-oxo-5-thia-1-azabicyclo[4.2.0]oct-2-ene-2-carboxylate

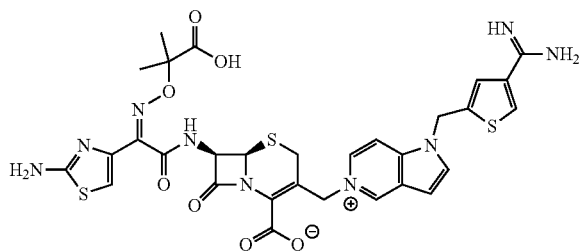 [SMILES: CC(C)(O/N=C(\C(=O)N[C@@H]1C(=O)N2C(C(=O)[O-])=C(C[n+]3ccc4c(ccn4Cc4cc(C(=N)N)cs4)c3)CS[C@H]12)c1csc(N)n1)C(=O)O]

Step 1: (4-Bromothiophen-2-yl)methanol

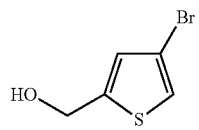

Sodium borohydride (2.08 g, 55.0 mmol) was added to a solution of 4-bromothiophene-2-carbaldehyde (10.0 g, 52.3 mmol) in anhydrous tetrahydrofuran (200 mL) at room temperature and the resulting reaction mixture was stirred at room temperature for 1.5 h. Then the reaction mixture was quenched carefully by adding saturated aq. ammonium chloride solution (50 mL). The reaction mixture was extracted with ethyl acetate (200 mL). Organic phase was separated, dried over $Na_2SO_4$. Solvent was evaporated, crude compound was dried under vacuum to give (4-bromothiophen-2-yl) methanol (10.56 g, crude) as white semi-solid which was used in the next step without further purification.
$^1$H NMR (400 MHz, $CDCl_3$): δ 4.79 (s, 2H), 6.92 (s, 1H), 7.17 (s, 1H).

Step 2: 5-(Hydroxymethyl)thiophene-3-carbonitrile

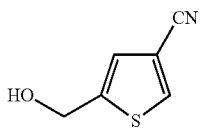

A mixture of (4-bromothiophen-2-yl) methanol (from step 1, 10.56 g crude, ~52.3 mmol), zinc cyanide (6.14 g, 52.34 mmol) in a 500 mL round bottom flask was degassed three times with nitrogen. Then anhydrous dimethylformamide (75 mL) was added, and the mixture was degassed with nitrogen. After that was added Palladium-tetrakis(triphenylphosphine) (3.01 g, 2.61 mmol) and degassing was repeated once again. The flask was fitted with a reflux condenser, and the reaction mixture was stirred at 80° C. (bath temperature) for 4 h under nitrogen. The mixture was cooled to room temperature, solvent was evaporated. The crude compound was purified by flash chromatography using RediSep silica 120 g flash column (10-30% ethyl acetate in hexanes as eluent) to give 5-(hydroxymethyl)thiophene-3-carbonitrile (5.15 g, 71% over two steps) as white solid.
$^1$H NMR (400 MHz, $CDCl_3$): δ 2.26 (t, 1H, J=5.9 Hz), 4.84 (d, 2H, J=5.9 Hz), 7.16 (s, 1H), 7.88 (d, 1H, J=1.6 Hz).

Step 3: 5-(Bromomethyl)thiophene-3-carbonitrile

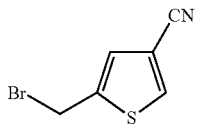

A solution of 5-(hydroxymethyl)thiophene-3-carbonitrile (from step 2, 5.15 g, 37.0 mmol) in anhydrous tetrahydrofuran (150 mL) was added triphenyl phosphine (10.19 g, 38.8 mmol) followed by carbon tetrabromide (12.88 g, 38.8 mmol). The reaction mixture was stirred at room temperature for 20 h under nitrogen. Solvent was evaporated and the crude compound was purified by flash chromatography using RediSep silica 120 g flash column (0-10% ethyl acetate in hexanes as eluent) to give 5-(bromomethyl)thiophene-3-carbonitrile (6.07 g, 81%) as a white solid.
$^1$H NMR (400 MHz, $CDCl_3$): δ 4.66 (s, 2H), 7.28 (d, 1H, J=0.8 Hz), 7.92 (d, 1H, J=1.6 Hz).

Step 4: 5-(1H-Pyrrolo[3,2-c]pyridin-1-ylmethyl)thiophene-3-carbonitrile

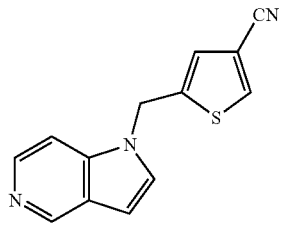 [SMILES: N#Cc1csc(Cn2ccc3cnccc32)c1]

To a solution of 1H-pyrrolo[3,2-c]pyridine (1.77 g, 15.00 mmol) in anhydrous dimethylformamide (75 mL) was added sodium hydride (60% suspension in mineral oil, 0.75 g, 18.75 mmol) at 0° C. in small portions under nitrogen. After the addition, reaction mixture was stirred for 15 minutes at 0° C. and then at room temperature for 10 minutes. Cooled to 0° C., 5-(bromomethyl)thiophene-3-carbonitrile (from step 3, 3.79 g, 18.75 mmol) was added in small portions. After the addition, reaction mixture was stirred for 10 minutes at 0° C. and then at room temperature for 1 h. Quenched with water (10 mL), solvent was evaporated under reduced pressure. Residue was partitioned between ethyl acetate (150 mL) and water (100 mL). Organic phase was separated, washed with brine and dried over $Na_2SO_4$. The crude compound was purified by flash chromatography using RediSep silica 80 g flash column (0-3% methanol in methylene chloride as eluent) to give 5-(1H-pyrrolo[3,2-c]pyridin-1-ylmethyl)thiophene-3-carbonitrile (2.17 g, 60%) as a brown solid.
$^1$H NMR (400 MHz, $CDCl_3$): δ 5.47 (s, 2H), 6.68 (d, 1H, J=3.1 Hz), 7.10 (s, 1H), 7.15 (d, 1H, J=3.5 Hz), 7.23 (d, 1H, J=5.8 Hz), 7.83 (s, 1H), 8.35 (d, 1H, J=5.9 Hz).
Mass: ES+ 240.01

Step 5: Methyl 5-(1H-pyrrolo[3,2-c]pyridin-1-ylmethyl)thiophene-3-carboximidate hydrochloride

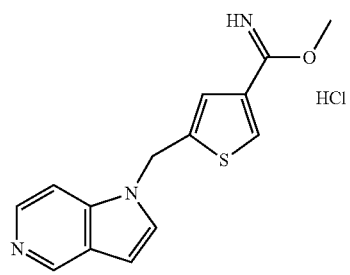 [SMILES: COC(=N)c1csc(Cn2ccc3cnccc32)c1 ; Cl]

Anhydrous hydrogen chloride gas was bubbled through a solution of 5-(1H-pyrrolo[3,2-c]pyridin-1-ylmethyl)thiophene-3-carbonitrile (from step 4, 1.05 g, 4.38 mmol) in anhydrous methanol (30 mL) at room temperature for 45 minutes. The reaction mixture was stirred at room temperature for 20 h. Solvent was evaporated and dried under vacuum to give methyl 5-(1H-pyrrolo[3,2-c]pyridin-1-ylmethyl)thiophene-3-carboximidate hydrochloride (1.05 g crude) as brown color gummy solid which was used in next step without further purification.

Mass: ES+ 272.06.

Step 6: 5-(1H-Pyrrolo[3,2-c]pyridin-1-ylmethyl)thiophene-3-carboximidamide

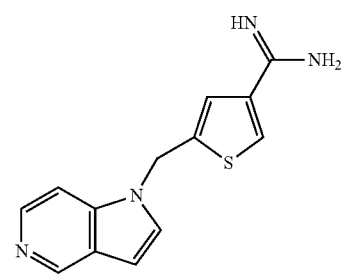

Anhydrous ammonia gas was bubbled through a solution of methyl 5-(1H-pyrrolo[3,2-c]pyridin-1-ylmethyl)thiophene-3-carboximidate hydrochloride (from step 5, 1.05 g crude, ~4.3 mmol) in anhydrous methanol (20 mL) at room temperature for 45 minutes. The reaction mixture was stirred at room temperature for 16 h. Solvent was evaporated and dried under vacuum to give 5-(1H-pyrrolo[3,2-c]pyridin-1-ylmethyl)thiophene-3-carboximidamide (1.72 g crude) as a brown solid which was used in the next step without further purification.

$^1$H NMR (400 MHz, DMSO-$d_6$): δ 5.90 (br s, 2H), 7.00 (br s, 1H), 7.42 (br s, 2H), 7.85 (s, 1H), 8.00 (br s, 1H), 8.19 (br s, 1H), 8.43 (br s, 1H), 8.65 (s, 1H), 9.19 (br s, 1H), 9.52 (br s, 1H).

Mass: ES+ 257.05.

Step 7: tert-Butyl {[5-(1H-pyrrolo[3,2-c]pyridin-1-ylmethyl)thiophen-3-yl]carbonoimidoyl}carbamate

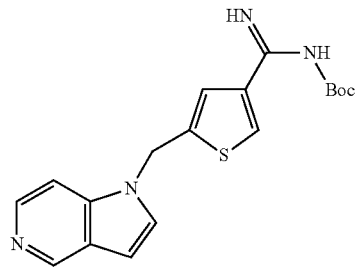 [SMILES: CC(C)(C)OC(=O)NC(=N)c1csc(Cn2ccc3cnccc32)c1]

To a solution of 5-(1H-pyrrolo[3,2-c]pyridin-1-ylmethyl)thiophene-3-carboximidamide (from step 6, 1.72 g crude, ~4.0 mmol) in 1,4-dioxane (50 mL) was added aqueous saturated sodium bicarbonate solution followed by di-tert-butyldicarbonate (3.50 g, 16.0 mmol). The reaction mixture was stirred at room temperature for 4 h. Solvent was evaporated, water (50 mL) was added and extracted with methylene chloride (2×50 mL). The organic phase was dried over Na$_2$SO$_4$. Solvent was evaporated and the crude compound was purified by flash chromatography using RediSep silica 40 g flash column (0-2% methanol in methylene chloride as eluent) to give tert-butyl {[5-(1H-pyrrolo[3,2-c]pyridin-1-ylmethyl)thiophen-3-yl]carbonoimidoyl}carbamate (0.17 g, 11% for three steps) as an off-white solid.

$^1$H NMR (400 MHz, CDCl$_3$): δ 1.53 (s, 9H), 5.42 (s, 2H), 6.64 (d, 1H, J=2.7 Hz), 7.15 (d, 1H, J=3.5 Hz), 7.23 (d, 1H, J=5.5 Hz), 7.41 (s, 1H), 7.86 (s, 1H), 8.28 (d, 1H, J=5.9 Hz), 8.89 (s, 1H).

Mass: ES+ 355.10.

Step 8: 5-{[(6R,7R)-7-{[(2Z)-2-(2-Amino-1,3-thiazol-4-yl)-2-{[((1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-pyrrolo[3,2-c]pyridin-5-ium iodide

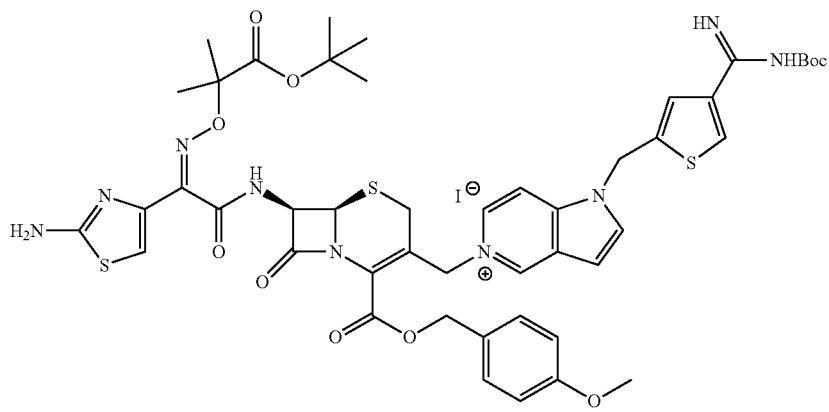

A mixture of tert-butyl {[5-(1H-pyrrolo[3,2-c]pyridin-1-ylmethyl)thiophen-3-yl]carbonoimidoyl}carbamate (from step 7, 107 mg, 0.30 mmol), 4-methoxybenzyl (6R,7R)-7-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-(chloromethyl)-8-oxo-5-thia-1-azabicyclo[4.2.0]oct-2-ene-2-carboxylate (234 mg, 0.30 mmol), and sodium iodide (90 mg, 0.60 mmol) was cooled to 0° C. in an ice-bath; dimethyl formamide (3 mL) was added, stirred for 45 minutes, then the mixture was stirred at −16° C. for 16 h under nitrogen. Sodium bisulphite (0.6 g) in sodium chloride solution (75 mL) was added at 15° C., stirred for 10 minutes. The solid separated was filtered off, washed with water and dried under vacuum to give 5-(((6R,7R)-2-((Z)-2-(2-aminothiazol-4-yl)-2-(((1-(tert-butoxy)-2-methyl-1-oxopropan-2-yl)oxy)imino)acetamido)-2-(((4-methoxybenzyl)oxy)carbonyl)-8-oxo-5-thia-1-azabicyclo[4.2.0]oct-2-en-3-yl)methyl)-1-((4-(N-(tert-butoxycarbonyl)carbamimidoyl)thiophen-2-yl)methyl)-1H-pyrrolo[3,2-c]pyridin-5-ium iodide (296 mg, crude) as yellow color solid which was used in the next step without further purification.

Mass: ES$^+$ 1100.52.

Step 9: (6R,7R)-7-{[(2Z)-2-(2-Amino-1,3-thiazol-4-yl)-2-{[(2-carboxypropan-2-yl)oxy]imino}acetyl]amino}-3-({1-[(4-carbamimidoylthiophen-2-yl)methyl]-1H-pyrrolo[3,2-c]pyridin-5-ium-5-yl}methyl)-8-oxo-5-thia-1-azabicyclo[4.2.0]oct-2-ene-2-carboxylate

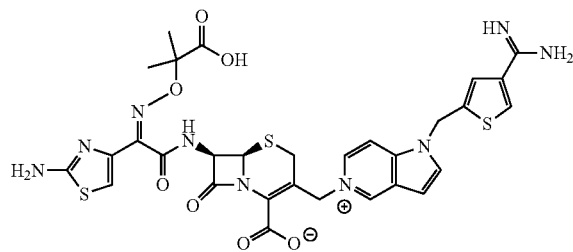 [SMILES: CC(C)(O/N=C(\C(=O)N[C@@H]1C(=O)N2C(C(=O)[O-])=C(C[n+]3ccc4c(ccn4Cc4cc(C(=N)N)cs4)c3)CS[C@H]12)c1csc(N)n1)C(=O)O]

To a solution of 5-{[(6R,7R)-7-{[(2Z)-2-(2-amino-1,3-thiazol-4-yl)-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-pyrrolo[3,2-c]pyridin-5-ium iodide (from step 8, 296 mg, crude, ~0.30 mmol)) in anhydrous methylene chloride (3 mL) was added anisole (0.8 mL) followed by trifluoroacetic acid (2.0 mL). The reaction mixture was stirred at room temperature for 3 h. Solvent was evaporated and diisopropyl ether (30 mL) was added. The solid separated was filtered, washed with diisopropyl ether and dried under vacuum. The light brown color solid (356 mg) was dissolved in water (20 mL) and filtered. The aqueous phase was lyophilized to give yellow solid (200 mg) which was purified by preparative HPLC (acetonitrile, water, 0.1% formic acid) to give (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidoylthiophen-2-yl)methyl]-1H-pyrrolo[3,2-c]pyridin-5-ium-5-yl}methyl)-8-oxo-5-thia-1-azabicyclo[4.2.0]oct-2-ene-2-carboxylate as a formic acid salt (30 mg, 14%).

$^1$H NMR (400 MHz, D$_2$O): δ 1.24 (s, 3H), 1.26 (s, 3H), 2.94 (d, 1H, J=18.0 Hz), 3.42 (d, 1H, J=18.0 Hz), 5.01-5.14 (m, 2H), 5.39 (d, 1H, J=14.5 Hz), 5.59-5.76 (m, 3H), 6.75 (s, 1H), 6.95 (d, 1H, J=3.5 Hz), 7.31 (s, 1H), 7.73 (d, 1H, J=3.5 Hz), 7.88 (d, 1H, J=7.0), 8.09 (d, 1H, J=1.6 Hz), 8.37 (d, 1H, J=7.0 Hz), 9.10 (s, 1H).

Mass: ES$^+$ 724.17.

Example 6 (Table 1, Compound 13)

(6R,7R)-7-{[(2Z)-2-(2-Amino-1,3-thiazol-4-yl)-2-{[(2-carboxypropan-2-yl)oxy]imino}acetyl]amino}-3-({1-[(4-carbamimidoylfuran-2-yl)methyl]-1H-pyrrolo[3,2-c]pyridin-5-ium-5-yl}methyl)-8-oxo-5-thia-1-azabicyclo[4.2.0]oct-2-ene-2-carboxylate

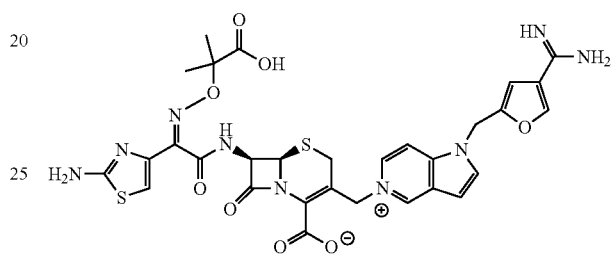

Step 1: (4-Bromofuran-2-yl)methanol

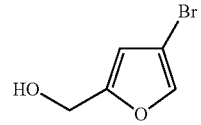

Sodium borohydride (1.21 g, 31.98 mmol) was added to a solution of 4-bromofuran-2-carbaldehyde (5.33 g, 30.46 mmol) in anhydrous tetrahydrofuran (120 mL) at room temperature and the resulting reaction mixture was stirred at room temperature for 1.5 h. Then the reaction mixture was quenched carefully by adding saturated aqueous ammonium chloride solution (50 mL) and extracted with ethyl acetate (200 mL). The organic phase was separated and dried over Na$_2$SO$_4$. Solvent was evaporated and the crude compound was dried under vacuum to give (4-bromofuran-2-yl) methanol (5.34 g) as white semi-solid, which was used in the next step without further purification.

$^1$H NMR (400 MHz, CDCl$_3$): δ 2.36 (br s, 1H), 4.55 (s, 2H), 6.34 (s, 1H), 7.39 (s, 1H).

Step 2: 5-(Hydroxymethyl)furan-3-carbonitrile

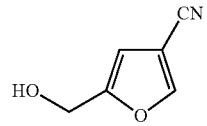

A mixture of (4-bromofuran-2-yl)methanol (from step 1, 3.50 g, 19.8 mmol) and zinc cyanide (2.32 g, 19.8 mmol) in a 250 mL round bottom flask was degassed three times with nitrogen. Anhydrous dimethylformamide (20 mL) was added, and the mixture was degassed with nitrogen. After that Pd(PPh$_3$)$_4$ (1.38 g, 1.20 mmol) was added and degassing was repeated once again. The flask was fitted with a reflux condenser, and the reaction mixture was stirred at 80° C. for 24 h under nitrogen. The mixture was cooled to room temperature, solvent was evaporated and residue was taken in ethyl acetate (150 mL), washed with water (100 mL), brine (100 mL) and dried over Na$_2$SO$_4$. Solvent was evaporated and the crude compound was purified by flash chromatography using RediSep silica 120 g flash column (0-30% ethyl acetate in hexanes as eluent) to give 5-(hydroxymethyl)furan-3-carbonitrile (0.58 g, 24%) as a white solid.

$^1$H NMR (400 MHz, CDCl$_3$): δ 1.97 (br s, 1H), 4.64 (d, 2H, J=6.3 Hz), 6.53 (s, 1H), 7.92 (s, 1H).

Step 3: 5-(Bromomethyl)furan-3-carbonitrile

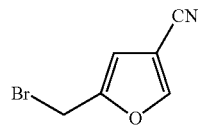

A solution of 5-(hydroxymethyl)furan-3-carbonitrile (from step 2, 0.92 g, 7.47 mmol) in anhydrous tetrahydrofuran (30 mL) was added triphenyl phosphine (2.15 g, 8.22 mmol) followed by carbon tetrabromide (2.72 g, 8.22 mmol). The reaction mixture was stirred at room temperature for 4 h under nitrogen. Solvent was evaporated and the crude compound was purified by flash chromatography using RediSep silica 80 g flash column (10% ethyl acetate in hexanes as eluent) to give 5-(bromomethyl)furan-3-carbonitrile (1.12 g, 81%) as a white solid.

$^1$H NMR (400 MHz, CDCl$_3$): δ 4.43 (s, 2H), 6.60 (s, 1H), 7.94 (s, 1H).

Step 4: 5-(1H-Pyrrolo[3,2-c]pyridin-1-ylmethyl)furan-3-carbonitrile

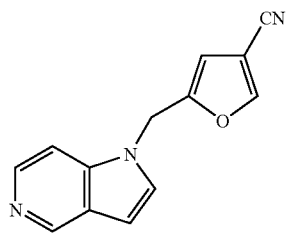 [SMILES: N#Cc1coc(Cn2ccc3cnccc32)c1]

To a solution of 1H-pyrrolo[3,2-c]pyridine (0.77 g, 6.50 mmol) in anhydrous dimethylformamide (30 mL) was added sodium hydride (60% suspension in mineral oil, 0.26 g, 6.50 mmol) at 0° C. in small portions under nitrogen. After the addition, the reaction mixture was stirred for 15 minutes at 0° C. and then at room temperature for 10 minutes then cooled to 0° C. and 5-(bromomethyl)furan-3-carbonitrile (from step 3, 1.10 g, 5.91 mmol) was added in small portions. After the addition, the reaction mixture was stirred for 10 minutes at 0° C. then at room temperature for 1 h. The mixture was quenched with water (5 mL). Solvent was evaporated under reduced pressure. Residue was partitioned between ethyl acetate (100 mL) and water (50 mL). The organic phase was separated, washed with brine and dried over Na$_2$SO$_4$. The crude compound was purified by flash chromatography using RediSep silica 40 g flash column (0-3% methanol in methylene chloride as eluent) to give 5-(1H-pyrrolo[3,2-c]pyridin-1-ylmethyl)furan-3-carbonitrile (1.065 g, 80%) as an off-white solid.

$^1$H NMR (400 MHz, CDCl$_3$): δ 5.29 (s, 2H), 6.46 (s, 1H), 6.66 (d, 1H, J=2.3 Hz), 7.15 (d, 1H, J=3.5 Hz), 7.27 (s, 1H), 7.88 (s, 1H), 8.37 (d, 1H, J=5.9 Hz), 8.94 (s, 1H).

Mass: ES$^+$ 224.10.

Step 5: Methyl 5-(1H-pyrrolo[3,2-c]pyridin-1-ylmethyl)furan-3-carboximidate hydrochloride

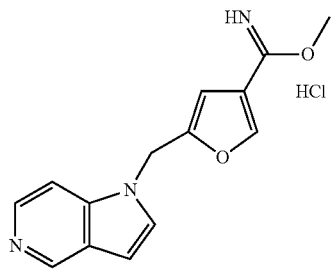 [SMILES: COC(=N)c1coc(Cn2ccc3cnccc32)c1 ; Cl]

Anhydrous hydrogen chloride gas was bubbled through a solution of 5-(1H-pyrrolo[3,2-c]pyridin-1-ylmethyl)furan-3-carbonitrile (from step 4, 1.05 g, 4.70 mmol) in anhydrous methanol (30 mL) at room temperature for 45 minutes; the reaction mixture was stirred at room temperature for 20 h. Solvent was evaporated and dried under vacuum to give methyl 5-(1H-pyrrolo[3,2-c]pyridin-1-ylmethyl)furan-3-carboximidate hydrochloride (1.05 g, crude) as a brown gummy solid. The compound was used in the next step without further purification. $^1$H NMR (400 MHz, CD$_3$OD): δ 4.28 (s, 3H), 5.82 (s, 2H), 7.16 (br s, 1H), 7.22 (br s, 1H), 7.98 (br s, 1H), 8.30 (br s, 1H), 8.46 (br s, 1H), 8.54 (s, 1H), 9.20 (s, 1H).

Mass: ES$^+$ 256.10.

Step 6: 5-(1H-Pyrrolo[3,2-c]pyridin-1-ylmethyl)furan-3-carboximidamide

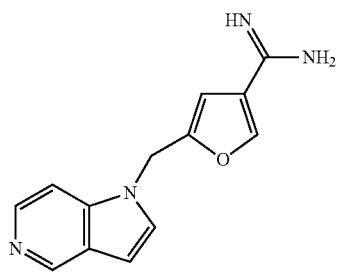 [SMILES: N=C(N)c1coc(Cn2ccc3cnccc32)c1]

Anhydrous ammonia gas was bubbled through a solution of methyl 5-(1H-pyrrolo[3,2-c]pyridin-1-ylmethyl)furan-3-carboximidate hydrochloride (from step 5, 1.0 g crude, ~4.7 mmol) in anhydrous methanol (30 mL) at room temperature for 45 minutes. The reaction mixture was stirred at room temperature for 16 h. Solvent was evaporated and dried under vacuum to give 5-(1H-pyrrolo[3,2-c]pyridin-1-ylmethyl)furan-3-carboximidamide (1.90 g, crude) as a brown solid.

The compound was used in the next step without further purification.

Mass: ES+ 241.11.

Step 7: tert-Butyl {[5-(1H-pyrrolo[3,2-c]pyridin-1-ylmethyl)furan-3-yl]carbonoimidoyl}carbamate

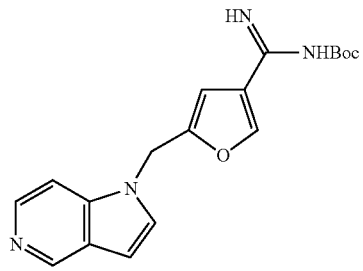 [SMILES: CC(C)(C)OC(=O)NC(=N)c1coc(Cn2ccc3cnccc32)c1]

To a solution of 5-(1H-pyrrolo[3,2-c]pyridin-1-ylmethyl)furan-3-carboximidamide (from step 6, 1.90 g crude, ~4.7 mmol) in 1,4-dioxane (5 mL) was added aqueous saturated sodium bicarbonate solution (5 mL) followed by di-tert-butyldicarbonate (4.10 g, 18.8 mmol) and the reaction mixture was stirred at room temperature for 4 h. Solvent was evaporated, water (50 mL) was added and extracted with methylene chloride (2×50 mL). The organic phase was dried over Na$_2$SO$_4$. Solvent was evaporated and the crude compound was purified by flash chromatography using RediSep silica 40 g flash column (2-5% methanol in methylene chloride as eluent) to give tert-butyl {[5-(1H-pyrrolo[3,2-c]pyridin-1-ylmethyl)furan-3-yl]carbonoimidoyl}carbamate (116 mg, 7% over steps) as an off-white solid.

$^1$H NMR (400 MHz, CDCl$_3$): δ 1.51 (s, 9H), 5.26 (s, 2H), 6.59 (s, 1H), 6.63 (dd, 1H, J=3.1, 0.8 Hz), 7.15 (d, 1H, J=3.5 Hz), 7.22 (d, 1H, J=5.9 Hz), 8.01 (s, 1H), 8.22 (d, 1H, J=5.9 Hz), 8.85 (s, 1H).

Mass: ES+ 341.23.

Step 8: 5-{[(6R,7R)-7-{[(2Z)-2-(2-Amino-1,3-thiazol-4-yl)-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]furan-2-yl}methyl)-1H-pyrrolo[3,2-c]pyridin-5-ium iodide A mixture of tert-butyl {[5-(1H-pyrrolo[3,2-c]pyridin-1-ylmethyl)furan-3-yl]carbonoimidoyl}carbamate (from step 7, 110 mg, 0.32 mmol), 4-methoxybenzyl (6R,7R)-7-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-(chloromethyl)-8-oxo-5-thia-1-azabicyclo[4.2.0]oct-2-ene-2-carboxylate (252 mg, 0.32 mmol), and sodium iodide (96 mg, 0.64 mmol) was cooled to 0° C. and dimethylformamide (3 mL) was added, stirred for 45 minutes then the mixture was stirred at −16° C. for 16 h under nitrogen. Sodium bisulphite (0.6 g) in sodium chloride solution (75 mL) was added at 15° C., stirred for 10 minutes, and the solid was filtered, washed with water and dried under vacuum to give 5-{[(6R,7R)-7-{[(2Z)-2-(2-amino-1,3-thiazol-4-yl)-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]furan-2-yl}methyl)-1H-pyrrolo[3,2-c]pyridin-5-ium iodide (328 mg, crude) as yellow solid which was used in the next step without further purification.

Mass: ES+ 1084.68.

Step 9: (6R,7R)-7-{[(2Z)-2-(2-Amino-1,3-thiazol-4-yl)-2-{[(2-carboxypropan-2-yl)oxy]imino}acetyl]amino}-3-({1-[(4-carbamimidoylfuran-2-yl)methyl]-1H-pyrrolo[3,2-c]pyridin-5-ium-5-yl}methyl)-8-oxo-5-thia-1-azabicyclo[4.2.0]oct-2-ene-2-carboxylate

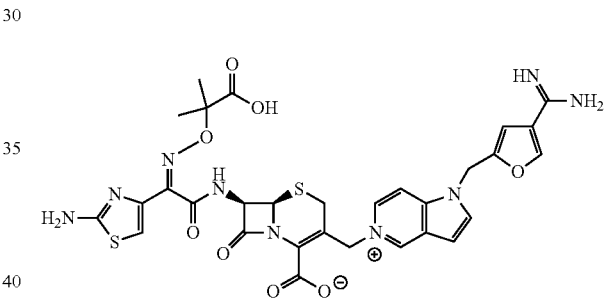

To a solution of 5-{[(6R,7R)-7-{[(2Z)-2-(2-amino-1,3-thiazol-4-yl)-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]furan-2-yl}methyl)-1H-pyrrolo[3,2-c]pyridin-5-ium iodide (from step 8, 328 mg, crude, ~0.32 mmol)) in anhydrous

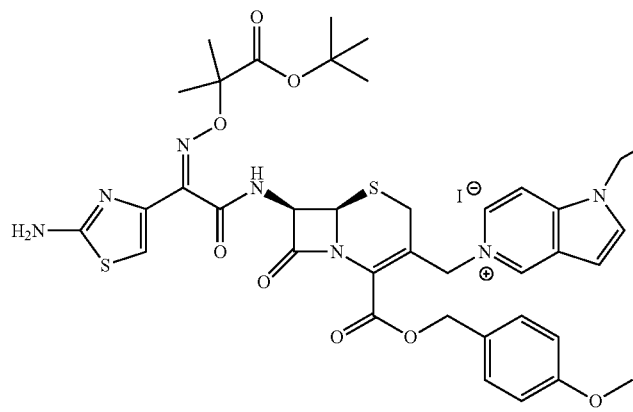

methylene chloride (3 mL) was added anisole (0.8 mL) followed by trifluoroacetic acid (2.0 mL). The reaction mixture was stirred at room temperature for 3 h and the solvent was evaporated. To the residue was added di-isopropyl ether (30 mL) and the solid separated was filtered off, washed with diisopropyl ether and dried under vacuum to get greenish yellow color solid (315 mg), which was dissolved in water (30 mL) and filtered. The aqueous phase was lyophilized to give yellow solid (160 mg), which was purified by preparative HPLC to give (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidoylfuran-2-yl)methyl]-1H-pyrrolo[3,2-c]pyridin-5-ium-5-yl}methyl)-8-oxo-5-thia-1-azabicyclo[4.2.0]oct-2-ene-2-carboxylate as formic acid salt (28 mg, 12% over two steps).

$^1$H NMR (400 MHz, D$_2$O): δ 1.27 (s, 3H), 1.28 (s, 3H), 2.97 (d, 1H, J=18.0 Hz), 3.44 (d, 1H, J=18.0 Hz), 5.04-5.16 (m, 2H), 5.42 (d, 1H, J=14.5 Hz), 5.66 (d, 1H, J=4.7 Hz), 6.72 (s, 1H), 6.84 (s, 1H), 6.96 (d, 1H, J=3.1 Hz), 7.74 (d, 1H, J=3.5 Hz), 7.96 (d, 1H, J=7.0 Hz), 8.14 (s, 1H), 8.43 (d, 1H, J=7.0 Hz), 9.14 (s, 1H). Seven protons were not observed in D$_2$O.

Mass: ES$^+$ 708.27.

Example 7 (Table 1, Compound 3)

(6R,7R)-7-{[(2Z)-2-(2-Amino-1,3-thiazol-4-yl)-2-{[(2-carboxypropan-2-yl)oxy]imino}acetyl]amino}-8-oxo-3-{[1-(4-{N-[(3R)-piperidin-3-yl]carbamimidoyl}benzyl)-1H-pyrrolo[3,2-c]pyridin-5-ium-5-yl]methyl}-5-thia-1-azabicyclo[4.2.0]oct-2-ene-2-carboxylate

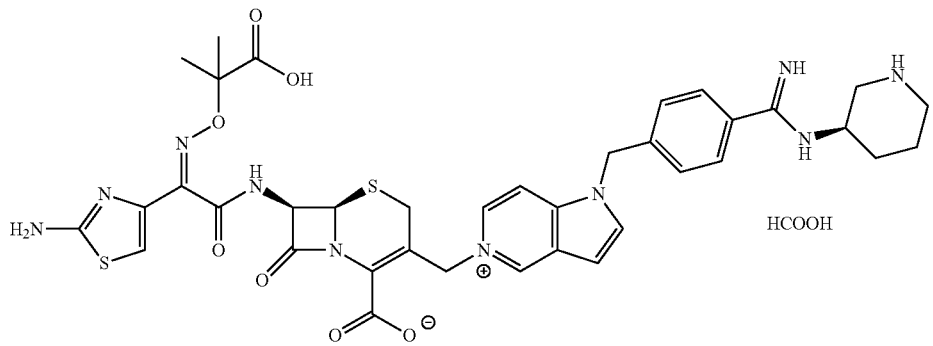 [SMILES: CC(C)(O/N=C(\C(=O)N[C@@H]1C(=O)N2C(C(=O)[O-])=C(C[n+]3ccc4c(ccn4Cc4ccc(C(=N)N[C@@H]5CCCNC5)cc4)c3)CS[C@H]12)c1csc(N)n1)C(=O)O ; "HCOOH"]

$^1$H NMR (400 MHz, CD$_3$OD): δ 1.23 (s, 3H), 1.29 (s, 3H), 1.81-2.02 (m, 4H), 2.89 (d, 1H, J=18.0 Hz), 2.99 (m, 1H), 3.16 (m, 1H), 3.40-3.51 (m, 2H), 3.63 (d, 1H, J=17.6 Hz), 4.21 (m, 1H), 4.95 (m, 1H), 5.18 (d, 1H, J=4.8 Hz), 5.66-5.83 (m, 3H), 5.93 (d, 1H, J=14.0 Hz), 6.78 (s, 1H), 7.14 (d, 1H, J=3.2 Hz), 7.44 (d, 2H, J=8.0 Hz), 7.70 (d, 1H, J=6.8 Hz), 7.85 (d, 1H, J=8.4 Hz), 8.07 (s, 1H), 8.34 (s, 1H), 9.29 (d, 1H, J=6.0 Hz), 9.43 (s, 1H). Seven protons were not observed in CD$_3$OD.

Mass: ES$^-$ 799.2.

Example 8 (Table 1, Compound 14)

(6R,7R)-7-{[(2Z)-2-(2-Amino-1,3-thiazol-4-yl)-2-{[(2-carboxypropan-2-yl)oxy]imino}acetyl]amino}-3-{[1-(4-carbamimidoyl-2-fluorobenzyl)-1H-pyrrolo[3,2-c]pyridin-5-ium-5-yl]methyl}-8-oxo-5-thia-1-azabicyclo[4.2.0]oct-2-ene-2-carboxylate

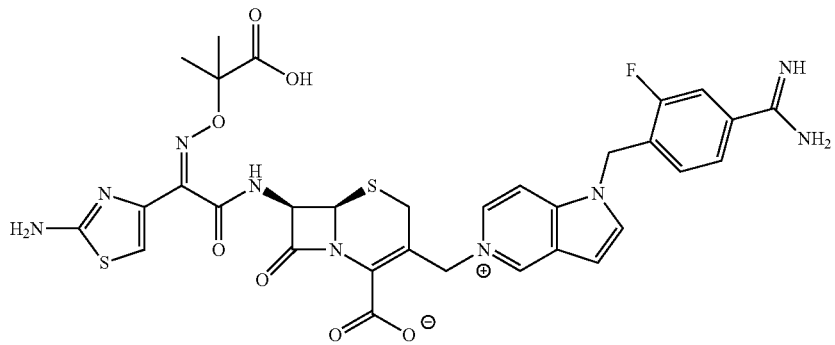 [SMILES: CC(C)(O/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1csc(N)n1)C(=O)O]

¹H NMR (400 MHz, D₂O): δ 1.23 (s, 6H), 2.93 (d, 1H, J=18.0 Hz), 3.38 (d, 1H, J=17.6 Hz), 5.08-5.12 (m, 2H), 5.34 (d, 1H, J=14.4 Hz), 5.57 (s, 2H), 5.64 (d, 1H, J=4.4 Hz), 6.75 (s, 1H), 6.92 (d, 1H, J=3.6 Hz), 7.15 (t, 1H, J=7.6 Hz), 7.36 (d, 1H, J=7.2 Hz), 7.41 (d, 1H, J=10.4 Hz), 7.67 (d, 1H, J=3.6 Hz), 7.77 (d, 1H, J=6.8 Hz), 8.27 (d, 1H, J=8.0 Hz), 9.05 (s, 1H). Seven protons were not observed in D₂O.

Mass: ES⁺ 736.41

Example 9 (Table 1, Compound 17)

(6R,7R)-7-{[(2Z)-2-(2-Amino-1,3-thiazol-4-yl)-2-{[(2-carboxypropan-2-yl)oxy]imino}acetyl]amino}-3-{[1-({3-[(diaminomethylidene)amino]-1,2-oxazol-5-yl}methyl)-1H-pyrrolo[3,2-c]pyridin-5-ium-5-yl]methyl}-8-oxo-5-thia-1-azabicyclo[4.2.0]oct-2-ene-2-carboxylate

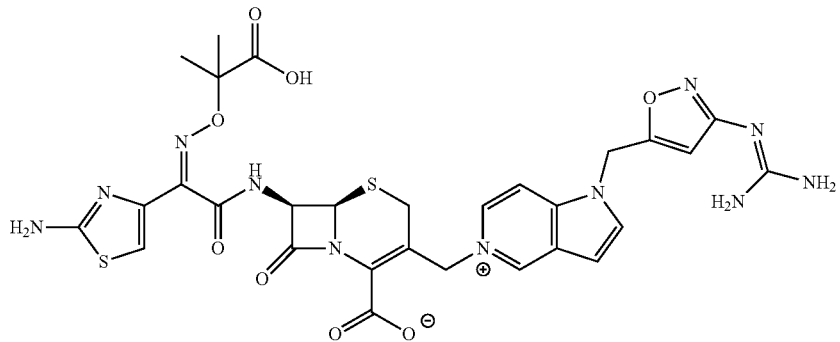 [SMILES: CC(C)(O/N=C(\C(=O)N[C@@H]1C(=O)N2C(C(=O)[O-])=C(C[n+]3ccc4c(ccn4Cc4cc(N=C(N)N)no4)c3)CS[C@H]12)c1csc(N)n1)C(=O)O]

¹H NMR (400 MHz, D₂O): δ 1.25 (s, 6H), 2.93 (d, 1H, J=17.6 Hz), 3.42 (d, 1H, J=18.0 Hz), 5.07-5.10 (m, 2H), 5.39 (d, 1H, J=13.6 Hz), 5.61 (s, 2H), 5.64 (d, 1H, J=4.8 Hz), 6.10 (s, 1H), 6.78 (s, 1H), 6.94 (d, 1H, J=3.2 Hz), 7.68 (d, 1H, J=3.6 Hz), 7.85 (d, 1H, J=6.4 Hz), 8.38 (d, 1H, J=6.8 Hz), 9.09 (s, 1H). Eight protons were not observed in D₂O.

Mass: ES⁺ 724.35

Example 10 (Table 1, Compound 18)

(6R,7R)-7-{[(2Z)-2-(2-Amino-1,3-thiazol-4-yl)-2-{[(2-carboxypropan-2-yl)oxy]imino}acetyl]amino}-3-({1-[(4-carbamimidoylthiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate

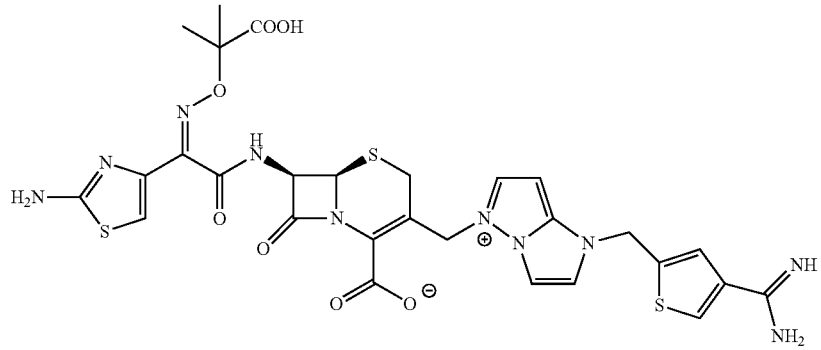 [SMILES: CC(C)(O/N=C(\C(=O)N[C@@H]1C(=O)N2C(C(=O)[O-])=C(C[n+]3ccc4n(Cc5cc(C(=N)N)cs5)ccn43)CS[C@H]12)c1csc(N)n1)C(=O)O]

Step 1: 5-(1H-Imidazo[1,2-b]pyrazol-1-ylmethyl)thiophene-3-carbonitrile

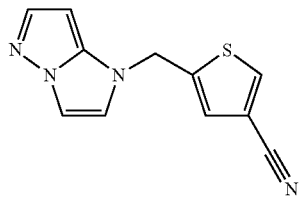 [SMILES: N#Cc1csc(Cn2ccn3nccc23)c1]

To a stirred solution of 1H-imidazo[1,2-b]pyrazole (0.25 g, 2.33 mmol) in anhydrous dimethylformamide (5 mL) was added sodium hydride (60% dispersion in mineral oil, 0.14 g, 3.50 mmol) in small portions at 0° C. The reaction mixture was stirred at 0° C. for 30 min and a solution of 5-(bromomethyl)thiophene-3-carbonitrile (0.495 g, 2.45 mmol) in anhydrous dimethylformamide (1.0 mL) was added slowly. The reaction mixture was stirred at 0° C. for 1 h then at room temperature for 2 h. The reaction was quenched using aqueous saturated ammonium chloride solution (2 mL) and the resulting mixture was partitioned between ethyl acetate (80 mL) and water (10 mL). The organic phase was separated, washed with water (10 mL), brine (10 mL), dried over sodium sulfate, filtered and concentrated under reduced pressure. The crude mixture was purified by flash column chromatography (silica gel, 230-400 mesh) using a 50 to 100% gradient of ethyl acetate in hexane to afford 5-(1H-imidazo[1,2-b]pyrazol-1-ylmethyl)thiophene-3-carbonitrile (0.28 g, 53%) as an off-white solid.

$^1$H NMR (400 MHz, DMSO-$d_6$): δ 5.38 (s, 2H), 5.72 (d, 1H, J=1.9 Hz), 7.29-7.32 (m, 1H), 7.46-7.48 (m, 1H), 7.57 (m, 2H), 8.49 (d, 1H, J=1.2 Hz)

Mass: ES$^+$ 229.09

Step 2: Ethyl 5-(1H-imidazo[1,2-b]pyrazol-1-ylmethyl)thiophene-3-carboximidate hydrochloride

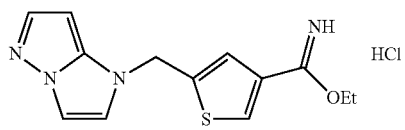

A solution of 5-(1H-imidazo[1,2-b]pyrazol-1-ylmethyl)thiophene-3-carbonitrile (from step 1, 0.39 g, 1.71 mmol) in anhydrous ethanol (30 mL) at 0° C. was purged with a stream of anhydrous hydrogen chloride gas for 15 min. The reaction flask was stoppered and the reaction mixture was stirred at room temperature for 24 h. The volatiles were removed under reduced pressure and the residue was further dried under high vacuum to afford ethyl 5-(1H-imidazo[1,2-b]pyrazol-1-ylmethyl)thiophene-3-carboximidate hydrochloride (0.60 g, crude) as a yellow solid which was used directly in the next step without further purification.

$^1$H NMR (400 MHz, DMSO-$d_6$): δ 1.45 (t, 3H, J=7.0 Hz), 4.55 (q, 2H, J=7.0 Hz), 5.46 (s, 2H), 5.83 (d, 1H, J=1.9 Hz), 7.40 (s, 1H), 7.58 (s, 1H), 7.65 (d, 1H, J=1.6 Hz), 7.81 (s, 1H), 8.78 (d, 1H, J=1.6 Hz). One proton was not observed in DMSO Mass: ES$^+$ 275.16

Step 3: 5-(1H-Imidazo[1,2-b]pyrazol-1-ylmethyl)thiophene-3-carboximidamide

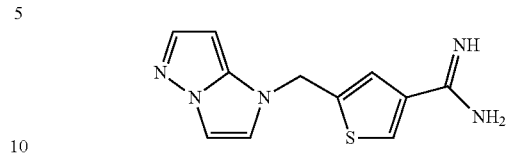

A solution of ethyl 5-(1H-imidazo[1,2-b]pyrazol-1-ylmethyl)thiophene-3-carboximidate hydrochloride (from step 2, crude, 0.6 g, 1.71 mmol) in anhydrous methanol (20 mL) at 0° C. was purged with a stream of anhydrous ammonia gas for 15 min. The reaction flask was sealed and the reaction mixture was allowed to warm to room temperature and stirred for 17 h. The volatiles were removed under reduced pressure and the residue was further dried under high vacuum to afford 5-(1H-imidazo[1,2-b]pyrazol-1-ylmethyl)thiophene-3-carboximidamide (1.0 g, crude) as a reddish solid which was used in the next step without further purification.

$^1$H NMR (400 MHz, DMSO-$d_6$): δ 5.40 (s, 2H), 5.69 (d, 1H, J=1.9 Hz), 7.29-7.32 (m, 1H), 7.44-7.48 (m, 1H), 7.59 (d, 1H, J=2.7 Hz), 7.69 (d, 1H, J=0.8 Hz), 8.50 (d, 1H, J=1.6 Hz). Three protons were not observed in DMSO.

Mass: ES$^+$ 246.09

Step 4: tert-Butyl {[5-(1H-imidazo[1,2-b]pyrazol-1-ylmethyl)thiophen-3-yl](imino)methyl}carbamate

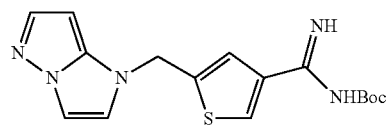

To a vigorously stirred solution of 5-(1H-imidazo[1,2-b]pyrazol-1-ylmethyl)thiophene-3-carboximidamide (from step 3, crude, 1.0 g, 1.71 mmol) in 1,4-dioxane (10 mL) was added aqueous saturated sodium bicarbonate solution (6 mL) followed by di-tert-butyl dicarbonate (1.5 g, 6.84 mmol). The reaction mixture was stirred at room temperature for 17 h. The majority of 1,4-dioxane was removed under reduced pressure and the mixture was partitioned between dichloromethane (50 mL) and water (30 mL). The phases were separated and the aqueous layer was re-extracted with dichloromethane (60 mL). The combined organic extracts were dried over sodium sulfate, filtered and concentrated under reduced pressure. The crude mixture was purified by flash column chromatography (silica gel, 230-400 mesh) using a 30 to 100% gradient of ethyl acetate in hexane to afford tert-butyl {[5-(1H-imidazo[1,2-b]pyrazol-1-ylmethyl)thiophen-3-yl](imino)methyl}carbamate (0.215 g, 36% over 3 steps) as a yellowish solid.

$^1$H NMR (400 MHz, DMSO-$d_6$): δ 1.41 (s, 9H), 5.32 (s, 2H), 5.65 (d, 1H, J=1.9 Hz), 7.24-7.30 (m, 1H), 7.39-7.46 (m, 1H), 7.54 (d, 1H, J=1.9 Hz), 7.60 (d, 1H, J=0.8 Hz), 8.21 (d, 1H, J=1.2 Hz), 8.85 (br s, 2H)

Mass: ES$^+$346.23, ES$^-$ 344.18

Step 5: 5-{[(6R,7R)-7-{[(2Z)-2-{2-[(tert-Butoxycarbonyl)amino]-1,3-thiazol-4-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-imidazo[1,2-b]pyrazol-5-ium iodide

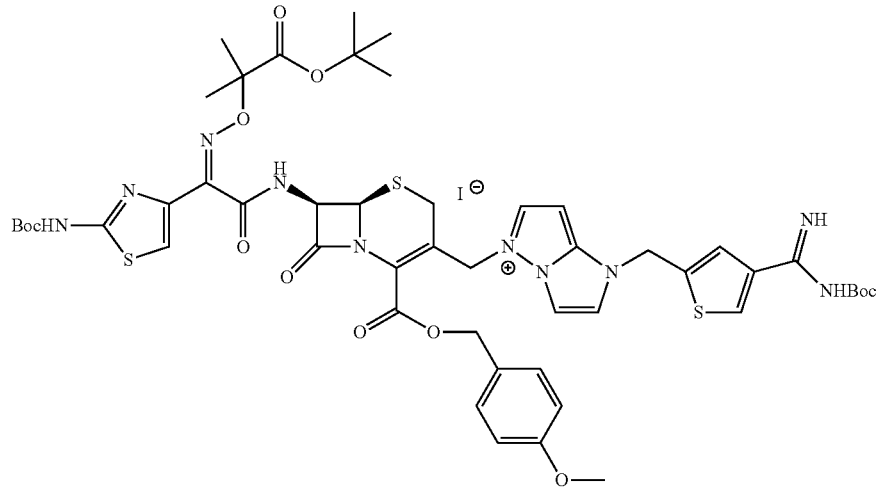 [SMILES: COc1ccc(COC(=O)C2=C(C[n+]3ccc4n(Cc5cc(C(=N)NC(=O)OC(C)(C)C)cs5)ccn43)CS[C@@H]3[C@H](NC(=O)/C(=N\OC(C)(C)C(=O)OC(C)(C)C)c4csc(NC(=O)OC(C)(C)C)n4)C(=O)N23)cc1 ; [I-]]

To a solution of tert-butyl {[5-(1H-imidazo[1,2-b]pyrazol-1-ylmethyl)thiophen-3-yl](imino)methyl}carbamate (from step 4, 0.118 g, 0.34 mmol) in anhydrous dimethylformamide (2 mL) was added (6R,7R)-7-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-(iodomethyl)-2-{[(4-methoxybenzyl)oxy]carbonyl}-8-oxo-5-thia-1-azabicyclo[4.2.0]oct-2-en-5-olate (0.303 g, 0.34 mmol) in one portion at room temperature. The reaction mixture was stirred at room temperature for 18 h. Anhydrous dimethylformamide (1 mL) was added and the reaction mixture was cooled to −40° C. Potassium iodide (0.317 g, 2.39 mmol) followed by acetyl chloride (0.107 g, 1.37 mmol) was then added at −40° C. and the reaction mixture was stirred at 0° C. for 1 h. Aqueous 5% sodium bisulphite solution (containing sodium metabisulphite, 10 mL) was added and the resulting mixture was stirred for 15 min at room temperature. The precipitated solid was collected by filtration, washed with water (3×10 mL) and air-dried. The crude product was further dried under high vacuum to afford 5-{[(6R,7R)-7-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-imidazo[1,2-b]pyrazol-5-ium iodide (0.37 g, crude) as a yellow solid which was used in the next step without further purification.

Mass: ES+ 1090.75

Step 6: (6R,7R)-7-{[(2Z)-2-(2-Amino-1,3-thiazol-4-yl)-2-{[(2-carboxypropan-2-yl)oxy]imino}acetyl]amino}-3-({1-[(4-carbamimidoylthiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate

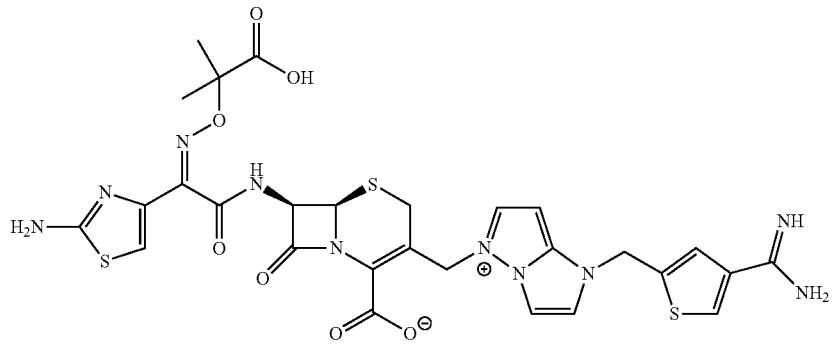 [SMILES: CC(C)(O/N=C(\C(=O)N[C@@H]1C(=O)N2C(C(=O)[O-])=C(C[n+]3ccc4n(Cc5cc(C(=N)N)cs5)ccn43)CS[C@H]12)c1csc(N)n1)C(=O)O]

To a stirred solution of 5-{[(6R,7R)-7-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-imidazo[1,2-b]pyrazol-5-ium iodide (0.37 g, 0.30 mmol) and anisole (1 mL) in anhydrous dichloromethane (7 mL) was added trifluoroacetic acid (3 mL) dropwise at 0° C. The reaction mixture was allowed to warm to room temperature and stirred for 3 h. The volatiles were then removed under reduced pressure and the residue was triturated using diisopropyl ether (15 mL). The precipitate was collected by filtration, washed with diisopropyl ether (5 mL) and dried under high vacuum to afford a yellow solid (0.33 g). The crude material was then taken in distilled water (20 mL) and the resulting suspension was stirred vigorously for 30 min at room temperature. The insoluble material was filtered off, the filtrate was collected and lyophilized. The crude product (0.16 g) was purified by prep HPLC to afford the trifluoroacetic acid salt of (6R,7R)-7-{[(2Z)-2-(2-amino-1,3-thiazol-4-yl)-2-{[(2-carboxypropan-2-yl)oxy]imino}acetyl]amino}-3-({1-[(4-carbamimidoylthiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate (15 mg; 6% over 2 steps).

$^1$H NMR (400 MHz, D$_2$O): δ 1.27 (s, 3H), 1.29 (s, 3H), 2.92 (d, 1H, J=18.0 Hz), 3.25 (d, 1H, J=18.0 Hz), 5.03 (d, 1H, J=5.1 Hz), 5.13 (s, 2H), 5.44 (s, 2H), 5.61 (d, 1H, J=4.7 Hz), 6.19 (d, 1H, J=3.5 Hz), 6.83 (s, 1H), 7.38-7.42 (m, 2H), 7.85-7.87 (m, 1H), 7.88 (d, 1H, J=4.3 Hz), 8.14 (s, 1H). Seven protons were not observed in D$_2$O.

Mass: ES$^+$ 712.37

Example 11 (Table 1, Compound 59)

(6R,7R)-7-{[(2Z)-2-(2-Amino-1,3-thiazol-4-yl)-2-(methoxyimino)acetyl]amino}-3-({1-[(4-carbamimidoylthiophen-2-yl)methyl]-1H-pyrrolo[3,2-c]pyridin-5-ium-5-yl}methyl)-8-oxo-5-thia-1-azabicyclo[4.2.0]oct-2-ene-2-carboxylate

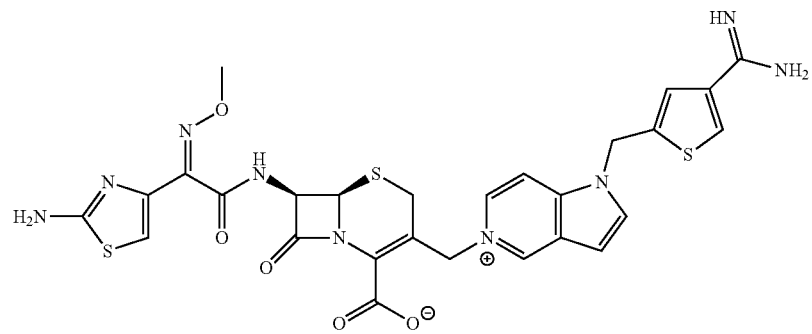 [SMILES: CO/N=C(\C(=O)N[C@@H]1C(=O)N2C(C(=O)[O-])=C(C[n+]3ccc4c(ccn4Cc4cc(C(=N)N)cs4)c3)CS[C@H]12)c1csc(N)n1]

40

Step 1: 5-{[(6R,7R)-7-{[(2Z)-2-{2-[(tert-Butoxycarbonyl)amino]-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-pyrrolo[3,2-c]pyridin-5-ium iodide

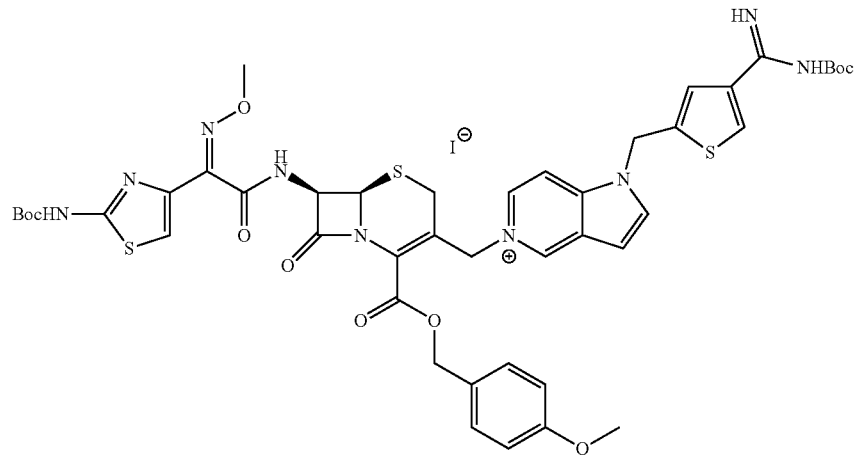 [SMILES: CO/N=C(\C(=O)N[C@@H]1C(=O)N2C(C(=O)OCc3ccc(OC)cc3)=C(C[n+]3ccc4c(ccn4Cc4cc(C(=N)NC(=O)OC(C)(C)C)cs4)c3)CS[C@H]12)c1csc(NC(=O)OC(C)(C)C)n1 ; [I-]]

To a solution tert-butyl {[5-(1H-pyrrolo[3,2-c]pyridin-1-ylmethyl)thiophen-3-yl]carbonoimidoyl}carbamate (0.12 g, 0.30 mmol) in dimethylformamide (2 mL) was added 4-methoxybenzyl (6R,7R)-7-{[(2Z)-2-{2-[(tert-butoxycarbonyl)amino]-1,3-thiazol-4-yl}-2-(methoxyimino)acetyl]amino}-3-(chloromethyl)-8-oxo-5-thia-1-azabicyclo[4.2.0]oct-2-ene-2-carboxylate (0.19 g, 0.30 mmol) at 0° C. The reaction mixture was then degassed under reduced pressure for 0.5 h, followed by adding NaI (0.09 g, 0.6 mmol) and stirred at room temperature overnight. Sodium bisulphite (0.6 g) in sodium chloride solution (75 mL) was added at 15° C. and stirred for 10 minutes. The solid was filtered, washed with water and dried under vacuum to a yellow solid (0.29 g), which was used in the next step without further purification.

Step 2: (6R,7R)-7-{[(2Z)-2-(2-Amino-1,3-thiazol-4-yl)-2-(methoxyimino)acetyl]amino}-3-({1-[(4-carbamimidoylthiophen-2-yl)methyl]-1H-pyrrolo[3,2-c]pyridin-5-ium-5-yl}methyl)-8-oxo-5-thia-1-azabicyclo[4.2.0]oct-2-ene-2-carboxylate

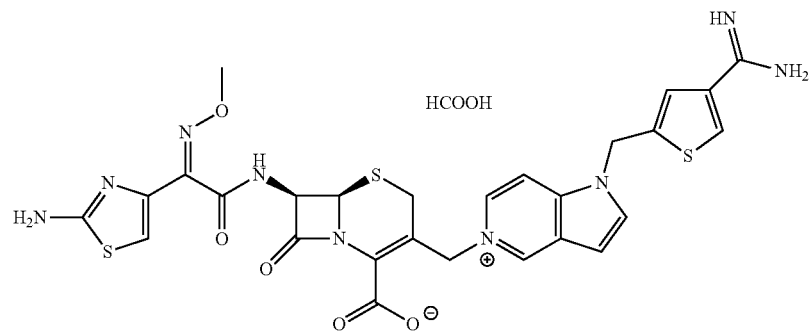 [SMILES: CO/N=C(\C(=O)N[C@@H]1C(=O)N2C(C(=O)[O-])=C(C[n+]3ccc4c(ccn4Cc4cc(C(=N)N)cs4)c3)CS[C@H]12)c1csc(N)n1 ; "HCOOH"]

To a solution of 5-{[(6R,7R)-7-{[(2Z)-2-{2-[(tert-butoxycarbonyl)amino]-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-pyrrolo[3,2-c]pyridin-5-ium iodide (0.29 g) in dry dichloromethane (2.5 mL) at 0° C. was added trifluoroacetic acid (2.5 mL) and anisole (0.82 mL, 7.75 mmol) and then stirred at room temperature for 2 h. Solvent was evaporated and diisopropyl ether (30 mL) was added. The solid separated was filtered, washed with di-isopropyl ether and dried under vacuum. The greenish yellow solid (315 mg) was dissolved in water (30 mL), filtered and the aqueous phase was lyophilized to give yellow solid (160 mg) which was purified by preparative HPLC to give (6R,7R)-7-{[(2Z)-2-(2-amino-1,3-thiazol-4-yl)-2-(methoxyimino)acetyl]amino}-3-({1-[(4-carbamimidoylthiophen-2-yl)methyl]-1H-pyrrolo[3,2-c]pyridin-5-ium-5-yl}methyl)-8-oxo-5-thia-1-azabicyclo[4.2.0]oct-2-ene-2-carboxylate as formic acid salt (0.007 g, 4%).

$^1$H NMR (400 MHz, D$_2$O): δ 3.05 (d, 1H, J=17.6 Hz), 3.45 (d, 1H, J=18.0 Hz), 3.84 (s, 3H), 5.11 (d, 1H, J=4.8 Hz), 5.21 (d, 1H, J=14.8 Hz), 5.35 (d, 1H, J=14.4 Hz), 5.70 (m, 3H), 6.84 (s, 1H), 6.98 (d, 1H, J=3.2 Hz), 7.34 (s, 1H), 7.73 (d, 1H, J=3.6 Hz), 7.88 (d, 1H, J=7.2 Hz), 8.12 (s, 1H), 8.31 (d, 1H, J=8.4 Hz), 9.08 (s, 1H). Six protons were not observed in D$_2$O.

Mass: ES$^+$ 652.15

Example 12 (Table 1, Compound 62)

(6R,7R)-7-{[(2Z)-2-(2-Amino-5-chloro-1,3-thiazol-4-yl)-2-(methoxyimino)acetyl]amino}-8-oxo-3-[(1-{[4-(N-phenylcarbamimidoyl)thiophen-2-yl]methyl}-1H-pyrrolo[3,2-c]pyridin-5-ium-5-yl)methyl]-5-thia-1-azabicyclo[4.2.0]oct-2-ene-2-carboxylate

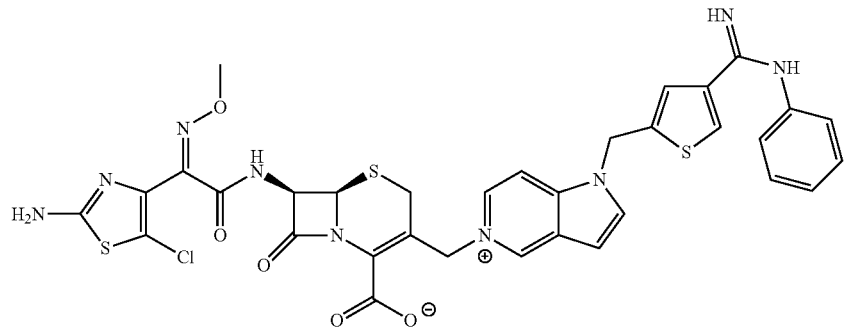 [SMILES: CO/N=C(\C(=O)N[C@@H]1C(=O)N2C(C(=O)[O-])=C(C[n+]3ccc4c(ccn4Cc4cc(C(=N)Nc5ccccc5)cs4)c3)CS[C@H]12)c1nc(N)sc1Cl]

Step 1: N-phenyl-5-(1H-pyrrolo[3,2-c]pyridin-1-ylmethyl)thiophene-3-carboximidamide

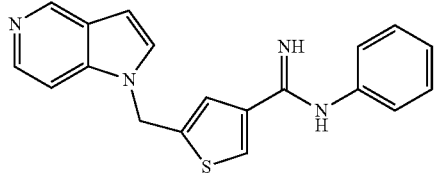 [SMILES: N=C(Nc1ccccc1)c1csc(Cn2ccc3cnccc32)c1]

To a solution of ethyl 5-(1H-pyrrolo[3,2-c]pyridin-1-ylmethyl)thiophene-3-carboximidate hydrochloride (0.5 g, 1.55 mmol) and triethylamine (0.56 mL, 4.0 mmol) in ethanol (5 mL) was added aniline (0.2.33 mmol) at room temperature. The reaction mixture was stirred at room temperature for 2 days and concentrated. The residue was purified by column chromatography using methanol: dichloromethane (15:85) as eluent to give N-phenyl-5-(1H-pyrrolo[3,2-c]pyridin-1-ylmethyl)thiophene-3-carboximidamide (0.28 g, 54%) as a beige solid.

$^1$H NMR (400 MHz, CD$_3$OD): δ 5.78 (s, 2H), 6.81 (d, 1H, J=4.4 Hz), 7.38-7.47 (m, 3H), 7.53-7.57 (m, 2H), 7.62 (m, 2H), 7.70 (d, 1H, J=6.4 Hz), 8.23 (d, 1H, J=6.4 Hz), 8.35 (s, 1H), 8.87 (s, 1H). Two protons were not observed in CD$_3$OD.

Step 2: 5-{[(6R,7R)-7-{[(2Z)-2-{2-[(tert-Butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{[4-(N-phenylcarbamimidoyl)thiophen-2-yl]methyl}-1H-pyrrolo[3,2-c]pyridin-5-ium iodide

To a solution N-phenyl-5-(1H-pyrrolo[3,2-c]pyridin-1-ylmethyl)thiophene-3-carboximidamide (0.10 g, 0.30 mmol) in dimethylformamide (2 mL) was added 4-methoxybenzyl (6R,7R)-7-{[(2Z)-2-{2-[(tert-butoxycarbonyl)amino]-5-chloro-1,3-thiazol-4-yl}-2-(methoxyimino)acetyl]amino}-3-(chloromethyl)-8-oxo-5-thia-1-azabicyclo[4.2.0]oct-2-ene-2-carboxylate (0.21 g, 0.30 mmol) at 0° C. The reaction mixture was then degassed under reduced pressure for 0.5 h, followed by adding NaI (0.09 g, 0.6 mmol) and stirred at room temperature overnight. Sodium bisulphite (0.6 g) in sodium chloride solution (75 mL) was added at 15° C. and stirred for 10 minutes. The solid was filtered off, washed with water and dried under vacuum to a yellow solid (0.28 g), which was used in the next step without further purification.

Step 3: (6R,7R)-7-{[(2Z)-2-(2-Amino-5-chloro-1,3-thiazol-4-yl)-2-(methoxyimino)acetyl]amino}-8-oxo-3-[(1-{[4-(N-phenylcarbamimidoyl)thiophen-2-yl]methyl}-1H-pyrrolo[3,2-c]pyridin-5-ium-5-yl)methyl]-5-thia-1-azabicyclo[4.2.0]oct-2-ene-2-carboxylate

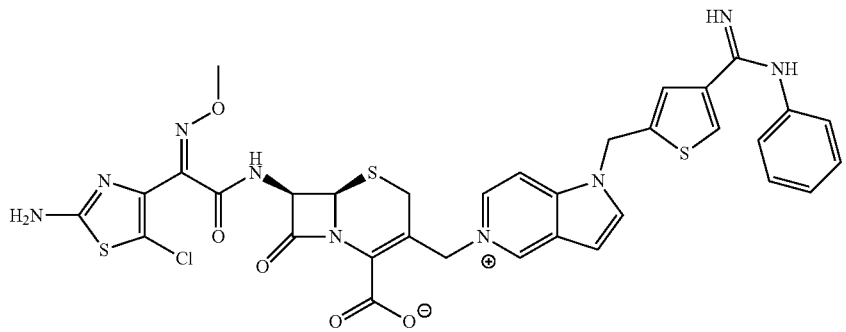 [SMILES: CO/N=C(\C(=O)N[C@@H]1C(=O)N2C(C(=O)[O-])=C(C[n+]3ccc4c(ccn4Cc4cc(C(=N)Nc5ccccc5)cs4)c3)CS[C@H]12)c1nc(N)sc1Cl]

To a solution of 5-{[(6R,7R)-7-{[(2Z)-2-{2-[(tert-butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{[4-(N-phenylcarbamimidoyl)thiophen-2-yl]methyl}-1H-pyrrolo[3,2-c]pyridin-5-ium iodide (0.28 g) in dry dichloromethane (2.5 mL) at 0° C. was added trifluoroacetic acid (2.5 mL) and anisole (0.82 mL, 7.75 mmol) and then stirred at room temperature for 2 h. Solvent was evaporated and diisopropyl ether (30 mL) was added. The solid was filtered, washed with diisopropyl ether and dried under vacuum. The greenish yellow solid (315 mg) was dissolved in water (30 mL), filtered and the aqueous phase was lyophilized to give yellow solid (160 mg) which was purified by preparative HPLC to give (6R,7R)-7-{[(2Z)-2-(2-amino-5-chloro-1,3-thiazol-4-yl)-2-(methoxyimino)acetyl]amino}-8-oxo-3-[(1-{[4-(N-phenylcarbamimidoyl)thiophen-2-yl]methyl}-1H-pyrrolo[3,2-c]pyridin-5-ium-5-yl)methyl]-5-thia-1-azabicyclo[4.2.0]oct-2-ene-2-carboxylate as formic acid salt (0.01 g, 5%).

$^1$H NMR (400 MHz, D$_2$O): δ 3.05 (d, 1H, J=18.0 Hz), 3.43 (d, 1H, J=18.0 Hz), 3.84 (s, 3H), 5.10 (d, 1H, J=4.8 Hz), 5.22 (d, 1H, J=15.2 Hz), 5.35 (d, 1H, J=14.4 Hz), 5.71 (d, 1H, J=4.8 Hz), 5.76 (s, 2H), 7.00 (d, 1H, J=3.2 Hz), 7.30 (d, 2H, J=7.2 Hz), 7.41-7.49 (m, 4H), 7.78 (d, 1H, J=3.2 Hz), 7.92 (d, 1H, J=7.6 Hz), 8.21 (s, 1H), 8.33 (d, 1H, J=8.0 Hz), 9.09 (s, 1H). Five protons were not observed in D$_2$O.

Mass: ES$^+$ 662.09

Example 13 (Table 1, Compound 63)

(6R,7R)-7-{[(2Z)-2-(2-Amino-5-chloro-1,3-thiazol-4-yl)-2-(methoxyimino)acetyl]amino}-8-oxo-3-[(1-{[4-(pyrrolidin-1-ylcarbonoimidoyl)thiophen-2-yl]methyl}-1H-pyrrolo[3,2-c]pyridin-5-ium-5-yl)methyl]-5-thia-1-azabicyclo[4.2.0]oct-2-ene-2-carboxylate

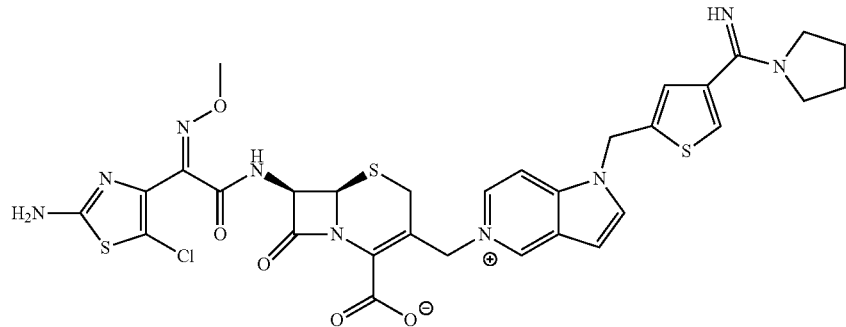 [SMILES: CO/N=C(\C(=O)N[C@@H]1C(=O)N2C(C(=O)[O-])=C(C[n+]3ccc4c(ccn4Cc4cc(C(=N)N5CCCC5)cs4)c3)CS[C@H]12)c1nc(N)sc1Cl]

Step 1: 1-(Pyrrolidin-1-yl)-1-[5-(1H-pyrrolo[3,2-c]pyridin-1-ylmethyl)thiophen-3-yl]methanimine

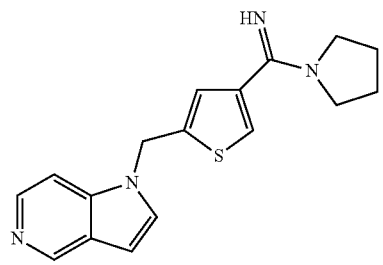 [SMILES: N=C(c1csc(Cn2ccc3cnccc32)c1)N1CCCC1]

To a solution of ethyl 5-(1H-pyrrolo[3,2-c]pyridin-1-ylmethyl)thiophene-3-carboximidate hydrochloride (0.5 g, 1.55 mmol) and triethylamine (0.56 mL, 4.0 mmol) in ethanol (5 mL) was added pyrrolidine (0.2 g, 2.81 mmol) at room temperature. The reaction mixture was stirred at room temperature for 2 days and concentrated. The residue was purified by column chromatography using methanol: dichloromethane (15:85) as eluent to give 1-(pyrrolidin-1-yl)-1-[5-(1H-pyrrolo[3,2-c]pyridin-1-ylmethyl)thiophen-3-yl]methanimine (0.26 g, 54%) as a beige solid.

$^1$H NMR (400 MHz, CD$_3$OD): δ 1.96 (m, 2H), 2.14 (m, 2H), 3.30 (m, 4H), 5.64 (s, 2H), 6.74 (d, 1H, J=4.0 Hz), 7.38 (s, 1H), 7.51 (d, 1H, J=3.6 Hz), 7.57 (d, 1H, J=6.0 Hz), 7.99 (s, 1H), 8.18 (d, 1H, J=5.6 Hz), 8.81 (s, 1H). One proton was not observed in CD$_3$OD.

Step 2: 5-{[(6R,7R)-7-{[(2Z)-2-{2-[(tert-Butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{[4-(pyrrolidin-1-ylcarbonoimidoyl)thiophen-2-yl]methyl}-1H-pyrrolo[3,2-c]pyridin-5-ium iodide

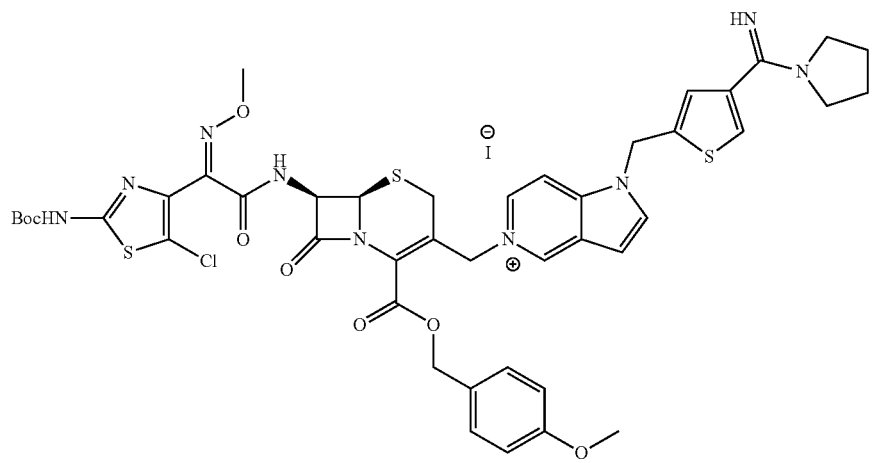 [SMILES: CO/N=C(\C(=O)N[C@@H]1C(=O)N2C(C(=O)OCc3ccc(OC)cc3)=C(C[n+]3ccc4c(ccn4Cc4cc(C(=N)N5CCCC5)cs4)c3)CS[C@H]12)c1nc(NC(=O)OC(C)(C)C)sc1Cl ; [I-]]

To a solution 1-(pyrrolidin-1-yl)-1-[5-(1H-pyrrolo[3,2-c]pyridin-1-ylmethyl)thiophen-3-yl]methanimine (0.093 g, 0.30 mmol) in dimethylformamide (2 mL) was added 4-methoxybenzyl (6R,7R)-7-{[(2Z)-2-{2-[(tert-butoxycarbonyl)amino]-5-chloro-1,3-thiazol-4-yl}-2-(methoxyimino)acetyl]amino}-3-(chloromethyl)-8-oxo-5-thia-1-azabicyclo[4.2.0]oct-2-ene-2-carboxylate (0.21 g, 0.30 mmol) at 0° C. The reaction mixture was then degassed under reduced pressure for 0.5 h, followed by adding NaI (0.09 g, 0.6 mmol) and stirred at room temperature overnight. Sodium bisulphite (0.6 g) in sodium chloride solution (75 mL) was added at 15° C. and stirred for 10 minutes. The solid separated was filtered, washed with water and dried under vacuum to a yellow solid (0.28 g), which was used in the next step without further purification.

Step 3: (6R,7R)-7-{[(2Z)-2-(2-Amino-5-chloro-1,3-thiazol-4-yl)-2-(methoxyimino)acetyl]amino}-8-oxo-3-[(1-{[4-(pyrrolidin-1-ylcarbonoimidoyl)thiophen-2-yl]methyl}-1H-pyrrolo[3,2-c]pyridin-5-ium-5-yl)methyl]-5-thia-1-azabicyclo[4.2.0]oct-2-ene-2-carboxylate

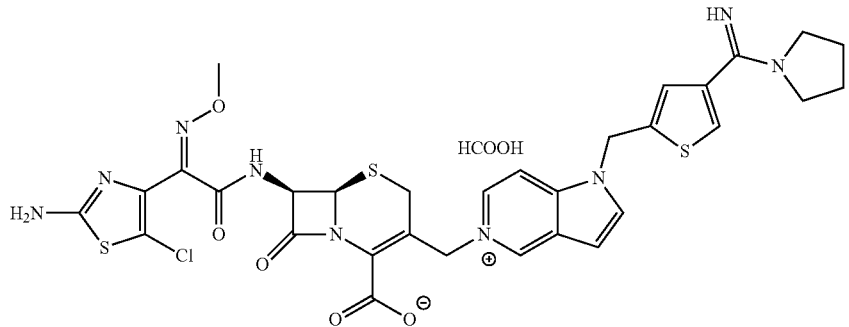 [SMILES: CO/N=C(\C(=O)N[C@@H]1C(=O)N2C(C(=O)[O-])=C(C[n+]3ccc4c(ccn4Cc4cc(C(=N)N5CCCC5)cs4)c3)CS[C@H]12)c1nc(N)sc1Cl ; "HCOOH"]

To a solution of 5-{[(6R,7R)-7-{[(2Z)-2-{2-[(tert-butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{[4-(pyrrolidin-1-ylcarbonoimidoyl)thiophen-2-yl]methyl}-1H-pyrrolo[3,2-c]pyridin-5-ium iodide (0.29 g) in dry dichloromethane (2.5 mL) at 0° C. was added trifluoroacetic acid (2.5 mL) and anisole (0.82 mL, 7.75 mmol) and then stirred at room temperature for 2 h. Solvent was evaporated and diisopropyl ether (30 mL) was added to the residue and the solid separated was filtered, washed with diisopropyl ether then dried under vacuum. The greenish yellow solid (315 mg) was dissolved in water (30 mL), filtered and the aqueous phase was lyophilized to give yellow solid (160 mg) which was purified by preparative HPLC to give (6R,7R)-7-{[(2Z)-2-(2-amino-5-chloro-1,3-thiazol-4-yl)-2-(methoxyimino)acetyl]amino}-8-oxo-3-[(1-{[4-(pyrrolidin-1-ylcarbonoimidoyl)thiophen-2-yl]methyl}-H-pyrrolo[3,2-c]pyridin-5-ium-5-yl)methyl]-5-thia-1-azabicyclo[4.2.0]oct-2-ene-2-carboxylate as formic acid salt (0.011 g, 5.7%).

$^1$H NMR (200 MHz, D$_2$O): δ 1.79 (m, 2H), 1.97 (m, 2H), 3.03 (d, 1H, J=18.0 Hz), 3.42 (m, 5H), 3.84 (s, 3H), 5.10 (d, 1H, J=4.4 Hz), 5.21 (d, 1H, J=14.8 Hz), 5.35 (d, 1H, J=14.4 Hz), 5.70 (m, 3H), 6.98 (d, 1H, J=3.2 Hz), 7.22 (s, 1H), 7.74 (d, 1H, J=3.2 Hz), 7.85 (s, 1H), 7.89 (d, 1H, J=7.2 Hz), 8.32 (d, 1H, 7.2 Hz), 9.08 (s, 1H). Four protons were not observed in D$_2$O.

Mass: ES$^+$ 740.13

Example 14 (Table 1, Compound 64)

(6R,7R)-7-{[(2Z)-2-(2-Amino-5-chloro-1,3-thiazol-4-yl)-2-(methoxyimino)acetyl]amino}-8-oxo-3-{[1-({4-[N-(1,3-thiazol-2-yl)carbamimidoyl]thiophen-2-yl}methyl)-1H-pyrrolo[3,2-c]pyridin-5-ium-5-yl]methyl}-5-thia-1-azabicyclo[4.2.0]oct-2-ene-2-carboxylate

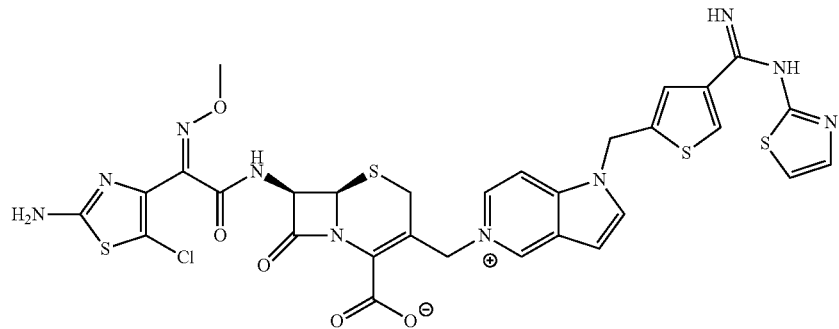 [SMILES: CO/N=C(\C(=O)N[C@@H]1C(=O)N2C(C(=O)[O-])=C(C[n+]3ccc4c(ccn4Cc4cc(C(=N)Nc5nccs5)cs4)c3)CS[C@H]12)c1nc(N)sc1Cl]

Step 1: 5-(1H-Pyrrolo[3,2-c]pyridin-1-ylmethyl)-N-(1,3-thiazol-2-yl)thiophene-3-carboximidamide

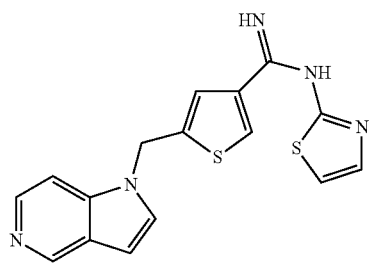 [SMILES: N=C(Nc1nccs1)c1csc(Cn2ccc3cnccc32)c1]

To a solution of ethyl 5-(1H-pyrrolo[3,2-c]pyridin-1-ylmethyl)thiophene-3-carboximidate hydrochloride (0.5 g, 1.55 mmol) and triethylamine (0.56 mL, 4.0 mmol) in ethanol (5 mL) was added 1,3-thiazol-2-amine (0.25 g, 2.33 mmol) at room temperature. The reaction mixture was stirred at room temperature for 2 days and concentrated. The residue was purified by column chromatography using methanol: dichloromethane (15:85) as eluent to give 5-(1H-pyrrolo[3,2-c]pyridin-1-ylmethyl)-N-(1,3-thiazol-2-yl)thiophene-3-carboximidamide (0.22 g, 42%) as a beige solid.

$^1$H NMR (400 MHz, CD$_3$OD): δ 5.43 (s, 2H), 6.65 (d, 1H, J=4.0 Hz), 7.16 (m, 2H), 7.27 (m, 2H), 7.44 (m, 1H, J=6.0 Hz), 7.64 (s, 1H), 8.32 (d, 1H, J=6.0 Hz), 8.92 (s, 1H).

Step 2: 5-{[(6R,7R)-7-{[(2Z)-2-{2-[(tert-Butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-({4-[N-(1,3-thiazol-2-yl)carbamimidoyl]thiophen-2-yl}methyl)-1H-pyrrolo[3,2-c]pyridin-5-ium iodide

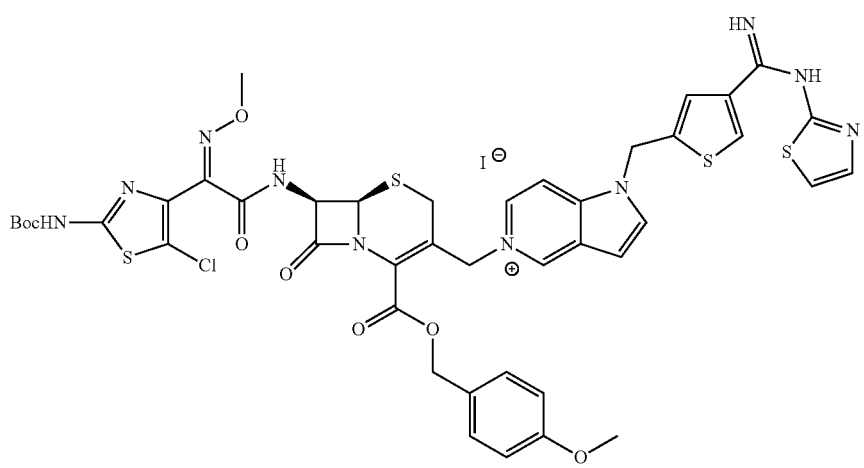 [SMILES: CO/N=C(\C(=O)N[C@@H]1C(=O)N2C(C(=O)OCc3ccc(OC)cc3)=C(C[n+]3ccc4c(ccn4Cc4cc(C(=N)Nc5nccs5)cs4)c3)CS[C@H]12)c1nc(NC(=O)OC(C)(C)C)sc1Cl ; [I-]]

To a solution of 5-(1H-pyrrolo[3,2-c]pyridin-1-ylmethyl)-N-(1,3-thiazol-2-yl)thiophene-3-carboximidamide (0.102 g, 0.30 mmol) in dimethylformamide (2 mL) was added 4-methoxybenzyl (6R,7R)-7-{[(2Z)-2-{2-[(tert-butoxycarbonyl)amino]-5-chloro-1,3-thiazol-4-yl}-2-(methoxyimino)acetyl]amino}-3-(chloromethyl)-8-oxo-5-thia-1-azabicyclo[4.2.0]oct-2-ene-2-carboxylate (0.21 g, 0.30 mmol) at 0° C. The reaction mixture was then degassed under reduced pressure for 0.5 h, followed by adding NaI (0.09 g, 0.6 mmol) and stirred at room temperature overnight. Sodium bisulphite (0.6 g) in sodium chloride solution (75 mL) was added at 0° C., stirred for 10 minutes and the solid separated was filtered, washed with water and dried under vacuum to a yellow solid (0.3 g), which was used in the next step without further purification.

Step 3: (6R,7R)-7-{[(2Z)-2-(2-Amino-5-chloro-1,3-thiazol-4-yl)-2-(methoxyimino)acetyl]amino}-8-oxo-3-{[1-({4-[N-(1,3-thiazol-2-yl)carbamimidoyl]thiophen-2-yl}methyl)-1H-pyrrolo[3,2-c]pyridin-5-ium-5-yl]methyl}-5-thia-1-azabicyclo[4.2.0]oct-2-ene-2-carboxylate

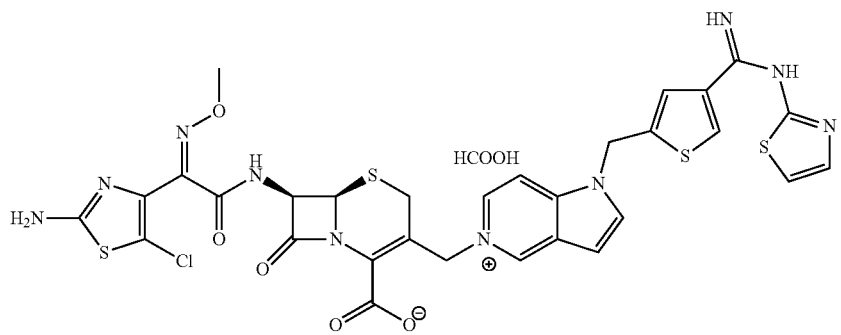 [SMILES: CO/N=C(\C(=O)N[C@@H]1C(=O)N2C(C(=O)[O-])=C(C[n+]3ccc4c(ccn4Cc4cc(C(=N)Nc5nccs5)cs4)c3)CS[C@H]12)c1nc(N)sc1Cl ; "HCOOH"]

To a solution of 5-{[(6R,7R)-7-{[(2Z)-2-{2-[(tert-butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-({4-[N-(1,3-thiazol-2-yl)carbamimidoyl]thiophen-2-yl}methyl)-1H-pyrrolo[3,2-c]pyridin-5-ium iodide (0.3 g) in dry dichloromethane (2.5 mL) at 0° C. was added trifluoroacetic acid (2.5 mL) and anisole (0.82 mL, 7.75 mmol) and then stirred at room temperature for 2 h, then the solvent was evaporated and diisopropyl ether (30 mL) was added. The solid was filtered, washed with diisopropyl ether and dried under vacuum. The greenish yellow solid (315 mg) was dissolved in water (30 mL), filtered and the aqueous phase was lyophilized to give yellow solid (160 mg) which was purified by preparative HPLC to give (6R,7R)-7-{[(2Z)-2-(2-amino-5-chloro-1,3-thiazol-4-yl)-2-(methoxyimino)acetyl]amino}-8-oxo-3-{[1-({4-[N-(1,3-thiazol-2-yl)carbamimidoyl]thiophen-2-yl}methyl)-1H-pyrrolo[3,2-c]pyridin-5-ium-5-yl]methyl}-5-thia-1-azabicyclo[4.2.0]oct-2-ene-2-carboxylate as formic acid salt (0.005 g, 2.5%).

$^1$H NMR (400 MHz, $D_2O$): δ 3.03 (d, 1H, J=17.6 Hz), 3.43 (d, 1H, J=17.2 Hz), 3.84 (s, 3H), 5.11 (d, 1H, J=4.8 Hz), 5.21 (d, 1H, J=13.6 Hz), 5.36 (d, 1H, J=14.0 Hz), 5.72 (m, 3H), 7.01 (d, 1H, J=4.2 Hz), 7.25 (d, 1H, J=3.6 Hz), 7.41 (d, 1H, J=7.6 Hz), 7.49 (m, 1H), 7.75 (m, 1H), 7.92 (d, 1H, J=7.2 Hz), 8.20 (s, 1H), 8.33 (d, 1H, J=7.6 Hz), 9.06 (s, 1H). Five protons were not observed in $D_2O$.

Mass: ES$^+$ 769.03

Example 15 (Table 1, Compound 60)

(6R,7R)-7-{[(2Z)-2-(2-Amino-5-chloro-1,3-thiazol-4-yl)-2-(methoxyimino)acetyl]amino}-3-({1-[(4-carbamimidoylthiophen-2-yl)methyl]-1H-pyrrolo[3,2-b]pyridin-4-ium-4-yl}methyl)-8-oxo-5-thia-1-azabicyclo[4.2.0]oct-2-ene-2-carboxylate

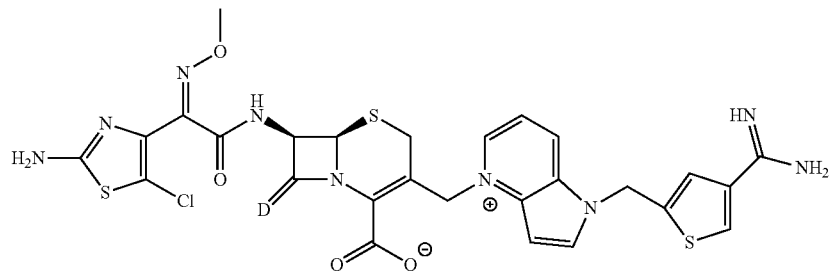

Step 1: 5-(1H-Pyrrolo[3,2-b]pyridin-1-ylmethyl)thiophene-3-carbonitrile

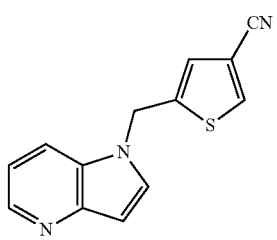 [SMILES: N#Cc1csc(Cn2ccc3ncccc32)c1]

To a solution of 1H-pyrrolo[3,2-b]pyridine (0.59 g, 5.00 mmol) in anhydrous dimethylformamide (10 mL) was added sodium hydride (60% suspension in mineral oil, 0.29 g, 7.25 mmol) at 0° C. in small portions under nitrogen. After the addition, the mixture was stirred for 10 minutes at 0° C. and then at room temperature for 10 minutes, cooled to 0° C. and was added 5-(bromomethyl)thiophene-3-carbonitrile (1.11 g, 5.50 mmol) in anhydrous tetrahydrofuran (10 mL) dropwise. After the addition, the reaction mixture was stirred at 0° C. for 1.5 h, quenched with ice-water (10 mL) and extracted with ethyl acetate (20 mL×2). The combined organic layers were washed with brine, dried over Na$_2$SO$_4$, filtered and evaporated. The residue was purified by column chromatography using DCM: MeOH (92:8) as eluent to afford 5-(1H-pyrrolo[3,2-b]pyridin-1-ylmethyl)thiophene-3-carbonitrile (1.0 g, 80%) as a brown solid.

$^1$H NMR (400 MHz, CDCl$_3$): δ 5.47 (s, 2H), 6.79 (d, 1H, J=4.0 Hz), 7.10 (s, 1H), 7.12 (m, 1H), 7.36 (d, 1H, J=3.6 Hz), 7.58 (d, 1H, J=10.4 Hz), 7.82 (s, 1H), 8.50 (d, 1H, J=6.0 Hz).

Step 2: Methyl 5-(1H-pyrrolo[3,2-b]pyridin-1-ylmethyl)thiophene-3-carboximidate hydrochloride

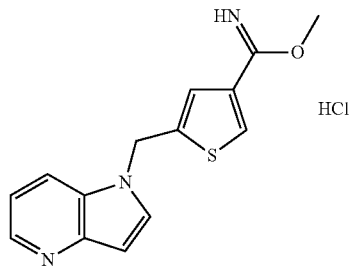 [SMILES: COC(=N)c1csc(Cn2ccc3ncccc32)c1 ; Cl]

Anhydrous hydrogen chloride gas was bubbled through a solution of 5-(1H-pyrrolo[3,2-b]pyridin-1-ylmethyl)thiophene-3-carbonitrile (1.0 g, 4.18 mmol) in anhydrous ethanol (30 mL) at 0° C. for 20 minutes. The reaction mixture was stirred at room temperature for 20 h and the solvent was evaporated and dried under vacuum to give methyl 5-(1H-pyrrolo[3,2-b]pyridin-1-ylmethyl)thiophene-3-carboximidate hydrochloride (0.97 g crude) as brown solid, which was used in next step without further purification.

Step 3: 5-(1H-Pyrrolo[3,2-b]pyridin-1-ylmethyl)thiophene-3-carboximidamide

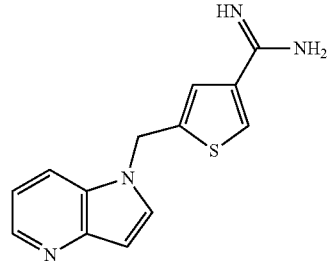 [SMILES: N=C(N)c1csc(Cn2ccc3ncccc32)c1]

Anhydrous ammonia gas was bubbled through a solution of methyl 5-(1H-pyrrolo[3,2-b]pyridin-1-ylmethyl)thiophene-3-carboximidate hydrochloride (0.97 g crude, ~4.1 mmol) in anhydrous methanol (40 mL) at 0° C. for 15 minutes. Then the reaction mixture was stirred at room temperature for 16 h. Solvent was evaporated and dried under vacuum to give 5-(1H-pyrrolo[3,2-b]pyridin-1-ylmethyl)thiophene-3-carboximidamide (1.2 g, crude) as a brown solid which was used in the next step without further purification.

Step 4: tert-Butyl {[5-(1H-pyrrolo[3,2-b]pyridin-1-ylmethyl)thiophen-3-yl]carbonoimidoyl}carbamate

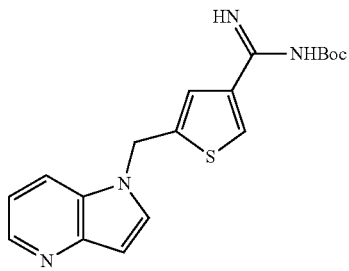 [SMILES: CC(C)(C)OC(=O)NC(=N)c1csc(Cn2ccc3ncccc32)c1]

To a solution of 5-(1H-pyrrolo[3,2-b]pyridin-1-ylmethyl)thiophene-3-carboximidamide (0.97 g, crude) in 1,4-dioxane (100 mL) was added aqueous saturated sodium carbonate solution (50 mL) followed by di-tert-butyldicarbonate (3.30 g, 15.12 mmol) at 0° C. The reaction mixture was stirred at room temperature for 16 h, the solvent was evaporated and was added water (50 mL) was added then extracted with ethyl acetate (2×50 mL). The organic phases were combined, washed with brine (2×50 mL) and dried over Na$_2$SO$_4$. The solvent was evaporated and the crude compound was purified by flash chromatography using RediSep silica 40 g flash column (0-6% methanol in methylene chloride as eluent) to give tert-butyl {[5-(1H-pyrrolo[3,2-b]pyridin-1-ylmethyl)thiophen-3-yl]carbonoimidoyl}carbamate (1.2 g, 61% over three steps) as an off-white solid.

$^1$H NMR (400 MHz, CDCl$_3$): δ 1.51 (s, 9H), 5.39 (s, 2H), 6.66 (d, 1H, J=4.00 Hz), 7.06 (m, 1H), 7.32 (d, 1H, J=3.2 Hz), 7.42 (s, 1H), 7.58 (d, 1H, J=10.4 Hz), 7.87 (s, 1H), 8.42 (d, 1H, J=5.6 Hz).

Step 5: 4-{[(6R,7R)-7-{[(2Z)-2-{2-[(tert-Butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-pyrrolo[3,2-b]pyridin-4-ium iodide

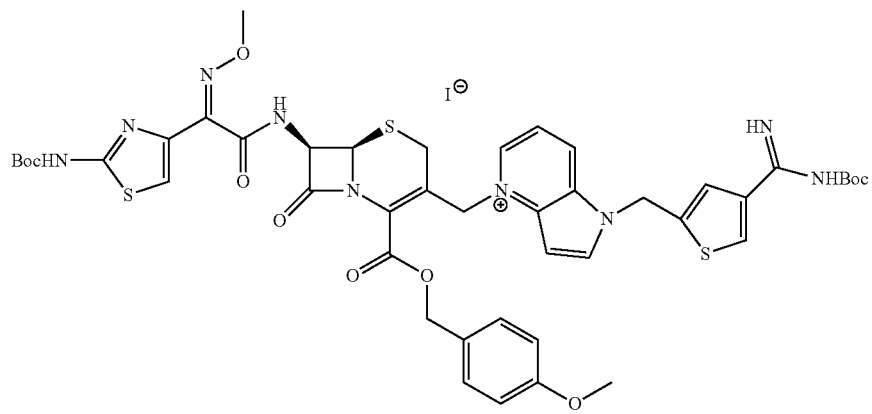 [SMILES: CO/N=C(\C(=O)N[C@@H]1C(=O)N2C(C(=O)OCc3ccc(OC)cc3)=C(C[n+]3cccc4c3ccn4Cc3cc(C(=N)NC(=O)OC(C)(C)C)cs3)CS[C@H]12)c1csc(NC(=O)OC(C)(C)C)n1 ; [I-]]

To a solution tert-butyl {[5-(1H-pyrrolo[3,2-b]pyridin-1-ylmethyl)thiophen-3-yl]carbonoimidoyl}carbamate (0.12 g, 0.30 mmol) in dimethylformamide (2 mL) was added 4-methoxybenzyl (6R,7R)-7-{[(2Z)-2-{2-[(tert-butoxycarbonyl)amino]-5-chloro-1,3-thiazol-4-yl}-2-(methoxyimino)acetyl]amino}-3-(chloromethyl)-8-oxo-5-thia-1-azabicyclo[4.2.0]oct-2-ene-2-carboxylate (0.21 g, 0.30 mmol) at 0° C. The reaction mixture was then degassed under reduced pressure for 0.5 h, followed by adding NaI (0.09 g, 0.6 mmol) and stirred at room temperature overnight. Sodium bisulphite (0.6 g) in sodium chloride solution (75 mL) was added at 15° C. and stirred for 10 minutes. The solid was filtered, washed with water and dried under vacuum to a yellow solid (0.3 g), which was used in the next step without further purification.

Step 6: (6R,7R)-7-{[(2Z)-2-(2-Amino-5-chloro-1,3-thiazol-4-yl)-2-(methoxyimino)acetyl]amino}-3-({1-[(4-carbamimidoylthiophen-2-yl)methyl]-1H-pyrrolo[3,2-b]pyridin-4-ium-4-yl}methyl)-8-oxo-5-thia-1-azabicyclo[4.2.0]oct-2-ene-2-carboxylate

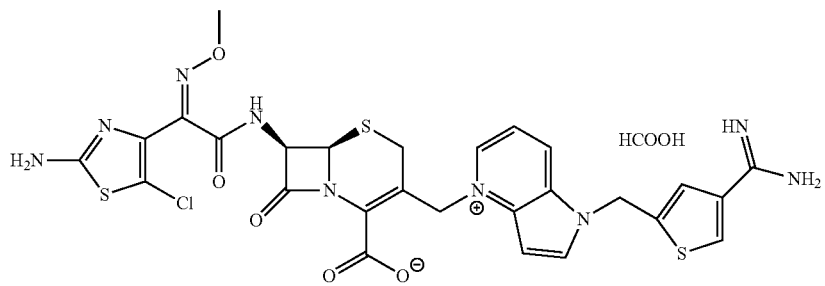 [SMILES: CO/N=C(\C(=O)N[C@@H]1C(=O)N2C(C(=O)[O-])=C(C[n+]3cccc4c3ccn4Cc3cc(C(=N)N)cs3)CS[C@H]12)c1nc(N)sc1Cl ; "HCOOH"]

To a solution of 4-{[(6R,7R)-7-{[(2Z)-2-{2-[(tert-butoxy-carbonyl)amino]-5-chloro-1,3-thiazol-4-yl}-2-(methoxy-imino)acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-pyrrolo[3,2-b]pyridin-4-ium iodide (0.3 mg, crude)) in dry dichloromethane (2.5 mL) at 0° C. was added trifluoroacetic acid (2.5 mL) and anisole (0.82 mL, 7.75 mmol) and then stirred at room temperature for 2 h. Solvent was evaporated, diisopropyl ether (30 mL) was added, and the solid separated was filtered, washed with diisopropyl ether and dried under vacuum. The greenish yellow solid (315 mg) was dissolved in water (30 mL), filtered and the aqueous phase was lyophilized to give yellow solid (165 mg), which was purified by preparative HPLC to give (6R,7R)-7-{[(2Z)-2-(2-amino-5-chloro-1,3-thiazol-4-yl)-2-(methoxyimino)acetyl]amino}-3-({1-[(4-carbamimidoylthiophen-2-yl)methyl]-1H-pyrrolo[3,2-b]pyridin-4-ium-4-yl}methyl)-8-oxo-5-thia-1-azabicyclo[4.2.0]oct-2-ene-2-carboxylate as formic acid salt (0.007 g, 3.9%).

$^1$H NMR (400 MHz, D$_2$O): δ 3.08 (d, 1H, J=18.0 Hz), 3.23 (d, 1H, J=17.6 Hz), 3.86 (s, 3H), 5.04 (d, 1H, J=4.8 Hz), 5.39 (d, 1H, J=15.2 Hz), 5.67 (d, 1H, J=14.8 Hz), 5.71 (d, 1H, J=4.4 Hz), 5.76 (s, 2H), 6.93 (d, 1H, J=3.6 Hz), 7.35 (s, 1H), 7.55 (m, 1H), 8.09 (d, 1H, J=3.2 Hz), 8.13 (s, 1H), 8.49 (m, 2H). Six protons were not observed in D$_2$O.

Mass: ES$^+$ 686.14

Example 16 (Table 1, Compound 61)

(6R,7R)-7-{[(2Z)-2-(2-Amino-5-chloro-1,3-thiazol-4-yl)-2-(methoxyimino)acetyl]amino}-3-({1-[(4-carbamimidoylthiophen-2-yl)methyl]-1H-pyrrolo[2,3-c]pyridin-6-ium-6-yl}methyl)-8-oxo-5-thia-1-azabicyclo[4.2.0]oct-2-ene-2-carboxylate

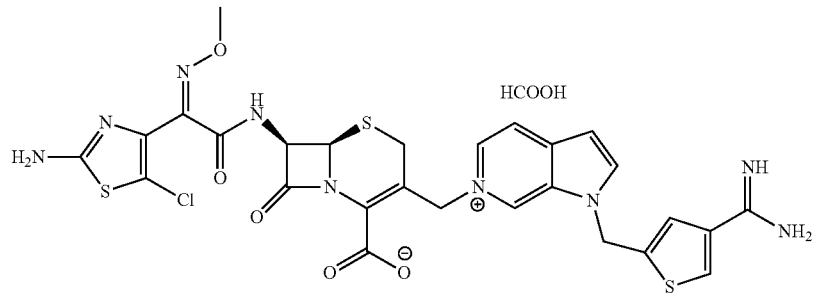 [SMILES: CO/N=C(\C(=O)N[C@@H]1C(=O)N2C(C(=O)[O-])=C(C[n+]3ccc4ccn(Cc5cc(C(=N)N)cs5)c4c3)CS[C@H]12)c1nc(N)sc1Cl ; "HCOOH"]

Step 1: 5-(1H-Pyrrolo[2,3-c]pyridin-1-ylmethyl)thiophene-3-carbonitrile

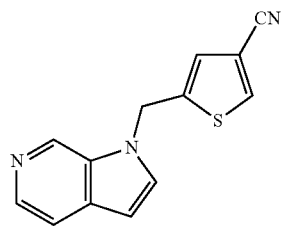 [SMILES: N#Cc1csc(Cn2ccc3ccncc32)c1]

To a solution of 1H-pyrrolo[2,3-c]pyridine (0.59 g, 5.00 mmol) in anhydrous dimethylformamide (10 mL) was added sodium hydride (60% suspension in mineral oil, 0.29 g, 7.25 mmol) at 0° C. in small portions under nitrogen. After the addition, reaction mixture was stirred for 10 minutes at 0° C., then at room temperature for 10 minutes, cooled to 0° C. then 5-(bromomethyl)thiophene-3-carbonitrile (1.11 g, 5.50 mmol) in anhydrous tetrahydrofuran (10 mL) was added dropwise. After the addition, reaction mixture was stirred at 0° C. for 1.5 h, quenched with ice-water (10 mL) and extracted with ethyl acetate (20 mL×2). The combined organic layers were washed with brine, dried over Na$_2$SO$_4$, filtered and evaporated. The residue was purified by column chromatography using DCM: MeOH (92:8) as eluent to afford 5-(1H-pyrrolo[2,3-c]pyridin-1-ylmethyl)thiophene-3-carbonitrile (0.88 g, 73%) as a brown solid. $^1$H NMR (400 MHz, CDCl$_3$): δ 5.56 (s, 2H), 6.59 (d, 1H, J=2.8 Hz), 7.13 (s, 1H), 7.27 (d, 1H, J=6.8 Hz), 7.54 (d, 1H, J=5.2 Hz), 7.82 (s, 1H), 8.29 (d, 1H, J=5.2 Hz), 8.73 (s, 1H).

Step 2: Methyl 5-(1H-pyrrolo[2,3-c]pyridin-1-ylmethyl)thiophene-3-carboximidate hydrochloride

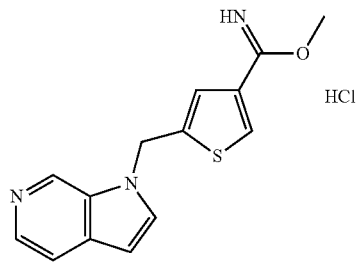 [SMILES: COC(=N)c1csc(Cn2ccc3ccncc32)c1 ; Cl]

Anhydrous hydrogen chloride gas was bubbled through a solution of 5-(1H-pyrrolo[2,3-c]pyridin-1-ylmethyl)thiophene-3-carbonitrile (0.8 g, 3.34 mmol) in anhydrous ethanol (30 mL) at 0° C. for 20 minutes. Then the reaction mixture was stirred at room temperature for 20 h. Solvent was evaporated and dried under vacuum to give methyl 5-(1H-pyrrolo[2,3-c]pyridin-1-ylmethyl)thiophene-3-carboximidate hydrochloride (1.0 g, crude) as brown solid, which was used in next step without further purification.

Step 3: 5-(1H-Pyrrolo[2,3-c]pyridin-1-ylmethyl)thiophene-3-carboximidamide

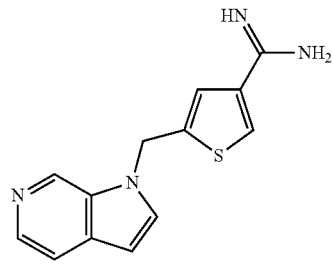 [SMILES: N=C(N)c1csc(Cn2ccc3ccncc32)c1]

Anhydrous ammonia gas was bubbled through a solution of methyl 5-(1H-pyrrolo[2,3-c]pyridin-1-ylmethyl)thiophene-3-carboximidate hydrochloride (1.0 g crude, ~4.1 mmol) in anhydrous methanol (40 mL) at 0° C. for 15 minutes. The reaction mixture was stirred at room temperature for 16 h. Solvent was evaporated and dried under vacuum to give 5-(1H-pyrrolo[2,3-c]pyridin-1-ylmethyl)thiophene-3-carboximidamide (0.73 g, crude) as a brown solid, which was used in the next step without further purification.

Step 4: tert-Butyl {[5-(1H-pyrrolo[2,3-c]pyridin-1-ylmethyl)thiophen-3-yl]carbonoimidoyl}carbamate

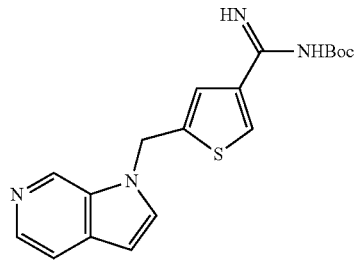 [SMILES: CC(C)(C)OC(=O)NC(=N)c1csc(Cn2ccc3ccncc32)c1]

To a solution of 5-(1H-pyrrolo[2,3-c]pyridin-1-ylmethyl)thiophene-3-carboximidamide (0.73 g crude) in 1,4-dioxane (100 mL) was added aqueous saturated sodium carbonate solution (50 mL) followed by di-tert-butyldicarbonate (2.9 g, 13.12 mmol) at 0° C. and stirred at room temperature for 16 h. The solvent was evaporated and was added water (50 mL) then extracted with ethyl acetate (2×50 mL). The organic phases were combined, washed with brine (2×50 mL), dried over $Na_2SO_4$, concentrated and the crude compound was purified by flash chromatography using RediSep silica 40 g flash column (0-6% methanol in methylene chloride as eluent) to give tert-butyl {[5-(1H-pyrrolo[2,3-c]pyridin-1-ylmethyl)thiophen-3-yl]carbonoimidoyl}carbamate (1.0 g, 51% over three steps) as an off-white solid.

$^1$H NMR (400 MHz, $CDCl_3$): δ 1.53 (s, 9H), 5.50 (s, 2H), 6.54 (d, 1H, J=3.2 Hz), 6.88 (d, 1H, J=3.6 Hz), 7.26 (s, 1H), 7.37 (d, 1H, J=3.6 Hz), 7.43 (s, 1H), 7.52 (d, 1H, J=4.8 Hz), 7.84 (s, 1H), 8.25 (d, 1H, J=5.6 Hz), 8.78 (s, 1H).

Step 5: 6-{[(6R,7R)-7-{[(2Z)-2-{2-[(tert-Butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-pyrrolo[2,3-c]pyridin-6-ium iodide

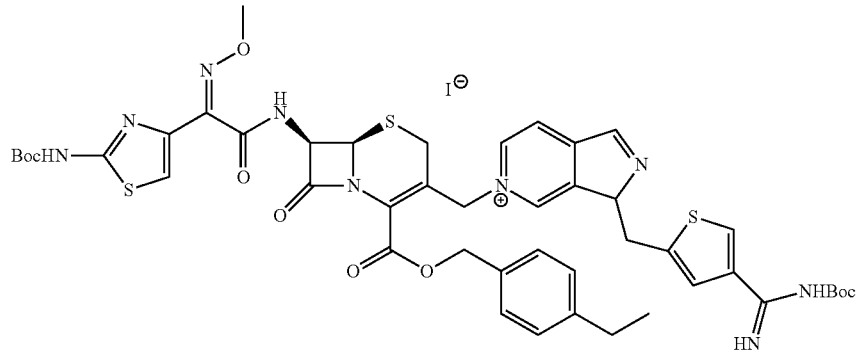 [SMILES: CCc1ccc(COC(=O)C2=C(C[n+]3ccc4c(c3)C(Cc3cc(C(=N)NC(=O)OC(C)(C)C)cs3)N=C4)CS[C@@H]3[C@H](NC(=O)/C(=N\OC)c4csc(NC(=O)OC(C)(C)C)n4)C(=O)N23)cc1 ; [I-]]

To a solution tert-butyl {[5-(1H-pyrrolo[2,3-c]pyridin-1-ylmethyl)thiophen-3-yl]carbonoimidoyl}carbamate (0.12 g, 0.30 mmol) in dimethylformamide (2 mL) was added 4-methoxybenzyl (6R,7R)-7-{[(2Z)-2-{2-[(tert-butoxycarbonyl)amino]-5-chloro-1,3-thiazol-4-yl})-2-(methoxyimino)acetyl]amino}-3-(chloromethyl)-8-oxo-5-thia-1-azabicyclo[4.2.0]oct-2-ene-2-carboxylate (0.21 g, 0.30 mmol) at 0° C. The reaction mixture was then degassed under reduced pressure for 0.5 h, treated with NaI (0.09 g, 0.6 mmol) and stirred at room temperature overnight. Sodium bisulphite (0.6 g) in sodium chloride solution (75 mL) was added to the reaction mixture at 15° C., stirred for 10 minutes and the solid separated was filtered, washed with water then dried under vacuum to a yellow solid (0.3 g), which was used in the next step without further purification.

Step 6: (6R,7R)-7-{[(2Z)-2-(2-Amino-5-chloro-1,3-thiazol-4-yl)-2-(methoxyimino)acetyl]amino}-3-({1-[(4-carbamimidoylthiophen-2-yl)methyl]-1H-pyrrolo[2,3-c]pyridin-6-ium-6-yl}methyl)-8-oxo-5-thia-1-azabicyclo[4.2.0]oct-2-ene-2-carboxylate formic acid salt

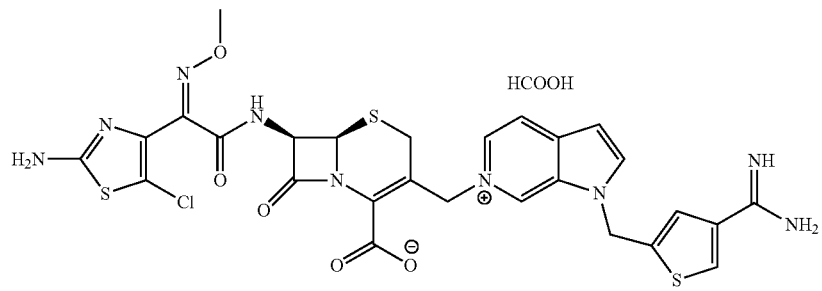 [SMILES: CO/N=C(\C(=O)N[C@@H]1C(=O)N2C(C(=O)[O-])=C(C[n+]3ccc4ccn(Cc5cc(C(=N)N)cs5)c4c3)CS[C@H]12)c1nc(N)sc1Cl ; "HCOOH"]

To a solution of 6-{[(6R,7R)-7-{[(2Z)-2-{2-[(tert-butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-({4-[N-(tert-butoxycarbonyl)carbamimidoyl]thiophen-2-yl}methyl)-1H-pyrrolo[2,3-c]pyridin-6-ium iodide (0.3 mg, crude)) in dry dichloromethane (2.5 mL) at 0° C. was added trifluoroacetic acid (2.5 mL) and anisole (0.82 mL, 7.75 mmol) then stirred at room temperature for 2 h. Solvent was evaporated, diisopropyl ether (30 mL) was added and solid was filtered, washed with diisopropyl ether then dried under vacuum. The greenish yellow solid (315 mg) was dissolved in water (30 mL), filtered and the aqueous phase was lyophilized to give yellow solid, which was purified by preparative HPLC to get (6R,7R)-7-{[(2Z)-2-(2-amino-5-chloro-1,3-thiazol-4-yl)-2-(methoxyimino)acetyl]amino}-3-({1-[(4-carbamimidoylthiophen-2-yl)methyl]-1H-pyrrolo[2,3-c]pyridin-6-ium-6-yl}methyl)-8-oxo-5-thia-1-azabicyclo[4.2.0]oct-2-ene-2-carboxylate yellow solid (165 mg) as formic acid salt (0.02 g, 11.2%).

$^1$H NMR (400 MHz, D$_2$O): δ 2.99 (d, 1H, J=18.0 Hz), 3.38 (d, 1H, J=18.0 Hz), 3.85 (s, 3H), 5.06 (d, 1H, J=5.2 Hz), 5.13 (d, 1H, J=14.4 Hz), 5.34 (d, 1H, J=14.0 Hz), 5.69-5.82 (m, 3H), 6.88 (d, 1H, J=3.2 Hz), 7.49 (s, 1H), 7.96 (d, 1H, J=6.8 Hz), 8.14 (d, 1H, J=6.8 Hz), 8.32 (s, 2H), 9.06 (s, 1H), Six protons were not observed in D$_2$O.

Mass: ES$^+$ 686.23

Example 17 (Table 1, Compound 28)

(6R,7R)-7-{[(2Z)-2-(2-Amino-5-chloro-1,3-thiazol-4-yl)-2-{[(2-carboxypropan-2-yl)oxy]imino}acetyl]amino}-3-({1-[(4-carbamimidoylthiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate

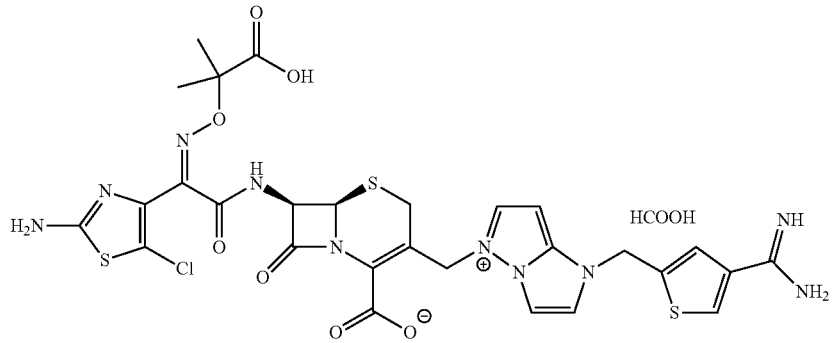 [SMILES: CC(C)(O/N=C(\C(=O)N[C@@H]1C(=O)N2C(C(=O)[O-])=C(C[n+]3ccc4n(Cc5cc(C(=N)N)cs5)ccn43)CS[C@H]12)c1nc(N)sc1Cl)C(=O)O ; "HCOOH"]

$^1$H NMR (400 MHz, D$_2$O) δ 1.24 (s, 3H), 1.27 (s, 3H), 2.88 (d, 1H, J=18.0 Hz), 3.24 (d, 1H, J=18.0 Hz), 5.02 (d, 1H, J=4.7 Hz), 5.13 (m, 2H), 5.45 (s, 2H), 5.61 (d, 1H, J=4.7 Hz), 6.20 (d, 1H, J=3.9 Hz), 7.40 (s, 2H), 7.87-7.89 (m, 2H), 8.14 (s, 1H). Seven protons were not observed in D$_2$O.

Mass: ES$^+$ 747.34 and 749.22

Example 18 (Table 1, Compound 4)

(6R,7R)-7-{[(2Z)-2-(2-Amino-1,3-thiazol-4-yl)-2-{[(2-carboxypropan-2-yl)oxy]imino}acetyl]amino}-3-{[1-(4-carbamimidamidobenzyl)-1H-pyrrolo[3,2-c]pyridin-5-ium-5-yl]methyl}-8-oxo-5-thia-1-azabicyclo[4.2.0]oct-2-ene-2-carboxylate

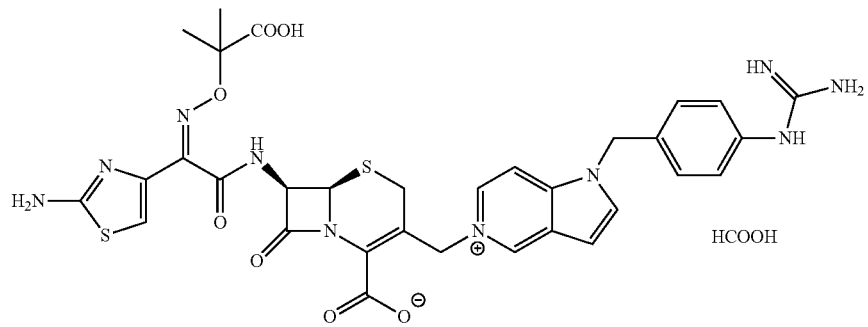 [SMILES: CC(C)(O/N=C(\C(=O)N[C@@H]1C(=O)N2C(C(=O)[O-])=C(C[n+]3ccc4c(ccn4Cc4ccc(NC(=N)N)cc4)c3)CS[C@H]12)c1csc(N)n1)C(=O)O ; "HCOOH"]

$^1$H NMR (400 MHz, D$_2$O): δ 1.27 (s, 3H), 1.28 (s, 3H), 2.92 (d, 1H, J=17.6 Hz), 3.38 (d, 1H, J=17.6 Hz), 5.08-5.12 (m, 2H), 5.33 (d, 1H, J=14.9 Hz), 5.44 (s, 2H), 5.64 (s, 1H), 6.80 (s, 1H), 6.91 (s, 1H), 7.11-7.17 (m, 4H), 7.67-7.71 (m, 2H), 8.16 (s, 0.4H, formic acid), 8.25 (m, 1H), 9.04 (s, 1H). Eight protons were not observed in D$_2$O.

Mass: ES$^+$ 733.32

Example 19 (Table 1, Compound 7)

(6R,7R)-3-[(1-{4-[N-(2-Aminoethyl)carbamimidoyl]benzyl}-1H-pyrrolo[3,2-c]pyridin-5-ium-5-yl)methyl]-7-{[(2Z)-2-(2-amino-1,3-thiazol-4-yl)-2-{[(2-carboxypropan-2-yl)oxy]imino}acetyl]amino}-8-oxo-5-thia-1-azabicyclo[4.2.0]oct-2-ene-2-carboxylate

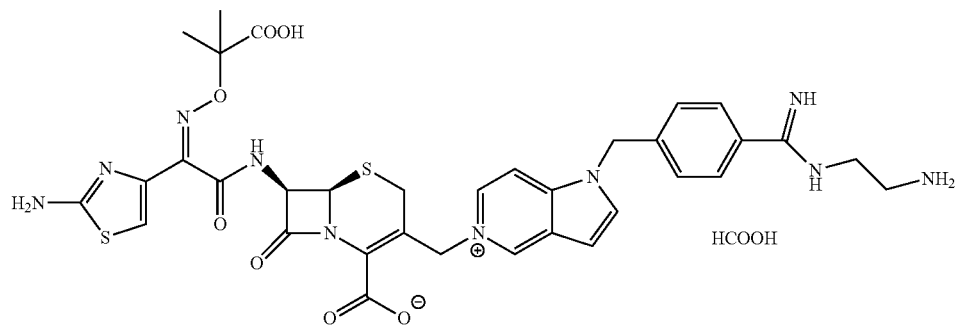 [SMILES: CC(C)(O/N=C(\C(=O)N[C@@H]1C(=O)N2C(C(=O)[O-])=C(C[n+]3ccc4c(ccn4Cc4ccc(C(=N)NCCN)cc4)c3)CS[C@H]12)c1csc(N)n1)C(=O)O ; "HCOOH"]

$^1$H NMR (400 MHz, D$_2$O): δ 1.20 (s, 3H), 1.21 (s, 3H), 2.92 (d, 1H, J=18.0 Hz), 3.21 (t, 2H, J=6.3 Hz), 3.38 (d, 1H, J=18.0 Hz), 3.63 (t, 2H, J=6.3 Hz), 5.06-5.11 (m, 2H), 5.32 (d, 1H, J=14.4 Hz), 5.52 (s, 2H), 5.59 (d, 1H, J=4.7 Hz), 6.73 (s, 1H), 6.92 (d, 1H, J=3.1 Hz), 7.21 (d, 2H, J=8.2 Hz), 7.52 (d, 2H, J=8.2 Hz), 7.66-7.69 (m, 2H), 8.23 (d, 1H, J=7.0 Hz), 9.05 (s, 1H). Eight protons were not observed in D$_2$O.

Mass: ES$^+$ 761.13

Example 20 (Table 1, Compound 8)

(6R,7R)-7-{[(2Z)-2-(2-Amino-1,3-thiazol-4-yl)-2-{[(2-carboxypropan-2-yl)oxy]imino}acetyl]amino}-3-({1-[4-(4,5-dihydro-1H-imidazol-2-yl)benzyl]-1H-pyrrolo[3,2-c]pyridin-5-ium-5-yl}methyl)-8-oxo-5-thia-1-azabicyclo[4.2.0]oct-2-ene-2-carboxylate

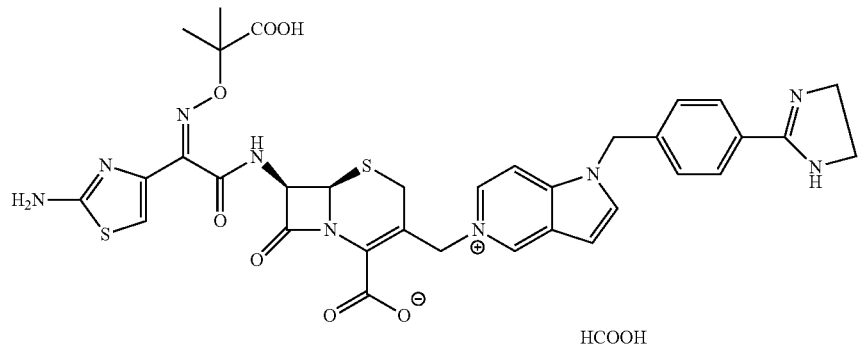 [SMILES: CC(C)(O/N=C(\C(=O)N[C@@H]1C(=O)N2C(C(=O)[O-])=C(C[n+]3ccc4c(ccn4Cc4ccc(C5=NCCN5)cc4)c3)CS[C@H]12)c1csc(N)n1)C(=O)O ; "HCOOH"]

$^1$H NMR (400 MHz, D$_2$O): δ 1.24 (s, 3H), 1.27 (s, 3H), 2.94 (d, 1H, J=17.5 Hz), 3.40 (d, 1H, J=17.5 Hz), 3.89 (s, 4H), 5.09-5.13 (m, 2H), 5.34 (d, 1H, J=14.8 Hz), 5.55 (s, 2H), 5.63 (d, 1H, J=4.7 Hz), 6.78 (s, 1H), 6.96 (s, 1H), 7.23 (d, 2H, J=7.1 Hz), 7.58 (d, 2H, J=7.1 Hz), 7.69-7.71 (m, 2H), 8.19 (s, 1H, formic acid), 8.25 (d, 1H, J=7.1 Hz), 9.08 (s, 1H). Five protons were not observed in D$_2$O.

Mass: ES$^+$ 744.27

Example 21 (Table 1, Compound 12)

(6R,7R)-7-{[(2Z)-2-(2-Amino-1,3-thiazol-4-yl)-2-{[(2-carboxypropan-2-yl)oxy]imino}acetyl]amino}-3-({1-[2-(4-carbamimidamidophenyl)ethyl]-1H-pyrrolo[3,2-c]pyridin-5-ium-5-yl}methyl)-8-oxo-5-thia-1-azabicyclo[4.2.0]oct-2-ene-2-carboxylate

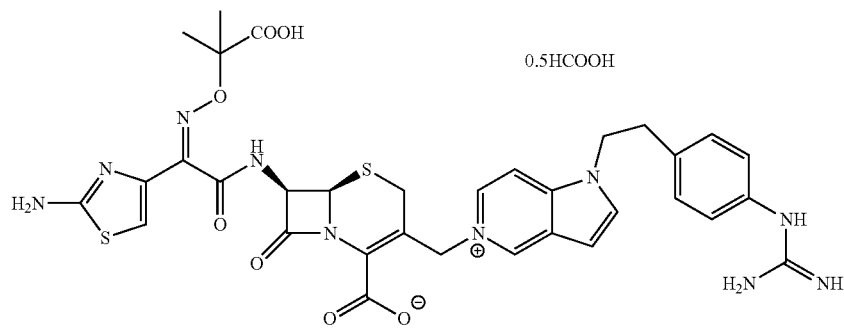 [SMILES: CC(C)(O/N=C(\C(=O)N[C@@H]1C(=O)N2C(C(=O)[O-])=C(C[n+]3ccc4c(ccn4CCc4ccc(NC(=N)N)cc4)c3)CS[C@H]12)c1csc(N)n1)C(=O)O]

$^1$H NMR (400 MHz, D$_2$O): δ 1.30 (s, 6H), 2.80 (d, 1H, J=17.6 Hz), 3.00 (m, 2H), 3.23 (d, 1H, J=17.6 Hz), 4.44 (m, 2H), 5.03-5.07 (m, 2H), 5.21 (d, 1H, J=14.1 Hz), 5.56 (d, 1H, J=4.3 Hz), 6.75-6.86 (m, 6H), 7.02 (d, 1H, J=6.7 Hz), 7.60 (s, 1H), 7.85 (d, 1H, J=6.7 Hz), 8.19 (s, 0.5H, formic acid), 8.90 (s, 1H). Eight protons were not observed in D$_2$O.

Mass: ES$^+$ 747.27

Example 22 (Table 1, Compound 16)

(6R,7R)-7-{[(2Z)-2-(2-Amino-1,3-thiazol-4-yl)-2-{[(2-carboxypropan-2-yl)oxy]imino}acetyl]amino}-3-({1-[(4-carbamimidoyl-1,3-thiazol-2-yl)methyl]-1H-pyrrolo[3,2-c]pyridin-5-ium-5-yl}methyl)-8-oxo-5-thia-1-azabicyclo[4.2.0]oct-2-ene-2-carboxylate

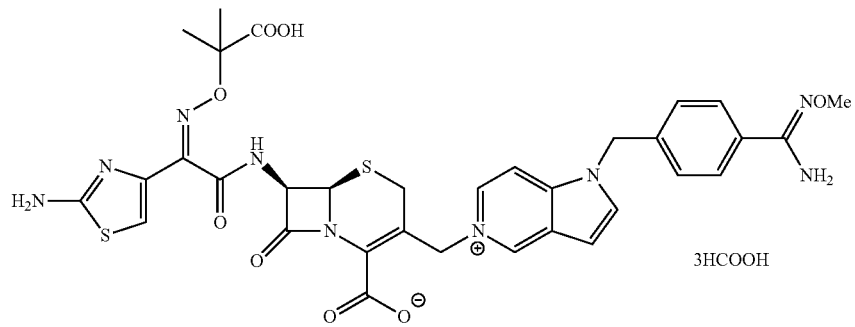

$^1$H NMR (400 MHz, D$_2$O): δ 1.29 (s, 3H), 1.32 (s, 3H), 2.98 (d, 1H, J=17.6 Hz), 3.40 (d, 1H, J=17.6 Hz), 5.09 (d, 1H, J=4.7 Hz), 5.14 (d, 1H, J=14.4 Hz), 5.34 (d, 1H, J=14.4 Hz), 5.67 (d, 1H, J=4.7 Hz), 5.85 (s, 2H), 6.91 (s, 1H), 6.97 (d, 1H, J=3.1 Hz), 7.74 (d, 1H, J=3.1 Hz), 7.86 (d, 1H, J=7.1 Hz), 8.09 (s, 0.4H, formic acid), 8.31 (d, 1H, J=7.1 Hz), 8.39 (s, 1H), 9.08 (s, 1H). Seven protons were not observed in D$_2$O.

Mass: ES$^+$ 725.37

Example 23 (Table 1, Compound 19)

(6R,7R)-7-{[(2Z)-2-(2-Amino-1,3-thiazol-4-yl)-2-{[(2-carboxypropan-2-yl)oxy]imino}acetyl]amino}-3-({1-[4-(N'-methoxycarbamimidoyl)benzyl]-1H-pyrrolo[3,2-c]pyridin-5-ium-5-yl}methyl)-8-oxo-5-thia-1-azabicyclo[4.2.0]oct-2-ene-2-carboxylate

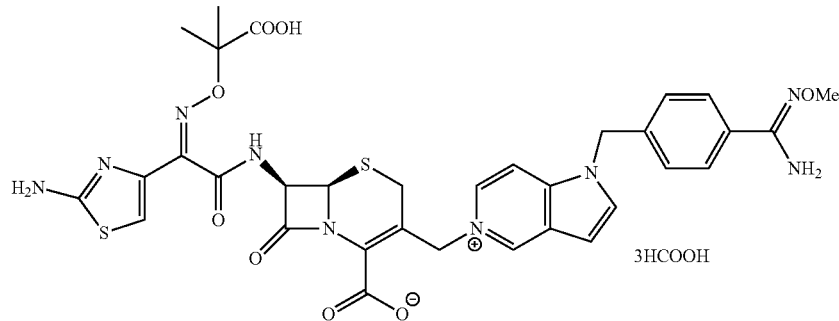

$^1$H NMR (400 MHz, D$_2$O): δ 1.25 (s, 3H), 1.26 (s, 3H), 2.94 (d, 1H, J=18.0 Hz), 3.35 (d, 1H, J=18.0 Hz), 3.64 (s, 3H), 5.07 (d, 1H, J=4.7 Hz), 5.09 (d, 1H, J=14.5 Hz), 5.30 (d, 1H, J=14.5 Hz), 5.45 (s, 2H), 5.65 (d, 1H, J=4.7 Hz), 6.77 (s, 1H), 6.91 (d, 1H, J=3.5 Hz), 7.11 (d, 2H, J=8.2 Hz), 7.38 (d, 2H, J=8.2 Hz), 7.64 (d, 1H, J=3.5 Hz), 7.69 (d, 1H, J=6.7 Hz), 8.19 (d, 1H, J=6.7 Hz), 8.26 (s, 3H, formic acid), 9.02 (s, 1H). Six protons were not observed in D$_2$O.

Mass: ES$^+$ 748.45

Example 24 (Table 1, Compound 30)

(6R,7R)-7-{[(2Z)-2-(2-Amino-1,3-thiazol-4-yl)-2-
{[(2-carboxypropan-2-yl)oxy]imino}acetyl]amino}-
3-({1-[(4-carbamimidoyl-1,3-oxazol-2-yl)methyl]-
1H-pyrrolo[3,2-c]pyridin-5-ium-5-yl}methyl)-8-oxo-
5-thia-1-azabicyclo[4.2.0]oct-2-ene-2-carboxylate

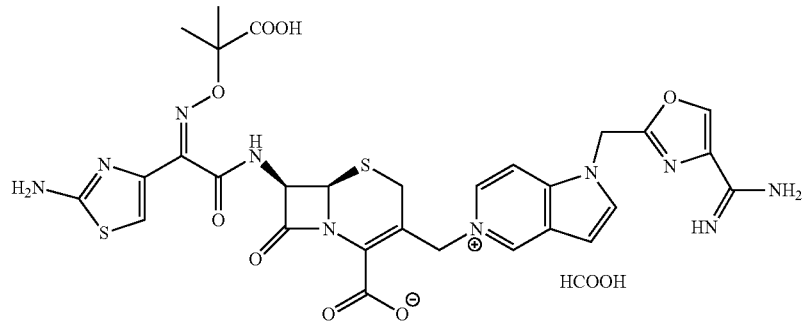 [SMILES: CC(C)(O/N=C(\C(=O)N[C@@H]1C(=O)N2C(C(=O)[O-])=C(C[n+]3ccc4c(ccn4Cc4nc(C(=N)N)co4)c3)CS[C@H]12)c1csc(N)n1)C(=O)O ; "HCOOH"]

$^1$H NMR (400 MHz, D$_2$O): δ 1.30 (s, 3H), 1.32 (s, 3H), 2.98 (d, 1H, J=18.0 Hz), 3.39 (d, 1H, J=18.0 Hz), 5.08 (d, 1H, J=4.7 Hz), 5.14 (d, 1H, J=14.9 Hz), 5.33 (d, 1H, J=14.9 Hz), 5.66 (d, 1H, J=4.7 Hz), 5.71 (s, 2H), 6.92 (s, 1H), 6.95 (d, 1H, J=3.5 Hz), 7.69 (d, 1H, J=3.5 Hz), 7.85 (d, 1H, J=7.0 Hz), 8.31 (d, 1H, J=7.0 Hz), 8.50 (s, 1H), 9.06 (s, 1H). Seven protons were not observed in D$_2$O.

Mass: ES$^+$ 709.29

Example 25 (Table 1, Compound 31)

(6R,7R)-7-{[(2Z)-2-(2-Amino-1,3-thiazol-4-yl)-2-
{[(2-carboxypropan-2-yl)oxy]imino}acetyl]amino}-
3-({1-[(4-{N-[(Z)-(dimethylamino)methylidene]
carbamimidoyl}-1,3-oxazol-2-yl)methyl]-1H-pyrrolo
[3,2-c]pyridin-5-ium-5-yl}methyl)-8-oxo-5-thia-1-
azabicyclo[4.2.0]oct-2-ene-2-carboxylate

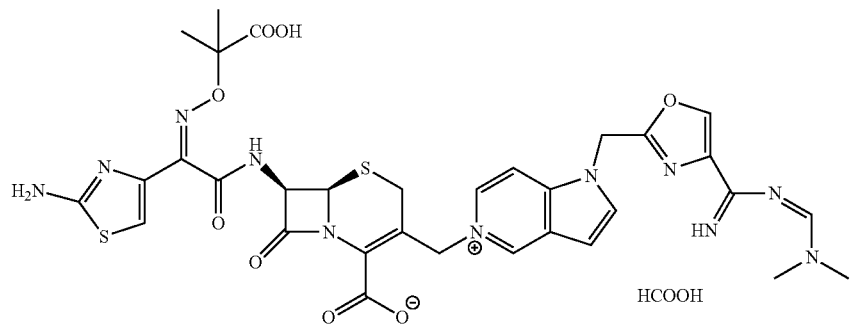 [SMILES: CN(C)/C=N\C(=N)c1coc(Cn2ccc3c[n+](CC4=C(C(=O)[O-])N5C(=O)[C@@H](NC(=O)/C(=N\OC(C)(C)C(=O)O)c6csc(N)n6)[C@H]5SC4)ccc32)n1 ; "HCOOH"]

$^1$H NMR (400 MHz, D$_2$O): δ 1.29 (s, 3H), 1.3 (s, 3H), 2.98 (d, 1H, J=18.0 Hz), 3.05 (s, 3H), 3.13 (s, 3H), 3.40 (d, 1H, J=18.0 Hz), 5.08 (d, 1H, J=4.7 Hz), 5.13 (d, 1H, J=14.9 Hz), 5.34 (d, 1H, J=14.9 Hz), 5.65 (d, 1H, J=4.7 Hz), 5.71 (s, 2H), 6.87 (s, 1H), 6.95 (d, 1H, J=3.2 Hz), 7.70 (d, 1H, J=3.6 Hz), 7.86 (d, 1H, J=7.4 Hz), 8.23 (s, 1H), 8.32 (d, 1H, J=6.7 Hz), 8.45 (s, 1H), 9.08 (s, 1H). Five protons were not observed in D$_2$O.

Mass: ES$^+$ 764.36

Example 26 (Table 1, Compound 29)

(6R,7R)-7-{[(2Z)-2-(2-Amino-1,3-thiazol-4-yl)-2-{[(2-carboxypropan-2-yl)oxy]imino}acetyl]amino}-3-[(1-{[3-(4,5-dihydro-1H-imidazol-2-yl)-1,2-oxazol-5-yl]methyl}-1H-pyrrolo[3,2-c]pyridin-5-ium-5-yl)methyl]-8-oxo-5-thia-1-azabicyclo[4.2.0]oct-2-ene-2-carboxylate

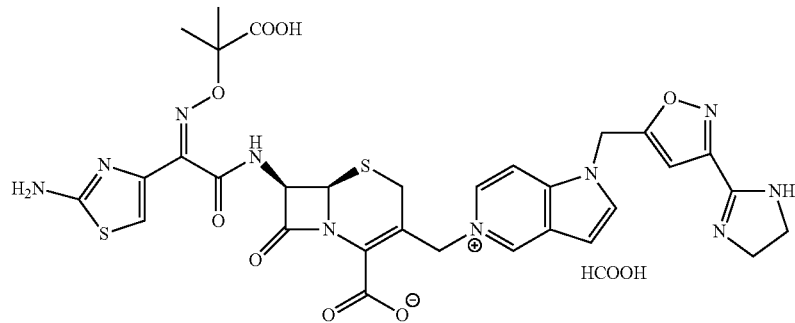 [SMILES: CC(C)(O/N=C(\C(=O)N[C@@H]1C(=O)N2C(C(=O)[O-])=C(C[n+]3ccc4c(ccn4Cc4cc(C5=NCCN5)no4)c3)CS[C@H]12)c1csc(N)n1)C(=O)O ; "HCOOH"]

$^1$H NMR (400 MHz, D$_2$O): δ 1.25 (s, 6H), 2.94 (d, 1H, J=17.2 Hz), 3.40 (d, 1H, J=17.2 Hz), 4.59 (s, 4H), 5.08-5.13 (m, 2H), 5.35 (d, 1H, J=14.4 Hz), 5.63 (d, 1H, J=5.1 Hz), 5.74 (s, 2H), 6.72 (m, 2H), 6.94 (d, 1H, J=1.2 Hz), 7.68 (d, 1H, J=3.1 Hz), 7.86 (d, 1H, J=7.1 Hz), 8.23 (s, 1H, formic acid), 8.34 (d, 1H, J=7.1 Hz), 9.07 (s, 1H). Five protons were not observed in D$_2$O.

Mass: ES$^+$ 735.21

Example 27 (Table 1, Compound 15)

(6R,7R)-7-{[(2Z)-2-(2-Amino-1,3-thiazol-4-yl)-2-{[(2-carboxypropan-2-yl)oxy]imino}acetyl]amino}-3-{[1-(4-carbamimidoyl-2-fluorobenzyl)-1H-imidazo[1,2-b]pyrazol-5-ium-5-yl]methyl}-8-oxo-5-thia-1-azabicyclo[4.2.0]oct-2-ene-2-carboxylate

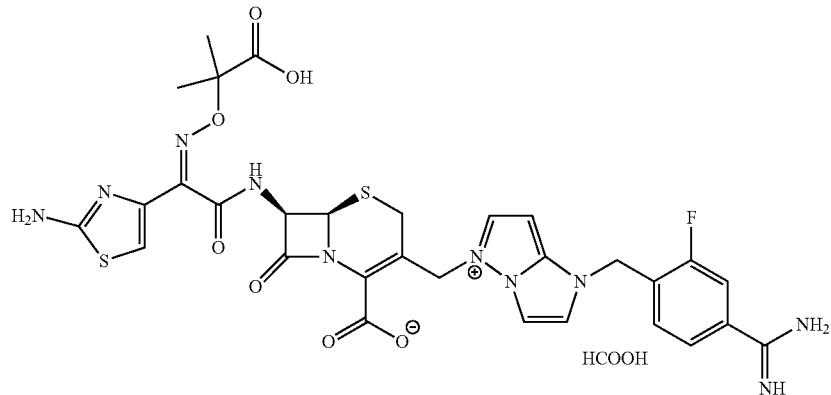 [SMILES: CC(C)(O/N=C(\C(=O)N[C@@H]1C(=O)N2C(C(=O)[O-])=C(C[n+]3ccc4n(Cc5ccc(C(=N)N)cc5F)ccn43)CS[C@H]12)c1csc(N)n1)C(=O)O ; "HCOOH"]

$^1$H NMR (400 MHz, D$_2$O): δ 1.29 (s, 3H), 1.31 (s, 3H), 2.95 (d, 1H, J=17.6 Hz), 3.24 (d, 1H, J=17.6 Hz), 5.04 (d, 1H, J=4.8 Hz), 5.14 (s, 2H), 5.37 (s, 2H), 5.62 (d, 1H, J=4.8 Hz), 6.23 (d, 1H, J=3.2 Hz), 6.92 (s, 1H), 7.40-7.48 (m, 4H), 7.84 (d, 1H, J=2.0 Hz), 7.88 (d, 1H, J=3.6 Hz). Seven protons were not observed in D$_2$O.

Mass: ES$^+$ 725.42

Example 28 (Table 1, Compound 6)

(6R,7R)-7-{[(2Z)-2-(2-Amino-1,3-thiazol-4-yl)-2-{[(2-carboxypropan-2-yl)oxy]imino}acetyl]amino}-3-({1-[4-(2-carbamimidamidoethoxy)benzyl]-1H-pyrrolo[3,2-c]pyridin-5-ium-5-yl}methyl)-8-oxo-5-thia-1-azabicyclo[4.2.0]oct-2-ene-2-carboxylate

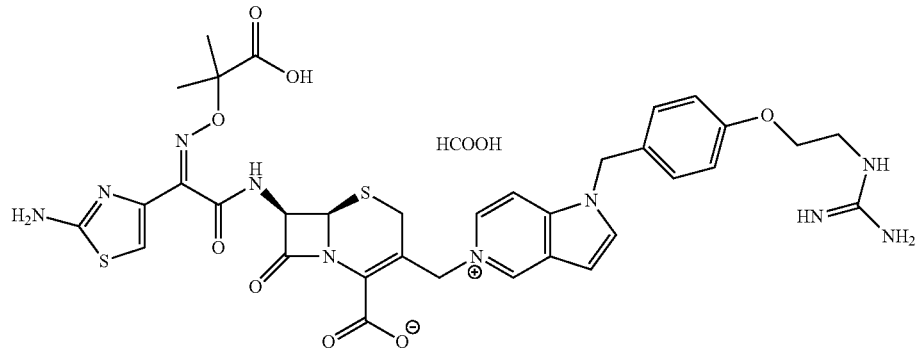 [SMILES: CC(C)(O/N=C(\C(=O)N[C@@H]1C(=O)N2C(C(=O)[O-])=C(C[n+]3ccc4c(ccn4Cc4ccc(OCCNC(=N)N)cc4)c3)CS[C@H]12)c1csc(N)n1)C(=O)O ; "HCOOH"]

$^1$H NMR (400 MHz, DMSO-d$_6$): δ 1.38 (s, 6H), 2.91 (d, 1H, J=18.4 Hz), 3.20-3.50 (m, 3H), 3.92 (s, 1H), 4.02 (s, 1H), 4.85 (d, 1H, J=13.2 Hz), 5.04 (d, 1H, J=5.2 Hz), 5.46 (s, 2H), 5.68 (d, 1H, J=13.2 Hz), 5.79 (d, 1H, J=4.8 Hz), 6.72 (s, 1H), 6.81 (d, 2H, J=8.8 Hz), 7.03 (d, 1H, J=3.2 Hz), 7.17 (s, 1H), 7.30 (d, 2H, J=8.0 Hz), 8.05 (d, 1H, J=6.0 Hz), 8.14 (s, 1H), 9.30 (br s, 1H), 9.44 (s, 1H). Eight protons were not observed in D$_2$O.

Mass: ES$^+$ 777.25

Example 29 (Table 1, Compound 20)

(6R,7R)-7-{[(2Z)-2-(5-Amino-1,2,4-thiadiazol-3-yl)-2-{[(2-carboxypropan-2-yl)oxy]imino}acetyl]amino}-3-{[1-(4-carbamimidoyl-2-fluorobenzyl)-1H-pyrrolo[3,2-c]pyridin-5-ium-5-yl]methyl}-8-oxo-5-thia-1-azabicyclo[4.2.0]oct-2-ene-2-carboxylate

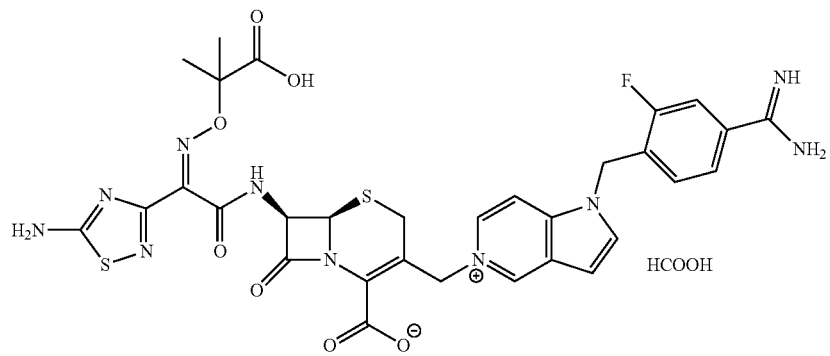 [SMILES: CC(C)(O/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1nsc(N)n1)C(=O)O ; "HCOOH"]

1H NMR (400 MHz, D$_2$O): δ 1.25 (s, 6H), 2.93 (d, 1H, J=17.6 Hz), 3.37 (d, 1H, J=18.0 Hz), 5.08-5.12 (m, 2H), 5.33 (d, 1H, J=14.4 Hz), 5.57 (s, 2H), 5.65 (d, 1H, J=4.4 Hz), 6.92 (d, 1H, J=3.6 Hz), 7.14 (t, 1H, J=8.0 Hz), 7.36 (d, 1H, J=8.4 Hz), 7.41 (d, 1H, J=10.0 Hz), 7.66 (d, 1H, J=3.2 Hz), 7.77 (d, 1H, J=6.8 Hz), 8.26 (d, 1H, J=6.8 Hz), 9.05 (s, 1H). Seven protons were not observed in D$_2$O.

Mass: ES$^+$ 737.36

Example 30 (Table 1, Compound 21)

(6R,7R)-7-{[(2Z)-2-(2-Amino-5-chloro-1,3-thiazol-4-yl)-2-{[(2-carboxypropan-2-yl)oxy]imino}acetyl]amino}-3-{[1-(4-carbamimidoyl-2-fluorobenzyl)-1H-pyrrolo[3,2-c]pyridin-5-ium-5-yl]methyl}-8-oxo-5-thia-1-azabicyclo[4.2.0]oct-2-ene-2-carboxylate

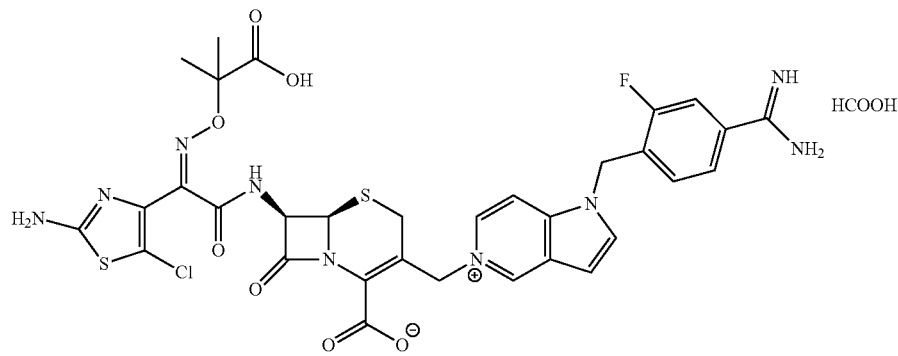 [SMILES: CC(C)(O/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1nc(N)sc1Cl)C(=O)O ; "HCOOH"]

$^1$H NMR (400 MHz, D$_2$O): δ 1.22 (s, 6H), 2.92 (d, 1H, J=18.0 Hz), 3.37 (d, 1H, J=19.2 Hz), 5.07-5.11 (m, 2H), 5.34 (d, 1H, J=14.4 Hz), 5.58 (s, 2H), 5.64 (d, 1H, J=4.4 Hz), 6.93 (d, 1H, J=4.0 Hz), 7.17 (t, 1H, J=7.6 Hz), 7.36 (d, 1H, J=8.8 Hz), 7.42 (d, 1H, J=10.0 Hz), 7.67 (d, 1H, J=3.6 Hz), 7.78 (d, 1H, J=6.4 Hz), 8.25 (d, 1H, J=6.8 Hz), 9.05 (s, 1H). Seven protons were not observed in D$_2$O.

Mass: ES$^+$ 770.36

Example 31 (Table 1, Compound 26)

(6R,7R)-7-{[(2Z)-2-(2-Amino-1,3-thiazol-4-yl)-2-{[(2-carboxypropan-2-yl)oxy]imino}acetyl]amino}-3-({1-[(4-carbamimidoyl-1,3-thiazol-2-yl)methyl]-1H-imidazo[1,2-b]pyrazol-5-ium-5-yl}methyl)-8-oxo-5-thia-1-azabicyclo[4.2.0]oct-2-ene-2-carboxylate

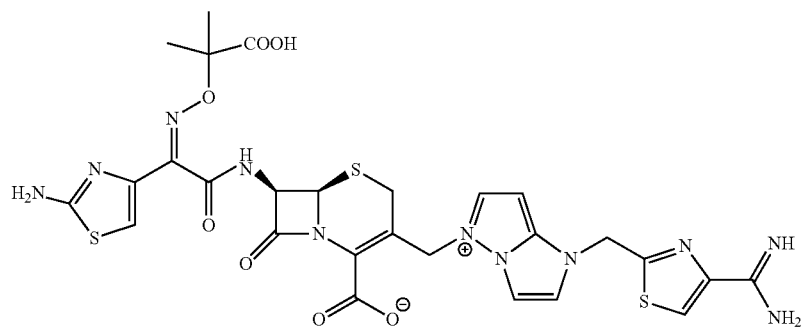 [SMILES: CC(C)(O/N=C(\C(=O)N[C@@H]1C(=O)N2C(C(=O)[O-])=C(C[n+]3ccc4n(Cc5nc(C(=N)N)cs5)ccn43)CS[C@H]12)c1csc(N)n1)C(=O)O]

$^1$H NMR (400 MHz, D$_2$O): δ 1.26 (s, 3H), 1.28 (s, 3H), 2.91 (d, 1H, J=18 Hz), 3.28 (d, 1H, J=18 Hz), 5.08 (s, 1H), 5.15 (s, 1H), 5.18 (s, 1H), 5.60-5.70 (m, 3H), 6.32 (s, 1H), 6.79 (s, 1H), 7.48 (s, 1H), 7.92-8.00 (m, 2H), 8.44 (s, 1H). Seven protons were not observed in D$_2$O.

Mass: ES$^+$ 714.27

Example 32 (Table 1, Compound 22)

(6R,7R)-7-({(2Z)-2-(2-Amino-1,3-thiazol-4-yl)-2-[(carboxymethoxy)imino]acetyl}amino)-3-{[1-(4-carbamimidoyl-2-fluorobenzyl)-1H-imidazo[1,2-b]pyrazol-5-ium-5-yl]methyl}-8-oxo-5-thia-1-azabicyclo[4.2.0]oct-2-ene-2-carboxylate

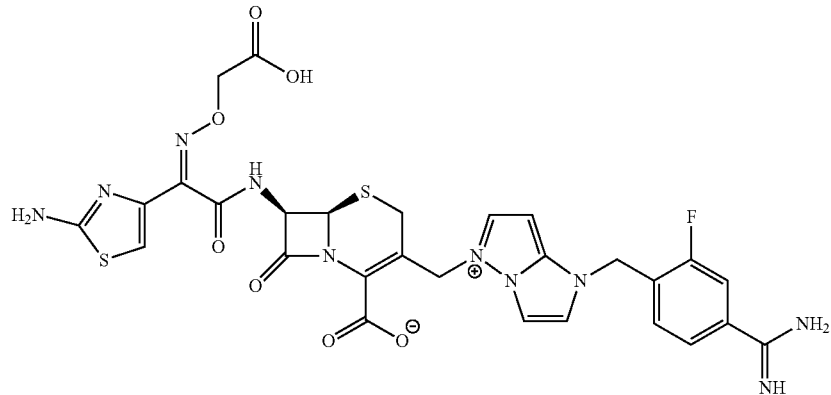 [SMILES: N=C(N)c1ccc(Cn2ccn3c2cc[n+]3CC2=C(C(=O)[O-])N3C(=O)[C@@H](NC(=O)/C(=N\OCC(=O)O)c4csc(N)n4)[C@H]3SC2)c(F)c1]

$^1$H NMR (400 MHz, D$_2$O): δ 2.97 (d, 1H, J=18 Hz), 3.25 (d, 1H, J=18 Hz), 5.04 (s, 1H), 5.15 (s, 2H), 5.38 (s, 2H), 5.66 (s, 1H), 6.23 (s, 1H), 6.96 (s, 1H), 7.38-7.52 (m, 4H), 7.83 (s, 1H), 7.88 (s, 1H). Seven protons were not observed in D$_2$O.
Mass: ES$^+$ 697.34

Example 33 (Table 1, Compound 23)

(6R,7R)-7-{[(2Z)-2-(2-Amino-5-chloro-1,3-thiazol-4-yl)-2-{[(2-carboxypropan-2-yl)oxy]imino}acetyl]amino}-3-{[1-(4-carbamimidoyl-2-fluorobenzyl)-1H-imidazo[1,2-b]pyrazol-5-ium-5-yl]methyl}-8-oxo-5-thia-1-azabicyclo[4.2.0]oct-2-ene-2-carboxylate

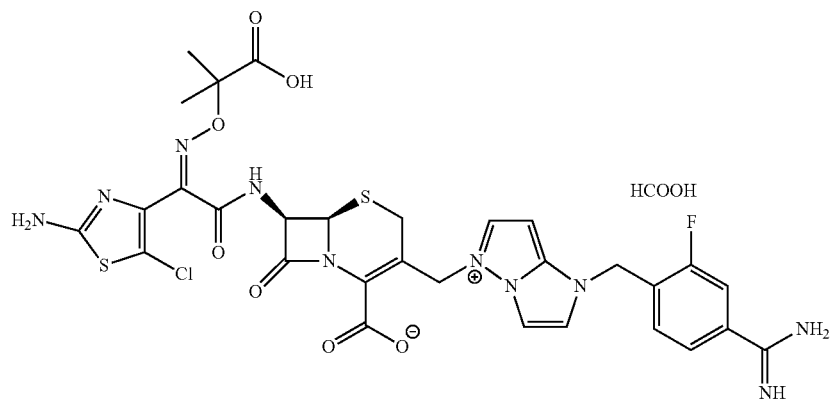 [SMILES: CC(C)(O/N=C(\C(=O)N[C@@H]1C(=O)N2C(C(=O)[O-])=C(C[n+]3ccc4n(Cc5ccc(C(=N)N)cc5F)ccn43)CS[C@H]12)c1nc(N)sc1Cl)C(=O)O ; "HCOOH"]

$^1$H NMR (400 MHz, D$_2$O): δ 1.27 (s, 3H), 1.30 (s, 3H), 2.90 (d, 1H, J=18 Hz), 3.20 (d, 1H, J=18 Hz), 5.00 (d, 1H, J=5.0 Hz), 5.13 (s, 2H), 5.32 (s, 2H), 5.61 (d, 1H, J=5.0 Hz), 6.24 (s, 1H), 7.40-7.55 (m, 4H), 7.90 (d, 2H, J=4.0 Hz), 8.20 (s, 0.2H). Six protons were not observed in D$_2$O.
Mass: ES$^+$ 760.29

Example 34 (Table 1, Compound 24)

(6R,7R)-7-{[(2Z)-2-(5-Amino-1,2,4-thiadiazol-3-yl)-2-{[(2-carboxypropan-2-yl)oxy]imino}acetyl]amino}-3-{[1-(4-carbamimidoyl-2-fluorobenzyl)-1H-imidazo[1,2-b]pyrazol-5-ium-5-yl]methyl}-8-oxo-5-thia-1-azabicyclo[4.2.0]oct-2-ene-2-carboxylate

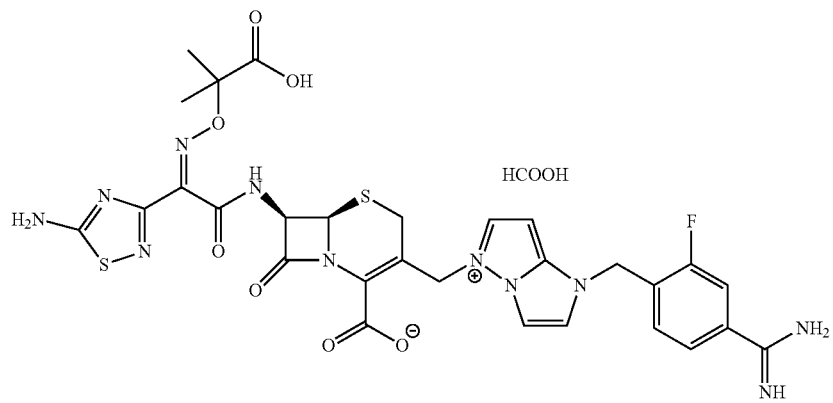 [SMILES: CC(C)(O/N=C(\C(=O)N[C@@H]1C(=O)N2C(C(=O)[O-])=C(C[n+]3ccc4n(Cc5ccc(C(=N)N)cc5F)ccn43)CS[C@H]12)c1nsc(N)n1)C(=O)O ; "HCOOH"]

$^1$H NMR (400 MHz, D$_2$O): δ 1.25 and 1.29 (2s, 6H), 2.90 (d, 1H, J=18 Hz), 3.24 (d, 1H, J=18 Hz), 5.06 (s, 1H), 5.16 (s, 2H), 5.38 (s, 2H), 5.64 (s, 1H), 6.25 (s, 1H), 7.40-7.50 (m, 4H), 7.90 (s, 2H), 8.27 (s, 2.75H). Six protons were not observed in D$_2$O.

Mass: ES$^+$ 726.27

Example 35 (Table 1, Compound 25)

(6R,7R)-7-{[(2Z)-2-(2-Amino-1,3-thiazol-4-yl)-2-{[(2-carboxypropan-2-yl)oxy]imino}acetyl]amino}-3-({1-[(4-carbamimidoylfuran-2-yl)methyl]-1H-imidazo[1,2-b]pyrazol-5-ium-5-yl}methyl)-8-oxo-5-thia-1-azabicyclo[4.2.0]oct-2-ene-2-carboxylate

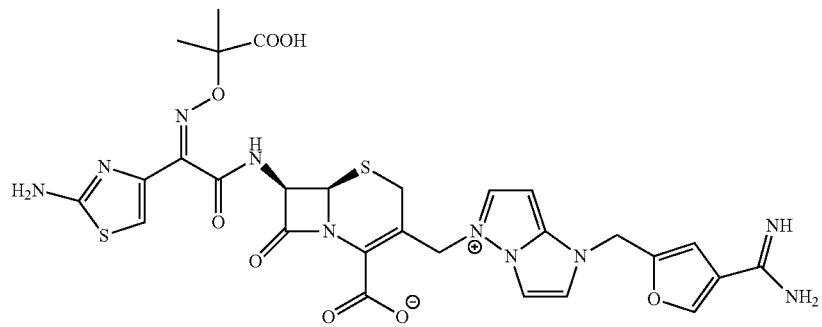 [SMILES: CC(C)(O/N=C(\C(=O)N[C@@H]1C(=O)N2C(C(=O)[O-])=C(C[n+]3ccc4n(Cc5cc(C(=N)N)co5)ccn43)CS[C@H]12)c1csc(N)n1)C(=O)O]

$^1$H NMR (400 MHz, D$_2$O): δ 1.30 (s, 3H), 1.32 (s, 3H), 2.95 (d, 1H, J=18 Hz), 3.24 (d, 1H, J=18 Hz), 5.03 (d, 1H, J=4.8 Hz), 5.13 (d, 2H, J=4.8 Hz), 5.29 (s, 2H), 5.62 (d, 1H, J=4.4 Hz), 6.26 (d, 1H, J=3.6 Hz), 6.85 (s, 1H), 6.92 (s, 1H), 7.38 (s, 1H), 7.82 (s, 1H), 7.89 (d, 1H, J=3.6 Hz), 8.13 (s, 1H). Seven protons were not observed in D$_2$O.

Mass: ES$^+$ 697.25

Example 36 (Table 1, Compound 10)

(6R,7R)-7-{[(2Z)-2-(2-Amino-1,3-thiazol-4-yl)-2-{[(2-carboxypropan-2-yl)oxy]imino}acetyl]amino}-3-({1-[4-(2-carbamimidamidoethoxy)benzyl]-2,3-dihydro-1H-imidazo[1,2-b]pyrazol-5-ium-5-yl}methyl)-8-oxo-5-thia-1-azabicyclo[4.2.0]oct-2-ene-2-carboxylate

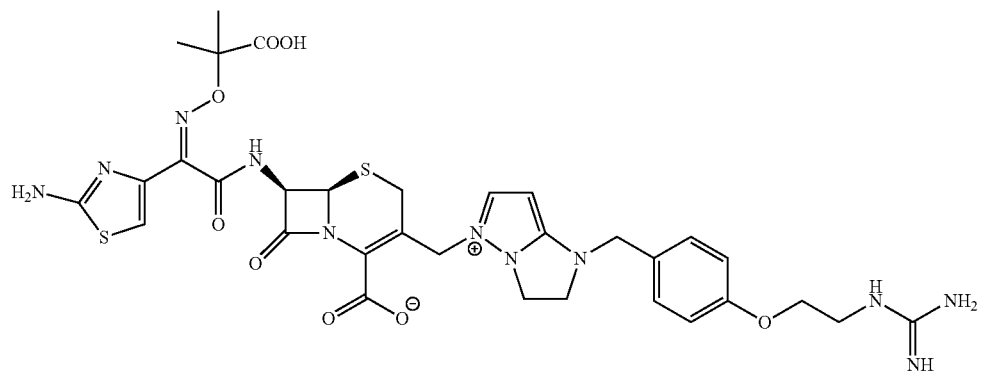 [SMILES: CC(C)(O/N=C(\C(=O)N[C@@H]1C(=O)N2C(C(=O)[O-])=C(C[n+]3ccc4n3CCN4Cc3ccc(OCCNC(=N)N)cc3)CS[C@H]12)c1csc(N)n1)C(=O)O]

$^1$H NMR (400 MHz, DMSO-$d_6$): δ 1.30 (s, 3H), 1.32 (s, 3H), 3.03 (d, 1H, J=17.6 Hz), 3.25 (d, 1H, J=17.6 Hz), 3.43 (t, 2H, J=4.7 Hz), 3.79 (t, 2H, J=8.2 Hz), 4.02-4.08 (m, 3H), 4.26 (m, 2H), 4.78 (d, 1H, J=15.3 Hz), 4.87 (d, 1H, J=15.7 Hz), 5.03 (d, 1H, J=5.1 Hz), 5.61 (dd, 2H, J=5.05 and 1.9 Hz), 6.84-6.86 (m, 3H), 7.17 (d, 2H, J=8.9 Hz), 7.78 (d, 1H, J=3.1 Hz), 8.18 (s, 1H). Eight protons were not observed in $D_2O$.
Mass: ES$^+$ 768.31

Example 37 (Table 1, Compound 49)

(6R,7R)-7-{[(2Z)-2-(2-Amino-1,3-thiazol-4-yl)-2-{[(2-carboxypropan-2-yl)oxy]imino}acetyl]amino}-3-{[1-(4-carbamimidoyl-2-chloro-6-fluorobenzyl)-1H-pyrrolo[3,2-c]pyridin-5-ium-5-yl]methyl}-8-oxo-5-thia-1-azabicyclo[4.2.0]oct-2-ene-2-carboxylate

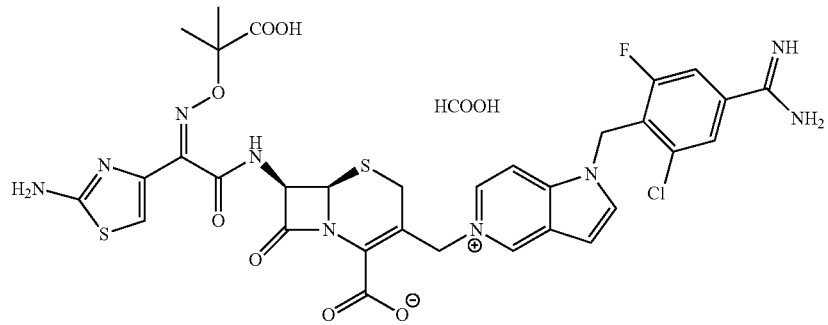 [SMILES: CC(C)(O/N=C(\C(=O)N[C@@H]1C(=O)N2C(C(=O)[O-])=C(C[n+]3ccc4c(ccn4Cc4c(F)cc(C(=N)N)cc4Cl)c3)CS[C@H]12)c1csc(N)n1)C(=O)O ; "HCOOH"]

$^1$H NMR (400 MHz, $D_2O$): δ 1.21 (s, 6H), 2.90 (d, 1H, J=17.6 Hz), 3.36 (d, 1H, J=18.0 Hz), 5.05-5.09 (m, 2H), 5.32 (d, 1H, J=14.4 Hz), 5.59 (s, 3H), 6.69 (s, 1H), 6.84 (d, 1H, J=3.2 Hz), 7.40 (d, 1H, J=9.6 Hz), 7.58 (d, 2H, J=10.0 Hz), 7.87 (d, 1H, J=7.2 Hz), 8.28 (d, 1H, J=7.2 Hz), 9.00 (s, 1H). Seven protons were not observed in $D_2O$.
Mass: ES$^+$ 770.28

Example 38 (Table 1, Compound 27)

(6R,7R)-7-{[(2Z)-2-(5-Amino-1,2,4-thiadiazol-3-yl)-2-{[(2-carboxypropan-2-yl)oxy]imino}acetyl]amino}-3-({1-[(4-carbamimidoylthiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate

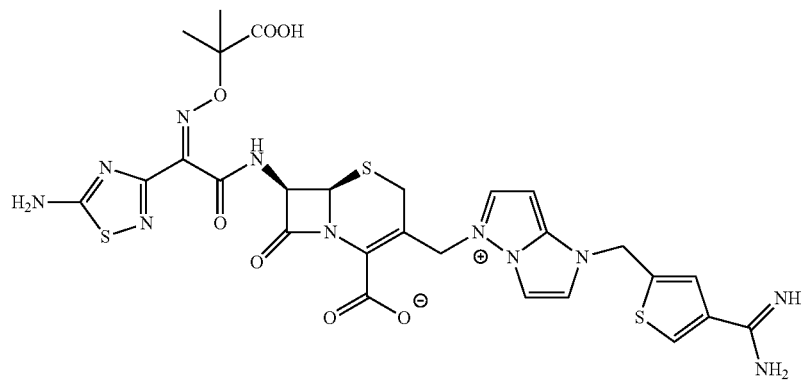 [SMILES: CC(C)(O/N=C(\C(=O)N[C@@H]1C(=O)N2C(C(=O)[O-])=C(C[n+]3ccc4n(Cc5cc(C(=N)N)cs5)ccn43)CS[C@H]12)c1nsc(N)n1)C(=O)O]

$^1$H NMR (400 MHz, D$_2$O): δ 1.28 (s, 3H), 1.30 (s, 3H), 2.90 (d, 1H, J=18.0 Hz), 3.22 (d, 1H, J=18.0 Hz), 5.01 (d, 1H, J=4.7 Hz), 5.12 (s, 2H), 5.43 (s, 2H), 5.62 (d, 1H, J=4.7 Hz), 6.17 (d, 1H, J=3.5 Hz), 7.38-7.40 (m, 2H), 7.80-7.88 (m, 2H), 8.12 (s, 1H). Seven protons were not observed in D$_2$O.

Mass: ES$^+$ 714.27

Example 39 (Table 1, Compound 51)

(6R,7R)-7-{[(2Z)-2-(2-Amino-5-chloro-1,3-thiazol-4-yl)-2-(methoxyimino)acetyl]amino}-3-({1-[(4-carbamimidoylthiophen-2-yl)methyl]-1H-imidazo[1,2-b]pyrazol-5-ium-5-yl}methyl)-8-oxo-5-thia-1-azabicyclo[4.2.0]oct-2-ene-2-carboxylate

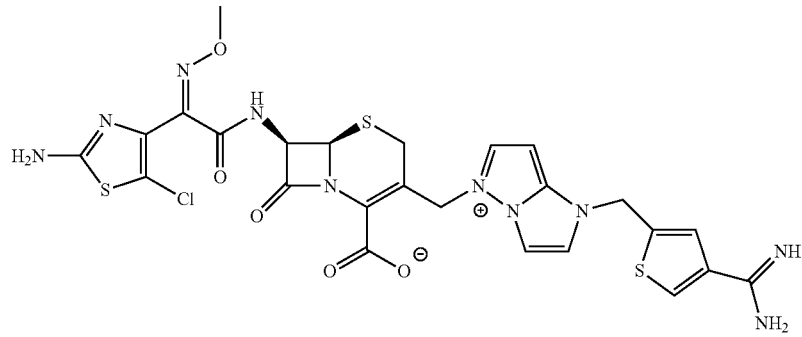 [SMILES: CO/N=C(\C(=O)N[C@@H]1C(=O)N2C(C(=O)[O-])=C(C[n+]3ccc4n(Cc5cc(C(=N)N)cs5)ccn43)CS[C@H]12)c1nc(N)sc1Cl]

$^1$H NMR (D$_2$O): δ 2.90 (d, 1H, J=17.6 Hz), 3.15 (d, 1H, J=17.6 Hz), 3.78 (s, 3H), 4.96 (d, 1H, J=4.8 Hz), 5.10 (d, 2H, J=3.6 Hz), 5.39 (s, 2H), 5.63 (d, 1H, J=4.8 Hz), 6.15 (d, 1H, J=3.6 Hz), 7.37 (d, 2H, J=10.8 Hz), 7.80 (d, 1H, J=2.4 Hz), 7.85 (d, 1H, J=2.4 Hz), 7.86 (s, 1H). Six protons were not observed in D$_2$O.

Mass: ES$^+$ 676.10

Example 40 (Table 1, Compound 50)

(6R,7R)-7-{[(2Z)-2-(2-Amino-5-chloro-1,3-thiazol-4-yl)-2-(methoxyimino)acetyl]amino}-3-({1-[(4-carbamimidoylthiophen-2-yl)methyl]-1H-pyrrolo[3,2-c]pyridin-5-ium-5-yl}methyl)-8-oxo-5-thia-1-azabicyclo[4.2.0]oct-2-ene-2-carboxylate

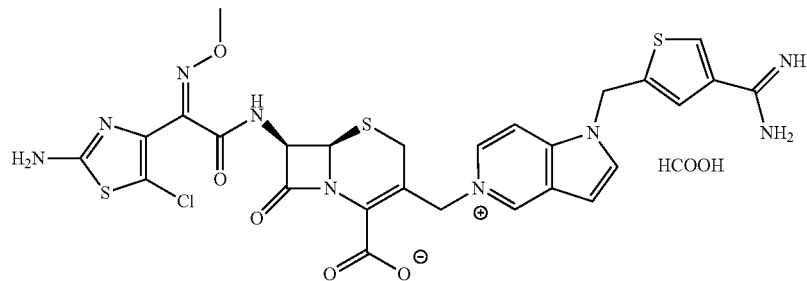 [SMILES: CO/N=C(\C(=O)N[C@@H]1C(=O)N2C(C(=O)[O-])=C(C[n+]3ccc4c(ccn4Cc4cc(C(=N)N)cs4)c3)CS[C@H]12)c1nc(N)sc1Cl ; "HCOOH"]

$^1$H NMR (D$_2$O): δ 3.04 (d, 1H, J=17.6 Hz), 3.42 (d, 1H, J=18.0 Hz), 3.84 (s, 3H), 5.10 (d, 1H, J=4.8 Hz), 5.21 (d, 1H, J=14.8 Hz), 5.34 (d, 1H, J=14.4 Hz), 5.70 (m, 3H), 6.98 (d, 1H, J=3.2 Hz), 7.35 (s, 1H), 7.74 (d, 1H, J=3.2 Hz), 7.89 (d, 1H, J=6.8 Hz), 8.12 (s, 1H), 8.31 (d, 1H, J=2.4 Hz), 9.08 (s, 1H). Six protons were not observed in D$_2$O.
Mass: ES$^+$ 686.17

Example 41 (Table 1, Compound 52)

(6R,7R)-7-{[(2Z)-2-(2-Amino-5-chloro-1,3-thiazol-4-yl)-2-(methoxyimino)acetyl]amino}-3-{[1-(4-carbamimidoyl-2-fluorobenzyl)-1H-pyrrolo[3,2-c]pyridin-5-ium-5-yl]methyl}-8-oxo-5-thia-1-azabicyclo[4.2.0]oct-2-ene-2-carboxylate

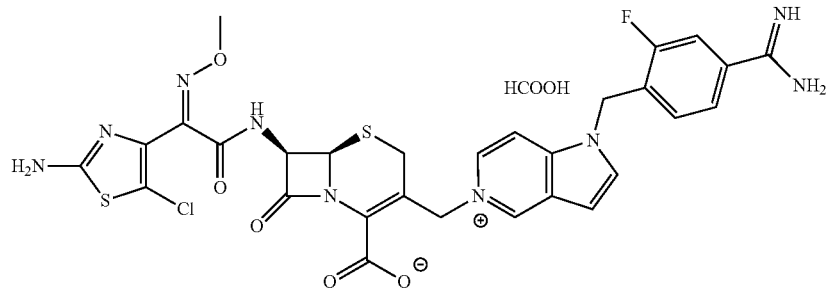 [SMILES: CO/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1nc(N)sc1Cl ; "HCOOH"]

$^1$H NMR (400 MHz, D$_2$O): δ 2.97 (d, 1H, J=18.0 Hz), 3.35 (d, 1H, J=17.6 Hz), 3.77 (s, 3H), 5.03 (d, 1H, J=4.8 Hz), 5.14 (d, 1H, J=15.2 Hz), 5.26 (d, 1H, J=14.0 Hz), 5.56 (s, 2H), 5.65 (d, 1H, J=4.8 Hz), 6.91 (d, 1H, J=3.6 Hz), 7.15 (t, 1H, J=8.0 Hz), 7.35 (d, 1H, J=7.6 Hz), 7.41 (d, 1H, J=10.4 Hz), 7.65 (d, 1H, J=3.2 Hz), 7.77 (d, 1H, J=7.2 Hz), 8.22 (d, 1H, J=8.4 Hz), 9.01 (s, 1H). Six protons were not observed in D$_2$O.
Mass: ES$^+$ 698.16

Example 42 (Table 1, Compound 54)

(6R,7R)-7-{[(2Z)-2-(2-Amino-5-chloro-1,3-thiazol-4-yl)-2-(methoxyimino)acetyl]amino}-8-oxo-3-{[1-(4-{N-[(3R)-piperidin-3-yl]carbamimidoyl}benzyl)-1H-pyrrol[3,2-c]pyridin-5-ium-5-yl]methyl}-5-thia-1-azabicyclo[4.2.0]oct-2-ene-2-carboxylate

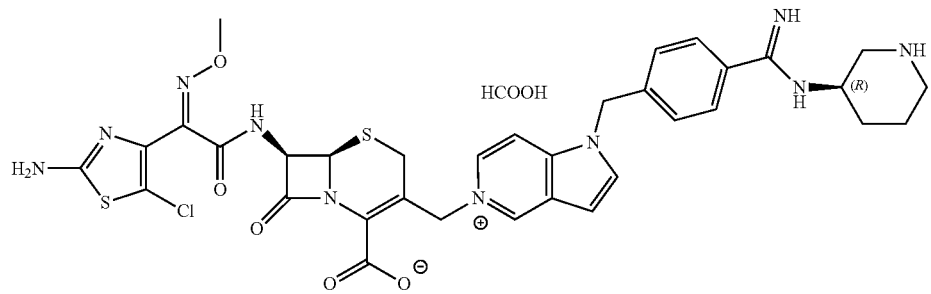

$^1$H NMR (400 MHz, D$_2$O): δ 1.56-1.92 (m, 2H), 1.88 (d, 1H, J=15.2 Hz), 2.07 (d, 1H, J=10.4 Hz), 2.83-3.01 (m, 3H), 3.21 (d, 1H, J=12.8 Hz), 3.32 (d, 1H, J=18.0 Hz), 3.47 (d, 1H, J=12.4 Hz), 3.74 (s, 3H), 3.92-3.97 (m, 1H), 4.99 (d, 1H, J=4.8 Hz), 5.13 (d, 1H, J=14.8 Hz), 5.23 (d, 1H, J=14.4 Hz), 5.51 (s, 2H), 5.60 (d, 1H, J=4.4 Hz), 6.90 (d, 1H, J=3.6 Hz), 7.17 (d, 2H, J=8.0 Hz), 7.47 (d, 2H, J=8.0 Hz), 7.63 (d, 1H, J=3.2 Hz), 7.66 (d, 1H, J=7.2 Hz), 8.16 (d, 1H, J=7.2 Hz), 9.00 (s, 1H). Six protons were not observed in D$_2$O.

Mass: ES$^+$ 763.22

Example 43 (Table 1, Compound 53)

(6R,7R)-7-{[(2Z)-2-(2-Amino-5-chloro-1,3-thiazol-4-yl)-2-(methoxyimino)acetyl]amino}-3-({-[(4-carbamimidoyl-1,3-thiazol-2-yl)methyl]-1H-imidazo[1,2-b]pyrazol-5-ium-5-yl}methyl)-8-oxo-5-thia-1-azabicyclo[4.2.0]oct-2-ene-2-carboxylate

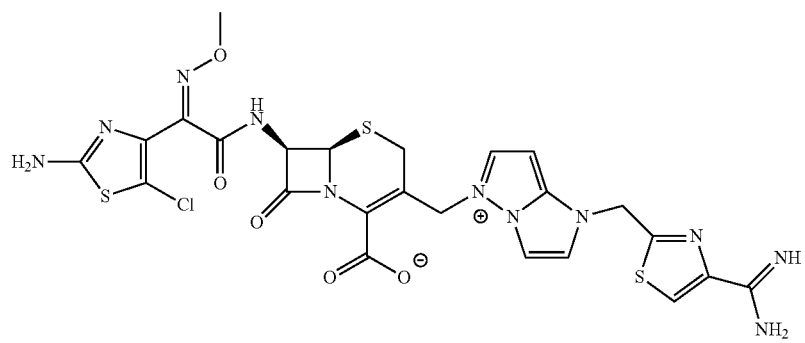 [SMILES: CO/N=C(\C(=O)N[C@@H]1C(=O)N2C(C(=O)[O-])=C(C[n+]3ccc4n(Cc5nc(C(=N)N)cs5)ccn43)CS[C@H]12)c1nc(N)sc1Cl]

$^1$H NMR (400 MHz, D$_2$O): δ 3.02 (d, 1H, J=16.4 Hz), 3.25 (d, 1H, J=18.4 Hz), 3.83 (s, 3H), 5.04 (s, 1H), 5.11 (d, 1H, J=16.5 Hz), 5.20 (d, 1H, J=15.4 Hz), 5.67 (s, 3H), 6.34 (m, 1H), 7.51 (m, 1H), 7.87 (m, 1H), 7.95 (m, 1H), 8.46 (s, 1H). Six protons were not observed in D$_2$O.

Mass: ES$^+$ 677.13

Example 44 (Table 1, Compound 55)

(6R,7R)-7-{[(2Z)-2-(2-Amino-1,3-thiazol-4-yl)-2-(methoxyimino)acetyl]amino}-3-{[1-(4-carbamimidoyl-2-fluorobenzyl)-1H-pyrrolo[3,2-c]pyridin-5-ium-5-yl]methyl}-8-oxo-5-thia-1-azabicyclo[4.2.0]oct-2-ene-2-carboxylate

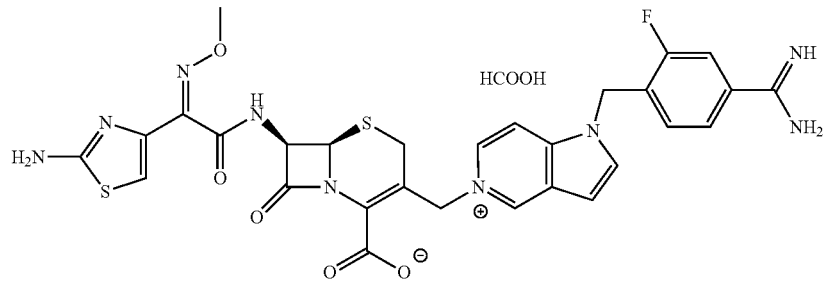 [SMILES: CO/N=C(\C(=O)N[C@@H]1C(=O)N2C(C(=O)[O-])=C(C[n+]3ccc4c(ccn4Cc4ccc(C(=N)N)cc4F)c3)CS[C@H]12)c1csc(N)n1 ; "HCOOH"]

$^1$H NMR (400 MHz, D$_2$O): δ 2.96 (d, 1H, J=17.6 Hz), 3.36 (d, 1H, J=18.0 Hz), 3.75 (s, 3H), 5.04 (d, 1H, J=4.8 Hz), 5.12 (d, 1H, J=14.8 Hz), 5.26 (d, 1H, J=14.8 Hz), 5.55 (s, 2H), 5.62 (d, 1H, J=4.8 Hz), 6.75 (s, 1H), 6.90 (d, 1H, J=2.8 Hz), 7.11 (t, 1H, J=8.0 Hz), 7.33 (d, 1H, J=8.0 Hz), 7.40 (d, 1H, J=10.8 Hz), 7.64 (d, 1H, J=3.2 Hz), 7.75 (d, 1H, J=6.8 Hz), 8.21 (d, 1H, J=7.2 Hz), 9.00 (s, 1H). Six protons were not observed in D$_2$O.

Mass: ES$^+$ 664.23

Example 45 (Table 1, Compound 58)

(6R,7R)-7-{[(2Z)-2-(2-amino-5-chloro-1,3-thiazol-4-yl)-2-(methoxyimino)acetyl]amino}-3-{[1-(4-carbamimidoyl-2-chloro-6-fluorobenzyl)-1H-pyrrolo[3,2-c]pyridin-5-ium-5-yl]methyl}-8-oxo-5-thia-1-azabicyclo[4.2.0]oct-2-ene-2-carboxylate

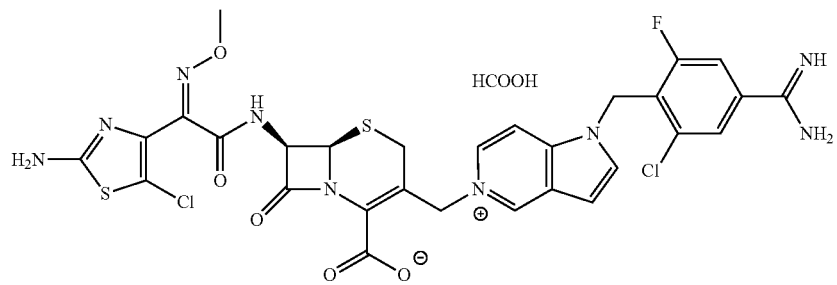 [SMILES: CO/N=C(\C(=O)N[C@@H]1C(=O)N2C(C(=O)[O-])=C(C[n+]3ccc4c(ccn4Cc4c(F)cc(C(=N)N)cc4Cl)c3)CS[C@H]12)c1nc(N)sc1Cl ; "HCOOH"]

Step 1: 3-Chloro-5-fluoro-4-formylbenzonitrile

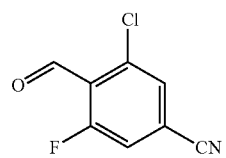 [SMILES: N#Cc1cc(F)c(C=O)c(Cl)c1]

To a solution of 3-chloro-5-fluorobenzonitrile (1.8 g, 11.57 mmol) in anhydrous tetrahydrofuran (40 mL) at −78° C. was added lithium diisopropylamide (2M, 6.4 mL, 12.73 mmol). After stirring at same temperature for 30 minutes was added dimethylformamide (1.02 g, 13.84 mmol). The reaction mixture was stirred at −78° C. for an additional 15 minutes, then was added acetic acid (2.7 mL) followed by water (40 mL) and the mixture was warmed to room temperature. After extraction with ethyl acetate (60 mL), the organic phase was washed with 1M HCl solution, brine, dried over Na$_2$SO$_4$, filtered and evaporated to give 3-chloro-5-fluoro-4-formylbenzonitrile (1.08 g, 51%) as a gummy solid.

$^1$H NMR (400 MHz, CDCl$_3$): δ 7.42 (m, 1H), 7.61 (d, 1H, J=2.8 Hz), 10.45 (s, 1H).

Step 2:
3-Chloro-5-fluoro-4-(hydroxymethyl)benzonitrile

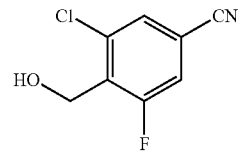 [SMILES: N#Cc1cc(F)c(CO)c(Cl)c1]

To a solution of 3-chloro-5-fluoro-4-formylbenzonitrile (from step 1, 1.08 g, 5.88 mmol) in methanol (6 mL) was added sodium borohydride (0.25 g, 6.61 mmol) at 0° C. After 15 minutes, the mixture was quenched with water (1 mL) and concentrated to obtain a yellow oil residue. Dissolved the residue in ethyl acetate (35 mL), washed with water (30 mL) and the aqueous layer was extracted again with ethyl acetate (20 mL). The extracts were combined, washed with brine, dried over Na$_2$SO$_4$, filtered and evaporated. The residue was purified by column chromatography (silica gel) eluting 1:1 ethyl acetate/hexanes as eluent to give 3-chloro-5-fluoro-4-(hydroxymethyl)benzonitrile (0.65 g, 60%) as an orange thick oil.

$^1$H NMR (400 MHz, CDCl$_3$): δ 4.88 (s, 2H), 7.33 (m, 1H), 7.54 (d, 1H, J=1.2 Hz).

Step 3:
4-(Bromomethyl)-3-chloro-5-fluorobenzonitrile

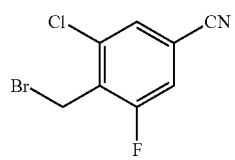 [SMILES: N#Cc1cc(F)c(CBr)c(Cl)c1]

To a solution of 3-chloro-5-fluoro-4-(hydroxymethyl) benzonitrile (from step 2, 0.65 g, 3.5 mmol) and carbon tetrabromide (1.25 g, 3.73 mmol) I dichloromethane (20 mL) was added triphenylphosphene (1.02 g, 2.73 mmol) slowly at 0° C. After stirring for 10 minutes at the same temperature, the solution was stirred overnight at room temperature. The solution was concentrated under reduced pressure and the residue was purified by column chromatography (silica gel) eluting with 1:20 ethyl acetate/hexanes as eluent to give 4-(bromomethyl)-3-chloro-5-fluorobenzonitrile (0.72 g, 83%) as a white solid.

$^1$H NMR (400 MHz, CDCl$_3$): δ 4.59 (s, 2H), 7.32 (m, 1H), 7.54 (s, 1H, J=1.2 Hz).

Step 4: 3-Chloro-5-fluoro-4-(1H-pyrrolo[3,2-c]pyridin-1-ylmethyl)benzonitrile

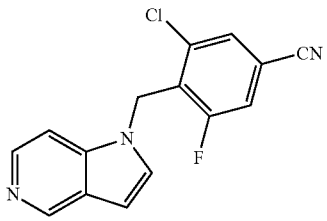 [SMILES: N#Cc1cc(F)c(Cn2ccc3cnccc32)c(Cl)c1]

An ice-cold mixture of 5-azaindole (0.34 g, 2.88 mmol) in N,N-dimethylformamide (10 mL) was treated with sodium hydride (60% in mineral oil, 0.172 g, 4.32 mmol) in portions, then stirred at room temperature for 15 minutes. The mixture was cooled to 0° C., and then treated with 4-(bromomethyl)-3-chloro-5-fluorobenzonitrile (from step 3, 0.73 g, 2.93 mmol) in tetrahydrofuran (10 mL). The resulting mixture was stirred at 0° C. for 1 hour then quenched with saturated ammonium chloride solution. The mixture was extracted with ethyl acetate, and the extracts were washed with brine, dried (sodium sulphate), filtered and concentrated in vacuo to brown oil, which was purified by column chromatography (silica gel) eluting with 5:3:2 dichloromethane/ethyl acetate/methanol as eluent to afford 3-chloro-5-fluoro-4-(1H-pyrrolo[3,2-c]pyridin-1-ylmethyl) benzonitrile (0.53 g, 65%) as a white solid.

$^1$H NMR (400 MHz, CDCl$_3$): δ 5.49 (d, 2H, J=1.9 Hz), 6.62 (d, 1H, J=3.2 Hz), 7.19 (d, 1H, J=2.8 Hz), 7.37-7.41 (m, 2H), 7.59 (s, 1H), 8.35 (d, 1H, J=6.0 Hz), 8.91 (s, 1H).

Step 5: Ethyl 3-chloro-5-fluoro-4-(1H-pyrrolo[3,2-c]pyridin-1-ylmethyl)benzenecarboximidate hydrochloride

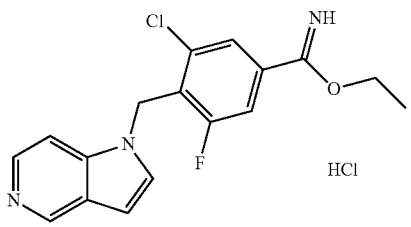 [SMILES: CCOC(=N)c1cc(F)c(Cn2ccc3cnccc32)c(Cl)c1 ; Cl]

Through a solution of 3-chloro-5-fluoro-4-(1H-pyrrolo[3,2-c]pyridin-1-ylmethyl)benzonitrile (from step 4, 0.53 g, 1.86 mmol) in anhydrous ethanol (20 mL) in a pressure vessel at 0° C. was bubbled a stream of anhydrous hydrogen chloride gas for 10 min. The reaction vessel was stoppered and stirred at room temperature for 18 h and the contents were transferred into a flask and evaporated under reduced pressure. The crude product was triturated with ether, then dried under vacuum to provide ethyl 3-chloro-5-fluoro-4-(1H-pyrrolo[3,2-c]pyridin-1-ylmethyl)benzenecarboximidate hydrochloride (0.64 g, 94%) as a white solid which was used in the next step without further purification.

Step 6: 3-Chloro-5-fluoro-4-(1H-pyrrolo[3,2-c]pyridin-1-ylmethyl)benzenecarboximidamide

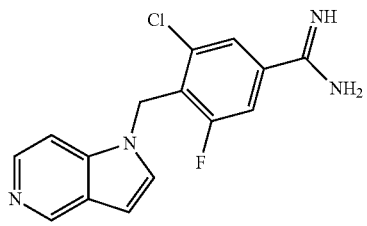 [SMILES: N=C(N)c1cc(F)c(Cn2ccc3cnccc32)c(Cl)c1]

A pressure vessel containing a suspension of ethyl 3-chloro-5-fluoro-4-(1H-pyrrolo[3,2-c]pyridin-1-ylmethyl) benzenecarboximidate hydrochloride (from step 5, 0.64 g, 1.74 mol) in methanol (20 mL) was saturated with ammonia gas and stoppered. The reaction mixture was stirred at room temperature for 24 h, then excess ammonia was vented out and the contents were concentrated under reduced pressure. The residue was triturated with hexanes and dried under vacuum to give 3-chloro-5-fluoro-4-(1H-pyrrolo[3,2-c]pyridin-1-ylmethyl)benzenecarboximidamide (0.69 g, 130%) as a grey solid which was used in the next step without further purification.

Step 7: tert-Butyl {[3-chloro-5-fluoro-4-(1H-pyrrolo[3,2-c]pyridin-1-ylmethyl)phenyl]carbonoimidoyl}carbamate

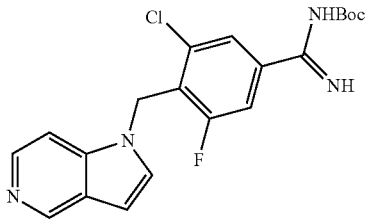 [SMILES: CC(C)(C)OC(=O)NC(=N)c1cc(F)c(Cn2ccc3cnccc32)c(Cl)c1]

A solution of 3-chloro-5-fluoro-4-(1H-pyrrolo[3,2-c]pyridin-1-ylmethyl)benzenecarboximidamide (from step 6, 0.69 g. 1.74 mmol) in 1,4-dioxane (50 mL) was treated with a saturated sodium carbonate solution (25 mL) followed by di-tert-butyl dicarbonate (2.51 g, 11.4 mmol) and stirred at room temperature for 40 h. The reaction mixture was concentrated under reduced pressure to remove the volatiles and the remaining solution was dissolved in ethyl acetate (60 mL), then washed with water (60 mL), brine solution (60 mL), dried and concentrated. The crude product was purified by silica gel column chromatography using ethyl acetate:methanol:ammonium hydroxide (60:39:1) as eluent to afford tert-butyl {[3-chloro-5-fluoro-4-(1H-pyrrolo[3,2-c]pyridin-1-ylmethyl)phenyl]carbonoimidoyl}carbamate (0.3 g, 33%).

$^1$H NMR (400 MHz, CDCl$_3$): δ 1.52 (s, 9H), 5.43 (s, 2H), 6.56 (d, 1, J=3.2 Hz), 7.18 (d, 1H, J=2.8 Hz), 7.37 (d, 1H, J=6.0 Hz), 7.58 (d, 1H, J=9.6 Hz), 7.80 (s, 1H), 8.22 (d, 1H, J=5.6 Hz), 8.82 (s, 1H).

Step 8: 5-{[(6R,7R)-7-{[(2Z)-2-{2-[(tert-Butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]-2-chloro-6-fluorobenzyl}-1H-pyrrolo[3,2-c]pyridin-5-ium iodide

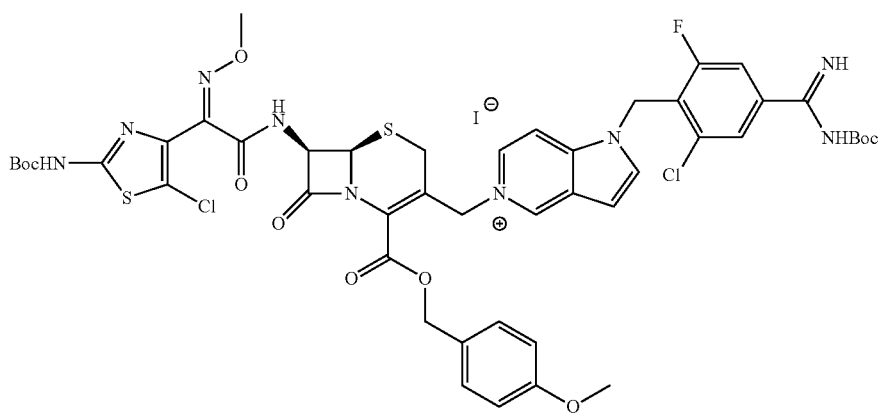

To a solution of tert-butyl {[3-chloro-5-fluoro-4-(1H-pyrrolo[3,2-c]pyridin-1-ylmethyl)phenyl]carbonoimidoyl}carbamate (from step 7, 0.12 g, 0.30 mmol) in dimethylformamide (1 mL) was added (6R,7R)-7-{[(2Z)-2-{2-[(tert-butoxycarbonyl)amino]-5-chloro-1,3-thiazol-4-yl}-2-(methoxyimino)acetyl]amino}-3-(iodomethyl)-2-{[(4-methoxybenzyl)oxy]carbonyl}-8-oxo-5-thionia-1-azabicyclo[4.2.0]oct-2-en-5-olate (0.24 g, 0.30 mmol) at 0° C. The reaction mixture was then degassed under reduced pressure for 0.5 h, and stirred at room temperature for 16 h. Dimethyl formamide (2 mL) was added and cooled to −40° C., followed by adding KI (0.35 g, 2.1 mmol) and acetyl chloride (0.09 mL, 1.2 mmol). After stirring at 0° C. for 1 h, ice water and ethyl acetate (30 mL) were poured to the reaction solution, and then NaHSO$_3$ solution (20 mL) was added. The aqueous solution was extracted with ethyl acetate (30 mL×2) and the organic layers were combined, washed with brine (3×50 mL), dried over Na$_2$SO$_4$, filtered and evaporated to give yellow solid (0.29 g), which was used in the next step without further purification.

Step 9: (6R,7R)-7-{[(2Z)-2-(2-Amino-5-chloro-1,3-thiazol-4-yl)-2-(methoxyimino)acetyl]amino}-3-{[1-(4-carbamimidoyl-2-chloro-6-fluorobenzyl)-1H-pyrrolo[3,2-c]pyridin-5-ium-5-yl]methyl}-8-oxo-5-thia-1-azabicyclo[4.2.0]oct-2-ene-2-carboxylate

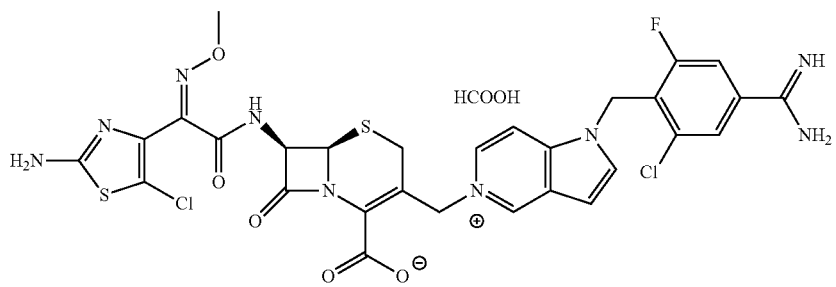

To a solution of 5-{[(6R,7R)-7-{[(2Z)-2-{2-[(tert-butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]-2-chloro-6-fluorobenzyl}-1H-pyrrolo[3,2-c]pyridin-5-ium iodide (0.29 g) in dry dichloromethane (6 mL) at −40° C. was added anisole (0.52 mL, 4.92 mmol) and then 2M AlCl₃ in CH₃NO₂ (2.46 mL, 4.92 mmol). The liquid was stirred at 0° C. for 30 min. To the reaction mixture were added diisopropyl ether (10 mL) and water (0.5 mL), and the resultant was stirred to generate a precipitate. The supernatant was removed by decantation. To the insoluble matter adhering to the vessel were added diluted aqueous hydrochloric acid solution (5 mL) and acetonitrile (10 mL). The resultant was stirred to dissolve the matter completely. Thereto was added HP20 resin (1.0 g), and stirred for 30 min, and then filtered. The filtrate was concentrated and lyophilized to give a crude product which was purified by HPLC to obtain (6R,7R)-7-{[(2Z)-2-(2-amino-5-chloro-1,3-thiazol-4-yl)-2-(methoxyimino)acetyl]amino}-3-{[1-(4-carbamimidoyl-2-chloro-6-fluorobenzyl)-1H-pyrrolo[3,2-c]pyridin-5-ium-5-yl]methyl}-8-oxo-5-thia-1-azabicyclo[4.2.0]oct-2-ene-2-carboxylate as formic acid salt (0.0135 g, 7.5%).

$^1$H NMR (400 MHz, D$_2$O): δ 2.94 (d, 1H, J=18.0 Hz), 3.33 (d, 1H, J=17.6 Hz), 3.73 (s, 3H), 5.00 (d, 1H, J=5.2 Hz), 5.11 (d, 1H, J=14.4 Hz), 5.26 (d, 1H, J=14.0 Hz), 5.58-5.62 (m, 3H), 6.84 (s, 1H), 7.39 (d, 1H, J=9.6 Hz), 7.58 (s, 2H), 7.89 (d, 1H, J=7.2 Hz), 8.25 (d, 1H, J=6.4 Hz), 8.97 (s, 1H). Six protons were not observed in D$_2$O.

Mass: ES⁺ 732.21

Example 46 (Table 1, Compound 56)

(6R,7R)-7-{[(2Z)-2-(2-Amino-5-chloro-1,3-thiazol-4-yl)-2-(methoxyimino)acetyl]amino}-3-({1-[(4-carbamimidoylfuran-2-yl)methyl]-1H-pyrrolo[3,2-c]pyridin-5-ium-5-yl}methyl)-8-oxo-5-thia-1-azabicyclo[4.2.0]oct-2-ene-2-carboxylate

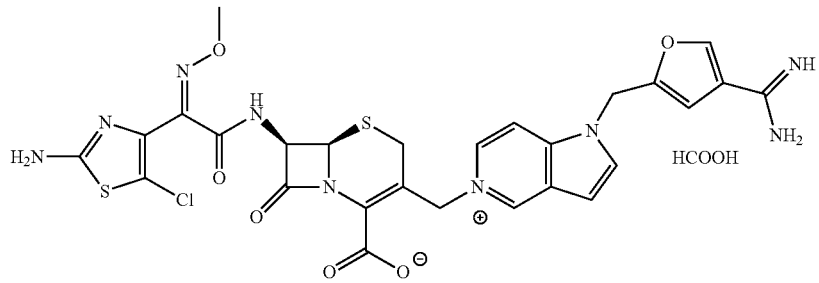

$^1$H NMR (400 MHz, D$_2$O): δ 2.91 (d, 1H, J=18.0 Hz), 3.34 (d, 1H, J=18.0 Hz), 3.77 (s, 3H), 5.03 (d, 1H, J=4.8 Hz), 5.15 (d, 1H, J=15.2 Hz), 5.26 (d, 1H, J=14.0 Hz), 5.47 (s, 2H), 5.65 (d, 1H, J=4.8 Hz), 6.74 (s, 1H), 6.88 (d, 1H, J=3.2 Hz), 7.64 (d, 1H, J=3.6 Hz), 7.86 (d, 1H, J=7.6 Hz), 8.04 (s, 1H), 8.25 (d, 1H, J=4.0 Hz), 8.99 (s, 1H). Six protons were not observed in D$_2$O.

Mass: ES⁺ 670.06

Example 47 (Table 1, Compound 65)

(6R,7R)-7-{[(2Z)-2-(2-Amino-5-chloro-1,3-thiazol-4-yl)-2-{[(2-carboxypropan-2-yl)oxy]imino}acetyl]amino}-3-({1-[(4-carbamimidoylthiophen-2-yl)methyl]-1H-pyrrolo[2,3-c]pyridin-6-ium-6-yl}methyl)-8-oxo-5-thia-1-azabicyclo[4.2.0]oct-2-ene-2-carboxylate

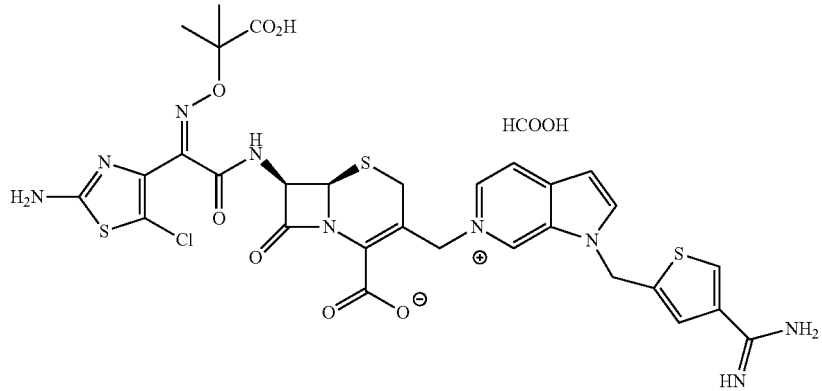

¹H NMR (400 MHz, D₂O): δ 1.33 (s, 3H), 1.35 (s, 3H), 2.95 (d, 1H, J=18.0 Hz), 3.38 (d, 1H, J=18.4 Hz), 5.07-5.11 (m, 2H), 5.39 (d, 1H, J=14.5 Hz), 5.67-5.78 (m, 3H), 6.88 (d, 1H, J=2.8 Hz), 7.47 (s, 1H), 7.96 (d, 1H, J=6.0 Hz), 8.12 (m, 3H), 9.10 (s, 1H). Seven protons were not observed in D₂O.

Mass: ES⁺ 758.17

Example 48 (Table 1, Compound 66)

(6R,7R)-7-{[(2Z)-2-(5-Amino-1,2,4-thiadiazol-3-yl)-2-{[(2-carboxypropan-2-yl)oxy]imino}acetyl]amino}-3-({1-[(4-carbamimidoylthiophen-2-yl)methyl]-1H-pyrrolo[2,3-c]pyridin-6-ium-6-yl}methyl)-8-oxo-5-thia-1-azabicyclo[4.2.0]oct-2-ene-2-carboxylate

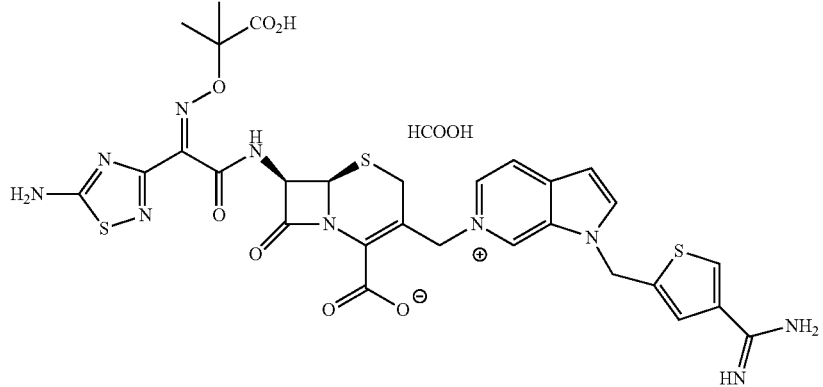

¹H NMR (400 MHz, D₂O): δ 1.37 (s, 3H), 1.39 (s, 3H), 2.97 (d, 1H, J=18.0 Hz), 3.38 (d, 1H, J=17.6 Hz), 5.08-5.13 (m, 2H), 5.37 (d, 1H, J=14.4 Hz), 5.69-5.80 (m, 3H), 6.85 (d, 1H, J=2.8 Hz), 7.46 (s, 1H), 7.94 (d, 1H, J=6.8 Hz), 8.09-8.16 (m, 3H), 9.08 (s, 1H). Seven protons were not observed in D₂O.

Mass: ES⁺ 725.16

Example 49 (Table 1, Compound 67)

(6R,7R)-7-{[(2Z)-2-(5-Amino-1,2,4-thiadiazol-3-yl)-2-(methoxyimino)acetyl]amino}-3-({1-[(4-carbamimidoylthiophen-2-yl)methyl]-1H-pyrrolo[2,3-c]pyridin-6-ium-6-yl}methyl)-8-oxo-5-thia-1-azabicyclo[4.2.0]oct-2-ene-2-carboxylate

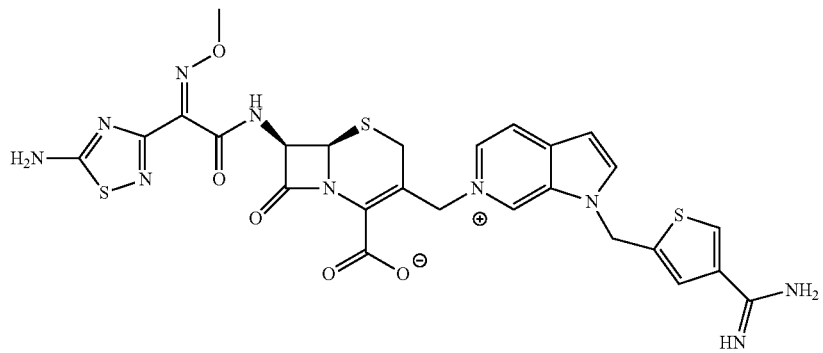

¹H NMR (400 MHz, D₂O): δ 2.96 (d, 1H, J=17.6 Hz), 3.38 (d, 1H, J=17.6 Hz), 3.95 (s, 3H), 5.06 (d, 1H, J=4.8 Hz), 5.12 (d, 1H, J=14.8 Hz), 5.31 (d, 1H, J=14.4 Hz), 5.53 (d, 1H, J=4.8 Hz), 5.72 (m, 2H), 6.88 (d, 1H, J=3.2 Hz), 7.50 (s, 1H), 7.95 (d, 1H, J=6.4 Hz), 8.11-8.30 (m, 3H), 8.99 (s, 1H). Six protons were not observed in D₂O.

Mass: ES⁺ 653.19

Example 50 (Table 1, Compound 68)

(6R,7R)-7-{[(2Z)-2-(5-amino-1,2,4-thiadiazol-3-yl)-2-{[(2-carboxypropan-2-yl)oxy]imino}acetyl]amino}-3-({1-[(4-carbamimidoylthiophen-2-yl)methyl]-1H-pyrrolo[3,2-b]pyridin-4-ium-4-yl}methyl)-8-oxo-5-thia-1-azabicyclo[4.2.0]oct-2-ene-2-carboxylate

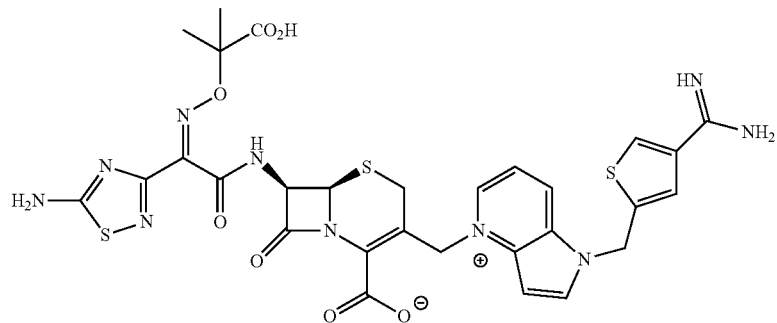

¹H NMR (400 MHz, D₂O): δ 1.40 (s, 6H), 3.03 (d, 1H, J=17.6 Hz), 3.24 (d, 1H, J=17.6 Hz), 5.06 (d, 1H, J=4.8 Hz), 5.42 (d, 1H, J=15.2 Hz), 5.58 (d, 1H, J=15.2 Hz), 5.71 (d, 1H, J=4.8 Hz), 5.76 (s, 2H), 6.95 (d, 1H, J=3.2 Hz), 7.34 (s, 1H), 7.54-7.58 (m, 1H), 8.08 (d, 1H, J=3.2 Hz), 8.12 (s, 1H), 8.48-8.53 (m, 2H). Seven protons were not observed in D₂O. Mass: ES⁺ 725.13

Example 51 (Table 1, Compound 71)

(6R,7R)-7-{[(2Z)-2-(2-Amino-5-chloro-1,3-thiazol-4-yl)-2-(methoxyimino)acetyl]amino}-3-{[1-(4-carbamimidoyl-2-chloro-6-fluorobenzyl)-1H-pyrrolo[3,2-b]pyridin-4-ium-4-yl]methyl}-8-oxo-5-thia-1-azabicyclo[4.2.0]oct-2-ene-2-carboxylate

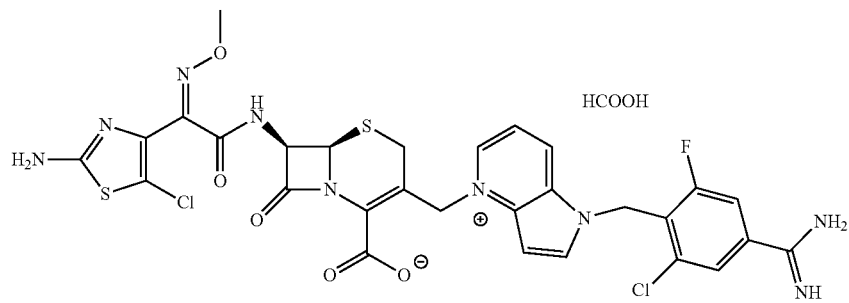

Step 1: 3-Chloro-5-fluoro-4-(1H-pyrrolo[3,2-b]pyridin-1-ylmethyl)benzonitrile

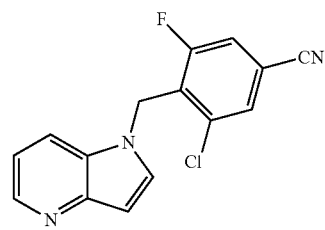 [SMILES: N#Cc1cc(F)c(Cn2ccc3ncccc32)c(Cl)c1]

An ice-cold mixture of 4-azaindole (0.47 g, 3.98 mmol) in N,N-dimethylformamide (10 mL) was treated with sodium hydride (60% in mineral oil, 0.23 g, 6.0 mmol) in portions, then stirred at room temperature for 15 minutes. The mixture was cooled to 0° C., then treated with 4-(bromomethyl)-3-chloro-5-fluorobenzonitrile (1.00 g, 4.00 mmol) in tetrahydrofuran (10 mL). The resulting mixture was stirred at 0° C. for 1 hour then quenched with saturated ammonium chloride solution. The mixture was extracted with ethyl acetate and the extracts were washed with brine, dried (sodium sulphate), filtered and concentrated in vacuo to brown oil, which was purified by column chromatography (silica gel) eluting with 5:3:2 dichloromethane/ethyl acetate/methanol as eluent to afford 3-chloro-5-fluoro-4-(1H-pyrrolo[3,2-b]pyridin-1-ylmethyl)benzonitrile (0.62 g, 54%) as brown solid.

¹H NMR (400 MHz, CDCl₃): δ 5.49 (d, 2H, J=1.9 Hz), 6.72 (d, 1H, J=3.4 Hz), 7.14 (dd, 1H, J=8.2, 4.7 Hz), 7.37 (d, 1H, J=8.7 Hz), 7.41 (d, 1H, J=3.4 Hz), 7.58 (br s, 1H,) 7.78 (d, 1H, J=8.4 Hz), 8.47 (d, 1H, J=4.7 Hz).

Step 2: Ethyl 3-chloro-5-fluoro-4-(1H-pyrrolo[3,2-b]pyridin-1-ylmethyl)benzenecarboximidate hydrochloride

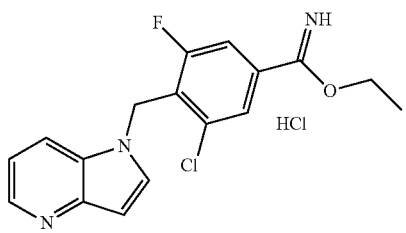 [SMILES: CCOC(=N)c1cc(F)c(Cn2ccc3ncccc32)c(Cl)c1 ; Cl]

Anhydrous hydrochloric acid was bubbled into an ice-cold brown suspension of 3-chloro-5-fluoro-4-(1H-pyrrolo[3,2-b]pyridin-1-ylmethyl)benzonitrile (0.65 g, 2.23 mmol) in anhydrous ethanol (30 mL) for 10 minutes. The mixture was sealed and stirred at room temperature overnight. The mixture was concentrated in vacuo to afford ethyl 3-chloro-5-fluoro-4-(1H-pyrrolo[3,2-b]pyridin-1-ylmethyl)benzenecarboximidate hydrochloride (0.83 g) as a brown solid, which was used in the next step without further purification.

$^1$H NMR (400 MHz, CD$_3$OD): δ 1.58 (t, 3H, J=7.2H), 4.59 (q, 2H, J=7.0 Hz), 6.09 (s, 2H), 7.15 (d, 1H, J=3.2 Hz), 7.92-8.04 (m, 2H), 8.16 (s, 1H), 8.34 (d, 1H, J=2.9 Hz), 8.83 (d, 1H, J=5.6 Hz), 9.03 (d, 1H, J=8.2 Hz).

Step 3: 3-Chloro-5-fluoro-4-(1H-pyrrolo[3,2-b]pyridin-1-ylmethyl)benzenecarboximidamide

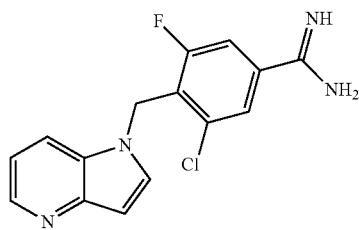 [SMILES: N=C(N)c1cc(F)c(Cn2ccc3ncccc32)c(Cl)c1]

Anhydrous ammonia was bubbled into an ice-cold solution of 3-chloro-5-fluoro-4-(1H-pyrrolo[3,2-b]pyridin-1-ylmethyl)benzenecarboximidate hydrochloride (0.83 g, 2.23 mmol) in anhydrous ethanol (30 mL) for 10 minutes. The mixture was sealed and stirred at room temperature overnight. The mixture was concentrated in vacuo to afford 3-chloro-5-fluoro-4-(1H-pyrrolo[3,2-b]pyridin-1-ylmethyl)benzenecarboximidamide as a brown solid (0.72 g), which was used in the next step without further purification.

$^1$H NMR (400 MHz, CD$_3$OD): δ 5.59 (s, 2H), 6.62 (br s, 1H), 7.22 (br s, 1H), 7.54-7.60 (m, 2H), 7.64-7.69 (m, 1H), 7.82-7.87 (m, 1H), 8.23-8.43 (br s, 1H).

Step 4: tert-Butyl {[3-chloro-5-fluoro-4-(1H-pyrrolo[3,2-b]pyridin-1-ylmethyl)phenyl]carbonoimidoyl}carbamate

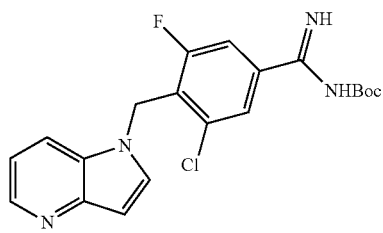 [SMILES: CC(C)(C)OC(=O)NC(=N)c1cc(F)c(Cn2ccc3ncccc32)c(Cl)c1]

An ice-cold solution of 3-chloro-5-fluoro-4-(1H-pyrrolo[3,2-b]pyridin-1-ylmethyl)benzenecarboximidamide (0.72 g, 2.38 mmol) in dioxane (40 mL) and saturated sodium carbonate solution (20 mL) was treated with di-tert-butyl dicarbonate (2.08 g, 9.53 mmol). The mixture was stirred at room temperature overnight, then concentrated in vacuo. The residue was diluted with ethyl acetate and washed with water and brine, then dried (sodium sulphate), filtered and concentrated to brown solid, which was purified by column chromatography (silica gel) eluting with 2-4% methanol in dichloromethane to afford tert-butyl {[3-chloro-5-fluoro-4-(1H-pyrrolo[3,2-b]pyridin-1-ylmethyl)phenyl]carbonoimidoyl}carbamate (0.20 g, 21%) as a yellow solid.

$^1$H NMR (400 MHz, CDCl$_3$): δ 1.55 (s, 9H), 5.47 (d, 2H, J=1.8 Hz), 6.60 (d, 1H, J=3.2 Hz), 7.19 (d, 1H, J=3.1 Hz), 7.41 (d, 1H, J=6.0 Hz), 7.55-7.60 (m, 1H), 7.78 (s, 1H), 8.31 (d, 1H, J=6.0 Hz), 8.88 (s, 1H).

Step 5: 4-{[(6R,7R)-7-{[(2Z)-2-{2-[(tert-Butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]-2-chloro-6-fluorobenzyl}-1H-pyrrolo[3,2-b]pyridin-4-ium iodide

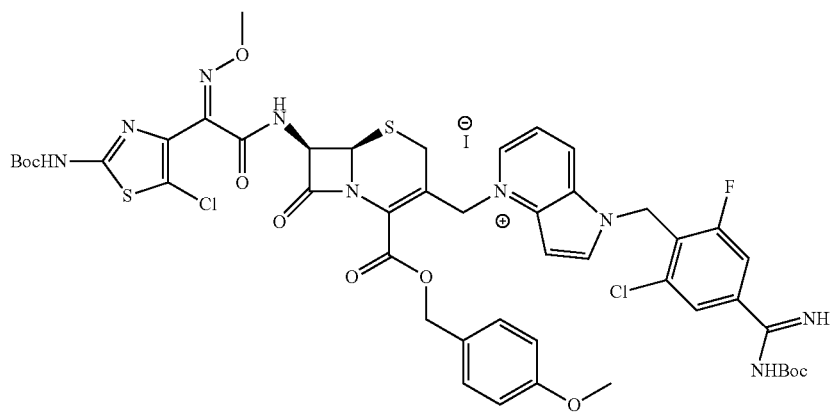

An ice-cold mixture of tert-butyl {[3-chloro-5-fluoro-4-(1H-pyrrolo[3,2-b]pyridin-1-ylmethyl)phenyl]carbonoimidoyl}carbamate (0.20 g, 0.50 mmol) in anhydrous N,N-dimethylformamide (2.0 mL) was degassed under reduced pressure for 5 minutes, then treated with 4-methoxybenzyl (6R,7R)-7-{[(2Z)-2-{2-[(tert-butoxycarbonyl)amino]-5-chloro-1,3-thiazol-4-yl}-2-(methoxyimino)acetyl]amino}-3-(chloromethyl)-8-oxo-5-thia-1-azabicyclo[4.2.0]oct-2-ene-2-carboxylate (0.34 g, 0.50 mmol). The resulting mixture was degassed for 30 minutes, and treated with sodium iodide (0.15 g, 1.00 mmol). The mixture was stirred at room temperature overnight, cooled to 0° C. and quenched with a 5% aqueous solution of sodium chloride and sodium thiosulfate to give an orange suspension. The solid was filtered, washed with water and dried in vacuo to afford 4-{[(6R,7R)-7-{[(2Z)-2-{2-[(tert-butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]-2-chloro-6-fluorobenzyl}-1H-pyrrolo[3,2-b]pyridin-4-ium iodide, which was used in the next step without further purification.

Step 6: (6R,7R)-7-{[(2Z)-2-(2-Amino-5-chloro-1,3-thiazol-4-yl)-2-(methoxyimino)acetyl]amino}-3-{[1-(4-carbamimidoyl-2-chloro-6-fluorobenzyl)-1H-pyrrolo[3,2-b]pyridin-4-ium-4-yl]methyl}-8-oxo-5-thia-1-azabicyclo[4.2.0]oct-2-ene-2-carboxylate

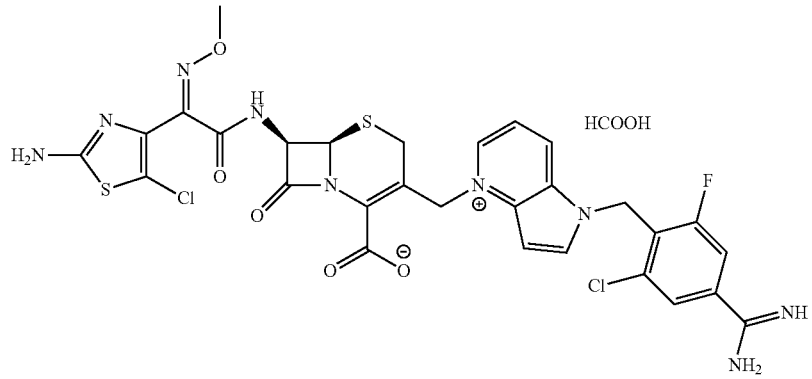 [SMILES: CO/N=C(\C(=O)N[C@@H]1C(=O)N2C(C(=O)[O-])=C(C[n+]3cccc4c3ccn4Cc3c(F)cc(C(=N)N)cc3Cl)CS[C@H]12)c1nc(N)sc1Cl ; "HCOOH"]

A solution of 4-{[(6R,7R)-7-{[(2Z)-2-{2-[(tert-butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]-2-chloro-6-fluorobenzyl}-1H-pyrrolo[3,2-b]pyridin-4-ium iodide (0.50 mmol) in dichloromethane (2.5 mL) and anisole (0.85 mL, 7.82 mmol) was cooled to 0° C., then treated with trifluoroacetic acid (2.5 mL, 32.6 mmol). The resulting brown solution was stirred at 0° C. for 10 minutes, then at room temperature for 2 hours. The mixture was concentrated in vacuo to a brown residue, which was washed with diethyl ether and the brown solid was purified by preparative HPLC (0.1% formic acid in water/acetonitrile) to afford (6R,7R)-7-{[(2Z)-2-(2-amino-5-chloro-1,3-thiazol-4-yl)-2-(methoxyimino)acetyl]amino}-3-{[1-(4-carbamimidoyl-2-chloro-6-fluorobenzyl)-1H-pyrrolo[3,2-b]pyridin-4-ium-4-yl]methyl}-8-oxo-5-thia-1-azabicyclo[4.2.0]oct-2-ene-2-carboxylate (0.050 g, 14% over 2 steps) as formic acid salt.

$^1$H NMR (400 MHz, D$_2$O): δ 3.18 (d, 1H, J=17.9 Hz), 3.32 (d, 1H, J=17.9 Hz), 3.95 (s, 3H) 5.12 (d, 1H, J=5.0 Hz), 5.50 (d, 1H, J=14.7 Hz), 5.71 (d, 1H, J=15.0 Hz), 5.80 (d, 1H, J=4.7 Hz), 5.85 (s, 2H), 7.01 (d, 1H, J=3.5 Hz), 7.62 (dd, 1H, J=9.7, 1.7 Hz), 7.70 (dd, 1H, J=8.2, 6.2 Hz), 7.80 (s, 1H), 8.15 (d, 1H, J=3.2 Hz), 8.62 (d, 1H, J=6.2 Hz), 8.69 (d, 1H, J=8.5 Hz).

Six protons were not observed in D$_2$O.

Mass: ES$^+$ 732.15.

Example 52 (Table 1, Compound 69)

(6R,7R)-7-{[(2Z)-2-(2-Amino-1,3-thiazol-4-yl)-2-(methoxyimino)acetyl]amino}-3-{[1-(4-carbamimidoyl-2-chloro-6-fluorobenzyl)-1H-pyrrolo[3,2-c]pyridin-5-ium-5-yl]methyl}-8-oxo-5-thia-1-azabicyclo[4.2.0]oct-2-ene-2-carboxylate

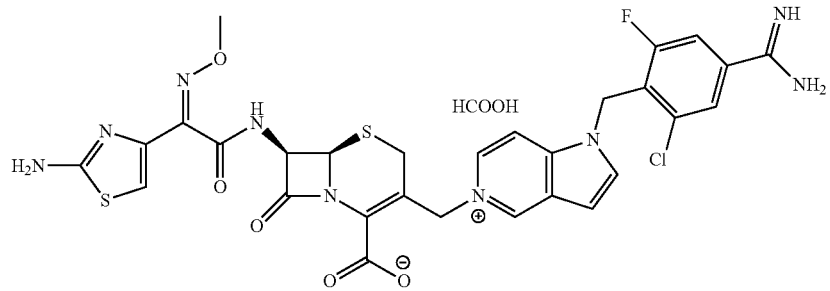 [SMILES: CO/N=C(\C(=O)N[C@@H]1C(=O)N2C(C(=O)[O-])=C(C[n+]3ccc4c(ccn4Cc4c(F)cc(C(=N)N)cc4Cl)c3)CS[C@H]12)c1csc(N)n1 ; "HCOOH"]

$^1$H NMR (400 MHz, D$_2$O): δ 3.14 (d, 1H, J=17.9 Hz), 3.58 (d, 1H, J=17.9 Hz), 3.93 (s, 3H), 5.22 (d, 1H, J=5.0 Hz), 5.29 (d, 1H, J=14.7 Hz), 5.48 (d, 1H, J=14.4 Hz), 5.74-5.79 (m, 3H), 6.82 (s, 1H), 7.02 (d, 1H, J=3.2 Hz), 7.60 (dd, 1H, J=9.7, 1.5 Hz), 7.73-7.81 (m, 2H), 8.06 (d, 1H, J=7.3 Hz), 8.44 (d, 1H, J=7.0 Hz), 9.17 (s, 1H). Six protons were not observed in D$_2$O.
Mass: ES$^+$ 698.19.

Example 53 (Table 1, Compound 70)

(6R,7R)-7-{[(2Z)-2-(2-Amino-5-chloro-1,3-thiazol-4-yl)-2-(methoxyimino)acetyl]amino}-3-{[1-(4-carbamimidoyl-2-chloro-6-fluorobenzyl)-1H-pyrrolo[2,3-c]pyridin-6-ium-6-yl]methyl}-8-oxo-5-thia-1-azabicyclo[4.2.0]oct-2-ene-2-carboxylate formic acid salt

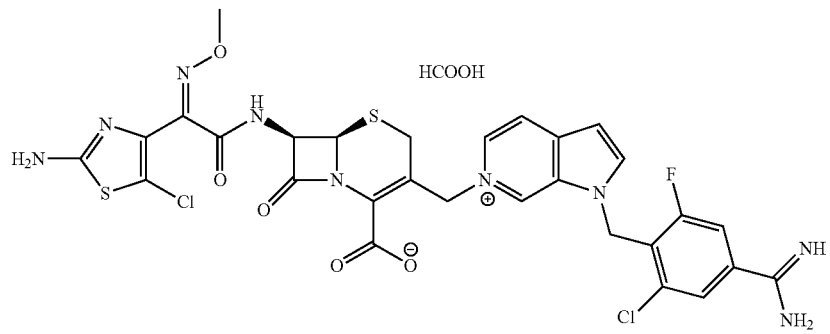 [SMILES: CO/N=C(\C(=O)N[C@@H]1C(=O)N2C(C(=O)[O-])=C(C[n+]3ccc4ccn(Cc5c(F)cc(C(=N)N)cc5Cl)c4c3)CS[C@H]12)c1nc(N)sc1Cl ; "HCOOH"]

Step 1: 3-Chloro-5-fluoro-4-(1H-pyrrolo[2,3-c]pyridin-1-ylmethyl)benzonitrile

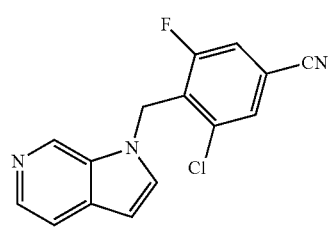 [SMILES: N#Cc1cc(F)c(Cn2ccc3ccncc32)c(Cl)c1]

An ice-cold mixture of 6-azaindole (0.98 g, 7.96 mmol) in N,N-dimethylformamide (10 mL) was treated with sodium hydride (60% in mineral oil, 0.46 g, 12.0 mmol) in portions, then stirred at room temperature for 15 minutes. The mixture was cooled to 0° C., then treated with 4-(bromomethyl)-3-chloro-5-fluorobenzonitrile (2.00 g, 8.05 mmol) in tetrahydrofuran (10 mL). The resulting mixture was stirred at 0° C. for 1 hour then quenched with saturated ammonium chloride solution. The mixture was extracted with ethyl acetate, and the extracts were washed with brine, dried (sodium sulphate), filtered and concentrated in vacuo to brown oil, which was purified by column chromatography (silica gel) eluting with 5:3:2 dichloromethane/ethyl acetate/methanol as eluent to afford 3-chloro-5-fluoro-4-(1H-pyrrolo[2,3-c]pyridin-1-ylmethyl)benzonitrile (1.14 g, 50%) as a brown solid.

$^1$H NMR (400 MHz, CDCl$_3$): δ 5.59 (d, 2H, J=1.9 Hz), 6.54 (dd, 1H) 7.31 (dd, 1H, J=3.15, 1.25 Hz), 7.38 (dd, 1H, J=8.7, 1.6 Hz), 7.51 (dd, 1H, J=5.4, 1.0 Hz), 7.59 (t, 1H, J=1.4 Hz), 8.27 (d, 1H, J=5.4 Hz), 8.92 (s, 1H).

Step 2: Ethyl 3-chloro-5-fluoro-4-(1H-pyrrolo[2,3-c]pyridin-1-ylmethyl)benzenecarboximidate hydrochloride

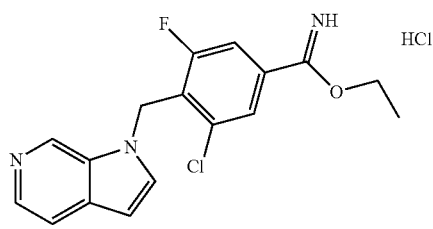 [SMILES: CCOC(=N)c1cc(F)c(Cn2ccc3ccncc32)c(Cl)c1 ; Cl]

Anhydrous hydrochloric acid was bubbled into an ice-cold brown suspension of 3-chloro-5-fluoro-4-(1H-pyrrolo[2,3-c]pyridin-1-ylmethyl)benzonitrile (1.14 g, 3.99 mmol) in anhydrous ethanol (30 mL) for 10 minutes. The mixture was sealed and stirred at room temperature overnight. The mixture was concentrated in vacuo to afford ethyl 3-chloro-5-fluoro-4-(1H-pyrrolo[2,3-c]pyridin-1-ylmethyl)benzenecarboximidate hydrochloride (1.16 g) as a brown solid, which was used in the next step without further purification.

Step 3: 3-Chloro-5-fluoro-4-(1H-pyrrolo[2,3-c]pyridin-1-ylmethyl)benzenecarboximidamide

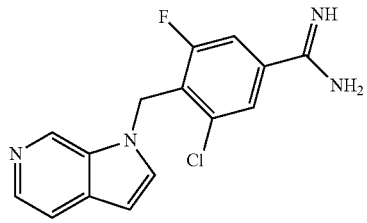 [SMILES: N=C(N)c1cc(F)c(Cn2ccc3ccncc32)c(Cl)c1]

Anhydrous ammonia was bubbled into an ice-cold solution of ethyl 3-chloro-5-fluoro-4-(1H-pyrrolo[2,3-c]pyridin-1-ylmethyl)benzenecarboximidate hydrochloride (1.6 g, 4.34 mmol) in anhydrous ethanol (30 mL) for 10 minutes. The mixture was sealed and stirred at room temperature overnight. The mixture was concentrated in vacuo to afford 3-chloro-5-fluoro-4-(1H-pyrrolo[2,3-c]pyridin-1-ylmethyl)benzenecarboximidamide as a brown solid (0.59 g), which was used in the next step without further purification.

$^1$H NMR (400 MHz, CD$_3$OD): δ 5.80 (s, 2H), 6.64-6.71 (m, 1H), 7.55-7.74 (m, 3H), 7.84-7.91 (m, 1H), 8.12 (s, 1H), 8.92 (s, 1H).

Step 4: tert-Butyl {[3-chloro-5-fluoro-4-(1H-pyrrolo[2,3-c]pyridin-1-ylmethyl)phenyl]carbonoimidoyl}carbamate

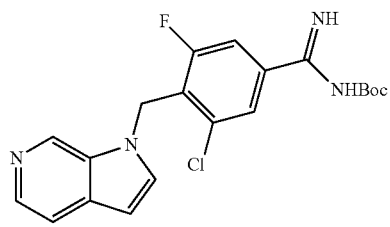 [SMILES: CC(C)(C)OC(=O)NC(=N)c1cc(F)c(Cn2ccc3ccncc32)c(Cl)c1]

An ice-cold solution of 3-chloro-5-fluoro-4-(1H-pyrrolo[2,3-c]pyridin-1-ylmethyl)benzenecarboximidamide (0.59 g, 1.95 mmol) in dioxane (40 mL) and saturated sodium carbonate solution (20 mL) was treated with di-tert-butyl dicarbonate (1.70 g, 7.78 mmol). The mixture was stirred at room temperature overnight and concentrated in vacuo. The residue was diluted with ethyl acetate, washed with water and brine, then dried (sodium sulphate), filtered and concentrated to a brown solid. The solid was purified by column chromatography (silica gel) eluting with 2-4% methanol in dichloromethane to afford tert-butyl {[3-chloro-5-fluoro-(1H-pyrrolo[2,3-c]pyridin-1-ylmethyl)phenyl]carbonoimidoyl}carbamate (0.64 g, 82%) as a yellow solid.

$^1$H NMR (400 MHz, CDCl$_3$): δ 1.55 (s, 9H), 5.53 (d, 2H, J=1.5 Hz), 6.49 (d, 1H, J=3.2 Hz), 7.30 (d, 1H, J=3.2 Hz), 7.48 (d, 1H, J=5.4 Hz), 7.57-7.63 (m, 1H), 7.81 (s, 1H), 8.21 (d, 1H, J=5.4 Hz), 8.91 (s, 1H).

Step 5: 6-{[(6R,7R)-7-{[(2Z)-2-{2-[(tert-Butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]-2-chloro-6-fluorobenzyl}-1H-pyrrolo[2,3-c]pyridin-6-ium iodide

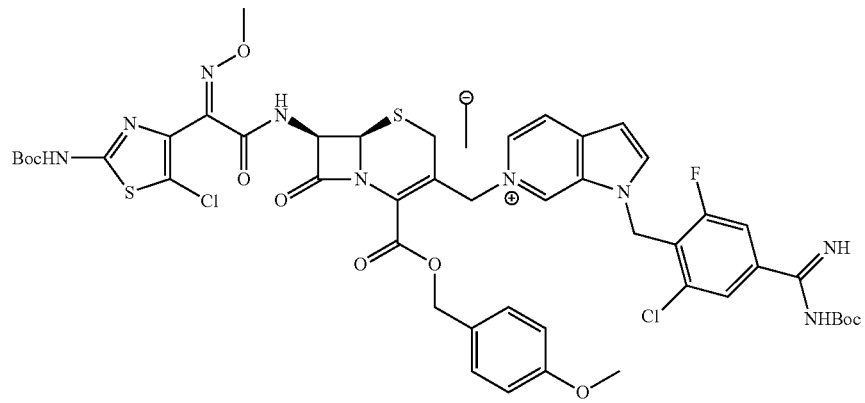

An ice-cold mixture of tert-butyl {[3-chloro-5-fluoro-4-(1H-pyrrolo[2,3-c]pyridin-1-ylmethyl)phenyl]carbonoimidoyl}carbamate (0.20 g, 0.50 mmol) in anhydrous N,N-dimethylformamide (2.0 mL) was degassed under reduced pressure for 5 minutes, then treated with 4-methoxybenzyl (6R,7R)-7-{[(2Z)-2-{2-[(tert-butoxycarbonyl)amino]-5-chloro-1,3-thiazol-4-yl}-2-(methoxyimino)acetyl]amino}-3-(chloromethyl)-8-oxo-5-thia-1-azabicyclo[4.2.0]oct-2-ene-2-carboxylate (0.34 g, 0.50 mmol). The resulting mixture was degassed for 30 minutes, then treated with sodium iodide (0.15 g, 1.00 mmol). The mixture was stirred at room temperature overnight, then cooled to 0° C. and quenched with a 5% aqueous solution of sodium chloride and sodium thiosulfate to give an orange suspension. The solid was filtered, washed with water and dried in vacuo to afford 6-{[(6R,7R)-7-{[(2Z)-2-{2-[(tert-butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]-2-chloro-6-fluorobenzyl}-1H-pyrrolo[2,3-c]pyridin-6-ium iodide, which was used in the next step without further purification.

Step 6: (6R,7R)-7-{[(2Z)-2-(2-Amino-5-chloro-1,3-thiazol-4-yl)-2-(methoxyimino)acetyl]amino}-3-{[1-(4-carbamimidoyl-2-chloro-6-fluorobenzyl)-1H-pyrrolo[2,3-c]pyridin-6-ium-6-yl]methyl}-8-oxo-5-thia-1-azabicyclo[4.2.0]oct-2-ene-2-carboxylate

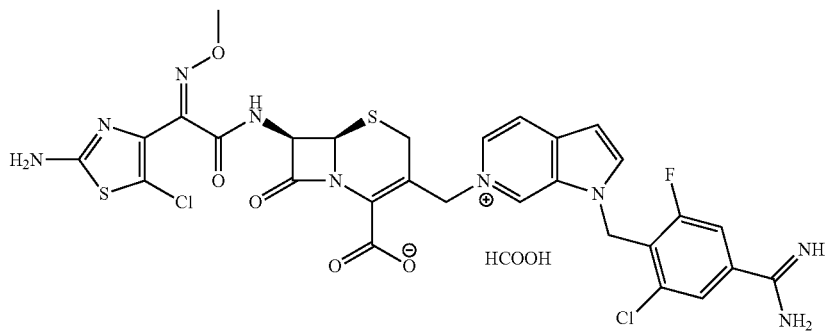 [SMILES: CO/N=C(\C(=O)N[C@@H]1C(=O)N2C(C(=O)[O-])=C(C[n+]3ccc4ccn(Cc5c(F)cc(C(=N)N)cc5Cl)c4c3)CS[C@H]12)c1nc(N)sc1Cl ; "HCOOH"]

A solution of 6-{[(6R,7R)-7-{[(2Z)-2-{2-[(tert-butoxycarbonyl)amino]-5-chloro-1,3-thiazol-4-yl}-2-(methoxyimino)acetyl]amino}-2-{[(4-methoxybenzyl)oxy]carbonyl}-8-oxo-5-thia-1-azabicyclo[4.2.0]oct-2-en-3-yl]methyl}-1-{4-[N-(tert-butoxycarbonyl)carbamimidoyl]-2-chloro-6-fluorobenzyl}-1H-pyrrolo[2,3-c]pyridin-6-ium iodide (0.50 mmol) in dichloromethane (2.5 mL) and anisole (0.85 mL, 7.82 mmol) was cooled to 0° C., then treated with trifluoroacetic acid (2.5 mL, 32.6 mmol). The resulting brown solution was stirred at 0° C. for 10 minutes, then at room temperature for 2 hours. The mixture was concentrated in vacuo to a brown residue, which was washed with diethyl ether to afford the crude product as brown solid. The solid was purified by preparative HPLC (0.1% formic acid in water/acetonitrile) to afford (6R,7R)-7-{[(2Z)-2-(2-Amino-5-chloro-1,3-thiazol-4-yl)-2-(methoxyimino)acetyl]amino}-3-{[1-(4-carbamimidoyl-2-chloro-6-fluorobenzyl)-1H-pyrrolo[2,3-c]pyridin-6-ium-6-yl]methyl}-8-oxo-5-thia-1-azabicyclo[4.2.0]oct-2-ene-2-carboxylate (0.025 g, 7% over 2 steps) as formic acid salt.

$^1$H NMR (400 MHz, D$_2$O): δ 3.18 (d, 1H, J=18.2 Hz), 3.59 (d, 1H, J=17.9 Hz), 3.95 (s, 3H), 5.21-5.32 (m, 2H), 5.56 (d, 1H, J=14.1 Hz), 5.79-5.90 (m, 3H), 6.96 (d, 1H, J=3.2 Hz), 7.62 (dd, 1H, J=9.5, 1.60 Hz), 7.78 (s, 1H), 8.05 (d, 1H, J=6.8 Hz), 8.20 (d, 1H, J=3.2 Hz), 8.24 (d, 1H, J=6.8 Hz), 9.09 (s, 1H). Six protons were not observed in D$_2$O.

Mass: ES$^+$ 732.04.

Example 54 (Table 1, Compound 72)

(6R,7R)-7-{[(2Z)-2-(2-Amino-5-chloro-1,3-thiazol-4-yl)-2-{[(2-carboxypropan-2-yl)oxy]imino}acetyl]amino}-3-{[1-(4-carbamimidoyl-2-chloro-6-fluorobenzyl)-1H-pyrrolo[2,3-c]pyridin-6-ium-6-yl]methyl}-8-oxo-5-thia-1-azabicyclo[4.2.0]oct-2-ene-2-carboxylate

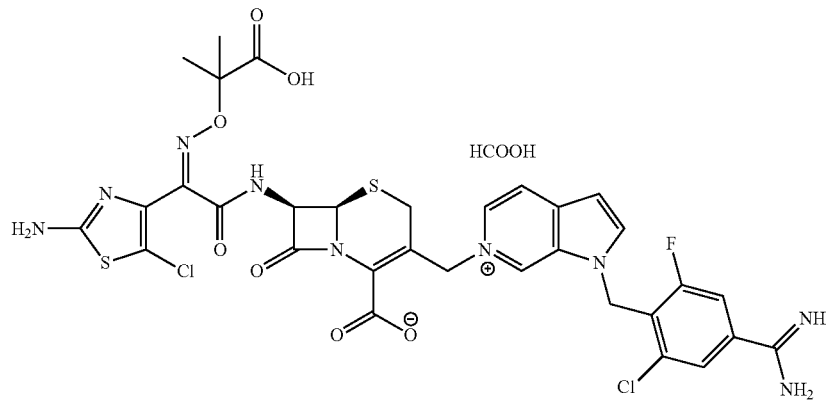 [SMILES: CC(C)(O/N=C(\C(=O)N[C@@H]1C(=O)N2C(C(=O)[O-])=C(C[n+]3ccc4ccn(Cc5c(F)cc(C(=N)N)cc5Cl)c4c3)CS[C@H]12)c1nc(N)sc1Cl)C(=O)O ; "HCOOH"]

$^1$H NMR (400 MHz, D$_2$O): δ 1.46 (s, 3H), 1.47 (s, 3H), 3.16 (d, 1H, J=18.2 Hz), 3.61 (d, 1H, J=17.9 Hz), 5.21 (d, 1H, J=14.1 Hz), 5.28 (d, 1H, J=5.0 Hz), 5.61 (d, 1H, J=14.4 Hz), 5.79-5.91 (m, 3H), 6.95 (d, 1H, J=2.6 Hz), 7.61 (d, 1H, J=10.0 Hz), 7.78 (s, 1H), 8.04 (d, 1H, J=6.8 Hz), 8.21 (d, 1H, J=2.4 Hz), 8.24 (d, 1H, J=6.8 Hz), 9.13 (s, 1H). Six protons were not observed in D$_2$O.

Mass: ES$^+$ 804.13

Example 55 (Table 1, Compound 73)

(6R,7R)-7-{[(2Z)-2-(2-Amino-1,3-thiazol-4-yl)-2-(methoxyimino)acetyl]amino}-3-{[1-(4-carbamimidoyl-2-chloro-6-fluorobenzyl)-1H-pyrrolo[2,3-c]pyridin-6-ium-6-yl]methyl}-8-oxo-5-thia-1-azabicyclo[4.2.0]oct-2-ene-2-carboxylate

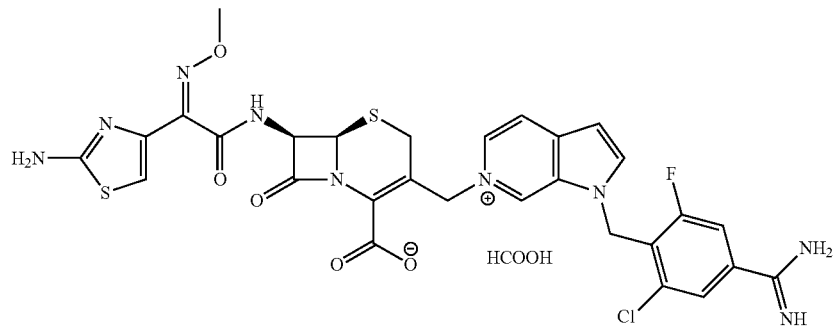 [SMILES: CO/N=C(\C(=O)N[C@@H]1C(=O)N2C(C(=O)[O-])=C(C[n+]3ccc4ccn(Cc5c(F)cc(C(=N)N)cc5Cl)c4c3)CS[C@H]12)c1csc(N)n1 ; "HCOOH"]

$^1$H NMR (400 MHz, D$_2$O): δ 3.16 (d, 1H, J=17.9 Hz), 3.63 (d, 1H, J=17.9 Hz), 3.94 (s, 3H), 5.19-5.33 (m, 2H), 5.58 (d, 1H, J=14.4 Hz), 5.78 (d, 1H, J=5.0 Hz), 5.82 (d, 2H, J=5.0 Hz), 6.95 (s, 2H), 7.60 (d, 1H, J=9.7 Hz), 7.73 (s, 1H), 8.04 (d, 1H, J=6.8 Hz), 8.16 (d, 1H, J=2.9 Hz), 8.24 (d, 1H, J=7.34 Hz), 9.13 (s, 1H). Six protons were not observed in D$_2$O.

Mass: ES$^+$ 698.13.

Example 56 (Table 1, Compound 74)

(6R,7R)-7-{[(2Z)-2-(5-Amino-1,2,4-thiadiazol-3-yl)-2-{[(2-carboxypropan-2-yl)oxy]imino}acetyl]amino}-3-{[1-(4-carbamimidoyl-2-chloro-6-fluorobenzyl)-1H-pyrrolo[2,3-c]pyridin-6-ium-6-yl]methyl}-8-oxo-5-thia-1-azabicyclo[4.2.0]oct-2-ene-2-carboxylate

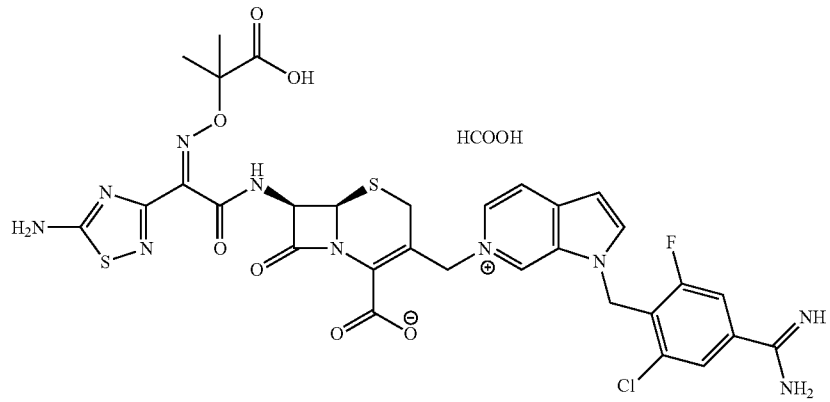 [SMILES: CC(C)(O/N=C(\C(=O)N[C@@H]1C(=O)N2C(C(=O)[O-])=C(C[n+]3ccc4ccn(Cc5c(F)cc(C(=N)N)cc5Cl)c4c3)CS[C@H]12)c1nsc(N)n1)C(=O)O ; "HCOOH"]

$^1$H NMR (400 MHz, D$_2$O): δ 1.46 (s, 6H), 3.15 (d, 1H, J=17.9 Hz), 3.61 (d, 1H, J=18.2 Hz), 5.20 (d, 1H, J=14.4 Hz), 5.28 (d, 1H, J=5.0 Hz), 5.61 (d, 1H, J=14.4 Hz), 5.80-5.88 (m, 3H), 6.95 (d, 1H, J=3.23 Hz), 7.60 (dd, 1H, J=9.4, 1.8 Hz), 7.76 (s, 1H), 8.03 (d, 1H, J=6.8 Hz), 8.20 (d, 1H, J=2.9 Hz), 8.24 (dd, 1H, J=6.8, 1.2 Hz), 9.13 (s, 1H). Six protons were not observed in D$_2$O.

Mass: ES$^+$ 771.18

Antibacterial Activity and Synergistic Activity:

Without limitation, the present cephem compounds alone, or in combination with one or more β-lactamase inhibitors, may provide improved antibacterial efficacy, particularly in antibiotic-resistant bacterial strains. It is believed that the present compounds may be structurally different from known compounds and, as a result, may be more basic in nature. It is an advantage that the present compounds may extend the spectrum of effective bacterial compounds, particularly against previously-resistant bacteria (e.g. ESKAPE organisms), and/or gram negative bacteria, without significant side effects. In a preferred embodiment, the present cephem compound may comprise reference compound ceftazidime, which may be used alone, or in combination with one or more β-lactamase inhibitors, such as NXL-104. As shown, the foregoing composition was tested for minimum inhibitory concentration (MIC, μg/mL) against bacteria listed in Tables 2-3.

TABLE 2

MIC values of selected compounds alone and in combination with NXL-104 against G(+) and G(-) isolates

| Isolate | Resistance Mechanism | CAZ | CAZ: NXL104 | Ex-1 | Ex-1: NXL104 | EX-2 | EX-2: NXL104 | Ex-5 | EX-5: NXL104 | Ex-6 | Ex-6: NXL104 |
|---|---|---|---|---|---|---|---|---|---|---|---|
| S. aureus 3132 | MSSA | 8.00 | 8.00 | | 2.00 | 2.00 | 2.00 | 2.00 | 2.00 | 4.00 | 4.00 |
| S. aureus 3136 | MSSA | 8.00 | 8.00 | 2.00 | 2.00 | 2.00 | 2.00 | 2.00 | 2.00 | 4.00 | 4.00 |
| S. aureus 3137 | MSSA | 32.00 | 32.00 | 8.00 | 8.00 | 32.00 | 32.00 | 32.00 | 4.00 | 32.00 | 8.00 |
| S. aureus 3144 | MSSA | 16.00 | 16.00 | 4.00 | 4.00 | 4.00 | 4.00 | 4.00 | 4.00 | 8.00 | 8.00 |
| S. aureus 3147 | MSSA | 8.00 | 8.00 | 2.00 | 2.00 | 2.00 | 2.00 | 2.00 | 2.00 | 4.00 | 4.00 |
| S. pneumoniae ATCC 700673 | Pen R | 16.00 | 8.00 | 2.00 | 2.00 | 8.00 | 8.00 | 2.00 | 2.00 | 2.00 | 2.00 |
| S. pneumoniae ATCC 6301 | Pen S | 0.12 | 0.12 | ≤0.06 | ≤0.06 | ≤0.06 | ≤0.06 | ≤0.06 | ≤0.06 | ≤0.06 | ≤0.06 |
| S. pneumoniae 2389 | Pen R | 16.00 | 16.00 | 4.00 | 4.00 | 8.00 | 8.00 | 2.00 | 1.00 | 2.00 | 2.00 |
| S. pneumoniae 2392 | Pen R | 16.00 | 16.00 | 2.00 | 2.00 | 8.00 | 8.00 | 2.00 | 1.00 | 2.00 | 2.00 |
| S. pneumoniae 2492 | Pen R | 8.00 | 8.00 | 2.00 | 2.00 | 8.00 | 8.00 | 2.00 | 2.00 | 2.00 | 2.00 |
| S. pneumoniae 2493 | Pen R | 16.00 | 16.00 | 4.00 | 4.00 | 8.00 | 8.00 | 2.00 | 2.00 | 2.00 | 2.00 |
| S. pneumoniae 2403 | Pen S | 0.12 | 0.12 | ≤0.06 | ≤0.06 | ≤0.06 | ≤0.06 | ≤0.06 | ≤0.06 | ≤0.06 | ≤0.06 |
| S. pneumoniae 2404 | Pen S | 32.00 | 32.00 | 0.25 | 0.12 | 0.25 | 0.25 | ≤0.06 | ≤0.06 | ≤0.06 | ≤0.06 |
| S. pneumoniae 2405 | Pen S | 0.25 | 0.25 | ≤0.06 | ≤0.06 | 0.12 | ≤0.06 | ≤0.06 | ≤0.06 | ≤0.06 | ≤0.06 |
| S. pneumoniae 2406 | Pen S | 0.12 | 0.12 | ≤0.06 | ≤0.06 | ≤0.06 | ≤0.06 | ≤0.06 | ≤0.06 | ≤0.06 | ≤0.06 |
| S. pneumoniae 2407 | Pen S | 4.00 | 32.00 | 0.12 | 0.12 | 0.12 | 0.12 | ≤0.06 | ≤0.06 | ≤0.06 | ≤0.06 |
| E. cloacae 2704 | P99 | 16.00 | 4.00 | 16.00 | 16.00 | 4.00 | 1.00 | 16.00 | 2.00 | 32.00 | 1.00 |
| E. cloacae 551 | Caz R, IMP S | 16.00 | 4.00 | 32.00 | 1.00 | 8.00 | 1.00 | 32.00 | 1.00 | 16.00 | 1.00 |
| E. cloacae 552 | Caz S, IMP S | 0.50 | 0.25 | 0.12 | 0.12 | 0.12 | 0.12 | 0.12 | ≤0.06 | 0.12 | 0.25 |
| E. cloacae 566 | Caz R, IMP S | >32 | 2.00 | 4.00 | 0.50 | 0.50 | 0.25 | 2.00 | 0.50 | 4.00 | 0.50 |
| E. cloacae 596 | Caz R, IMP S | 4.00 | 1.00 | 4.00 | 0.50 | 0.50 | 0.25 | 8.00 | 0.25 | 8.00 | 0.50 |
| E. cloacae 2044 | Caz S, IMP S | 1.00 | 0.25 | 0.25 | 0.12 | 0.25 | 0.12 | 0.50 | 0.12 | 0.12 | ≤0.06 |
| C. freundii 15 | Caz R, IMP S | 8.00 | 2.00 | 16.00 | 0.50 | 4.00 | 0.50 | 16.00 | 0.50 | 8.00 | 0.50 |

TABLE 2-continued

MIC values of selected compounds alone and in combination with NXL-104 against G(+) and G(−) isolates

| Isolate | Resistance Mechanism | CAZ | CAZ: NXL104 | Ex-1 | Ex-1: NXL104 | EX-2 | EX-2: NXL104 | Ex-5 | EX-5: NXL104 | Ex-6 | Ex-6: NXL104 |
|---|---|---|---|---|---|---|---|---|---|---|---|
| *C. freundii* 579 | Caz R, IMP S | 4.00 | 2.00 | 4.00 | 0.25 | 2.00 | 0.50 | 4.00 | 0.25 | 2.00 | 0.25 |
| *C. freundii* 580 | Caz R, IMP S | 8.00 | 2.00 | 16.00 | 0.50 | 4.00 | 0.50 | 8.00 | 0.25 | 4.00 | 0.25 |
| *C. freundii* 2003 | Caz R, IMP S | 4.00 | 1.00 | 8.00 | 0.25 | 2.00 | 0.50 | 8.00 | 0.25 | 4.00 | 0.50 |
| *C. freundii* 2487 | Caz R, IMP S | 16.00 | 8.00 | 32.00 | 1.00 | 8.00 | 1.00 | 32.00 | 1.00 | 8.00 | 1.00 |
| *K. pneumoniae* 4104 | KPC-3, TEM-1 | 32.00 | 8.00 | 16.00 | 2.00 | 8.00 | 2.00 | 32.00 | 2.00 | 32.00 | 2.00 |
| *K. pneumoniae* 4105 | KPC-3, TEM-1, SHV-11 | 32.00 | 4.00 | 16.00 | 2.00 | 32.00 | 2.00 | 32.00 | 1.00 | 32.00 | 1.00 |
| *K. pneumoniae* 4106 | KPC-3, TEM-1, SHV-12, SHV-141 | 16.00 | 4.00 | 8.00 | 1.00 | 8.00 | 2.00 | 16.00 | 1.00 | 16.00 | 1.00 |
| *K. pneumoniae* 4107 | KPC-2, TEM-1, SHV-11 | 32.00 | 8.00 | 16.00 | 2.00 | 16.00 | 4.00 | 32.00 | 2.00 | 32.00 | 2.00 |
| *K. pneumoniae* 4108 | KPC-3, TEM-166, SHV-12, SHV-141 | 16.00 | 4.00 | 4.00 | 0.50 | 4.00 | 1.00 | 8.00 | 0.50 | 16.00 | 0.50 |
| *K. pneumoniae* 4109 | SHV-1, SHV-12 | 2.00 | 0.50 | 2.00 | 0.12 | 0.50 | 0.12 | 8.00 | 0.12 | 8.00 | 0.12 |
| *M. morganii* 2409 | High level cephase (ACC 43: 769-776, 1999), β-Lactamase producing | 16.00 | 4.00 | 8.00 | 1.00 | 8.00 | 1.00 | 16.00 | 0.50 | 16.00 | 1.00 |
| *K. pneumoniae* 2689 | KPC-2 | 32.00 | 4.00 | 8.00 | 2.00 | 8.00 | 2.00 | 8.00 | 1.00 | 16.00 | 1.00 |
| *E. coli* 2671 | VIM-19 | 32.00 | 32.00 | 16.00 | 16.00 | 4.00 | 4.00 | 16.00 | 16.00 | 32.00 | 32.00 |
| *K. pneumoniae* 2697 | IMP-4 | 8.00 | 2.00 | 4.00 | 0.50 | 4.00 | 1.00 | 16.00 | 0.50 | 16.00 | 0.50 |
| *E. coli* 4080 | TEM-10 | 16.00 | 4.00 | 4.00 | 1.00 | 8.00 | 1.00 | 16.00 | 0.50 | 16.00 | 0.50 |
| *E. coli* 4098 | CTX-M-15, TEM-1 | 2.00 | 0.50 | 4.00 | 0.25 | 1.00 | 0.25 | >32 | 0.12 | 32.00 | 0.12 |
| *E. coli* 4101 | CTX-M-14, TEM-1 | 0.50 | 0.25 | 0.50 | 0.12 | 0.50 | 0.12 | 0.50 | 0.12 | 0.50 | ≤0.06 |
| *E. coli* 4102 | CTX-M-14 | 1.00 | 0.25 | 1.00 | 0.12 | 1.00 | 0.12 | 1.00 | ≤0.06 | 2.00 | 0.12 |
| *E. coli* 102 | TEM-1 | 0.12 | 0.12 | ≤0.06 | ≤0.06 | ≤0.06 | ≤0.06 | ≤0.06 | ≤0.06 | ≤0.06 | ≤0.06 |
| *K. baumanii* 2579 | OXA-25 | >32 | >32 | 32.00 | 8.00 | >32 | 32.00 | >32 | 8.00 | >32 | 16.00 |
| *K. baumanii* 4091 | OXA-23 | >32 | 16.00 | 16.00 | 4.00 | 8.00 | 2.00 | 8.00 | 2.00 | 16.00 | 4.00 |
| *K. baumanii* 4094 | OXA-51 | >32 | 32.00 | 16.00 | 32.00 | 32.00 | 8.00 | 16.00 | 4.00 | 16.00 | 8.00 |
| *K. baumanii* 4095 | OXA-48 | 0.50 | 0.50 | 0.50 | 0.25 | 0.25 | 0.25 | 0.25 | 0.25 | 0.12 | 0.25 |
| *E. coli* 2668 | OXA-48 | 1.00 | 0.50 | 1.00 | 0.12 | 0.50 | 0.25 | 1.00 | ≤0.06 | 0.50 | 0.12 |
| *P. aeruginosa* 2573 | OXA-10 (Class D) | 8.00 | 8.00 | 4.00 | 2.00 | 2.00 | 4.00 | 4.00 | 4.00 | 2.00 | 2.00 |

TABLE 3

MIC values of selected compounds alone and in combination with NXL-104 against KPC-producing organisms

| Isolate | Resistance Mechanism | CAZ | CAZ: NXL104 | Ex-1 | Ex-1: NXL104 | Ex-12 | Ex-12: NXL104 | Ex-4 | Ex-4: NXL104 |
|---|---|---|---|---|---|---|---|---|---|
| *E. cloacae* 2689 | KPC-2 | >32 | 2 | 32 | 1 | 32 | 1 | 4 | 0.5 |
| *E. cloacae* 2705 | VIM-1, KPC-3type | >32 | >32 | >32 | >32 | >32 | >32 | >32 | >32 |
| *E. cloacae* 2706 | VIM-1, KPC-3 | >32 | 32 | >32 | 32 | >32 | >32 | >32 | 32 |
| *E. cloacae* 2709 | KPC-3, VIM-1 | >32 | 8 | 32 | 4 | 32 | 4 | 8 | 4 |
| *E. cloacae* 2710 | KPC-3, VIM-1 | >32 | >32 | >32 | >32 | >32 | >32 | >32 | >32 |
| *E. coli* 2666 | KPC-2 | >32 | 4 | 32 | 1 | 16 | 1 | 32 | 2 |
| *E. coli* 4103 | KPC-2, TEM-1, CMY-type | >32 | 16 | >32 | 4 | >32 | 4 | >32 | 8 |
| *K. pneumoniae* 2689 | KPC-2 | >32 | 4 | 16 | 1 | 16 | 1 | 16 | 1 |
| *K. pneumoniae* 2690 | KPC-2 | >32 | 4 | 32 | 1 | 8 | 1 | 16 | 2 |
| *K. pneumoniae* 2711 | KPC-3, VIM-1 | >32 | 2 | 4 | 0.25 | 4 | 0.5 | 8 | 1 |
| *K. pneumoniae* 2712 | KPC-3, VIM-1 | >32 | 16 | >32 | 4 | >32 | 4 | >32 | 4 |
| *K. pneumoniae* 2713 | KPC-3, VIM-1 | >32 | 8 | >32 | 1 | >32 | 2 | >32 | 2 |
| *K. pneumoniae* 4088 | KPC-3 | >32 | 8 | >32 | 4 | >32 | 2 | >32 | 4 |
| *K. pneumoniae* 4104 | KPC-3, TEM-1 | >32 | 2 | 32 | 1 | 16 | 1 | 16 | 1 |

TABLE 3-continued

MIC values of selected compounds alone and in combination with NXL-104 against KPC-producing organisms

| | | | | | | | | | |
|---|---|---|---|---|---|---|---|---|---|
| K. pneumoniae 4105 | KPC-3, TEM-1, SHV-11 | >32 | 4 | 32 | 2 | 32 | 2 | >32 | 2 |
| K. pneumoniae 4106 | KPC-3, TEM-1, SHV-12, SHV-141 | >32 | 8 | 32 | 2 | 32 | 2 | 32 | 4 |
| K. pneumoniae 4107 | KPC-2, TEM-1, SHV-11 | >32 | 4 | 32 | 1 | 16 | 1 | 32 | 2 |
| K. pneumoniae 4108 | KPC-3, TEM-166, SHV-12, SHV-141 | >32 | 4 | 32 | 2 | 32 | 1 | >32 | 2 |
| P. aeruginosa 2686 | KPC-2 | >32 | 16 | >32 | 8 | 32 | 32 | 32 | 8 |

| Isolate | Ex-14 | Ex-14: NXL104 | Ex-2 | Ex-2: NXL104 | Ex-5 | Ex-5: NXL104 | Ex-6 | Ex-6: NXL104 |
|---|---|---|---|---|---|---|---|---|
| E. cloacae 2689 | 16 | 0.5 | 8 | 0.5 | 16 | 0.5 | 16 | 1 |
| E. cloacae 2705 | >32 | >32 | >32 | >32 | >32 | >32 | >32 | >32 |
| E. cloacae 2706 | >32 | 32 | >32 | 32 | >32 | 32 | >32 | 32 |
| E. cloacae 2709 | 32 | 4 | 16 | 4 | 32 | 4 | 32 | 4 |
| E. cloacae 2710 | >32 | >32 | >32 | >32 | >32 | >32 | >32 | >32 |
| E. coli 2666 | 32 | 1 | 32 | 2 | 16 | 1 | 16 | 1 |
| E. coli 4103 | >32 | 8 | >32 | 8 | >32 | 4 | >32 | 4 |
| K. pneumoniae 2689 | 32 | 1 | 32 | 2 | 8 | 1 | 16 | 1 |
| K. pneumoniae 2690 | 32 | 1 | 32 | 2 | 8 | .5 | 16 | 1 |
| K. pneumoniae 2711 | 4 | 0.5 | 4 | 0.5 | 2 | 0.25 | 4 | 0.5 |
| K. pneumoniae 2712 | >32 | 4 | >32 | 4 | >32 | 4 | >32 | 4 |
| K. pneumoniae 2713 | >32 | 2 | >32 | 2 | >32 | 2 | >32 | 2 |
| K. pneumoniae 4088 | >32 | 4 | >32 | 4 | 32 | 2 | >32 | 2 |
| K. pneumoniae 4104 | 32 | 1 | 32 | 2 | 16 | 0.5 | 32 | 0.5 |
| K. pneumoniae 4105 | >32 | 2 | >32 | 2 | 32 | 1 | 32 | 2 |
| K. pneumoniae 4106 | >32 | 4 | >32 | 4 | 32 | 2 | 32 | 2 |
| K. pneumoniae 4107 | 16 | 2 | >32 | 2 | 16 | 1 | 16 | 1 |
| K. pneumoniae 4108 | >32 | 2 | >32 | 2 | 32 | 1 | 32 | 1 |
| P. aeruginosa 2686 | >32 | 16 | >32 | 16 | 32 | 8 | 32 | 8 |

We claim:

1. A compound of formula (I) or a pharmaceutically acceptable salt thereof:

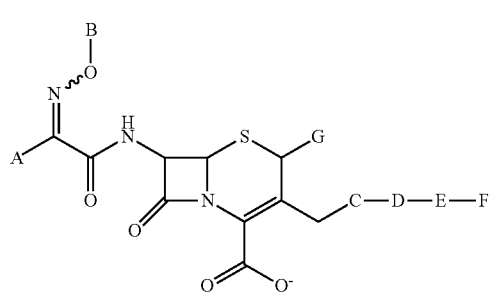

(I)

wherein in the formula (I), (i) A is defined by the formula (Ia):

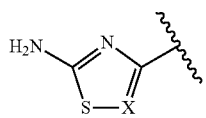

(Ia)

Where X is N, C(H), C(F) or C(Cl);

(ii) B is defined as hydrogen, methyl, ethyl or represented by the formula (Ib)

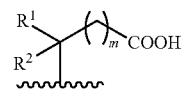

(Ib)

wherein, $R^1$ and $R^2$ is independently hydrogen or lower alkyl; or wherein $R^1$ and $R^2$ together may form a 3 to 6-membered spiro ring system; and
m is 0 or 1
(iii) C represents a quaternized bicyclic nitrogen containing aromatic heterocyclic ring represented by the formulae (Ic) to (Iz)
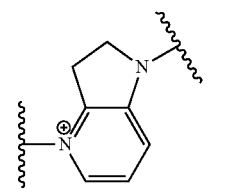 (Ic)
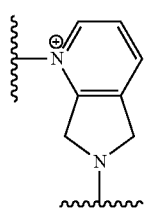 (Id)
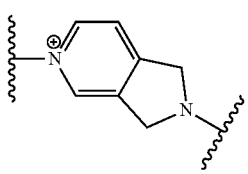 (Ie)
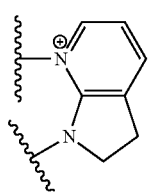 (If)
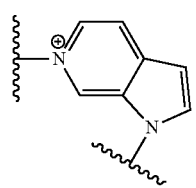 (Ig)
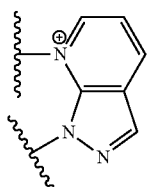 (Ih)
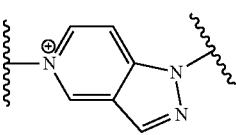 (Ii)
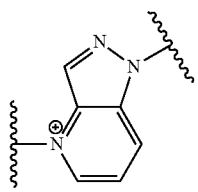 (Ij)
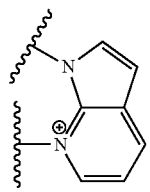 (Ik)
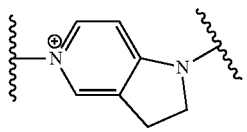 (Il)
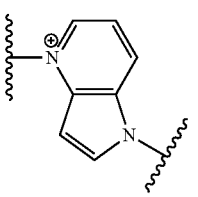 (Im)
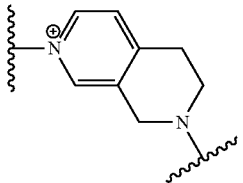 (In)
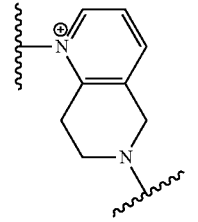 (Io)
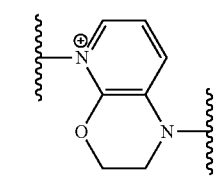 (Ip)
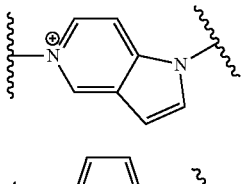 (Iq)
(Ir)

221
-continued

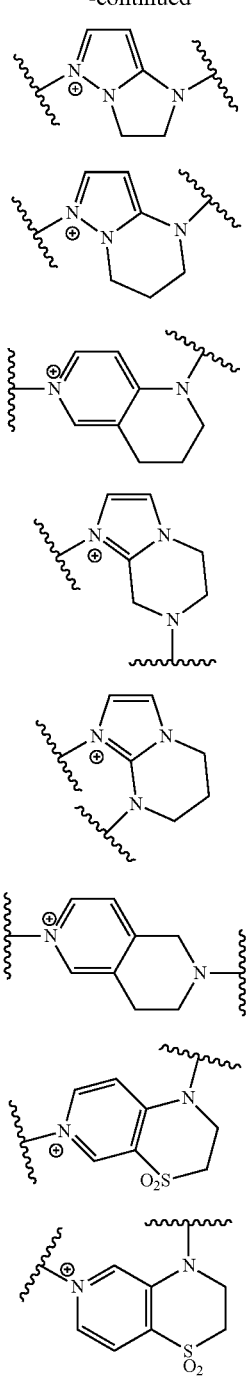

(Is)
(It)
(Iu)
(Iv)
(Iw)
(Ix)
(Iy)
(Iz)

(iv) D represents CH$_2$, CH$_2$CH$_2$ or CH$_2$CO
(v) E represents a substituted benzene ring or a substituted 5- or 6-membered aromatic heterocyclic ring having at least one heteroatom selected from O, S and N, wherein the heteroaromatic ring includes pyrrolyl, imidazolyl, pyrazolyl, pyridazinyl, pyrimidinyl, pyrazinyl, triazolyl, isoxazolyl, oxazolyl, oxadiazolyl, isothiazolyl, thiazolyl, thiadiazolyl, furyl, and thienyl;
(vi) F is substituted amidine or substituted guanidine; and
(vii) G is hydrogen, methyl, ethyl, C$_{3-6}$ alkyl, C$_{3-6}$ cycloalkyl or a substituted 5- or 6-membered aliphatic or a substituted 5- or 6-membered aromatic heterocy-

222 clic ring, wherein the heterocyclic ring is substituted with at least 1-2 hetero atoms selected from N, O, and S (α or β).

2. A compound as recited in claim 1, where E is selected from a substituted aryl or a 5- and 6-membered aromatic heterocyclic rings

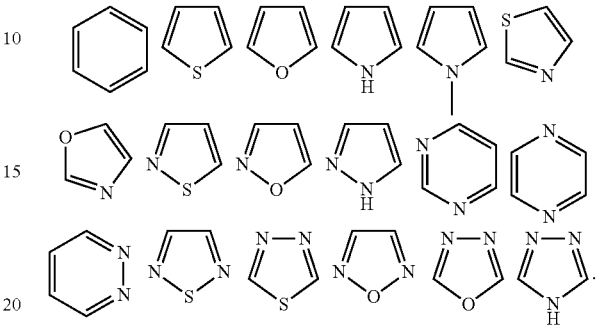

3. A compound as recited in claim 2, wherein the optional substituents include chloro, fluoro, cyano, hydroxy, amino, carboxy, acetyl, methoxy, ethoxy, trifluoromethyl, pyrrolidinyloxy, and piperidinyloxy.

4. A compound as recited in claim 1, wherein the preferred examples of "-C-D-E-F" include the following organic residues

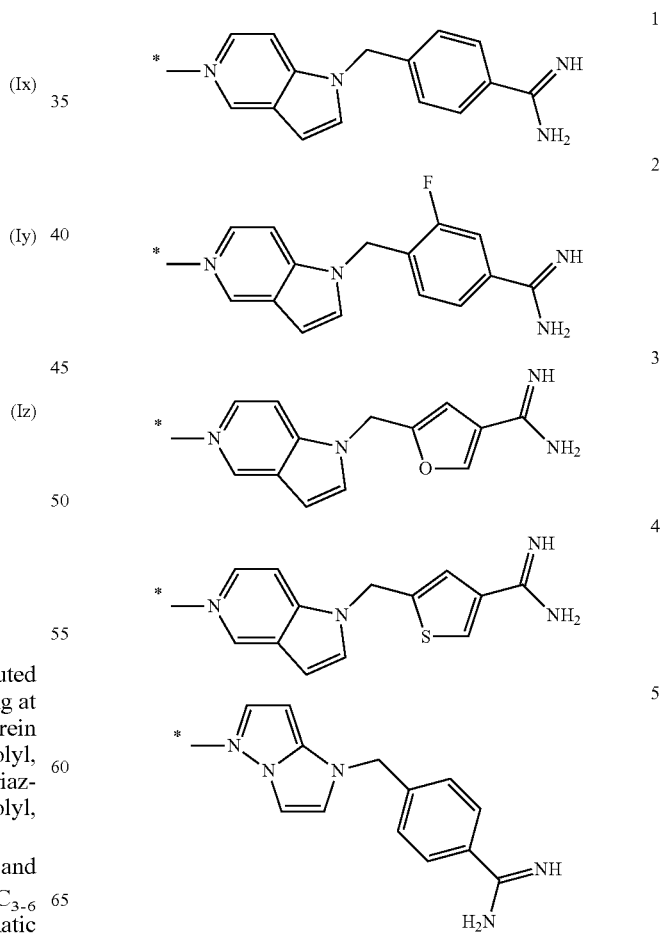

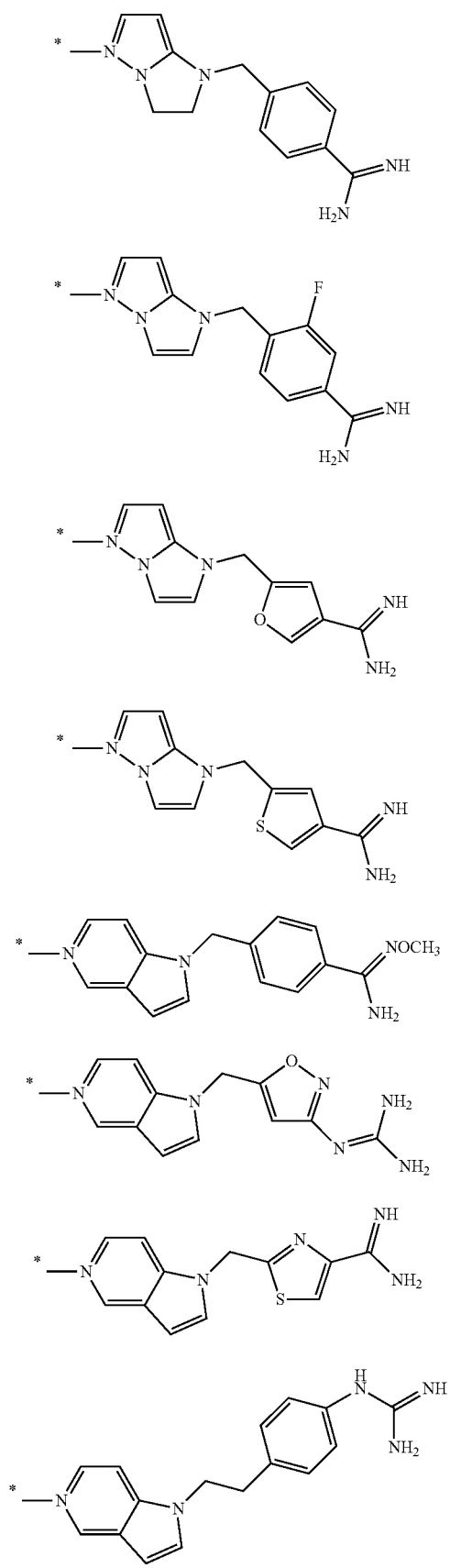
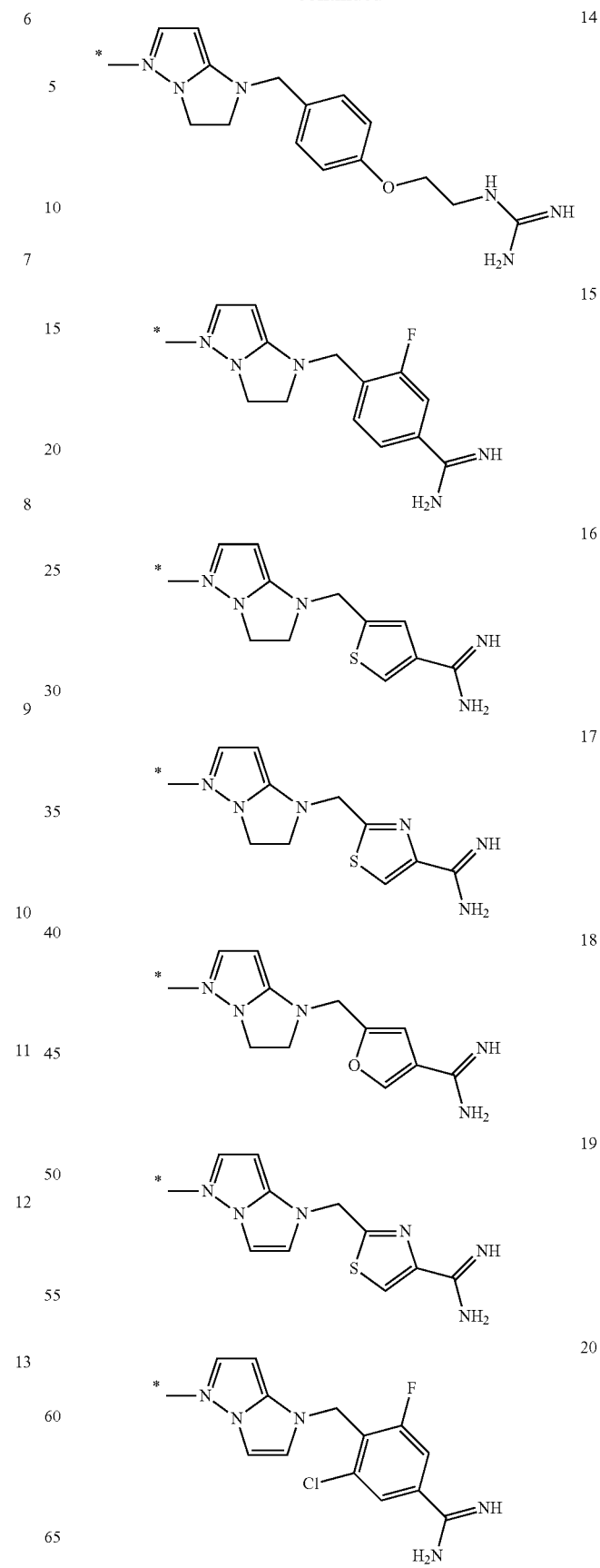

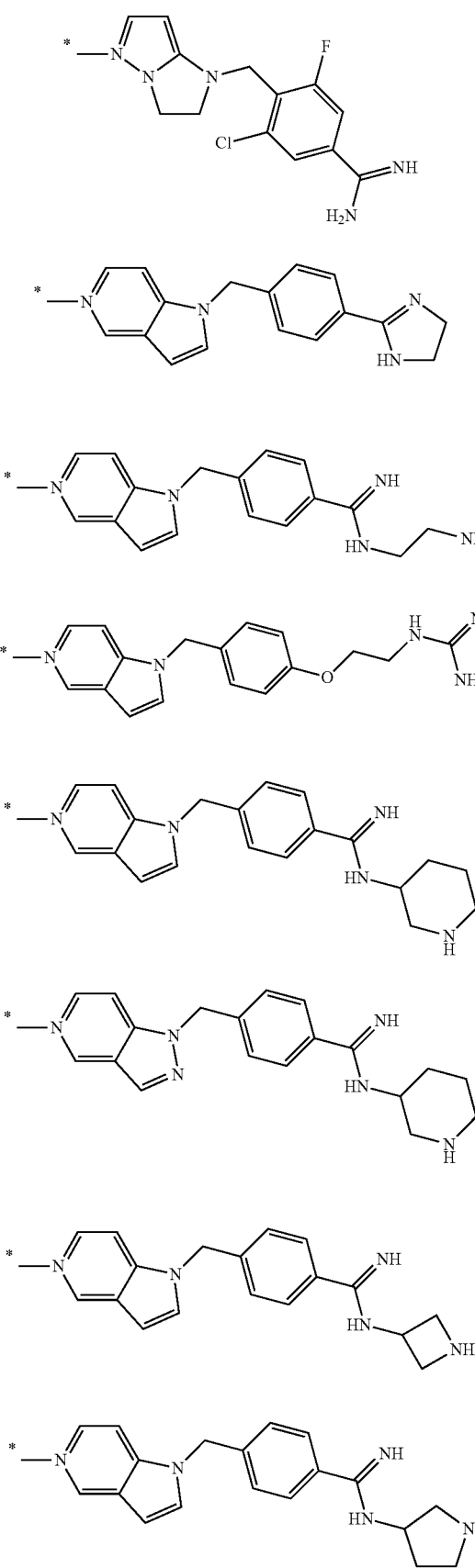
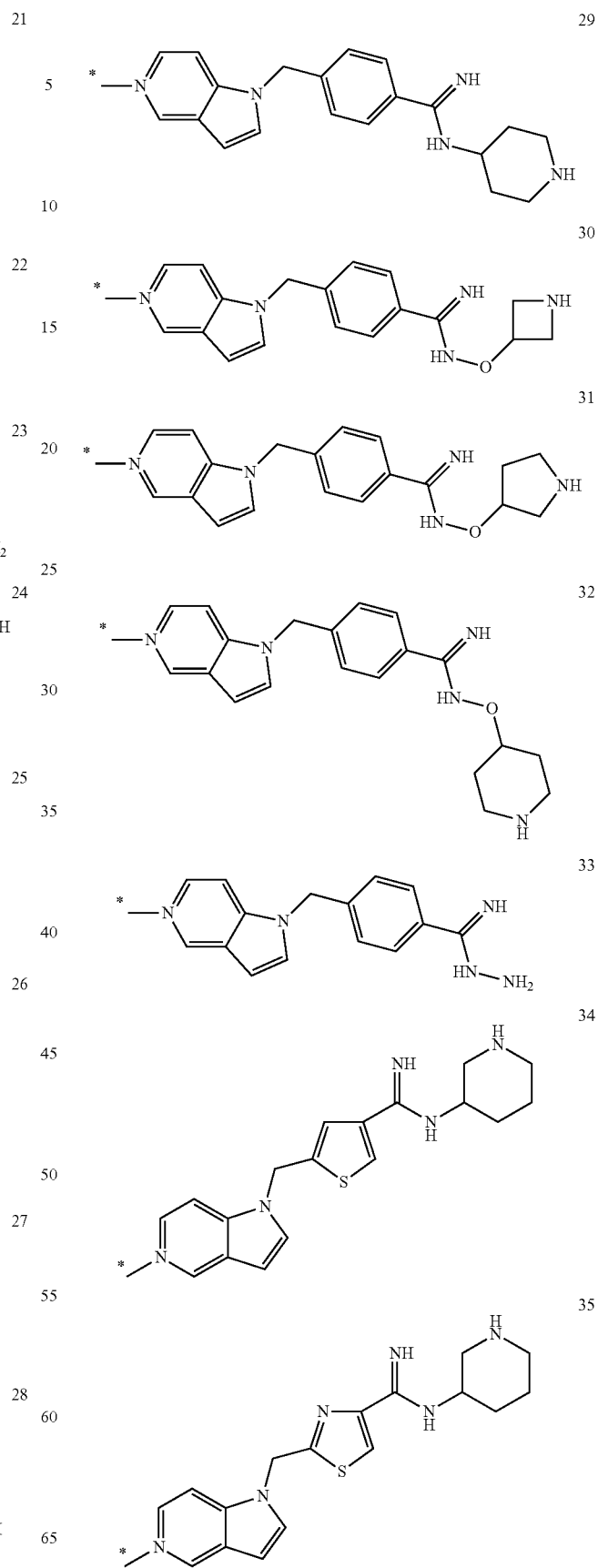

36
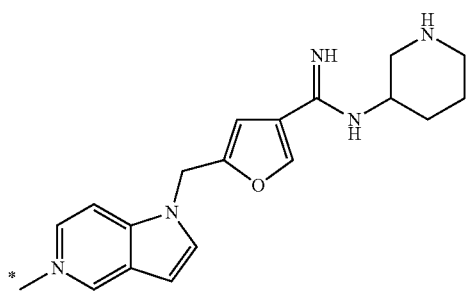
37
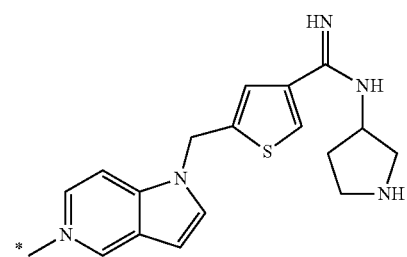
38
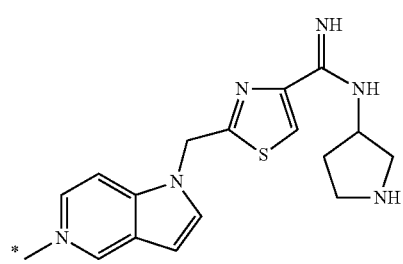
39
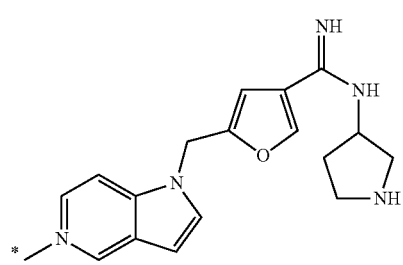
40
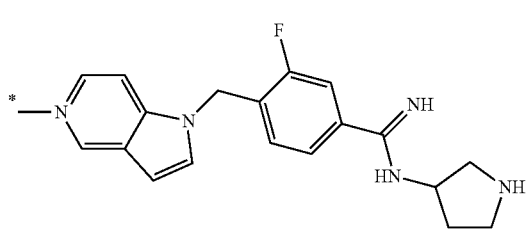
41
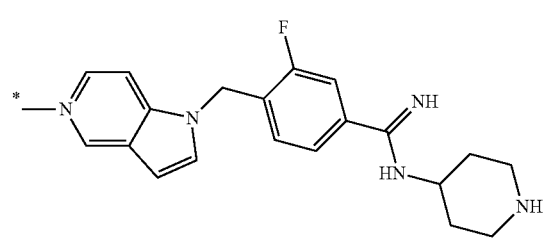
42
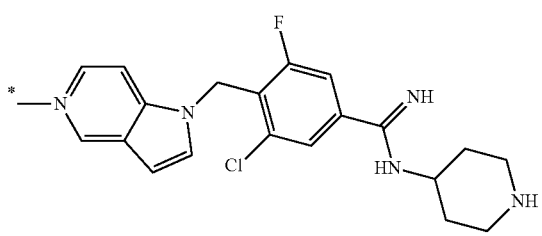
43
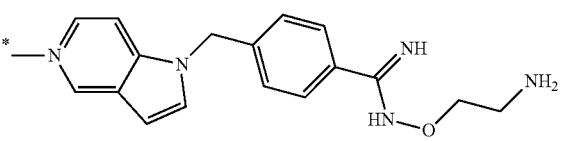
44
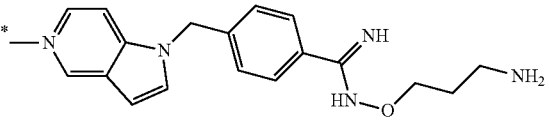
45
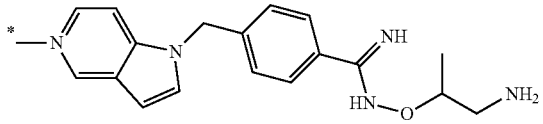
46
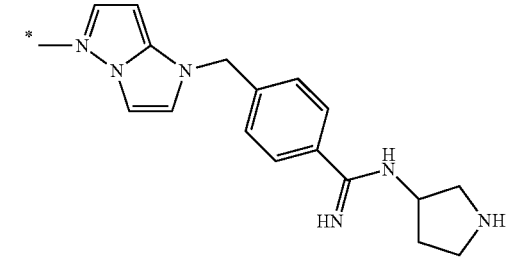
47
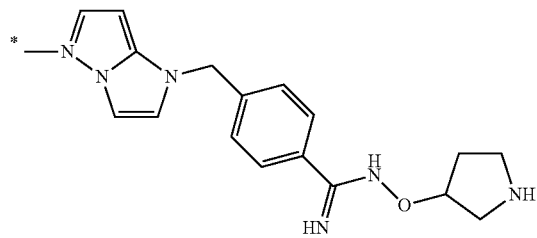
48
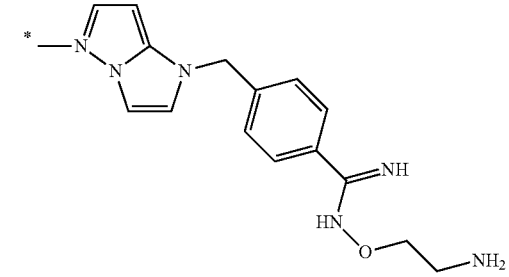

229
-continued
230
-continued

-continued

233
-continued
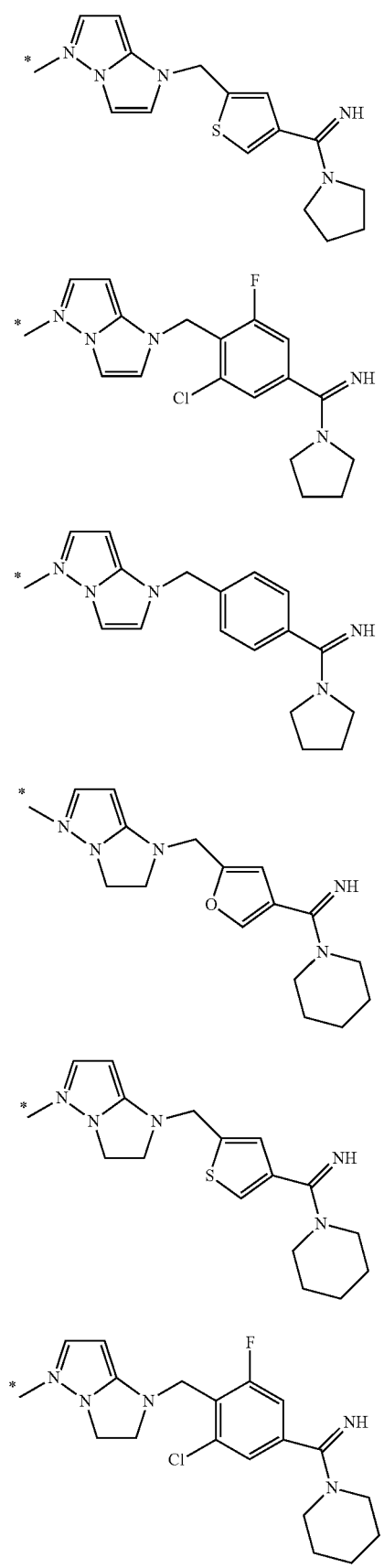
234
-continued
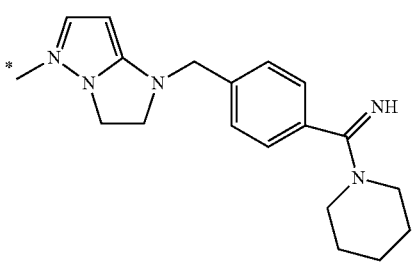
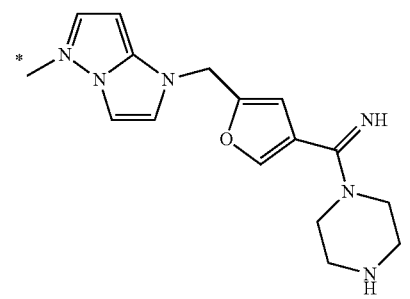
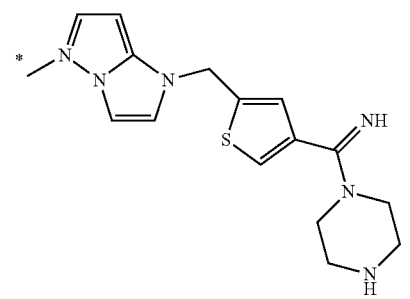
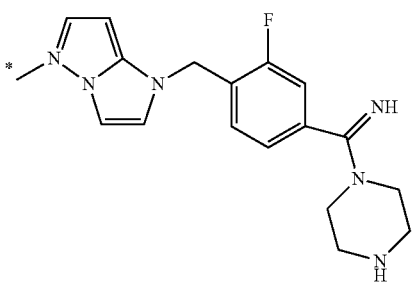
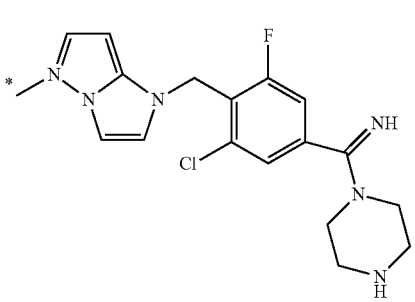
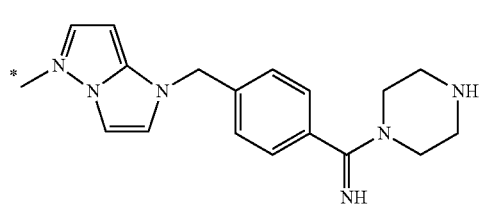

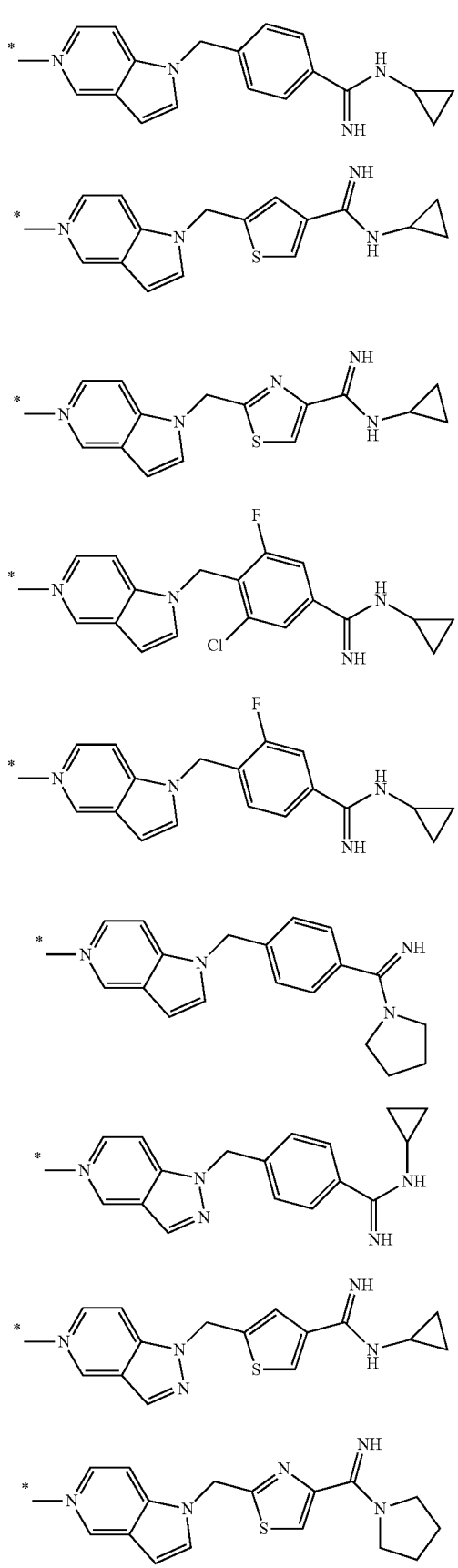

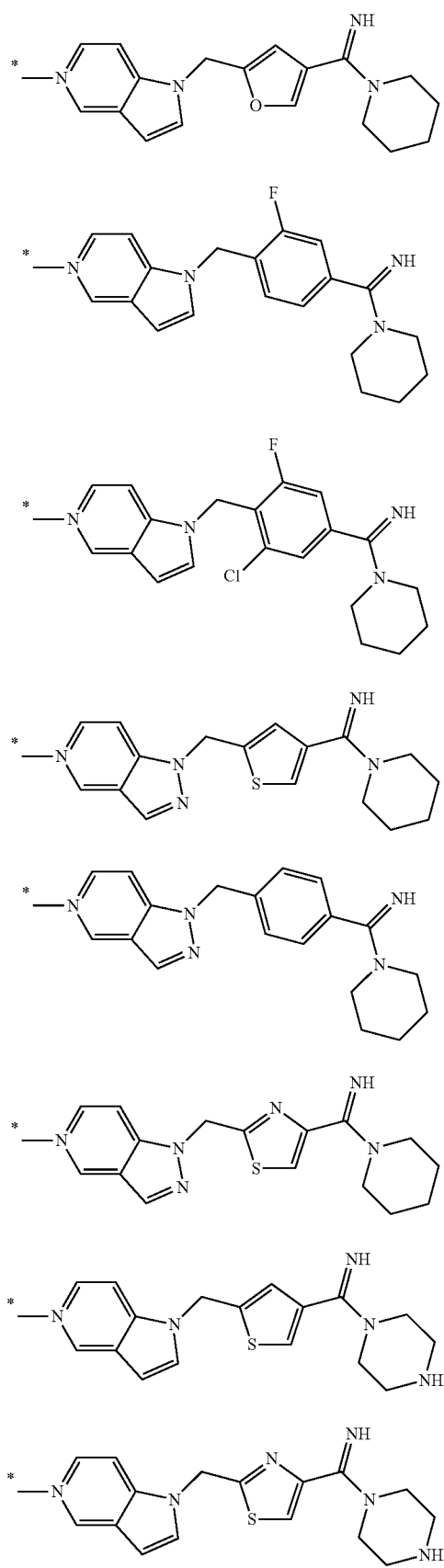
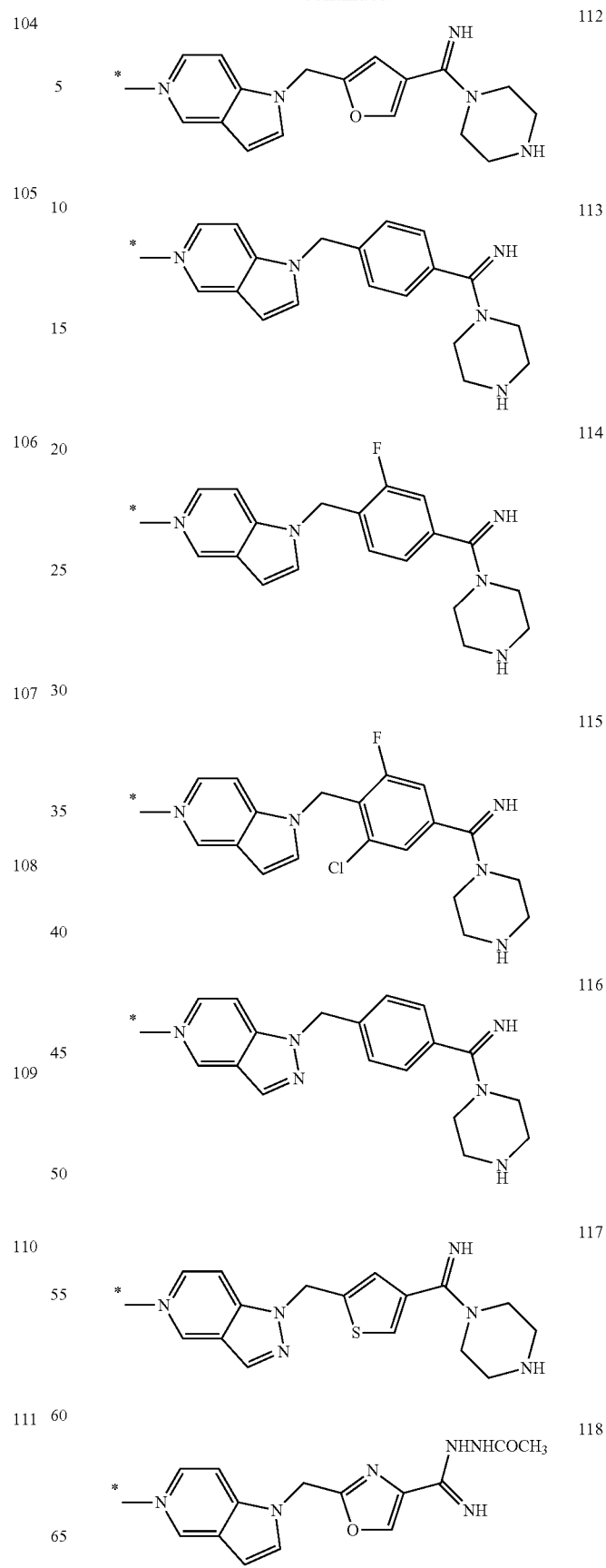

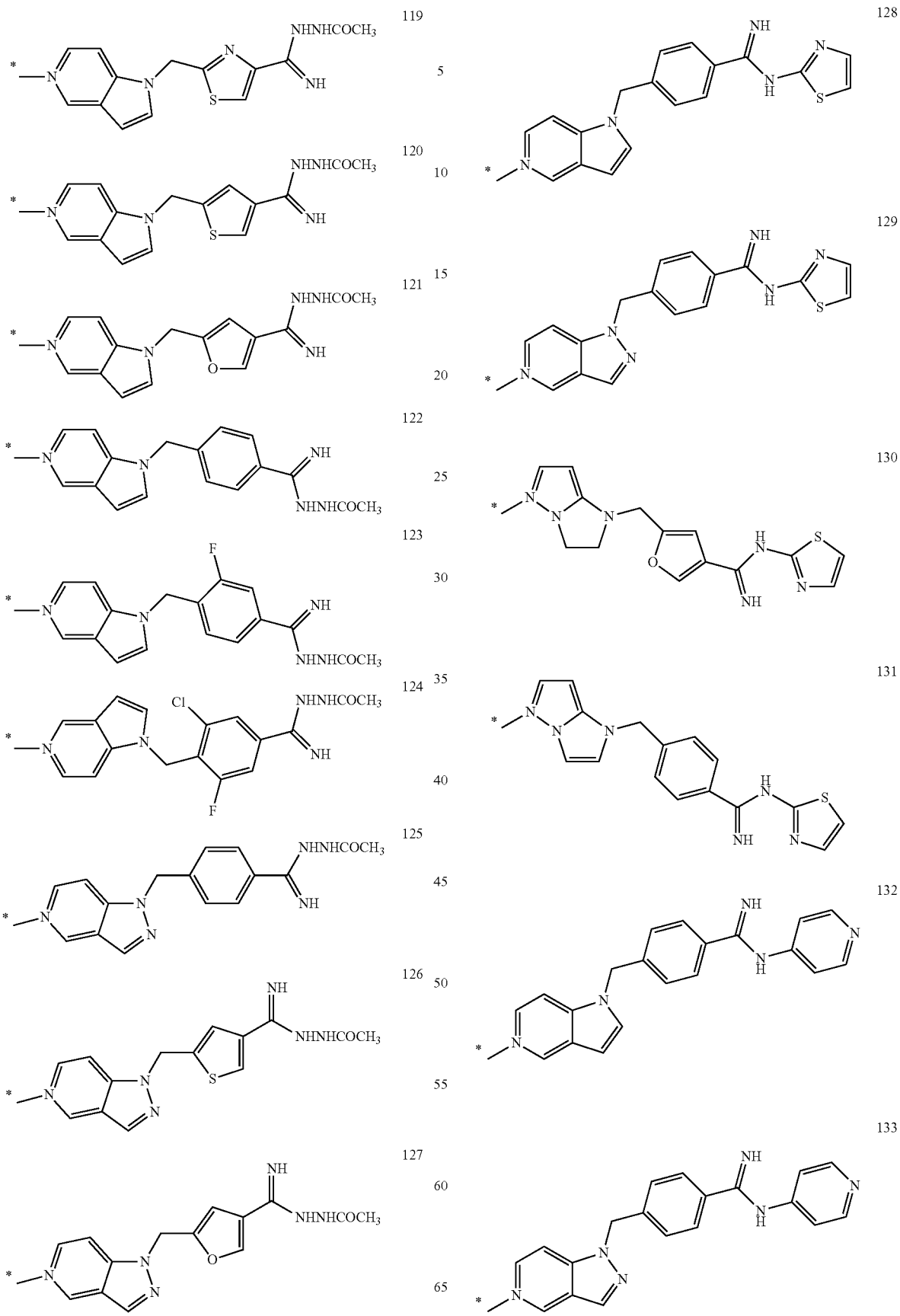

| | |
|---|---|
| 134 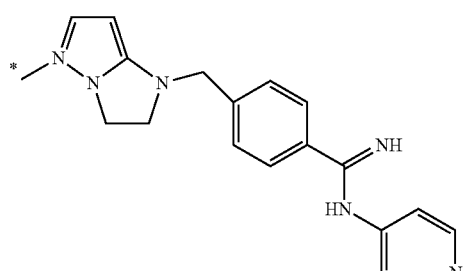 | 141 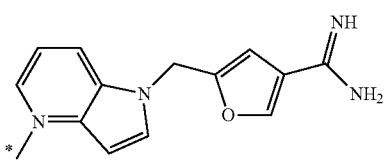 |
| 135 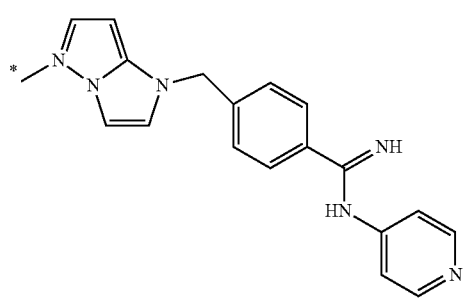 | 142 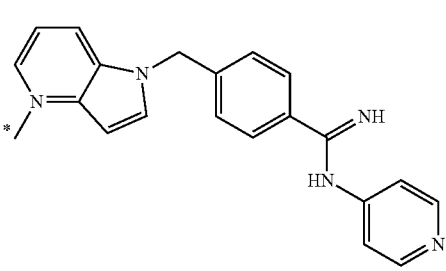 |
| 136 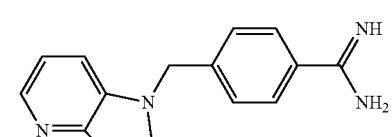 | 143 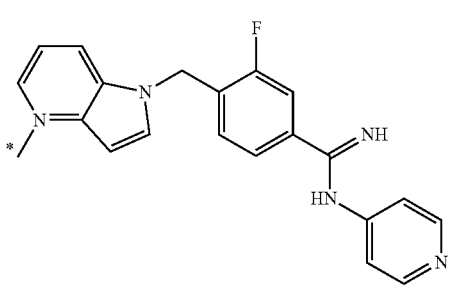 |
| 137 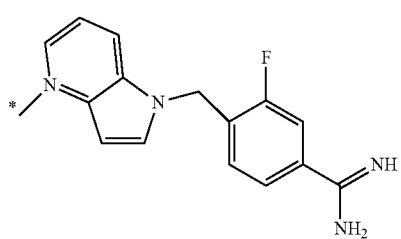 | 144 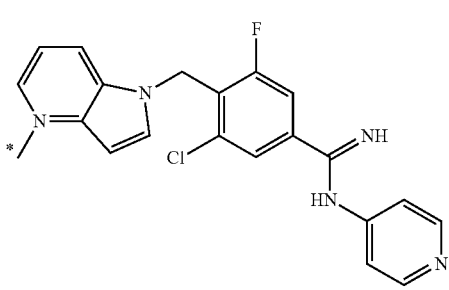 |
| 138 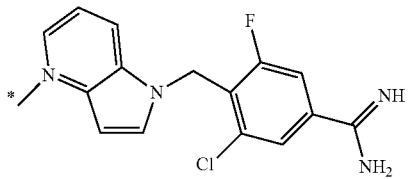 | 145 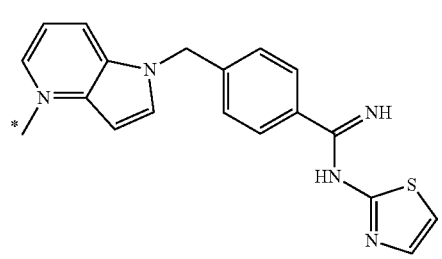 |
| 139 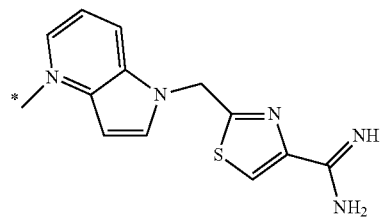 | 146 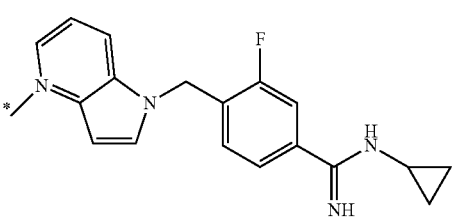 |
| 140 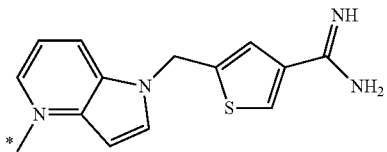 | |

147 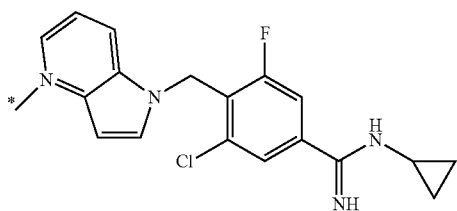
148 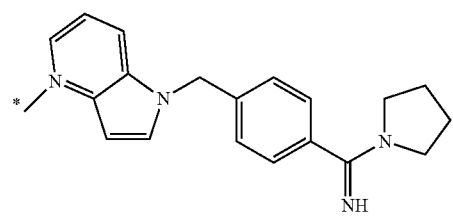
149 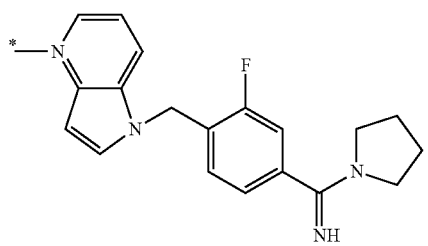
150 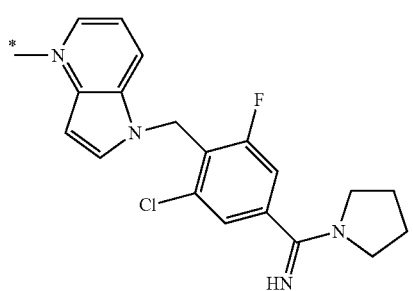
151 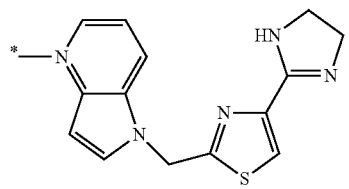
152 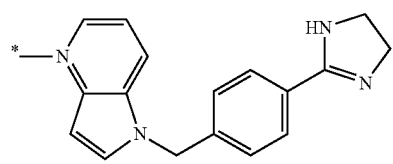
153 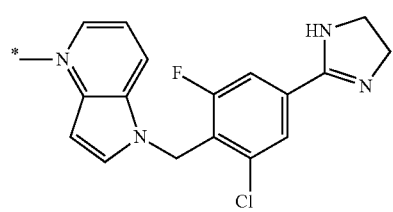
154 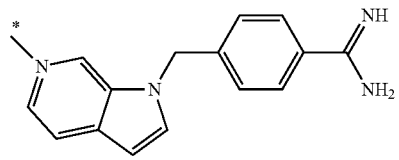
155 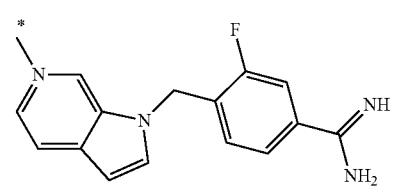
156 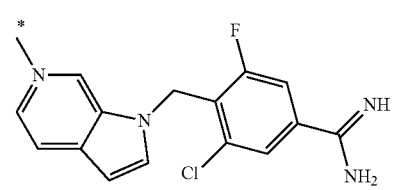
157 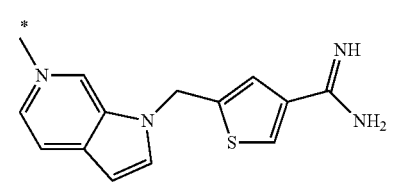
158 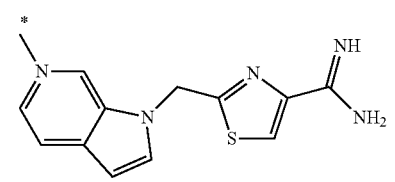
159 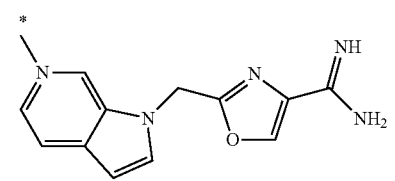
160 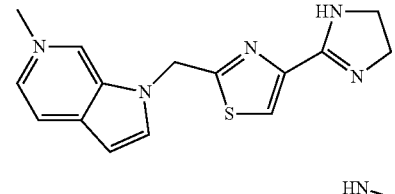
161 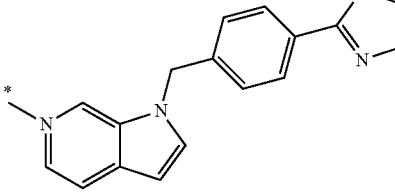

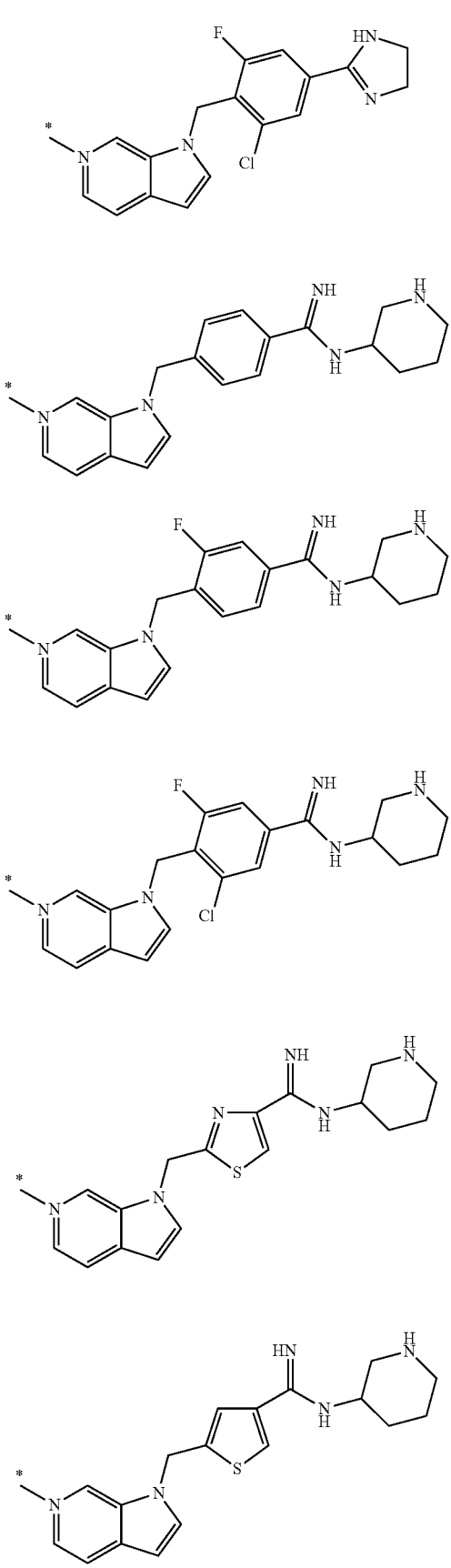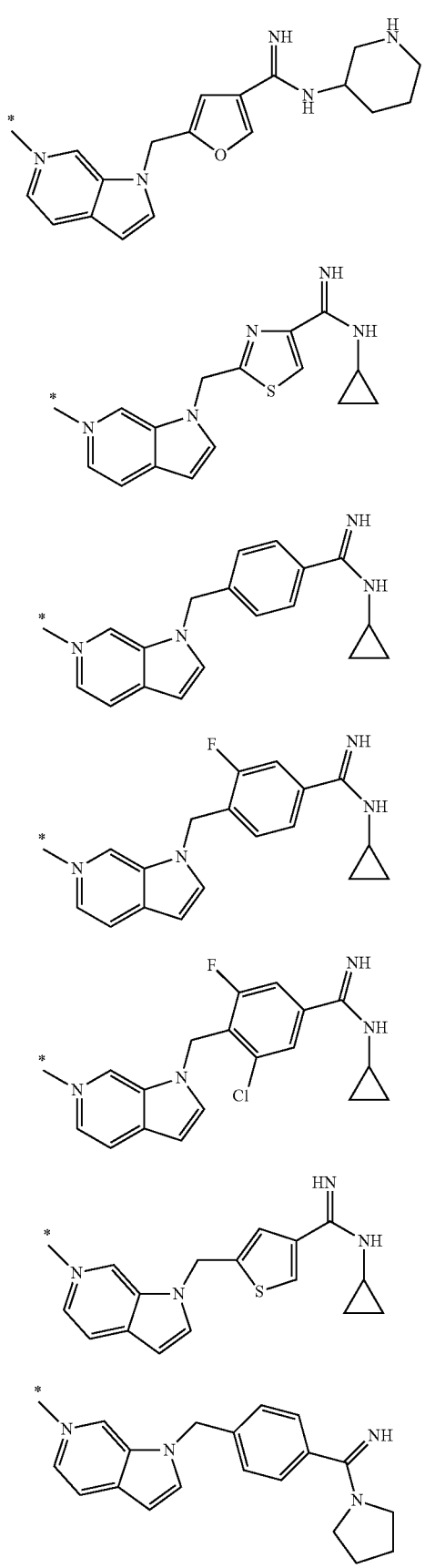

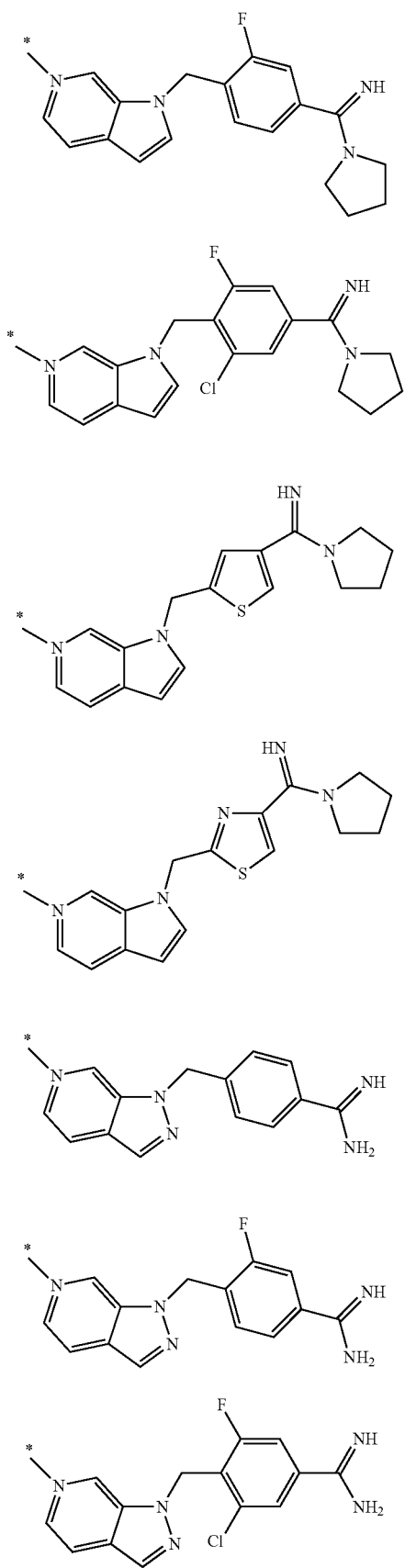
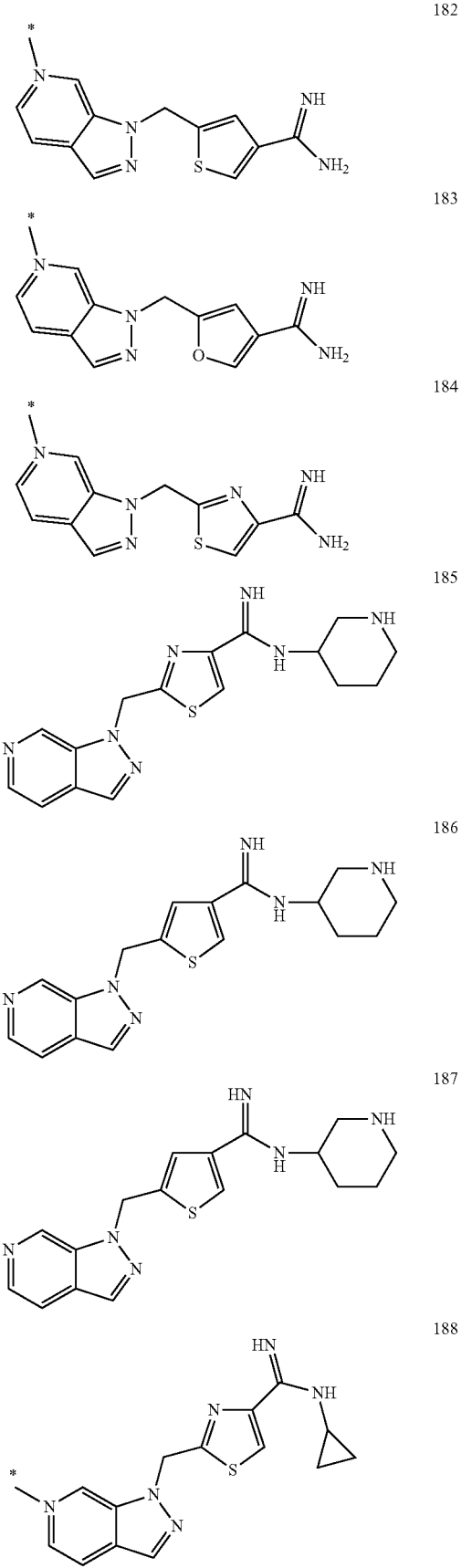

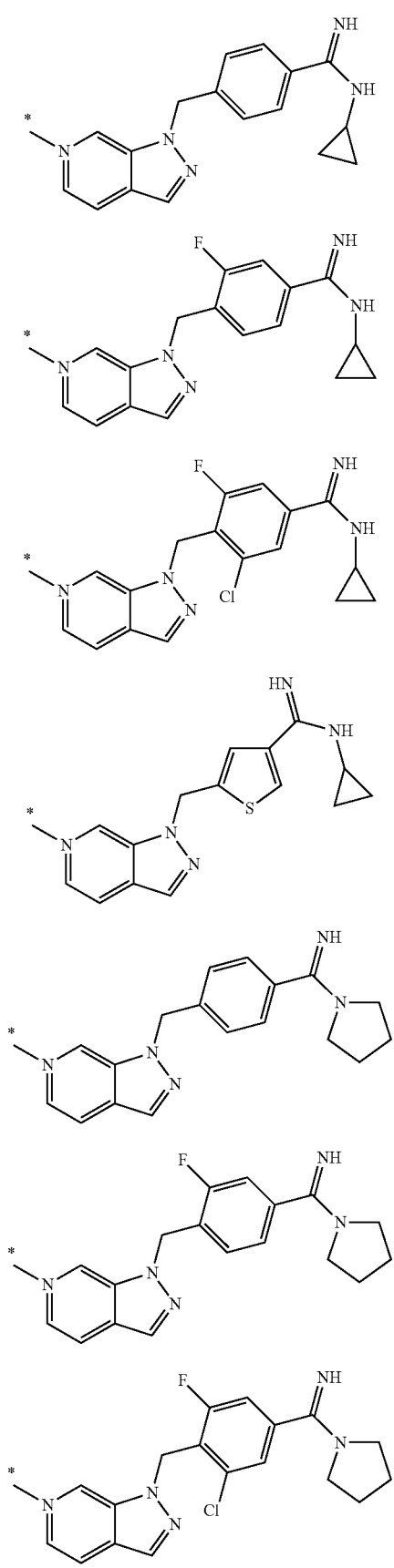
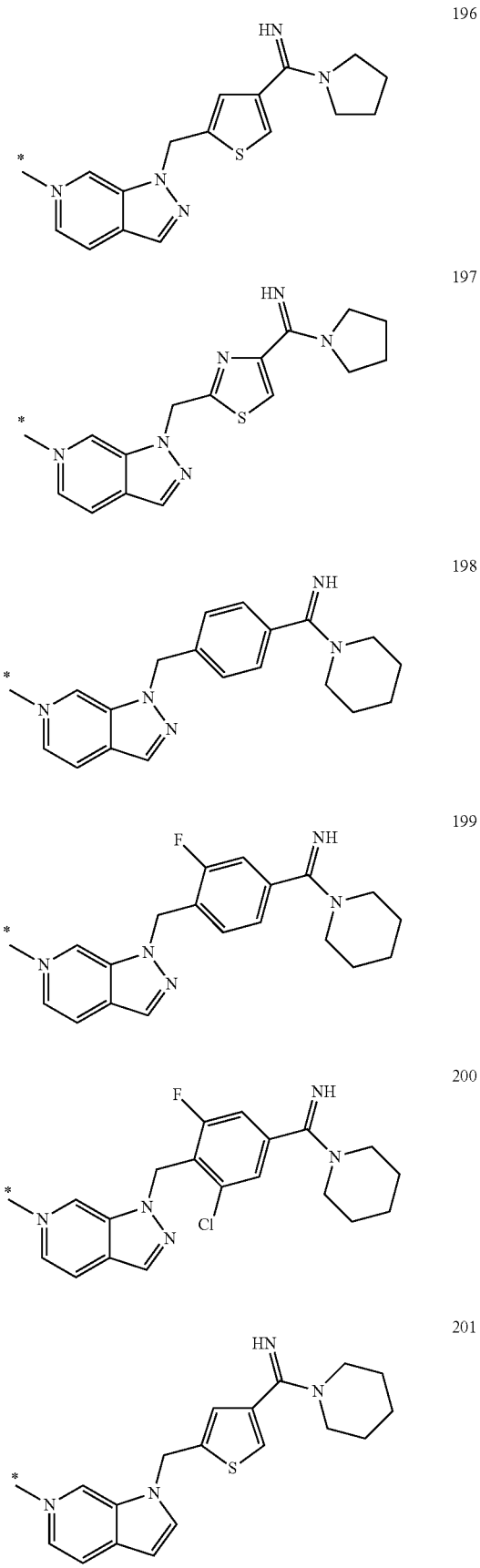

202 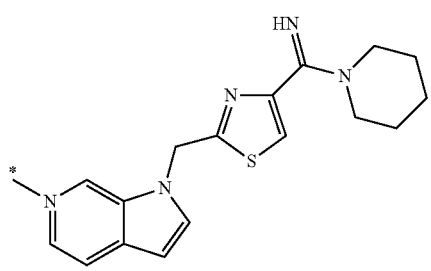
203 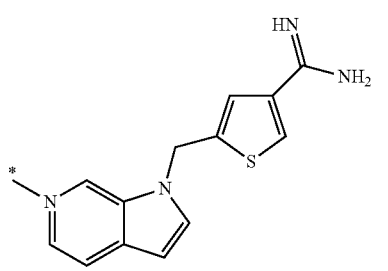
204 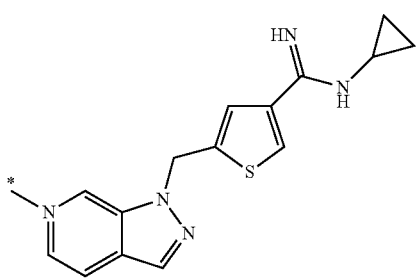
205 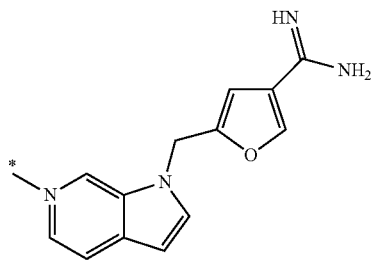
206 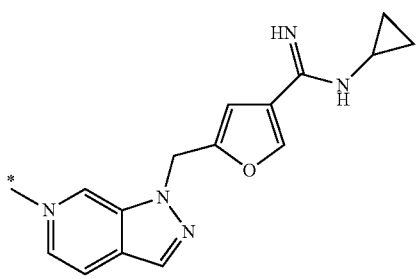
207 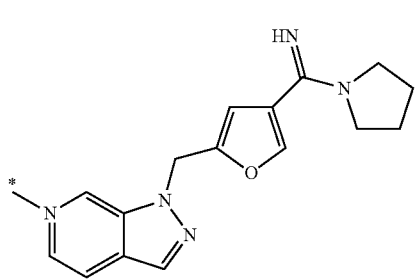
208 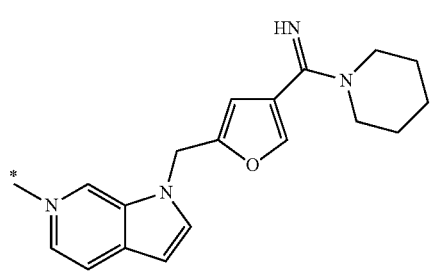
209 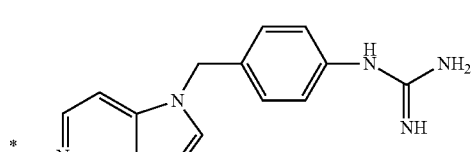
210 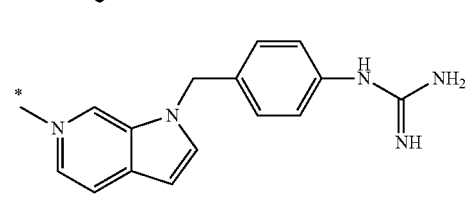
211 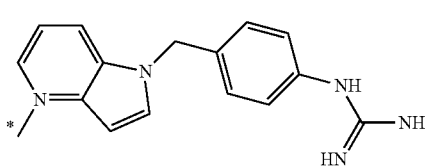
212 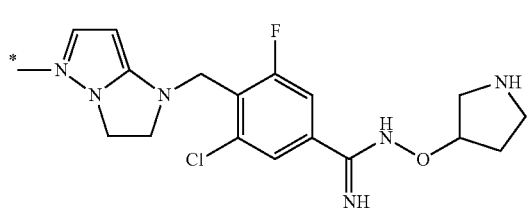
213 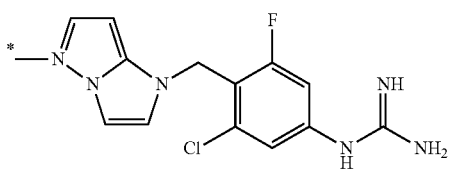
214 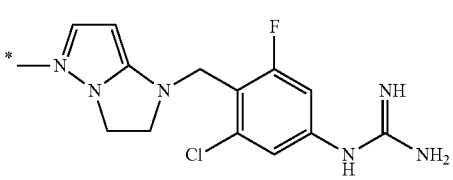
215 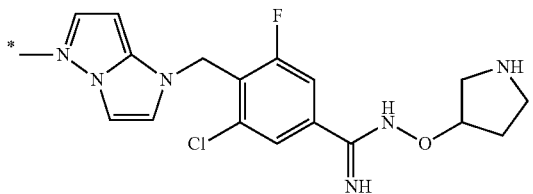

| 216 | 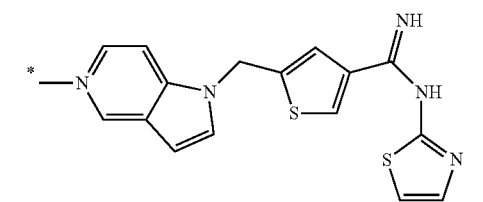 | 223 | 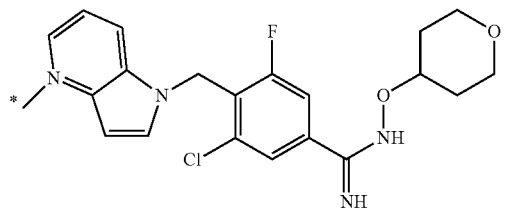 |
| 217 | 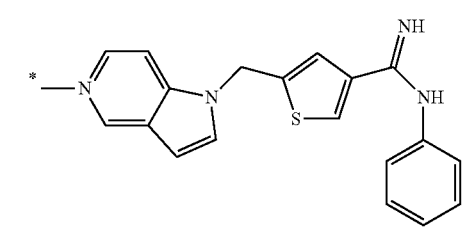 | 224 | 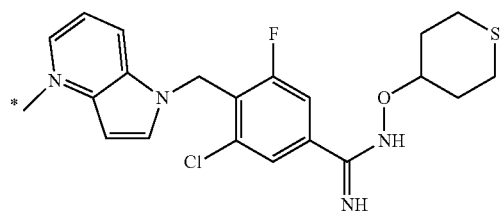 |
| 218 | 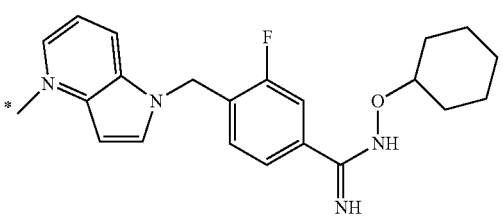 | 225 | 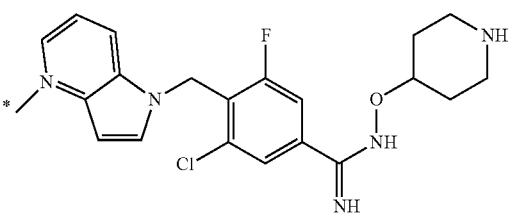 |
| 219 | 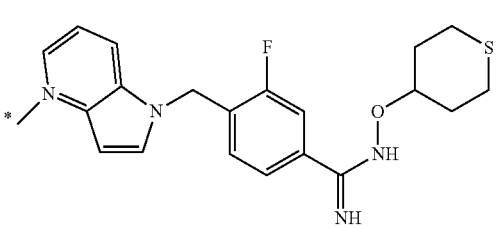 | 226 | 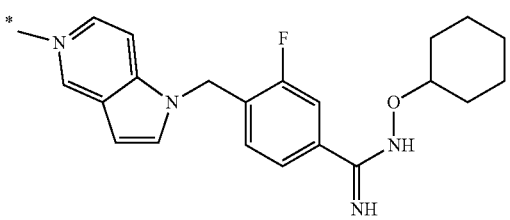 |
| 220 | 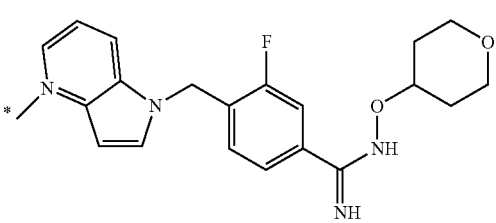 | 227 | 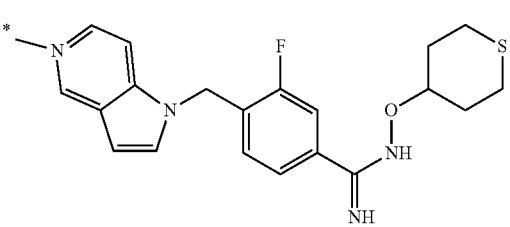 |
| 221 | 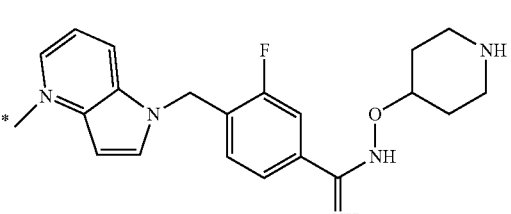 | 228 | 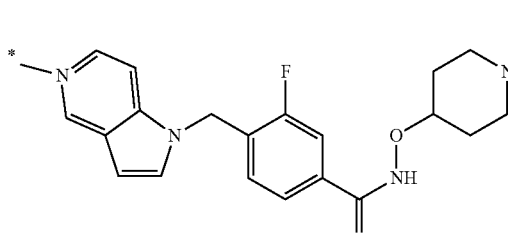 |
| 222 | 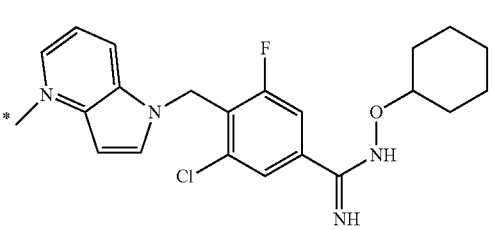 | 229 | 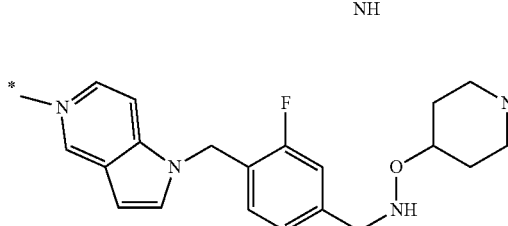 |

230
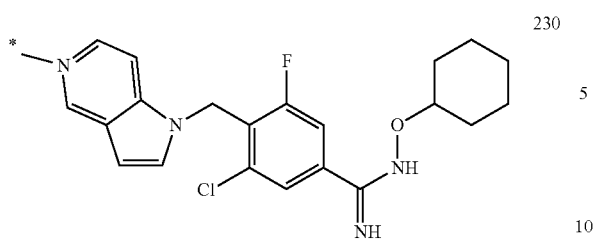
231
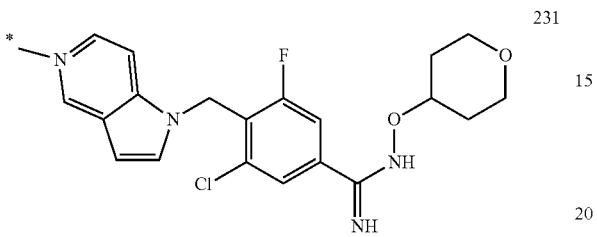
232
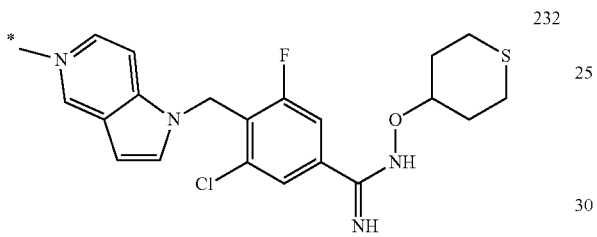
233
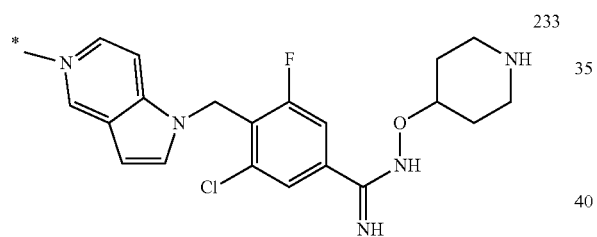
234
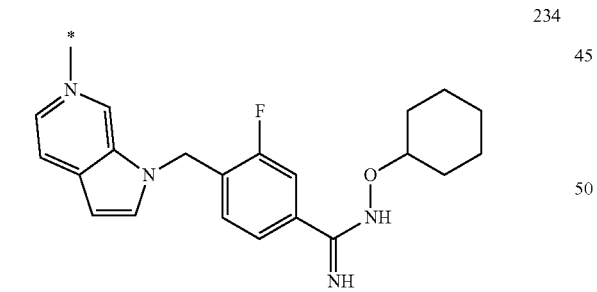
235
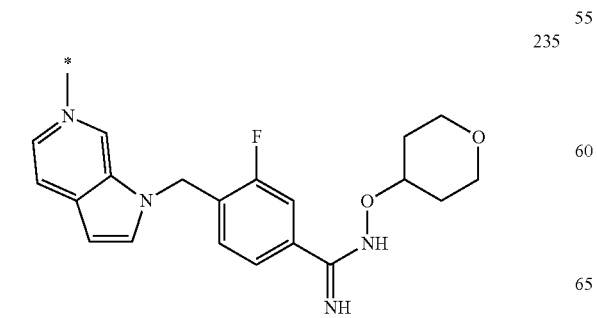
236
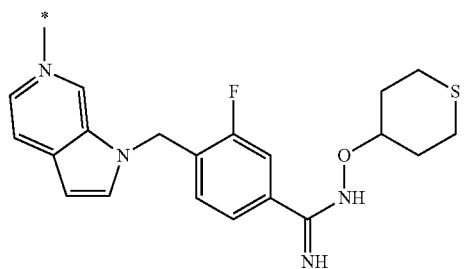
237
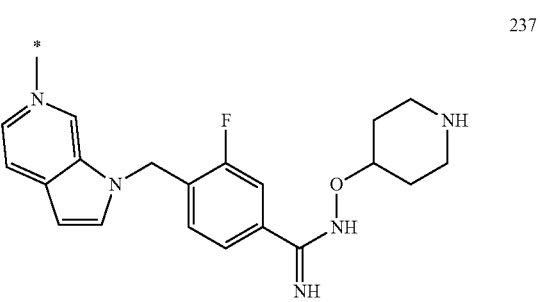
238
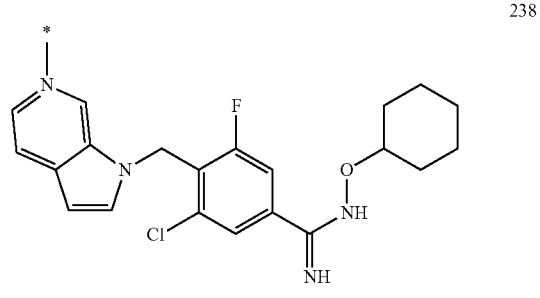
239
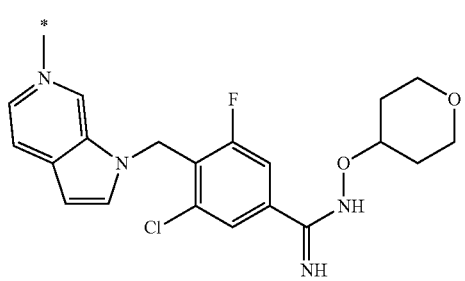
240
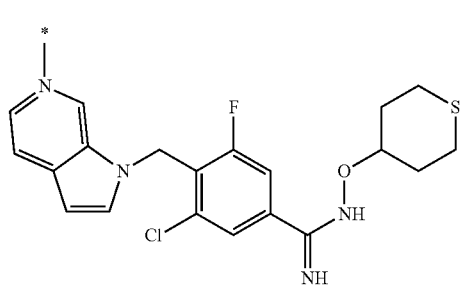

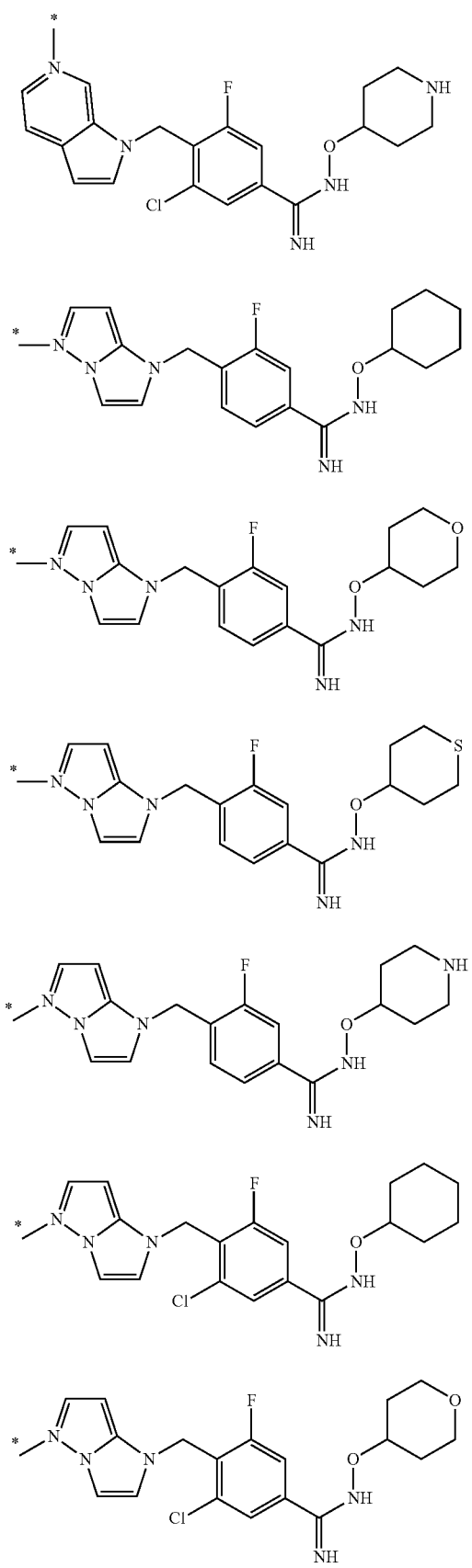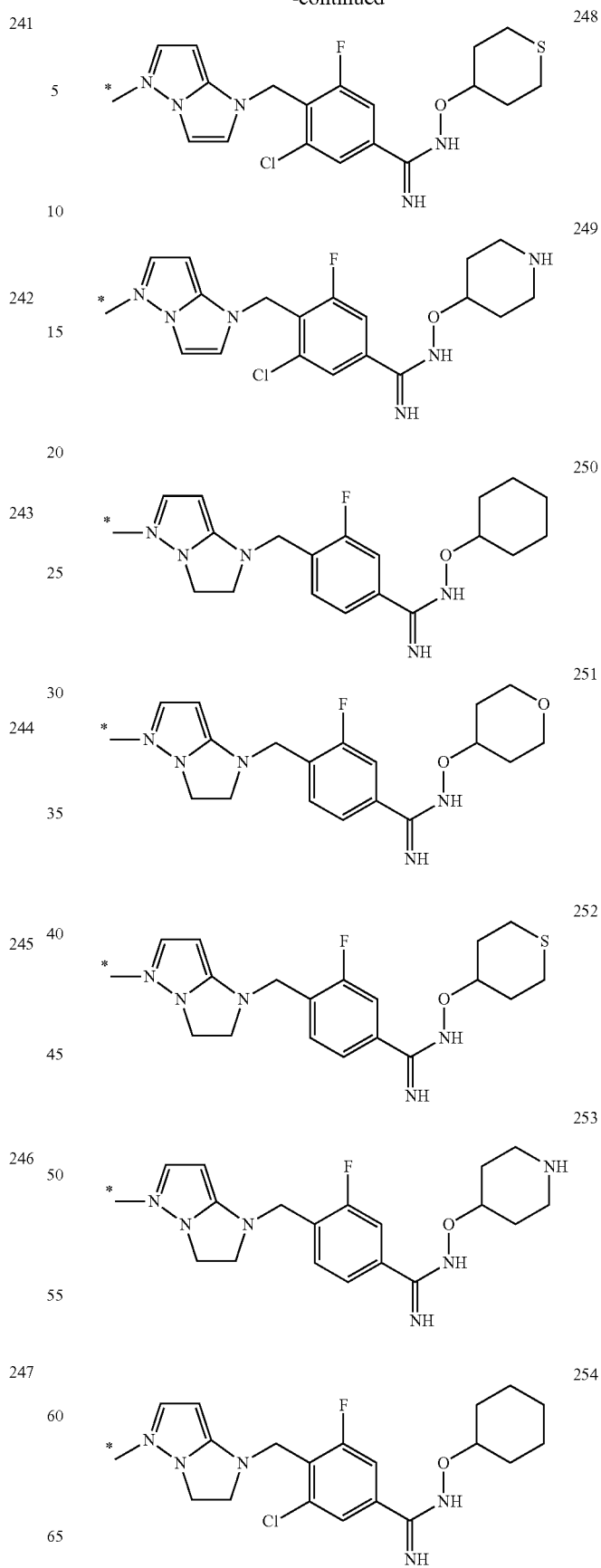

255 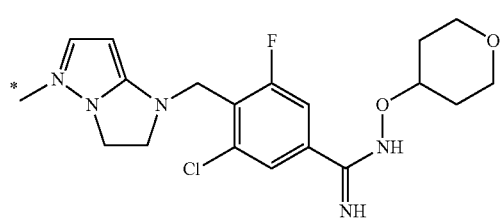
256 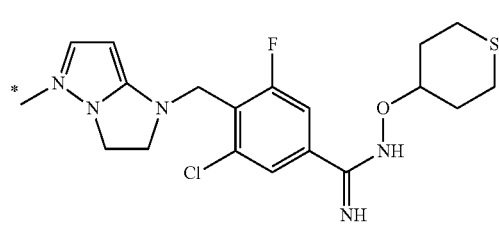
257 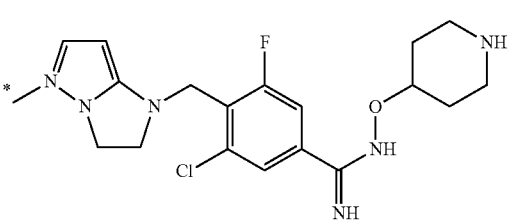
258 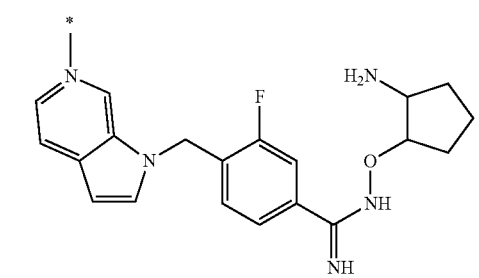
259 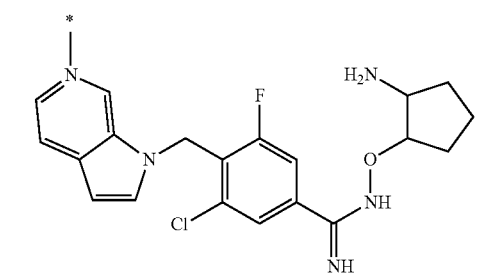
260 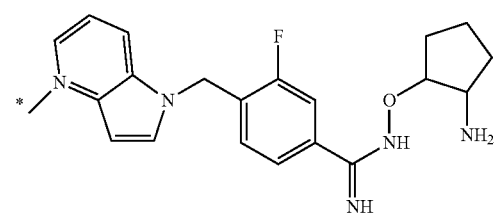
261 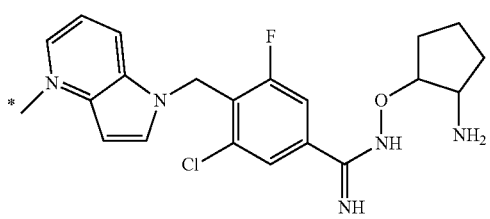
262 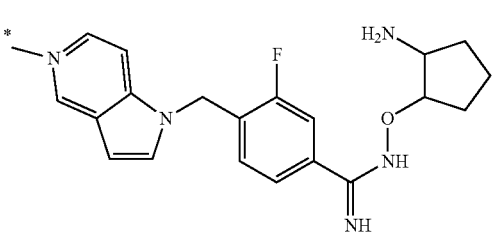
263 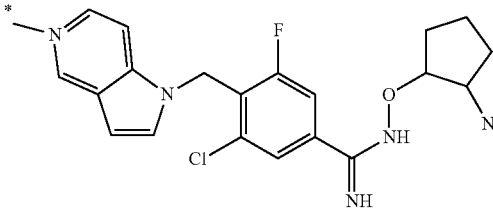
264 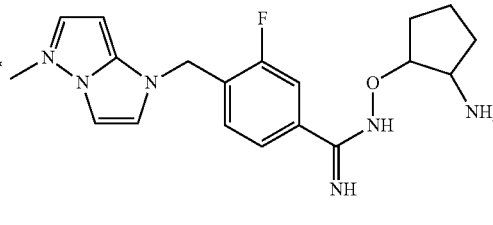
265 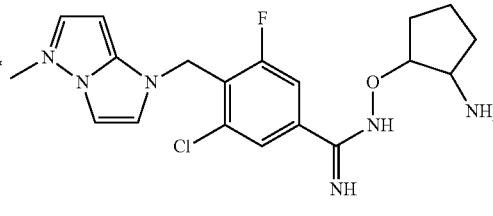
266 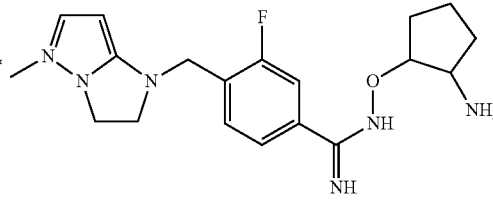
267 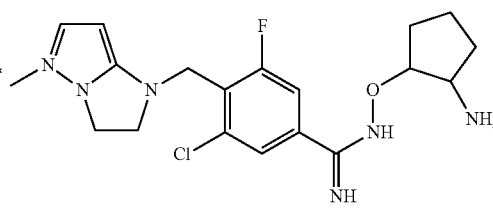

261
-continued
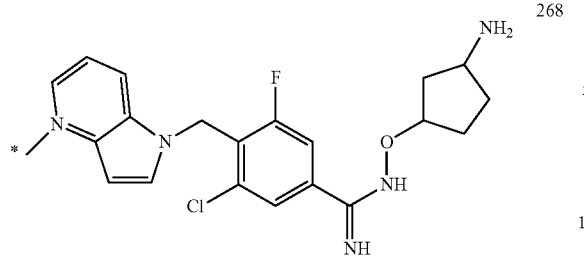
268
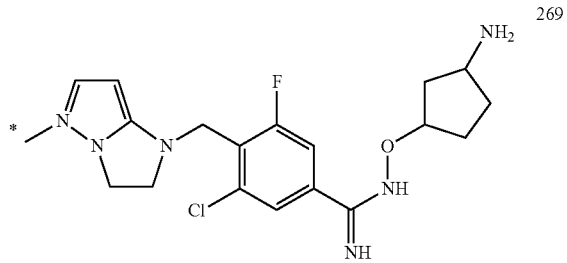
269
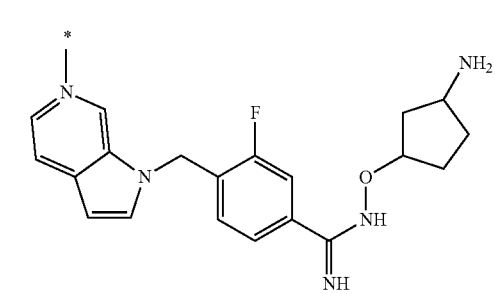
270
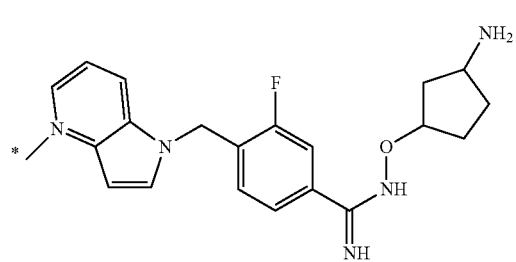
271
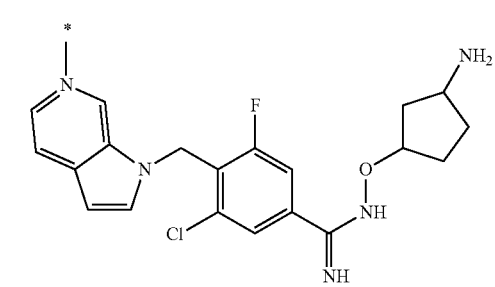
272
262
-continued
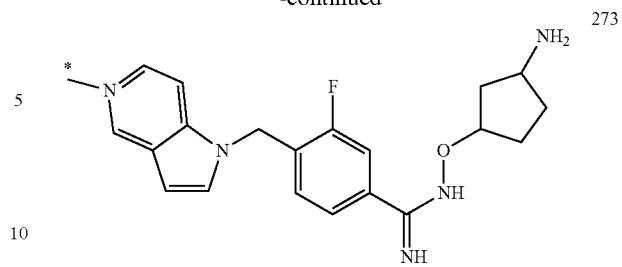
273
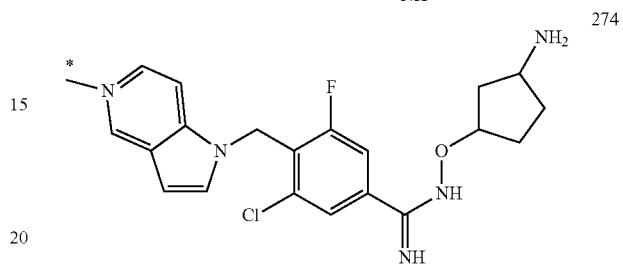
274
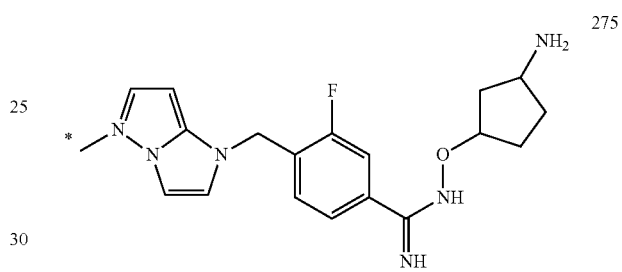
275
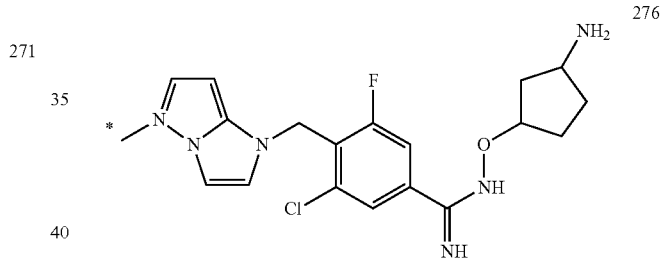
276
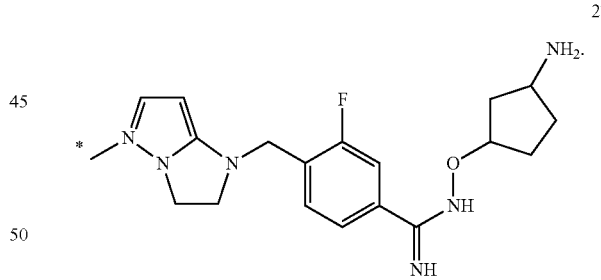
277
5. The compound of formula (I) as recited in claim 1, which is selected from the following group of compounds:
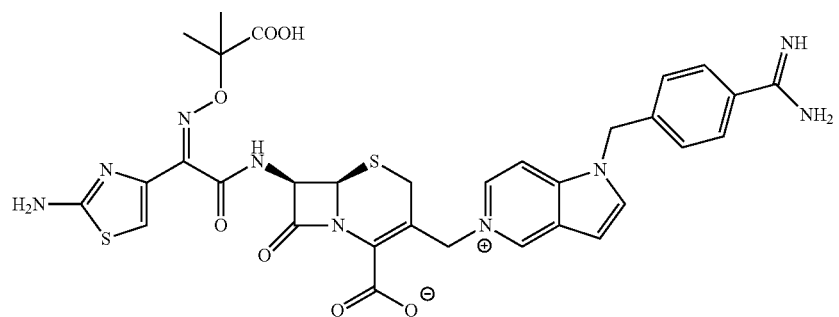

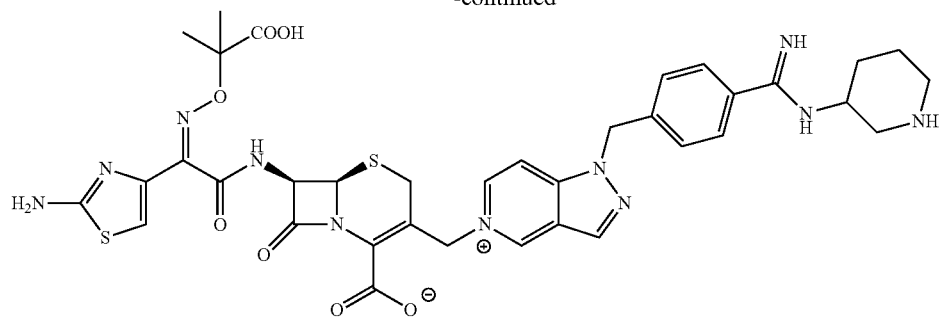
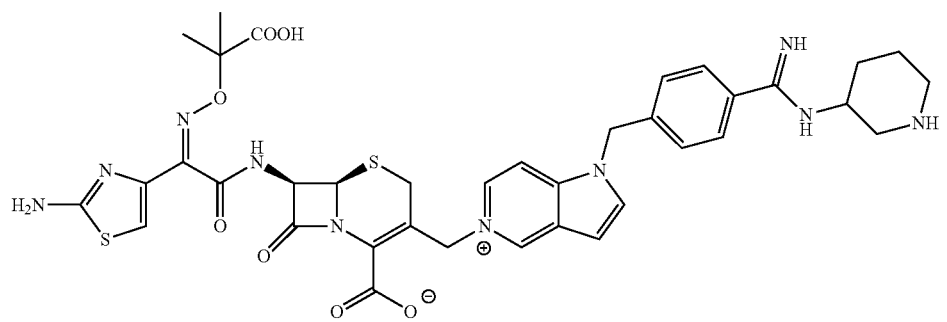
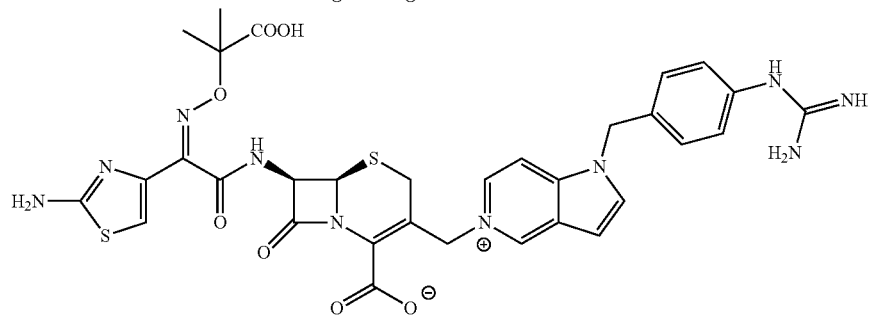
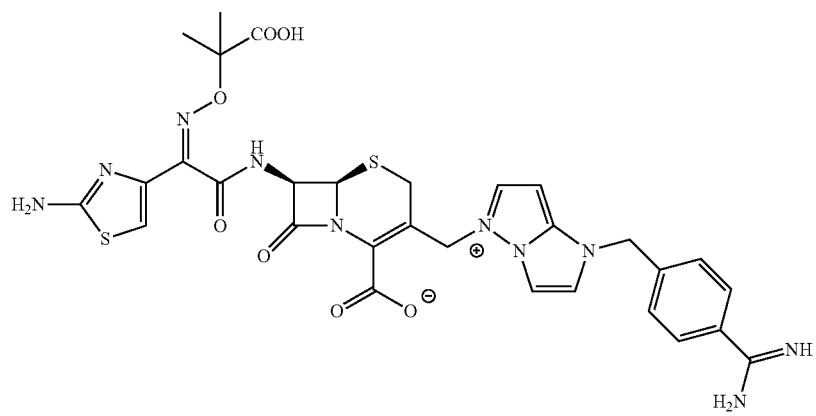
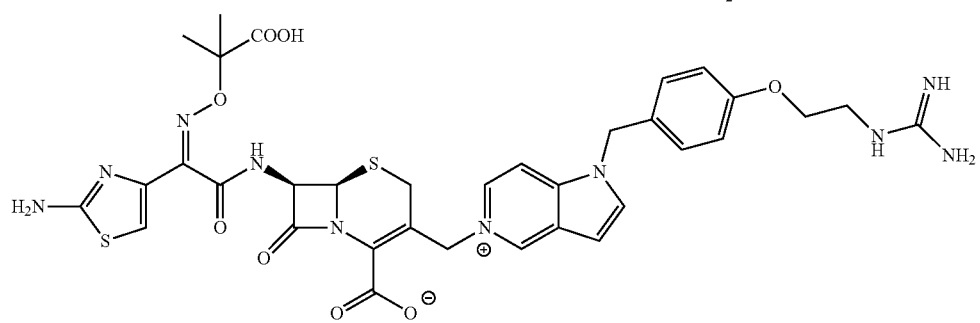

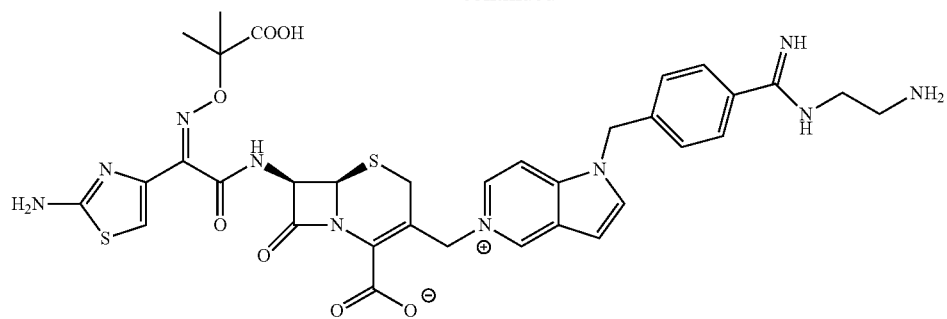
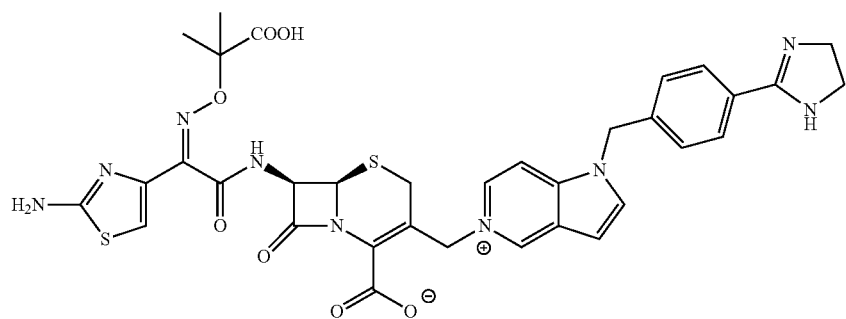
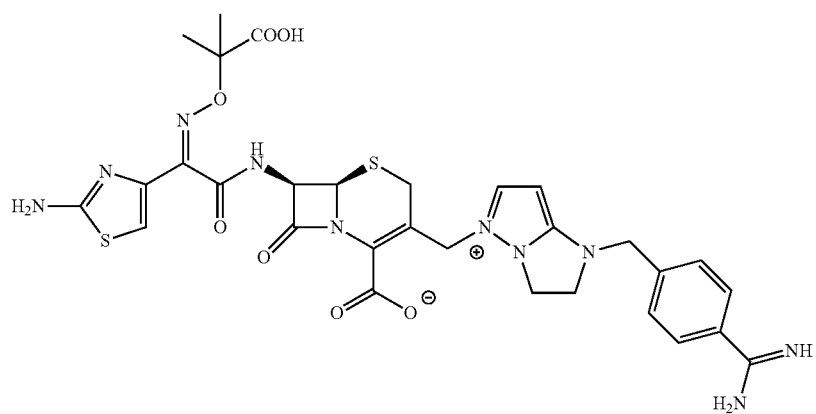
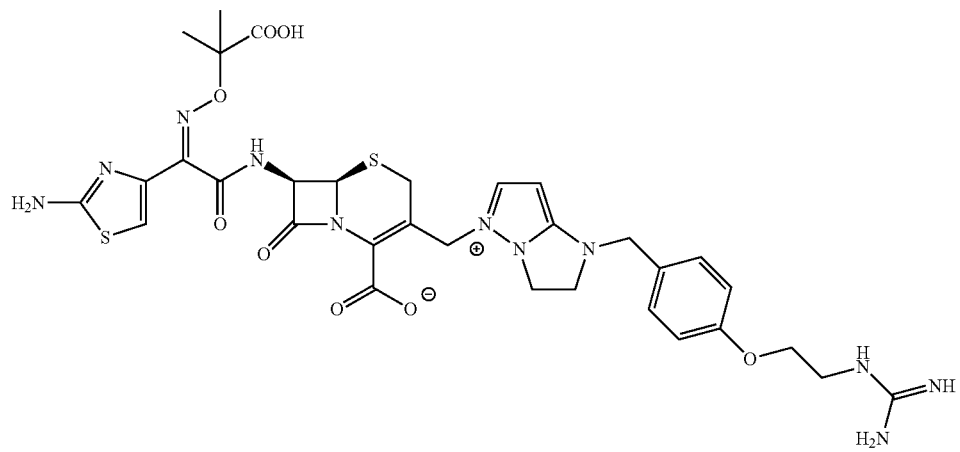

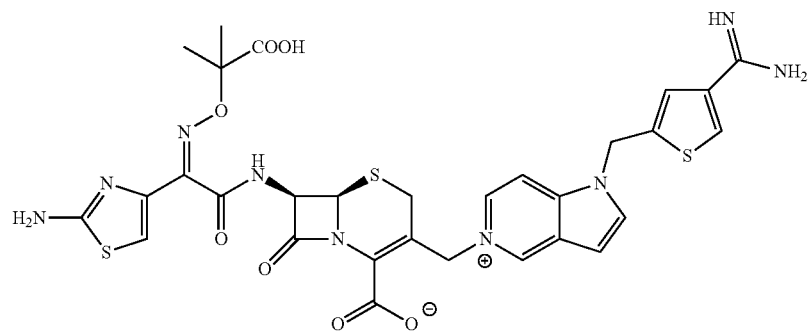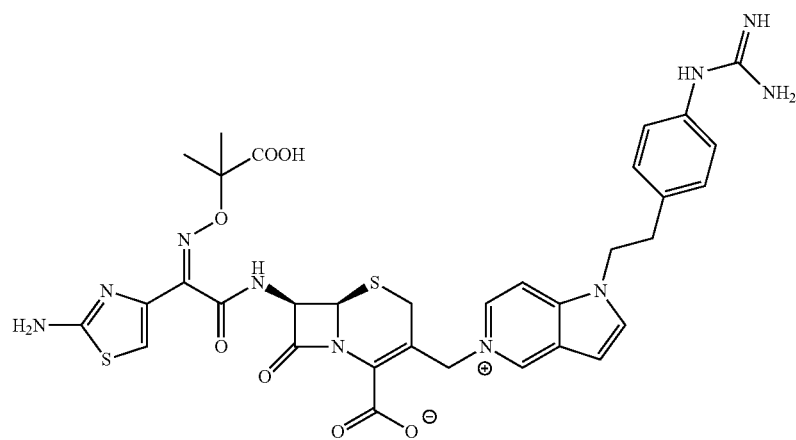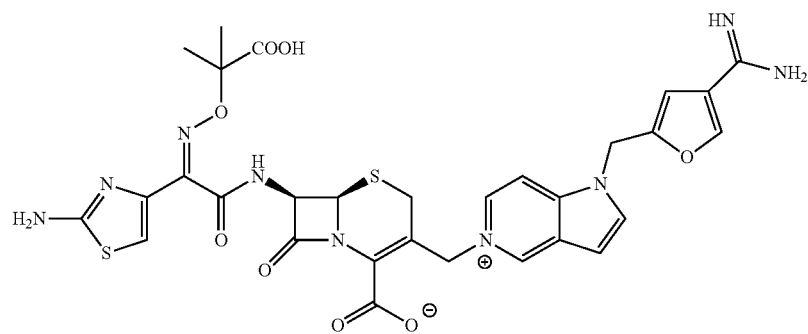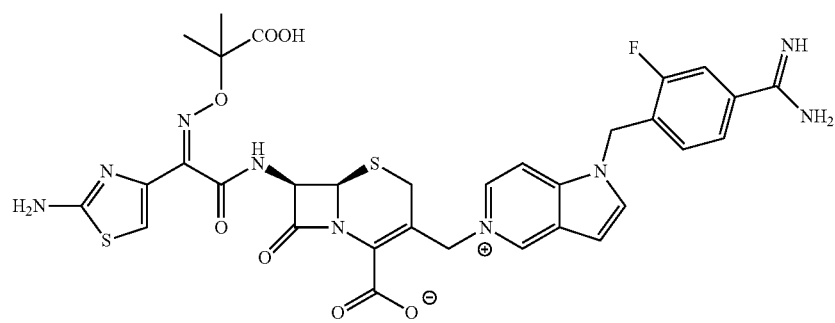

-continued
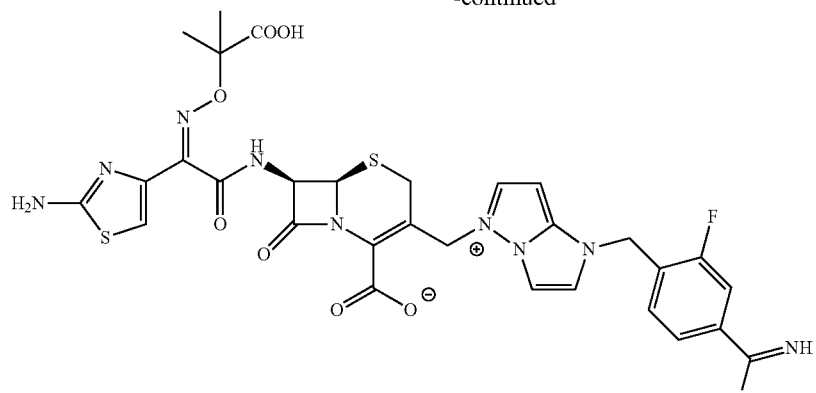
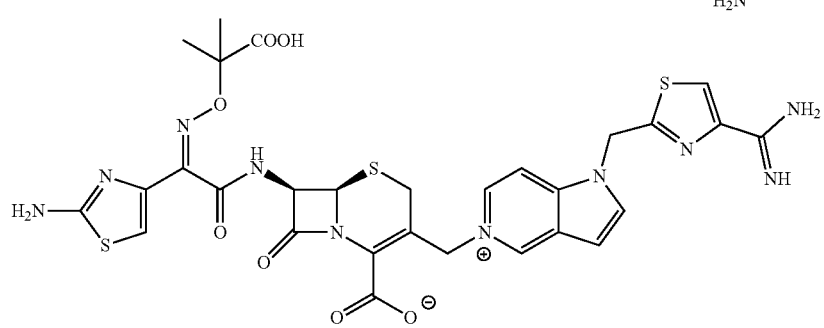
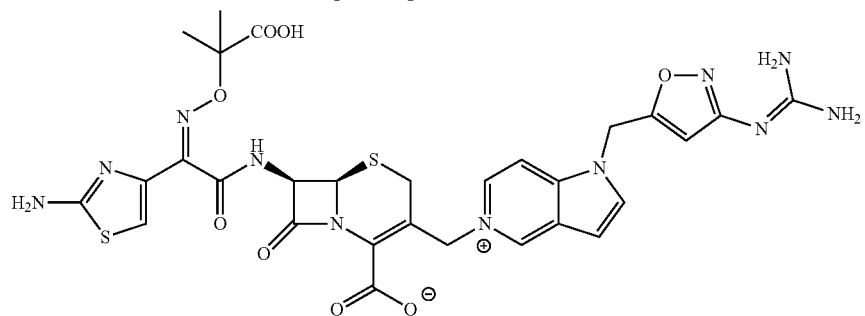
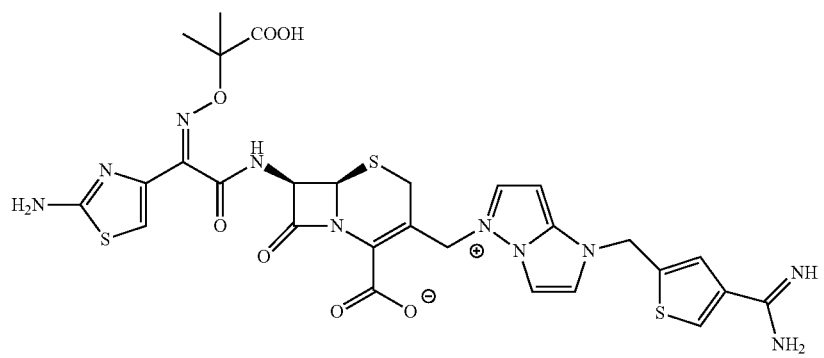
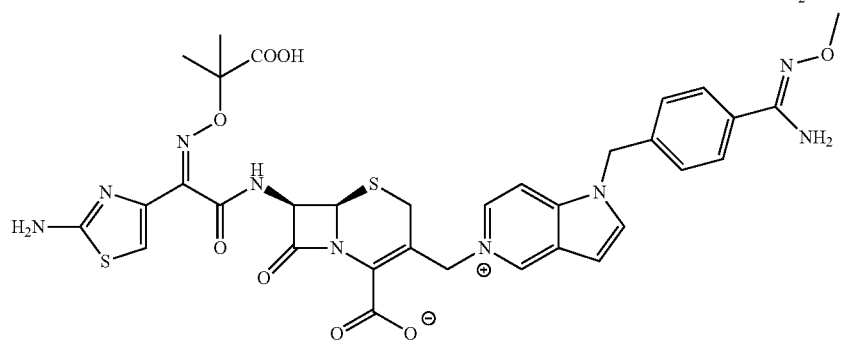

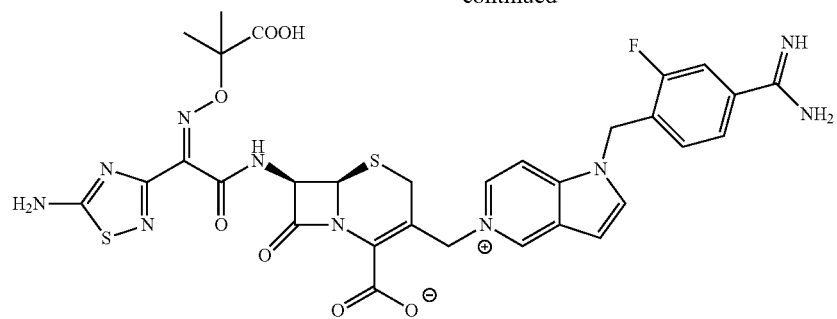
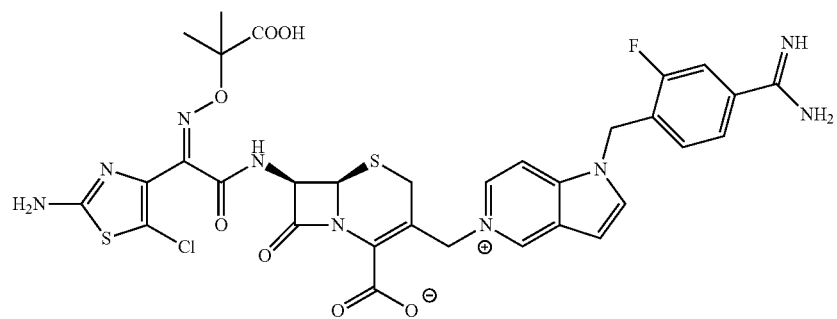
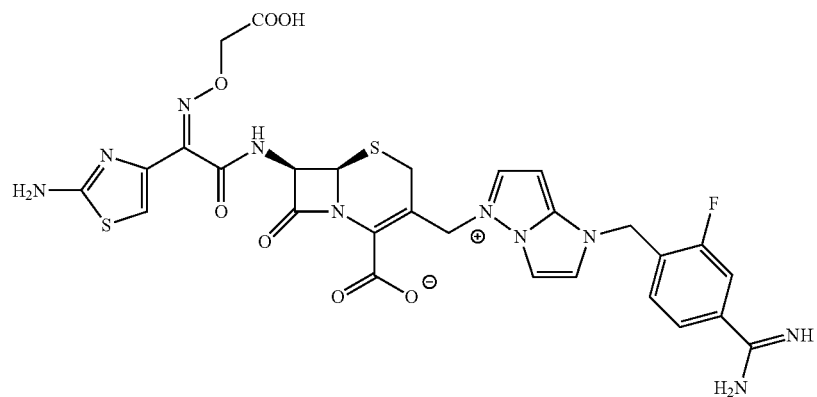
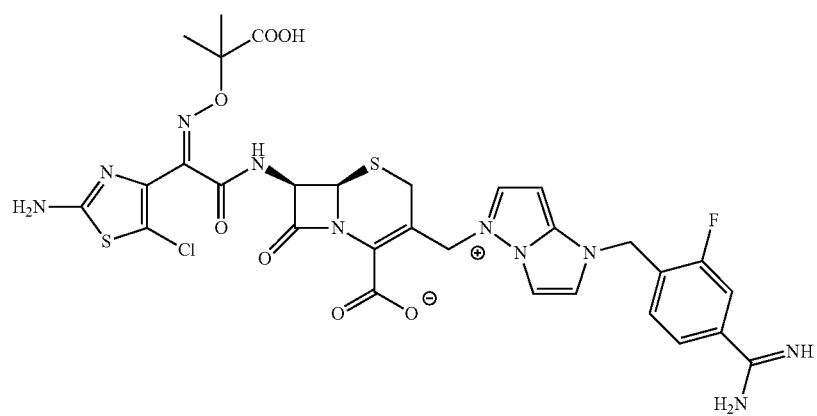

-continued
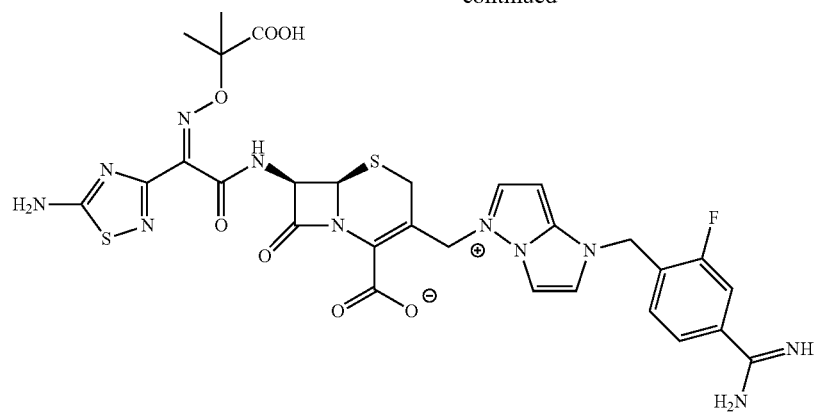
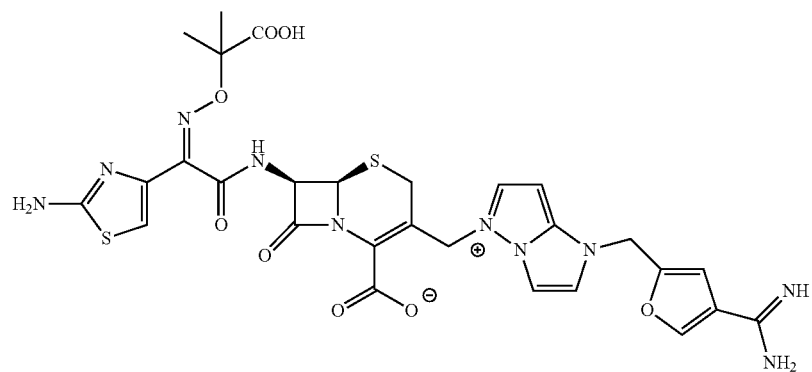
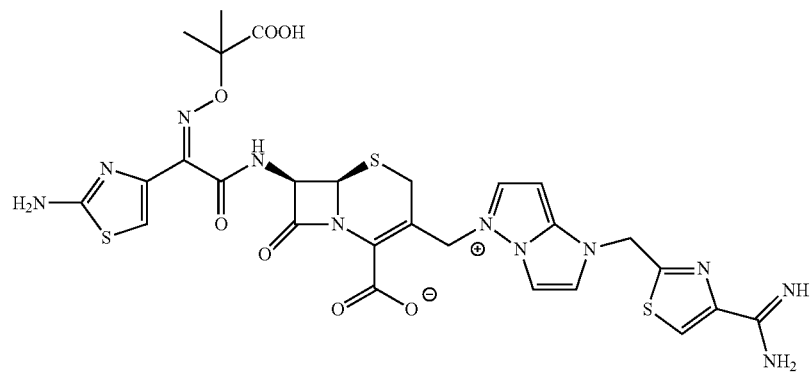
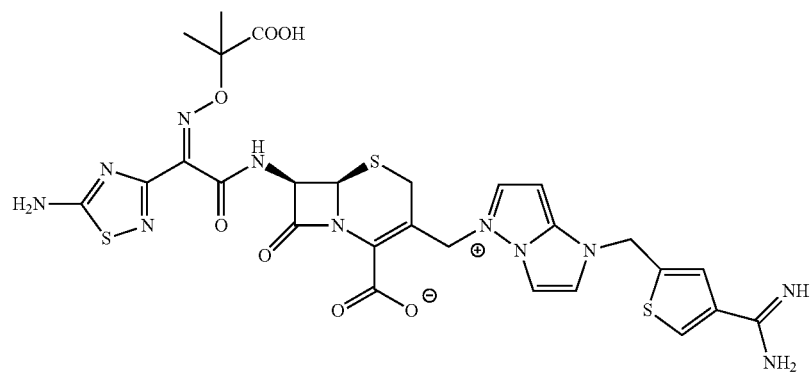

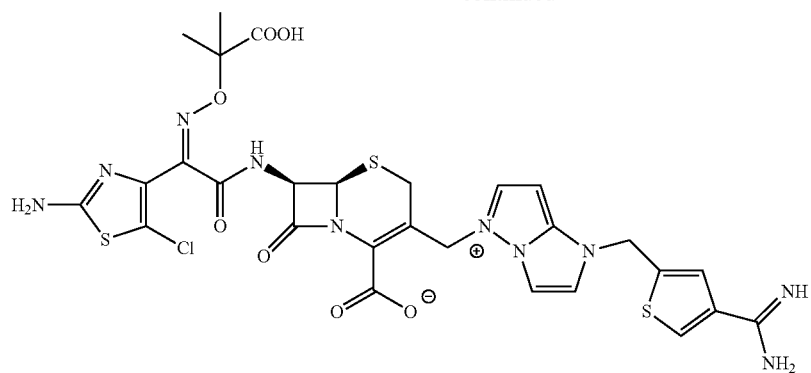
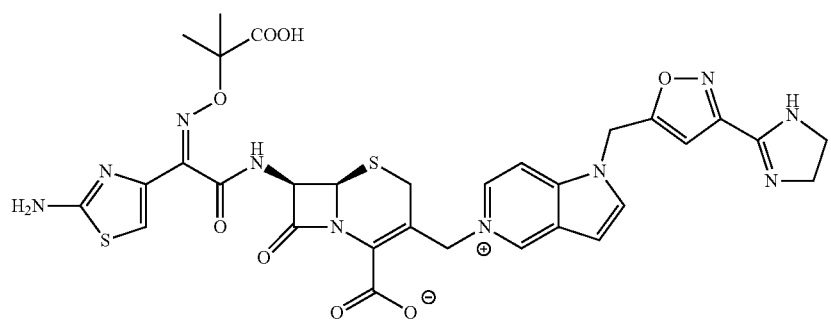
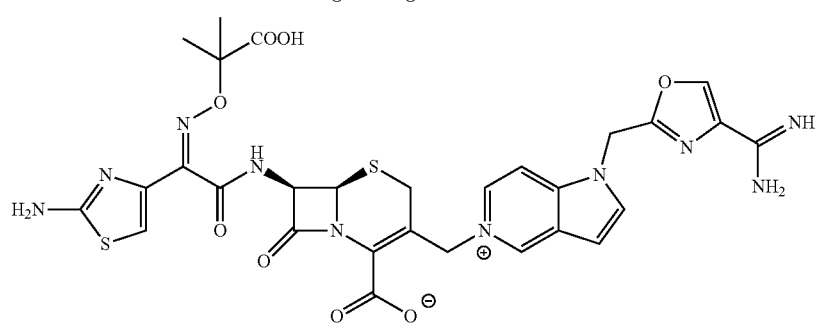
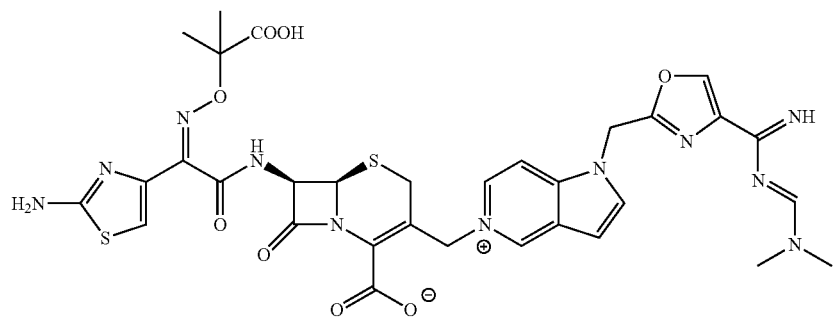
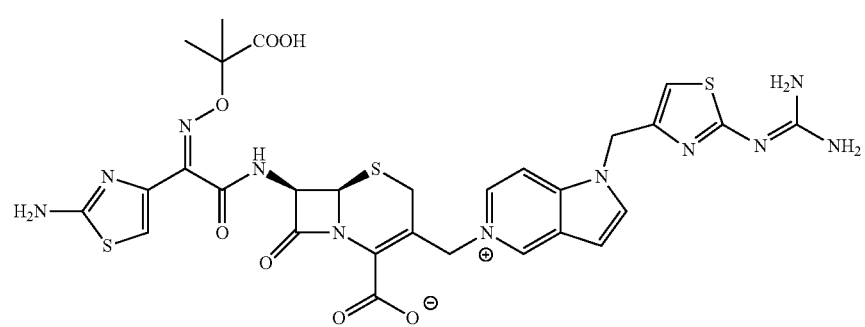

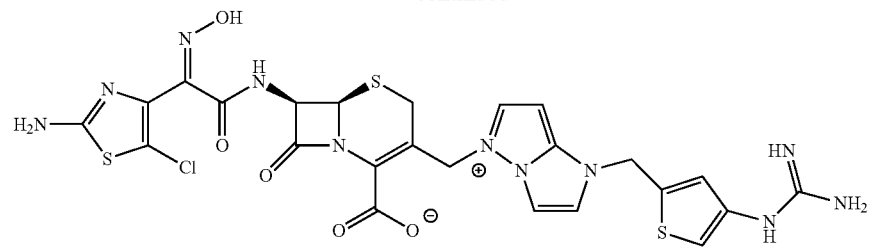
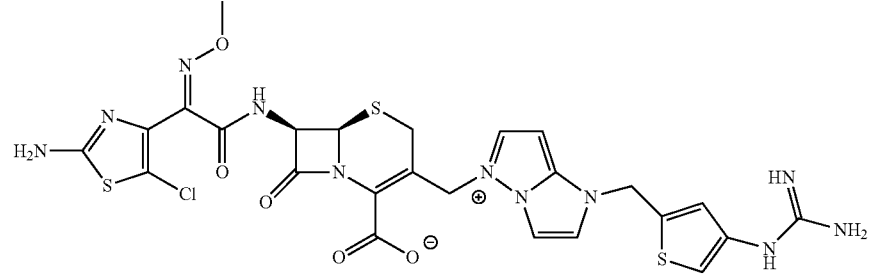
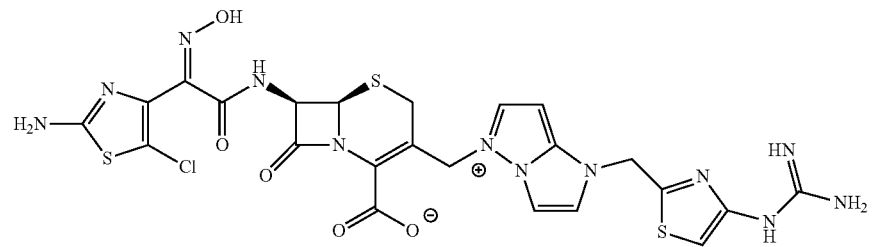
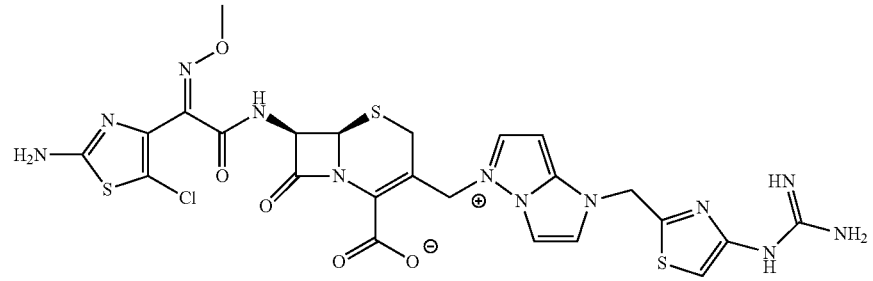
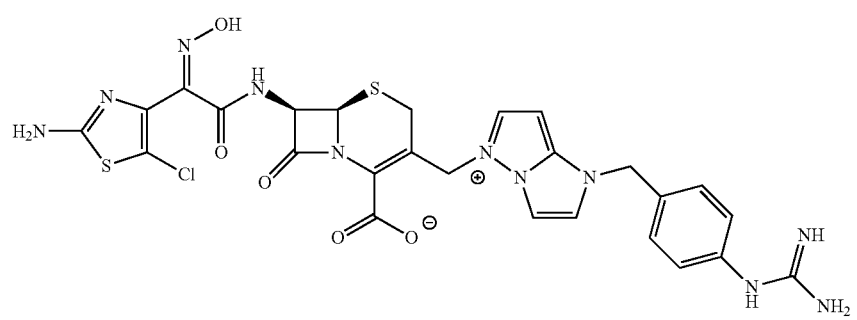
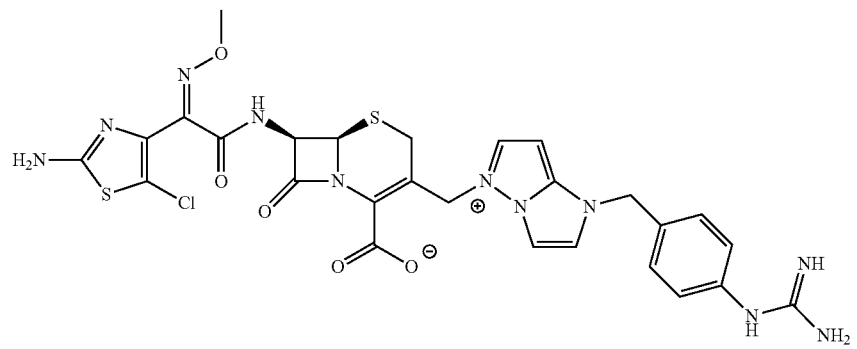

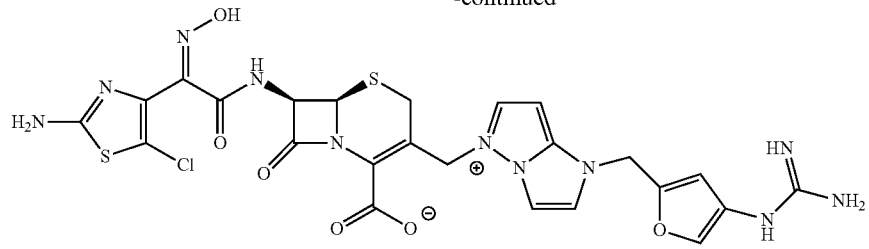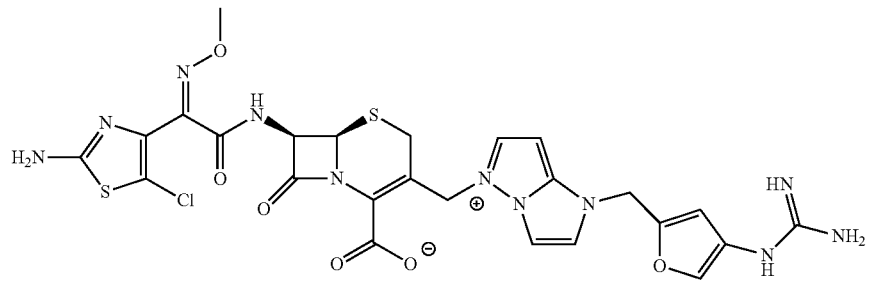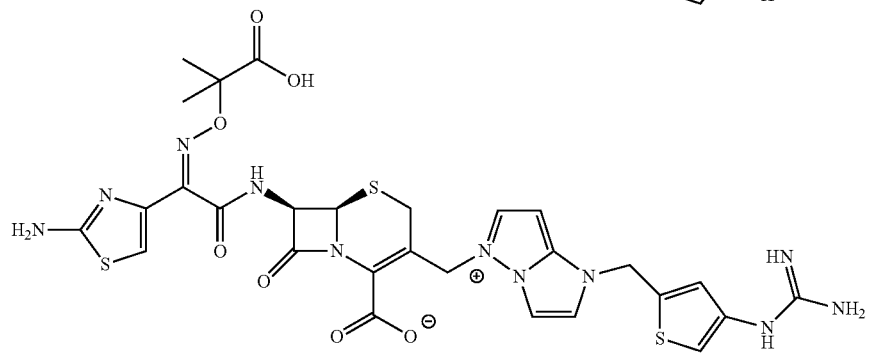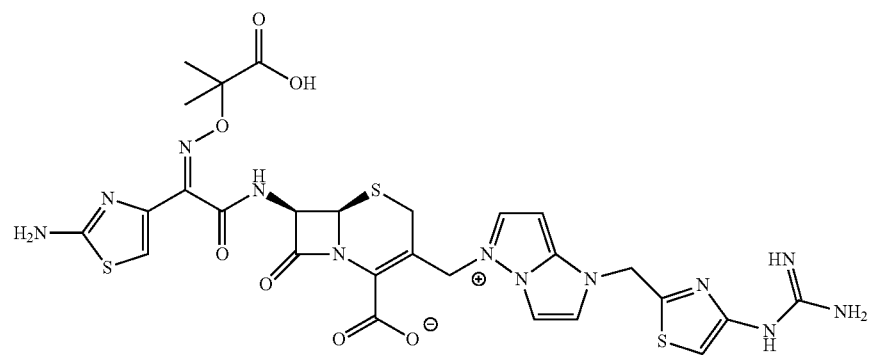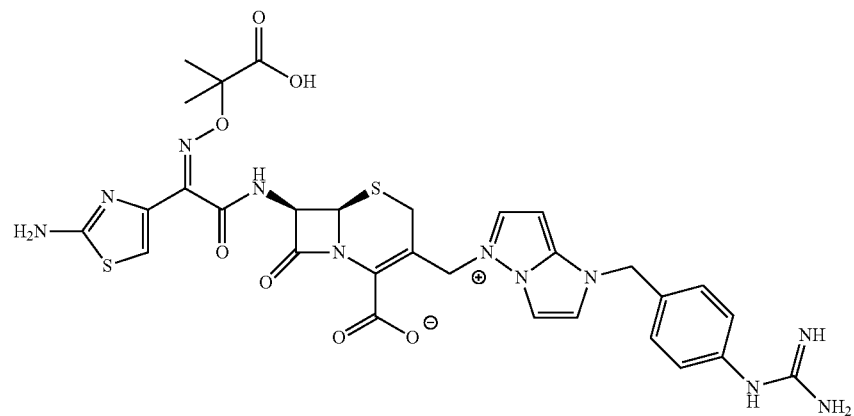

-continued
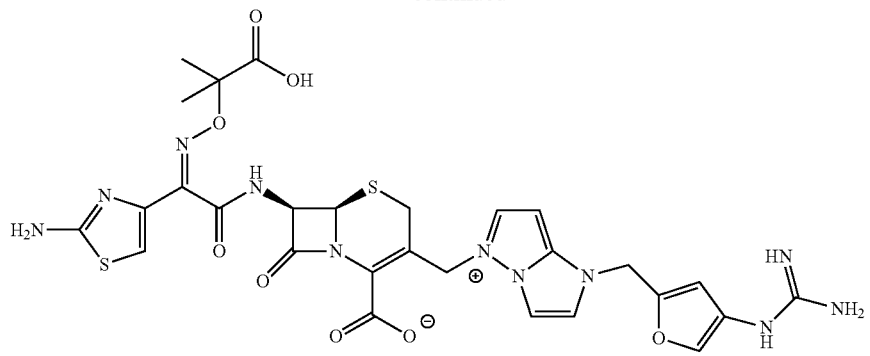
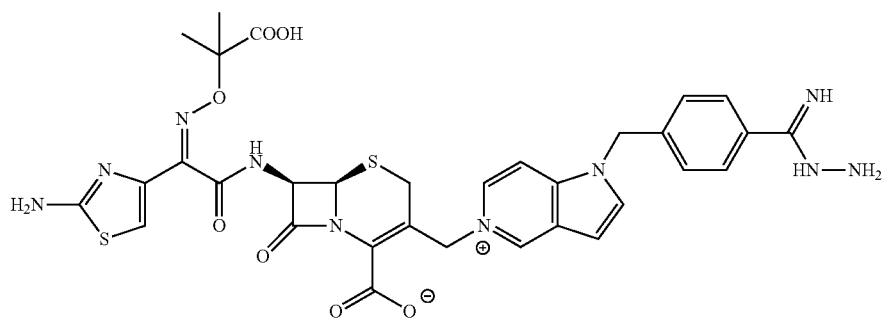
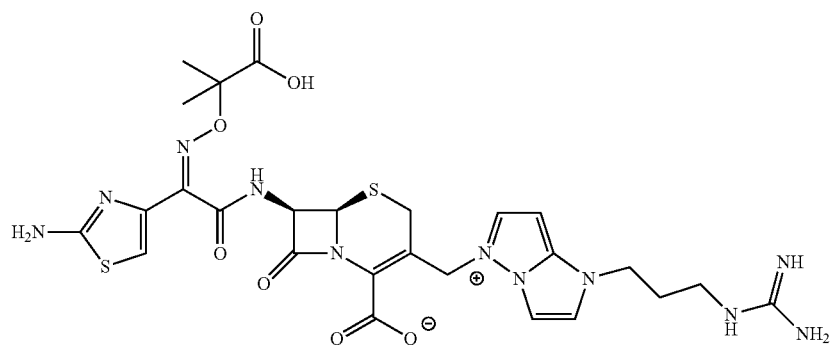
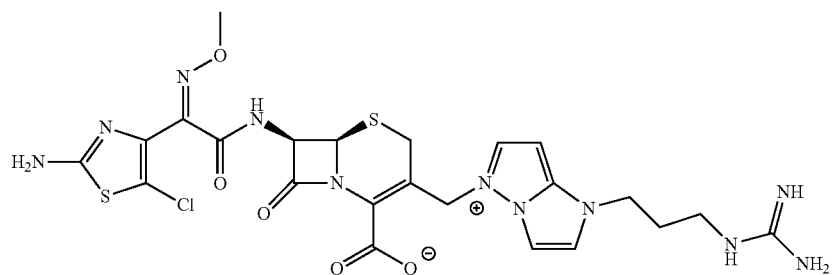
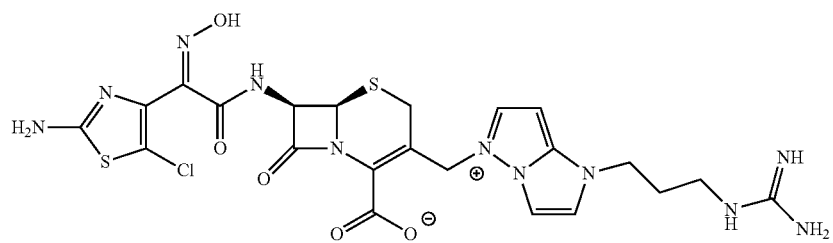

-continued
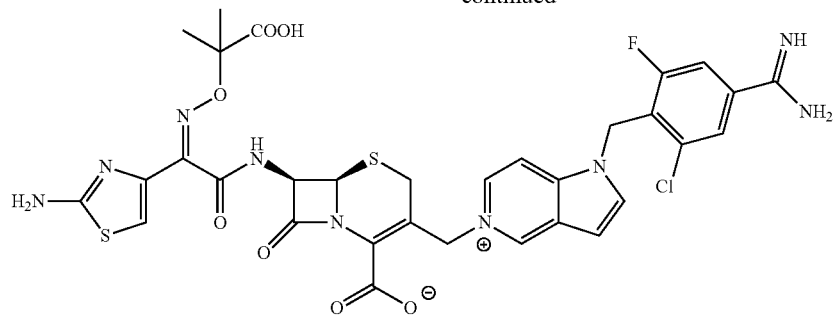
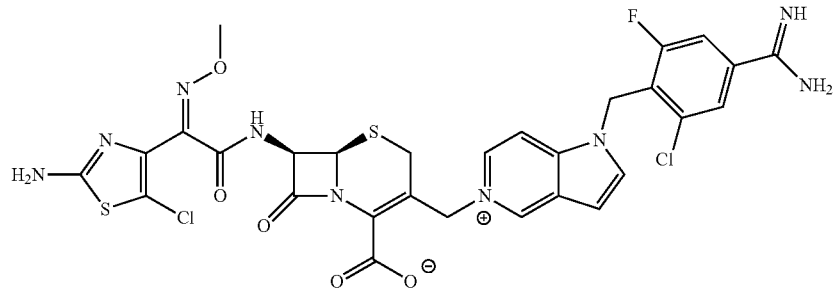
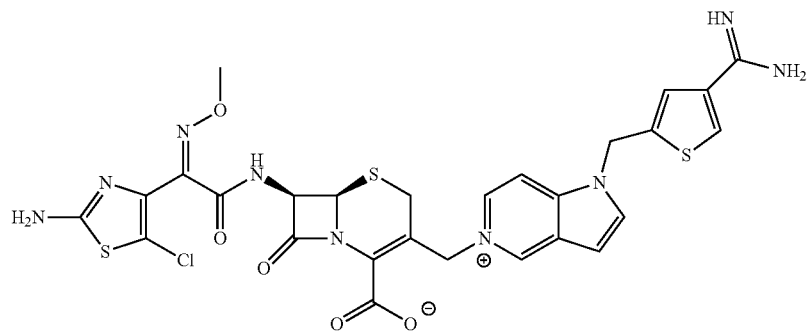
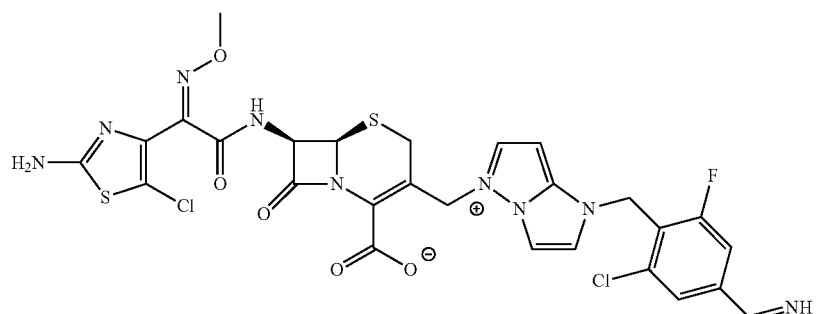
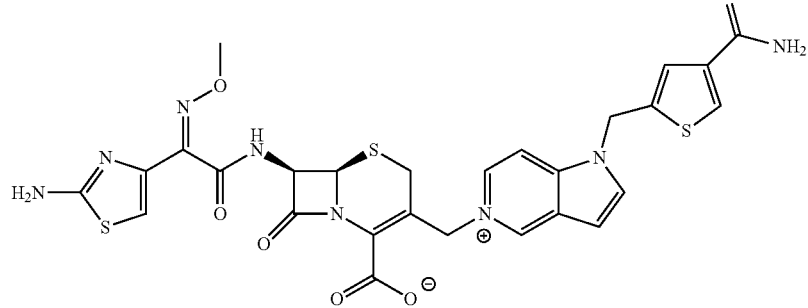

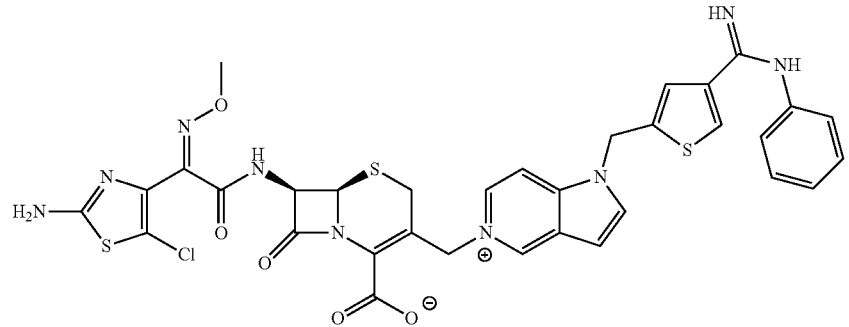
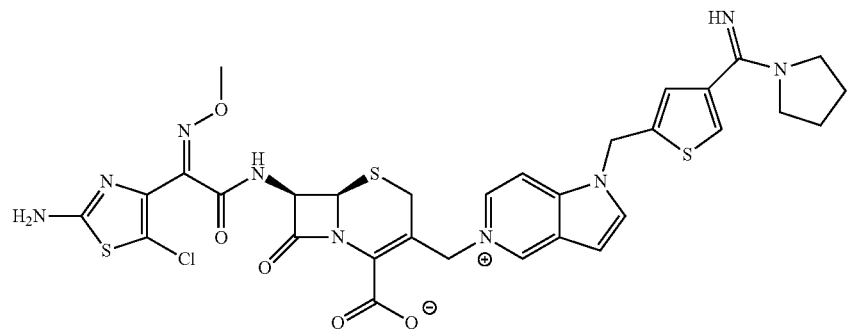
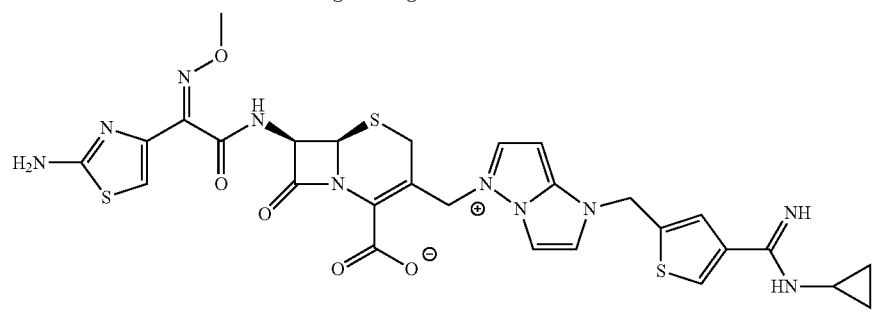
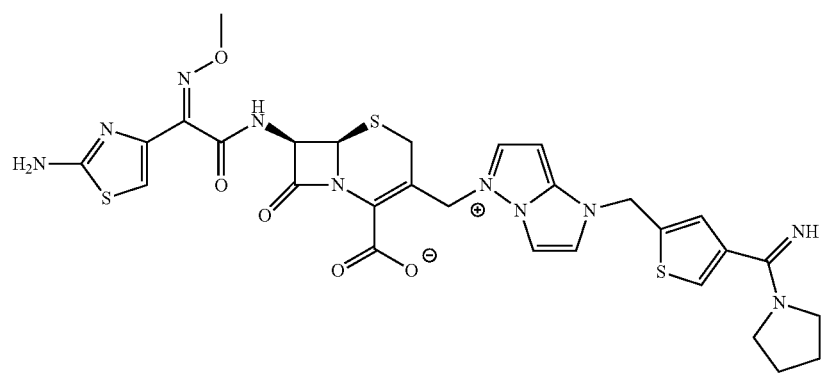
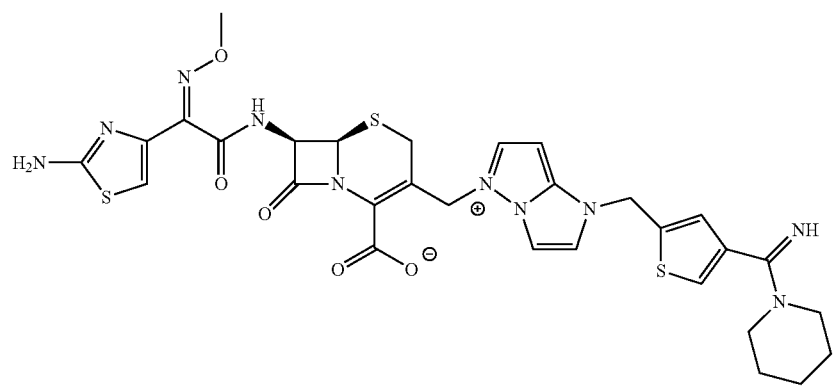

-continued
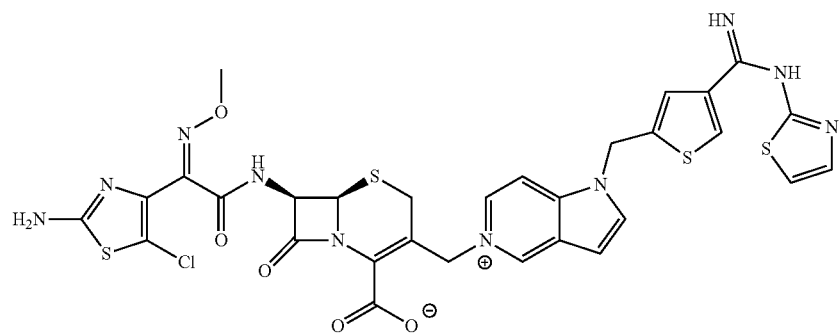
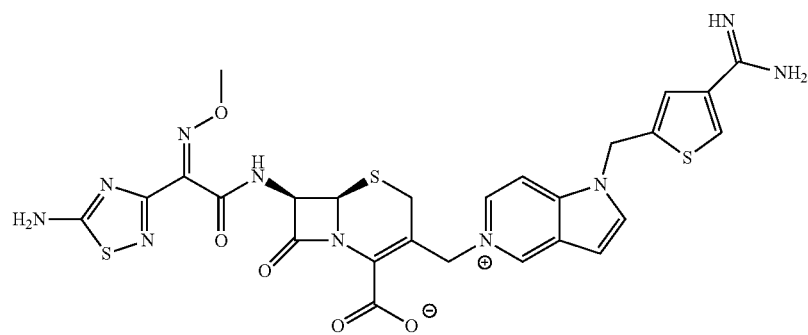
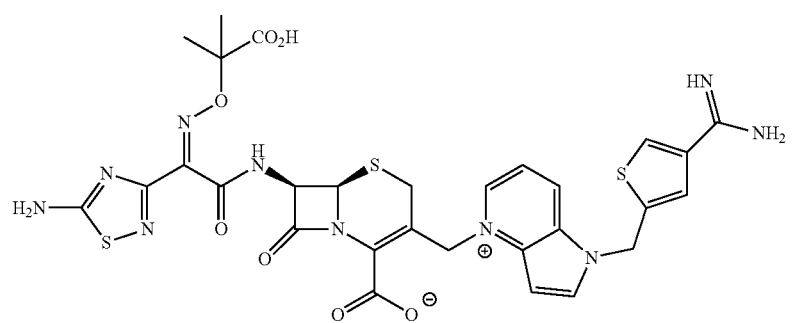
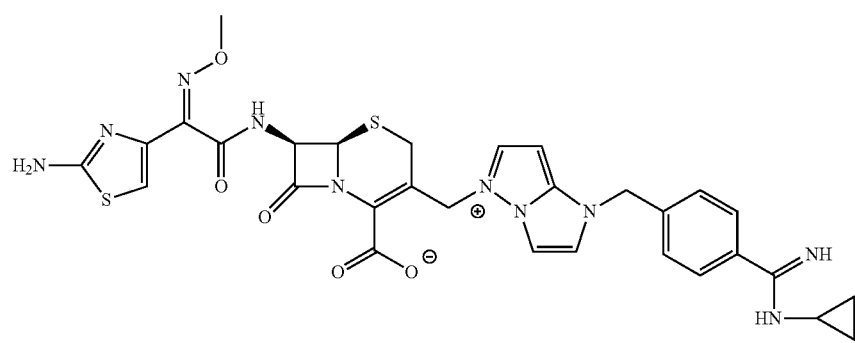
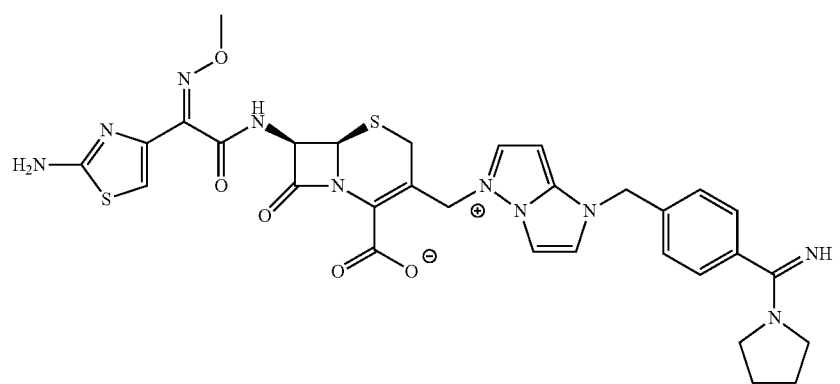

-continued
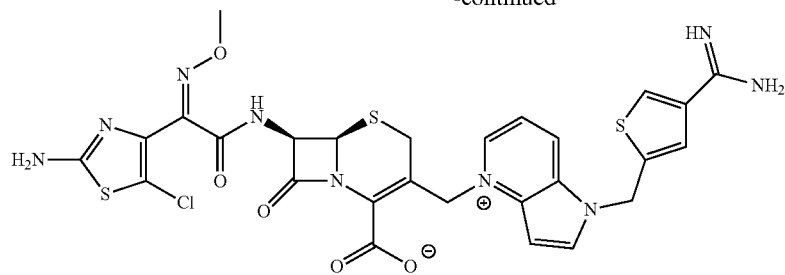
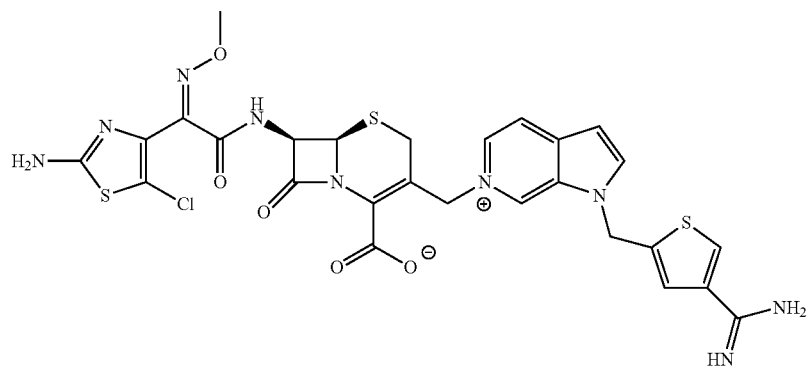
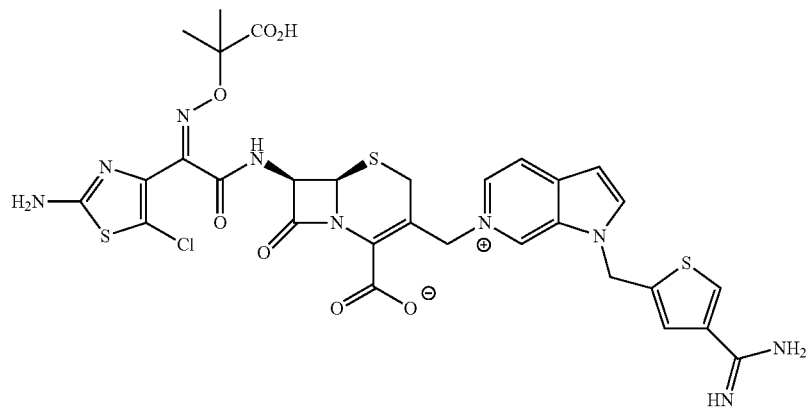
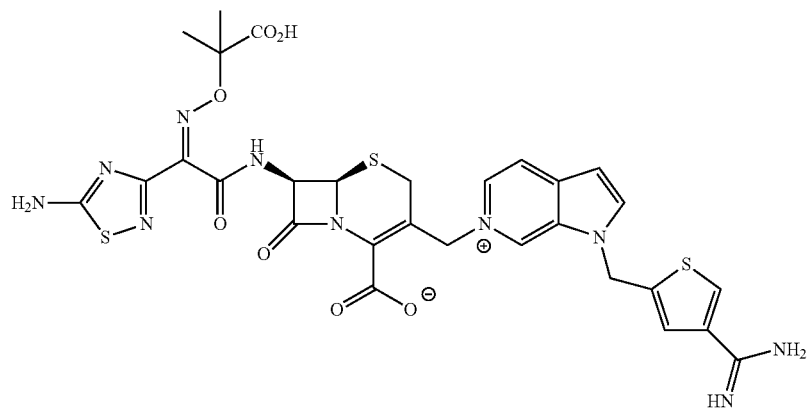

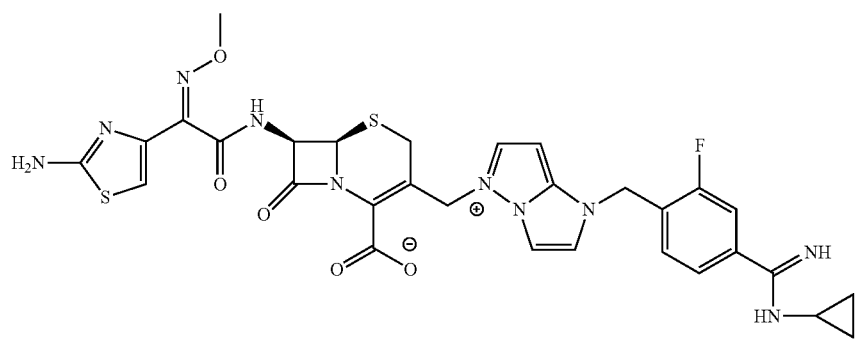
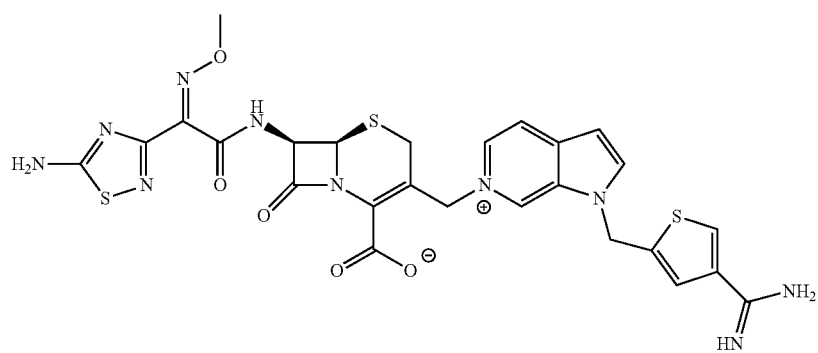
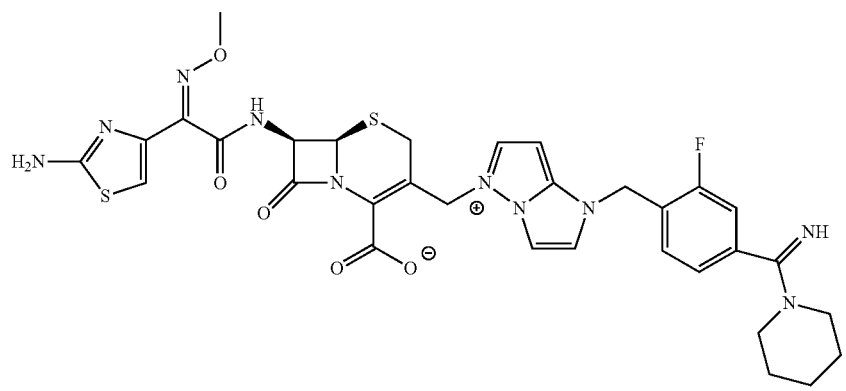
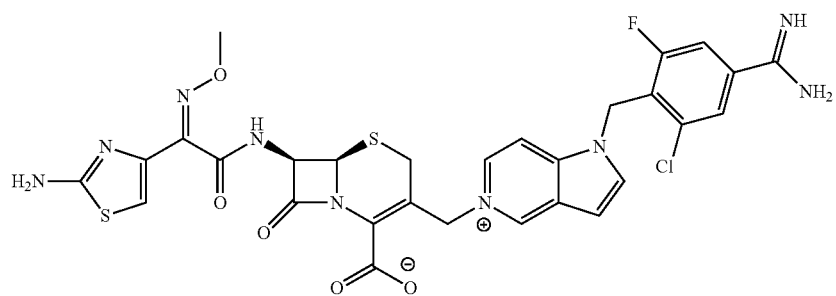
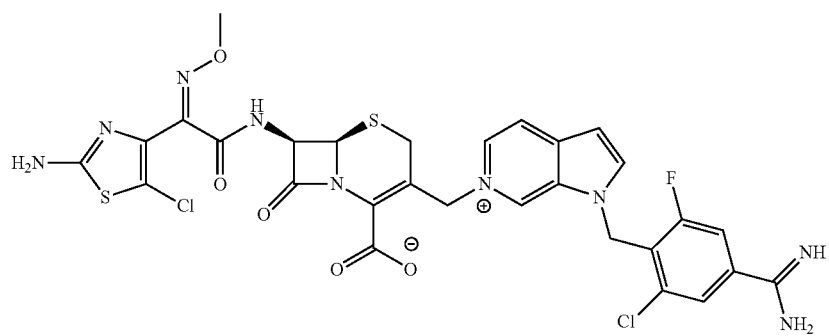

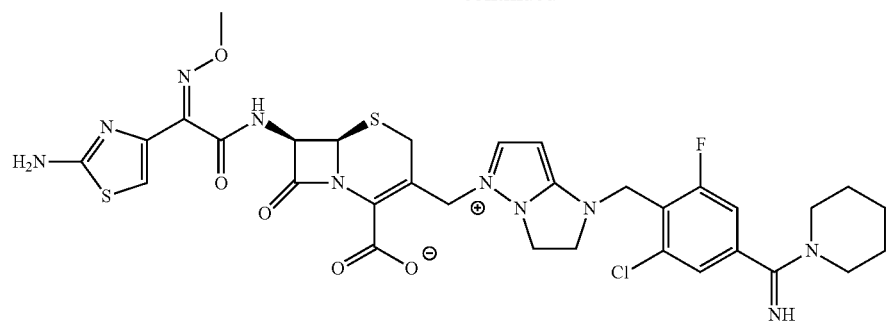
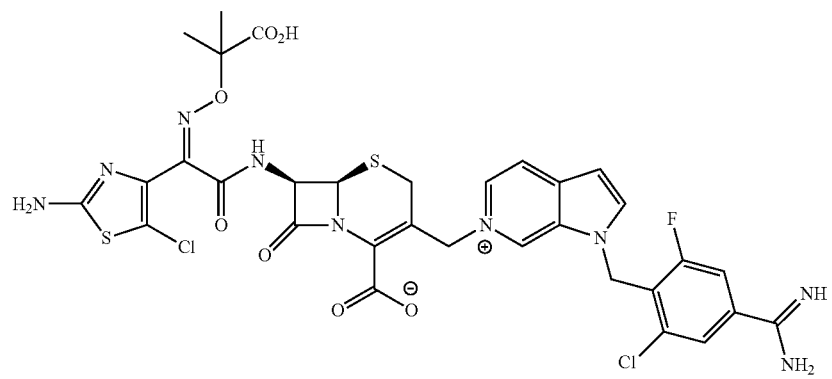
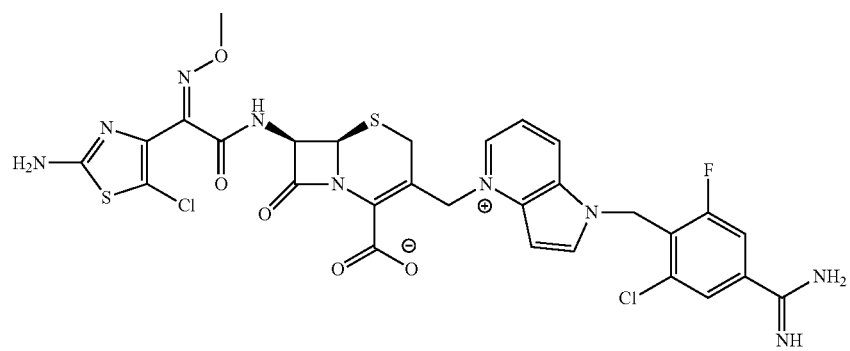
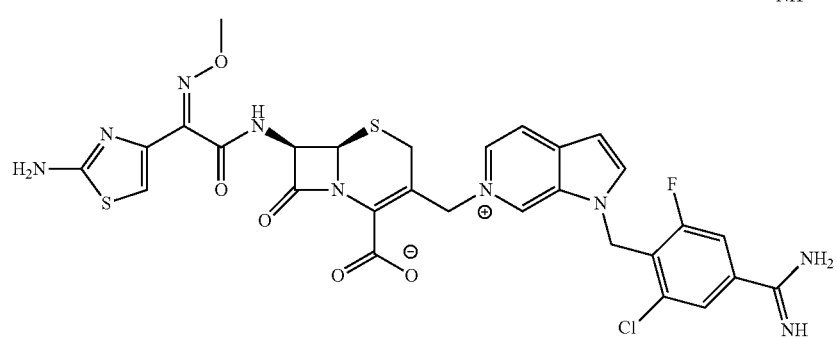
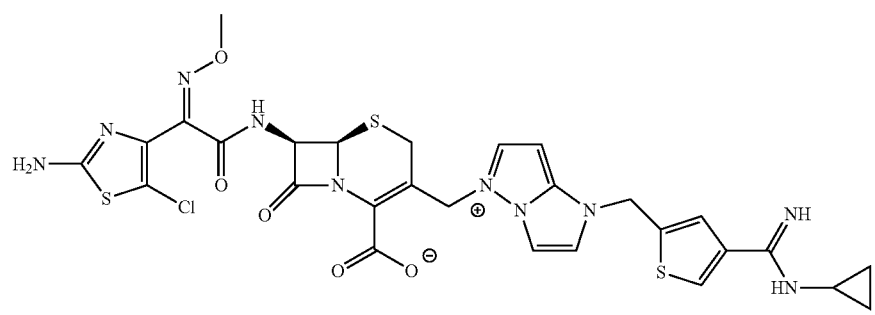

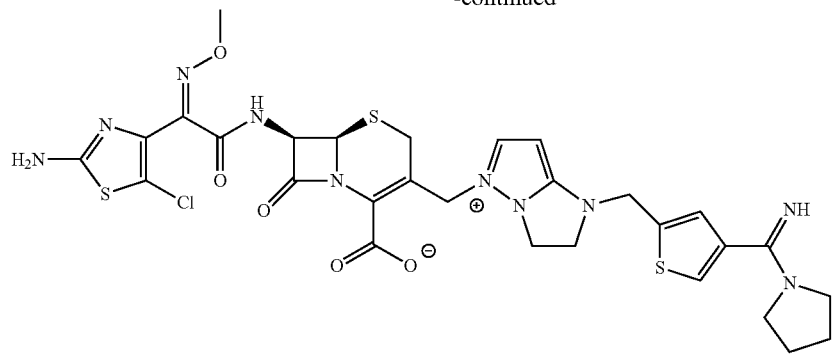
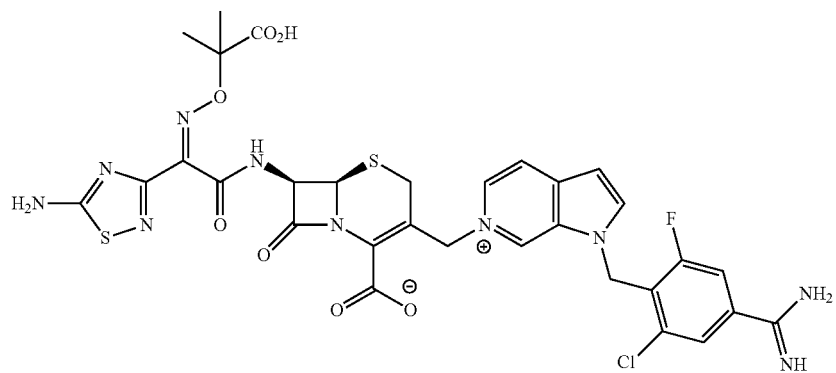
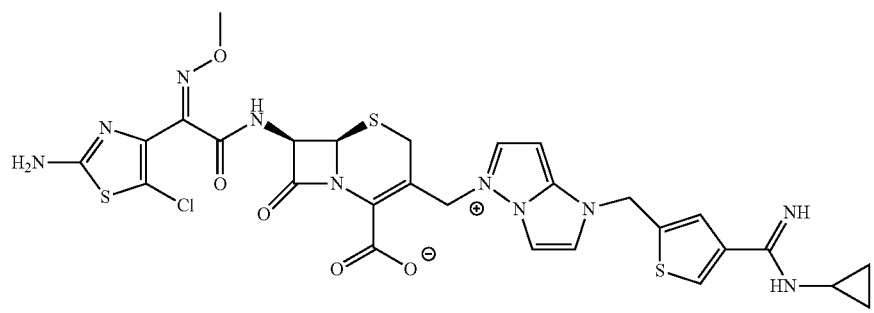
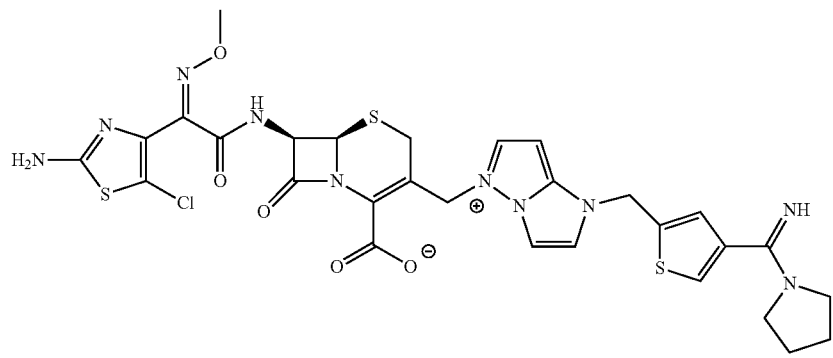

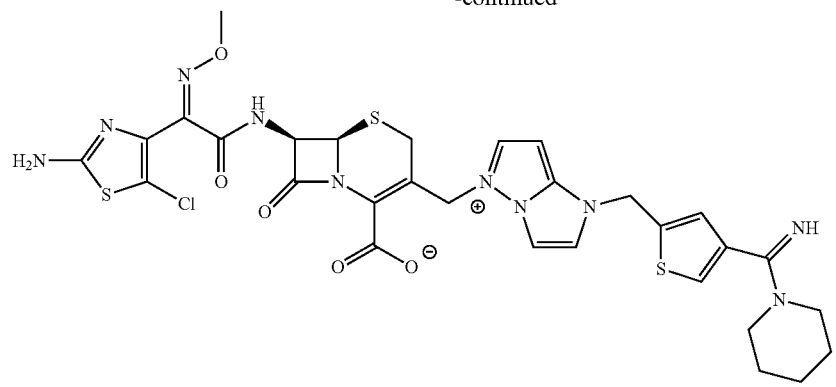
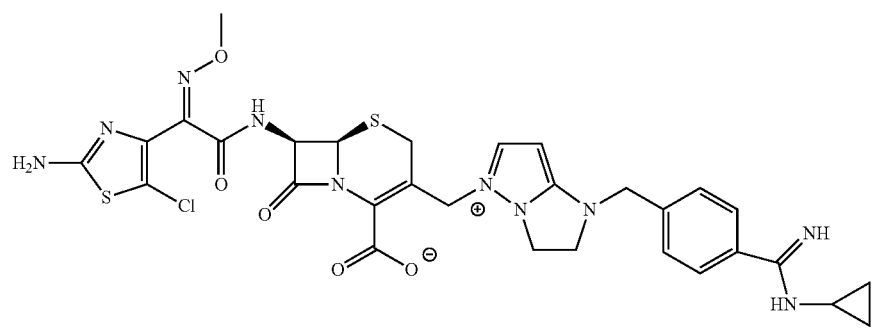
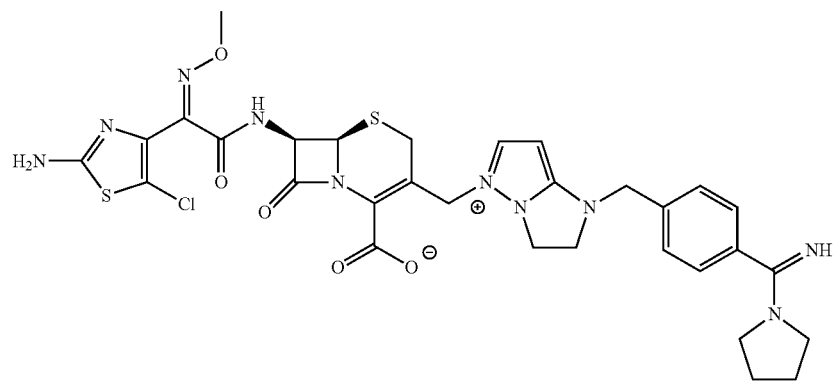
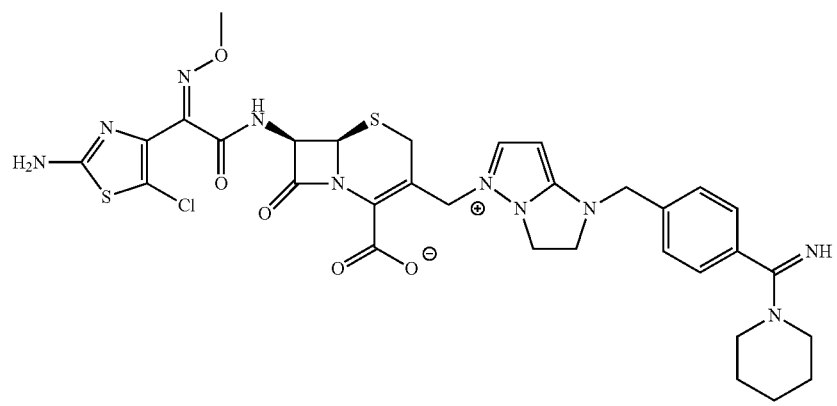

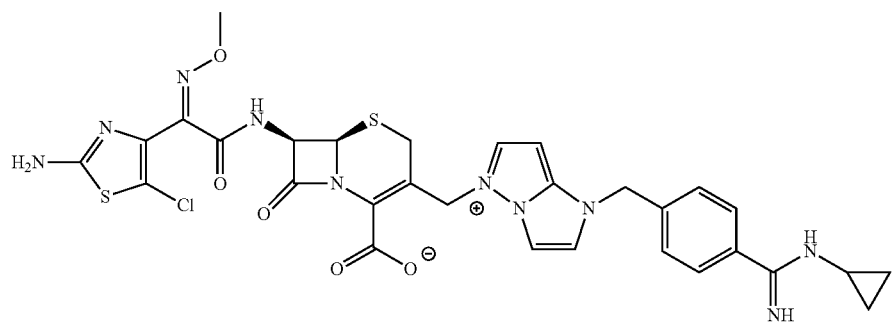
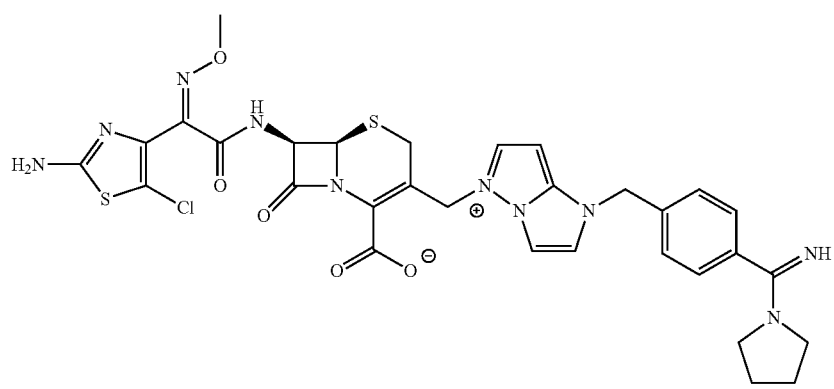
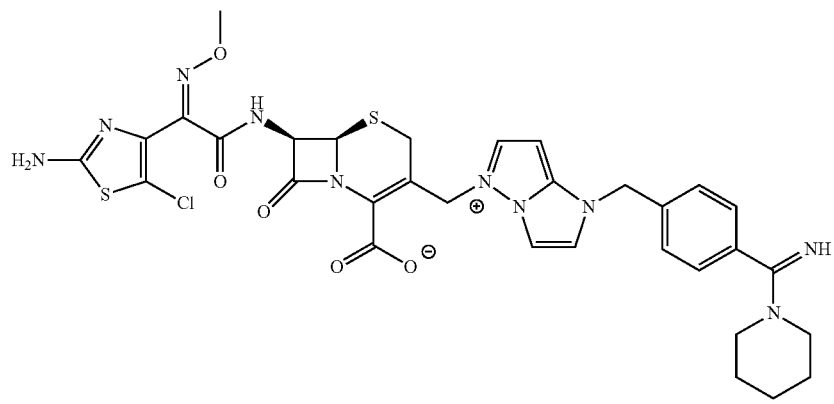
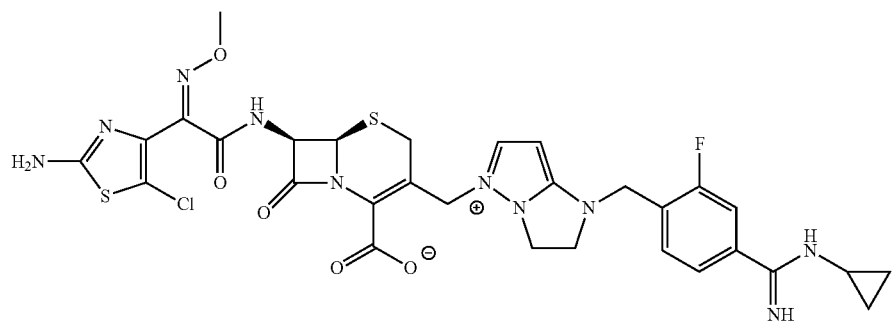

-continued
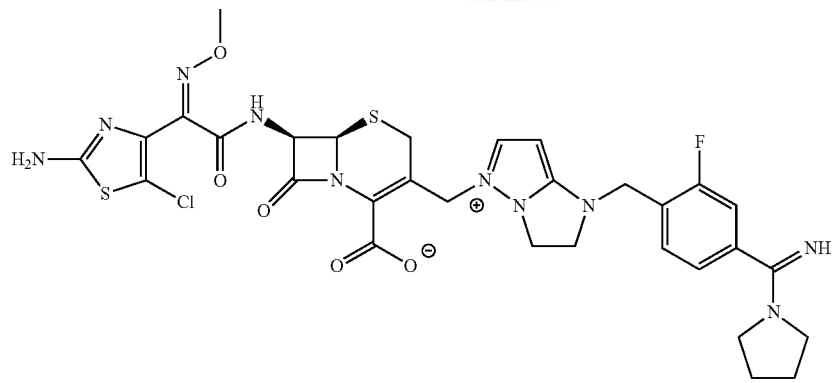
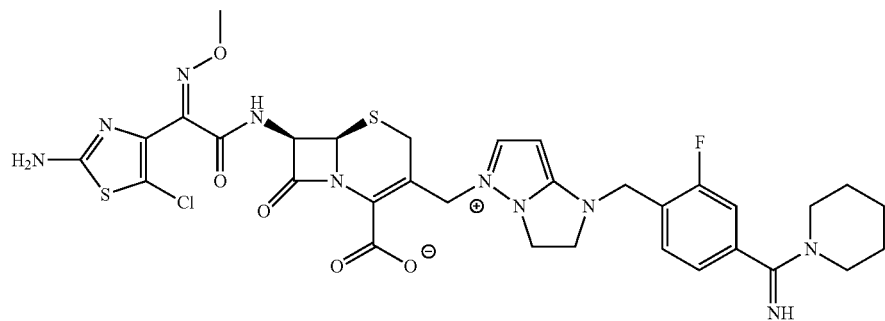
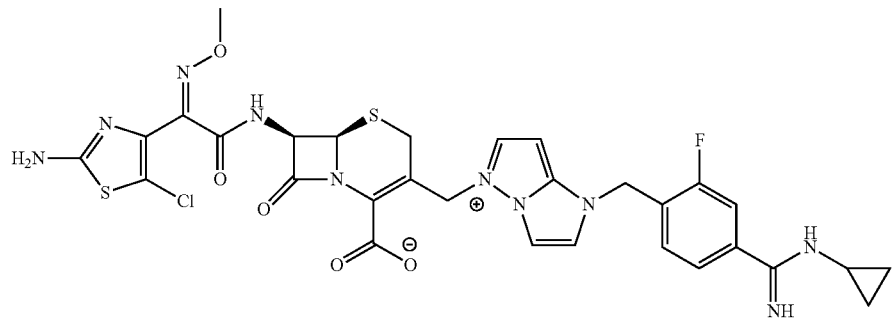
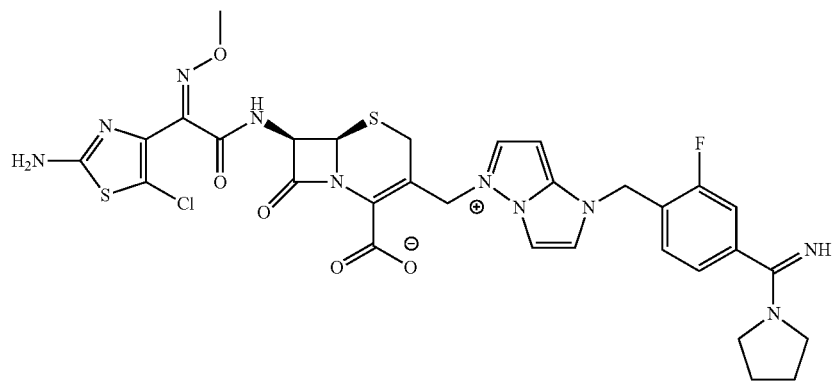

-continued
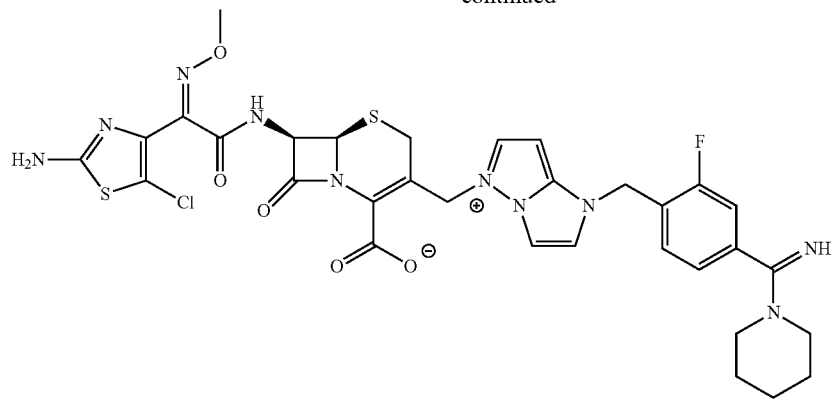
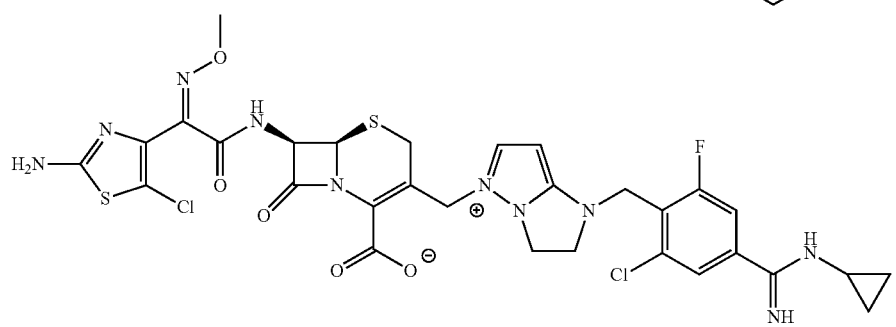
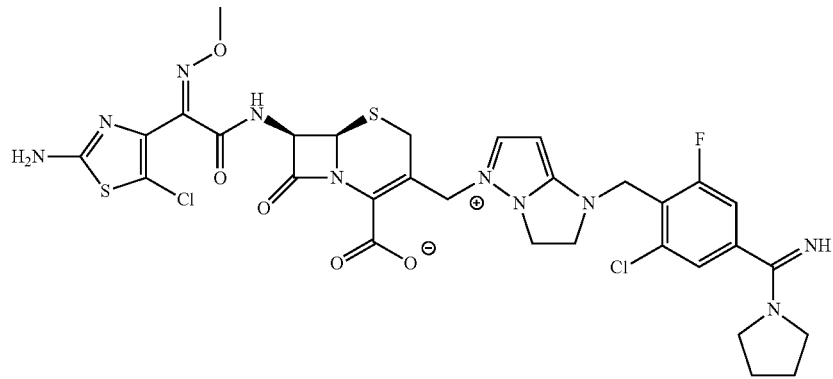
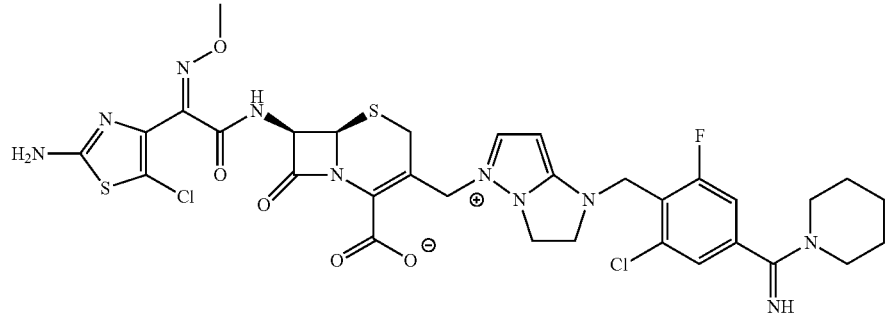
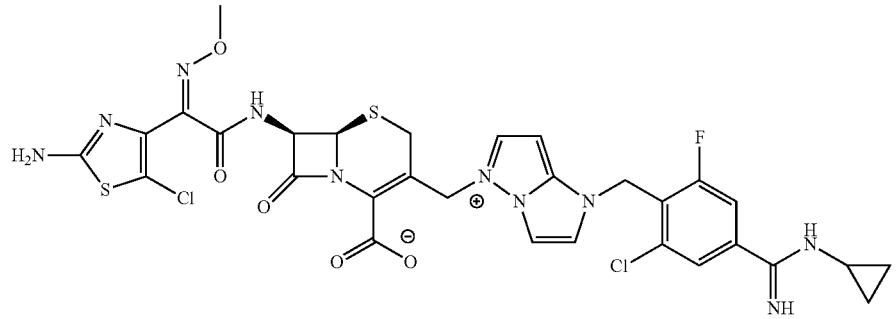

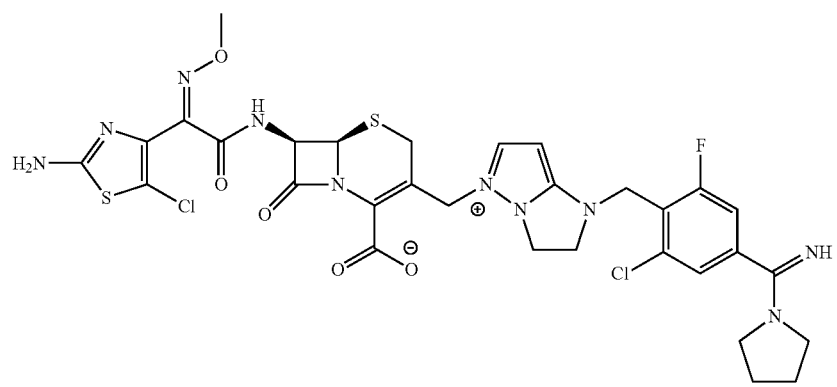
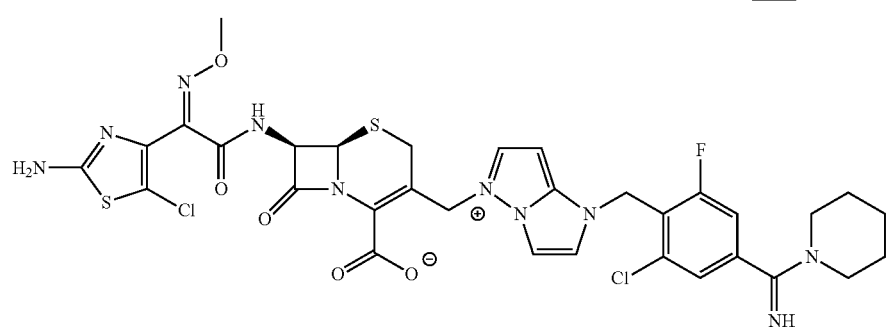
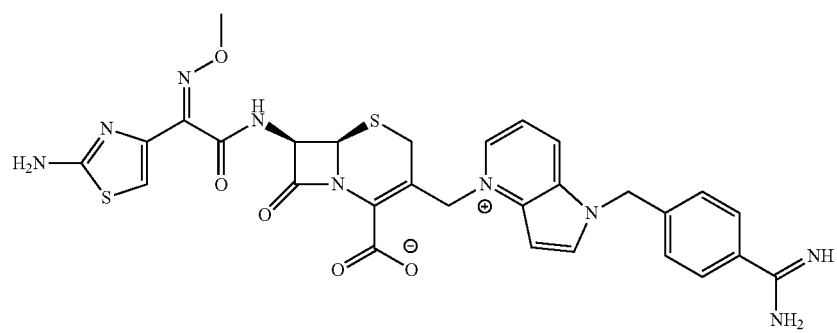
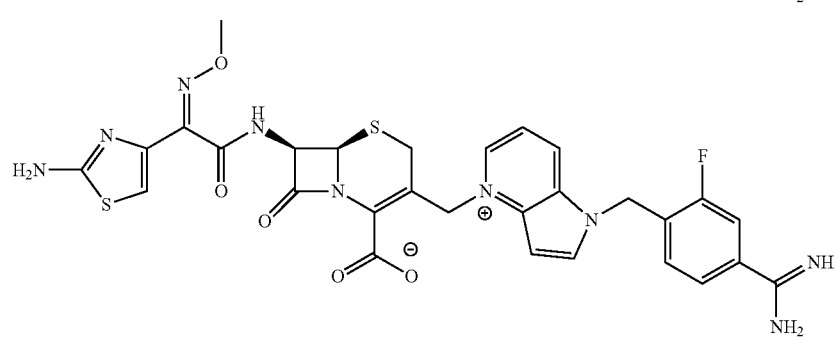
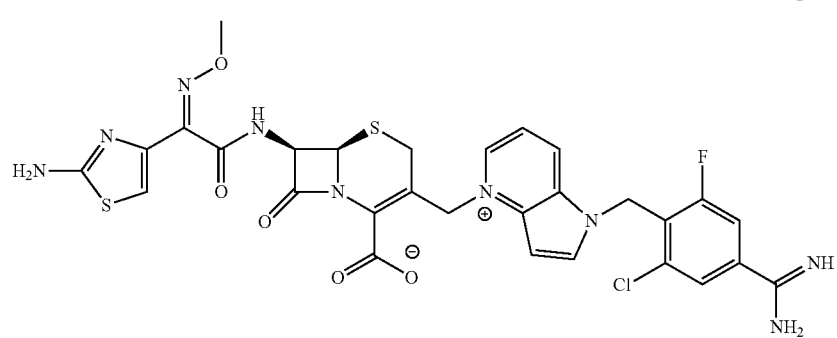

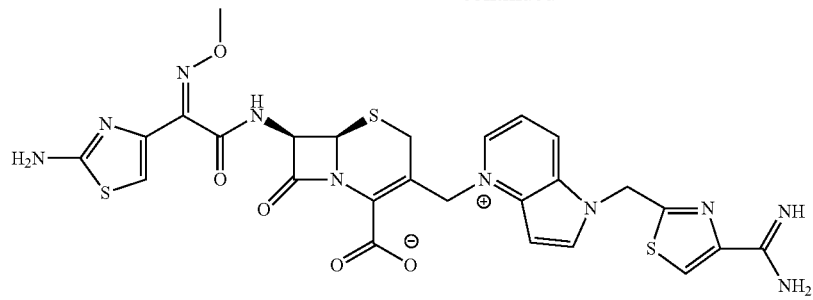
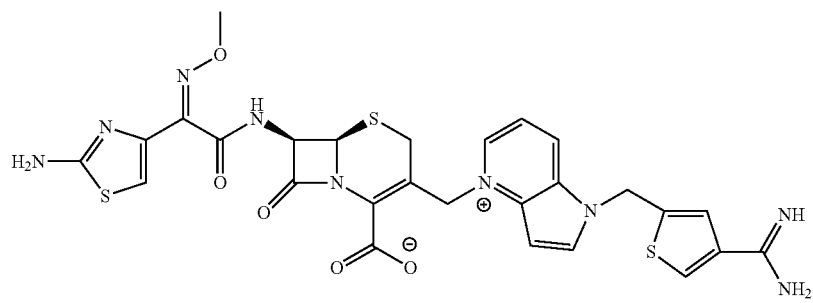
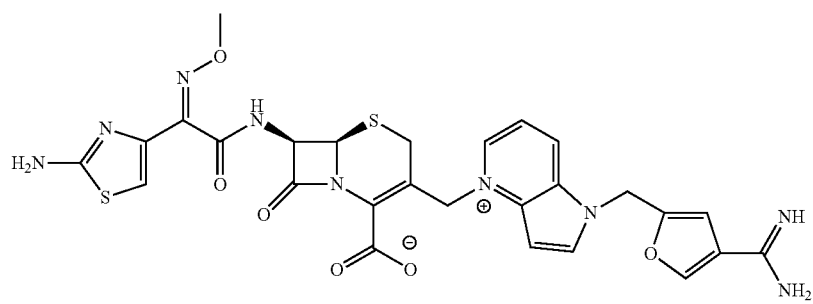
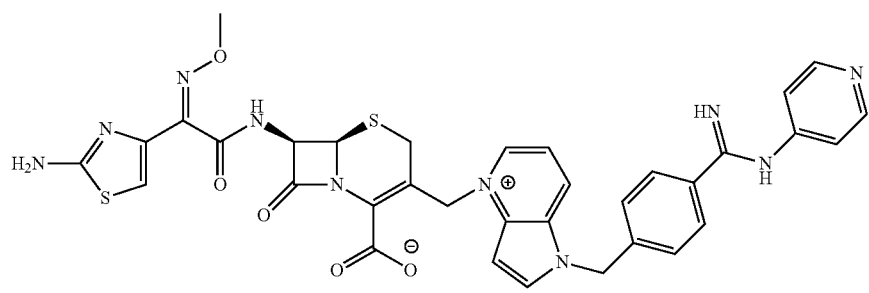
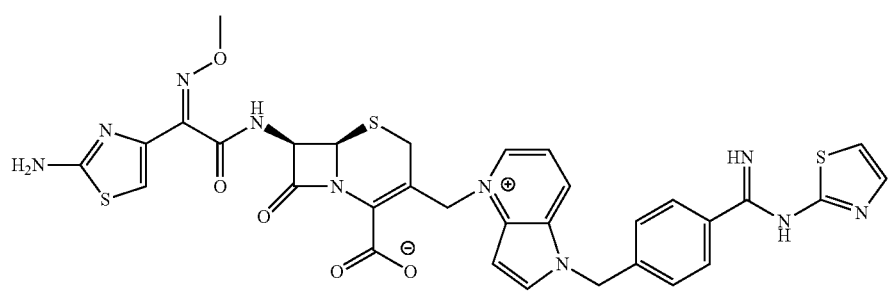

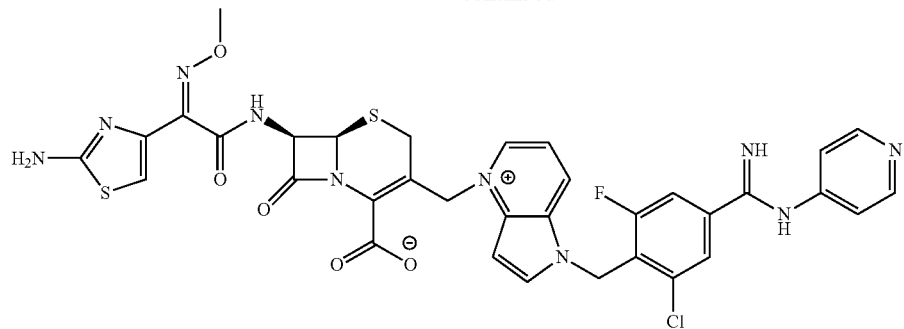
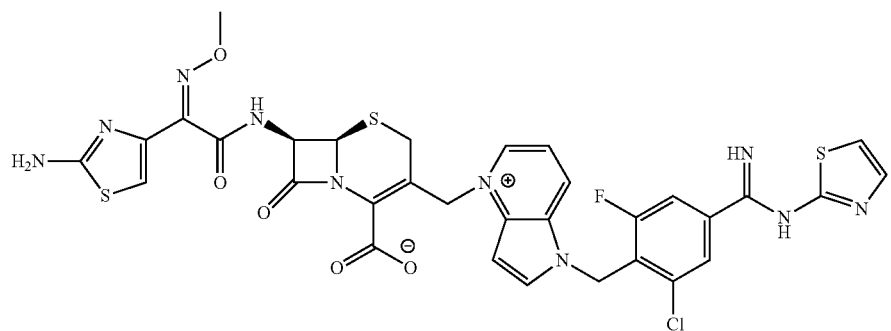
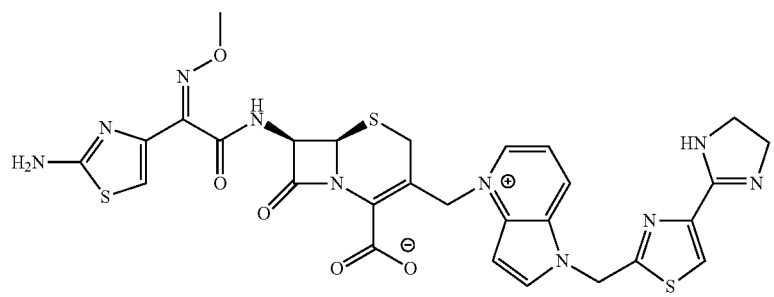
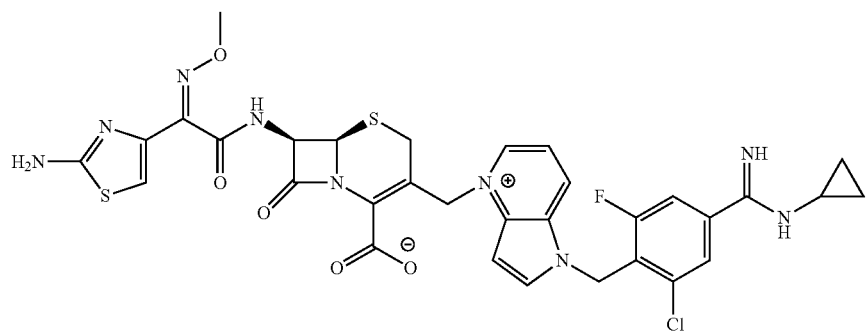
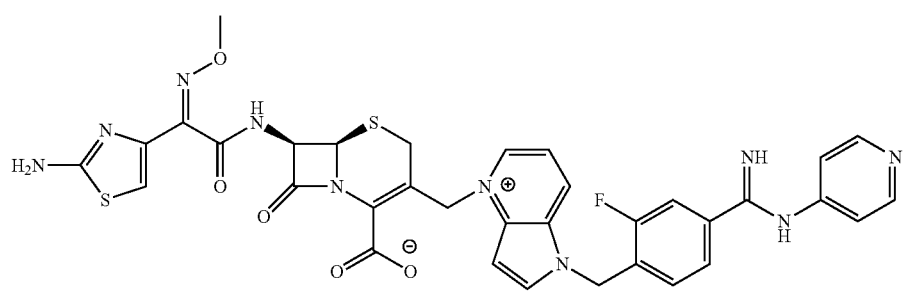

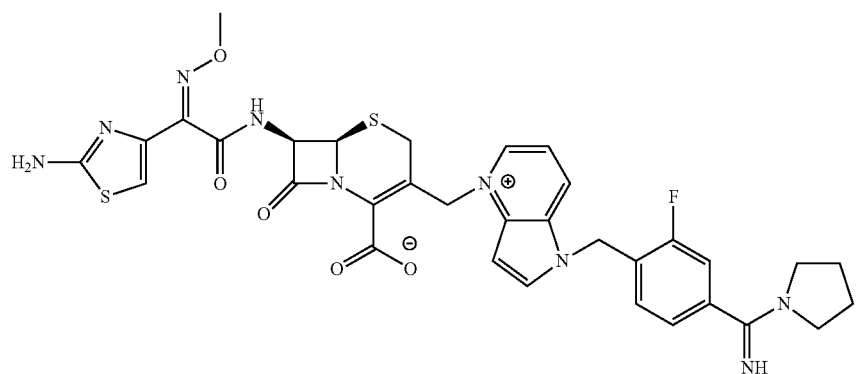
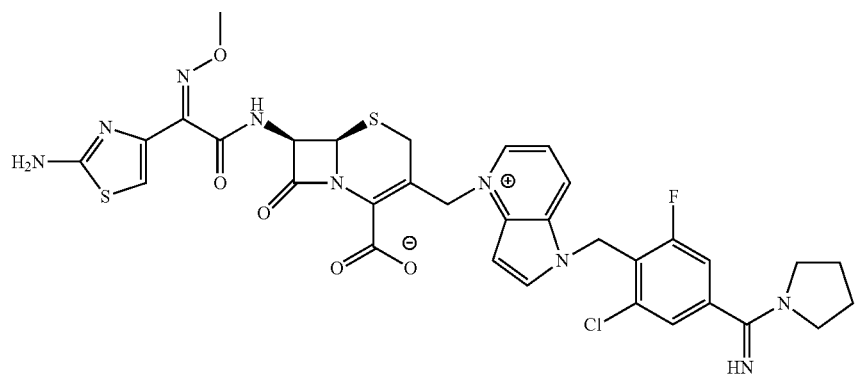
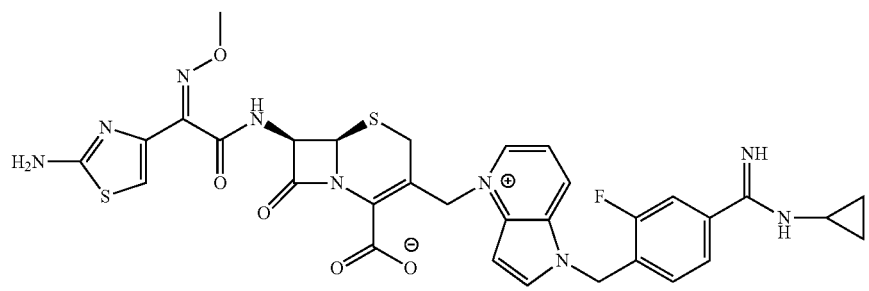
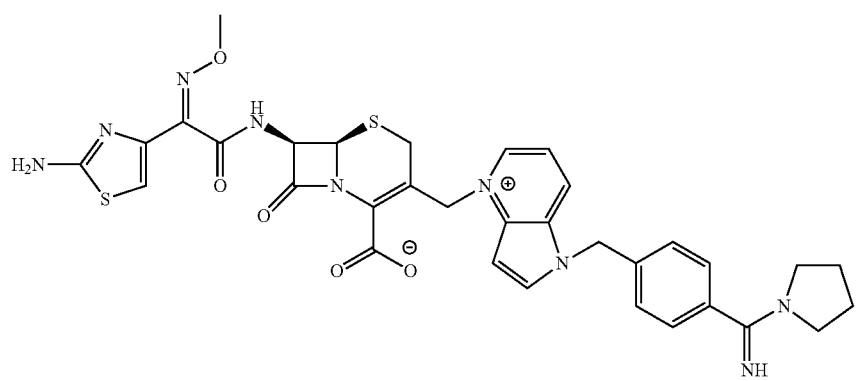

-continued
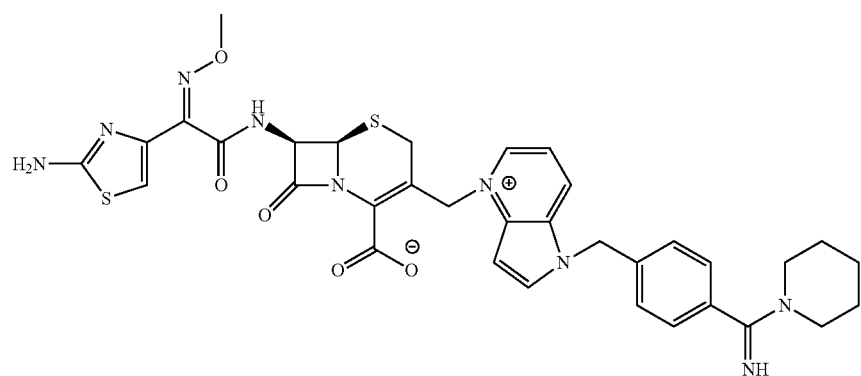
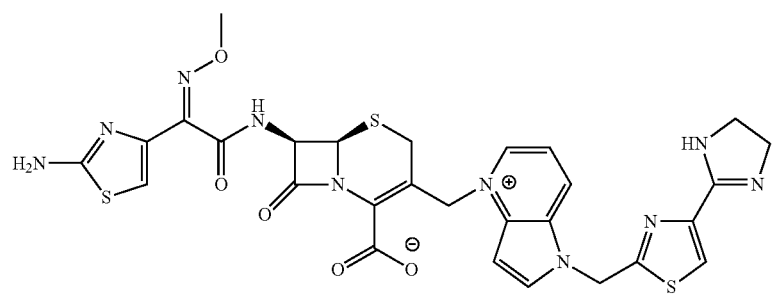
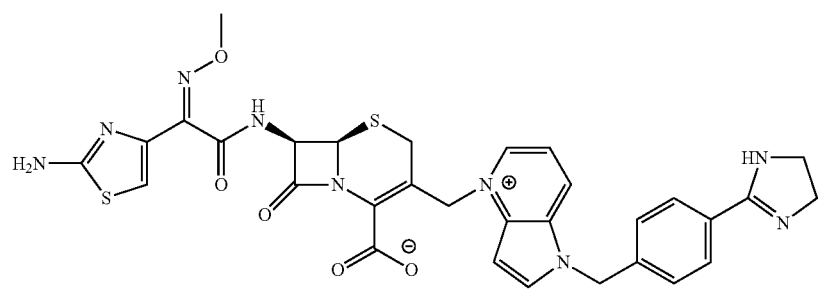
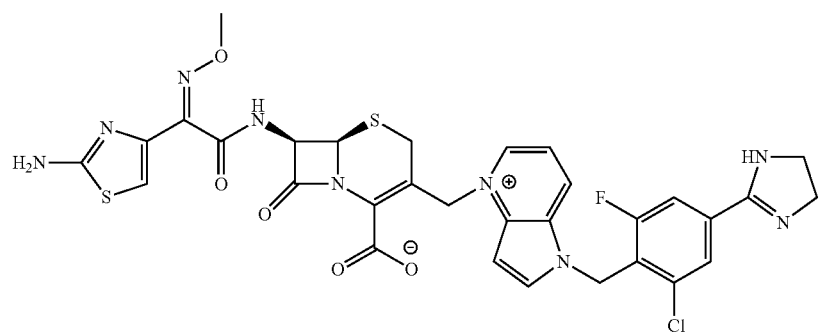
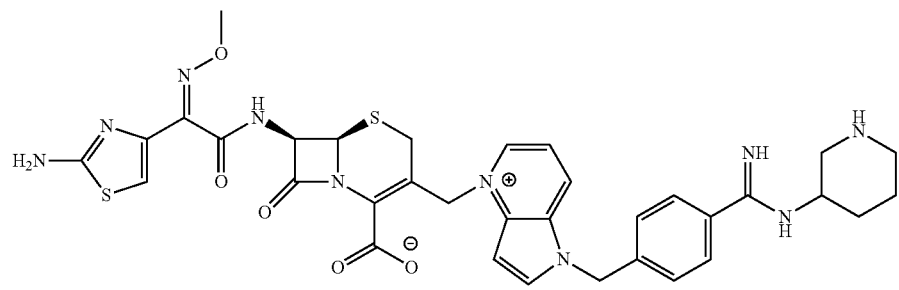

-continued
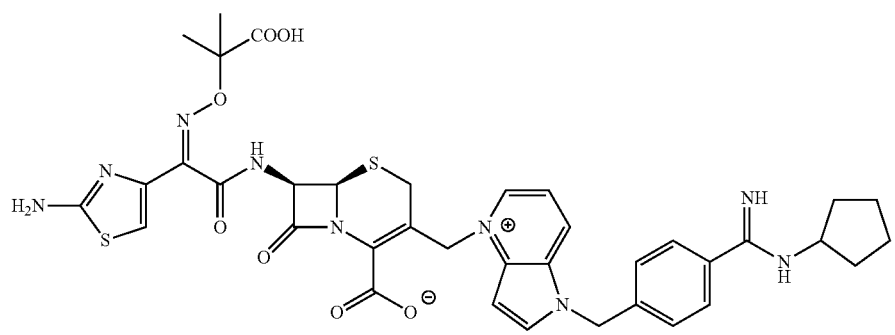
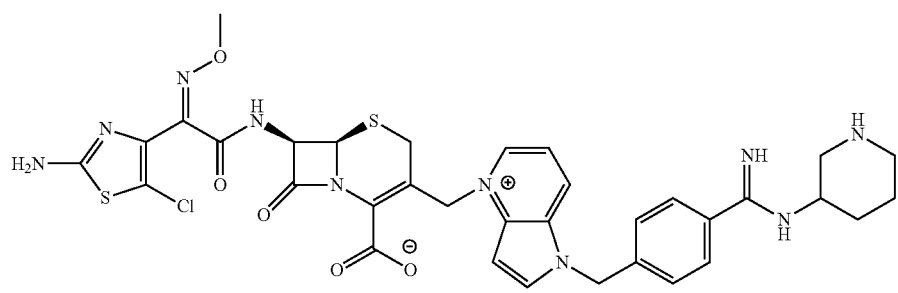
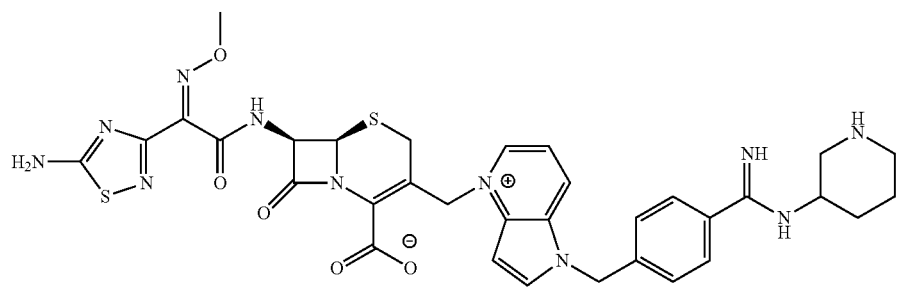
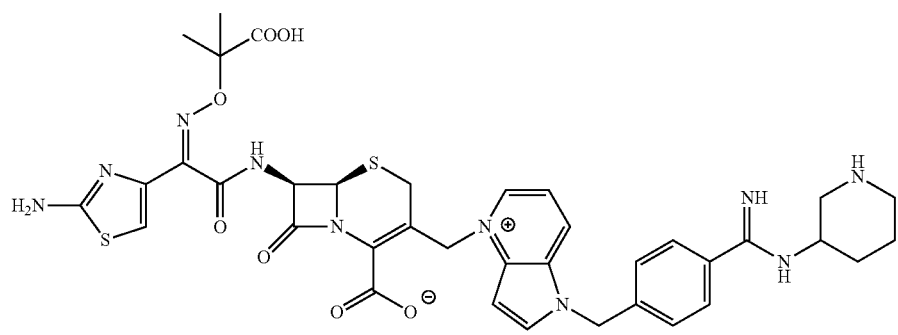
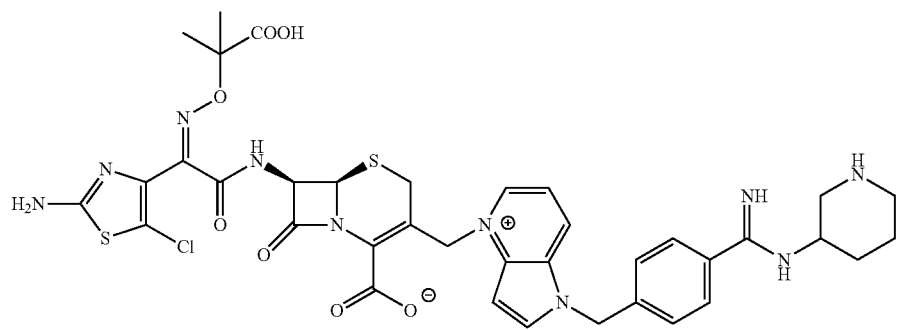

-continued
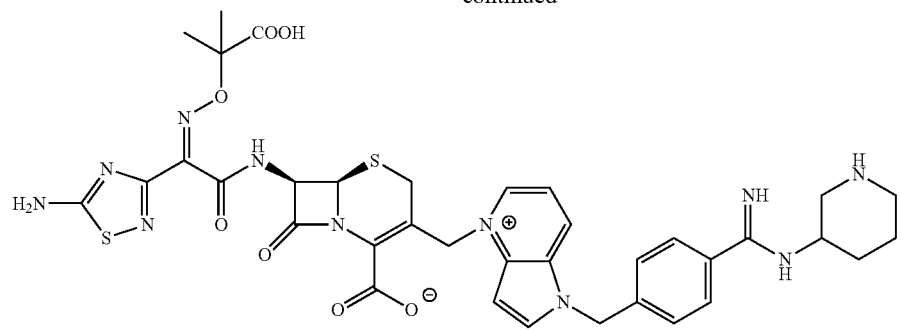
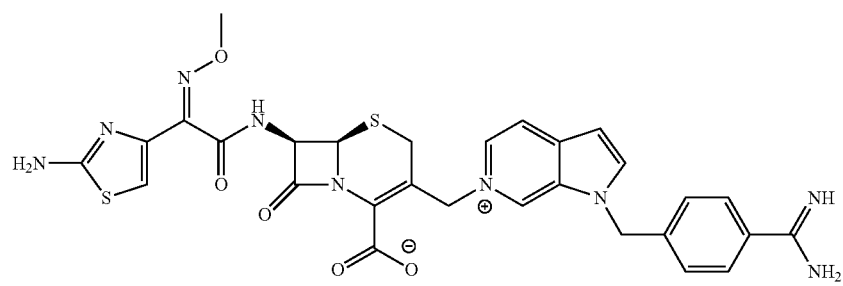
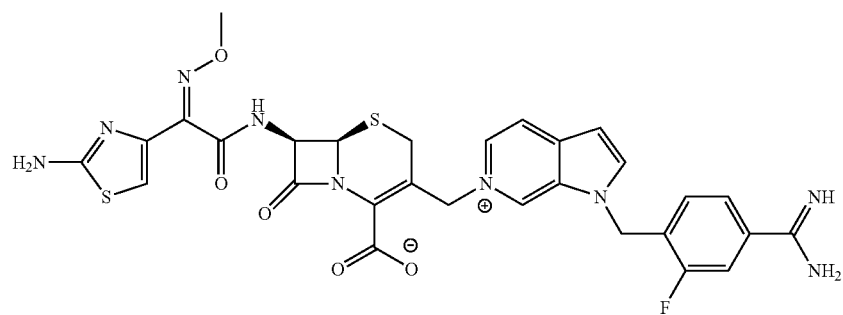
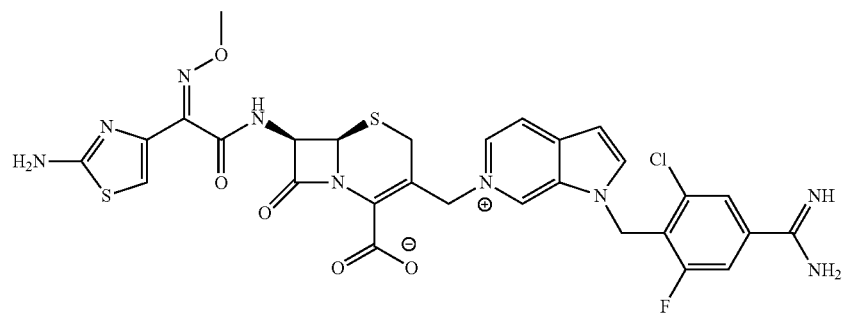
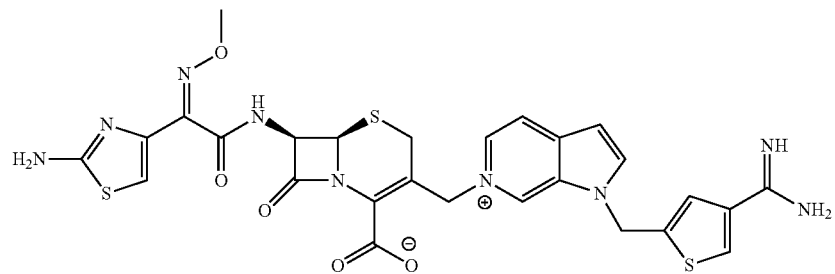

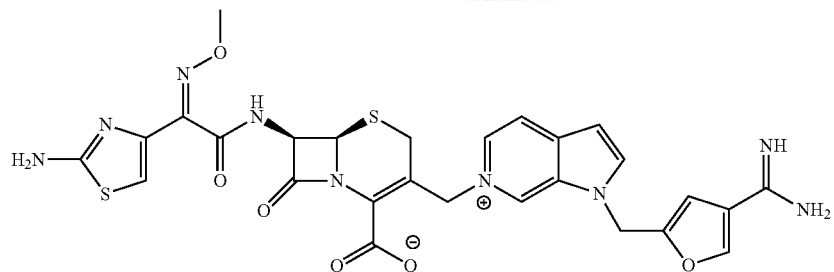
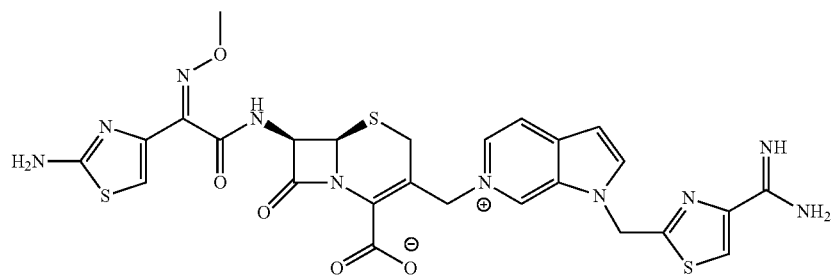
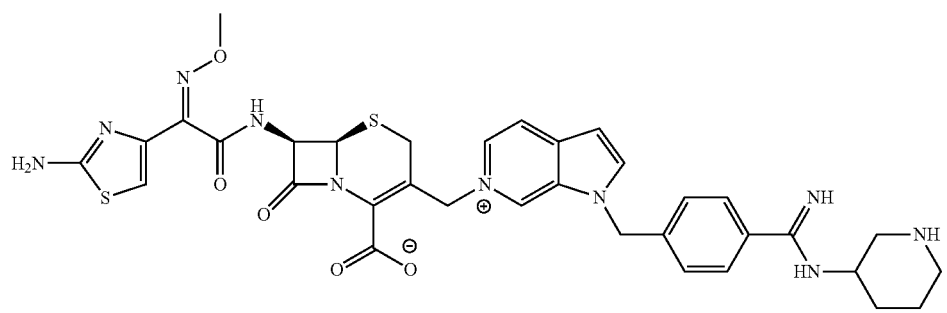
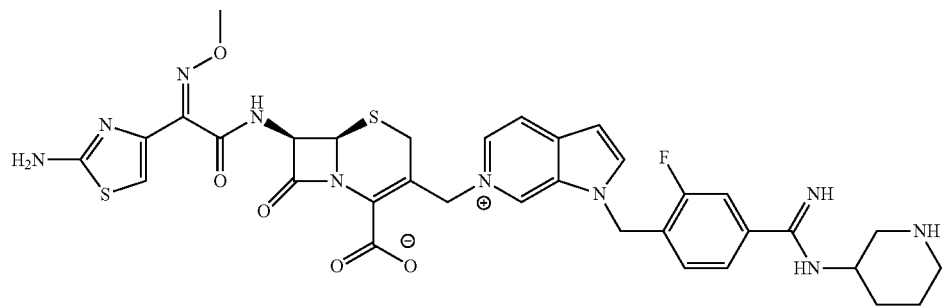
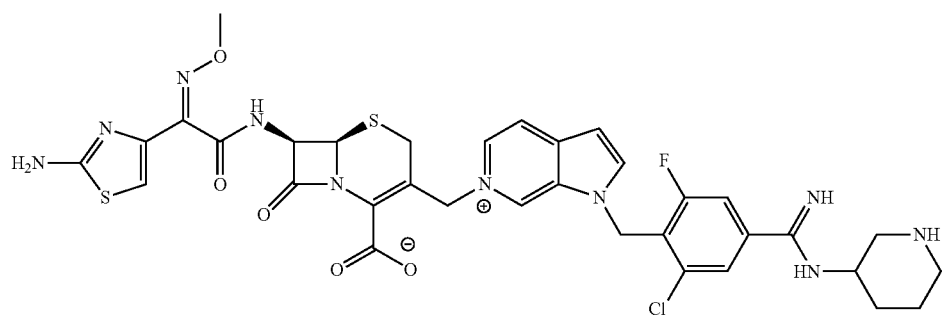

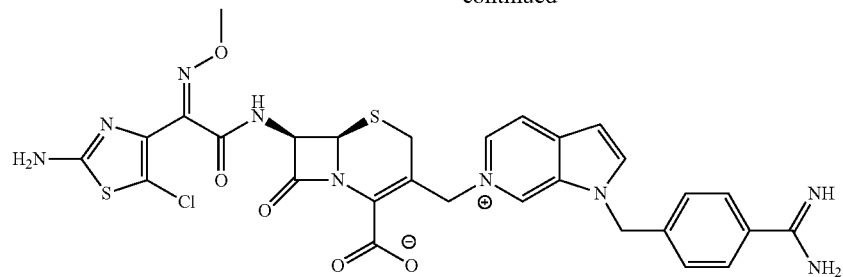
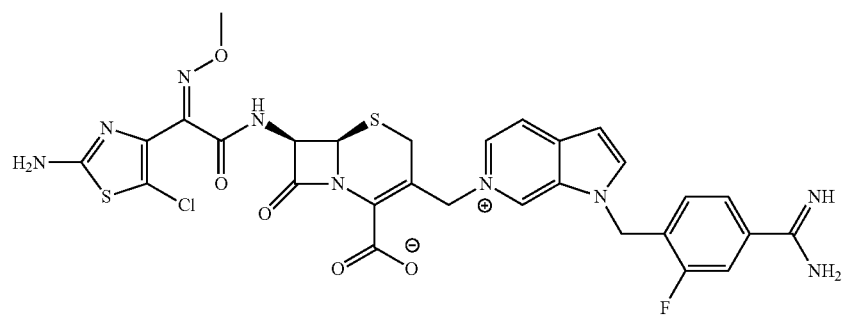
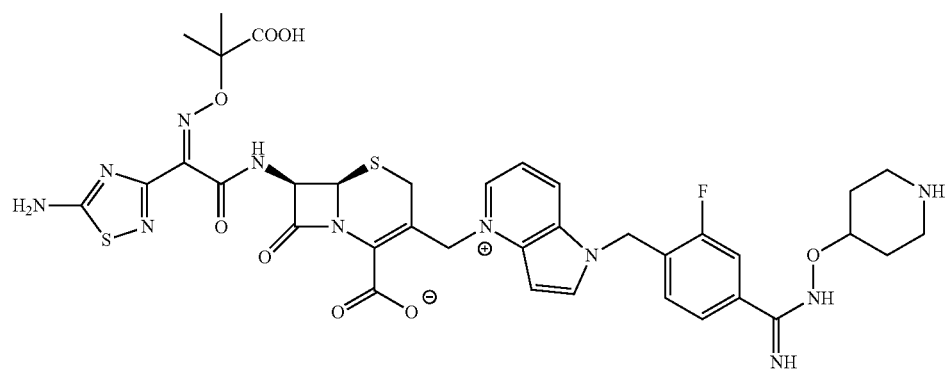
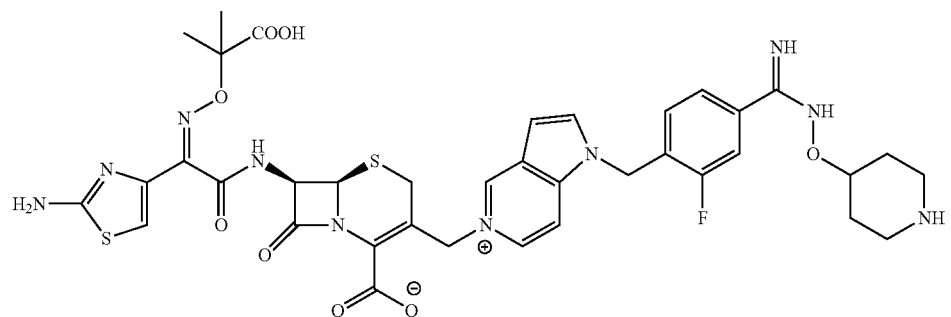
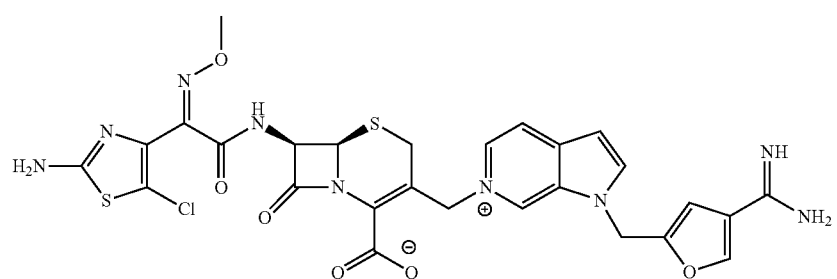

-continued
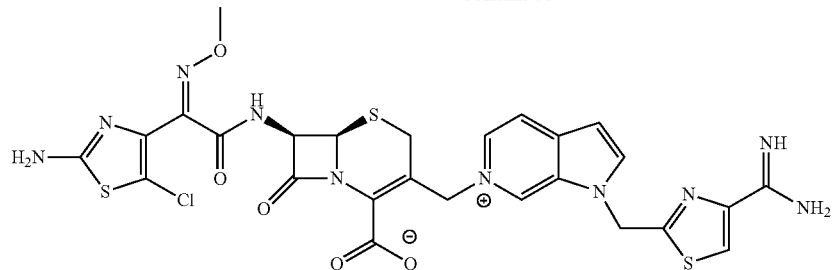
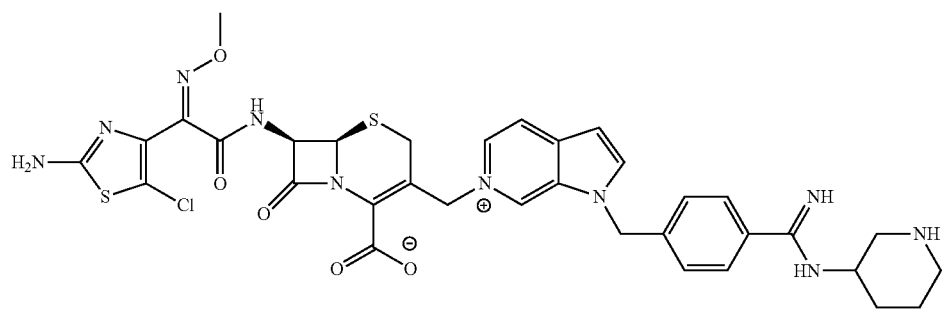
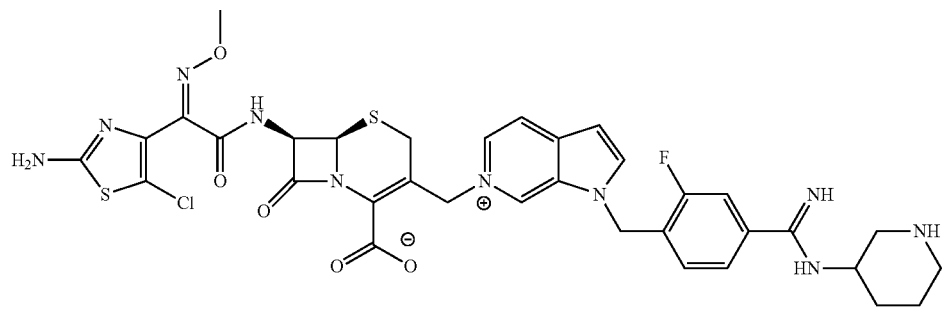
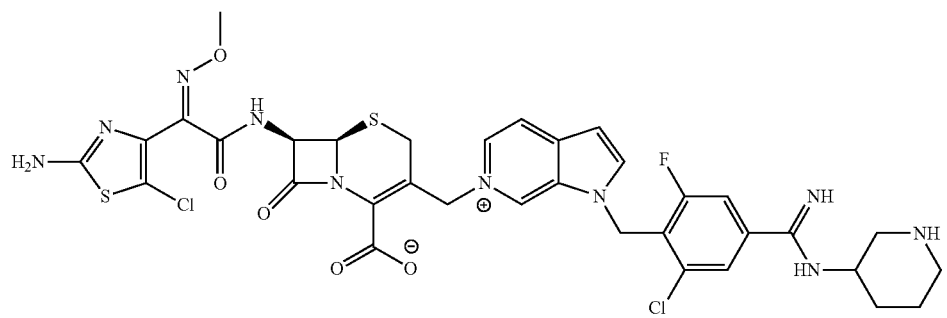
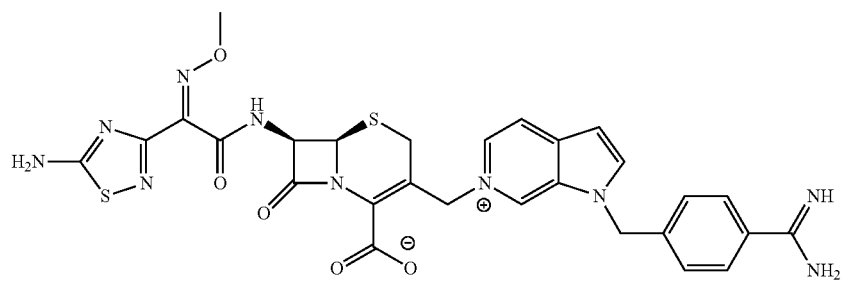

-continued
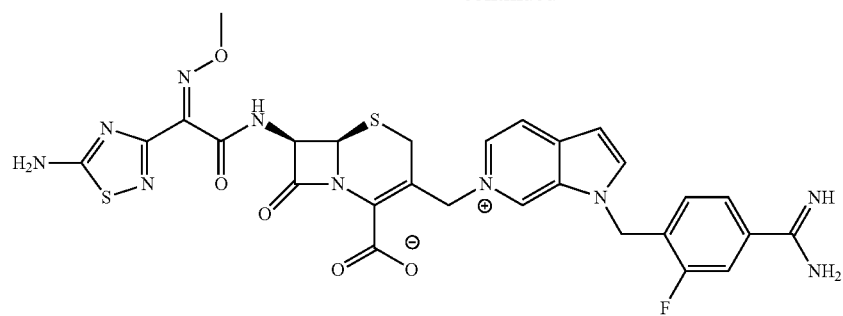
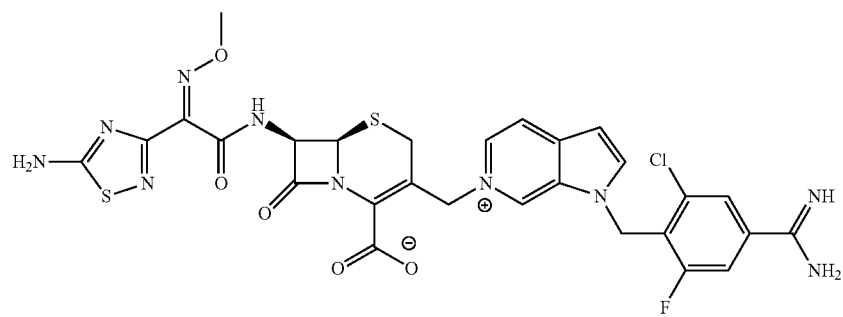
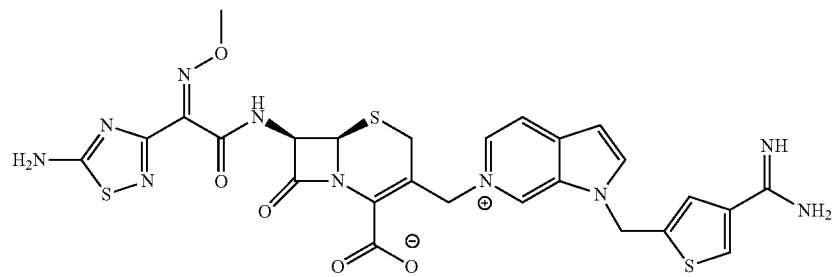
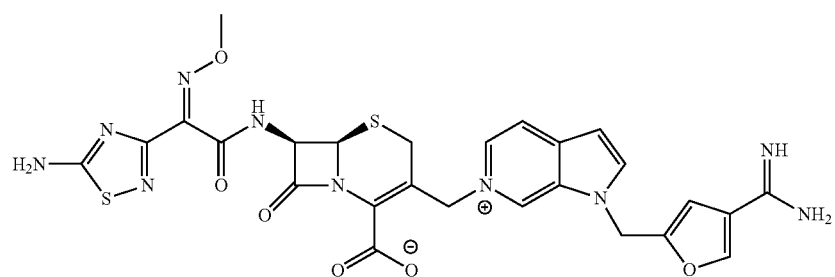
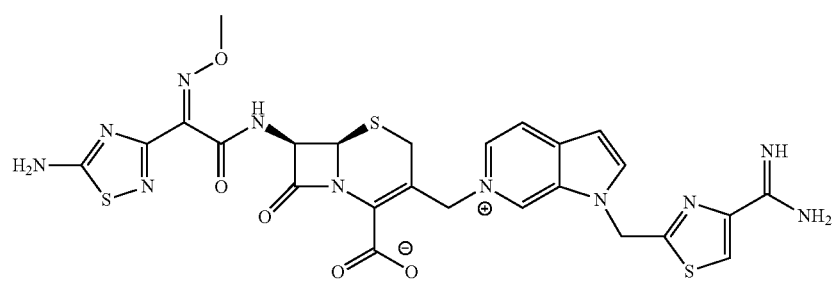

-continued
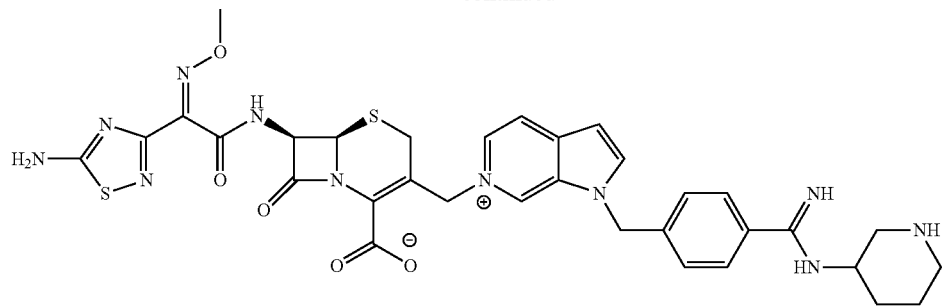
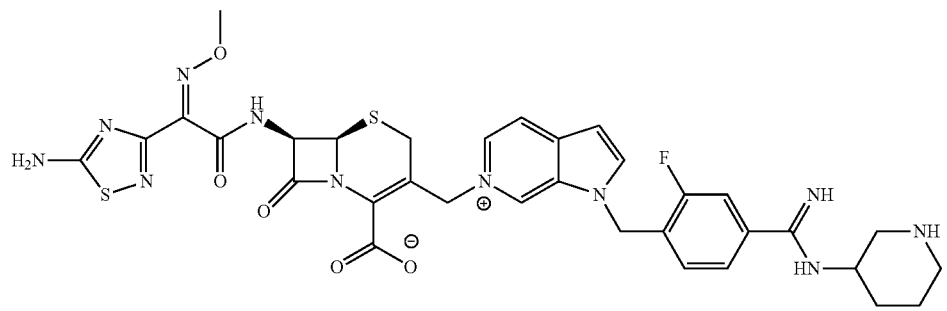
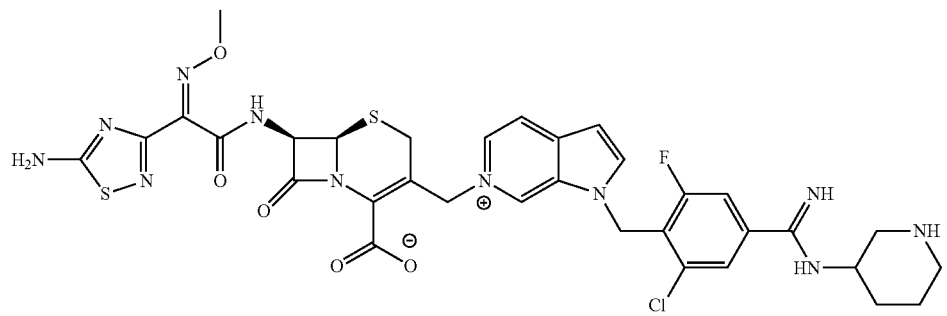
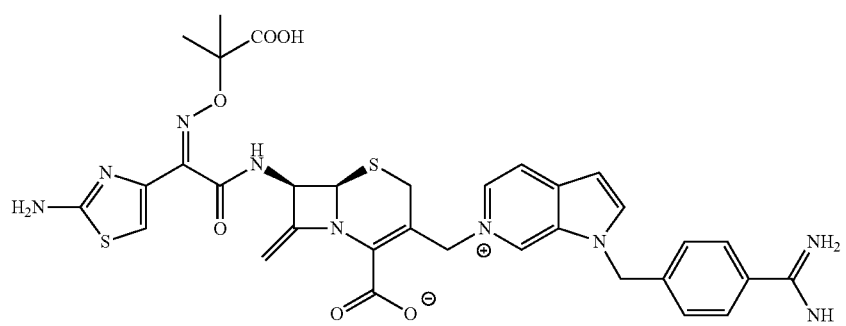
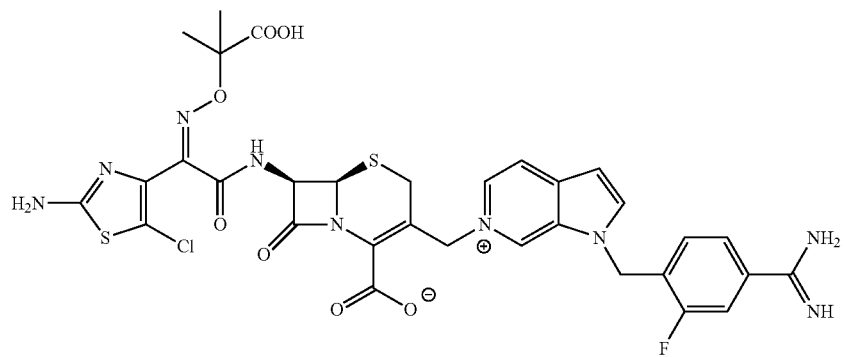

-continued
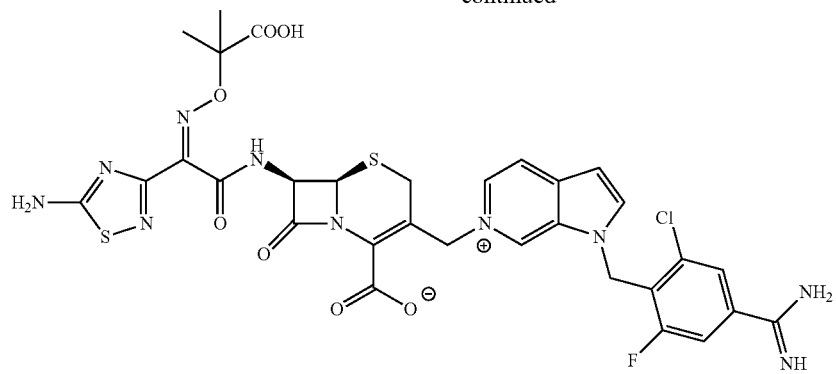
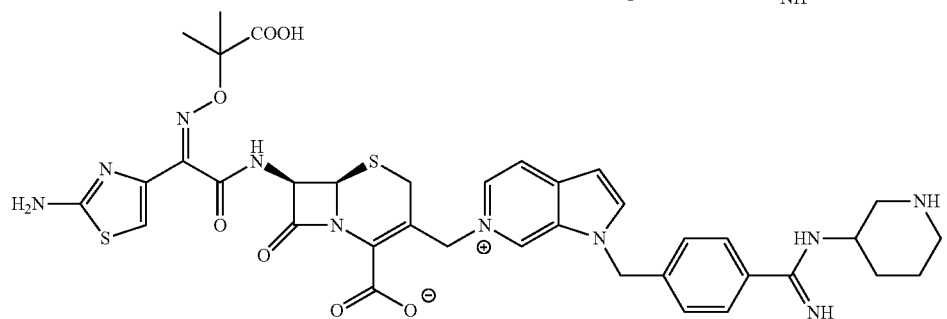
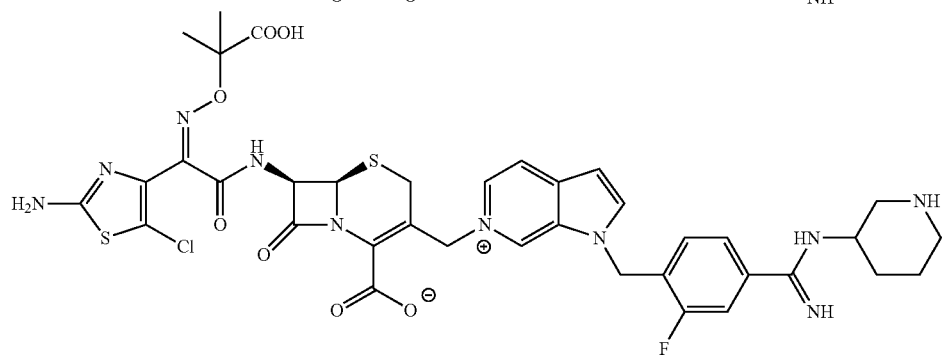
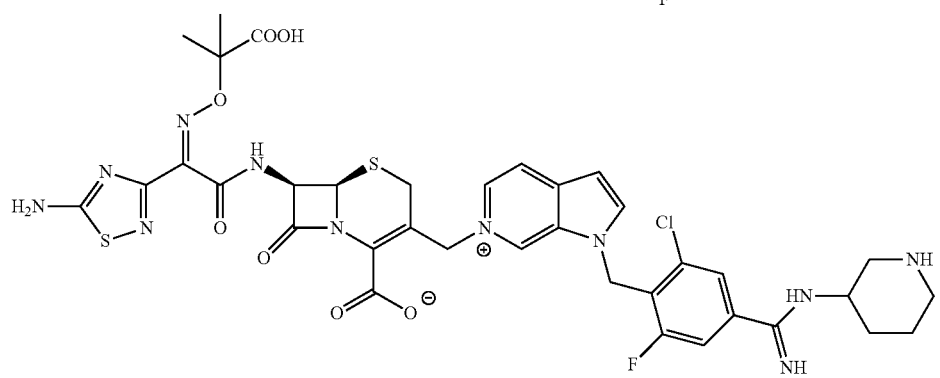
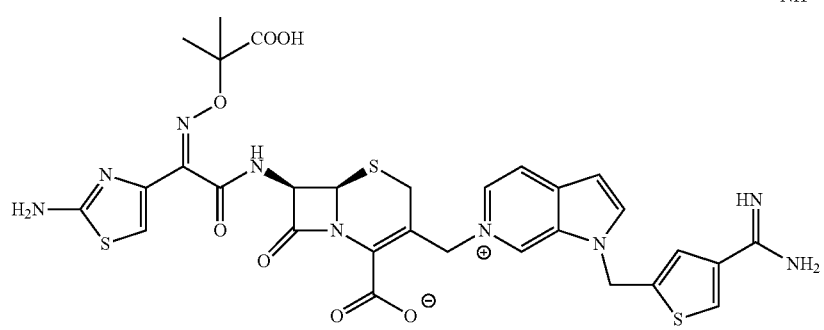

-continued
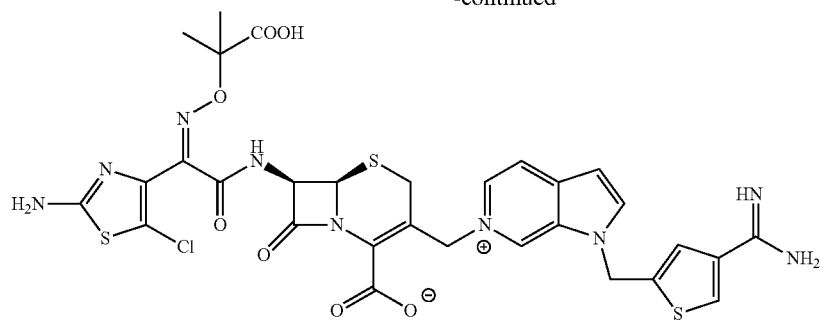
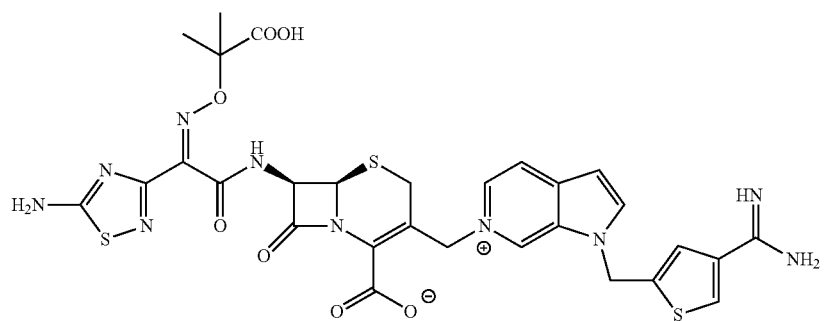
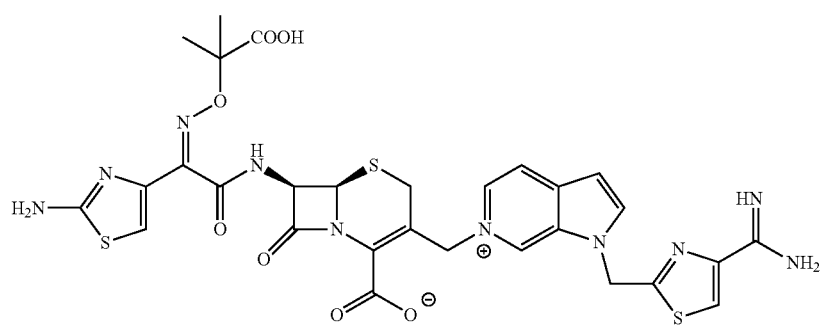
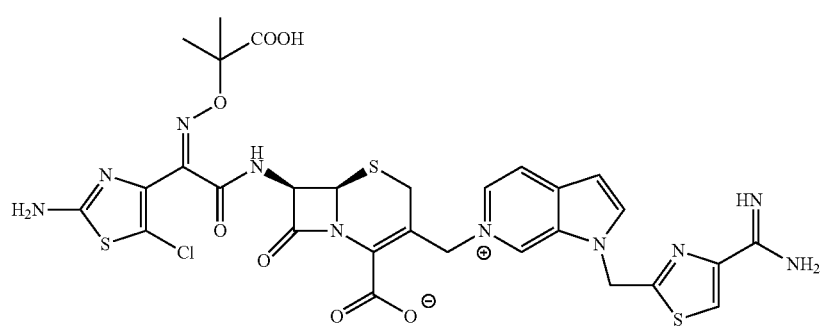
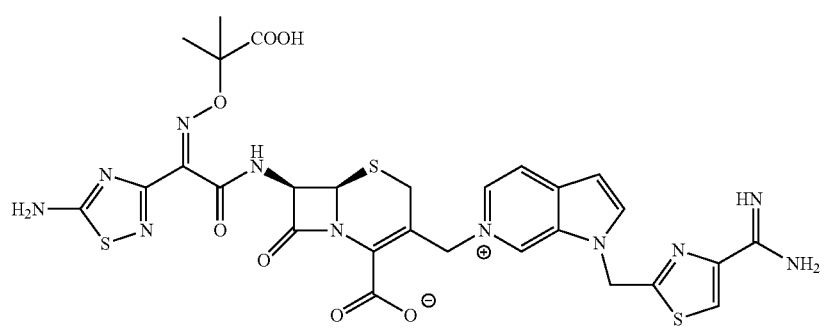

-continued
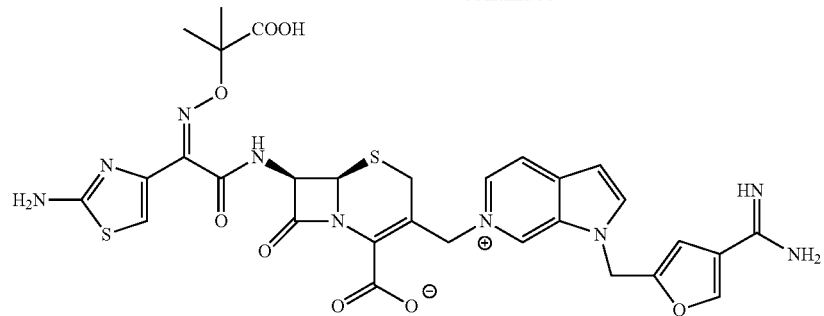
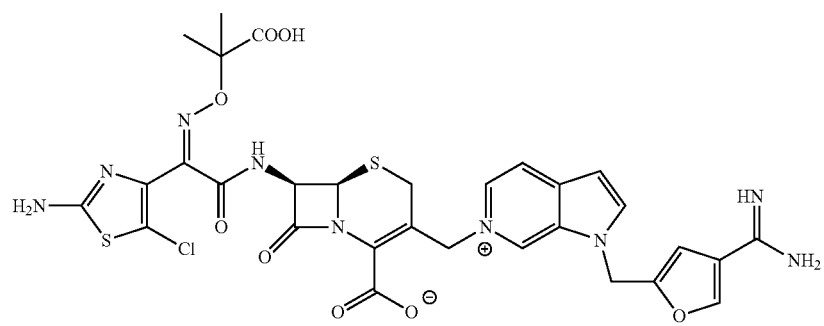
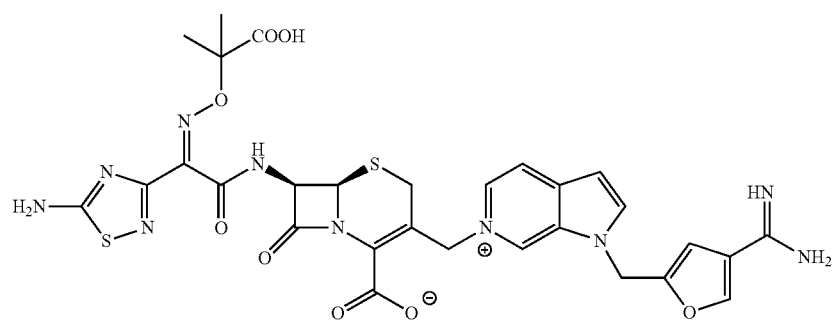
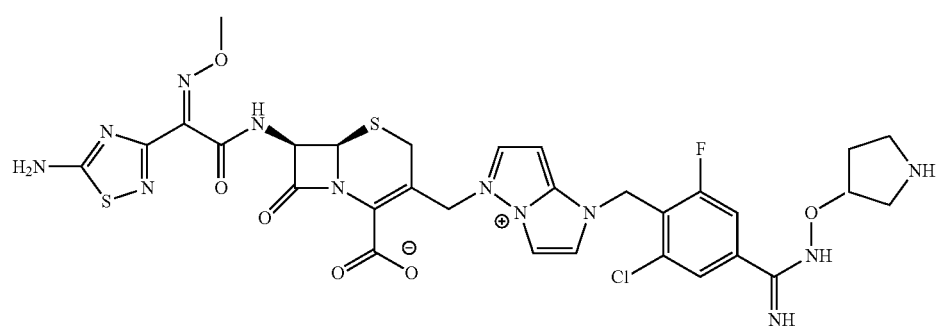
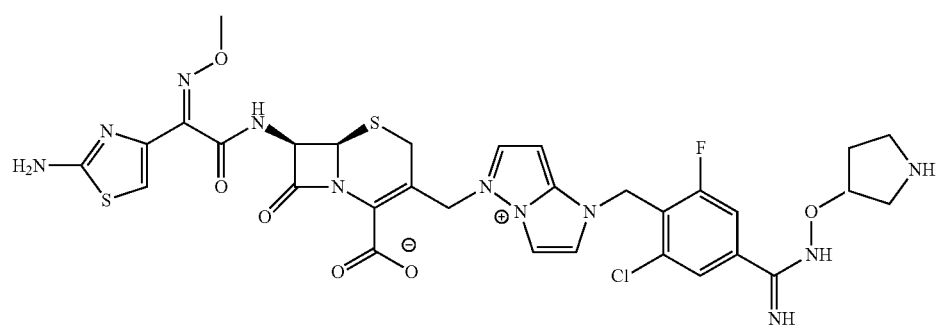

-continued
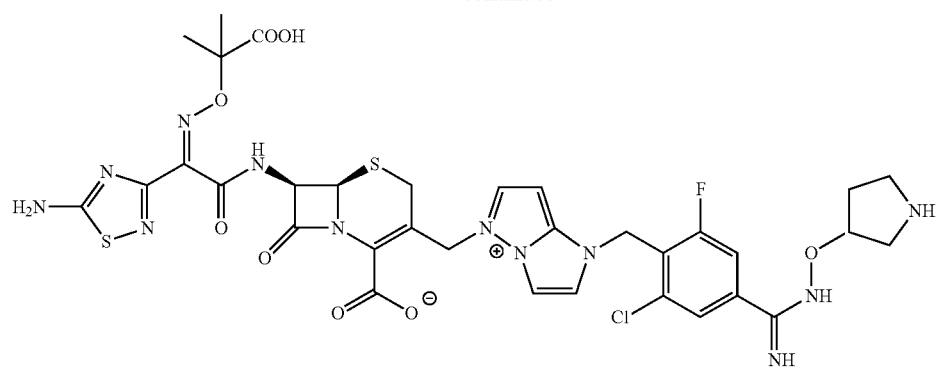
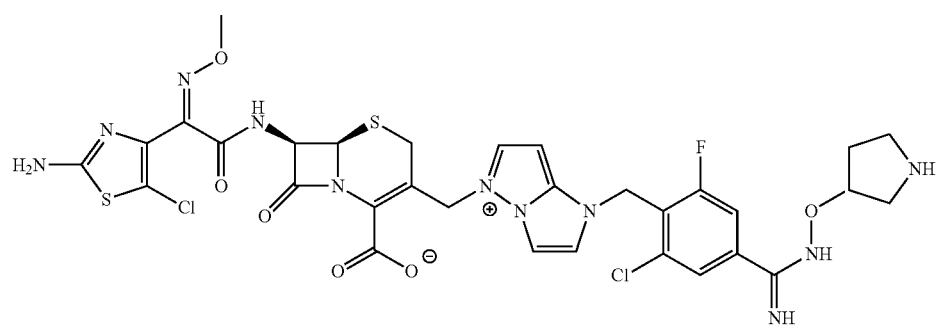
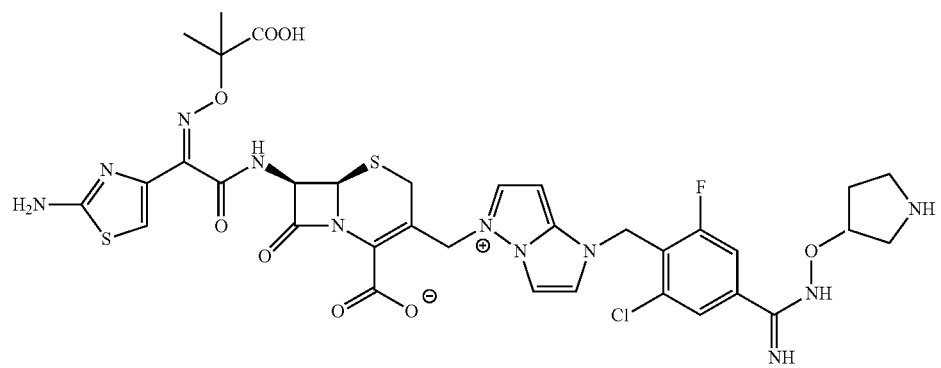
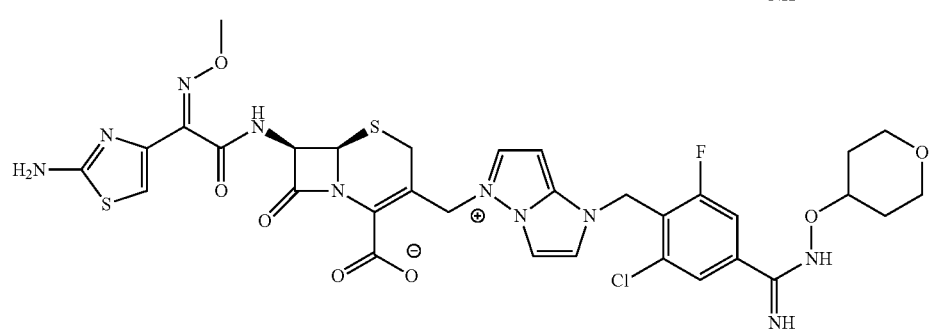
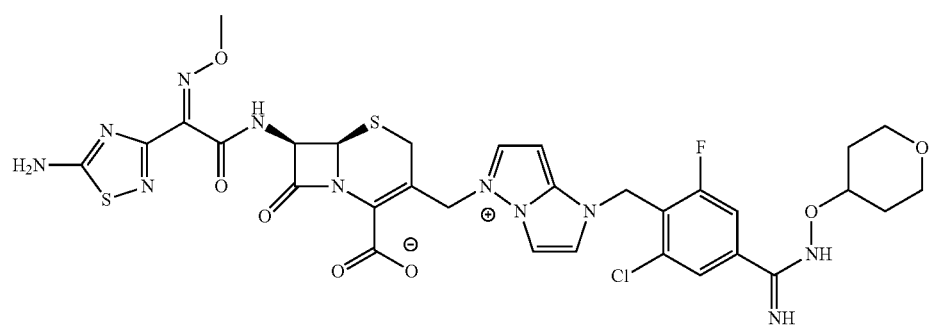

-continued
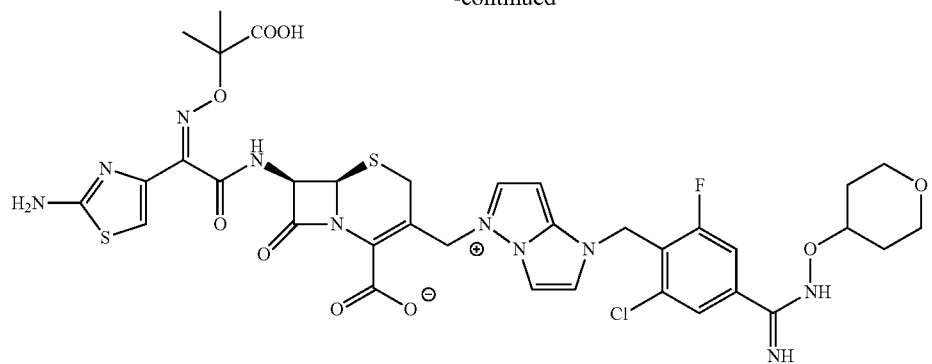
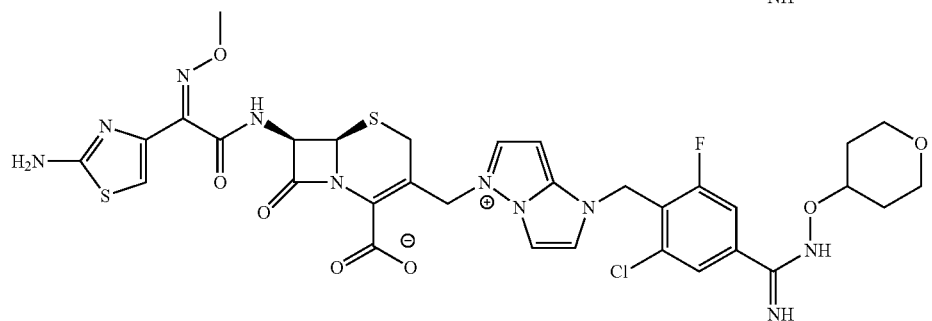
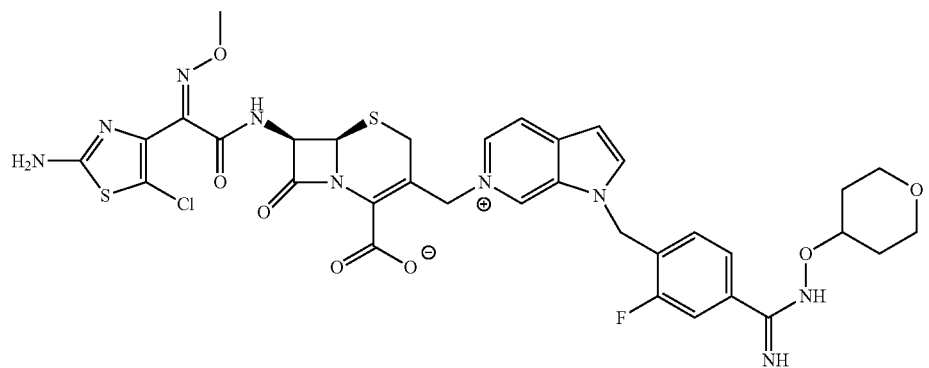
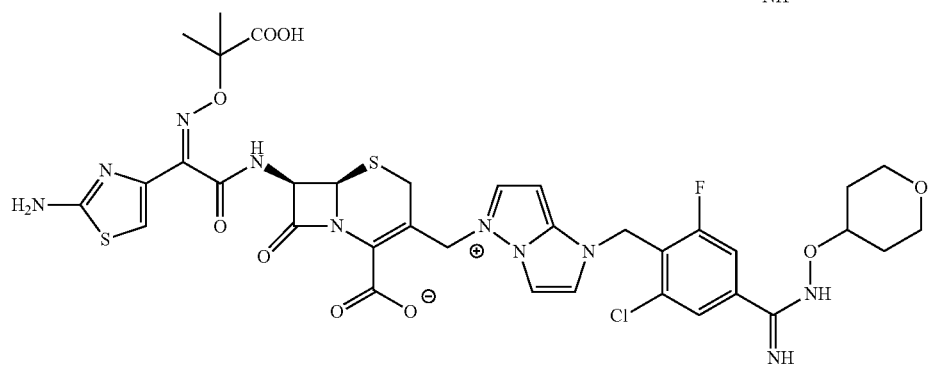
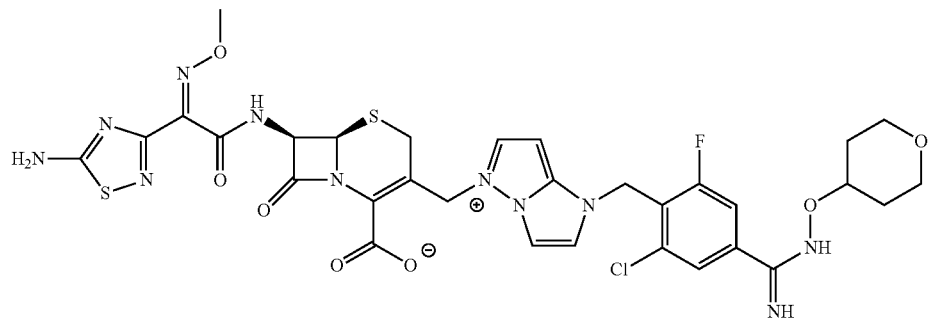

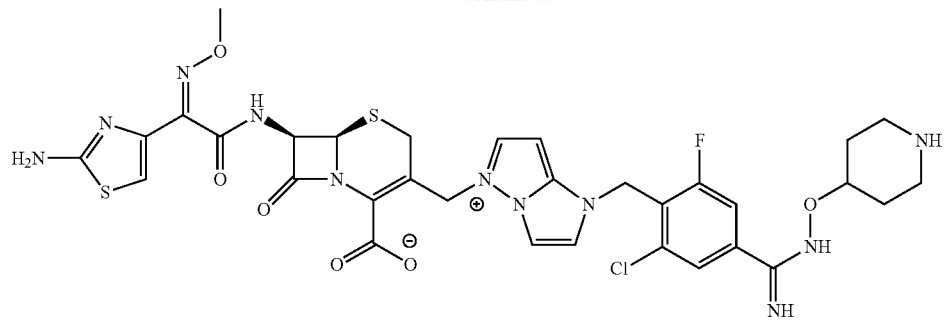
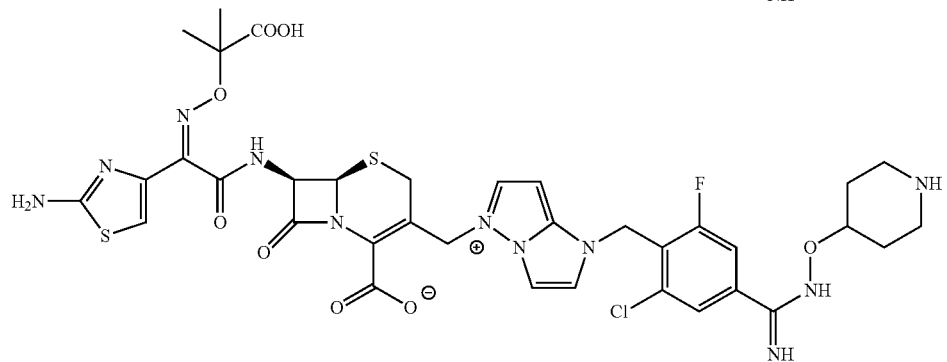
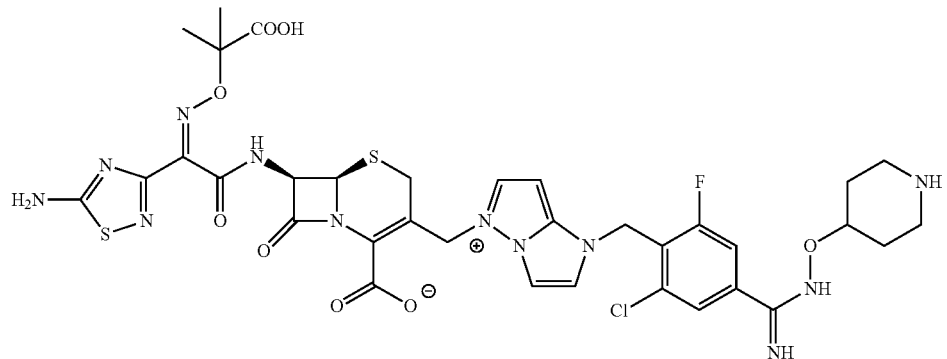
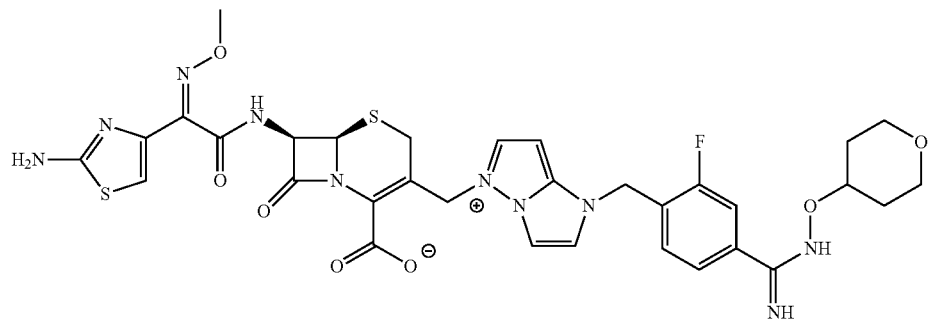
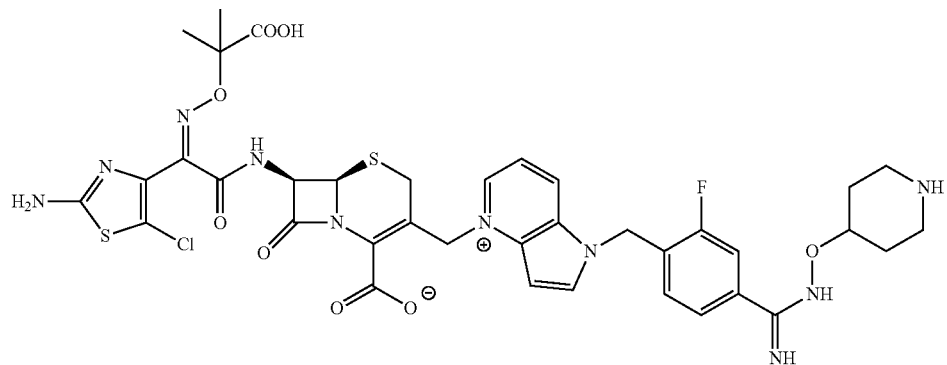

-continued

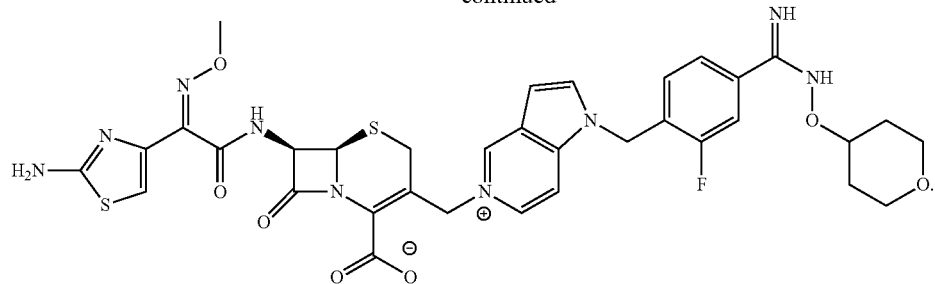

6. A method of treating a bacterial infection comprising administering to a mammal in need thereof an antibacterially effective amount of a compound as recited in claim 1.

7. A pharmaceutical composition containing as an active ingredient, at least one compound as recited in claim 1.

8. A method of treating a bacterial infection comprising administering to a mammal in need thereof a combination of (i) an antibacterially effective amount of a compound as recited in claim 1, and (ii) a therapeutically effective amount of a β-lactamase inhibitor selected from the group consisting of:

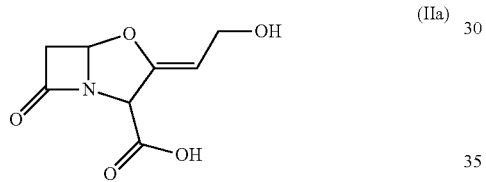
(IIa)

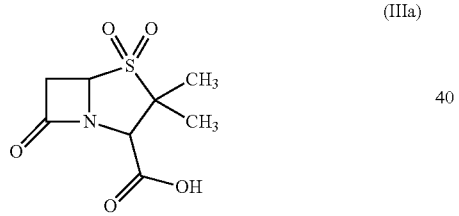
(IIIa)

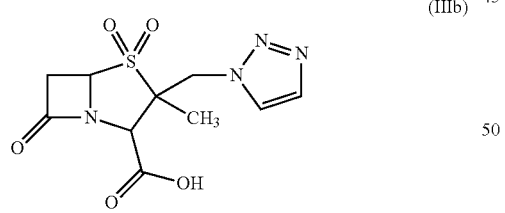
(IIIb)

(IVa)

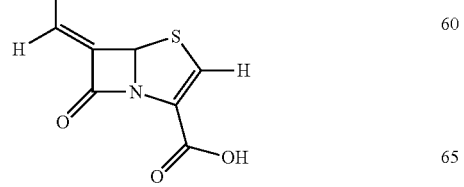

-continued

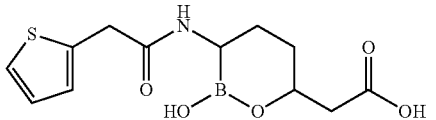
(Va)

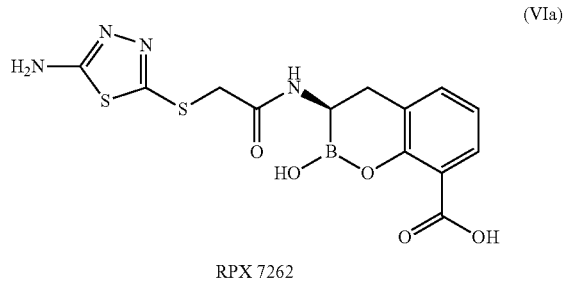
(VIa)

RPX 7262

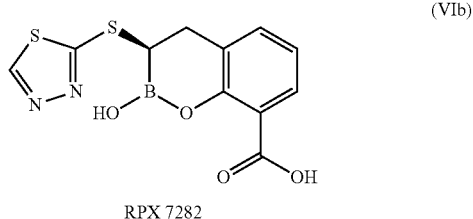
(VIb)

RPX 7282

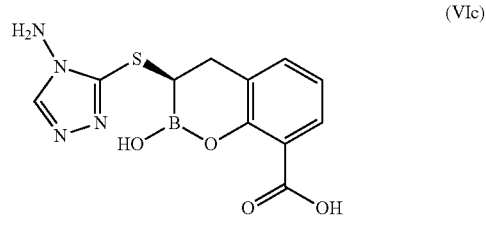
(VIc)

RPX 7381

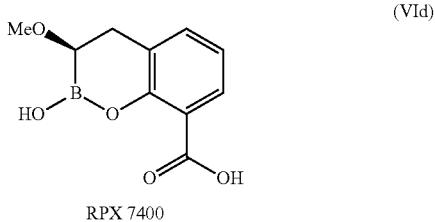
(VId)

RPX 7400

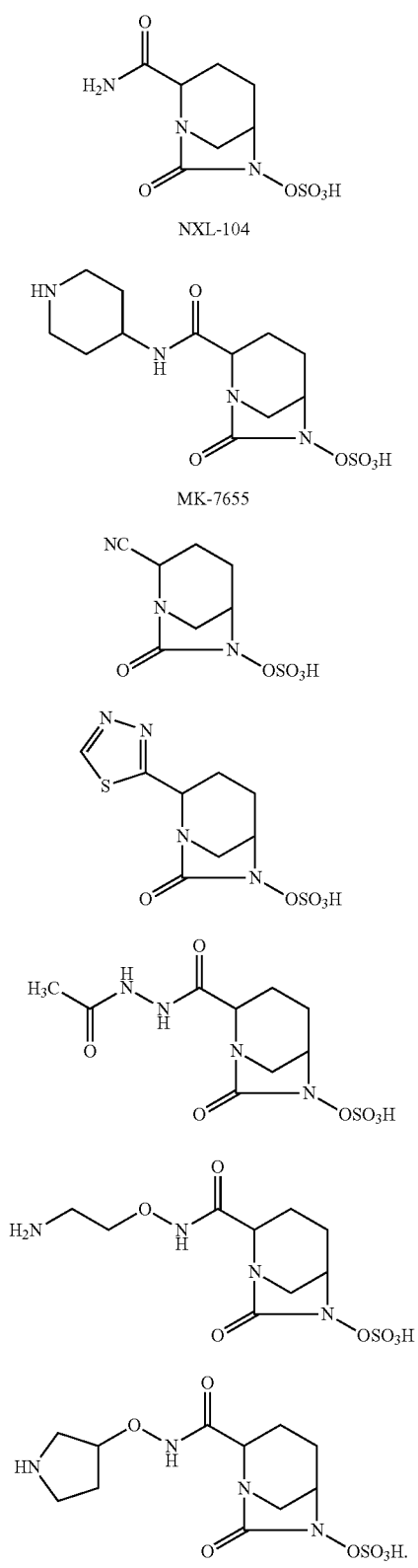
9. A pharmaceutical composition containing as an active ingredient at least (i) one compound as recited in claim 1 and (ii) a therapeutically effective amount of a β-lactamase inhibitor selected from the group consisting of:

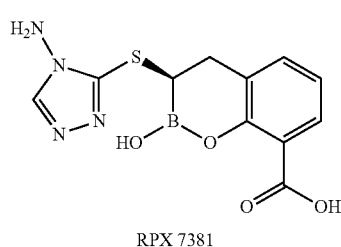

RPX 7381

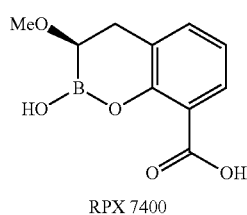

RPX 7400

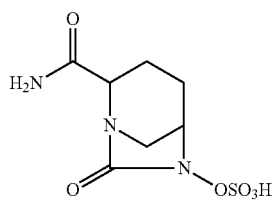

(VIIa, NXL-104)

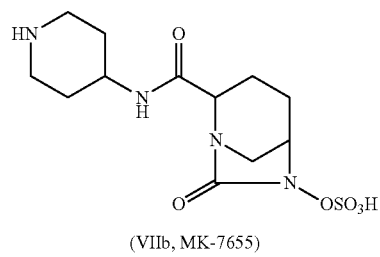

(VIIb, MK-7655)

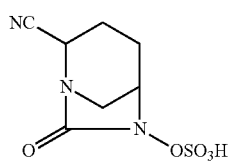

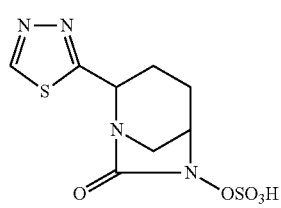

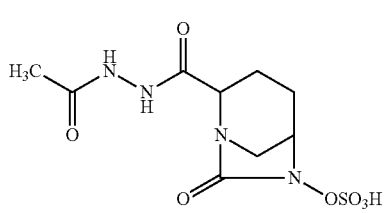

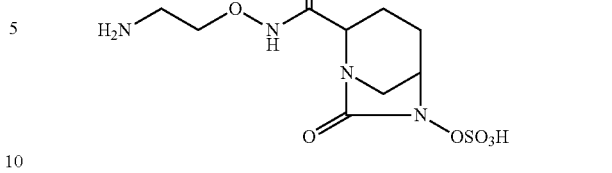

(VIc)

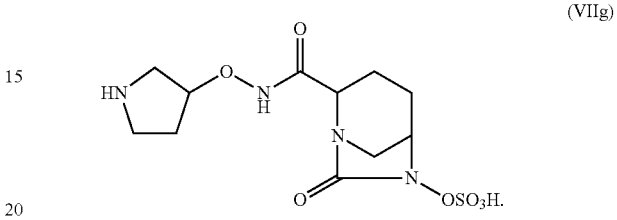

(VId)

10. The method as recited in claim 8, wherein (i) and (ii) are administered simultaneously, sequentially, or separated in time.

11. The pharmaceutical composition as recited in claim 9, wherein the ratio of the weight of (i) to the weight of (ii) is in the range of from about 1:20 to about 20:1.

12. A process for preparing a compound of formula (I) as recited in claim 1, the process comprising one of the following processes:

Process I wherein the intermediate VIII (q =0, Y =chloride) is coupled with intermediate (IX) to provide the intermediate (X) followed by removal of protecting groups to provide the compound of formula (I)

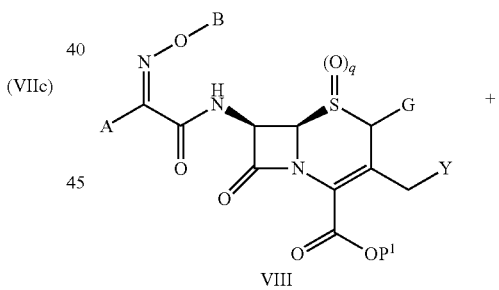

VIII

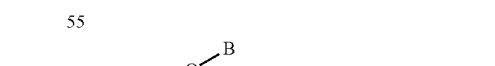

(IX)

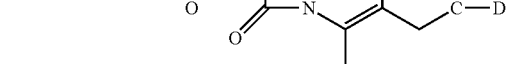

(X)

-continued
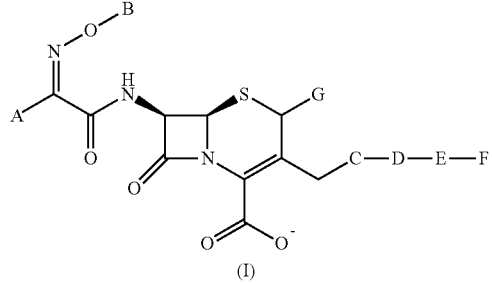
or
Process II wherein the intermediate VIII (q=1, Y=iodide) is coupled with intermediate (IX) and subsequently reducing the sulfoxide to sulfide providing the intermediate (XI) by removal of the protecting groups provides the compound of formula (I)
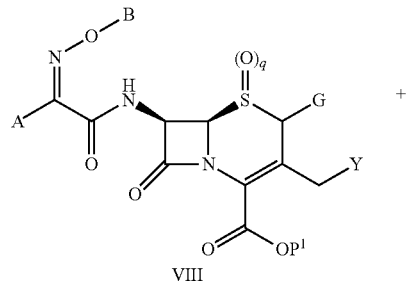
-continued
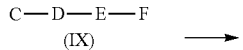
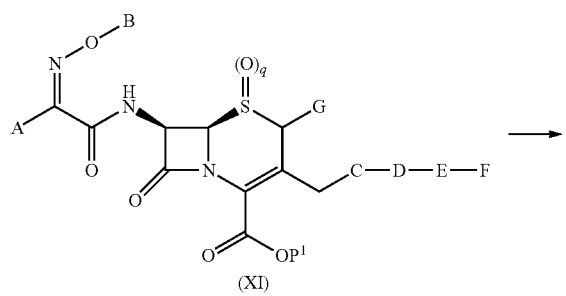
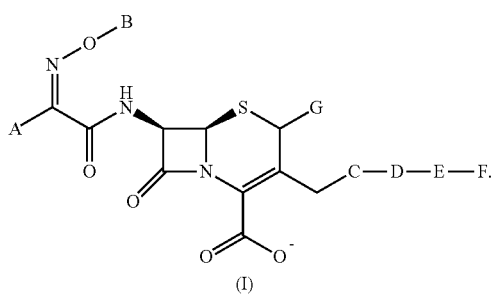
* * * * *

UNITED STATES PATENT AND TRADEMARK OFFICE
CERTIFICATE OF CORRECTION

PATENT NO. : 9,751,894 B2
APPLICATION NO. : 15/369181
DATED : September 5, 2017
INVENTOR(S) : Samarendra Nath Maiti et al.

It is certified that error appears in the above-identified patent and that said Letters Patent is hereby corrected as shown below:

In Claim 5, Columns 327-328, please delete the fourth listed compound:

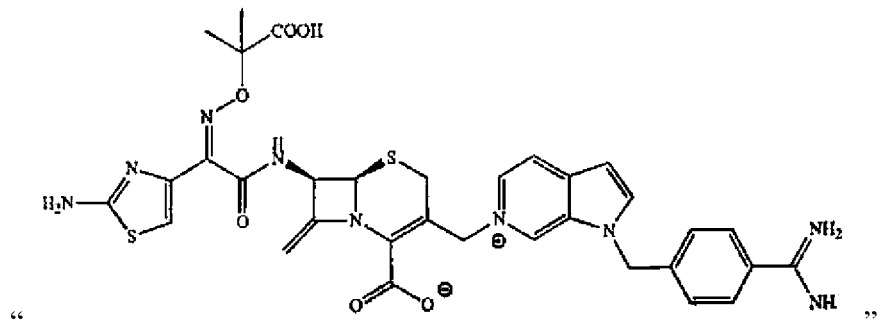

And insert:

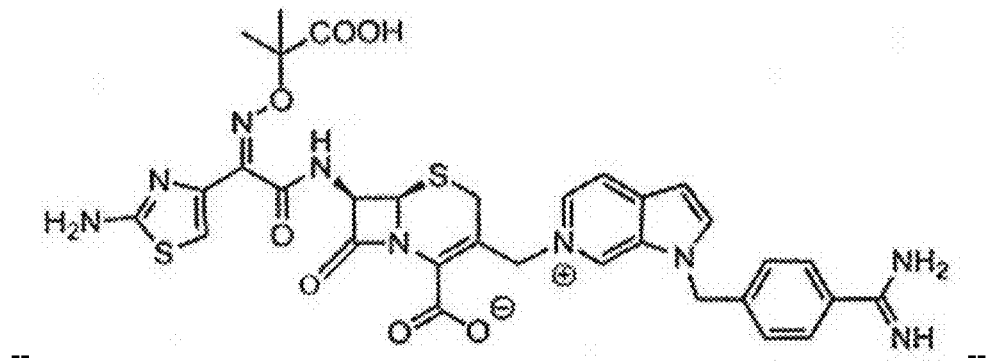

--

In Claim 5, Columns 335-336, please delete the fourth listed compound:

Signed and Sealed this
Nineteenth Day of December, 2017

Joseph Matal
*Performing the Functions and Duties of the
Under Secretary of Commerce for Intellectual Property and
Director of the United States Patent and Trademark Office*

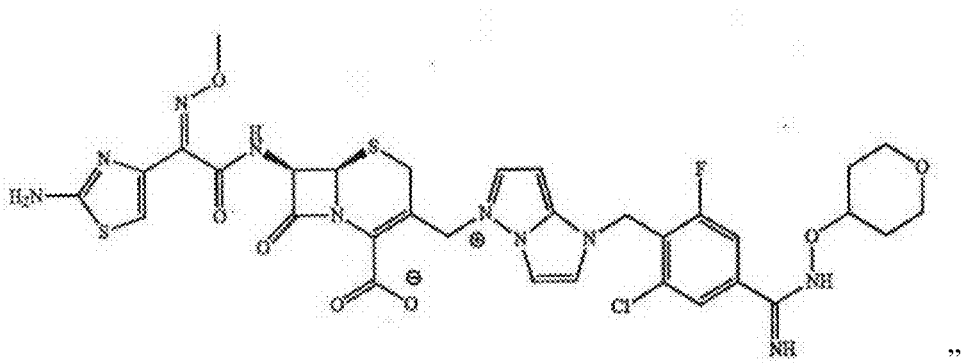
"
And insert:
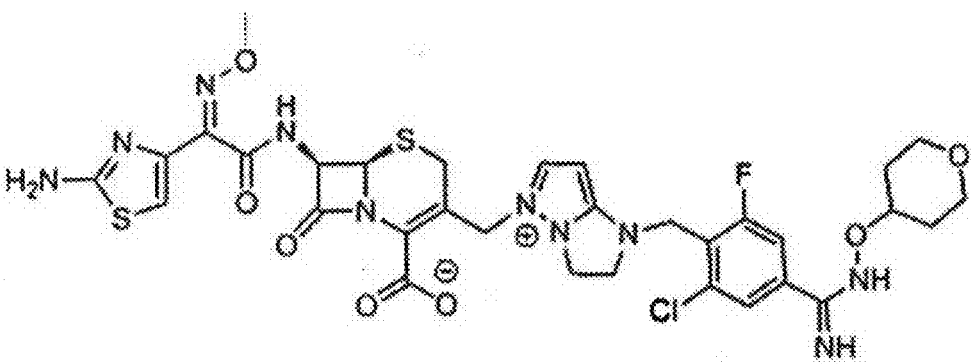
--  --
In Claim 5, Columns 335-336, please delete the fifth listed compound:
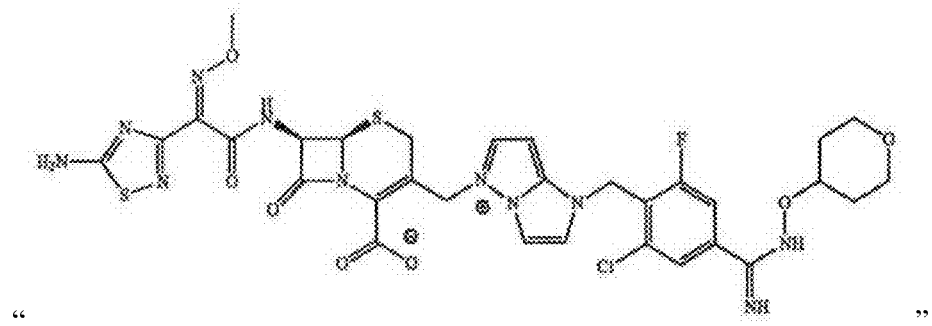
"  "
And insert:

CERTIFICATE OF CORRECTION (continued)
U.S. Pat. No. 9,751,894 B2

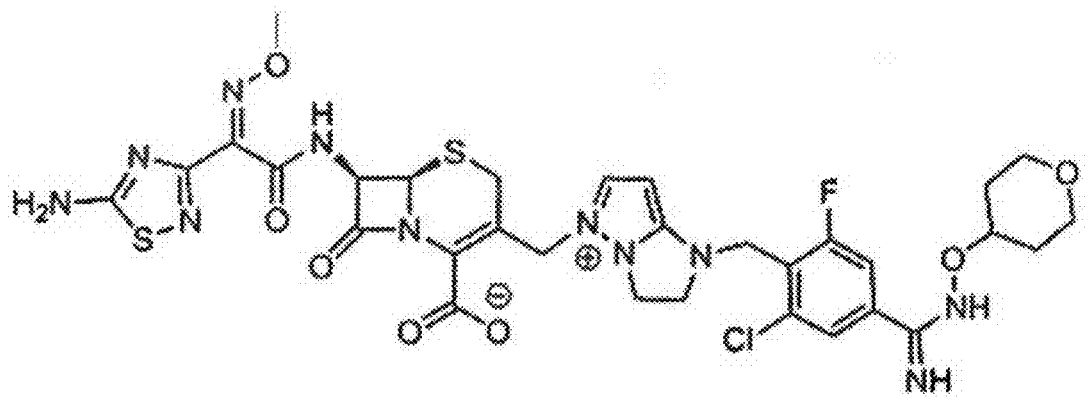

--  --

In Claim 5, Columns 337-338, please delete the first listed compound:

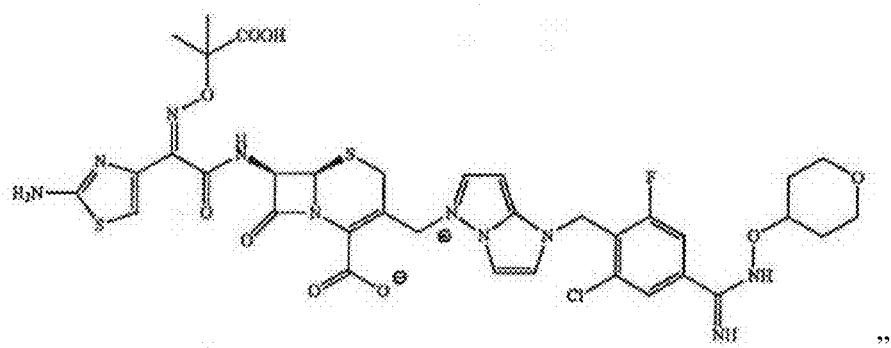

"  "

And insert:

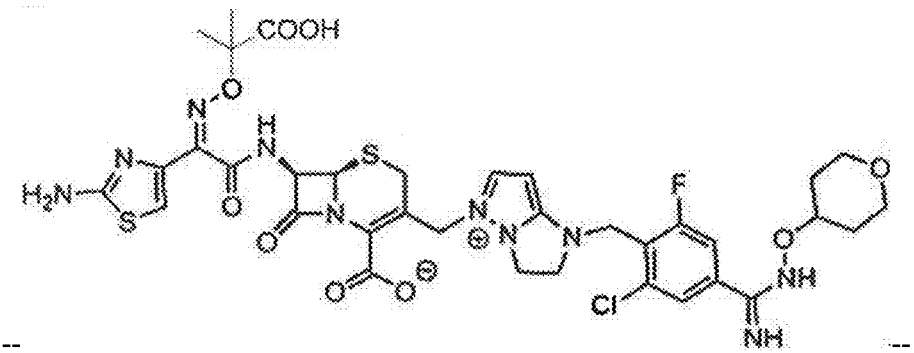

--  --